United States Patent
Suzuki et al.

(10) Patent No.: US 8,946,211 B2
(45) Date of Patent: Feb. 3, 2015

(54) FUSED AMINODIHYDROTHIAZINE DERIVATIVES

(71) Applicant: Eisai R&D Management Co., Ltd., Tokyo (JP)

(72) Inventors: Yuichi Suzuki, Tsukuba (JP); Takafumi Motoki, Tsukuba (JP); Toshihiko Kaneko, Tsukuba (JP); Mamoru Takaishi, Tsukuba (JP); Tasuku Ishida, Tsukuba (JP); Yoichi Kita, Tsukuba (JP); Kunitoshi Takeda, Tsukuba (JP); Noboru Yamamoto, London (GB); Afzal Khan, London (GB); Paschalis Dimopoulos, London (GB)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 13/804,691

(22) Filed: Mar. 14, 2013

(65) Prior Publication Data
US 2013/0203741 A1 Aug. 8, 2013

Related U.S. Application Data

(60) Continuation of application No. 13/333,238, filed on Dec. 21, 2011, which is a division of application No. 12/355,154, filed on Jan. 16, 2009, now Pat. No. 8,158,620.

(60) Provisional application No. 61/085,024, filed on Jul. 31, 2008, provisional application No. 61/021,939, filed on Jan. 18, 2008.

(30) Foreign Application Priority Data

Jan. 18, 2008 (JP) .................. 2008-008680
Jul. 31, 2008 (JP) .................. 2008-197204

(51) Int. Cl.
*C07D 513/02* (2006.01)
*A61K 31/542* (2006.01)

(52) U.S. Cl.
USPC .......................... 514/224.2; 544/48

(58) Field of Classification Search
USPC .......................... 544/48; 514/224.2
See application file for complete search history.

(56) References Cited

U.S. PATENT DOCUMENTS

| 3,227,713 | A | 1/1966 | Behner et al. |
|---|---|---|---|
| 3,235,551 | A | 2/1966 | Schubert et al. |
| 7,648,983 | B2 | 1/2010 | Audia et al. |
| 8,338,407 | B2 | 2/2012 | Hall et al. |
| 8,158,620 | B2 | 4/2012 | Suzuki et al. |
| 8,198,269 | B2 | 6/2012 | Motoki et al. |
| 2004/0110743 | A1 | 6/2004 | Miyamato et al. |
| 2006/0052406 | A1 | 3/2006 | Fisher et al. |
| 2007/0021454 | A1 | 1/2007 | Coburn et al. |
| 2008/0139538 | A1 | 6/2008 | McGaughey et al. |
| 2009/0082560 | A1 | 3/2009 | Kobayashi et al. |
| 2009/0209755 | A1 | 8/2009 | Suzuki et al. |
| 2010/0075957 | A1 | 3/2010 | Tamura et al. |
| 2010/0093999 | A1 | 4/2010 | Motoki et al. |
| 2010/0160290 | A1 | 6/2010 | Kobayashi et al. |
| 2010/0317850 | A1 | 12/2010 | Suzuki et al. |
| 2011/0009395 | A1 | 1/2011 | Audia et al. |
| 2011/0152253 | A1 | 6/2011 | Motoki et al. |
| 2011/0207723 | A1 | 8/2011 | Motoki et al. |
| 2012/0094984 | A1 | 4/2012 | Suzuki et al. |

(Continued)

FOREIGN PATENT DOCUMENTS

| EP | 1 942 105 | 7/2008 |
|---|---|---|
| EP | 2 233 474 | 9/2010 |

(Continued)

OTHER PUBLICATIONS

Bobrov et al., "Interaction of Quinone Oxide with Thiourea" *Chemistry and Chemical Technology*, 33(10):15-18 (1990) (original and English language translation).

(Continued)

*Primary Examiner* — Kahsay Habte
(74) *Attorney, Agent, or Firm* — Fish & Richardson P.C.

(57) ABSTRACT

A compound represented by the general formula:

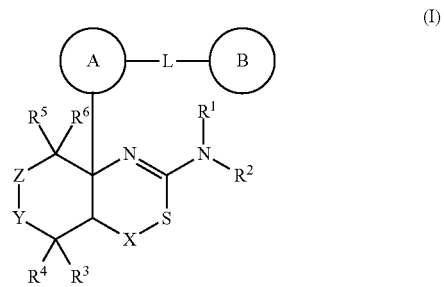

(I)

or a pharmaceutically acceptable salt thereof or a solvate thereof, wherein Ring A is a $C_{6-14}$ aryl group or the like, L is —$NR^eCO$— or the like (wherein $R^e$ is a hydrogen atom or the like), Ring B is a $C_{6-14}$ aryl group or the like, X is a $C_{1-3}$ alkylene group or the like, Y is a single bond or the like, Z is a $C_{1-3}$ alkylene group or the like, $R^1$ and $R^2$ are each independently a hydrogen atom or the like, and $R^3$, $R^4$, $R^5$ and $R^6$ are independently a hydrogen atom, a halogen atom or the like, has an Aβ production inhibitory effect or a BACE1 inhibitory effect and is useful as a prophylactic or therapeutic agent for a neurodegenerative disease caused by Aβ and typified by Alzheimer-type dementia.

10 Claims, No Drawings

(56) References Cited

U.S. PATENT DOCUMENTS

| | | |
|---|---|---|
| 2012/0190672 A1 | 7/2012 | Hall et al. |
| 2012/0190848 A1 | 7/2012 | Mitasev et al. |
| 2012/0202804 A1 | 8/2012 | Ellard et al. |
| 2012/0202828 A1 | 8/2012 | Castro Pineiro et al. |

FOREIGN PATENT DOCUMENTS

| | | |
|---|---|---|
| JP | 09-067355 | 3/1997 |
| JP | 2004-149429 | 5/2004 |
| WO | 96/14842 | 5/1996 |
| WO | WO 01/87293 | 11/2001 |
| WO | WO 02/096897 | 12/2002 |
| WO | WO 2004/014843 | 2/2004 |
| WO | WO 2004/043916 | 5/2004 |
| WO | WO 2005/058311 | 6/2005 |
| WO | WO 2005/097767 | 10/2005 |
| WO | WO 2006/041404 | 4/2006 |
| WO | WO 2006/041405 | 4/2006 |
| WO | WO 2007/011810 | 1/2007 |
| WO | WO 2007/049532 | 5/2007 |
| WO | WO 2008/133273 | 11/2008 |
| WO | WO 2008/133274 | 11/2008 |
| WO | WO 2010/013302 | 2/2010 |
| WO | WO 2010/013794 | 2/2010 |
| WO | WO 2011/009897 | 1/2011 |
| WO | WO 2011/009898 | 1/2011 |
| WO | WO 2012/093148 | 7/2012 |
| WO | WO 2012/098213 | 7/2012 |
| WO | WO 2012/098461 | 7/2012 |
| WO | WO 2012/100179 | 7/2012 |

OTHER PUBLICATIONS

Cohen et al., "Synthesis of 2-Amino-5,6-dihydro-4H-1,3-thiazines and Related Compounds by Acid Catalyzed Cyclization of Allylic Isothiuronium Salts," *Journal of Heterocyclic Chemistry*, 14:717-723 (1977).
Forman et al., "Differential Effects of the Swedish Mutant Amyloid Precursor Protein on β-Amyloid Accumulation and Secretion in Neurons and Nonneuronal Cells," *The Journal of Biological Chemistry*, 272(51):32247-32253 (1997).
Glenner et al., "Alzheimer's Disease: Initial report of the purification and characterization of a novel cerebrovascular amyloid protein," *Biochemical and Biophysical Research Communications*, 120(3):885-890 (1984).
Gong et al., "Alzheimer's disease-affected brain: Presence of oligomeric Aβ ligands (ADDLs) suggests a molecular basis for reversible memory loss," *Proceeding National Academy of Science USA*, 100(18):10417-10422 (2003).
Gouras et al., "Intraneuronal Aβ42 Accumulation in Human Brain," *American Journal of Pathology*, 156(1):15-20 (2000).
Hock et al., "Antibodies against β-Amyloid Slow Cognitive Decline in Alzheimer's Disease," *Neuron*, 38:547-554 (2003).
Jarrett et al., "The Carboxy Terminus of the β Amyloid Protein is Critical for the Seeding of Amyloid Formation: Implications for the Pathogenesis of Alzheimer's Disease," *Biochemistry*, 32(18):4693-4697 (1993).
Khimiya i Khimicheskaya Tekhologiya, 33(10):15-18 (1990).
Kuo et al., "A Synthesis of Estrone via Novel Intermediates, Mechanism of the Coupling Reaction of a Vinyl Carbinol with a β Diketone," *Journal of Organic Chemistry*, 33(8):3126-3132 (1968).
Masters et al., "Amyloid plaque core protein in Alzheimer disease and Down syndrome," *Proceeding National Academy of Science USA*, 82:4245-4249 (1985).
Meredith et al., "P-Glycoprotein Efflux and Other Factors Limit Brain Amyloid β Reduction by β-Site Amyloid Precursor Protein-Cleaving Enzyme 1 Inhibitors in Mice," *J. Pharmacol. Exp. Ther*, 326(2):502-513 (2008).
Sankaranarayanan et al., "In Vivo β-Secretase 1 Inhibition Leads to Brain Aβ Lowering and Increased α-Secretase Processing of Amyloid Precursor Protein without Effect on Neuregulin-1," *J. Pharmacol. Exp. Ther*, 324(3):957-969 (2008).
Scheuner et al., "Secreted amyloid β-protein similar to that in the senile plaques of Alzheimer's disease is increased in vivo by the presenilin 1 and 2 and APP mutations linked to familial Alzheimer's disease," *Nature Medicine*, 2(8):864-870 (1996).
Acceptance of Complete Specification from South African Application No. 2010/04799 (Aug. 16, 2011).
Amended Claims and Observations for Chinese App. Ser. No. 200980101688.X dated Jan. 22, 2013, 13 pages (with English translation).
Amended Claims and Specification Filed with Response to Office Action from Chilean Application No. 96-2009 and English Translation (Nov. 4, 2011).
Amendment and Response to Office Action from Mexican Application No. MX/a/2010/007337 and English Translation (Jan. 3, 2012).
Amendment and Response to Office Action from Singapore Application No. 201102027-8 (Dec. 28, 2011).
Amendment and Response to Office Action from U.S. Appl. No. 12/568,151 (Dec. 22, 2011).
Amendment filed with Request for Continued Examination from U.S. Appl. No. 12/355,154 (Jan. 5, 2012).
Amendment in Reply to Office Action of Jun. 3, 2011 in U.S. Appl. No. 12/355,154 (Sep. 2, 2011).
Argument and Amended Claims for Mexico App. Ser. No. MX/a/2011/003189 dated Feb. 14, 2013, 31 pages (with English translation).
Argument and Amendment in Response to Office Action from Japanese Application No. 2009-5500550 and English Translation (Apr. 12, 2010).
Argument and Amendment in Response to Office Action from New Zealand Application No. 586796 (Apr. 28, 2011).
Argument and Amendment in Response to Office Action from Pakistan Application No. 43/2009 (May 21, 2010).
Communication for Europe App. Ser. No. 09788008.2 dated Feb. 4, 2013, 7 pages.
Decision of Grant dated Feb. 23, 2012 for Ukraine App. Ser. No. a201010101 and English Translation.
Decision of Granting Patent from Japanese Application No. 2009-550050 and English Translation (May 7, 2010).
Decision of Grant for Ukraine App. Ser. No. A201010101 dated Nov. 22, 2012, 16 pages (with English translation).
English Translation of Office Action from Mexican Application No. MX/a/2010/007337 (2011).
European Search Report for App. Ser. No. EP 09 81 7719, dated Feb. 14, 2012.
Examination Report and Notice of Acceptance of Complete Specification from New Zealand Application No. 586796 (Oct. 6, 2011).
Examination Report for Australia App. Ser. No. 2009277485 dated Feb. 7, 2013, 2 pages.
Examination Report from Australian App. Ser. No. 2009205072, dated Jul. 19, 2012.
Examination Report from Chilean App. Ser. No. 702-2-011, dated May 14, 2012 and English Translation.
Examination Report from GCC App. Ser. No. 12680 and English translation (Sep. 15, 2012).
Examination Report from GCC App. Ser. No. 14375 and English translation (Jul. 18, 2012).
Examiner's Report and Amendments/Observations for Chile App. Ser. No. 702-2011 dated Oct. 11, 2013 and Jan. 28, 2013, 56 pages (with English translation).
Extended Search Report from European Application No. 09701914.5 (Sep. 30, 2011).
International Preliminary Report on Patentability from PCT Application No. PCT/JP2009/050511 (Aug. 31, 2010).
International Search Report from PCT Application No. PCT/JP2009/050511 (Mar. 24, 2009).
Newspaper Publication of Venezuelan Application No. 2009-000078 (2011).
Notice of Acceptance for Australia App. Ser. No. 2009205072 dated Jan. 10, 2013, 3 pages.
Notice of Acceptance for New Zealand App. Ser. No. 591878 (May 17, 2012).

(56) References Cited

OTHER PUBLICATIONS

Notice of Acceptance from South African App. Ser. No. 2011/02172 (Jul. 30, 2012).
Notice of Allowance for U.S. Appl. No. 13/354,716 dated Oct. 2, 2012, 5 pages.
Notice of Allowance from Canadian App. Ser. No. 2,711,655 (Nov. 1, 2012).
Notice of Allowance from U.S. Appl. No. 13/055,830 (Oct. 26, 2012).
Notice of Allowance from U.S. Appl. No. 12/355,154 (Feb. 17, 2012).
Notice of Allowance from U.S. Appl. No. 12/355,154 (Jan. 18, 2012).
Notice of Allowance from U.S. Appl. No. 12/355,154 (Oct. 5, 2011).
Notice of Allowance from U.S. Appl. No. 12/568,151 (Jan. 4, 2012).
Notification of Examination from Ukraine App. Ser. No. a201010101 and English translation (Aug. 3, 2012).
Office Action for Chinese App. Ser. No. 200980101688.X dated Dec. 5, 2012, 6 pages (with English translation).
Office Action for Chinese App. Ser. No. 200980129365.1 dated Dec. 5, 2012, 8 pages (with English translation).
Office Action for Israel App. Ser. No. 206952 dated Jan. 6, 2013, 3 pages (with English translation).
Office Action for Mexico App. Ser. No. MX/a/2011/003189 dated Nov. 27, 2012, 4 pages (with English translation).
Office Action from Canadian App. Ser. No. 2,711,655, dated Jun. 5, 2012.
Office Action from Chilean Application No. 96-2009 and English Translation (2011).
Office Action from Chilean Application No. 96-2009 and English Translation (Aug. 1, 2011).
Office Action from Chilean Application No. 96-2009 and English Translation (Dec. 12, 2011).
Office Action from Chinese Application No. 200980101688.X and English Translation (Apr. 1, 2012).
Office Action from Japanese Application No. 2009-550050 and English translation (Feb. 9, 2011).
Office Action from Mexican Application No. MX/a/2010/007337 and English Translation (Oct. 19, 2011).
Office Action from Mexican Application No. MX/a/2011/003189 and English Translation (Jun. 25, 2012).
Office Action from New Zealand Application No. 586796 (Feb. 21, 2011).
Office Action from Pakistan Application No. 43/2009 (Mar. 26, 2010).
Office Action from Russian App. Ser. No. 2010134403, dated May 14, 2012 and English Translation.
Office Action from U.S. Appl. No. 12/355,154 (Jun. 3, 2011).
Office Action from U.S. Appl. No. 12/568,151 (Oct. 24, 2011).
Official Acceptance Notice for Pakistan Application No. 43/2009 (Jun. 10, 2010).
Official Decision of Grant from Russian App. Ser. No. 2010134403 (Oct. 8, 2012).
Preliminary Office Action and Response for Israel App. Ser. No. 211933 dated Oct. 11, 2012 and Feb. 10, 2013, 5 pages (with English translation).
Reply and Amended Claims from Ukraine App. Ser. No. A201010101 and English translation (Oct. 18, 2012).
Reply and Amendments from Australian App. Ser. No. 2009205072 (Nov. 22, 2012).
Reply from GCC App. Ser. No. 12680 and English translation (Oct. 3, 2012).
Reply from GCC App. Ser. No. 14375 and English translation (Aug. 11, 2012).
Response to Communication pursuant to Rules 70(2) and 70a(2) for European App. Ser. No. 09817719.9 (Jul. 26, 2012).
Response to Examiner's Action for Philippine App. Ser. No. Jan. 2010-501531 dated Jan. 29, 2013, 1 page.
Response to Examiner's report for Chilean App. Ser. No. 702-2011 and English translation (Aug. 8, 2012).
Response to Office Action from Chilean Application No. 96-2009 and English Translation (Nov. 4, 2011).
Response to Office Action from Chilean Application No. 96-2009 and English Translation (Mar. 22, 2012).
Response to Office Action from Chinese Application No. 200980101688.X and English Translation (Jun. 15, 2012).
Response to Office Action in Mexican App. Ser. No. MX/a/2011/003189 and English translation (Aug. 28, 2012).
Response to Office Action in Russian App. Ser. No. 2010134403 and English translation (Aug. 14, 2012).
Response to Restriction Requirement from U.S. Appl. No. 12/355,154 (May 19, 2011).
Response to Written opinion for Singapore App. Ser. No. 201102027-8 dated Feb. 5, 2013, 3 pages.
Response to Written Opinion from Singapore Application No. 201102027-8 (Jul. 5, 2012).
Restriction Requirement from U.S. Appl. No. 12/355,154 (Apr. 19, 2011).
Substantive Examination Report for Philippine App. Ser. No. 1-2010-501531 dated Dec. 10, 2012, 1 page.
Supplemental Amendment in Reply to Office Action of Jun. 3, 2011 in U.S. Appl. No. 12/355,154 (Sep. 27, 2011).
Technical Report for Peru App. Ser. No. 52/2009 dated Feb. 6, 2013, 15 pages (with English translation).
Written Opinion from Singapore App. Ser. No. 201102027-8 (Aug. 24, 2011).
Written Opinion from Singapore App. Ser. No. 201102027-8 (Mar. 15, 2012).
Written Opinion from Singapore App. Ser. No. 201102027-8 (Oct. 10, 2012).
Examination Response filed in CN App. Ser. No. 200980138381.7, dated Jun. 19, 2013, 25 pages (with English translation).
Examination Response filed in CN App. Ser. No. 200980138381.7, dated Aug. 1, 2013, 15 pages (with English translation).
Examination Response filed in ID App. Ser. No. W-00 201101110, dated Jul. 8, 2013, 4 pages (with English translation).
Examination Response filed in RU App. Ser. No. 2011117341, dated Jul. 24, 2013, 29 pages (with English translation).
Notice of Acceptance issued in AU App. Ser. No. 2008221906, dated Mar. 28, 2012, 3 pages.
Official Communication issued in EP App. Ser. No. 09701914.5, dated Jun. 27, 2013, 5 pages.
Official Letter issued in TW App. Ser. No. 98101564, dated Jun. 24, 2013, 9 pages (with English translation).
Official Notice issued in VN App. Ser. No. 1-2011-00844, dated Jun. 24, 2013, 3 pages (with English translation).
Amendment filed in IL App. Ser. No. 211933, dated Nov. 21, 2013, 11 pages.
Argument and Amendment filed in CN App. Ser. No. 200980129365.1, dated Sep. 26, 2013, 11 pages (with English translation).
Argument and Amendment filed in EP App. Ser. No. 09701914.5, dated Nov. 6, 2013, 45 pages.
Argument and Amendment filed in JP App. Ser. No. 2010-533357, dated Nov. 7, 2013, 8 pages (with English translation).
Argument and Amendment filed in TW App. Ser. No. 98101564, dated Sep. 23, 2013, 950 pages (with English translation).
Decision of Grant in RU App. Ser. No. 2011117341, dated Aug. 23, 2013, 20 pages (with English Translation).
Decision of Granting Patent in JP App. Ser. No. 2010-533357, dated Dec. 13, 2013, 6 pages (with English translation).
Examination Report issued in PH App. Ser. No. Jan. 2011-500586, dated Aug. 29, 2013, 6 pages (with English Translation).
First Examination Report in AU App. Ser. No. 2009300836, dated Oct. 24, 2013, 2 pages.
Notice of Allowance in GCC App. Ser. No. 12680, dated Nov. 18, 2013, 2 pages (with English translation).
Notice of Allowance in ID App. Ser. No. W-00 2011 01110, dated Jul. 22, 2013, 4 pages (with English translation).
Notice of Allowance in TW App. Ser. No. 98101564, dated Nov. 28, 2013, 3 pages (with English translation).
Notification to Grant Patent Right issued in CN App. Ser. No. 200980138381.7, dated Aug. 20, 2013, 4 pages (with English Translation).

(56) References Cited

OTHER PUBLICATIONS

Office Action in JP App. Ser. No. 2010-533357, dated Sep. 13, 2013, 4 pages (with English translation).
Office Action issued in IL App. Ser. No. 211933, dated Aug. 8, 2013, 5 pages (with English Translation).
Substantive Examination Adverse Report in MY App. Ser. No. PI 2010003293, dated Nov. 15, 2013, 3 pages.
Technical Report issued in PE App. Ser. No. 781-2011, dated Sep. 6, 2013, 7 pages (with English Translation).
Office Action mailed Dec. 20, 2013 in Japanese App. Ser. No. 2010-531835, 9 pages (with English translation).
Notice before Allowance dated Dec. 22, 2013 in IL App. Ser. No. 206952, 11 pages (with English translation).
Response (Argument and Amendment) as filed on Dec. 30, 2013 in MY App. Ser. No. 2010003293, 9 pages.
Response (Notice of Entitlement and Amendment) as filed on Jan. 15, 2014 in AU App. Ser. No. 2009300836, 9 pages.
Decision of Grant in TW App. Ser. No. 1423970, dated Jan. 21, 2014, 2 pages (with English translation).
Decision of Grant in CN App. Ser. No. 200980129365.1, dated Jan. 17, 2014, 5 pages (with English translation).
Official Action in EP App. Ser. No. 09817719.9, dated Feb. 12, 2014, 4 pages.
Response (Argument and Amendment) filed in JP App. Ser. No. 2010-531835, dated Feb. 18, 2014, 65 pages (with English translation).
Official Action in EG App. Ser. No. 2010071213, dated Mar. 21, 2014, 7 pages (with English translation).
Office Action in EP App. Ser. No. 09701914.5, dated May 20, 2014, 4 pages.
Amendment filed in EP App. Ser. No. 09817719.9, dated Jun. 6, 2014, 27 pages.
Response to office action filed in EG App. Ser. No. PCT 1213/2010, dated Jun. 23, 2014, 1013 pages (with English translation).
Office Action in JP App. Ser. No. 2010-531835, mailed Aug. 1, 2014, 4 pages (with English translation).

FUSED AMINODIHYDROTHIAZINE DERIVATIVES

RELATED APPLICATIONS

The present application is a continuation of U.S. application Ser. No. 13/333,238, filed on Dec. 21, 2011, which is a divisional of U.S. application Ser. No. 12/355,154, filed on Jan. 16, 2009, issued as U.S. Pat. No. 8,158,620, which claims priority from U.S. provisional application Ser. No. 61/021,939 filed on Jan. 18, 2008, U.S. provisional application Ser. No. 61/085,024 filed on Jul. 31, 2008, Japanese patent application no. 2008-008680 filed on Jan. 18, 2008, and Japanese patent application no. 2008-197204 filed on Jul. 31, 2008, all of the contents of which are incorporated herein by reference.

BACKGROUND OF THE INVENTION

1. Field of the Invention

The present invention relates to a fused aminodihydrothiazine derivative and pharmaceutical use thereof. More particularly, the present invention relates to a fused aminodihydrothiazine derivative which has an amyloid-β (hereinafter referred to as Aβ) protein production inhibitory effect or a beta-site amyloid-β precursor protein cleavage enzyme 1 (hereinafter referred to as BACE1 or beta-secretase) inhibitory effect and is effective for treating a neurodegenerative disease caused by Aβ protein, in particular, Alzheimer-type dementia, Down's syndrome or the like, and to a pharmaceutical composition comprising the fused aminodihydrothiazine derivative as an active ingredient.

2. Description of Related Art

Alzheimer's disease is a disease characterized by degeneration and loss of neurons as well as formation of senile plaques and neurofibrillary degeneration. Currently, Alzheimer's disease is treated only with symptomatic treatment using a symptom improving agent typified by an acetylcholinesterase inhibitor, and a fundamental remedy to inhibit progression of the disease has not yet been developed. It is necessary to develop a method for controlling the cause of the onset of pathology in order to create a fundamental remedy for Alzheimer's disease.

It is assumed that Aβ-proteins as metabolites of amyloid precursor proteins (hereinafter referred to as APP) are highly involved in degeneration and loss of neurons and onset of symptoms of dementia (see Non-Patent Documents 3 and 4, for example). Aβ-proteins have, as main components, Aβ40 consisting of 40 amino acids and Aβ42 with two amino acids added at the C-terminal. The Aβ40 and Aβ42 are known to have high aggregability (see Non-Patent Document 5, for example) and to be main components of senile plaques (see Non-Patent Documents 5, 6 and 7, for example). Further, it is known that the Aβ40 and Aβ42 are increased by mutation in APP and presenilin genes which is observed in familial Alzheimer's disease (see Non-Patent Documents 8, 9 and 10, for example). Accordingly, a compound that reduces production of Aβ40 and Aβ42 is expected as a progression inhibitor or prophylactic agent for Alzheimer's disease.

Aβ is produced by cleaving APP by beta-secretase (BACE1) and subsequently by gamma-secretase. For this reason, attempts have been made to create gamma-secretase and beta-secretase inhibitors in order to inhibit Aβ production. Already known beta-secretase inhibitors are reported in Patent Documents 1 to 13 and Non-Patent Documents 1 and 2 shown below and the like. In particular, Patent Document 1 describes an aminodihydrothiazine derivative and a compound having BACE1 inhibitory activity.

[Patent Document 1] WO 2007/049532
[Patent Document 2] U.S. Pat. No. 3,235,551
[Patent Document 3] U.S. Pat. No. 3,227,713
[Patent Document 4] JP-A-09-067355
[Patent Document 5] WO 01/87293
[Patent Document 6] WO 04/014843
[Patent Document 7] JP-A-2004-149429
[Patent Document 8] WO 02/96897
[Patent Document 9] WO 04/043916
[Patent Document 10] WO 2005/058311
[Patent Document 11] WO 2005/097767
[Patent Document 12] WO 2006/041404
[Patent Document 13] WO 2006/041405
[Non-Patent Document 1] Journal of Heterocyclic Chemistry, vol. 14, p. 717-723 (1977)
[Non-Patent Document 2] Journal of Organic Chemistry, vol. 33, p. 3126-3132 (1968)
[Non-Patent Document 3] Klein W L, and seven others, Alzheimer's disease-affected brain: Presence of oligomeric Aβ ligands (ADDLs) suggests a molecular basis for reversible memory loss, Proceeding National Academy of Science USA, Sep. 2, 2003; 100 (18), p. 10417-10422.
[Non-Patent Document 4] Nitsch R M, and sixteen others, Antibodies against β-amyloid slow cognitive decline in Alzheimer's disease, Neuron, 2003, May 22; 38, p. 547-554.
[Non-Patent Document 5] Jarrett J T, and two others, The carboxy terminus of the β amyloid protein is critical for the seeding of amyloid formation: Implications for the pathogenesis of Alzheimers' disease, Biochemistry, 1993, 32 (18), p. 4693-4697.
[Non-Patent Document 6] Glenner G G, and one other, Alzheimer's disease: initial report of the purification and characterization of a novel cerebrovascular amyloid protein, Biochemical and biophysical research communications, May 16, 1984, 120 (3), p. 885-890.
[Non-Patent Document 7] Masters C L, and five others, Amyloid plaque core protein in Alzheimer disease and Down syndrome, Proceeding National Academy of Science USA, 1985, June, 82 (12), p. 4245-4249.
[Non-Patent Document 8] Gouras G K, and eleven others, Intraneuronal Aβ42 accumulation in human brain, American Journal of Pathology, 2000, January, 156 (1), p. 15-20.
[Non-Patent Document 9] Scheuner D, and twenty others, Secreted amyloid β-protein similar to that in the senile plaques of Alzheimer's disease is increased in vivo by the presenilin 1 and 2 and APP mutations linked to familial Alzheimer's disease, Nature Medicine, 1996, August, 2 (8), p. 864-870.
[Non-Patent Document 10] Forman M S, and four others, Differential effects of the swedish mutant amyloid precursor protein on β-amyloid accumulation and secretion in neurons and nonneuronal cells, The Journal of Biological Chemistry, Dec. 19, 1997, 272 (51), p. 32247-32253.

BRIEF SUMMARY OF THE INVENTION

An object of the present invention is to provide a fused aminodihydrothiazine compound which is a compound differing from an aminodihydrothiazine derivative and a compound having BACE1 inhibitory activity described in Patent Document 1 and which has an Aβ production inhibitory effect or a BACE1 inhibitory effect and is useful as a prophylactic or therapeutic agent for a neurodegenerative disease caused by Aβ and typified by Alzheimer-type dementia, and pharmaceutical use thereof.

The present invention relates to:

[1] A compound represented by the formula (I):

[Formula 1]

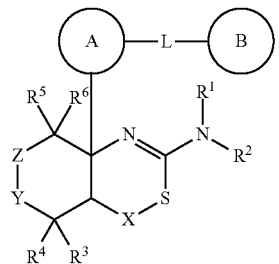

(I)

or a pharmaceutically acceptable salt thereof or a solvate thereof, wherein

Ring A is a $C_{6-14}$ aryl group which may have 1 to 3 substituents selected from Substituent Group α, a 5- to 6-membered heteroaryl group which may have 1 to 3 substituents selected from Substituent Group α or a 9- to 10-membered benzo-fused heterocyclic group which may have 1 to 3 substituents selected from Substituent Group α, L is a single bond, an oxygen atom, a formula —NR$^e$CO— (wherein R$^e$ is a hydrogen atom or a $C_{1-6}$ alkyl group which may have 1 to 3 substituents selected from Substituent Group α), a formula —NR$^e$SO$_2$— (wherein R$^e$ is a hydrogen atom or a $C_{1-6}$ alkyl group which may have 1 to 3 substituents selected from Substituent Group α), a formula —NR$^e$— (wherein R$^e$ is a hydrogen atom or a $C_{1-6}$ alkyl group which may have 1 to 3 substituents selected from Substituent Group α), a $C_{1-6}$ alkylene group which may have 1 to 3 substituents selected from Substituent Group α, a $C_{2-6}$ alkenylene group which may have 1 to 3 substituents selected from Substituent Group α or a $C_{2-6}$ alkynylene group which may have 1 to 3 substituents selected from Substituent Group α, Ring B is a $C_{3-8}$ cycloalkyl group which may have 1 to 3 substituents selected from Substituent Group α, a $C_{6-14}$ aryl group which may have 1 to 3 substituents selected from Substituent Group α or a 5- to 10-membered heterocyclic group which may have 1 to 3 substituents selected from Substituent Group α, X is a single bond or a $C_{1-3}$ alkylene group which may have 1 to 3 substituents selected from Substituent Group α, Y is a single bond, —NR$^Y$— (wherein R$^Y$ is a hydrogen atom, a $C_{1-6}$ alkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a $C_{6-14}$ aryl group which may have 1 to 3 substituents selected from Substituent Group α or a 5- to 10-membered heterocyclic group which may have 1 to 3 substituents selected from Substituent Group α), an oxygen atom, a sulfur atom, a sulfoxide or a sulfone, Z is a single bond, a $C_{1-3}$ alkylene group which may have 1 to 3 substituents selected from Substituent Group α or a $C_{2-3}$ alkenylene group which may have 1 to 3 substituents selected from Substituent Group α, R$^1$ and R$^2$ are each independently a hydrogen atom, a $C_{1-6}$ alkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a 3- to 10-membered carbocyclic group which may have 1 to 3 substituents selected from Substituent Group α or a 5- to 10-membered heterocyclic group which may have 1 to 3 substituents selected from Substituent Group α, and R$^3$, R$^4$, R$^5$ and R$^6$ are independently a hydrogen atom, a halogen atom, a hydroxy group, a $C_{1-6}$ alkyl group which may have 1 to 3 substituents selected from Substituent Group α, a $C_{1-6}$ alkoxy group which may have 1 to 3 substituents selected from Substituent Group α, a 3- to 10-membered carbocyclic group which may have 1 to 3 substituents selected from Substituent Group α or a 5- to 10-membered heterocyclic group which may have 1 to 3 substituents selected from Substituent Group α, or R$^4$ and R$^6$ together may form a ring represented by the formula (II):

[Formula 2]

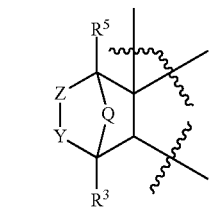

(II)

wherein Y, Z, R$^5$ and R$^3$ are the same as defined above and Q is an oxygen atom, a methylene group or an ethylene group

[Substituent Group α: a hydrogen atom, a halogen atom, a hydroxy group, a nitro group, a $C_{1-6}$ alkylthio group, a $C_{6-14}$ aryl group, a $C_{6-14}$ aryloxycarbonyl group, a $C_{6-14}$ arylcarbonyl group, a cyano group, a $C_{3-8}$ cycloalkoxy group, a $C_{3-8}$ cycloalkyl group, a $C_{3-8}$ cycloalkylthio group, a sulfonylamino group (wherein the sulfonylamino group may be substituted with a $C_{1-6}$ alkyl group), a $C_{2-6}$ alkenyl group which may have 1 to 3 substituents selected from Substituent Group β, a $C_{2-6}$ alkynyl group which may have 1 to 3 substituents selected from Substituent Group β, a carbamoyl group which may be substituted with one or two $C_{1-6}$ alkyl groups, a $C_{1-6}$ alkoxy group which may have 1 to 3 substituents selected from Substituent Group β, a $C_{1-6}$ alkyl group which may have 1 to 3 substituents selected from Substituent Group β and a 5- to 10-membered heterocyclic group which may have 1 to 3 substituents selected from Substituent Group β, Substituent Group β: a halogen atom, a cyano group, a hydroxy group, a $C_{1-6}$ alkoxy group, a $C_{1-6}$ alkyl group, a $C_{3-8}$ cycloalkyl group and an oxo group];

[2] The compound or pharmaceutically acceptable salt thereof or solvate thereof according to [1] above, wherein X is a methylene which may have 1 to 2 substituents selected from Substituent Group α;

[3] The compound or pharmaceutically acceptable salt thereof or solvate thereof according to [1] or [2] above, wherein Y is a single bond and Z is a $C_{1-3}$ alkylene which may have 1 to 3 substituents selected from Substituent Group α;

[4] The compound or pharmaceutically acceptable salt thereof or solvate thereof according to [1] or [2] above, wherein Y is an oxygen atom and Z is a C$_{1-3}$ alkylene which may have 1 to 3 substituents selected from Substituent Group α;

[5] The compound or pharmaceutically acceptable salt thereof or solvate thereof according to [1] or [2] above, wherein Y is an oxygen atom and Z is a single bond;

[6] The compound or pharmaceutically acceptable salt thereof or solvate thereof according to [1] or [2] above, wherein Y is —NR$^Y$— (wherein R$^Y$ is a C$_{1-6}$ alkyl group which may have 1 to 3 substituents selected from Substituent Group α, a C$_{1-6}$ alkylcarbonyl group which may have 1 to 3 substituents selected from Substituent Group α, a C$_{6-14}$ arylcarbonyl group which may have 1 to 3 substituents selected from Substituent Group α, a C$_{6-14}$ arylsulfonyl group which may have 1 to 3 substituents selected from Substituent Group α, a C$_{6-14}$ aryl group which may have 1 to 3 substituents selected from Substituent Group α or a 5- to 10-membered heterocyclic group which may have 1 to 3 substituents selected from Substituent Group α), a sulfur atom, a sulfoxide or a sulfone and Z is a single bond, a C$_{1-3}$ alkylene which may have 1 to 3 substituents selected from Substituent Group α;

[7] The compound or pharmaceutically acceptable salt thereof or solvate thereof according to any one of [1] to [6] above, wherein L is a single bond, a formula —NR$^e$CO— (wherein R$^e$ is a hydrogen atom or a C$_{1-6}$ alkyl group which may have 1 to 3 substituents selected from Substituent Group α) or a formula —NR$^e$SO$_2$— (wherein R$^e$ is a hydrogen atom or a C$_{1-6}$ alkyl group which may have 1 to 3 substituents selected from Substituent Group α);

[8] The compound or pharmaceutically acceptable salt thereof or solvate thereof according to any one of [1] to [6] above, wherein L is a single bond, an oxygen atom, a C$_{1-6}$ alkylene group which may have 1 to 3 substituents selected from Substituent Group α, a C$_{2-6}$ alkenylene group which may have 1 to 3 substituents selected from Substituent Group α or a C$_{2-6}$ alkynylene group which may have 1 to 3 substituents selected from Substituent Group α;

[9] The compound or pharmaceutically acceptable salt thereof or solvate thereof according to any one of [1] to [6] above, wherein L is a formula —NR$^e$CO— (wherein R$^e$ is a hydrogen atom or a C$_{1-6}$ alkyl group which may have 1 to 3 substituents selected from Substituent Group α);

[10] The compound or pharmaceutically acceptable salt thereof or solvate thereof according to any one of claims 1 to 9, wherein the compound is selected from the following compounds:

1) (+)-N-{3-[(4aR*,8aS*)-2-amino-4a,5,6,7,8,8a-hexahydro-4H-benzo[d][1,3]thiazin-8a-yl]-4-fluorophenyl}-5-chloropyridine-2-carboxamide,
2) (+)-N-{3-[(4aR*,7aS*)-2-amino-4a,5,6,7,7a-hexahydrocyclopenta[d][1,3]thiazin-7a-yl]-4-fluorophenyl}-5-chloropyridine-2-carboxamide,
3) N-{3-[(4aR*,7aS*)-2-amino-4a,5,6,7,7a-hexahydrocyclopenta[d][1,3]thiazin-7a-yl]-4-fluorophenyl}pyridine-2-carboxamide,
4) N-{3-[(4aR*,7aS*)-2-amino-4a,5,6,7,7a-hexahydrocyclopenta[d][1,3]thiazin-7a-yl]-4-fluorophenyl}-5-fluoropyridine-2-carboxamide,
5) N-[3-((4aR*,8aS*)-2-amino-4a,5,6,7,8,8a-hexahydro-4H-benzo[d][1,3]thiazin-8a-yl)-4-fluorophenyl]-5-cyanopyridine-2-carboxamide,
6) N-[3-((4aR*,7aS*)-2-amino-4a,5,6,7,7a-hexahydrocyclopenta[d][1,3]thiazin-7a-yl-4-fluorophenyl]-5-difluoromethoxypyrazine-2-carboxamide,
7) N-[3-((4aR*,7aS*)-2-amino-4a,5,6,7,7a-hexahydrocyclopenta[d][1,3]thiazin-7a-yl)-4-fluorophenyl]-5-fluoromethoxypyrazine-2-carboxamide,
8) N-[3-((4aR*,7aS*)-2-amino-4,4a,5,6,7,7a-hexahydrocyclopenta[d][1,3]thiazin-7a-yl)-4-fluorophenyl]-5-cyanopyridine-2-carboxamide,
9) N-[3-((4aR*,7aS*)-2-amino-4,4a,5,6,7,7a-hexahydrocyclopenta[d][1,3]thiazin-7a-yl)-4-fluorophenyl]-5-fluoromethoxypyridine-2-carboxamide,
10) N-[3-((4aS*,7aS*)-2-amino-4a,5-dihydro-4H-furo[3,4-d][1,3]thiazin-7a-yl)-4-fluorophenyl]-5-cyanopyridine-2-carboxamide,
11) N-[3-((4aS*,7aS*)-2-amino-4a,5-dihydro-4H-furo[3,4-d][1,3]thiazin-7a-yl)-4-fluorophenyl]-5-difluoromethoxypyrazine-2-carboxamide,
12) N-[3-((4aS*,7aS*)-2-amino-4a,5-dihydro-4H-furo[3,4-d][1,3]thiazin-7a-yl)-4-fluorophenyl]-5-chloropyridine-2-carboxamide,
13) N-[3-((7S*,7aS*)-2-amino-4a,5-dihydro-4H-furo[3,4-d][1,3]thiazin-7a-yl)-4-fluorophenyl]-5-fluoromethoxypyrazine-2-carboxamide,
14) N-[3-((4aS*,8aS*)-2-amino-4a,5,7,8-tetrahydro-4H-6-oxa-3-thia-1-azanaphthalen-8a-yl)-4-fluorophenyl]-5-cyanopyridine-2-carboxamide,
15) N-[3-((4aS*,8aS*)-2-amino-4a,5,7,8-tetrahydro-4H-6-oxa-3-thia-1-azanaphthalen-8a-yl)-4-fluorophenyl]-5-difluoromethoxypyrazine-2-carboxamide,
16) N-[3-((4aS*,8aS*)-2-amino-4a,5,7,8-tetrahydro-4H-6-oxa-3-thia-1-azanaphthalen-8a-yl)-4-fluorophenyl]-5-chloropyridine-2-carboxamide,
17) (+)-N-[3-((4aR*,6S*,7aS*)-2-amino-6-methoxy-4,4a,5,6,7,7a-hexahydrocyclopenta[d][1,3]thiazin-7a-yl)-4-fluorophenyl]-5-cyanopyridine-2-carboxamide,
18) (+)-N-[3-((4aR*,6R*,7aS*)-2-amino-6-methoxy-4,4a,5,6,7,7a-hexahydrocyclopenta[d][1,3]thiazin-7a-yl)-4-fluorophenyl]-5-cyanopyridine-2-carboxamide,
19) (+)-N-[3-((4aR*,9aS*)-2-amino-4,4a,5,6,7,8,9,9a-octahydrocyclohepta[d][1,3]thiazin-9a-yl)-4-fluorophenyl]-5-cyanopyridine-2-carboxamide,
20) N-[3-((4aR*,7aS*)-2-amino-4,4a,5,6,7,7a-hexahydrocyclopenta[d][1,3]thiazin-7a-yl)-4-methoxyphenyl]-5-chloropyridine-2-carboxamide,
21) N-[3-((4aS*,7aS*)-2-amino-4a,5-dihydro-4H-furo[3,4-d][1,3]thiazin-7a-yl)-4-fluorophenyl]-5-difluoromethylpyrazine-2-carboxamide,
22) (4aR*,7aS*)-7a-[3-(2-fluoropyridin-3-yl)phenyl]-6-phenyl-4,4a,5,6,7,7a-hexahydropyrrolo[3,4-d][1,3]thiazin-2-ylamine,
23) (4aR*,7aS*)-7a-[3-(2-fluoropyridin-3-yl)phenyl]-6-pyrimidin-2-yl-4,4a,5,6,7,7a-hexahydropyrrolo[3,4-d][1,3]thiazin-2-ylamine,
24) N-[3-((4aS*,5R*,7aS*)-2-amino-5-methyl-4a,5-dihydro-4H-furo[3,4-d][1,3]thiazin-7a-yl)-4-fluorophenyl]-5-cyanopyridine-2-carboxamide,
25) N-[3-((4aS*,5R*,7aS*)-2-amino-5-methyl-4a,5-dihydro-4H-furo[3,4-d][1,3]thiazin-7a-yl)-4-fluorophenyl]-5-difluoromethylpyrazine-2-carboxamide,
26) N-[3-((4aS*,8aS*)-2-amino-4a,5,7,8-tetrahydro-4H-6-oxa-3-thia-1-azanaphthalen-8a-yl)-4-fluorophenyl]-5-fluoromethoxypyrazine-2-carboxamide,
27) N-[3-((4aS*,5R*,7aS*)-2-amino-5-ethyl-4a,5-dihydro-4H-furo[3,4-d][1,3]thiazin-7a-yl)-4-fluorophenyl]-5-difluoromethoxypyrazine-2-carboxamide,
28) N-[3-((4aS,5S,7aS)-2-amino-5-fluoromethyl-4a,5-dihydro-4H-furo[3,4-d][1,3]thiazin-7a-yl)-4-fluorophenyl]-5-difluoromethoxypyrazine-2-carboxamide,
29) N-[3-((4aS,5S,7aS)-2-amino-5-fluoromethyl-4a,5-dihydro-4H-furo[3,4-d][1,3]thiazin-7a-yl)-4-fluorophenyl]-5-fluoromethoxylpyrazine-2-carboxamide, 30) N-[3-((4aS*,5S*,7aS*)-2-amino-5-fluoromethyl-4a,5-dihydro-4H-furo[3,4-d][1,3]thiazin-7a-yl)-4-fluorophenyl]-5-cyanopyridine-2-carboxamide, 31) N-[3-((4aS*,5S*,8aS*)-2-amino-5-fluoromethyl-4a,5,7,8-tetrahydro-4H-6-oxa-3-thia-1-azanaphtalen-8a-yl)-4-fluorophenyl]-5-cyanopyridine-2-carboxamide, 32) N-[3-((4aS*,5S*,8aS*)-2-amino-5-fluoromethyl-4a,5,7,8-tetrahydro-4H-6-oxa-3-thia-1-azanaphtalen-8a-yl)-4-fluorophenyl]-5-fluoromethoxypyrazine-2-carboxamide, 33) N-[3-((4aS*,5S*,8aS*)-2-amino-5-fluoromethyl-4a,5,7,8-tetrahydro-4H-6-oxa-3-thia-1-azanaphtalen-8a-yl)-4-fluorophenyl]-5-chloropyridine-2-carboxamide, 34) N-[3-((4aS*,6S*,7aS*)-2-amino-6-methoxy-4a,5,6,7-tetrahydro-4H-cyclopenta[d][1,3]thiazine-7a-yl)-4-fluorophenyl]-5-difluoromethylpyrazine-2-carboxamide, 35) N-[3-((4aR*,6R*,7aS*)-2-amino-6-methoxy-4a,5,6,7-tetrahydro-4H-cyclopenta[d][1,3]thiazine-7a-yl)-4-fluorophenyl]-5-difluoromethylpyrazine-2-carboxamide, and 36) N-[3-((4aR*,6S*,7aS*)-2-amino-6-fluoro-4a,5,6,7-tetrahydro-4H-cyclopenta[d][1,3]thiazine-7a-yl)-4-fluorophenyl]-5-difluoromethylpyrazine-2-carboxamide;

[11] A pharmaceutical composition comprising the compound or pharmaceutically acceptable salt thereof or solvate thereof according to any one of [1] to [10] above as an active ingredient;

[12] The pharmaceutical composition according to [11] above for inhibiting production of amyloid-β protein;

[13] The pharmaceutical composition according to [11] above for inhibiting beta-site amyloid-β precursor protein cleaving enzyme 1 (BACE1);

[14] The pharmaceutical composition according to any one of [11] to [13] above for treating a neurodegenerative disease; and

[15] The pharmaceutical composition according to [14] above, wherein the neurodegenerative disease is Alzheimer-type dementia or Down's syndrome.

DETAILED DESCRIPTION OF THE INVENTION

Meanings of symbols, terms and the like used in the present specification will be explained and the present invention will be described in detail below.

In the present specification, a structural formula of a compound may represent a certain isomer for convenience. However, the present invention includes all isomers and isomer mixtures such as geometric isomers which can be generated from the structure of a compound, optical isomers based on asymmetric carbon, stereoisomers and tautomers. The present invention is not limited to the description of a chemical formula for convenience and may include any one of the isomers or mixtures thereof. Accordingly, the compound of the present invention may have an asymmetric carbon atom in the molecule and exist as an optically active compound or racemate, and the present invention includes each of the optically active compound and the racemate without limitations. Although crystal polymorphs of the compound may be present, the compound is similarly not limited thereto and may be present as a single crystal form or a mixture of single crystal forms. The compound may be an anhydride or a hydrate. Any of these forms is included in the claims of the present specification.

The "halogen atom" herein refers to a fluorine atom, a chlorine atom, a bromine atom, an iodine atom or the like and is preferably a fluorine atom or a chlorine atom.

The "$C_{1-6}$ alkyl group" refers to an alkyl group having 1 to 6 carbon atoms. Preferable examples of the group include linear or branched alkyl groups such as a methyl group, an ethyl group, an n-propyl group, an isopropyl group, an n-butyl group, an isobutyl group, a t-butyl group, an n-pentyl group, an isopentyl group, a neopentyl group, an n-hexyl group, a 1-methylpropyl group, an 1,2-dimethylpropyl group, a 1-ethylpropyl group, a 1-methyl-2-ethylpropyl group, a 1-ethyl-2-methylpropyl group, a 1,1,2-trimethylpropyl group, a 1-methylbutyl group, a 2-methylbutyl group, a 1,1-dimethylbutyl group, a 2,2-dimethylbutyl group, a 2-ethylbutyl group, a 1,3-dimethylbutyl group, a 2-methylpentyl group and a 3-methylpentyl group. The group is more preferably a methyl group, an ethyl group or an n-propyl group.

The "$C_{2-6}$ alkenyl group" refers to an alkenyl group having 2 to 6 carbon atoms. Preferable examples of the group include linear or branched alkenyl groups such as a vinyl group, an allyl group, a 1-propenyl group, an isopropenyl group, a 1-buten-1-yl group, a 1-buten-2-yl group, a 1-buten-3-yl group, a 2-buten-1-yl group and a 2-buten-2-yl group.

The "$C_{2-6}$ alkynyl group" refers to an alkynyl group having 2 to 6 carbon atoms. Preferable examples of the group include linear or branched alkynyl groups such as an ethynyl group, a 1-propynyl group, a 2-propynyl group, a butynyl group, a pentynyl group and a hexynyl group.

The "$C_{1-6}$ alkoxy group" refers to an alkyl group having 1 to 6 carbon atoms in which one hydrogen atom is replaced by an oxygen atom. Examples of the group include a methoxy group, an ethoxy group, an n-propoxy group, an isopropoxy group, an n-butoxy group, an isobutoxy group, a sec-butoxy group, a t-butoxy group, an n-pentoxy group, an isopentoxy group, a sec-pentoxy group, a t-pentoxy group, an n-hexoxy group, an isohexoxy group, a 1,2-dimethylpropoxy group, a 2-ethylpropoxy group, a 1-methyl-2-ethylpropoxy group, a 1-ethyl-2-methylpropoxy group, a 1,1,2-trimethylpropoxy group, a 1,1-dimethylbutoxy group, a 2,2-dimethylbutoxy group, a 2-ethylbutoxy group, a 1,3-dimethylbutoxy group, a 2-methylpentoxy group, a 3-methylpentoxy group and a hexyloxy group.

The "$C_{1-6}$ alkylthio group" refers to an alkyl group having 1 to 6 carbon atoms in which one hydrogen atom is replaced by a sulfur atom. Examples of the group include a methylthio group, an ethylthio group, an n-propylthio group, an isopropylthio group, an n-butylthio group, an isobutylthio group, a t-butylthio group, an n-pentylthio group, an isopentylthio group, a neopentylthio group, an n-hexylthio group and a 1-methylpropylthio group.

The "$C_{1-6}$ alkylsulfonyl group" refers to an alkyl group having 1 to 6 carbon atoms in which one hydrogen atom is replaced by a sulfonyl group. Examples of the group include a methylsulfonyl group, an ethylsulfonyl group, an n-propylsulfonyl group, an isopropylsulfonyl group, an n-butylsulfonyl group, an isobutylsulfonyl group, a t-butylsulfonyl group, an n-pentylsulfonyl group, an isopentylsulfonyl group, a neopentylsulfonyl group, an n-hexylsulfonyl group and a 1-methylpropylsulfonyl group.

The "$C_{1-6}$ alkylcarbonyl group" refers to an alkyl group having 1 to 6 carbon atoms in which one hydrogen atom is replaced by a carbonyl group. Preferable examples of the group include an acetyl group, a propionyl group and a butyryl group.

The "$C_{6-14}$ aryl group" refers to an aromatic hydrocarbon ring group having 6 to 14 carbon atoms. Examples of the group include a phenyl group, a naphthyl group and an anthryl group. A phenyl group is particularly preferable.

The "$C_{7-12}$ aralkyl group" refers to a group having 7 to 12 carbon atoms in which an aromatic hydrocarbon ring such as a phenyl group or a naphthyl group is substituted with a $C_{1-6}$ alkyl group. Examples of the group include a benzyl group, a phenethyl group, a phenylpropyl group and a naphthylmethyl group. A benzyl group is particularly preferable.

The "$C_{6-14}$ aryloxycarbonyl group" refers to a group in which oxycarbonyl is bonded to an aromatic hydrocarbon ring group having 6 to 14 carbon atoms. Preferable examples of the group include a phenyloxycarbonyl group, a naphthyloxycarbonyl group and an anthryloxycarbonyl group. A phenyloxycarbonyl group is more preferable.

The "$C_{6-14}$ arylcarbonyl group" refers to a group in which a carbonyl group is bonded to an aromatic hydrocarbon ring group having 6 to 14 carbon atoms. Preferable examples of the group include a benzoyl group and a naphthoyl group. A benzoyl group is more preferable.

The "$C_{6-14}$ arylsulfonyl group" refers to a group in which a sulfonyl group is bonded to an aromatic hydrocarbon ring group having 6 to 14 carbon atoms. Preferable examples of the group include a benzenesulfonyl group and a naphthylsulfonyl group. A benzenesulfonyl group is more preferable.

The "$C_{3-8}$ cycloalkyl group" refers to a cyclic alkyl group having 3 to 8 carbon atoms. Preferable examples of the group include a cyclopropyl group, a cyclobutyl group, a cyclopentyl group, a cyclohexyl group, a cycloheptyl group and a cyclooctyl group.

The "$C_{3-8}$ cycloalkoxy group" refers to a cyclic alkyl group having 3 to 8 carbon atoms in which one hydrogen atom is replaced by an oxygen atom. Examples of the group include a cyclopropoxy group, a cyclobutoxy group, a cyclopentoxy group, a cyclohexoxy group, a cycloheptyloxy group and a cyclooctyloxy group.

The "$C_{3-8}$ cycloalkylthio group" refers to a cyclic alkyl group having 3 to 8 carbon atoms in which one hydrogen atom is replaced by a sulfur atom. Examples of the group include a cyclopropylthio group, a cyclobutylthio group, a cyclopentylthio group, a cyclohexylthio group, a cycloheptylthio group and a cyclooctylthio group.

The "5- to 10-membered heterocyclic group" refers to a heteroatom-containing cyclic group having 5 to 10 members in total. Preferable examples of the group include a piperidinyl group, a pyrrolidinyl group, an azepinyl group, an azocanyl group, a piperazinyl group, a 1,4-diazepanyl group, a morpholinyl group, a thiomorpholinyl group, a pyrrolyl group, an imidazolyl group, a pyrazolyl group, a pyridinyl group, a pyridazinyl group, a pyrimidinyl group, a pyrazinyl group, a triazolyl group, a triazinyl group, a tetrazolyl group, an isoxazolyl group, an oxazolyl group, an oxadiazolyl group, an isothiazolyl group, a thiazolyl group, a thiadiazolyl group, a furyl group, a thienyl group, a quinolinyl group, an isoquinolinyl group, a benzofuryl group, a benzopyranyl group, a benzimidazolyl group, a benzotriazolyl group, a benzisothiazolyl group, an indolinyl group, an isoindolinyl group, a chromanyl group, an isochromanyl group, a 1,3-dioxaindanyl group and a 1,4-dioxatetralinyl group.

The "5- to 6-membered heteroaryl group" refers to the "5- to 10-membered heterocyclic group" which is a heteroatom-containing aromatic cyclic group having 5 to 6 members in total. Examples of the group include a pyrrolyl group, an imidazolyl group, a pyrazolyl group, a pyridinyl group, a pyridazinyl group, a pyrimidinyl group, a pyrazinyl group, a triazolyl group, a triazinyl group, a tetrazolyl group, an isoxazolyl group, an oxazolyl group, an oxadiazolyl group, an isothiazolyl group, a thiazolyl group, a thiadiazolyl group, a furyl group and a thienyl group.

The "9- to 10-membered benzo-fused heterocyclic group" refers to the "5- to 10-membered heterocyclic group" which is a heteroatom-containing cyclic group having 9 to 10 members in total fused with a benzene ring. Preferable examples of the group include an indolinyl group, an isoindolinyl group, a chromanyl group, an isochromanyl group, a 1,3-dioxaindanyl group and a 1,4-dioxatetralinyl group.

The "3- to 10-membered carbocyclic group" refers to a carbocyclic group having 3 to 10 members in total. Preferable examples of the group include a cyclopropyl group, a cyclobutyl group, a cyclopentyl group, a cyclohexyl group, a cycloheptyl group, a cyclooctyl group, a spiro[3.4]octanyl group, a decanyl group, an indanyl group, a 1-acenaphthenyl group, a cyclopentacyclooctenyl group, a benzocyclooctenyl group, an indenyl group, a tetrahydronaphthyl group, a 6,7,8,9-tetrahydro-5H-benzocycloheptenyl group and a 1,4-dihydronaphthalenyl group.

The "$C_{1-6}$ alkylene group" refers to a divalent group derived by excluding any one hydrogen atom from the "$C_{1-6}$ alkyl group" as defined above. Examples of the group include a methylene group, a 1,2-ethylene group, a 1,1-ethylene group, a 1,3-propylene group, a tetramethylene group, a pentamethylene group and a hexamethylene group.

The "$C_{2-6}$ alkenylene group" refers to a divalent group derived by excluding any one hydrogen atom from the "$C_{2-6}$ alkenyl group" as defined above. Examples of the group include a 1,2-vinylene group (ethenylene group), a propenylene group, a butenylene group, a pentenylene group and a hexenylene group.

The "$C_{2-6}$ alkynylene group" refers to a divalent group derived by excluding any one hydrogen atom from the "$C_{2-6}$ alkynyl group" as defined above. Examples of the group include an ethynylene group, a propynylene group, a butynylene group, a pentynylene group and a hexynylene group.

Examples of the "$C_{1-3}$ alkylene group" include a methylene group, an ethylene group and a propylene group.

Examples of the "$C_{2-3}$ alkenylene group" include a 1,2-vinylene group (ethenylene group) and a propenylene group.

Examples of the "$C_{2-3}$ alkynylene group" include an ethynylene group and a propynylene group.

Examples of the sulfonylamino group which may be substituted with a $C_{1-6}$ alkyl group in the "sulfonylamino group (wherein the sulfonylamino group may be substituted with a $C_{1-6}$ alkyl group)" include a methylsulfonylmethylamino group, an ethylsulfonylmethylamino group and an ethylsulfonylethylamino group.

"Substituent Group α" refers to a hydrogen atom, a halogen atom, a hydroxy group, a nitro group, a $C_{1-6}$ alkylthio group, a $C_{6-14}$ aryl group, a $C_{6-14}$ aryloxycarbonyl group, a $C_{6-14}$ arylcarbonyl group, a cyano group, a $C_{3-8}$ cycloalkoxy group, a $C_{3-8}$ cycloalkyl group, a $C_{3-8}$ cycloalkylthio group, a sulfonylamino group (wherein the sulfonylamino group may be substituted with a $C_{1-6}$ alkyl group), a $C_{2-6}$ alkenyl group which may have 1 to 3 substituents selected from Substituent Group β, a $C_{2-6}$ alkynyl group which may have 1 to 3 substituents selected from Substituent Group 0, a carbamoyl group which may be substituted with one or two $C_{1-6}$ alkyl groups, a $C_{1-6}$ alkoxy group which may have 1 to 3 substituents selected from Substituent Group β, a $C_{1-6}$ alkyl group which may have 1 to 3 substituents selected from Substituent Group β and a 5- to 10-membered heterocyclic group which may have 1 to 3 substituents selected from Substituent Group β.

"Substituent Group β" refers to a halogen atom, a cyano group, a hydroxy group, a $C_{1-6}$ alkoxy group, a $C_{1-6}$ alkyl group, a $C_{3-8}$ cycloalkyl group and an oxo group.

The fused aminodihydrothiazine derivative of the formula (I) according to the present invention may be a pharmaceutically acceptable salt. Specific examples of the pharmaceutically acceptable salt include inorganic acid salts (such as sulfates, nitrates, perchlorates, phosphates, carbonates, bicarbonates, hydrofluorides, hydrochlorides, hydrobromides and hydroiodides), organic carboxylates (such as acetates, oxalates, maleates, tartrates, fumarates and citrates), organic sulfonates (such as methanesulfonates, trifluoromethanesulfonates, ethanesulfonates, benzenesulfonates, toluenesulfonates and camphorsulfonates), amino acid salts (such as aspartates and glutamates), quaternary amine salts, alkali metal salts (such as sodium salts and potassium salts) and alkali earth metal salts (such as magnesium salts and calcium salts).

The fused aminodihydrothiazine derivative of the formula (I) or pharmaceutically acceptable salt according to the present invention may be a solvate thereof. Examples of the solvate include a hydrate.

The compound (1) is not limited to a specific isomer and includes all possible isomers (such as a keto-enol isomer, an imine-enamine isomer, a diastereoisomer, an optical isomer and a rotamer) and racemates. For example, the compound (1) wherein $R^1$ is hydrogen includes the following tautomers.
[Formula 3]

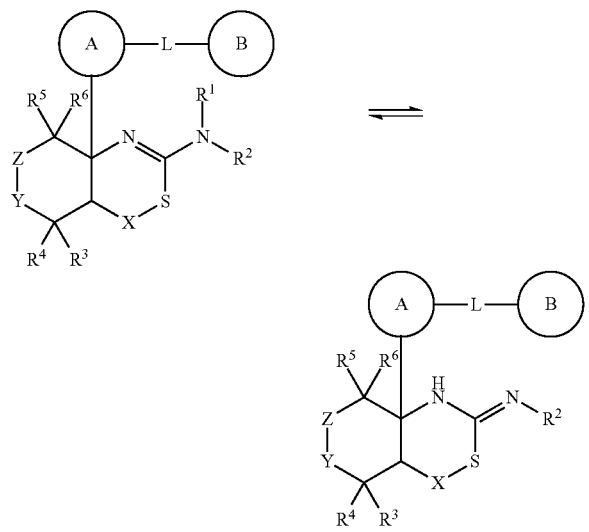

The fused aminodihydrothiazine derivative of the formula (I) according to the present invention is preferably a compound of the formula (I), wherein X is a methylene which may have 1 to 2 substituents selected from Substituent Group α. A compound of the formula (I), wherein Y is a single bond and Z is a $C_{1-3}$ alkylene which may have 1 to 3 substituents selected from Substituent Group α; wherein Y is an oxygen atom and Z is a $C_{1-3}$ alkylene which may have 1 to 3 substituents selected from Substituent Group α; or wherein Y is an oxygen atom and Z is a single bond, is particularly preferable.

The fused aminodihydrothiazine derivative of the formula (I) according to the present invention is preferably a compound of the formula (I), wherein L is a single bond, a formula —NR$^e$CO— (wherein R$^e$ is a hydrogen atom or a $C_{1-6}$ alkyl group which may have 1 to 3 substituents selected from Substituent Group α) or a formula —NR$^e$SO$_2$— (wherein R$^e$ is a hydrogen atom or a $C_{1-6}$ alkyl group which may have 1 to 3 substituents selected from Substituent Group α); or wherein L is a single bond, an oxygen atom, a $C_{1-6}$ alkylene group which may have 1 to 3 substituents selected from Substituent Group α, a $C_{2-6}$ alkenylene group which may have 1 to 3 substituents selected from Substituent Group α or a $C_{2-6}$ alkynylene group which may have 1 to 3 substituents selected from Substituent Group α. A compound, wherein L is a formula —NR$^e$CO— (wherein R$^e$ is a hydrogen atom or a $C_{1-6}$ alkyl group which may have 1 to 3 substituents selected from Substituent Group α), is particularly preferable.

Preferable compounds in the present invention include the following compounds:
1) (+)-N-{3-[(4aR*,8aS*)-2-amino-4a,5,6,7,8,8a-hexahydro-4H-benzo[d][1,3]thiazin-8a-yl]-4-fluorophenyl}-5-chloropyridine-2-carboxamide,
2) (+)-N-{3-[(4aR*,7aS*)-2-amino-4,4a,5,6,7,7a-hexahydrocyclopenta[d][1,3]thiazin-7a-yl]-4-fluorophenyl}-5-chloropyridine-2-carboxamide,
3) N-{3-[(4aR*,7aS*)-2-amino-4,4a,5,6,7,7a-hexahydrocyclopenta[d][1,3]thiazin-7a-yl]-4-fluorophenyl}pyridine-2-carboxamide,
4) N-{3-[(4aR*,7aS*)-2-amino-4,4a,5,6,7,7a-hexahydrocyclopenta[d][1,3]thiazin-7a-yl]-4-fluorophenyl}-5-fluoropyridine-2-carboxamide,
5) N-[3-((4aR*,8aS*)-2-amino-4a,5,6,7,8,8a-hexahydro-4H-benzo[d][1,3]thiazin-8a-yl)-4-fluorophenyl]-5-cyanopyridine-2-carboxamide,
6) N-[3-((4aR*,7aS*)-2-amino-4,4a,5,6,7,7a-hexahydrocyclopenta[d][1,3]thiazin-7a-yl-4-fluorophenyl]-5-difluoromethoxypyrazine-2-carboxamide,
7) N-[3-((4aR*,7aS*)-2-amino-4,4a,5,6,7,7a-hexahydrocyclopenta[d][1,3]thiazin-7a-yl)-4-fluorophenyl]-5-fluoromethoxypyrazine-2-carboxamide,
8) N-[3-((4aR*,7aS*)-2-amino-4,4a,5,6,7,7a-hexahydrocyclopenta[d][1,3]thiazin-7a-yl)-4-fluorophenyl]-5-cyanopyridine-2-carboxamide,
9) N-[3-((4aR*,7aS*)-2-amino-4,4a,5,6,7,7a-hexahydrocyclopenta[d][1,3]thiazin-7a-yl)-4-fluorophenyl]-5-fluoromethoxypyridine-2-carboxamide,
10) N-[3-((4aS*,7aS*)-2-amino-4a,5-dihydro-4H-furo[3,4-d][1,3]thiazin-7a-yl)-4-fluorophenyl]-5-cyanopyridine-2-carboxamide,
11) N-[3-((4aS*,7aS*)-2-amino-4a,5-dihydro-4H-furo[3,4-d][1,3]thiazin-7a-yl)-4-fluorophenyl]-5-difluoromethoxypyrazine-2-carboxamide,
12) N-[3-((4aS*,7aS*)-2-amino-4a,5-dihydro-4H-furo[3,4-d][1,3]thiazin-7a-yl)-4-fluorophenyl]-5-chloropyridine-2-carboxamide,
13) N-[3-((7S*,7aS*)-2-amino-4a,5-dihydro-4H-furo[3,4-d][1,3]thiazin-7a-yl)-4-fluorophenyl]-5-fluoromethoxypyrazine-2-carboxamide,
14) N-[3-((4aS*,8aS*)-2-amino-4a,5,7,8-tetrahydro-4H-6-oxa-3-thia-1-azanaphthalen-8a-yl)-4-fluorophenyl]-5-cyanopyridine-2-carboxamide,
15) N-[3-((4aS*,8aS*)-2-amino-4a,5,7,8-tetrahydro-4H-6-oxa-3-thia-1-azanaphthalen-8a-yl)-4-fluorophenyl]-5-difluoromethoxypyrazine-2-carboxamide,
16) N-[3-((4aS*,8aS*)-2-amino-4a,5,7,8-tetrahydro-4H-6-oxa-3-thia-1-azanaphthalen-8a-yl)-4-fluorophenyl]-5-chloropyridine-2-carboxamide,
17) (+)-N-[3-((4aR*,6S*,7aS*)-2-amino-6-methoxy-4,4a,5,6,7,7a-hexahydrocyclopenta[d][1,3]thiazin-7a-yl)-4-fluorophenyl]-5-cyanopyridine-2-carboxamide,
18) (+)-N-[3-((4aR*,6R*,7aS*)-2-amino-6-methoxy-4,4a,5,6,7,7a-hexahydrocyclopenta[d][1,3]thiazin-7a-yl)-4-fluorophenyl]-5-cyanopyridine-2-carboxamide,
19) (+)-N-[3-((4aR*,9aS*)-2-amino-4,4a,5,6,7,8,9,9a-octahydrocyclohepta[d][1,3]thiazin-9a-yl)-4-fluorophenyl]-5-cyanopyridine-2-carboxamide,
20) N-[3-((4aR*,7aS*)-2-amino-4,4a,5,6,7,7a-hexahydrocyclopenta[d][1,3]thiazin-7a-yl)-4-methoxyphenyl]-5-chloropyridine-2-carboxamide,
21) N-[3-((4aS*,7aS*)-2-amino-4a,5-dihydro-4H-furo[3,4-d][1,3]thiazin-7a-yl)-4-fluorophenyl]-5-difluoromethylpyrazine-2-carboxamide, 22) (4aR*,7aS*)-7a-[3-(2-fluoro-pyridin-3-yl)phenyl]-6-phenyl-4,4a,5,6,7,7a-hexahydropyrrolo[3,4-d][1,3]thiazin-2-ylamine,
23) (4aR*,7aS*)-7a-[3-(2-fluoropyridin-3-yl)phenyl]-6-pyrimidin-2-yl-4,4a,5,6,7,7a-hexahydropyrrolo[3,4-d][1,3]thiazin-2-ylamine,
24) N-[3-((4aS*,5R*,7aS*)-2-amino-5-methyl-4a,5-dihydro-4H-furo[3,4-d][1,3]thiazin-7a-yl)-4-fluorophenyl]-5-cyanopyridine-2-carboxamide,
25) N-[3-((4aS*,5R*,7aS*)-2-amino-5-methyl-4a,5-dihydro-4H-furo[3,4-d][1,3]thiazin-7a-yl)-4-fluorophenyl]-5-difluoromethylpyrazine-2-carboxamide,
26) N-[3-((4aS*,8aS*)-2-amino-4a,5,7,8-tetrahydro-4H-6-oxa-3-thia-1-azanaphthalen-8a-yl)-4-fluorophenyl]-5-fluoromethoxypyrazine-2-carboxamide,
27) N-[3-((4aS*,5R*,7aS*)-2-amino-5-ethyl-4a,5-dihydro-4H-furo[3,4-d][1,3]thiazin-7a-yl)-4-fluorophenyl]-5-difluoromethoxypyrazine-2-carboxamide,
28) N-[3-((4aS,5S,7aS)-2-amino-5-fluoromethyl-4a,5-dihydro-4H-furo[3,4-d][1,3]thiazin-7a-yl)-4-fluorophenyl]-5-difluoromethylpyrazine-2-carboxamide,
29) N-[3-((4aS,5S,7aS)-2-amino-5-fluoromethyl-4a,5-dihydro-4H-furo[3,4-d][1,3]thiazin-7a-yl)-4-fluorophenyl]-5-fluoromethoxylpyrazine-2-carboxamide,
30) N-[3-((4aS*,5S*,7aS*)-2-amino-5-fluoromethyl-4a,5-dihydro-4H-furo[3,4-d][1,3]thiazin-7a-yl)-4-fluorophenyl]-5-cyanopyridine-2-carboxamide,
31) N-[3-((4aS*,5S*,8aS*)-2-amino-5-fluoromethyl-4a,5,7,8-tetrahydro-4H-6-oxa-3-thia-1-aza-naphtalene-8a-yl)-4-fluorophenyl]-5-cyanopyridine-2-carboxamide,
32) N-[3-((4aS*,5S*,8aS*)-2-amino-5-fluoromethyl-4a,5,7,8-tetrahydro-4H-6-oxa-3-thia-1-aza-naphtalene-8a-yl)-4-fluorophenyl]-5-fluoromethoxypyrazine-2-carboxamide,
33) N-[3-((4aS*,5S*,8aS*)-2-amino-5-fluoromethyl-4a,5,7,8-tetrahydro-4H-6-oxa-3-thia-1-aza-naphtalene-8a-yl)-4-fluorophenyl]-5-chloropyridine-2-carboxamide,
34) N-[3-((4aS*,6S*,7aS*)-2-amino-6-methoxy-4a,5,6,7-tetrahydro-4H-cyclopenta[d][1,3]thiazine-7a-yl)-4-fluorophenyl]-5-difluoromethylpyrazine-2-carboxamide,
35) N-[3-((4aR*,6R*,7aS*)-2-amino-6-methoxy-4a,5,6,7-tetrahydro-4H-cyclopenta[d][1,3]thiazine-7a-yl)-4-fluorophenyl]-5-difluoromethylpyrazine-2-carboxamide, and
36) N-[3-((4aR*,6S*,7aS*)-2-amino-6-fluoro-4a,5,6,7-tetrahydro-4H-cyclopenta[d][1,3]thiazine-7a-yl)-4-fluorophenyl]-5-difluoromethylpyrazine-2-carboxamide.

Next, methods for preparing the compound of the formula (I) [hereinafter referred to as compound (I); a compound represented by another formula is similarly described] or pharmaceutically acceptable salt thereof according to the present invention will be described.

The compound represented by the formula (I):
[Formula 4]

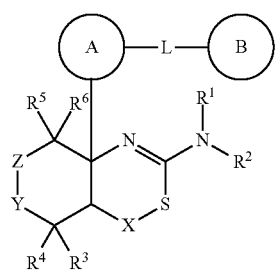

(wherein Ring A, Ring B, $R^1$, $R^2$, $R^3$, $R^4$, $R^5$, $R^6$, L, X, Y and Z are as defined above) or the intermediate thereof are synthesized by, for example, General Preparation Methods 1 to 15 as described below.

The "leaving group" in the raw material compound used in preparation of the compound (I) according to the present invention may be any leaving group used for nucleophilic substitution reaction. Preferable examples of the leaving group include a halogen atom, a $C_{1-6}$ alkylsulfonyloxy group which may be substituted with the above Substituent Group α and an arylsulfonyloxy group which may be substituted with the above Substituent Group α. Specific examples of the leaving group include a chlorine atom, a bromine atom, an iodine atom, a methanesulfonyloxy group, a trifluoromethanesulfonyloxy group and a p-toluenesulfonyloxy group.

1. General Preparation Method 1:
[Formula 5]

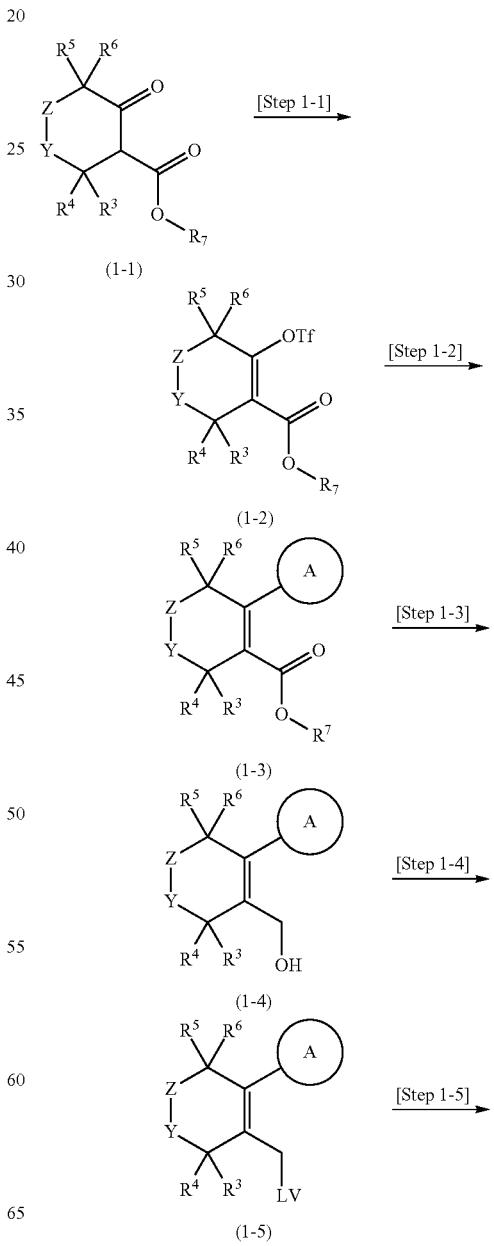

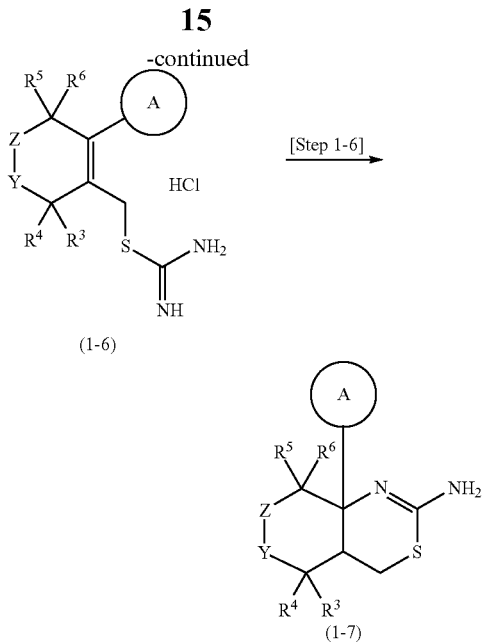

(1-6)

(1-7)

In the formula, R⁷ represents a $C_{1-6}$ alkyl group such as a methyl group or an ethyl group, a $C_{7-12}$ aralkyl group such as a benzyl group, or the like, LV is a leaving group and represents a halogen atom (such as a chlorine atom, a bromine atom or an iodine atom), for example, or a sulfonyloxy group such as a methanesulfonyloxy group, a p-toluenesulfonyloxy group or a trifluoromethanesulfonyloxy group (represented by TfO in the formula), for example, and Ring A, $R^3$, $R^4$, $R^5$, $R^6$, Y and Z are as defined above.

General Preparation Method 1 is a method for preparing a compound (1-7) which is a synthetic intermediate of the compound (I) according to the present invention from a compound (1-1) as a raw material through multiple steps of Step 1-1 to Step 1-6.

The compound (1-1) can be a commercially available product used as is, can also be prepared from a commercially available product by a method known to a person skilled in the art, and can further be prepared by a method described in Preparation Examples among Examples.

Step 1-1:

This step is a step of obtaining a compound (1-2) by trifluoromethanesulfonylation of the compound (1-1).

The reaction in this step can be performed under the same conditions as those usually used in trifluoromethanesulfonylation reaction of a carbonyl compound (such as the conditions described in J. Org. Chem., 57, 6972-6975 (1992), Tetrahedron Letters., 40, 8133-8136 (1999) and Tetrahedron., 61, 4128-4140 (2005)).

Specifically, the compound (1-2) can be obtained by causing a base to act on the compound (1-1), and then reacting the compound with N-phenyltrifluoromethanesulfonimide or trifluoromethanesulfonic anhydride, for example. This reaction can be performed by causing one or more equivalents of a base to act on the compound (1-1) in an organic solvent such as ether, tetrahydrofuran, 1,4-dioxane, 1,2-dimethoxyethane, dichloromethane, 1,2-dichloroethane, benzene or toluene, for example. Examples of the base used include sodium hydride, LDA (lithium diisopropylamide), lithium bis(trimethylsilyl) amide, diisopropylethylamine, pyridine and 2,6-lutidine. The reaction time is not particularly limited and is usually 5 minutes to 24 hours, and preferably 5 minutes to 12 hours. The reaction temperature is usually −100° C. to room temperature, and more preferably −78° C. to room temperature.

Step 1-2:

This step is a step of obtaining a compound (1-3) by coupling reaction of the compound (1-2) using a transition metal.

This reaction can be performed under the conditions usually used in coupling reaction using a transition metal (such as Suzuki-Miyaura reaction or Stille reaction).

Examples of the reaction using an organoboron reagent as an organometallic compound include reactions in documents such as Tetrahedron: Asymmetry 16 (2005) 2, 528-539 and Org. Lett. 6 (2004) 2, 277-279. Examples of the reaction using an organotin reagent include reaction in a document such as Tetrahedron 61 (2005) 16, 4128-4140. Examples of the reaction using an organozinc reagent as an organometallic compound include reaction in a document such as Tetrahedron 61 (2005) 16, 4128-4140. The organometallic catalyst used in this reaction is not particularly limited. Preferable examples of the organometallic catalyst include tetrakis(triphenylphosphine)palladium (0), dichlorobis(triphenylphosphine)palladium (II), [1,1′-bis(diphenylphosphino) ferrocene]palladium (II)dichloride, bis(tert-butylphosphine) palladium (0), palladium (II) acetate and [1,3-bis (diphenylphosphino)propane]nickel (II). The amount of the organometallic catalyst used is about 0.001 to 0.1 equivalent with respect to the raw material. The organometallic compound is not particularly limited. Preferable examples of the organometallic compound include organotin reagents such as aryltri-n-butyltin, and organoboron reagents such as arylboronic acid. The amount of the organometallic compound used is one to five equivalents with respect to the raw material. The solvent used in this reaction is not particularly limited insofar as it does not inhibit the reaction. Preferable examples of the solvent include benzene, toluene, xylene, N,N-dimethylformamide, 1-methyl-2-pyrrolidone, tetrahydrofuran, 1,4-dioxane, acetonitrile and propionitrile. The reaction temperature is not particularly limited and is usually ice-cold temperature to solvent reflux temperature, and preferably room temperature to solvent reflux temperature, for example. The reaction time is not particularly limited and is usually 0.5 to 48 hours, and preferably 0.5 to 24 hours.

A more preferable result such as an improved yield may be achieved by carrying out this reaction in the presence of a base. Such a base is not particularly limited. Preferable examples of the base include bases such as sodium carbonate, potassium carbonate, cesium carbonate, potassium phosphate and solutions thereof, and triethylamine.

Step 1-3:

This step is a step of obtaining an alcohol compound (1-4) by subjecting the ester compound (1-3) to reduction reaction. The alcohol compound (1-4) can be obtained from the ester compound (1-3) by a method known to a person skilled in the art.

Examples of the reducing agent used in the reaction include lithium aluminum hydride, lithium borohydride and diisobutylaluminum hydride. The reaction temperature is not particularly limited and is usually −78° C. to solvent reflux temperature, and preferably −78° C. to room temperature. The solvent used in the reaction is not particularly limited insofar as it does not inhibit the reaction and allows the starting material to be dissolved therein to a certain extent. Preferable examples of the solvent include tetrahydrofuran, diethyl ether, toluene and dichloromethane.

Step 1-4:

This step is a step of obtaining a compound (1-5) by converting the hydroxyl group of the compound (1-4) to a leaving group.

Examples of the leaving group include halogen atoms (such as a chlorine atom, a bromine atom and an iodine atom) and sulfonyloxy groups such as a methanesulfonyloxy group, a p-toluenesulfonyloxy group and a trifluoromethanesulfonyloxy group.

The reaction can be performed under the same conditions as those usually used in reaction of converting a hydroxyl group to such a leaving group. When the leaving group is a halogen atom, for example, the compound (1-5) can be prepared by reacting the compound (1-4) with thionyl chloride, thionyl bromide, phosphorus tribromide or tetrahalogenomethane-triphenylphosphine, for example. The solvent used in the reaction is not particularly limited insofar as it does not inhibit the reaction and allows the starting material to be dissolved therein to a certain extent. Preferable examples of the solvent include benzene, toluene, xylene, dichloromethane and chloroform. The reaction temperature is usually −78° C. to solvent reflux temperature, and preferably ice-cold temperature to solvent reflux temperature. The reaction time is not particularly limited and is usually 5 minutes to 48 hours, and preferably 5 minutes to 12 hours.

When the leaving group is a sulfonyloxy group, the compound (1-5) can be prepared by reacting the compound (1-4) with methanesulfonyl chloride, p-toluenesulfonyl chloride or trifluoromethanesulfonic anhydride, for example.

The solvent used in the reaction is not particularly limited insofar as it does not inhibit the reaction and allows the starting material to be dissolved therein to a certain extent. Preferable examples of the solvent include tetrahydrofuran, toluene, xylene, dichloromethane, chloroform and N,N-dimethylformamide. The reaction temperature is usually −78° C. to solvent reflux temperature, and preferably −78° C. to room temperature. A favorable result such as an improved yield may be achieved by addition of a base. The base used is not particularly limited insofar as it does not inhibit the reaction. Preferable examples of the base include sodium carbonate, potassium carbonate, triethylamine, pyridine and diisopropylethylamine.

Step 1-5:

This step is a step of obtaining a compound (1-6) from the compound (1-5). The thiourea compound (1-6) can be obtained from the compound (1-5) by a method known to a person skilled in the art.

Specifically, the compound (1-6) can be obtained by reacting the compound (1-5) with thiourea in a solvent, for example. This reaction can be performed by causing one or more equivalents of thiourea to act on the compound (1-5) in an organic solvent such as ethanol, 1-propanol, 2-propanol, 1-butanol, tetrahydrofuran, 1,4-dioxane or N,N-dimethylformamide, for example. The reaction time is not particularly limited and is usually 5 minutes to 24 hours, and preferably 5 minutes to 12 hours. The reaction temperature is usually 0° C. to 150° C., and more preferably room temperature to 100° C.

Step 1-6:

This step is a method of obtaining the compound (1-7) by cyclizing the compound (1-6) with an acid.

This reaction is not particularly limited insofar as it does not inhibit the reaction and allows the starting material to be dissolved therein to a certain extent. For example, the reaction can be performed by causing one equivalent to a large excess of an appropriate acid to act on the compound (1-6) in the presence or absence of a solvent such as benzene, toluene or dichloromethane. Further, an acid may also be used as a solvent. Examples of the acid used include sulfuric acid, trifluoroacetic acid, methanesulfonic acid, trifluoromethanesulfonic acid and mixtures thereof. The reaction time is not particularly limited and is usually 1 to 72 hours, and preferably 1 to 48 hours. The reaction temperature is usually ice-cold temperature to solvent reflux temperature.

The amino group in the compound (1-7) can be converted to corresponding —$NR^1R^2$ in the formula (I), in which $R^1$ and $R^2$ are substituted, by further reacting the compound (1-7) with a corresponding halide compound or the like such as a $C_{1-6}$ alkyl halide, a $C_{1-6}$ alkylcarbonyl halide, a $C_{6-14}$ arylcarbonyl halide, a $C_{1-6}$ alkylsulfonyl halide, a $C_{6-14}$ arylsulfonyl halide, a 3- to 10-membered carbocyclic halide or a 5- to 10-membered heterocyclic halide.

2. General Preparation Method 2:

Method 2A:

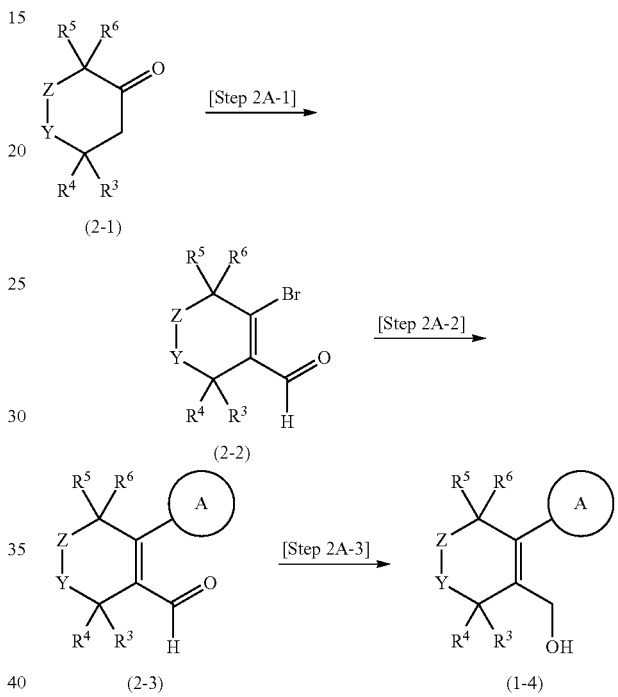

In the formula, Ring A, $R^3$, $R^4$, $R^5$, $R^6$, Y and Z are as defined above.

General Preparation Method 2 consists of the above Method 2A and the later-described Method 2B. Method 2A is a method for preparing a compound of the general formula (I-4) which is a synthetic intermediate of the compound (I) according to the present invention from a compound (2-1) as a raw material through multiple steps of Step 2A-1 to Step 2A-3.

The compound (2-1) can be a commercially available product used as is, can also be prepared from a commercially available product by a method known to a person skilled in the art, and can further be prepared by a method described in Preparation Examples among Examples.

Step 2A-1:

This step is a step of obtaining a compound (2-2) from the compound (2-1). This reaction can be performed under the same conditions as those usually used in reaction of synthesizing a compound (2-2) from a carbonyl compound (such as the conditions described in J. Org. Chem., 47, 3597-3607 (1982)).

Step 2A-2:

This step is a step of synthesizing a compound (2-3) from the compound (2-2) as a raw material using a method described in the above preparation method (Step 1-2).

Step 2A-3:

This step is a step of obtaining the alcohol compound (1-4) by subjecting the aldehyde compound (2-3) to reduction reaction.

The alcohol compound (1-4) can be obtained from the aldehyde compound (2-3) by a method known to a person skilled in the art. Examples of the reducing agent used in the reaction include sodium borohydride, sodium cyanoborohydride and sodium triacetoxyborohydride. The reaction temperature is not particularly limited and is usually −78° C. to solvent reflux temperature, and preferably −20° C. to room temperature. The solvent used in the reaction is not particularly limited insofar as it does not inhibit the reaction and allows the starting material to be dissolved therein to a certain extent. Preferable examples of the solvent include methanol, ethanol, tetrahydrofuran, ether, toluene and dichloromethane.

Method 2B:

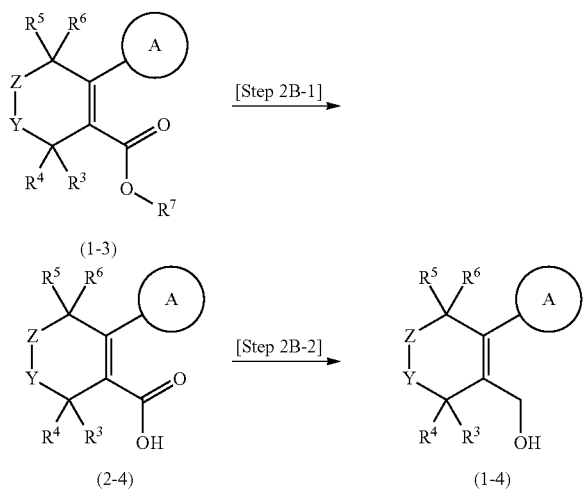

In the formula, Ring A, $R^3$, $R^4$, $R^5$, $R^6$, $R^7$, Y and Z are as defined above.

As shown in the above method 2B, the compound (1-4) can also be prepared by converting a compound (1-3) to a compound (2-4) and subjecting the compound to reduction reaction.

The compound (1-3) can be prepared from a commercially available product by General Preparation Method 1, and can also be prepared by a method described in Preparation Examples among Examples.

Step 2B-1:

This step is a step of obtaining the compound (2-4) by alkaline hydrolysis of the compound (1-3). The reaction can be performed under the same reaction conditions as those described in J. Med. Chem., 33 (9), 2621-2629 (1990), for example.

Specifically, the compound (2-4) can be obtained by adding a base such as sodium hydroxide to a solution of the compound (1-3), stirring the mixture for several hours to one day, and then treating the solution with an acid such as a citric acid solution, for example.

The solvent used in the reaction is not particularly limited insofar as it does not inhibit the reaction and allows the starting material to be dissolved therein to a certain extent. Examples of the solvent include methanol, ethanol, 2-propanol, tetrahydrofuran and 1,4-dioxane. The base used is not particularly limited and is preferably sodium hydroxide, potassium hydroxide or lithium hydroxide, for example. The amount of the base used is one equivalent to a large excess, and preferably 1 to 20 equivalents with respect to the compound (1-3). The reaction time is not particularly limited and is usually 1 to 24 hours, and preferably 1 to 6 hours. The reaction temperature is not particularly limited and is usually room temperature to solvent reflux temperature.

Step 2B-2:

This step is a step of obtaining the compound (1-4) by subjecting the compound (2-4) to reduction reaction.

The compound (1-4) can be obtained by converting the compound (2-4) to a mixed acid anhydride and then reacting the mixed acid anhydride with sodium borohydride. The mixed acid anhydride can be synthesized by a method known to a person skilled in the art. The synthesis is performed by reacting the compound (2-4) with a chloroformate such as ethyl chloroformate in the presence of a base such as triethylamine, for example. One to two equivalents of the chloroformate and the base are used with respect to the compound (2-4). The reaction temperature is −30° C. to room temperature, and preferably −20° C. to room temperature.

The step of reacting the mixed acid anhydride with a reducing agent such as sodium borohydride is performed by reaction in a solvent such as tetrahydrofuran or 1,2-dimethoxyethane or in a mixed solution of the solvent and water, for example. One equivalent to a large excess of the reducing agent such as sodium borohydride is used with respect to the mixed acid anhydride.

The reaction time is not particularly limited and is usually 0.5 to 48 hours, and preferably 0.5 to 24 hours. The reaction temperature is not particularly limited and is usually −78° C. to solvent reflux temperature, and preferably −20° C. to room temperature. The solvent used in the reaction is not particularly limited insofar as it does not inhibit the reaction and allows the starting material to be dissolved therein to a certain extent. Preferable examples of the solvent include tetrahydrofuran and ether.

3. General Preparation Method 3:

[Formula 8]

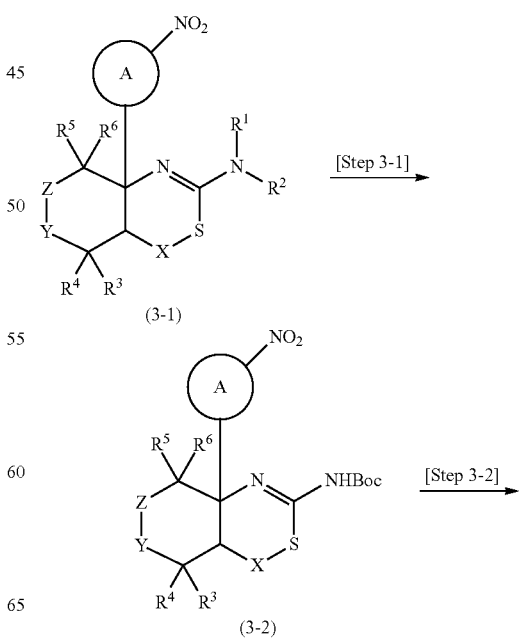

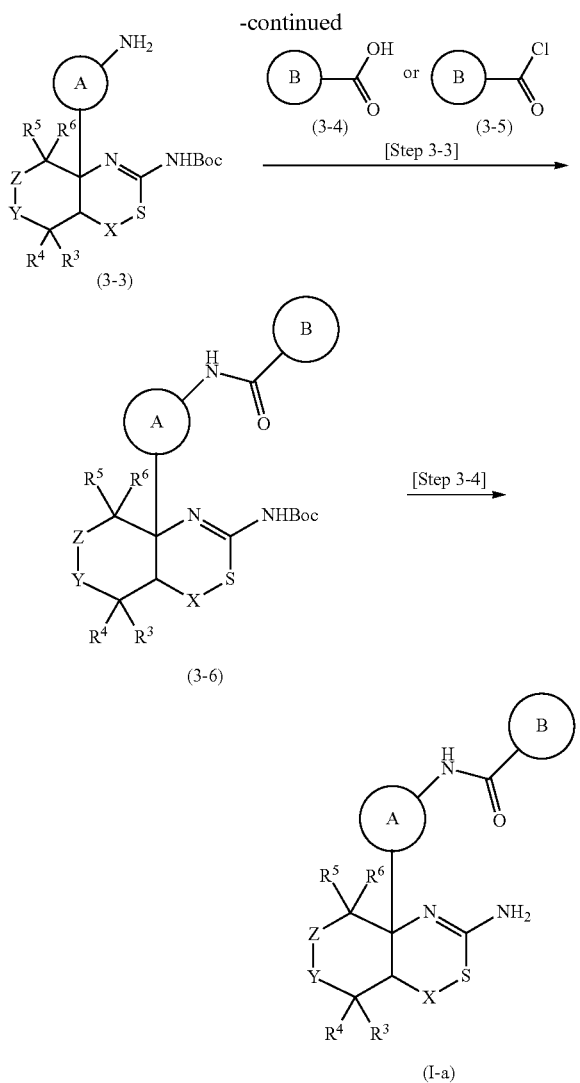

In the formula, Ring A, $R^1$, $R^2$, $R^3$, $R^4$, $R^5$, $R^6$, X, Y, Z and Ring B are as defined above.

General Preparation Method 3 is a method for preparing the compound of the general formula (I) according to the present invention, wherein L is —NHCO— and $R^1$ and $R^2$ are hydrogen atoms, from a compound (3-1) as a raw material through multiple steps of Step 3-1 to Step 3-4.

The compound (3-1) can be prepared from a commercially available product by the above General Preparation Method 1 or a combination of three preparation methods, General Preparation Method 1, General Preparation Method 2 and General Preparation Method 4, and can also be prepared by a method described in Preparation Examples among Examples. Compounds (3-4) and (3-5) each can be a commercially available product used as is, can also be prepared from a commercially available product by a method known to a person skilled in the art, and can further be prepared by a method described in Preparation Examples among Examples.

Step 3-1:

This step is a step of obtaining a compound (3-2) by t-butoxycarbonylation of the amino group of the compound (3-1) when $R^1$ and $R^2$ are both hydrogen.

The reaction can be performed under the same conditions as those generally used in t-butoxycarbonylation of an amino compound such as the conditions described in a document such as T. W. Green and P. G. M. Wuts, "Protective Groups in Organic Chemistry, Second Edition", John Wiley & Sons (1991), P. 327-330. The compound (3-2) can be obtained by reacting the compound (3-1) with di-tert-butyl dicarbonate using triethylamine as a base in a solvent such as tetrahydrofuran, for example.

Step 3-2:

This step is a step of obtaining a compound (3-3) from the compound (3-2).

The compound (3-3) is synthesized by reducing the nitro compound (3-2) by a synthesis method known to a person skilled in the art. Examples of the method include reduction by catalytic hydrogenation using a noble metal catalyst such as Raney nickel, palladium, ruthenium, rhodium or platinum. In this case, reduction reaction with iron under neutral conditions using ammonium chloride is preferable, for example.

Step 3-3:

This step is a step of obtaining a compound (3-6) by condensing the compound (3-3) with the compound (3-4) using a condensing agent. Alternatively, this step is a step of obtaining a compound (3-6) by condensing the compound (3-3) with the compound (3-5) by acylation reaction.

The condensation reaction of the compound (3-3) with the compound (3-4) using a condensing agent can be performed under the same conditions as those usually used and described in the following documents. Examples of the known method include those in Rosowsky, A.; Forsch, R. A.; Moran, R. G.; Freisheim, J. H.; J. Med. Chem., 34 (1), 227-234 (1991), Brzostwska, M.; Brossi, A.; Flippen-Anderson, J. L.; Heterocycles, 32 (10), 1968-1972 (1991), and Romero, D. L.; Morge, R. A.; Biles, C.; Berrios-Pena, N.; May, P. D.; Palmer, J. R.; Johnson, P. D.; Smith, H. W.; Busso, M.; Tan, C.-K.; Voorman, R. L.; Reusser, F.; Althaus, I. W.; Downey, K. M.; So, A. G.; Resnick, L.; Tarpley, W. G., Aristoff, P. A.; J. Med. Chem., 37 (7), 998-1014 (1994).

The compound (3-3) may be a free form or a salt.

The solvent in this reaction is not particularly limited insofar as it does not inhibit the reaction. Examples of the solvent include tetrahydrofuran, 1,4-dioxane, ethyl acetate, methyl acetate, dichloromethane, chloroform, N,N-dimethylformamide, toluene and xylene. Examples of the condensing agent include CDI (N,N'-carbonyldiimidazole), Bop (1H-1,2,3-benzotriazol-1-yloxy(tri(dimethylamino))phosphonium hexafluorophosphate), WSC (1-ethyl-3-(3-dimethylaminopropyl)carbodiimide hydrochloride), DCC (N,N-dicyclohexylcarbodiimide), diethylphosphoryl cyanide, PyBOP (benzotriazol-1-yloxytris(pyrrolidino)phosphonium hexafluorophosphate) and EDC.HCl (1-ethyl-3-(3-dimethylaminopropyl)carbodiimide hydrochloride). One equivalent to a large excess of the compound (3-4) is used with respect to the compound (3-3). One equivalent to a large excess of an organic base such as triethylamine may be added where necessary.

The reaction time is not particularly limited and is usually 0.5 to 48 hours, and preferably 0.5 to 24 hours. The reaction temperature varies according to the raw material used, the solvent and the like and is not particularly limited. Ice-cold temperature to solvent reflux temperature is preferable.

The compound of the formula (I) according to the present invention, wherein at least one of $R^1$ and $R^2$ is a $C_{1-6}$ alkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a 3- to 10-membered carbocyclic group which may have 1 to 3 substituents selected from Substituent Group α or a 5- to 10-membered heterocyclic group which may have 1 to 3 substituents selected from Substituent Group α, can be obtained by further reacting the compound (I-a) obtained in General Preparation Method 3 with a corresponding halide compound such as a $C_{1-6}$ alkyl halide.

Alternatively, —NHCO— of L in the compound (I-a) of the present invention can be converted to —NR$^e$CO— (wherein R$^e$ is a $C_{1-6}$ alkyl group which may have 1 to 3 substituents selected from Substituent Group α) by further reacting the compound (I-a) obtained in General Preparation Method 3 with a corresponding halide compound such as a $C_{1-6}$ alkyl halide.

The compound of the formula (I) according to the present invention, wherein L is —NR$^e$SO$_2$—, can be obtained using a corresponding sulfonyl halide compound in place of the compound (3-4) or (3-5) used in General Preparation Method 3.

In General Preparation Method 3, the compound (3-6) can also be prepared from the compound (3-3) and the compound (3-4) by a method described in the following alternative method (1) or (2).

Alternative Method (1):

The compound (3-6) can be obtained by converting the compound (3-4) to a mixed acid anhydride and then reacting the mixed acid anhydride with the compound (3-3). The mixed acid anhydride can be synthesized by a means known to a person skilled in the art. The synthesis is performed by reacting the compound (3-4) with a chloroformate such as ethyl chloroformate in the presence of a base such as triethylamine, for example. One to two equivalents of the chloroformate and the base are used with respect to the compound (3-4). The reaction temperature is −30° C. to room temperature, and preferably −20° C. to room temperature.

The step of condensing the mixed acid anhydride with the compound (3-3) is performed by reacting the mixed acid anhydride with the compound (3-3) in a solvent such as dichloromethane, tetrahydrofuran or N,N-dimethylformamide, for example. One equivalent to a large excess of the compound (3-3) is used with respect to the mixed acid anhydride.

The reaction time is not particularly limited and is usually 0.5 to 48 hours, and preferably 0.5 to 12 hours. The reaction temperature is −20° C. to 50° C., and preferably −20° C. to room temperature.

Alternative Method (2):

The compound (3-6) can be obtained by converting the compound (3-4) to an active ester and then reacting the active ester with the compound (3-3). The step of obtaining the active ester is performed by reacting the compound (3-4) with an active ester synthesis reagent in a solvent such as 1,4-dioxane, tetrahydrofuran or N,N-dimethylformamide in the presence of a condensing agent such as DCC, for example. Examples of the active ester synthesis reagent include N-hydroxysuccinimide. One to 1.5 equivalents of the active ester synthesis reagent and the condensing agent are used with respect to the compound (3-4). The reaction time is not particularly limited and is usually 0.5 to 48 hours, and preferably 0.5 to 24 hours.

The reaction temperature is −20° C. to 50° C., and preferably −20° C. to room temperature.

The step of condensing the active ester with the compound (3-3) is performed by reacting the active ester with the compound (3-3) in a solvent such as dichloromethane, tetrahydrofuran or N,N-dimethylformamide, for example. One equivalent to a large excess of the compound (3-3) is used with respect to the active ester. The reaction time is not particularly limited and is usually 0.5 to 48 hours, and preferably 0.5 to 24 hours. The reaction temperature is −20° C. to 50° C., and preferably −20° C. to room temperature.

In this acylation reaction, the compound (3-6) can be obtained from the compounds (3-3) and (3-5) by a method known to a person skilled in the art.

Examples of the base used in the reaction include triethylamine, pyridine, potassium carbonate and diisopropylethylamine. The reaction temperature is not particularly limited and is usually −78° C. to solvent reflux temperature, and preferably −20° C. to room temperature. The solvent used in the reaction is not particularly limited insofar as it does not inhibit the reaction and allows the starting material to be dissolved therein to a certain extent. Preferable examples of the solvent include tetrahydrofuran, ether, toluene and dichloromethane.

Step 3-4:

This step is a step of obtaining the compound (I-a) by deprotection reaction of the t-butoxycarbonyl group of the compound (3-6).

The reaction can be performed under the same conditions as those generally used in deprotection reaction of a t-butoxycarbonyl group such as the conditions described in a document such as T. W. Green and P. G. M. Wuts, "Protective Groups in Organic Chemistry, Second Edition", John Wiley & Sons (1991), P. 327-330. The compound (I-a) can be obtained by reacting trifluoroacetic acid with the compound (3-6) in a solvent such as dichloromethane, for example.

4. General Preparation Method 4:

[Formula 9]

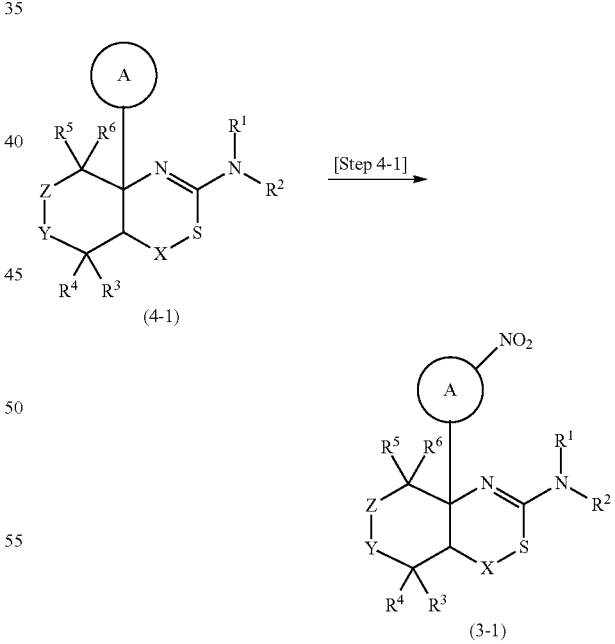

In the formula, Ring A, R$^1$, R$^2$, R$^3$, R$^4$, R$^5$, R$^6$, X, Y and Z are as defined above.

General Preparation Method 4 is a method for preparing a compound of the general formula (3-1) which is a synthetic intermediate of the compound according to the present invention and is used in General Preparation Method 3 from a compound (4-1) as a raw material through Step 4-1.

The compound (4-1) can be prepared from a commercially available product by General Preparation Method 1, General Preparation Method 5 or a combination of General Preparation Method 1 and General Preparation Method 2, and can also be prepared by a method described in Preparation Examples among Examples.

Step 4-1:

This step is a step of obtaining the compound (3-1) by nitration reaction of the compound (4-1). In this nitration reaction, the compound (3-1) can be obtained from the compound (4-1) by a method known to a person skilled in the art. Examples of the nitrating agent used in the reaction include potassium nitrate/concentrated sulfuric acid and fuming nitric acid/acetic anhydride. The reaction temperature is not particularly limited and is usually −20° C. to room temperature.

5. General Preparation Method 5:

[Formula 10]

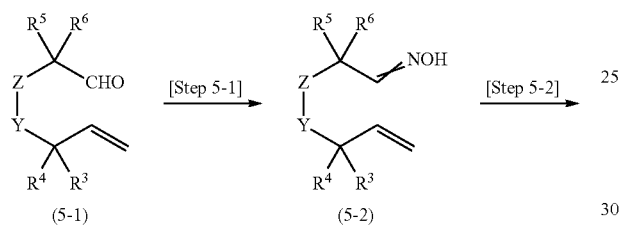

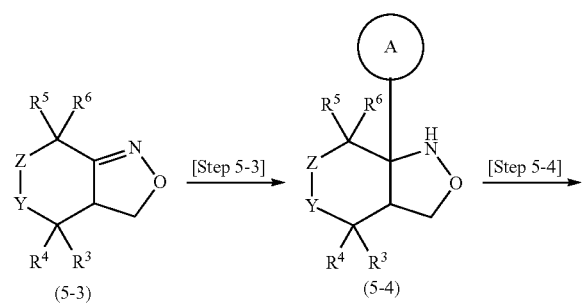

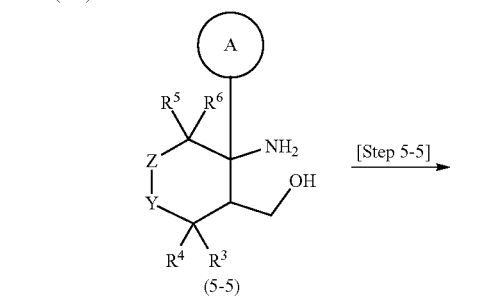

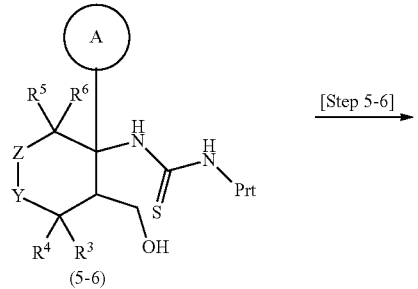

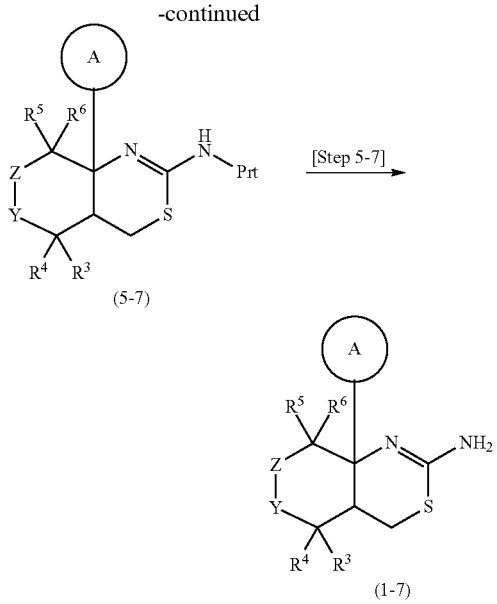

In the formula, Prt represents a protecting group such as a benzoyl group, an acetyl group or a 8-fluorenemethyloxycarbonyl group (Fmoc group), and Ring A, $R^3$, $R^4$, $R^5$, $R^6$, Y and Z are as defined above.

General Preparation Method 5 is a method for preparing a compound (1-7) which is a synthetic intermediate of the compound (I) according to the present invention from a compound (5-1) as a raw material through multiple steps of Step 5-1 to Step 5-7.

The compound (5-1) can be prepared from a commercially available product by the later-described General Preparation Method 6 or 7, can also be prepared from a commercially available product by a method known to a person skilled in the art, and can further be prepared by a method described in Preparation Examples among Examples.

Step 5-1:

This step is a step of obtaining a compound (5-2) by oximation of the compound (5-1).

The reaction in this step can be performed under the same conditions as those usually used in oximation reaction of a carbonyl compound such as the conditions described in Org. Lett. 9 (2007) 5, 753-756, Tetrahedron: Asymmetry 5 (1994) 6, 1018-1028 and Tetrahedron 54 (1998) 22, 5868-5882.

Specifically, the compound (5-2) can be obtained by reacting the compound (5-1) with hydroxylamine or a hydroxylamine salt (such as hydroxylamine hydrochloride or hydroxylamine sulfate) in the presence of a base or in the absence of a base, for example.

The solvent used in this reaction is not particularly limited insofar as it does not inhibit the reaction. Preferable examples of the solvent include organic solvents such as ethanol, methanol, tetrahydrofuran, 1,4-dioxane, 1,2-dimethoxyethane and dichloromethane, and mixtures of these solvents and water. Examples of the base used include sodium acetate, pyridine, sodium hydroxide, cesium hydroxide, barium hydroxide and 2,6-lutidine. The reaction time is not particularly limited and is usually 5 minutes to 24 hours, and preferably 5 minutes to 12 hours. The reaction temperature is usually −20° C. to solvent reflux temperature, and more preferably 0° C. to solvent reflux temperature.

Step 5-2:

This step is a step of obtaining a compound (5-3) by converting the compound (5-2) to a nitrile oxide derivative and performing 1,3-dipolar cycloaddition reaction with the olefin moiety in the same molecule.

The reaction in this step can be performed under the same conditions as those usually used in 1,3-dipolar cycloaddition reaction such as the conditions described in a document such as Org. Lett. 9 (2007) 5, 753-756, Tetrahedron: Asymmetry 5 (1994) 6, 1018-1028 and Tetrahedron 54 (1998) 22, 5868-5882. Examples of the reagent for converting the oxime compound to the nitrile oxide include N-chlorosuccinimide and sodium hypochlorite. The solvent used in this reaction is not particularly limited insofar as it does not inhibit the reaction. Preferable examples of the solvent include dichloromethane, chloroform, benzene, toluene, xylene, N,N-dimethylformamide, tetrahydrofuran and 1,4-dioxane. The reaction temperature is not particularly limited and is usually ice-cold temperature to solvent reflux temperature. The reaction time is not particularly limited and is usually 0.5 to 48 hours, and preferably 0.5 to 24 hours.

A more preferable result such as an improved yield may be achieved by carrying out this reaction in the presence of a base. Such a base is not particularly limited. Examples of the base include bases such as sodium carbonate, potassium carbonate, cesium carbonate, potassium phosphate and solutions thereof, and triethylamine and pyridine.

Step 5-3:

This step is a step of obtaining a compound (5-4) by addition reaction of an aryllithium reagent (including heterocyclic) or a Grignard reagent (including heterocyclic) with the compound (5-3).

The reaction in this step can be performed under the same conditions as those described in J. Am. Chem. Soc. 2005, 127, 5376-5383, Bull. Chem. Soc. Jpn., 66, 2730-2737 (1993) and SYNLETT. 2004, No. 8, pp 1408-1413, for example.

The aryllithium reagent (including heterocyclic) or the Grignard reagent (including heterocyclic) can be prepared by a method known to a person skilled in the art. Specifically, a corresponding aryl (including heterocyclic) lithium reagent or aryl (including heterocyclic) magnesium reagent can be prepared by halogen-metal exchange between an aryl halide compound and a commercially available organometallic reagent such as an alkyllithium reagent such as n-, sec- or tert-butyllithium or a Grignard reagent such as isopropylmagnesium bromide, or metallic magnesium, for example.

The solvent used in this step varies according to the starting material and the reagent used, and is not particularly limited insofar as it does not inhibit the reaction, allows the starting material to be dissolved therein to a certain extent, and is always inert during the reaction. Preferable examples of the solvent include organic solvents such as diethyl ether, tetrahydrofuran, 1,4-dioxane, 1,2-dimethoxyethane, benzene and toluene, and mixed solvents thereof. The reaction time is not particularly limited and is usually 0.1 to 48 hours, and preferably 0.1 to 12 hours. The reaction temperature varies according to the starting material, the reagent used and the like, and is preferably maintained to be low, for example, at −78° C. to minimize formation of a by-product.

Favorable results such as an improved yield and a reduced reaction time may be achieved by addition of TMEDA (tetramethylethylenediamine), HMPA (hexamethylphosphoramide) or a Lewis acid such as a boron trifluoride-diethyl ether complex (BF3.OEt2) as an additive, for example.

Step 5-4:

This step is a step of obtaining a compound (5-5) by subjecting the compound (5-4) to reductive cleavage reaction of the N—O bond.

The reductive cleavage reaction of the N—O bond can be performed under the conditions using zinc-acetic acid, a metal catalyst such as hydrogen-platinum oxide, or lithium aluminum hydride, for example.

The reaction using zinc such as zinc-acetic acid can be performed under the same conditions as those described in J. Org. Chem. 2003, 68, 1207-1215 and Org. Lett. 7 (2005) 25, 5741-5742, for example. Examples of the acid used include acetic acid, formic acid and hydrochloric acid. The solvent used in the reaction is not particularly limited insofar as it does not inhibit the reaction and allows the starting material to be dissolved therein to a certain extent. Examples of the solvent include methanol, ethanol, 1,4-dioxane, THF and water. The above acid may also be used as a solvent. The reaction temperature is usually −20° C. to solvent reflux temperature, and preferably ice-cold temperature to solvent reflux temperature. The reaction time is not particularly limited and is usually 5 minutes to 48 hours, and preferably 5 minutes to 24 hours.

The reaction using a metal catalyst such as hydrogen-platinum oxide can be performed under the same conditions as those described in Tetrahedron: Asymmetry 5 (1994) 6, 1018-1028 and Tetrahedron, Vol. 53, No. 16, pp 5752-5746, 1997, for example. The compound (5-5) can be obtained by hydrogenating the compound (5-4) using platinum oxide as a catalyst in a solvent such as methanol, for example.

The reaction using lithium aluminum hydride can be performed under the same conditions as those described in Bull. Chem. Soc. Jpn., 66, 2730-2737 (1993), for example. The compound (5-5) can be obtained by reducing the compound (5-4) using lithium aluminum hydride in a solvent such as ether, for example.

Step 5-5:

This step is a step of obtaining a compound (5-6) from the compound (5-5). The thiourea derivative (5-6) can be obtained from the compound (5-5) by a method known to a person skilled in the art.

When the protecting group is a benzoyl group, the compound (5-6) can be obtained in this step by reacting the compound (5-5) with benzoyl isothiocyanate in a solvent such as dichloromethane or toluene. This reaction can be performed under the same conditions as those described in J. Org. Chem. 1994, 59, 1911-1917, for example. The solvent used in the reaction is not particularly limited insofar as it does not inhibit the reaction and allows the starting material to be dissolved therein to a certain extent. Examples of the solvent include dichloromethane, chloroform, toluene, methanol, ethanol, 1,4-dioxane and THF. The reaction temperature is usually −20° C. to solvent reflux temperature, and preferably ice-cold temperature to solvent reflux temperature. The reaction time is not particularly limited and is usually 5 minutes to 48 hours, and preferably 5 minutes to 24 hours.

When the protecting group is a 8-fluorenemethyloxycarbonyl group (Fmoc group), the compound (5-6) can be obtained in this step by reacting the compound (5-5) with fluorenemethyloxycarbonyl isothiocyanate in a solvent such as dichloromethane or toluene. This reaction can be performed under the same conditions as those described in J. Org. Chem. 1998, 63, 196-200, for example. The solvent used in the reaction is not particularly limited insofar as it does not inhibit the reaction and allows the starting material to be dissolved therein to a certain extent. Examples of the solvent include dichloromethane, chloroform, toluene, methanol, ethanol, 1,4-dioxane and THF. The reaction temperature is usually −20° C. to solvent reflux temperature, and preferably ice-cold temperature to solvent reflux temperature. The reaction time is not particularly limited and is usually 5 minutes to 48 hours, and preferably 5 minutes to 24 hours.

Step 5-6:

This step is a method of obtaining a compound (5-7) by cyclizing the compound (5-6).

In this reaction, the compound (5-6) can be cyclized under various conditions to obtain the compound (5-7) by selecting a protecting group of the compound (5-6).

When the protecting group is an Fmoc group or a benzoyl group, for example, the compound (5-7) can be obtained in this reaction by heating the compound (5-6) in a solvent such as methanol in the presence of an acid such as concentrated hydrochloric acid, for example. The solvent used in the reaction is not particularly limited insofar as it does not inhibit the reaction and allows the starting material to be dissolved therein to a certain extent. Examples of the solvent include solvents such as methanol, ethanol, 1-propanol and water, mixed solvents thereof, and acids used as a solvent. The reaction can be performed by causing one equivalent to a large excess of an appropriate acid to act in the presence or absence of such a solvent. Examples of the acid used include concentrated hydrochloric acid, hydrobromic acid, sulfuric acid, trifluoroacetic acid, methanesulfonic acid, trifluoromethanesulfonic acid and mixtures thereof. The reaction time is not particularly limited and is usually 0.5 to 72 hours, and preferably 0.5 to 24 hours. The reaction temperature is usually ice-cold temperature to solvent reflux temperature.

When the protecting group is an Fmoc group or a benzoyl group, the compound (5-7) can be obtained by an alternative method 1 of reacting the compound (5-6) with trifluoromethanesulfonic anhydride in a solvent such as dichloromethane in the presence of a base such as pyridine. This reaction can be performed under the same conditions as those described in Chem Bio Chem. 2005, 6, 186-191, for example. The solvent used in the reaction is not particularly limited insofar as it does not inhibit the reaction and allows the starting material to be dissolved therein to a certain extent. Examples of the solvent include solvents such as dichloromethane, 1,2-dichloroethane, THF, 1,2-dimethoxyethane and toluene, and mixed solvents thereof. The reaction can be performed using 1 to 20 equivalents of an appropriate base in such a solvent. Examples of the base used include pyridine, 2,6-lutidine, sodium carbonate, potassium carbonate and mixtures thereof. The reaction time is not particularly limited and is usually 0.5 to 24 hours, and preferably 0.5 to 12 hours. The reaction temperature is usually −78° C. to room temperature.

When the protecting group is a benzoyl group, the compound (5-7) can be obtained by an alternative method 2 of reacting the compound (5-6) with triphenylphosphine and carbon tetrabromide (or bromine) in a solvent such as dichloromethane. The reaction conditions are the same as those of bromination of a primary alcohol which are known to a person skilled in the art.

Step 5-7:

This step is a method of obtaining the compound (1-7) by deprotecting the protecting group of the compound (5-7). The compound (1-7) can be obtained under deprotection conditions known to a person skilled in the art.

When the protecting group is an Fmoc group, for example, the compound (1-7) can be obtained under the same conditions as those generally used in deprotection of a protecting group of an amine compound (such as the conditions described in a document such as T. W. Green and P. G. M. Wuts, "Protective Groups in Organic Chemistry, Third Edition", John Wiley & Sons, p. 506-507 and J. Org. Chem. 1998, 63, 196-200). In this reaction, the compound (1-7) can be obtained by reacting the compound (5-7) with an excess of an amine such as pyrrolidine in a solvent such as acetonitrile, for example. The solvent used in the reaction is not particularly limited insofar as it does not inhibit the reaction and allows the starting material to be dissolved therein to a certain extent. Examples of the solvent include dichloromethane, THF and acetonitrile. The reaction can be performed by causing one equivalent to a large excess of an appropriate base to act in the presence of such a solvent. Examples of the base used include piperidine, morpholine, pyrrolidine, TBAF and DBU. The reaction time is not particularly limited and is usually 0.5 to 72 hours, and preferably 0.5 to 24 hours. The reaction temperature is usually ice-cold temperature to solvent reflux temperature.

Favorable results such as an improved yield and a reduced reaction time may be achieved by addition of a thiol compound such as 1-octanethiol as an additive, for example.

When the protecting group is a benzoyl group, the compound (1-7) can be obtained in this reaction by heating the compound (5-7) in a solvent such as methanol in the presence of a base such as DBU, for example. This reaction can be performed under the same conditions as those described in Synth. Commun. 32 (2), 265-272 (2002), for example. The solvent used in the reaction is not particularly limited insofar as it does not inhibit the reaction and allows the starting material to be dissolved therein to a certain extent. Examples of the solvent include solvents such as methanol, ethanol and 1-propanol. The reaction can be performed using 1 to 20 equivalents of an appropriate base in such a solvent. Examples of the base used include DBU. The reaction time is not particularly limited and is usually 0.5 to 24 hours, and preferably 0.5 to 12 hours. The reaction temperature is usually room temperature to solvent reflux temperature.

6. General Preparation Method 6:

[Formula 11]

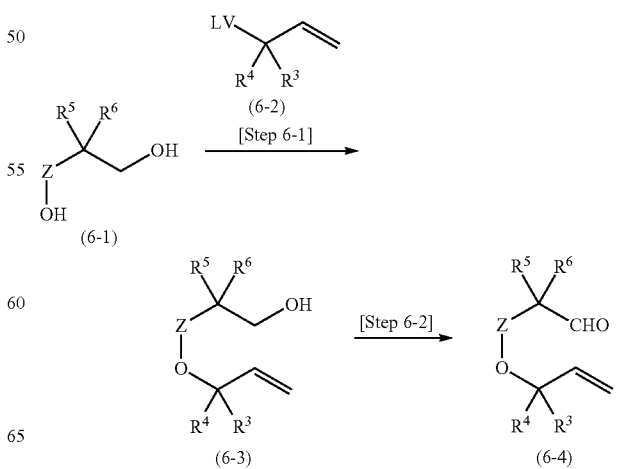

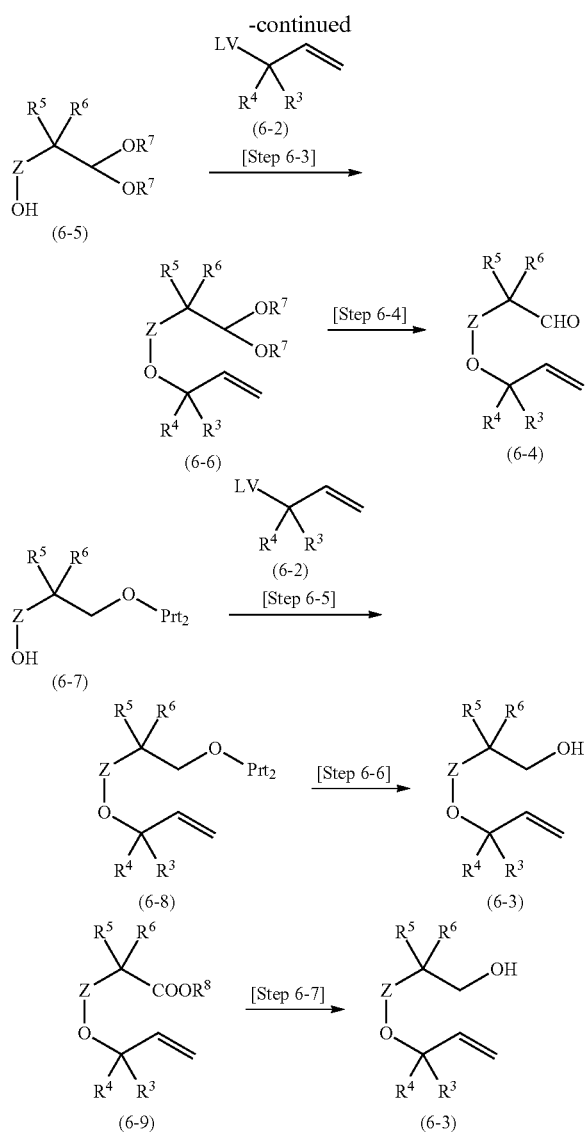

In the formula, $Prt_2$ represents a primary hydroxyl protecting group, $R^8$ represents a $C_{1-6}$ alkyl group, and Z, $R^3$, $R^4$, $R^5$, $R^6$, $R^7$ and LV are as defined above.

General Preparation Method 6 is a method for preparing a compound (6-4) which is a compound (5-1) as a starting material for General Preparation Method 5, wherein Y is an oxygen atom.

Compounds (6-1), (6-2), (6-5), (6-7) and (6-9) each can be a commercially available product used as is, can also be prepared from a commercially available product by a method known to a person skilled in the art, and can further be prepared by a method described in Preparation Examples among Examples.

Step 6-1:

This step is a step of obtaining a compound (6-3) by reaction of the compound (6-1) with the compound (6-2).

This reaction can be performed under the same conditions as those usually used in O-alkylation reaction of an alcohol compound (such as the conditions described in Tetrahedron Lett. 46 (2005) 45, 7751-7755). In this reaction, the compound (6-3) can be obtained by adding a base such as sodium hydride to a solution of the compound (6-1) in THF to prepare an alkoxide, and then reacting the alkoxide with the compound (6-2), for example. The solvent used in the reaction is not particularly limited insofar as it does not inhibit the reaction and allows the starting material to be dissolved therein to a certain extent. Examples of the solvent include solvents such as THF, DMF and dimethyl sulfoxide. The reaction can be performed by causing 1 to 3 equivalents of an appropriate base to act in the presence of such a solvent. Examples of the base used include sodium hydride, potassium hydride and t-butoxypotassium. The reaction time is not particularly limited and is usually 0.5 to 72 hours, and preferably 0.5 to 12 hours. The reaction temperature is usually −20° C. to 50° C.

A more preferable result such as an improved yield may be achieved by adding a salt such as tetrabutylammonium iodide in this reaction.

Step 6-2:

This step is a step of obtaining an aldehyde compound (6-4) by subjecting the alcohol compound (6-3) to oxidation reaction. The aldehyde compound can be obtained from the alcohol compound by a method known to a person skilled in the art.

Examples of the known oxidation method used in the reaction include Swern oxidation, Corey-Kim oxidation, Moffatt oxidation, PCC oxidation, PDC oxidation, Dess-Martin oxidation, $SO_3$-pyridine oxidation and TEMPO oxidation.

The solvent used in the reaction is not particularly limited insofar as it does not inhibit the reaction and allows the starting material to be dissolved therein to a certain extent. Examples of the solvent include dimethyl sulfoxide, tetrahydrofuran, toluene, dichloromethane and chloroform.

The reaction temperature is not particularly limited and is usually −78° C. to solvent reflux temperature, and preferably −78° C. to room temperature. The reaction time is not particularly limited and is usually 0.5 to 48 hours, and preferably 0.5 to 24 hours.

Step 6-3:

This step is a step of synthesizing a compound (6-6) from the compound (6-5) as a raw material using a method described in the above preparation method (Step 6-1).

Step 6-4:

This step is a step of obtaining the compound (6-4) by deprotecting the acetal group of the compound (6-6).

This reaction can be performed under the same conditions as those generally used in deprotection of an aldehyde group such as the conditions described in a document such as T. W. Green and P. G. M. Wuts, "Protective Groups in Organic Chemistry, Third Edition", John Wiley & Sons, P. 293-329.

Step 6-5:

This step is a step of synthesizing a compound (6-8) from the compound (6-7) as a raw material using a method described in the above preparation method (Step 6-1).

Step 6-6:

This step is a step of obtaining the compound (6-3) by deprotecting the hydroxyl protecting group of the compound (6-8). The hydroxyl protecting group used in this step is not particularly limited.

This reaction can be performed under the same conditions as those generally used in deprotection of an alcohol protecting group such as the conditions described in a document such as T. W. Green and P. G. M. Wuts, "Protective Groups in Organic Chemistry, Third Edition", John Wiley & Sons, P. 17-245.

Step 6-7:

This step is a step of synthesizing the compound (6-3) from the compound (6-9) as a raw material using a method described in the above preparation method ((Step 1-3) or (Steps 2B-1 and 2)).

7. General Preparation Method 7:

[Formula 12]

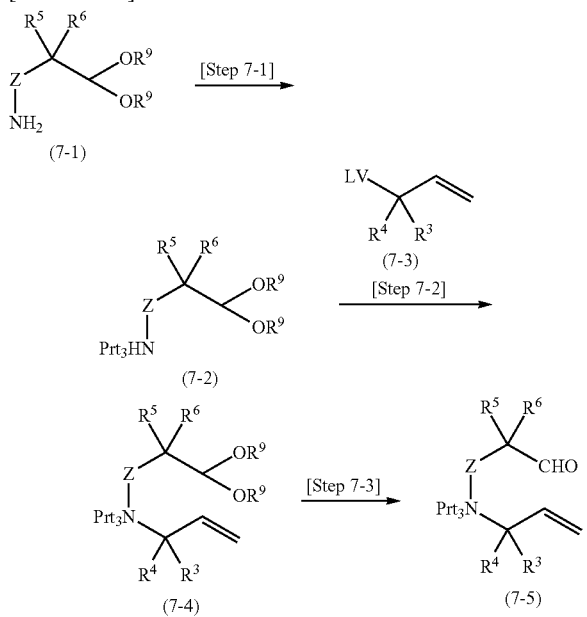

In the formula, $R^9$ represents a $C_{1-6}$ alkyl group, or two $R^9$ together may form a ring, $Prt_3$ represents a protecting group such as a 2,4-dimethoxybenzyl group, and Z, $R^3$, $R^4$, $R^5$, $R^6$, Z and LV are as defined above.

General Preparation Method 7 is a method for preparing a compound (7-5) which is a compound (5-1) as a starting material for General Preparation Method 5, wherein Y is a nitrogen atom.

Compounds (7-1) and (7-3) each can be a commercially available product used as is, can also be prepared from a commercially available product by a method known to a person skilled in the art, and can further be prepared by a method described in Preparation Examples among Examples.

Step 7-1:

This step is a step of obtaining a compound (7-2) by protecting the amino group of the compound (7-1).

This reaction can be performed under the same conditions as those generally used in protection of an amino group such as the conditions described in a document such as T. W. Green and P. G. M. Wuts, "Protective Groups in Organic Chemistry, Third Edition", John Wiley & Sons, P. 494-572 and J. Med. Chem. 2007, 50, 5493-5508.

Step 7-2:

This step is a step of obtaining a compound (7-4) by N-alkylation reaction of the compound (7-2) with the compound (7-3).

This reaction can be performed under the same conditions as those usually used in N-alkylation reaction of a compound (7-2) (such as the conditions described in J. Med. Chem. 2007, 50, 5493-5508). In this reaction, the compound (7-4) can be obtained by adding a base such as powdery sodium hydroxide to a solution of the compound (7-2) in toluene, and then reacting the mixture with the compound (7-3), for example. The solvent used in the reaction is not particularly limited insofar as it does not inhibit the reaction and allows the starting material to be dissolved therein to a certain extent. Examples of the solvent include solvents such as toluene, THF, DMF and dimethyl sulfoxide. The reaction can be performed by causing 1 to 5 equivalents of an appropriate base to act in the presence of such a solvent. Examples of the base used include sodium hydroxide, potassium hydroxide, sodium hydride, potassium hydride and t-butoxypotassium. The reaction time is not particularly limited and is usually 0.5 to 72 hours, and preferably 0.5 to 24 hours. The reaction temperature is usually −20° C. to 100° C.

A more preferable result such as an improved yield may be achieved by adding a salt such as tetrabutylammonium iodide in this reaction.

Step 7-3:

This step is a step of obtaining the compound (7-5) by deprotecting the acetal group of the compound (7-4).

This reaction can be performed under the same conditions as those generally used in deprotection of an aldehyde group such as the conditions described in a document such as T. W. Green and P. G. M. Wuts, "Protective Groups in Organic Chemistry, Third Edition", John Wiley & Sons, P. 293-329.

8. General Preparation Method 8:

[Formula 13]

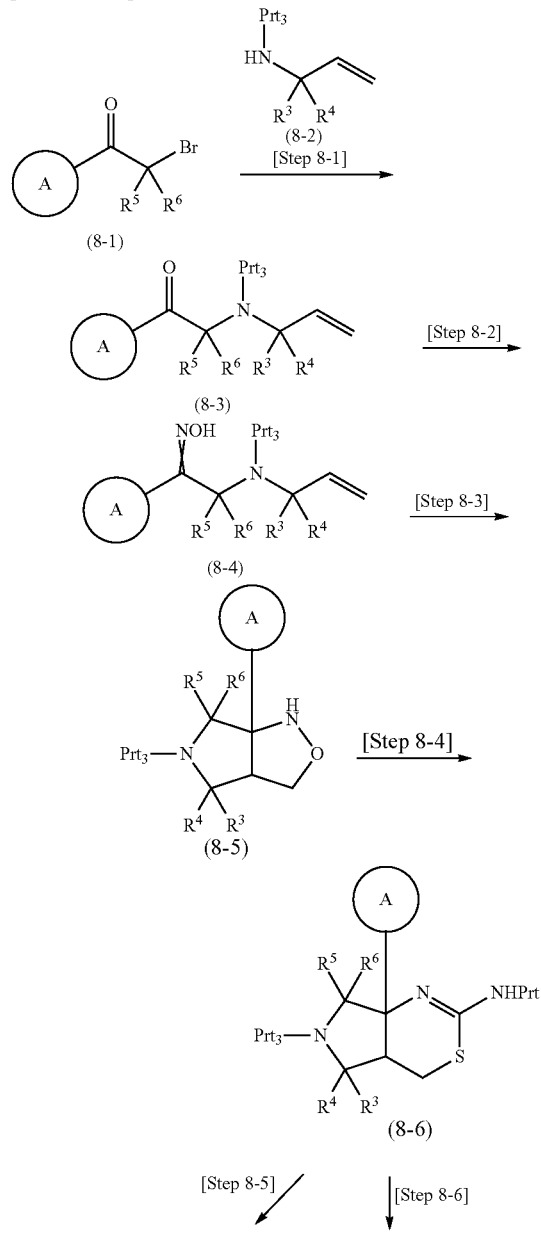

-continued

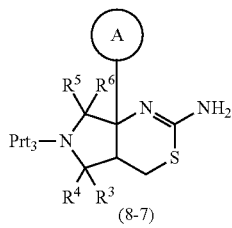

(8-7)

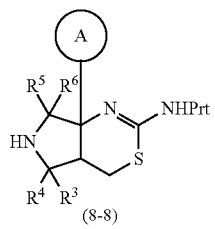

(8-8)

In the formula, Prt represents a protecting group such as a benzoyl group, an acetyl group or a 8-fluorenemethyloxycarbonyl group (Fmoc group), $Prt_3$ represents a protecting group such as a 2,4-dimethoxybenzyl group, and Ring A, $R^3$, $R^4$, $R^5$ and $R^6$ are as defined above.

General Preparation Method 8 is steps of the method for preparing compounds of the general formulas (8-7) and (8-8) which are synthetic intermediates of the compound (I) according to the present invention in General Preparation Method 5, wherein Y is a nitrogen atom and Z is a single bond. These compounds can be prepared from a compound (8-1) as a raw material by the steps shown above.

The compound (8-1) can be a commercially available product used as is, can also be prepared from a commercially available product by a method known to a person skilled in the art, and can further be prepared by a method described in Preparation Examples among Examples. A compound (8-2) can be prepared from a commercially available product by a method known to a person skilled in the art, and can further be prepared by a method described in Preparation Examples among Examples.

Step 8-1:

This step is a step of obtaining a compound (8-3) by reaction of the compound (8-1) with the compound (8-2). This reaction can be performed under the same conditions as those usually used in N-alkylation reaction of an amino compound (such as the conditions described in J. Med. Chem. 2002, 45, 3794-3804 and J. Med. Chem. 2000, 43, 3808-3812). In this reaction, the compound (8-3) can be obtained by reacting the compound (8-1) with the compound (8-2) in a solvent such as dichloromethane in the presence of a base such as N,N-diisopropylethylamine, for example. The solvent used in the reaction is not particularly limited insofar as it does not inhibit the reaction and allows the starting material to be dissolved therein to a certain extent. Examples of the solvent include dichloromethane, THF, acetonitrile and DMF. The reaction can be performed by causing 1 to 10 equivalents of an appropriate base to act in such a solvent. Examples of the base used include N,N-diisopropylethylamine, triethylamine, sodium carbonate and potassium carbonate. The reaction time is not particularly limited and is usually 0.5 to 72 hours, and preferably 0.5 to 12 hours. The reaction temperature is usually ice-cold temperature to 50° C.

Step 8-2:

This step is a step of obtaining a compound (8-4) by oximation of the compound (8-3).

The reaction in this step can be performed under the same conditions as those usually used in oximation reaction of a carbonyl compound such as the conditions described in J. Med. Chem. 2002, 45, 3794-3804 and J. Med. Chem. 2000, 43, 3808-3812.

Specifically, the compound (8-4) can be obtained by reacting the compound (8-3) with hydroxylamine or a hydroxylamine salt (such as hydroxylamine hydrochloride or hydroxylamine sulfate) in the presence of a base or in the absence of a base, for example. The solvent used in this reaction is not particularly limited insofar as it does not inhibit the reaction. Preferable examples of the solvent include organic solvents such as ethanol, methanol, tetrahydrofuran, 1,4-dioxane, 1,2-dimethoxyethane and dichloromethane, and mixtures of these solvents and water. Examples of the base used include sodium carbonate, potassium carbonate, sodium acetate, pyridine, sodium hydroxide, cesium hydroxide, barium hydroxide and 2,6-lutidine. The reaction time is not particularly limited and is usually 5 minutes to 24 hours, and preferably 5 minutes to 12 hours. The reaction temperature is usually 0° C. to solvent reflux temperature, and more preferably room temperature to solvent reflux temperature.

Step 8-3:

This step is a step of obtaining a compound (8-5) by subjecting the oxime compound (8-4) to 1,3-dipolar cycloaddition reaction.

The reaction in this step can be performed under the same conditions as those usually used in 1,3-dipolar cycloaddition reaction such as the conditions described in J. Org. Chem. 1993, 58, 4538-4546 and Tetrahedron Letters, Vol. 29, No. 41, pp 5312-5316.

Specifically, the compound (8-5) can be obtained by heating the compound (8-4) under reflux in a toluene solvent, for example. The solvent used in this reaction is not particularly limited insofar as it does not inhibit the reaction. Preferable examples of the solvent include organic solvents such as toluene, xylene and chlorobenzene. The reaction time is not particularly limited and is usually 5 minutes to 24 hours, and preferably 5 minutes to 12 hours. The reaction temperature is usually 0° C. to solvent reflux temperature, and more preferably room temperature to solvent reflux temperature.

Favorable results such as an improved yield and a reduced reaction time may be achieved by addition of a Lewis acid such as zinc chloride as an additive, for example.

Favorable results such as a reduced reaction time and an improved yield may be obtained by performing this reaction using a microwave reactor.

Step 8-4:

The compound (8-6) can be synthesized from the compound (8-5) using a series of methods described in the above preparation method ((Step 5-4) to (Step 5-6)).

Step 8-5:

This step is a step of synthesizing the compound (8-7) from the compound (8-6) as a raw material using a method described in the above preparation method (Step 5-7).

Step 8-6:

This step is a step of obtaining the compound (8-8) by deprotecting the amino group of the compound (8-6). The amino protecting group used in this step is not particularly limited. When $Prt_3$ is a 2,4-dimethoxybenzyl group, for example, this step can be performed under the same conditions as those generally used (such as the conditions described in a document such as Tetrahedron Vol. 47, No. 26, pp 4591-4602, 1991). When $Prt_3$ is a 2,4-dimethoxybenzyl group in this step, the solvent used in this step is not particularly limited insofar as it does not inhibit the reaction and allows the starting material to be dissolved therein to a certain extent. For example, the first-stage reaction solvent may be methylene chloride or chloroform, and the second-stage reaction solvent may be methanol. The reaction temperature in this step is usually 0° C. to room temperature. The reaction time in this step is not particularly limited and is usually 0.5 to 24 hours, and preferably 0.5 to 12 hours.

9. General Preparation Method 9:

[Formula 14]

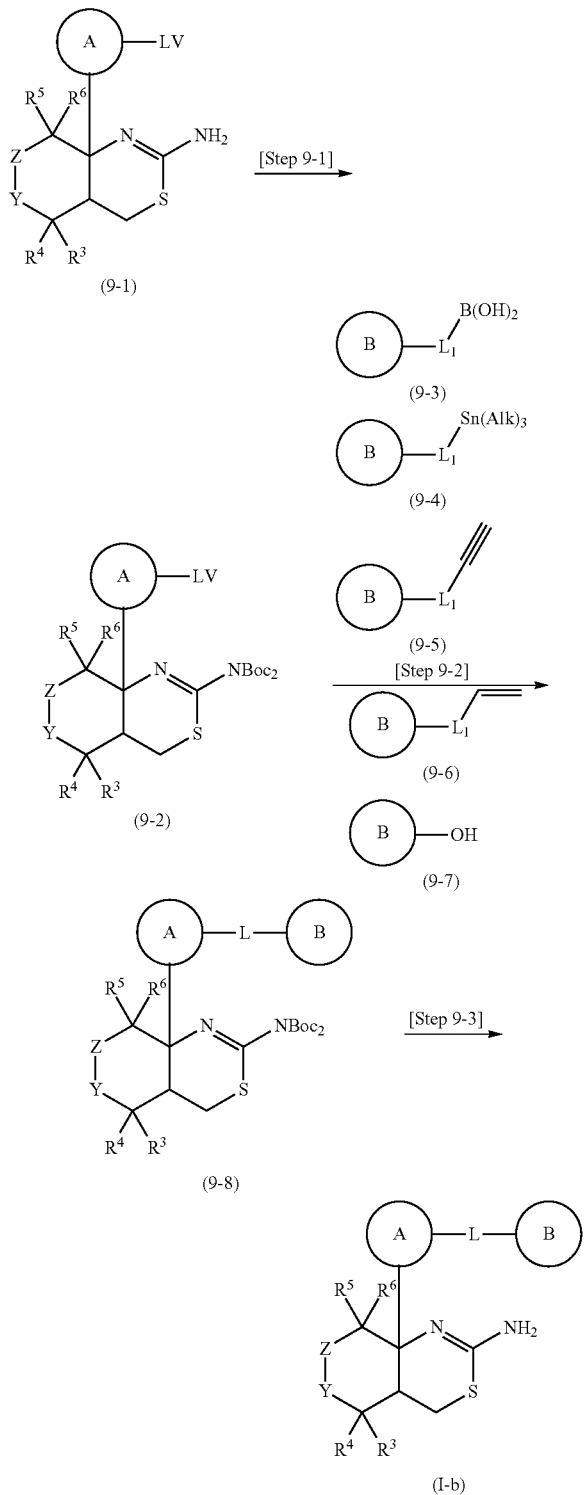

In the formula, $L_1$ represents a single bond or a $C_{1-6}$ alkylene group in compounds (9-3) and (9-4) and represents a single bond or a $C_{1-4}$ alkylene group in compounds (9-5) and (9-6), L represents a single bond, an oxygen atom, a $C_{1-6}$ alkylene group, a $C_{2-6}$ alkenylene group or a $C_{2-6}$ alkynylene group, Alk represents a $C_{1-6}$ alkyl group, and Ring A, Ring B, $R^3$, $R^4$, $R^5$, $R^6$, Y, Z and LV are as defined above.

General Preparation Method 9 is a method for preparing the compound (I-b) of the general formula (I) according to the present invention, wherein L is a single bond, an oxygen atom, a $C_{1-6}$ alkylene group, a $C_{2-6}$ alkenylene group or a $C_{2-6}$ alkynylene group and $R^1$ and $R^2$ are hydrogen atoms, from a compound (9-1) as a raw material by the above steps.

The compound (9-1) can be prepared from a commercially available product by General Preparation Method 1, General Preparation Method 5 or a combination of General Preparation Method 1 and Method 2B of General Preparation Method 2, and can also be prepared by a method described in Preparation Examples among Examples. The compounds (9-3), (9-4), (9-5), (9-6) and (9-7) each can be a commercially available product used as is, can also be prepared from a commercially available product by a method known to a person skilled in the art, and can further be prepared by a method described in Preparation Examples among Examples.

Step 9-1:

This step is a step of obtaining a compound (9-2) by di-t-butoxycarbonylating the compound (9-1). This reaction can be performed under the same conditions as those generally used in t-butoxycarbonylation of an amide compound such as the conditions described in T. W. Green and P. G. M. Wuts, "Protective Groups in Organic Chemistry, Third Edition", John Wiley & Sons, P. 642-643 and J. Org. Chem. 2005, 70, 2445-2454. The compound (9-2) can be obtained by reacting the compound (9-1) with di-tert-butyl dicarbonate using 4-dimethylaminopyridine as a base in a solvent such as THF, for example.

The solvent used in this reaction is not particularly limited insofar as it does not inhibit the reaction. Preferable examples of the solvent include organic solvents such as tetrahydrofuran, 1,4-dioxane, 1,2-dimethoxyethane, dichloromethane, DMF and acetonitrile, and mixed solvents thereof. Examples of the base used include triethylamine, 4-dimethylaminopyridine, DBU and mixtures thereof. A catalytic amount to an excess of, and more preferably 0.1 to 5 equivalents of the base is used with respect to the compound (9-1). Two equivalents to an excess of, and more preferably 2 to 10 equivalents of di-tert-butyl dicarbonate is used with respect to the compound (9-1). The reaction time is not particularly limited and is usually 5 minutes to 24 hours, and preferably 5 minutes to 12 hours. The reaction temperature is usually −20° C. to solvent reflux temperature, and more preferably 0° C. to solvent reflux temperature.

Step 9-2:

This step is a step of obtaining a compound (9-8) by coupling reaction of the compound (9-2) with the compound (9-3), (9-4), (9-5), (9-6) or (9-7) using a transition metal. This reaction can be performed under the conditions usually used in coupling reaction using a transition metal (such as Suzuki-Miyaura reaction, Stille reaction, Sonogashira reaction, Heck reaction or aryl ether synthesis reaction of Buckwald et al.).

Examples of the Suzuki-Miyaura reaction include reactions in documents such as J. Org. Chem. 2007, 72, 7207-7213, J. Am. Chem. Soc. 2000, 122, 4020-4028 and J. Org. Chem. 2007, 72, 5960-5967. Examples of the Stille coupling reaction include reaction in a document such as J. Am. Chem. Soc. 1990, 112, 3093-3100. Examples of the Sonogashira reaction include reactions in documents such as J. Org. Chem. 2007, 72, 8547-8550 and J. Org. Chem. 2008, 73, 234-240. Examples of the Heck reaction include reaction in a document such as J. Am. Chem. Soc. 2005, 127, 16900-16911. Examples of the aryl ether synthesis reaction of Buckwald et al. include reaction in a document such as Buckwald, S. L. et al., J Am Chem Soc (1999) 121 (18), 4369-4378. The organometallic catalyst used in this reaction is not particularly limited. Preferable examples of the organometallic catalyst include metal catalysts such as tetrakis(triphenylphosphine) palladium (0), dichlorobis(triphenylphosphine)palladium (II), [1,1'-bis(diphenylphosphino)ferrocene]palladium (II)dichloride, bis(tert-butylphosphine)palladium (0), palladium (II) acetate and [1,3-bis(diphenylphosphino)propane]nickel (II), and mixtures of these metal catalysts. The amount of the organometallic catalyst used is about 0.001 to 0.5 equivalent with respect to the raw material. The amount of the compound (9-3), (9-4), (9-5), (9-6) or (9-7) used is not particularly limited and is usually 1 to 5 equivalents with respect to the compound (9-2). The solvent used in this reaction is not particularly limited insofar as it does not inhibit the reaction. Preferable examples of the solvent include benzene, toluene, xylene, N,N-dimethylformamide, 1-methyl-2-pyrrolidone, tetrahydrofuran, 1,2-dimethoxyethane, 1,4-dioxane, acetonitrile and propionitrile. The reaction temperature is not particularly limited and is usually ice-cold temperature to solvent reflux temperature, and preferably room temperature to solvent reflux temperature, for example. The reaction time is not particularly limited and is usually 0.5 to 48 hours, and preferably 0.5 to 24 hours.

A more preferable result such as an improved yield may be achieved by carrying out this reaction in the presence of a base or a salt. Such a base or salt is not particularly limited. Preferable examples of the base or salt include bases or salts such as sodium carbonate, potassium carbonate, barium hydroxide, cesium carbonate, potassium phosphate, potassium fluoride and solutions thereof, and triethylamine, N,N-diisopropylethylamine, lithium chloride and copper (I) iodide.

Step 9-3:

This step is a step of synthesizing the compound (I-b) from the compound (9-8) as a raw material using a method described in the above preparation method (Step 3-4).

The compound of the formula (I) according to the present invention, wherein at least one of $R^1$ and $R^2$ is a $C_{1-6}$ alkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a 3- to 10-membered carbocyclic group which may have 1 to 3 substituents selected from Substituent Group α or a 5- to 10-membered heterocyclic group which may have 1 to 3 substituents selected from Substituent Group α, can be obtained by further reacting the compound (I-b) obtained in General Preparation Method 9 with a corresponding halide compound such as a $C_{1-6}$ alkyl halide.

10. General Preparation Method 10:

[Formula 15]

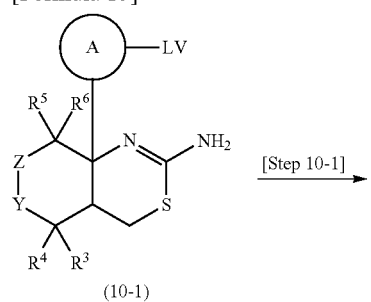

(10-1)

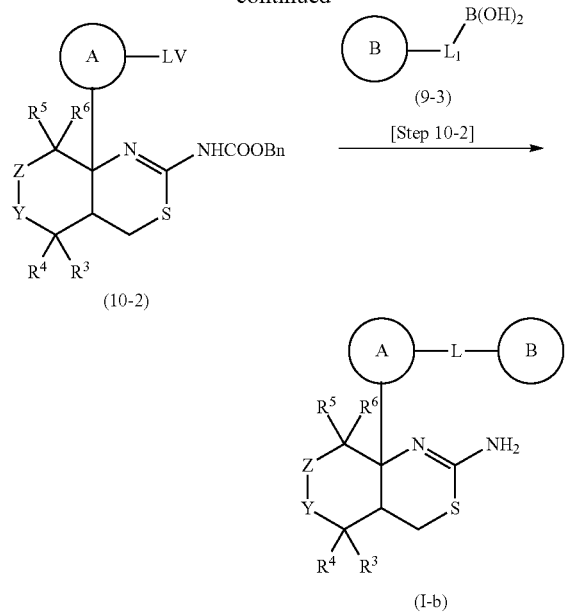

In the formula, Ring A, Ring B, $R^3$, $R^4$, $R^5$, $R^6$, Z, Y, $L_1$, L and LV are as defined above.

General Preparation Method 10 is a method for preparing the compound (I-b) of the general formula (I) according to the present invention, wherein L is a single bond and $R^1$ and $R^2$ are hydrogen atoms, from a compound (10-1).

The compound (10-1) can be prepared from a commercially available product by General Preparation Method 1, General Preparation Method 5 or a combination of General Preparation Method 1 and Method 2B of General Preparation Method 2, and can also be prepared by a method described in Preparation Examples among Examples.

Step 10-1:

This step is a step of obtaining a compound (10-2) by benzyloxycarbonylation of the compound (10-1).

The reaction can be performed under the same conditions as those generally used in benzyloxycarbonylation of an amino compound such as the conditions described in a document such as T. W. Green and P. G. M. Wuts, "Protective Groups in Organic Chemistry, Third Edition", John Wiley & Sons, P. 531-537. The compound (10-2) can be obtained by reacting the compound (10-1) with benzyl chloroformate in a mixed solvent of 1,4-dioxane and a saturated sodium bicarbonate solution, for example.

Step 10-2:

This step is a step of synthesizing the compound (I-b) from the compound (10-2) as a raw material using the same method as Suzuki-Miyaura reaction described in the above preparation method (Step 9-2).

The compound of the formula (I) according to the present invention, wherein at least one of $R^1$ and $R^2$ is a $C_{1-6}$ alkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a 3- to 10-membered carbocyclic group which may have 1 to 3 substituents selected from Substituent Group α or a 5- to 10-membered heterocyclic group which may have 1 to 3 substituents selected from Substituent Group α, can be obtained by further reacting the compound (I-b) obtained in General Preparation Method 10 with a corresponding halide compound such as a $C_{1-6}$ alkyl halide.

11. General Preparation Method 11:

[Formula 16]

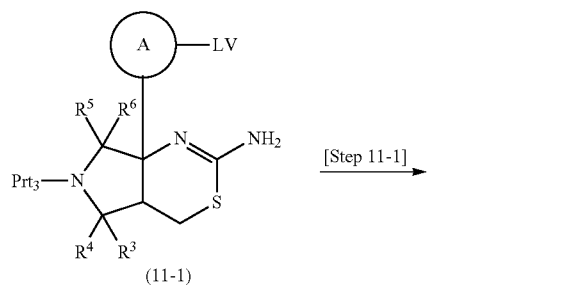

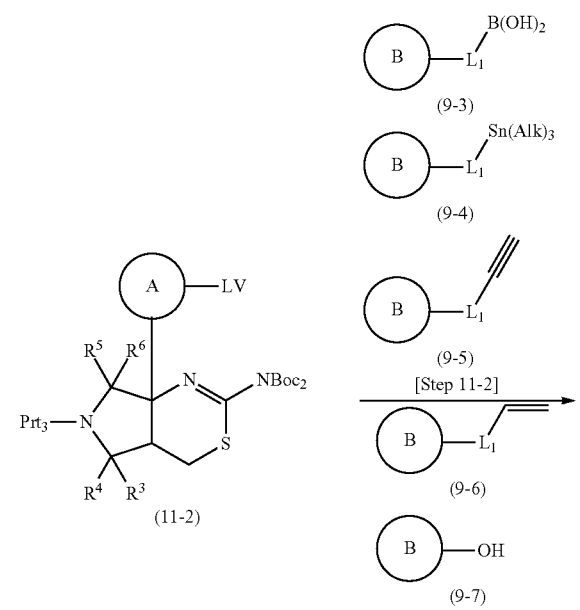

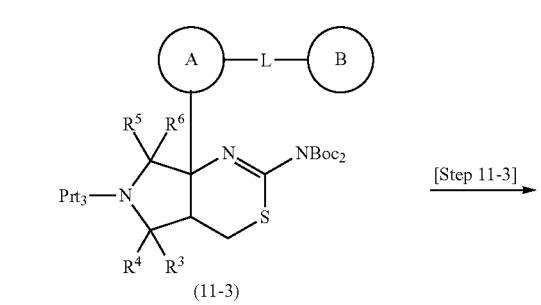

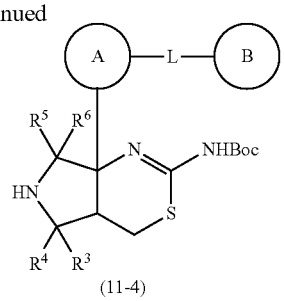

(11-4)

In the formula, Ring A, Ring B, $R^3$, $R^4$, $R^5$, $R^6$, L1, L, LV, Alk and $Prt_3$ are as defined above.

General Preparation Method 11 shows General Preparation Method 9 in the case where Y is a nitrogen atom and Z is a single bond in the general formula. The method is a method for preparing a compound (11-4) which is a synthetic intermediate of the compound (I) according to the present invention from a compound (11-1).

The compound (11-1) can be prepared from a commercially available product by General Preparation Method 5 or General Preparation Method 8, and can also be prepared by a method described in Preparation Examples among Examples.

Step 11-1:

This step is a step of synthesizing a compound (11-2) from the compound (11-1) as a raw material using a method described in the above preparation method (Step 9-1).

Step 11-2:

This step is a step of synthesizing a compound (11-3) from the compound (11-2) as a raw material using a method described in the above preparation method (Step 9-2).

Step 11-3:

This step is a step of obtaining the compound (11-4) by deprotecting the amino group of the compound (11-3). The amino protecting group used in this step is not particularly limited. When $Prt_3$ is a 2,4-dimethoxybenzyl group, for example, this step can be performed under the same conditions as those generally used (such as the conditions described in a document such as Tetrahedron Vol. 47, No. 26, pp 4591-4602, 1991). In this step, when $Prt_3$ is a 2,4-dimethoxybenzyl group, one Boc group can be deprotected simultaneously with deprotection of the 2,4-dimethoxybenzyl group. When $Prt_3$ is a 2,4-dimethoxybenzyl group in this step, the solvent used in this step is not particularly limited insofar as it does not inhibit the reaction and allows the starting material to be dissolved therein to a certain extent. For example, the first-step reaction solvent may be methylene chloride or chloroform, and the second-step reaction solvent may be methanol. The reaction temperature in this step is usually 0° C. to room temperature. The reaction time in this step is not particularly limited and is usually 0.5 to 24 hours, and preferably 0.5 to 12 hours.

12. General Preparation Method 12:

[Formula 17]

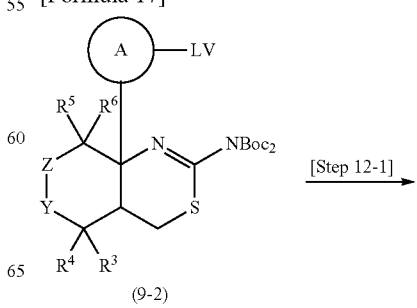

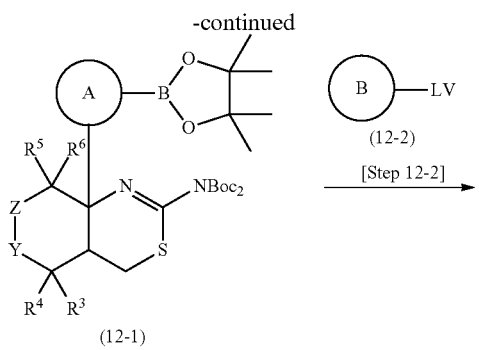

(12-1)

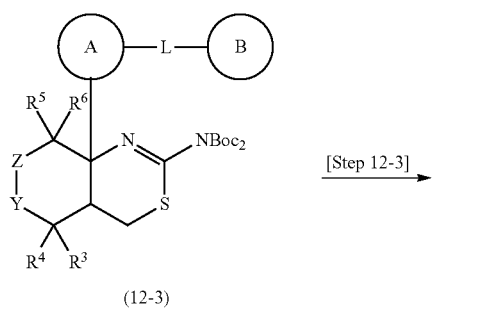

(12-3)

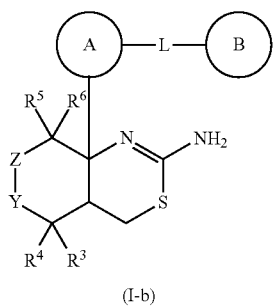

(I-b)

In the formula, Ring A, Ring B, $R^3$, $R^4$, $R^5$, $R^6$, Y, Z, L and LV are as defined above.

General Preparation Method 12 is a method for preparing the compound (I-b) of the general formula (I) according to the present invention, wherein L is a single bond and $R^1$ and $R^2$ are hydrogen atoms, from a compound (9-2).

The compound (9-2) can be prepared from a commercially available product by General Preparation Method 9, and can also be prepared by a method described in Preparation Examples among Examples. A compound (12-2) can be a commercially available product used as is, can also be prepared from a commercially available product by a method known to a person skilled in the art, and can further be prepared by a method described in Preparation Examples among Examples.

Step 12-1:

This step is a step of obtaining a compound (12-1) by coupling reaction of the compound (9-2) using a transition metal.

The reaction in this step can be performed under the same conditions as those usually used in coupling reaction using a transition metal such as the conditions described in Org. Lett. 2007, Vol. 9, No. 4, 558-562 and Bioorg. Med. Chem., 14 (2006) 4944-4957. Specifically, the compound (12-1) can be obtained by reacting the compound (9-2) with bis(pinacolato)diborane under heating conditions in a solvent such as DMF in the presence of a catalyst such as potassium acetate or [1,1'-bis(diphenylphosphino)ferrocene]palladium (II)dichloride, for example.

The organometallic catalyst used in this reaction is not particularly limited. Preferable examples of the organometallic catalyst include metal catalysts such as dichlorobis(triphenylphosphine)palladium (II), [1,1'-bis(diphenylphosphino)ferrocene]palladium (II)dichloride, bis(tert-butylphosphine)palladium (0), palladium (II) acetate and [1,3-bis(diphenylphosphino)propane]nickel (II). The amount of the organometallic catalyst used is about 0.001 to 0.5 equivalent with respect to the raw material. The solvent used in this reaction is not particularly limited insofar as it does not inhibit the reaction. Preferable examples of the solvent include benzene, toluene, xylene, N,N-dimethylformamide, 1-methyl-2-pyrrolidone, dimethyl sulfoxide, tetrahydrofuran, 1,2-dimethoxyethane, 1,4-dioxane, acetonitrile and propionitrile. The reaction temperature is not particularly limited and is usually ice-cold temperature to solvent reflux temperature, and preferably room temperature to solvent reflux temperature, for example. The reaction time is not particularly limited and is usually 0.5 to 72 hours, and preferably 0.5 to 24 hours.

A more preferable result such as an improved yield may be achieved by carrying out this reaction in the presence of a base. Such a base is not particularly limited. Preferable examples of the base include bases such as potassium acetate, sodium acetate, sodium carbonate, potassium carbonate, cesium carbonate, potassium phosphate, potassium fluoride, triethylamine and N,N-diisopropylethylamine.

Step 12-2:

This step is a step of synthesizing a compound (12-3) from the compound (12-1) as a raw material using a method described in the above preparation method (Step 9-2).

Step 12-3:

This step is a step of synthesizing the compound (I-b) from the compound (12-3) as a raw material using a method described in the above preparation method (Step 3-4).

The compound of the formula (I) according to the present invention, wherein at least one of $R^1$ and $R^2$ is a $C_{1-6}$ alkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a 3- to 10-membered carbocyclic group which may have 1 to 3 substituents selected from Substituent Group α or a 5- to 10-membered heterocyclic group which may have 1 to 3 substituents selected from Substituent Group α, can be obtained by further reacting the compound (I-b) obtained in General Preparation Method 12 with a corresponding halide compound such as a $C_{1-6}$ alkyl halide.

13. General Preparation Method 13:

[Formula 18]

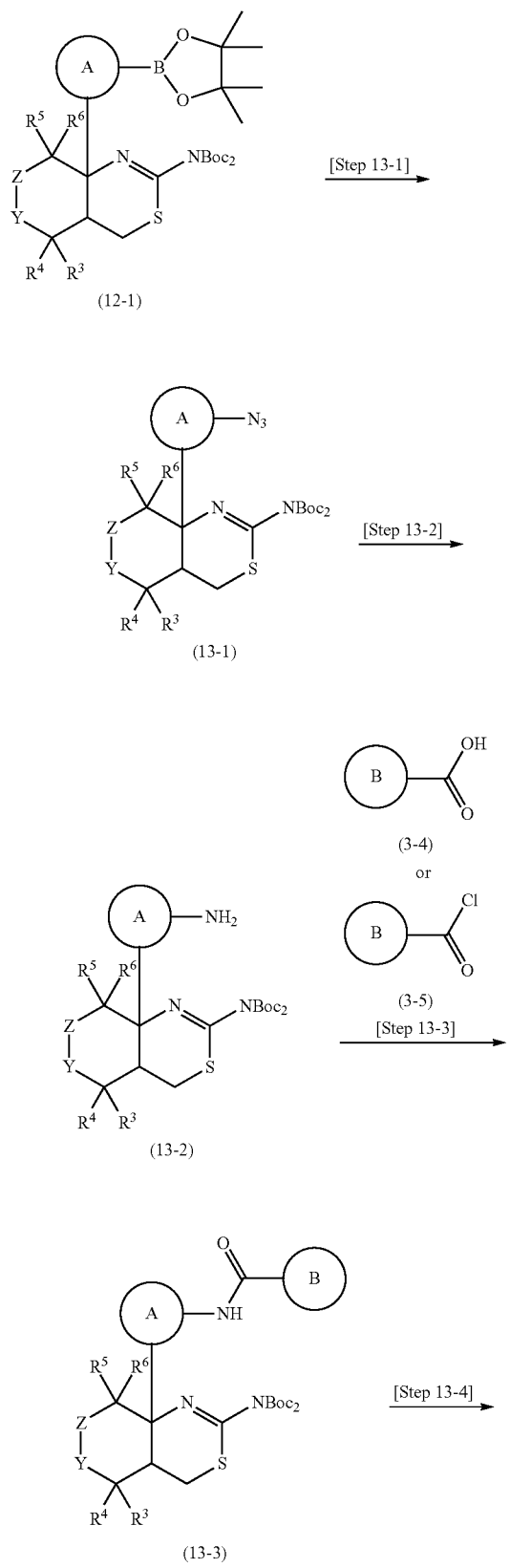
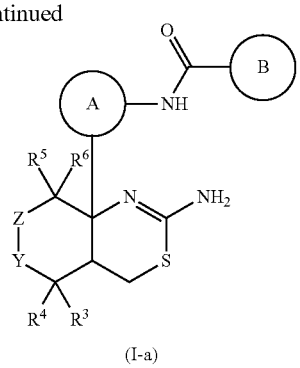

In the formula, Ring A, Ring B, $R^3$, $R^4$, $R^5$, $R^6$, Y and Z are as defined above.

General Preparation Method 13 is a method for preparing the compound (I-a) of the general formula (I) according to the present invention, wherein L is —NHCO— and $R^1$ and $R^2$ are hydrogen atoms, from a compound (12-1).

The compound (12-1) can be prepared from a commercially available product by General Preparation Method 12, and can also be prepared by a method described in Preparation Examples among Examples.

Step 13-1:

This step is a step of obtaining a compound (13-1) by reaction of the compound (12-1) with sodium azide in the presence of a copper catalyst.

The reaction in this step can be performed under the same conditions as those described in Org. Lett. 2007, Vol. 9, No. 5, 761-764 and Tetrahedron Lett. 2007, 48, 3525-3529, for example. Specifically, the compound (13-1) can be obtained by reacting the compound (12-1) with sodium azide at room temperature using a solvent such as methanol in the presence of a catalyst such as copper (II)acetate, for example.

The catalyst used in this reaction is not particularly limited. Preferable examples of the catalyst include metal catalysts such as copper (II)acetate, copper (II) sulfate, copper (I) iodide and copper (I) chloride. The amount of the catalyst used is not particularly limited and is usually about 0.1 to 0.5 equivalent with respect to the raw material. The solvent used in this reaction is not particularly limited insofar as it does not inhibit the reaction and allows the starting material to be dissolved therein to a certain extent. Preferable examples of the solvent include methanol, N,N-dimethylformamide, 1-methyl-2-pyrrolidone, tetrahydrofuran, 1,2-dimethoxyethane, 1,4-dioxane, acetonitrile, propionitrile and dichloromethane. The reaction temperature is not particularly limited and is usually ice-cold temperature to solvent reflux temperature, and preferably room temperature to solvent reflux temperature, for example. The reaction time is not particularly limited and is usually 0.5 to 100 hours, and preferably 1 to 72 hours.

A more preferable result such as an improved yield may be achieved by carrying out this reaction in an oxygen atmosphere.

Step 13-2:

This step is a step of obtaining a compound (13-2) by reduction reaction the azide of the compound (13-1). The reaction in this step can be performed under the same conditions as those described in J. Org. Chem. 2003, 68, 4693-4699, for example. Specifically, the compound (13-2) can be obtained by dissolving the compound (13-1) in a solvent such as methanol, and reacting the solution with sodium borohydride, for example.

Step 13-3:

This step is a step of synthesizing a compound (13-3) from the compound (13-2) as a raw material using a method described in the above preparation method (Step 3-3).

Step 13-4:

This step is a step of synthesizing the compound (I-a) from the compound (13-3) as a raw material using a method described in the above preparation method (Step 3-4).

The compound of the formula (I) according to the present invention, wherein at least one of $R^1$ and $R^2$ is a $C_{1-6}$ alkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a 3- to 10-membered carbocyclic group which may have 1 to 3 substituents selected from Substituent Group α or a 5- to 10-membered heterocyclic group which may have 1 to 3 substituents selected from Substituent Group α, can be obtained by further reacting the compound (I-a) obtained in General Preparation Method 13 with a corresponding halide compound such as a $C_{1-6}$ alkyl halide.

Alternatively, —NHCO— of L in the compound (I-a) of the present invention can be converted to —NR$^e$CO— (wherein R$^e$ is a $C_{1-6}$ alkyl group which may have 1 to 3 substituents selected from Substituent Group α) by further reacting the compound (I-a) obtained in General Preparation Method 13 with a corresponding halide compound such as a $C_{1-6}$ alkyl halide.

The compound of the formula (I) according to the present invention, wherein L is —NR$^e$SO$_2$—, can be obtained using a corresponding sulfonyl halide compound in place of the compound (3-4) or (3-5) used in General Preparation Method 13.

14. General Preparation Method 14:

[Formula 19-1]

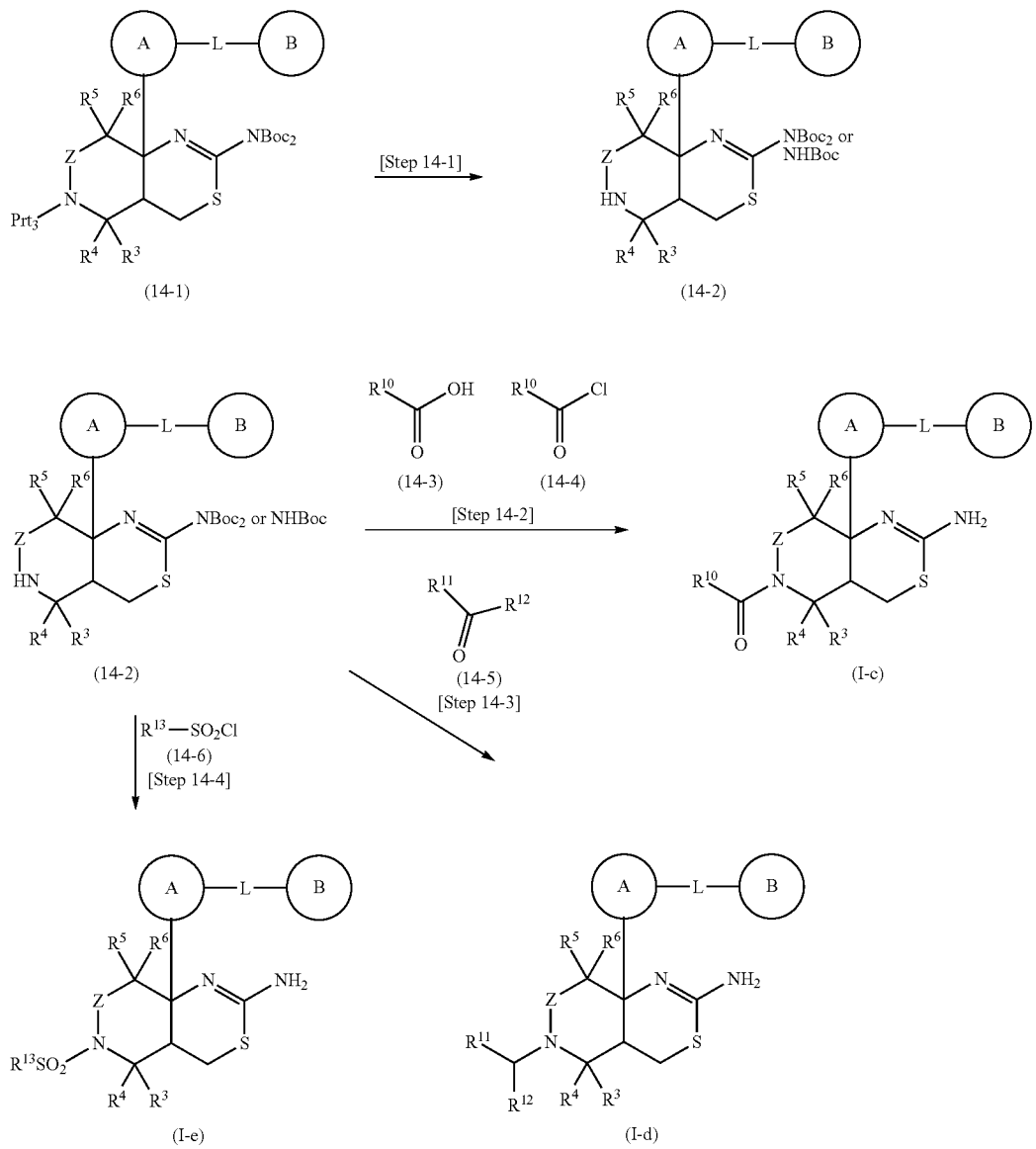

[Formula 19-2]

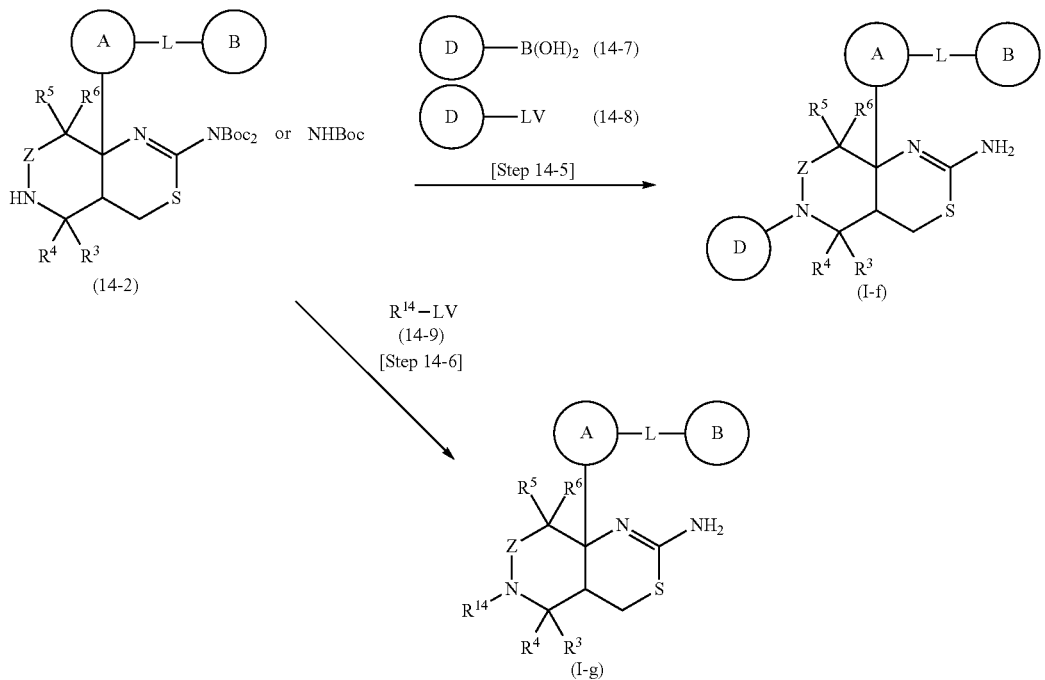

In the formula, Ring A, Ring B, $R^3$, $R^4$, $R^5$, $R^6$, L, Z, $Prt_3$ and LV are as defined above; Ring D represents a $C_{6-14}$ aryl group which may have 1 to 3 substituents selected from Substituent Group α or a 5- to 6-membered heteroaryl group which may have 1 to 3 substituents selected from Substituent Group α; $R^{10}$ represents a $C_{6-14}$ aryl group which may have 1 to 3 substituents selected from Substituent Group α, a 5- to 10-membered heterocyclic group which may have 1 to 3 substituents selected from Substituent Group α, a $C_{3-8}$ cycloalkyl group which may have 1 to 3 substituents selected from Substituent Group α, a $C_{1-6}$ alkyl group which may have 1 to 3 substituents selected from Substituent Group α or a 3- to 10-membered carbocyclic group which may have 1 to 3 substituents selected from Substituent Group α; $R^{11}$ and $R^{12}$ are each independently a hydrogen atom, a $C_{6-14}$ aryl group which may have 1 to 3 substituents selected from Substituent Group α, a 5- to 10-membered heterocyclic group which may have 1 to 3 substituents selected from Substituent Group α, a $C_{3-8}$ cycloalkyl group which may have 1 to 3 substituents selected from Substituent Group α, a $C_{1-6}$ alkyl group which may have 1 to 3 substituents selected from Substituent Group α or a 3- to 10-membered carbocyclic group which may have 1 to 3 substituents selected from Substituent Group α, or $R^{11}$ and $R^{12}$ together may form a ring; $R^{13}$ represents a $C_{6-14}$ aryl group which may have 1 to 3 substituents selected from Substituent Group α, a 5- to 10-membered heterocyclic group which may have 1 to 3 substituents selected from Substituent Group α, a $C_{3-8}$ cycloalkyl group which may have 1 to 3 substituents selected from Substituent Group α, a $C_{1-6}$ alkyl group which may have 1 to 3 substituents selected from Substituent Group α or a 3- to 10-membered carbocyclic group which may have 1 to 3 substituents selected from Substituent Group α; and $R^{14}$ represents a $C_{7-12}$ aralkyl group which may have 1 to 3 substituents selected from Substituent Group α.

General Preparation Method 14 is a method for preparing the compounds (I-c) to (I-g) of the general formula (I) according to the present invention, wherein Y is a nitrogen atom and $R^1$ and $R^2$ are hydrogen atoms, from a compound (14-1).

The compound (14-1) can be prepared from a commercially available product by General Preparation Method 5, General Preparation Method 8, General Preparation Method 9, General Preparation Method 10, General Preparation Method 11, General Preparation Method 12 or a combination thereof, and can also be prepared by a method described in Preparation Examples among Examples.

Compounds (14-3), (14-4), (14-5), (14-6), (14-7), (14-8) and (14-9) each can be a commercially available product used as is, can also be prepared from a commercially available product by a method known to a person skilled in the art, and can further be prepared by a method described in Preparation Examples among Examples.

Step 14-1:

This step is a step of obtaining a compound (14-2) by deprotecting the amino group of the compound (14-1).

The reaction can be performed under the same conditions as those generally used in deprotection of a protecting group of an amino compound such as the conditions described in a document such as T. W. Green and P. G. M. Wuts, "Protective Groups in Organic Chemistry, Third Edition", John Wiley & Sons, P. 494-572.

The amino protecting group used in this step is not particularly limited. When $Prt_3$ is a 2,4-dimethoxybenzyl group, for example, this step can be performed under the same conditions as those generally used (such as the conditions described in a document such as Tetrahedron Vol. 47, No. 26, pp 4591-4602, 1991). One Boc group can be deprotected simultaneously with deprotection of the 2,4-dimethoxybenzyl group. The solvent used in this step is not particularly limited insofar as it does not inhibit the reaction and allows the starting material to be dissolved therein to a certain extent.

For example, the first-step reaction solvent may be methylene chloride or chloroform, and the second-step reaction solvent may be methanol. The reaction temperature in this step is usually 0° C. to room temperature. The reaction time in this step is not particularly limited and is usually 0.5 to 24 hours, and preferably 0.5 to 12 hours.

When $Prt_3$ is a benzyloxycarbonyl group, the compound (14-2) can be obtained by deprotecting the compound (14-1) by hydrogenation using palladium-carbon as a catalyst in a solvent such as an alcohol, for example.

Step 14-2:

This step is a step of synthesizing the compound (I-c) from the compound (14-2) as a raw material using a method described in the above preparation method ((Step 3-3) and (Step 3-4)).

Step 14-3:

This step is a step of synthesizing the compound (I-d) using a method described in the above preparation method (Step 3-4) after reductive amination reaction of the compound (14-2) with the compound (14-5).

The reductive amination reaction can be performed under the same conditions as those usually used in reductive amination reaction of a carbonyl compound with an amine compound. The reduction reaction in this step is not particularly limited. Examples of the reduction reaction include reductive amination reaction using a reducing agent such as borane or a boron hydride complex compound. Examples of the reductive amination reaction using a boron hydride complex compound include a method described in a document such as J. Org. Chem. 1996, 61, 3849. Examples of the boron hydride complex compound that can be used include sodium borohydride, sodium cyanoborohydride and sodium triacetoxyborohydride.

When the boron hydride complex compound is used as a reducing agent, the solvent is not particularly limited insofar as it does not inhibit the reaction and allows the starting material to be dissolved therein to a certain extent. Specific examples of the solvent that can be used include methanol, ethanol, tetrahydrofuran, N,N-dimethylformamide, dichloromethane and 1,2-dichloroethane. A more preferable result such as an improved yield can be achieved by carrying out this reaction in the presence of an acid. Such an acid is not particularly limited. Preferable examples of the acid include mineral acids such as hydrochloric acid, organic acids such as acetic acid, and Lewis acids such as zinc chloride, a boron trifluoride-diethyl ether complex and titanium (IV)tetraisopropoxide.

Step 14-4:

This step is a step of synthesizing the compound (I-e) using a method described in the above preparation method (Step 3-4) after sulfonylation of the amino group of the compound (14-2). For the sulfonylation, reaction using a sulfonyl chloride derivative is known to a person skilled in the art.

Step 14-5:

This step is a step of synthesizing the compound (I-f) using a method described in the above preparation method (Step 3-4) after coupling reaction of the compound (14-2) with the compound (14-7) or (14-8). Reaction such as coupling using a transition metal complex or the like or nucleophilic aromatic substitution (SNAr reaction) is used in this step.

The coupling reaction in this step can be performed under the same conditions as those described in Org. Lett. 2007, Vol. 9, No. 5, 761-764 and Org. Lett. 2003, Vol. 5, No. 23, 4397-4400, for example. Specifically, the coupling reaction can be performed by reacting the compound (14-2) with the compound (14-7) at room temperature to 50° C. using a solvent such as dichloromethane in the presence of molecular sieve 4A and a catalyst such as copper (II)acetate, for example.

The catalyst used in this reaction is not particularly limited. Preferable examples of the catalyst include metal catalysts such as copper (II)acetate, copper (II) sulfate, copper (I) iodide and copper (I) chloride. The amount of the catalyst used is not particularly limited and is usually about 0.1 to 0.5 equivalent with respect to the raw material. The solvent used in this reaction is not particularly limited insofar as it does not inhibit the reaction and allows the starting material to be dissolved therein to a certain extent. Preferable examples of the solvent include N,N-dimethylformamide, 1-methyl-2-pyrrolidone, tetrahydrofuran, 1,2-dimethoxyethane, 1,4-dioxane, acetonitrile, propionitrile and dichloromethane. The reaction temperature is not particularly limited and is usually ice-cold temperature to solvent reflux temperature, and preferably room temperature to solvent reflux temperature, for example. The reaction time is not particularly limited and is usually 0.5 to 100 hours, and preferably 1 to 72 hours.

A more preferable result such as an improved yield may be achieved by carrying out this reaction in an oxygen atmosphere.

When this step is coupling using a transition metal complex or the like as a catalyst, the reaction can be performed using the compound (14-2) and the compound (14-8) which is an aryl halide derivative, a heteroaryl halide derivative, an aryloxy trifluoromethanesulfonate derivative or a heteroaryloxy trifluoromethanesulfonate derivative under the same conditions as those usually used (such as the conditions described in a document such as Org. Lett. 2002, Vol. 4, No. 4, 581). The aryl halide derivative, the heteroaryl halide derivative, the aryloxy trifluoromethanesulfonate derivative or the heteroaryloxy trifluoromethanesulfonate derivative used in this step can be a commercially available product used as is, and can also be prepared from a commercially available product by a method known to a person skilled in the art. Examples of the transition metal complex used in this step include dichlorobis(triphenylphosphine)palladium (II), tetrakis(triphenylphosphine)palladium (0), tris(dibenzylideneacetone) palladium (0) and a copper-diol ligand complex. In this reaction, a phosphorus ligand (such as preferably triphenylphosphine, tri-o-tolylphosphine, tri-tert-butylphosphine, 2,2'-bis(diphenylphosphino)-1,1'-binaphthyl or 1,1'-bis (diphenylphosphino)ferrocene) may be further added in order to obtain favorable results (such as a reduced reaction temperature, a reduced reaction time and an improved yield). When the transition metal complex used is a palladium complex, the reaction in this step is preferably performed under a nitrogen or argon atmosphere. The solvent used in this step is not particularly limited insofar as it does not inhibit the reaction and allows the starting material to be dissolved therein to a certain extent. For example, when the transition metal complex used is a palladium complex, N,N-dimethylformamide, N-methyl-2-pyrrolidone, 1,4-dioxane, toluene, xylene or the like can be used. When the transition metal complex used is a copper-diol complex, 2-propanol or the like can be used. The reaction temperature in this step is usually room temperature to solvent reflux temperature. The reaction time in this step is not particularly limited and is usually 0.5 to 72 hours, and preferably 0.5 to 24 hours.

When this step is nucleophilic aromatic substitution (SNAr reaction), the reaction can be performed using the compound (14-2) and the compound (14-8) which is an aryl halide derivative, a heteroaryl halide derivative, an aryloxy trifluoromethanesulfonate derivative or a heteroaryloxy trifluoromethanesulfonate derivative in the presence of a base under the same conditions as those usually used. The aryl halide derivative, the heteroaryl halide derivative, the aryloxy trifluoromethanesulfonate derivative or the heteroaryloxy trifluoromethanesulfonate derivative used in this step can be a commercially available product used as is, and can also be prepared from a commercially available product by a method known to a person skilled in the art. The nucleophilic aromatic substitution (SNAr reaction) used in this step can be performed under the same conditions as those generally used (such as the conditions according to methods described in documents such as Org. Prep. Proceed. int. 39 (2007) 4, 399-402, Bioorg. Med. Chem. Lett. 15 (2005) 9, 2409-2413 and Bioorg. Med. Chem. Lett. 15 (2005) 3, 719-723). The solvent used in this step is not particularly limited insofar as it does not inhibit the reaction and allows the starting material to be dissolved therein to a certain extent. Examples of the solvent that can be used include N,N-dimethylformamide, N-methyl-2-pyrrolidone, dimethyl sulfoxide and acetonitrile. The base used in this step is not particularly limited. Examples of the base include potassium carbonate, sodium carbonate, sodium hydride and tetrabutylammonium fluoride. Potassium carbonate, sodium carbonate and tetrabutylammonium fluoride are preferably used. The reaction temperature in this step is usually room temperature to solvent reflux temperature. The reaction time in this step is not particularly limited and is usually 0.5 to 24 hours, and preferably 0.5 to 12 hours.

Step 14-6:

This step is a step of synthesizing the compound (I-g) from the compound (14-2) as a raw material using a method described in the above preparation method ((Step 8-1) and (Step 3-4)).

The compound of the formula (I) according to the present invention, wherein at least one of $R^1$ and $R^2$ is a $C_{1-6}$ alkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a 3- to 10-membered carbocyclic group which may have 1 to 3 substituents selected from Substituent Group α or a 5- to 10-membered heterocyclic group which may have 1 to 3 substituents selected from Substituent Group α, can be obtained by further reacting any of the compounds (I-c) to (I-g) obtained in General Preparation Method 14 with a corresponding halide compound such as a $C_{1-6}$ alkyl halide.

The compound of the formula (I) according to the present invention obtained in this manner can be converted to a pharmaceutically acceptable salt by a conventional method where necessary. The salt can be prepared by a method in which methods typically used in the field of organic synthetic chemistry and the like are appropriately combined. Specific examples of the method include neutralization titration of a free solution of the compound of the present invention with an acid solution. The compound of the formula (I) according to the present invention can be converted to a solvate by subjecting the compound to solvate forming reaction known per se where necessary.

The fused aminodihydrothiazine derivative or pharmaceutically acceptable salt thereof or solvate thereof according to the present invention has an extremely excellent Aβ production inhibitory effect or BACE1 inhibitory effect and is extremely useful as a prophylactic or therapeutic agent for a neurodegenerative disease caused by Aβ and typified by Alzheimer-type dementia.

The fused aminodihydrothiazine derivative or pharmaceutically acceptable salt thereof or solvate thereof according to the present invention can be formulated by a conventional method. Preferable examples of the dosage form include tablets, coated tablets such as film tablets and sugar-coated tablets, fine granules, granules, powders, capsules, syrups, troches, inhalants, suppositories, injections, ointments, eye drops, nasal drops, ear drops, cataplasms and lotions.

These solid preparations such as tablets, capsules, granules and powders can contain generally 0.01 to 100 wt %, and preferably 0.1 to 100 wt % of the fused aminodihydrothiazine derivative or pharmaceutically acceptable salt thereof or solvate thereof according to the present invention as an active ingredient.

The active ingredient is formulated by blending ingredients generally used as materials for a pharmaceutical preparation and adding an excipient, a disintegrant, a binder, a lubricant, a colorant and a corrective typically used, and adding a stabilizer, an emulsifier, an absorbefacient, a surfactant, a pH adjuster, a preservative and an antioxidant where necessary, for example, using a conventional method.

Examples of such ingredients include animal and vegetable oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; a silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil and a polyoxyethylene-polyoxypropylene block copolymer; water-soluble polymers such as hydroxyethylcellulose, polyacrylic acid, a carboxyvinyl polymer, polyethylene glycol, polyvinylpyrrolidone and methylcellulose; lower alcohols such as ethanol and isopropanol; polyhydric alcohols such as glycerol, propylene glycol, dipropylene glycol and sorbitol; sugars such as glucose and sucrose; inorganic powders such as silicic anhydride, magnesium aluminum silicate and aluminum silicate; and purified water. Examples of the excipient used include lactose, corn starch, saccharose, glucose, mannitol, sorbitol, crystalline cellulose and silicon dioxide. Examples of the binder used include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, a polypropylene glycol-polyoxyethylene block copolymer and meglumine. Examples of the disintegrant used include starch, agar, gelatin powder, crystalline cellulose, calcium carbonate, sodium bicarbonate, calcium citrate, dextrin, pectin and carboxymethylcellulose calcium. Examples of the lubricant used include magnesium stearate, talc, polyethylene glycol, silica and hydrogenated vegetable oil. Examples of the colorant used include those permitted to be added to pharmaceuticals. Examples of the corrective used include cocoa powder, menthol, empasm, mentha oil, borneol and cinnamon powder. Obviously, the ingredients are not limited to the above additive ingredients.

For example, an oral preparation is prepared by adding the fused aminodihydrothiazine derivative or pharmaceutically acceptable salt thereof or solvate thereof according to the present invention as an active ingredient, an excipient and, where necessary, a binder, a disintegrant, a lubricant, a colorant, a corrective and the like, and then forming the mixture into powder, fine granules, granules, tablets, coated tablets, capsules or the like by a conventional method. Obviously, tablets or granules may be appropriately coated, for example, sugar coated, where necessary.

For example, a syrup or an injection preparation is prepared by adding a pH adjuster, a solubilizer, an isotonizing agent and the like, and a solubilizing agent, a stabilizer and the like where necessary by a conventional method. The injection may be a previously prepared solution, or may be powder itself or powder containing a suitable additive, which is dissolved before use. The injection can contain usually 0.01 to 100 wt %, and preferably 0.1 to 100 wt % of the active ingredient. Further, a liquid preparation for oral administration such as a suspension or a syrup can contain usually 0.01 to 100 wt %, and preferably 0.1 to 100 wt % of the active ingredient.

For example, an external preparation can be prepared by any conventional method without specific limitations. As a base material, any of various materials usually used for a pharmaceutical, a quasi drug, a cosmetic or the like can be used. Examples of the base material include materials such as animal and vegetable oils, mineral oils, ester oils, waxes, higher alcohols, fatty acids, silicone oils, surfactants, phospholipids, alcohols, polyhydric alcohols, water-soluble polymers, clay minerals and purified water. A pH adjuster, an antioxidant, a chelator, a preservative and fungicide, a colorant, a flavor or the like can be added where necessary. Further, ingredients such as an ingredient having a differentiation inducing effect, a blood flow enhancer, a bactericide, an antiphlogistic, a cell activator, vitamin, amino acid, a humectant and a keratolytic agent can be blended where necessary.

The dose of the fused aminodihydrothiazine derivative or pharmaceutically acceptable salt thereof or solvate thereof according to the present invention varies according to the degree of symptoms, age, sex, body weight, mode of administration, type of salt and specific type of disease, for example. Typically, the active ingredient is orally administered to an adult at about 30 µg to 10 g, preferably 100 µg to 5 g, and more preferably 100 µg to 1 g per day, or is administered to an adult by injection at about 30 µg to 1 g, preferably 100 µg to 500 mg, and more preferably 100 µg to 300 mg per day, in one or several doses, respectively.

The present invention will be described more specifically below with reference to Examples, Preparation Examples and Test Example. However, the present invention is not limited thereto. The abbreviations used in Examples are conventional abbreviations known to a person skilled in the art. Some abbreviations are shown below.

THF: Tetrahydrofuran

DMF: N,N-Dimethylformamide

TFA: Trifluoroacetic acid

EDC.HCl: 1-Ethyl-3-(3-dimethylaminopropyl)carbodiimide hydrochloride pTLC: Preparative thin-layer chromatography LC-MS: Liquid chromatography-mass spectrometry PyBOP: Benzotriazol-1-yloxytris(pyrrolidino)phosphonium hexafluorophosphate Pd2 DBA3: Tris(dibenzylideneacetone)dipalladium Pd(t-Bu3P)2: Bis(tri-t-butylphosphine)palladium Chemical shifts in proton nuclear magnetic resonance spectra are recorded in δ units (ppm) relative to tetramethylsilane and coupling constants are recorded in Hertz (Hz). Patterns are designated as s: singlet, d: doublet, t; triplet, br; broad.

The "room temperature" in the following Examples and Preparation Examples typically refers to about 10° C. to about 35° C. "%" indicates wt % unless otherwise specified.

Preparation Example 1

Synthesis of tert-butyl(±)-[(4aR*,8aS*)-8a-(5-amino-2-fluorophenyl)-4a,5,6,7,8,8a-hexahydro-4H-benzo[d][1,3]thiazin-2-yl]carbamate

[Formula 20]

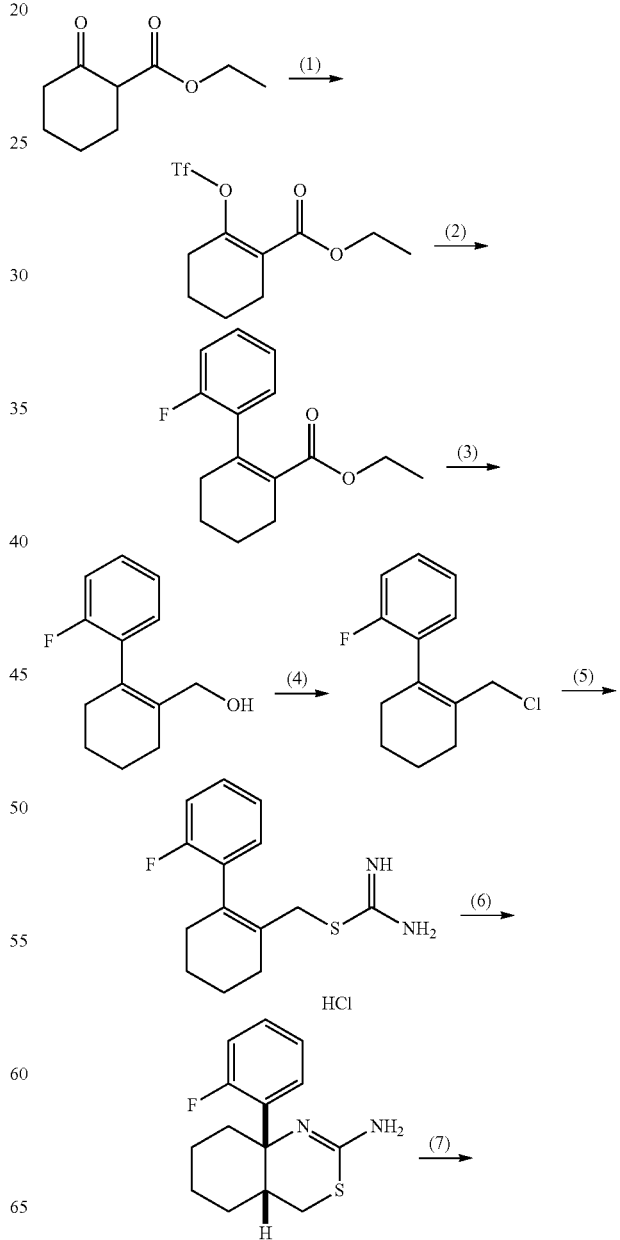

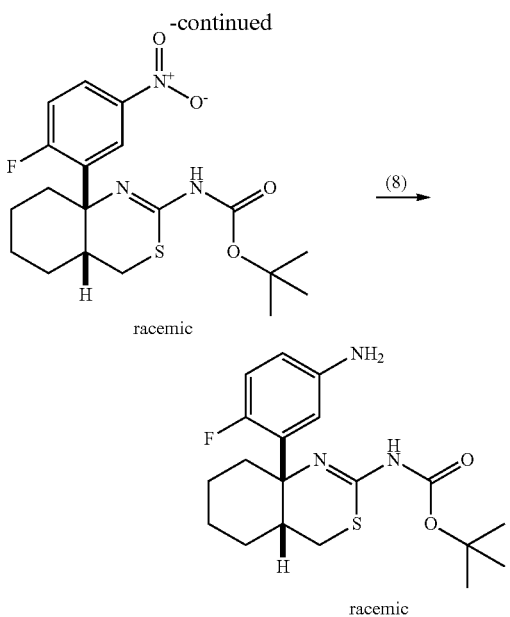

(1) Synthesis of ethyl 2-trifluoromethanesulfonyloxycyclohex-1-enecarboxylate Diisopropylethylamine (38.0 mL) was added to a solution of ethyl 2-oxocyclohexanecarboxylate (8.00 g) in dichloromethane (100 mL) under a nitrogen atmosphere at −78° C. After stirring at the same temperature for 10 minutes, trifluoromethanesulfonic anhydride (8.80 mL) was added. The mixture was stirred overnight with gradual warming to room temperature. The mixture was washed with water and further washed with a 5% citric acid solution (150 mL) twice. The organic layer was dried over anhydrous magnesium sulfate. The drying agent was removed by filtration and the filtrate was concentrated under reduced pressure to obtain the title compound as a crude product (15.5 g). The crude product was used for the next reaction without further purification.

$^1$H-NMR (400 MHz, CDCl$_3$) δδ (ppm): 1.33 (t, J=7.2 Hz, 3H), 1.66 (m, 2H), 1.78 (m, 2H), 2.40 (m, 2H), 2.48 (m, 2H), 4.28 (q, J=7.2 Hz, 2H).

(2) Synthesis of ethyl 2-(2-fluorophenyl)cyclohex-1-enecarboxylate

Ethanol (100 mL) was added to a solution of ethyl 2-trifluoromethanesulfonyloxycyclohex-1-enecarboxylate obtained in Preparation Example 1-(1) (17.0 g) in toluene (200 mL). 2-Fluorophenylboronic acid (7.74 g) and tetrakis(triphenylphosphine)palladium (1.60 g) were added. A 1 N sodium carbonate solution (55.3 mL) was added, followed by replacement of the reaction atmosphere with nitrogen. The reaction solution was heated to 80° C. and stirred for eight hours. After returning to room temperature, the excess of ethanol was evaporated under reduced pressure and the residue was extracted with ethyl acetate. The organic layer was dried over anhydrous magnesium sulfate. The drying agent was removed by filtration and the filtrate was concentrated under reduced pressure. The residue was purified by silica gel column chromatography to obtain the title compound (10.5 g).

$^1$H-NMR (400 MHz, CDCl$_3$) δ (ppm): 0.87 (t, J=7.2 Hz, 3H), 1.75 (m, 4H), 2.36 (m, 2H), 2.46 (m, 2H), 3.89 (q, J=7.2 Hz, 2H), 6.99-7.08 (m, 3H), 7.22 (m, 1H).

(3) Synthesis of [2-(2-fluorophenyl)cyclohex-1-enyl]methanol

Lithium aluminum hydride (1.90 g) was added to a recovery flask, and THF (300 mL) was added thereto in an ice bath. A solution of ethyl 2-(2-fluorophenyl)cyclohex-1-enecarboxylate obtained in Preparation Example 1-(2) (10.3 g) in THF (100 mL) was added dropwise to the reaction solution at the same temperature, and the mixture was stirred for one hour. Water (1.90 mL), a 5 N sodium hydroxide solution (1.90 mL) and water (5.70 mL) were sequentially added to the reaction solution. Anhydrous magnesium sulfate was further added, followed by extraction with ethyl acetate. The insoluble matter was separated by filtration and the filtrate was concentrated under reduced pressure to obtain the title compound (8.88 g).

$^1$H-NMR (400 MHz, CDCl$_3$) δ (ppm): 1.22 (dt, J=2.0, 5.2 Hz, 1H), 1.75 (br, 4H), 2.25 (br, 2H), 2.30 (br, 2H), 3.86 (d, J=5.2 Hz, 2H), 7.04 (t, J=9.2 Hz, 1H), 7.08-7.13 (m, 2H), 7.22 (m, 1H).

(4) Synthesis of 1-(2-chloromethylcyclohex-1-enyl)-2-fluorobenzene

N,N-Diisopropylethylamine (14.7 mL) was added to a solution of [2-(2-fluorophenyl)cyclohex-1-enyl]methanol obtained in Preparation Example 1-(3) (8.88 g) in dichloromethane (300 mL). Methanesulfonyl chloride (4.00 mL) was added dropwise to the reaction solution in an ice bath. The reaction solution was gradually warmed to room temperature and stirred overnight. Water was added to the reaction solution, followed by extraction with chloroform. The organic layer was dried over anhydrous magnesium sulfate. The drying agent was removed by filtration and the filtrate was concentrated under reduced pressure. The resulting crude product was purified by silica gel column chromatography to obtain the title compound (5.88 g).

$^1$H-NMR (400 MHz, CDCl$_3$) δ (ppm): 1.75 (brs, 4H), 2.27 (m, 4H), 3.89 (brs, 2H), 7.03-7.29 (m, 4H).

(5) Synthesis of 2-[2-(2-fluorophenyl)cyclohex-1-enylmethyl]isothiourea hydrochloride Thiourea (2.09 g) was added to a solution of 1-(2-chloromethylcyclohex-1-enyl)-2-fluorobenzene obtained in Preparation Example 1-(4) (5.88 g) in ethanol (200 mL). The reaction solution was heated to 80° C. and stirred for 270 minutes. Thiourea (399 mg) was added to the reaction solution, followed by stirring at the same temperature for one hour. After cooling to room temperature, the solvent was evaporated under reduced pressure. Diethyl ether and ethyl acetate were added to the residual syrup. A white solid was precipitated by ultrasonic treatment. After standing at room temperature for 30 minutes, the supernatant was removed. Further, the solid was washed with diethyl ether and the supernatant was removed again. The resulting solid was dried under reduced pressure to obtain the title compound (6.38 g).

$^1$H-NMR (400 MHz, DMSO-d$_6$) δ (ppm): 1.69 (s, 4H), 2.20 (s, 2H), 2.21 (s, 2H), 3.60 (s, 2H), 7.17 (dt, J=2.0, 7.6 Hz, 1H), 7.24 (m, 2H), 7.38 (m, 1H), 9.04 (brs, 3H).

(6) Synthesis of (±)-(4aR*,8aS*)-8a-(2-fluorophenyl)-4a,5,6,7,8,8a-hexahydro-4H-benzo[d][1,3]thiazin-2-ylamine 2-[2-(2-Fluorophenyl)cyclohex-1-enylmethyl]isothiourea hydrochloride obtained in Preparation Example 1-(5) (6.38 g)

was dissolved in TFA (32.0 mL) under ice-cooling, and trifluoromethanesulfonic acid (6.40 mL) was added dropwise at the same temperature. The reaction solution was stirred overnight with gradual warming to room temperature. The reaction solution was poured into ice, diluted with diethyl ether and then neutralized with sodium bicarbonate. The generated reaction mixture was extracted with ethyl acetate, and the organic layer was dried over anhydrous magnesium sulfate. The drying agent was removed by filtration and the filtrate was concentrated under reduced pressure to obtain a crude product. The crude product was purified by NH-silica gel column chromatography to obtain the title compound (4.58 g).

$^1$H-NMR (400 MHz, CDCl$_3$) δ (ppm): 1.47-1.83 (m, 7H), 2.26 (m, 1H), 2.52 (dd, J=2.8, 12.0 Hz, 1H), 2.70 (ddd, J=4.0, 6.8, 12.0 Hz, 1H), 2.86 (dd, J=4.4, 12.4 Hz, 1H), 7.01 (ddd, J=1.2, 8.0, 12.8 Hz, 1H), 7.08 (dt, J=1.2, 7.6 Hz, 1H), 7.21 (m, 1H), 7.28 (dt, J=2.0, 8.0 Hz, 1H).

(7) Synthesis of tert-butyl(±)-[(4aR*,8aS*)-8a-(2-fluoro-5-nitrophenyl)-4a,5,6,7,8,8a-hexahydro-4H-benzo[d][1,3]thiazin-2-yl]carbamate The compound obtained in Preparation Example 1-(6) (3.50 g) was added to concentrated sulfuric acid (25.0 mL) in an ice bath. Fuming nitric acid (specific gravity: 1.53, 800 μL) was added dropwise to the reaction solution, followed by stirring at the same temperature for 30 minutes. The reaction mixture was poured into ice and neutralized with a 5 N sodium hydroxide solution. The generated solid was collected by filtration through a glass filter and washed with water. The solid was dissolved in a mixed solvent of THF and ethyl acetate, and the solution was dried over anhydrous magnesium sulfate. The drying agent was removed by filtration and the filtrate was evaporated under reduced pressure at room temperature or lower to obtain a crude product of a reaction intermediate. Triethylamine (9.20 mL) was added to a solution of the crude product in THF (100 mL). Di-tert-butyl dicarbonate (8.64 g) was added to the reaction solution, followed by stirring for two days. A saturated sodium bicarbonate solution was added to the reaction solution, followed by extraction with ethyl acetate. The organic layer was dried over anhydrous magnesium sulfate. The drying agent was removed by filtration and the filtrate was concentrated under reduced pressure. The residue was purified by silica gel column chromatography to obtain the title compound (4.70 g).

$^1$H-NMR (400 MHz, CDCl$_3$) δ (ppm): 1.55 (s, 9H), 1.65-1.88 (m, 7H), 2.23 (m, 1H), 2.55 (dd, J=2.8, 12.8 Hz, 1H), 2.83 (m, 2H), 7.23 (m, 1H), 8.20 (m, 2H).

(8) Synthesis of tert-butyl(±)-[(4aR*,8aS*)-8a-(5-amino-2-fluorophenyl)-4a,5,6,7,8,8a-hexahydro-4H-benzo[d][1,3]thiazin-2-yl]carbamate 10% palladium-carbon (15.8 mg) was added to a solution of the compound obtained in Preparation Example 1-(7) (58.0 mg) in methanol (14.5 mL). The atmosphere of the reaction system was replaced with hydrogen, followed by stirring at room temperature for two hours. The reaction solution was filtered through celite and the filtrate was concentrated under reduced pressure to obtain a crude product of the title compound (58.0 mg). The resulting crude product was used for the next reaction without further purification.

$^1$H-NMR (400 MHz, CDCl$_3$) δ (ppm): 1.53 (s, 9H), 1.64-1.87 (m, 7H), 2.35 (m, 1H), 2.47 (dd, J=2.8, 12.8 Hz, 1H), 2.88 (m, 2H), 3.64 (s, 2H), 6.54 (m, 2H), 6.85 (m, 1H).

Preparation Example 2

Synthesis of tert-butyl[(4aR*,8aS*)-8a-(5-amino-2-fluorophenyl)-4a,5,6,7,8,8a-hexahydro-4H-benzo[d][1,3]thiazin-2-yl]carbamate

[Formula 21]

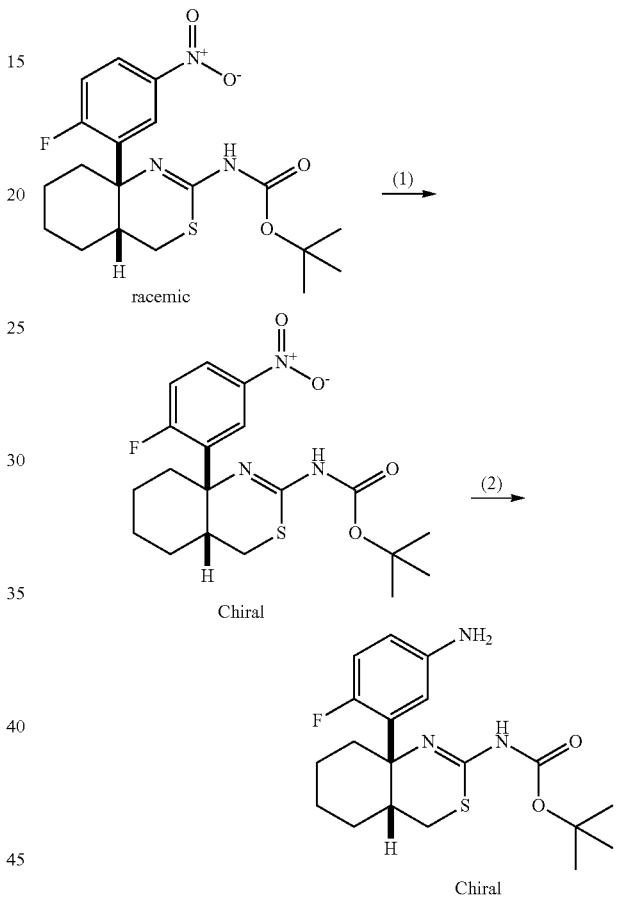

(1) Synthesis of tert-butyl(+)-[(4aR*,8aS*)-8a-(2-fluoro-5-nitrophenyl)-4a,5,6,7,8,8a-hexahydro-4H-benzo[d][1,3]thiazin-2-yl]carbamate The compound obtained in Preparation Example 1-(7) (80.0 mg) was optically resolved by CHIRALPAK™ OJ-H manufactured by Daicel Chemical Industries, Ltd. (2 cm×25 cm, mobile phase: hexane:ethanol=8:2, flow rate: 20 mL/min). The components having a retention time of 9.38 to 18.3 minutes were collected to obtain the title compound. The same operation was repeated to obtain the title compound (433 mg; >99% ee) from the racemate (1.00 g).

(2) Synthesis of tert-butyl[(4aR*,8aS*)-8a-(5-amino-2-fluorophenyl)-4a,5,6,7,8,8a-hexahydro-4H-benzo[d][1,3]thiazin-2-yl]carbamate A solution of sodium dithionite (923 mg) in water (20.0 mL) was added dropwise to a solution of the compound obtained in Preparation Example 2-(1) (433 mg) in ethanol (100 mL) at room temperature. The reaction solution was stirred for 30 minutes, and then ethanol was evaporated under reduced pressure at room temperature or lower. The residue was neutralized with a sodium bicarbonate solution, followed by extraction with ethyl acetate. The organic layer was dried over anhydrous magnesium sulfate. The drying agent was removed by filtration and the filtrate was concentrated under reduced pressure. The resulting crude product was purified by NH-silica gel column chromatography to obtain the title compound (111 mg).

¹H-NMR (400 MHz, CDCl₃) δ (ppm): 1.53 (s, 9H), 1.57-2.05 (m, 7H), 2.36 (dt, J=4.4, 14.4 Hz, 1H), 2.47 (dd, J=2.8, 12.4 Hz, 1H), 2.84 (m, 1H), 2.90 (dd, J=4.0, 12.4 Hz, 1H), 3.64 (s, 2H), 6.55 (m, 2H), 6.85 (m, 1H).

Preparation Example 3

Synthesis of tert-butyl(−)-[(4aR*,7aS*)-7a-(5-amino-2-fluorophenyl)-4,4a,5,6,7,7a-hexahydrocyclopenta[d][1,3]thiazin-2-yl]carbamate

[Formula 22]

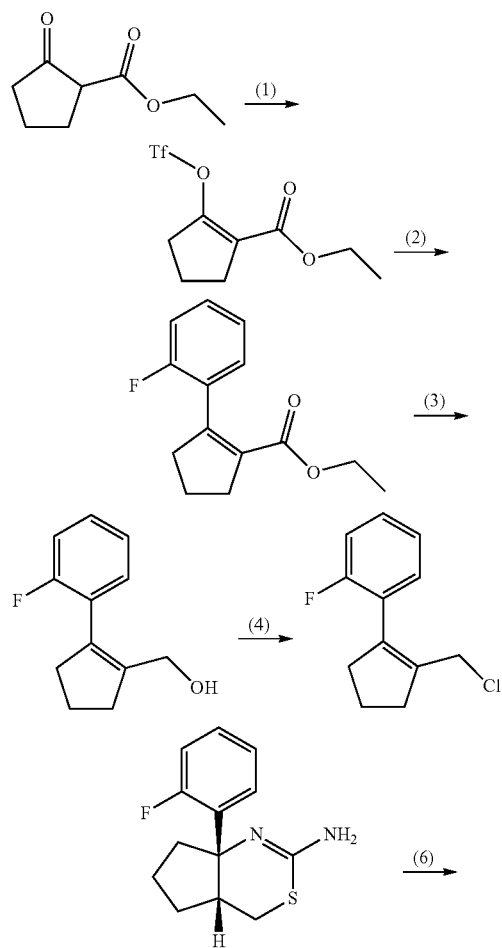

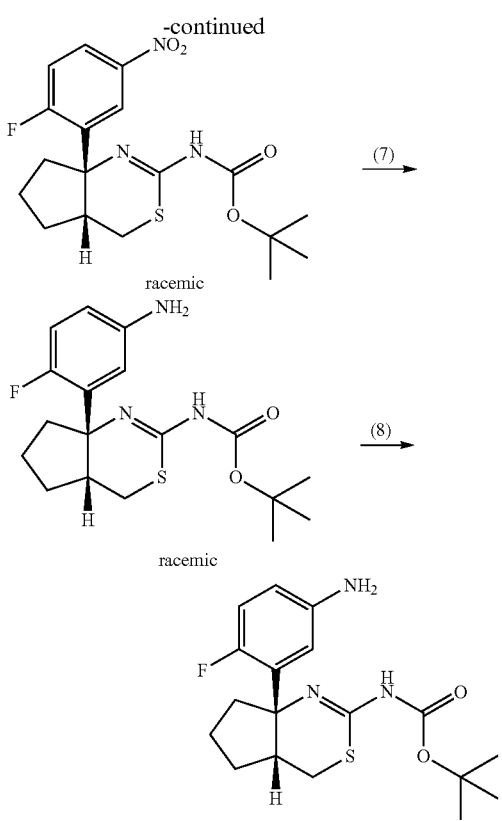

(1) Synthesis of ethyl 2-trifluoromethanesulfonyloxycyclopent-1-enecarboxylate

N,N-Diisopropylethylamine (27.2 mL) was added to a solution of ethyl 2-oxo-cyclopentanecarboxylate (5.00 g) in dichloromethane (100 mL) at −78° C. for 10 minutes. Trifluoromethanesulfonic anhydride (5.92 mL) was added dropwise to the reaction solution at the same temperature. The reaction solution was stirred overnight with gradual warming to room temperature. Water was added to the reaction mixture, followed by washing with a 5% citric acid solution (150 mL) twice. The organic layer was dried over anhydrous magnesium sulfate. The drying agent was removed by filtration and toluene (200 mL) was added to the filtrate. Dichloromethane was evaporated under reduced pressure at room temperature or lower to obtain a solution of the title compound in toluene. The compound was used for the next reaction without further purification.

¹H-NMR (400 MHz, CDCl₃) δ (ppm): 1.33 (t, J=6.0 Hz, 3H), 2.02 (m, 2H), 2.72 (m, 4H), 4.27 (q, J=6.0 Hz, 2H).

(2) Synthesis of ethyl 2-(2-fluorophenyl)cyclopent-1-enecarboxylate

2-Fluorobenzeneboronic acid (4.48 g) and tetrakis(triphenylphosphine)palladium (740 mg) were added to a solution of ethyl 2-trifluoromethanesulfonyloxycyclopent-1-enecarboxylate obtained in Preparation Example 3-(1) in toluene. Then, ethanol (100 mL) and a 1 N sodium carbonate solution (32 mL) were added to the reaction solution, followed by replacement of the reaction atmosphere with nitrogen. The reaction solution was heated to 85° C. and stirred overnight. The reaction solution was cooled to room temperature, followed by extraction with ethyl acetate. The organic layer was dried over anhydrous magnesium sulfate. The drying agent was removed by filtration and the filtrate was concentrated under reduced pressure. The residue was purified by silica gel column chromatography to obtain the title compound (7.60 g).

ESI-MS; m/z 235 [M+H].

$^1$H-NMR (400 MHz, CDCl$_3$) δ (ppm): 1.06 (t, J=7.2 Hz, 3H), 2.02 (m, 2H), 2.83 (t, J=7.6 Hz, 4H), 4.05 (q, J=7.2 Hz, 2H), 7.04 (m, 1H), 7.10 (dt, J=1.2, 7.2 Hz, 1H), 7.19-7.29 (m, 2H).

(3) Synthesis of [2-(2-fluorophenyl)cyclopent-1-enyl]methanol

A solution of ethyl 2-(2-fluorophenyl)cyclopent-1-enecarboxylate obtained in Preparation Example 3-(2) (7.60 g) in THF (100 mL) was added dropwise to a suspension of lithium aluminum hydride (1.34 g) in THF (300 mL) in an ice bath. The reaction solution was stirred at the same temperature for one hour. Then, water (1.35 mL), a 5 N sodium hydroxide solution (1.35 mL) and water (4.05 mL) were sequentially added dropwise in an ice bath. Anhydrous magnesium sulfate was added to the generated reaction mixture, followed by extraction with ethyl acetate. The reaction mixture was filtered through celite and the filtrate was concentrated under reduced pressure to obtain a residue. The residue was purified by silica gel column chromatography to obtain the title compound (6.50 g).

$^1$H-NMR (400 MHz, CDCl$_3$) δ (ppm): 1.34 (dt, J=1.6, 5.8 Hz, 1H), 2.00 (m, 2H), 2.65 (m, 2H), 2.75 (m, 2H), 4.15 (d, J=5.8 Hz, 2H), 7.03-7.27 (m, 4H).

(4) Synthesis of 1-(2-chloromethylcyclopent-1-enyl)-2-fluorobenzene

N,N-Diisopropylethylamine (17.2 mL) was added to a solution of [2-(2-fluorophenyl)cyclopent-1-enyl]methanol obtained in Preparation Example 3-(3) (6.50 g) in dichloromethane (300 mL) in an ice bath. Methanesulfonyl chloride (2.88 mL) was added to the reaction solution at the same temperature. Then, the reaction solution was warmed to room temperature and stirred overnight. Water was added to the reaction mixture, followed by extraction with chloroform. The organic layer was dried over anhydrous magnesium sulfate. The drying agent was removed by filtration and the filtrate was concentrated under reduced pressure. The residue was purified by silica gel column chromatography to obtain the title compound (7.23 g).

$^1$H-NMR (400 MHz, CDCl$_3$) δ (ppm): 2.02 (m, 2H), 2.67 (m, 2H), 2.77 (m, 2H), 4.11 (s, 2H), 7.07 (m, 1H), 7.15 (m, 1H), 7.23-7.30 (m, 2H).

(5) Synthesis of (±)-(4aR*, 7aS*)-7a-(2-fluorophenyl)-4,4a,5,6,7,7a-hexahydrocyclopenta[d][1,3]thiazin-2-ylamine Thiourea (2.60 g) was added to a solution of 1-(2-chloromethylcyclopent-1-enyl)-2-fluorobenzene obtained in Preparation Example 3-(4) (7.20 g) in ethanol (100 mL), and the mixture was stirred with heating under reflux for five hours. The reaction solution was cooled to room temperature and the solvent was evaporated under reduced pressure. The residual syrup was washed with heptane, followed by drying under reduced pressure. Trifluoroacetic acid (50.0 mL) and trifluoromethanesulfonic acid (10.0 mL) were added to the residue in an ice bath. Then, the reaction mixture was warmed to room temperature and stirred for four days. The reaction solution was poured into ice, diluted with ether and then neutralized with sodium bicarbonate, followed by extraction with ethyl acetate. The organic layer was dried over anhydrous magnesium sulfate. The drying agent was removed by filtration and the filtrate was concentrated under reduced pressure to obtain a residue. The residue was purified by NH-silica gel column chromatography to obtain the title compound (4.98 g).

$^1$H-NMR (400 MHz, CDCl$_3$) δ (ppm): 1.69-1.95 (m, 5H), 2.62 (m, 1H), 2.74 (dd, J=4.0, 12.4 Hz, 1H), 2.77 (m, 1H), 2.94 (dd, J=3.2, 12.4 Hz, 1H), 7.00 (ddd, J=1.6, 8.4, 12.8 Hz, 1H), 7.09 (ddd, J=1.2, 7.2, 7.6 Hz, 1H), 7.20 (m, 1H), 7.33 (ddd, J=2.0, 8.4, 8.8 Hz, 1H).

(6) Synthesis of tert-butyl(±)-[(4aR*,7aS*)-7a-(2-fluoro-5-nitrophenyl)-4,4a,5,6,7,7a-hexahydrocyclopenta[d][1,3]thiazin-2-yl]carbamate The compound obtained in Preparation Example 3-(5) (1.00 g) was dissolved in sulfuric acid (6.00 mL) in an ice bath. Fuming nitric acid (215 µL, specific gravity: 1.53) was added dropwise to the reaction solution at the same temperature, followed by stirring for 30 minutes. The reaction mixture was poured into ice and neutralized with a 5 N sodium hydroxide solution. The generated solid was collected by filtration through a glass filter and then dissolved in a mixed solvent of THF and ethyl acetate. The solution was dried over anhydrous magnesium sulfate. The drying agent was removed by filtration and the filtrate was evaporated under reduced pressure to obtain a reaction intermediate. Triethylamine (2.77 mL) and di-tert-butyl dicarbonate (2.47 g) were added to a solution of the intermediate in THF (50 mL), followed by stirring for two days. A saturated sodium bicarbonate solution was added to the reaction mixture, followed by extraction with ethyl acetate. The organic layer was dried over anhydrous magnesium sulfate. The drying agent was removed by filtration and the filtrate was concentrated under reduced pressure to obtain a residue. The residue was purified by silica gel column chromatography to obtain the title compound (1.00 g).

$^1$H-NMR (400 MHz, CDCl$_3$) δ (ppm): 1.53 (s, 9H), 1.80-2.16 (m, 5H), 2.52 (m, 1H), 2.76 (m, 1H), 2.97 (m, 2H), 7.22 (m, 1H), 8.20 (m, 1H), 8.25 (m, 1H).

(7) Synthesis of tert-butyl(±)-[(4aR*,7aS*)-7a-(5-amino-2-fluorophenyl)-4,4a,5,6,7,7a-hexahydrocyclopenta[d][1,3]thiazin-2-yl]carbamate A saturated ammonium chloride solution (2.10 mL) and iron powder (905 mg) were added to a solution of the compound obtained in Preparation Example 3-(6) (800 mg) in ethanol (21.0 mL), and the mixture was stirred with heating under reflux for 30 minutes. The reaction solution was cooled to room temperature and then the solvent was evaporated under reduced pressure. The residue was purified by NH-silica gel column chromatography to obtain the title compound (545 mg).

$^1$H-NMR (400 MHz, CDCl$_3$) δ (ppm): 1.51 (s, 9H), 1.87-2.08 (m, 5H), 2.62 (m, 1H), 2.70 (dd, J=4.4, 14.0 Hz, 1H), 3.02 (dd, J=3.4, 14.0 Hz, 1H), 3.03 (m, 1H), 3.63 (s, 2H), 6.55 (m, 1H), 6.59 (dd, J=2.6, 7.0 Hz, 1H), 6.85 (dd, J=8.4, 12.0 Hz, 1H).

(8) Synthesis of tert-butyl(−)-[(4aR*,7aS*)-7a-(5-amino-2-fluorophenyl)-4,4a,5,6,7,7a-hexahydrocyclopenta[d][1,3]thiazin-2-yl]carbamate The compound obtained in Preparation Example 3-(7) (50 mg) was optically resolved by CHIRALPAK™ AD-H manufactured by Daicel Chemical Industries, Ltd. (2 cm×25 cm, mobile phase: hexane:ethanol=9:1, flow rate: 20 mL/min), and the components having a retention time of 17.1 to 22.8 minutes were collected. This operation was repeated to obtain the title compound (200 mg; >99% ee) from 500 mg of the racemate.

Preparation Example 4

Synthesis of tert-butyl[(4aR*,8aS*)-8a-(3-aminophenyl)-4a,5,6,7,8,8a-hexahydro-4H-benzo[d][1,3]thiazin-2-yl]carbamate

[Formula 23]

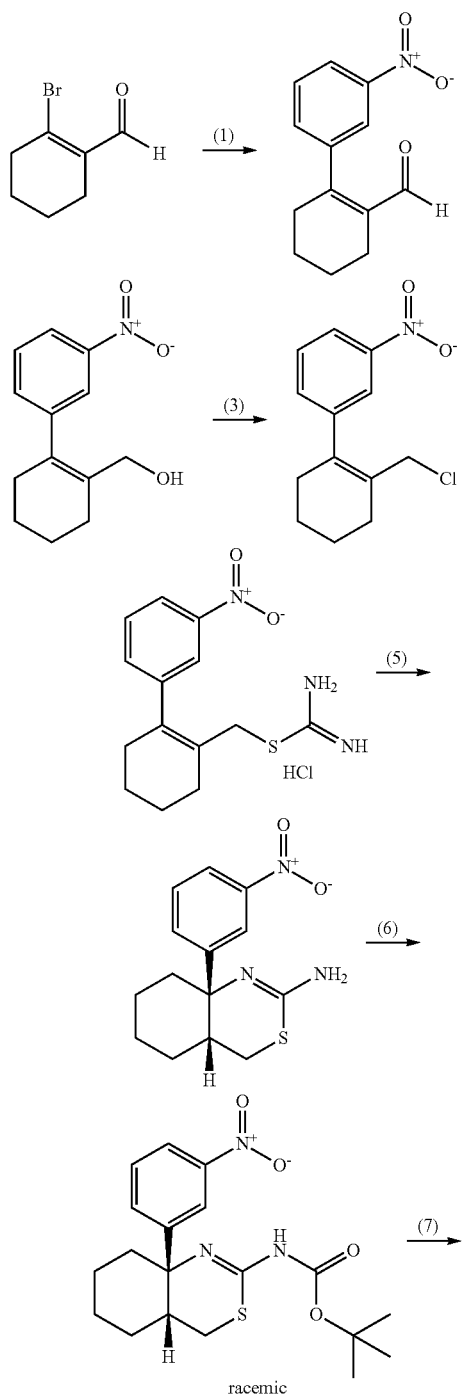

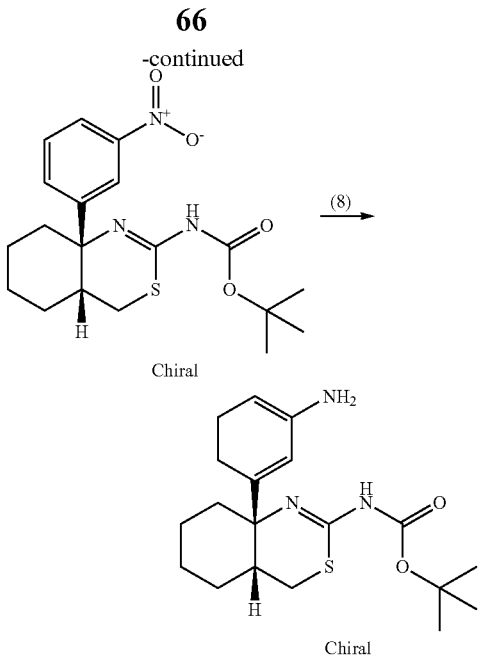

(1) Synthesis of 2-(3-nitrophenyl)cyclohex-1-enecarbaldehyde

Ethanol (11.1 mL) was added to a solution of 2-bromocyclohex-1-enecarbaldehyde (2.22 g) in toluene (22.2 mL). 3-Nitrophenylboronic acid (2.34 g), tetrakis(triphenylphosphine)palladium (270 mg) and a 1 N sodium carbonate solution (14.0 mL) were added to the mixture. The atmosphere of the reaction system was replaced with nitrogen. Then, the reaction solution was stirred with heating under reflux for three hours. The reaction solution was cooled to room temperature, followed by extraction with ethyl acetate. The organic layer was dried over anhydrous magnesium sulfate. The drying agent was removed by filtration and the filtrate was concentrated under reduced pressure to obtain a residue. The residue was purified by silica gel column chromatography to obtain the title compound (2.00 g).

$^1$H-NMR (400 MHz, CDCl$_3$) δ (ppm): 1.76 (m, 2H), 1.83 (m, 2H), 2.39 (m, 2H), 2.56 (m, 2H), 7.58 (m, 2H), 8.14 (m, 1H), 8.24 (m, 1H), 9.46 (s, 1H).

(2) Synthesis of [2-(3-nitrophenyl)cyclohex-1-enyl]methanol

Cerium chloride heptahydrate (1.22 g) was added to a mixed solution of 2-(3-nitrophenyl)cyclohex-1-enecarbaldehyde obtained in Preparation Example 4-(1) (630 mg) in methanol (60.0 mL) and THF (20.0 mL) in an ice bath. Sodium borohydride (130 mg) was added to the reaction solution at the same temperature, followed by stirring for 30 minutes. A saturated ammonium chloride solution was added to the reaction mixture, followed by extraction with ethyl acetate. The organic layer was washed with a saturated sodium chloride solution. The organic layer was dried over anhydrous magnesium sulfate. The drying agent was removed by filtration and the filtrate was concentrated under reduced pressure to obtain a crude product. The resulting crude product was purified by NH-silica gel column chromatography to obtain the title compound (610 mg).

$^1$H-NMR (400 MHz, CDCl$_3$) δ (ppm): 1.28 (t, J=5.2 Hz, 1H), 1.77 (m, 4H), 2.30 (s, 4H), 3.93 (d, J=5.2 Hz, 2H), 7.50 (m, 2H), 8.04 (m, 1H), 8.11 (dt, J=2.0, 7.2 Hz, 1H).

(3) Synthesis of 1-(2-chloromethylcyclohex-1-enyl)-3-nitrobenzene

N,N-Diisopropylethylamine (3.64 mL) was added to a solution of [2-(3-nitrophenyl)cyclohex-1-enyl]methanol obtained in Preparation Example 4-(2) (1.67 g) in dichloromethane (109 mL) in an ice bath. Then, methanesulfonyl chloride (668 μL) was added dropwise. The reaction mixture was warmed to room temperature and stirred overnight. Water was added to the reaction mixture, followed by extraction with ethyl acetate. The organic layer was dried over anhydrous magnesium sulfate. The drying agent was removed by filtration and the filtrate was concentrated under reduced pressure. The residue was purified by silica gel column chromatography to obtain the title compound (1.56 g).

$^1$H-NMR (400 MHz, CDCl$_3$) δ (ppm): 1.78 (m, 4H), 2.32 (s, 4H), 3.86 (s, 2H), 7.54 (t, J=7.6 Hz, 1H), 7.60 (m, 1H), 8.10 (m, 1H), 8.15 (m, 1H).

(4) Synthesis of 2-[2-(3-nitrophenyl)cyclohex-1-enylmethyl]isothiourea hydrochloride Thiourea (495 mg) was added to a solution of 1-(2-chloromethylcyclohex-1-enyl)-3-nitrobenzene obtained in Preparation Example 4-(3) (1.56 g) in ethanol (71.6 mL), and the mixture was stirred with heating under reflux for four hours. The reaction solution was cooled to room temperature and then the solvent was evaporated under reduced pressure. The residual solid was washed with ether to obtain the title compound (2.04 g).

$^1$H-NMR (400 MHz, DMSO-d$_6$) δ (ppm): 1.70 (s, 4H), 2.22 (s, 2H), 2.30 (s, 2H), 3.68 (s, 2H), 7.65 (dt, J=1.2, 7.6 Hz, 1H), 7.71 (t, J=8.0 Hz, 1H), 7.99 (t, J=2.0 Hz, 1H), 8.19 (ddd, J=1.6, 2.4, 8.4 Hz, 1H), 9.02 (brs, 3H).

(5) Synthesis of (±)-(4aR*,8aS*)-8a-(3-nitrophenyl)-4a,5,6,7,8,8a-hexahydro-4H-benzo[d][1,3]thiazin-2-ylamine Trifluoromethanesulfonic acid (1.00 mL) was added to a solution of 2-[2-(3-nitrophenyl)cyclohex-1-enylmethyl]isothiourea hydrochloride obtained in Preparation Example 4-(4) (2.04 g) in TFA (10.0 mL) in an ice bath. The reaction solution was warmed to room temperature, followed by stirring overnight. Trifluoromethanesulfonic acid (1.00 mL) was further added to the reaction solution, followed by stirring for two days. After confirming completion of the reaction, the reaction mixture was carefully poured into a mixed solution of a saturated sodium bicarbonate solution and ether in an ice bath. The aqueous layer was extracted with ethyl acetate, and the organic layer was washed with a saturated sodium bicarbonate solution and a saturated sodium chloride solution. The organic layer was dried over anhydrous magnesium sulfate. The drying agent was removed by filtration and the filtrate was concentrated under reduced pressure to obtain a crude product. The resulting crude product was purified by NH-silica gel column chromatography to obtain the title compound (1.62 g).

$^1$H-NMR (400 MHz, CDCl$_3$) δ (ppm): 1.47-1.86 (m, 8H), 2.23 (ddd, J=4.0, 6.4, 11.6 Hz, 1H), 2.51 (dd, J=2.8, 12.0 Hz, 1H), 2.78 (dd, J=4.4, 12.0 Hz, 1H), 4.45 (s, 2H), 7.49 (t, J=8.0 Hz, 1H), 7.67 (ddd, J=1.2, 2.0, 8.0 Hz, 1H), 8.08 (ddd, J=1.2, 2.4, 8.0 Hz, 1H), 8.19 (t, J=2.0 Hz, 1H).

(6) Synthesis of tert-butyl(±)-[(4aR*,8aS*)-8a-(3-nitrophenyl)-4a,5,6,7,8,8a-hexahydro-4H-benzo[d][1,3]thiazin-2-yl]carbamate Triethylamine (3.08 mL) was added to a solution of the compound obtained in Preparation Example 4-(5) (1.62 g) in THF (30.0 mL). Di-tert-butyl dicarbonate (1.33 g) was added to the reaction solution, followed by stirring at room temperature for three days. The reaction solution was concentrated under reduced pressure. The residue was purified by NH-silica gel column chromatography to obtain the title compound (2.28 g).

$^1$H-NMR (400 MHz, CDCl$_3$) δ (ppm): 1.46-1.95 (m, 8H), 1.54 (s, 9H), 2.46 (m, 1H), 2.48 (dd, J=2.4, 13.2 Hz, 1H), 2.74 (dd, J=4.4, 12.8 Hz, 1H), 7.57 (t, J=8.0 Hz, 1H), 7.70 (d, J=8.0 Hz, 1H), 8.18 (m, 2H).

(7) Synthesis of tert-butyl(−)-[(4aR*,8aS*)-8a-(3-nitrophenyl)-4a,5,6,7,8,8a-hexahydro-4H-benzo[d][1,3]thiazin-2-yl]carbamate The compound obtained in Preparation Example 4-(6) (70.0 mg) was dissolved in ethanol (1.2 mL) and optically resolved by CHIRALPAK™ OJ-H manufactured by Daicel Chemical Industries, Ltd. (2 cm×25 cm, mobile phase: hexane:ethanol=8:2, flow rate: 20 mL/min). The components having a retention time of 12.0 to 21.51 minutes were collected to obtain the title (−)-isomer. This operation was repeated to obtain the title (−)-isomer (144 mg) from 290 mg of the raw material.

(8) Synthesis of tert-butyl[(4aR*,8aS*)-8a-(3-aminophenyl)-4a,5,6,7,8,8a-hexahydro-4H-benzo[d][1,3]thiazin-2-yl]carbamate A saturated solution of sodium dithionite (879 mg) was added to a solution of tert-butyl(−)-[(4aR*,8aS*)-8a-(3-nitrophenyl)-4a,5,6,7,8,8a-hexahydro-4H-benzo[d][1,3]thiazin-2-yl]carbamate (395 mg) in ethanol (20 mL) at room temperature. After stirring at room temperature for 10 minutes, ethanol (10 mL) was further added to the reaction solution. After stirring at room temperature for five minutes, water (10 mL) was further added. The reaction solution was warmed to 40° C. and stirred for 30 minutes. After confirming completion of the reaction, the reaction solution was cooled to room temperature. The excess of ethanol in the reaction solution was evaporated under reduced pressure and then the aqueous layer was extracted with ethyl acetate. The organic layer was washed with a saturated sodium chloride solution and dried over anhydrous magnesium sulfate. The drying agent was removed by filtration and then the filtrate was concentrated under reduced pressure. The residue was purified by NH-silica gel column chromatography to obtain the title compound (110 mg).

$^1$H-NMR (400 MHz, CDCl$_3$) δ (ppm): 1.53 (s, 9H), 1.61-1.99 (m, 8H), 2.38 (dd, J=2.4, 13.2 Hz, 1H), 2.39 (m, 1H), 2.89 (dd, J=4.8, 13.2 Hz, 1H), 3.74 (s, 2H), 6.60 (m, 2H), 6.66 (d, J=8.4 Hz, 1H), 7.15 (t, J=7.6 Hz, 1H).

Preparation Example 5

Synthesis of tert-butyl(−)-[(4aR*,8aS*)-8a-(5-amino-2,3-difluorophenyl)-4a,5,6,7,8,8a-hexahydro-4H-benzo[d][1,3]thiazin-2-yl]carbamate

[Formula 24]

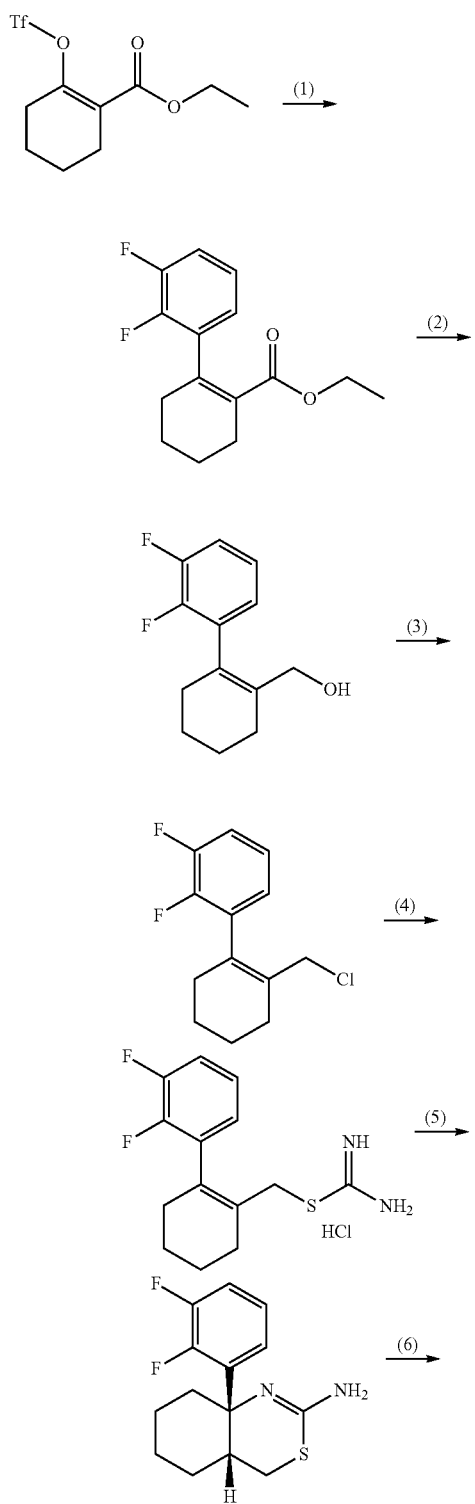

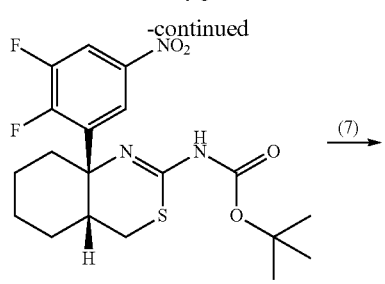

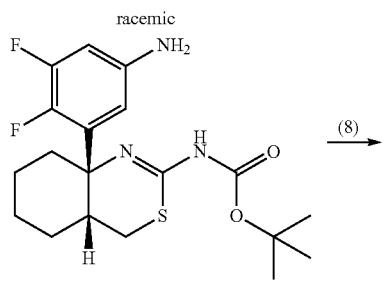

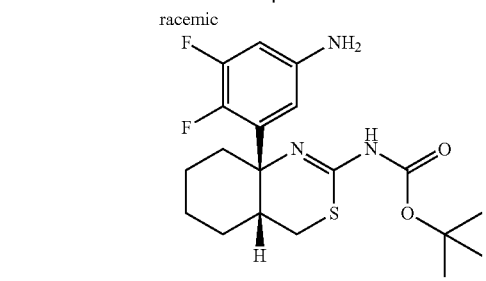

(1) Synthesis of ethyl 2-(2,3-difluorophenyl)cyclohex-1-enecarboxylate

The title compound (675 mg) was obtained from ethyl 2-trifluoromethanesulfonyloxycyclohex-1-enecarboxylate obtained in Preparation Example 1-(1) (1.00 g) and 2,3-difluorophenylboronic acid (627 mg) according to the method of Preparation Example 1-(2).

$^1$H-NMR (400 MHz, CDCl$_3$) δ (ppm): 0.92 (t, J=7.2 Hz, 3H), 1.76 (m, 4H), 2.34 (m, 2H), 2.46 (m, 2H), 3.92 (q, J=7.2 Hz, 2H), 6.82 (m, 1H), 7.02 (m, 2H).

(2) Synthesis of [2-(2,3-difluorophenyl)cyclohex-1-enyl]methanol

The title compound (490 mg) was obtained from ethyl 2-(2,3-difluorophenyl)cyclohex-1-enecarboxylate obtained in Preparation Example 5-(1) (675 mg) according to the method of Preparation Example 1-(3).

$^1$H-NMR (400 MHz, CDCl$_3$) δ (ppm): 1.19 (dt, J=1.6, 5.8 Hz, 1H), 1.75 (m, 4H), 2.24 (m, 2H), 2.30 (m, 2H), 3.86 (d, J=5.8 Hz, 2H), 6.87 (m, 1H), 7.04 (m, 2H).

(3) Synthesis of 1-(2-chloromethylcyclohex-1-enyl)-2,3-difluorobenzene

The title compound (588 mg) was obtained from [2-(2,3-difluorophenyl)cyclohex-1-enyl]methanol obtained in Preparation Example 5-(2) (490 mg) according to the method of Preparation Example 1-(4).

$^1$H-NMR (400 MHz, CDCl$_3$) δ (ppm): 1.77 (s, 4H), 2.29 (brs, 4H), 3.85 (s, 2H), 6.96 (m, 1H), 7.07 (m, 2H).

(4) Synthesis of 2-[2-(2,3-difluorophenyl)cyclohex-1-enylmethyl]isothiourea hydrochloride The title compound (635 mg) was obtained from 1-(2-chloromethylcyclohex-1-enyl)-2,3-difluorobenzene obtained in Preparation Example 5-(3) (588 mg) and thiourea (193 mg) according to the method of Preparation Example 1-(5).

$^1$H-NMR (400 MHz, DMSO-$d_6$) δ (ppm): 1.67 (s, 4H), 2.19 (s, 2H), 2.20 (s, 2H), 3.62 (s, 2H), 6.97 (m, 1H), 7.22 (m, 1H), 7.38 (m, 1H), 8.99 (s, 3H).

(5) Synthesis of (±)-(4aR*,8aS*)-8a-(2,3-difluorophenyl)-4a,5,6,7,8,8a-hexahydro-4H-benzo[d][1,3]thiazin-2-ylamine The title compound (447 mg) was obtained from 2-[2-(2,3-difluorophenyl)cyclohex-1-enylmethyl]isothiourea hydrochloride obtained in Preparation Example 5-(4) (635 mg) according to the method of Preparation Example 1-(6).

$^1$H-NMR (400 MHz, CDCl$_3$) δ (ppm): 1.48-1.81 (m, 7H), 2.22 (m, 1H), 2.55 (dd, J=2.8, 12.0 Hz, 1H), 2.66 (m, 1H), 2.87 (dd, J=4.4, 12.0 Hz, 1H), 4.45 (s, 2H), 7.03 (m, 3H).

(6) Synthesis of tert-butyl(±)-[(4aR*,8aS*)-8a-(2,3-difluoro-5-nitrophenyl)-4a,5,6,7,8,8a-hexahydro-4H-benzo[d][1,3]thiazin-2-yl]carbamate The title compound (530 mg) was obtained from (±)-(4aR*,8aS*)-8a-(2,3-difluorophenyl)-4a,5,6,7,8,8a-hexahydro-4H-benzo[d][1,3]thiazin-2-ylamine obtained in Preparation Example 5-(5) (420 mg) according to the method of Preparation Example 1-(7).

$^1$H-NMR (400 MHz, CDCl$_3$) δ (ppm): 1.54 (s, 9H), 1.54-1.90 (m, 7H), 2.19 (m, 1H), 2.58 (dd, J=2.8, 12.8 Hz, 1H), 2.79 (m, 1H), 2.82 (m, 1H), 8.05 (m, 2H).

(7) Synthesis of tert-butyl(±)-[(4aR*,8aS*)-8a-(5-amino-2,3-difluorophenyl)-4a,5,6,7,8,8a-hexahydro-4H-benzo[d][1,3]thiazin-2-yl]carbamate The title compound (174 mg) was obtained from tert-butyl (±)-[(4aR*,8aS*)-8a-(2,3-difluoro-5-nitrophenyl)-4a,5,6,7,8,8a-hexahydro-4H-benzo[d][1,3]thiazin-2-yl]carbamate obtained in Preparation Example 5-(6) (530 mg) according to the method of Preparation Example 3-(7).

ESI-MS; m/z 398 [M+H].

$^1$H-NMR (400 MHz, CDCl$_3$) δ (ppm): 1.54 (s, 9H), 1.63-1.92 (m, 7H), 2.31 (m, 1H), 2.51 (dd, J=2.4, 12.8 Hz, 1H), 2.81 (m, 1H), 2.92 (dd, J=4.0, 12.8 Hz, 1H), 3.72 (s, 2H), 6.29 (m, 1H), 6.42 (ddd, J=2.8, 6.0, 11.2 Hz, 1H).

(8) Synthesis of tert-butyl(−)-[(4aR*,8aS*)-8a-(5-amino-2,3-difluorophenyl)-4a,5,6,7,8,8a-hexahydro-4H-benzo[d][1,3]thiazin-2-yl]carbamate tert-Butyl(±)-[(4aR*,8aS*)-8a-(5-amino-2,3-difluorophenyl)-4a,5,6,7,8,8a-hexahydro-4H-benzo[d][1,3]thiazin-2-yl]carbamate obtained in Preparation Example 5-(7) (150 mg) was optically resolved by CHIRALPAK™ AD-H manufactured by Daicel Chemical Industries, Ltd. (2 cm×25 cm, mobile phase: hexane:ethanol=8:2, flow rate: 20 mL/min). The components having a retention time of 9.13 to 12.4 minutes were collected to obtain the title compound (42 mg).

Preparation Example 6

Synthesis of tert-butyl(±)-[(4aR*,7aS*)-7a-(5-amino-2-methoxyphenyl)-4,4a,5,6,7,7a-hexahydrocyclopenta[d][1,3]thiazin-2-yl]carbamate

[Formula 25]

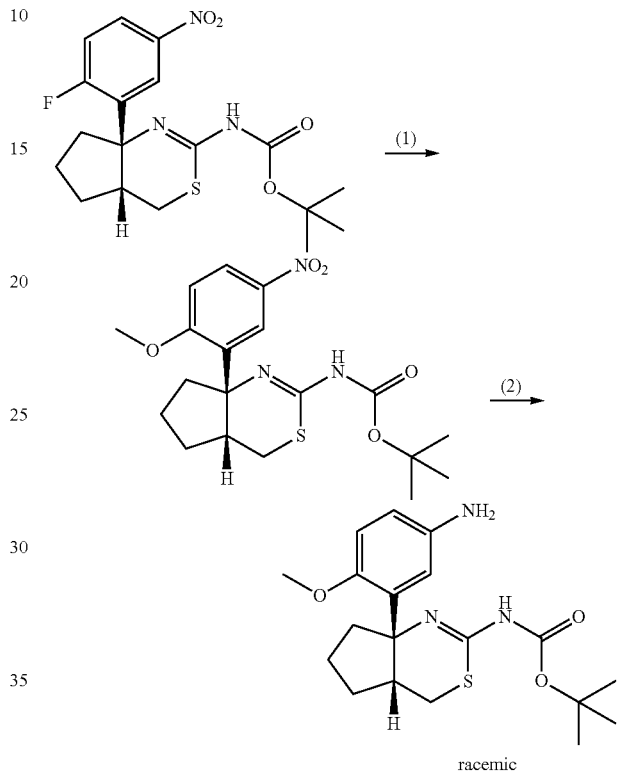

racemic

(1) Synthesis of tert-butyl(±)-[(4aR*,7aS*)-7a-(2-methoxy-5-nitrophenyl)-4,4a,5,6,7,7a-hexahydrocyclopenta[d][1,3]thiazin-2-yl]carbamate A 28% solution of sodium methoxide in methanol (100 μL) was added to a solution of the compound obtained in Preparation Example 3-(6) (97 mg) in methanol (2.0 mL). The reaction solution was stirred at room temperature for one hour and stirred at 45° C. for five hours. The reaction solution was concentrated under reduced pressure. The residue was purified by silica gel column chromatography to obtain the title compound (75.8 mg).

$^1$H-NMR (400 MHz, CDCl$_3$) δ (ppm): 1.50 (s, 9H), 1.75-2.36 (m, 6H), 2.82-2.91 (m, 1H), 3.13-3.22 (m, 1H), 3.22-3.29 (m, 1H), 4.03 (s, 3H), 7.02 (d, J=9.2 Hz, 1H), 8.14 (d, J=2.8 Hz, 1H), 8.23 (dd, J=9.2, 2.8 Hz, 1H).

(2) Synthesis of tert-butyl(±)-[(4aR*,7aS*)-7a-(5-amino-2-methoxyphenyl)-4,4a,5,6,7,7a-hexahydrocyclopenta[d][1,3]thiazin-2-yl]carbamate Iron (83.1 mg) and a saturated ammonium chloride solution (168 μL) were added to a solution of the compound obtained in Preparation Example 6-(1) (75.8 mg) in ethanol (1.68 mL). The reaction solution was heated under reflux at an external temperature of 100° C. for 20 minutes. After cooling to room temperature, ethyl acetate was added to the reaction solution. The insoluble matter was filtered off. Water was added to the filtrate, followed by extraction with ethyl acetate. The organic layer was concentrated. The residue was purified by NH-silica gel chromatography to obtain the title compound (50 mg).

¹H-NMR (400 MHz, CDCl₃) δ (ppm): 1.50 (s, 9H), 1.78-2.15 (m, 5H), 2.49-2.61 (m, 1H), 2.67-2.74 (dd, J=13.1, 4.3 Hz, 1H), 3.09-3.16 (dd, J=13.1, 4.3 Hz, 1H), 3.16-3.25 (m, 1H), 3.42-3.54 (brs, 2H), 3.79 (s, 3H), 6.59-6.62 (m, 2H), 6.73-6.77 (m, 1H).

Preparation Example 7

Synthesis of tert-butyl(−)-[(4aR*,9aS*)-9a-(5-amino-2-fluorophenyl)-4,4a,5,6,7,8,9,9a-octahydro-cyclohepta[d][1,3]thiazin-2-yl]carbamate

[Formula 26]

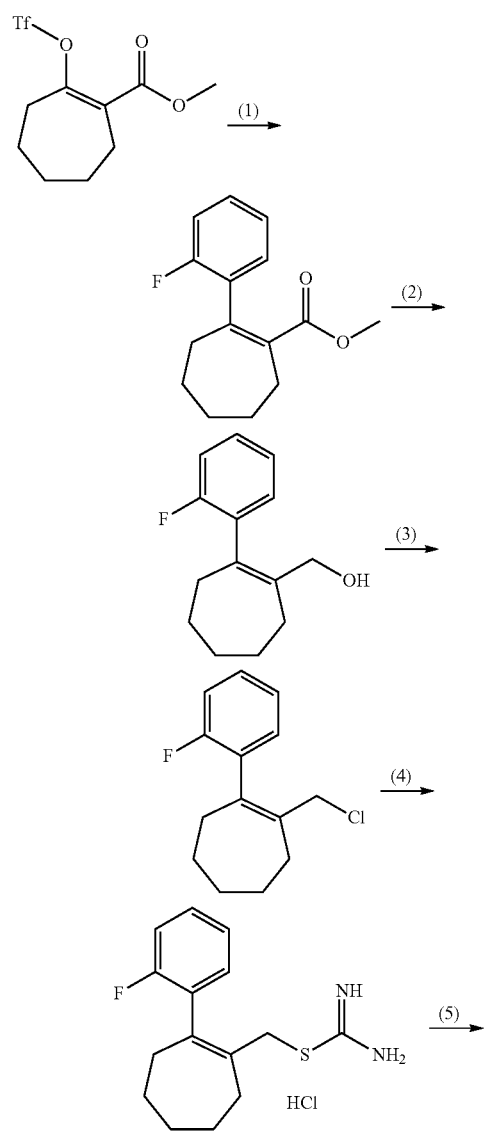

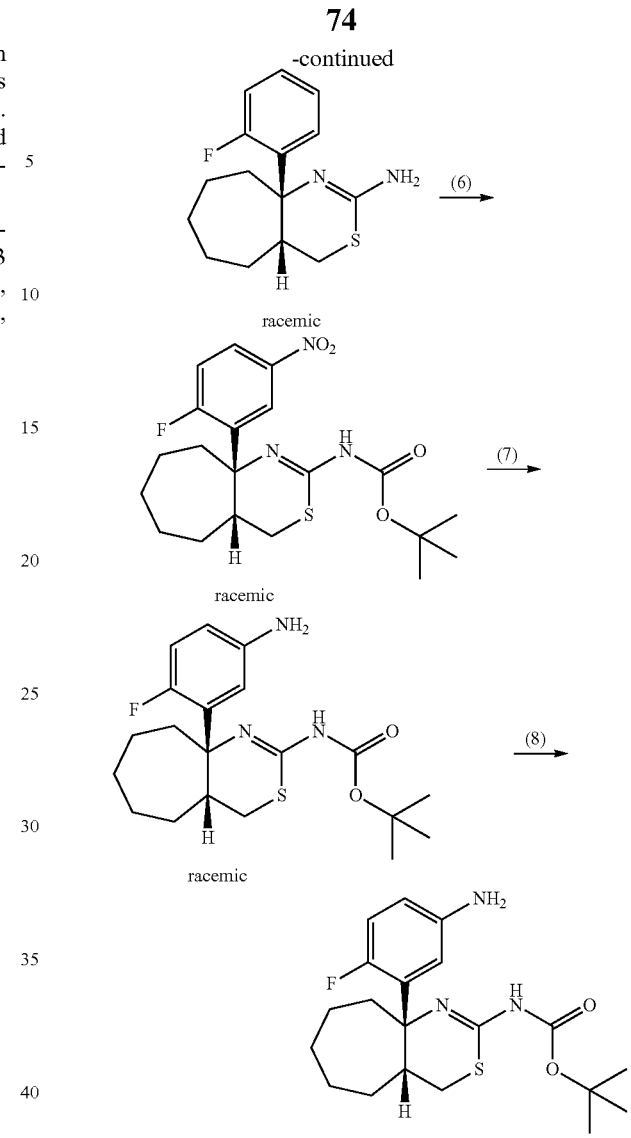

(1) Synthesis of methyl 2-(2-fluorophenyl)-cyclohept-1-enecarboxylate

The title compound (10.2 g) was obtained from methyl 2-trifluoromethanesulfonyloxycyclohept-1-enecarboxylate prepared according to Preparation Example 1-(1) (16.0 g) and 2-fluorophenylboronic acid (4.50 g) according to the method of Preparation Example 1-(2).

ESI-MS; m/z 249 [M+H].

(2) Synthesis of [2-(2-fluorophenyl)-cyclohept-1-enyl]methanol

The title compound (4.50 g) was obtained from methyl 2-(2-fluorophenyl)-cyclohept-1-enecarboxylate obtained in Preparation Example 7-(1) (10.2 g) according to the method of Preparation Example 1-(3).

¹H-NMR (400 MHz, CDCl₃) δ (ppm): 1.21 (dt, J=2.0, 6.0 Hz, 1H), 1.56-1.67 (m, 4H), 1.84 (m, 2H), 2.46 (m, 4H), 3.89 (m, 2H), 7.04 (m, 1H), 7.09 (m, 2H), 7.21 (m, 1H).

(3) Synthesis of 1-chloromethyl-2-(2-fluorophenyl)-cyclopeptene

The title compound (1.56 g) was obtained from [2-(2-fluorophenyl)-cyclohept-1-enyl]methanol obtained in Preparation Example 7-(2) (2.10 g) according to the method of Preparation Example 1-(4).

$^1$H-NMR (400 MHz, CDCl$_3$) δ (ppm): 1.55-1.68 (m, 4H), 1.83 (m, 2H), 2.46 (m, 4H), 3.92 (d, J=3.2 Hz, 2H), 7.05 (ddd, J=1.6, 8.0, 9.6 Hz, 1H), 7.11 (dt, J=1.2, 7.2 Hz, 1H), 7.20 (dt, J=2.0, 7.2 Hz, 1H), 7.26 (m, 1H).

(4) Synthesis of 2-[2-(2-fluorophenyl)-cyclohept-1-enylmethyl]isothiourea hydrochloride The title compound (2.01 g) was obtained from 1-chloromethyl-2-(2-fluorophenyl)-cyclopeptene obtained in Preparation Example 7-(3) (1.56 g) and thiourea (507 mg) according to the method of Preparation Example 1-(5).

$^1$H-NMR (400 MHz, DMSO-d$_6$) δ (ppm): 1.54 (m, 4H), 1.77 (m, 2H), 2.37 (m, 4H), 3.65 (m, 2H), 7.11 (dt, J=2.0, 7.2 Hz, 1H), 7.19 (m, 1H), 7.23 (m, 1H), 7.35 (m, 1H), 8.99 (s, 3H).

(5) Synthesis of (±)-(4aR*,9aS*)-9a-(2-fluorophenyl)-4,4a,5,6,7,8,9,9a-octahydro-cyclohepta[d][1,3]thiazin-2-ylamine The title compound (1.35 g) was obtained from 2-[2-(2-fluorophenyl)-cyclohept-1-enylmethyl]isothiourea hydrochloride obtained in Preparation Example 7-(4) (2.00 g) according to the method of Preparation Example 1-(6).

ESI-MS; m/z 279 [M+H].

$^1$H-NMR (400 MHz, CDCl$_3$) δ (ppm): 1.48-1.89 (m, 9H), 2.40 (m, 1H), 2.50 (dd, J=3.6, 12.0 Hz, 1H), 2.65 (m, 1H), 2.77 (dd, J=3.6, 12.0 Hz, 1H), 7.00 (ddd, J=1.6, 8.0, 12.8 Hz, 1H), 7.07 (dt, J=1.6, 7.6 Hz, 1H), 7.17-7.24 (m, 2H).

(6) Synthesis of tert-butyl(±)-[(4aR*,9aS*)-9a-(2-fluoro-5-nitrophenyl)-4,4a,5,6,7,8,9,9a-octahydro-cyclohepta[d][1,3]thiazin-2-yl]carbamate The title compound (1.83 g) was obtained from (±)-(4aR*,9aS*)-9a-(2-fluorophenyl)-4,4a,5,6,7,8,9,9a-octahydro-cyclohepta[d][1,3]thiazin-2-ylamine obtained in Preparation Example 7-(5) (1.35 g) according to the method of Preparation Example 1-(7).

$^1$H-NMR (400 MHz, CDCl$_3$) δ (ppm): 1.50-1.98 (m, 9H), 1.54 (s, 9H), 2.38 (m, 1H), 2.53 (dd, J=3.2, 12.8 Hz, 1H), 2.70 (3.2, 9.6 Hz, 1H), 2.82 (m, 1H), 7.23 (m, 1H), 8.19 (m, 2H).

(7) Synthesis of tert-butyl(±)-[(4aR*,9aS*)-9a-(5-amino-2-fluorophenyl)-4,4a,5,6,7,8,9,9a-octahydro-cyclohepta[d][1,3]thiazin-2-yl]carbamate The title compound (1.36 g) was obtained from tert-butyl (±)-[(4aR*,9aS*)-9a-(2-fluoro-5-nitrophenyl)-4,4a,5,6,7,8, 9,9a-octahydro-cyclohepta[d][1,3]thiazin-2-yl]carbamate obtained in Preparation Example 7-(6) (1.83 g) according to the method of Preparation Example 3-(7).

$^1$H-NMR (400 MHz, CDCl$_3$) δ (ppm): 1.53 (s, 9H), 1.57-1.99 (m, 9H), 2.45 (m, 2H), 2.83 (m, 2H), 3.64 (s, 2H), 6.53 (m, 2H), 6.84 (m, 1H).

(8) Synthesis of tert-butyl(−)-[(4aR*,9aS*)-9a-(5-amino-2-fluorophenyl)-4,4a,5,6,7,8,9,9a-octahydro-cyclohepta[d][1,3]thiazin-2-yl]carbamate tert-Butyl(±)-[(4aR*,9aS*)-9a-(5-amino-2-fluorophenyl)-4,4a,5,6,7,8,9,9a-octahydrocyclohepta[d][1,3]thiazin-2-yl]carbamate obtained in Preparation Example 7-(7) (140 mg) was optically resolved by CHIRALPAK™ AD-H manufactured by Daicel Chemical Industries, Ltd. (2 cm×25 cm, mobile phase: hexane:ethanol=8:2, flow rate: 10 mL/min). The components having a retention time of 14.3 to 17.9 minutes were collected to obtain the title compound (60 mg).

Preparation Example 8

Synthesis of tert-butyl(−)-[(4aS*,8aS*)-8a-(5-amino-2-fluorophenyl)-4a,7,8,8a-tetrahydro-4H,5H-6-oxa-3-thia-1-azanaphthalen-2-yl]carbamate

[Formula 27]

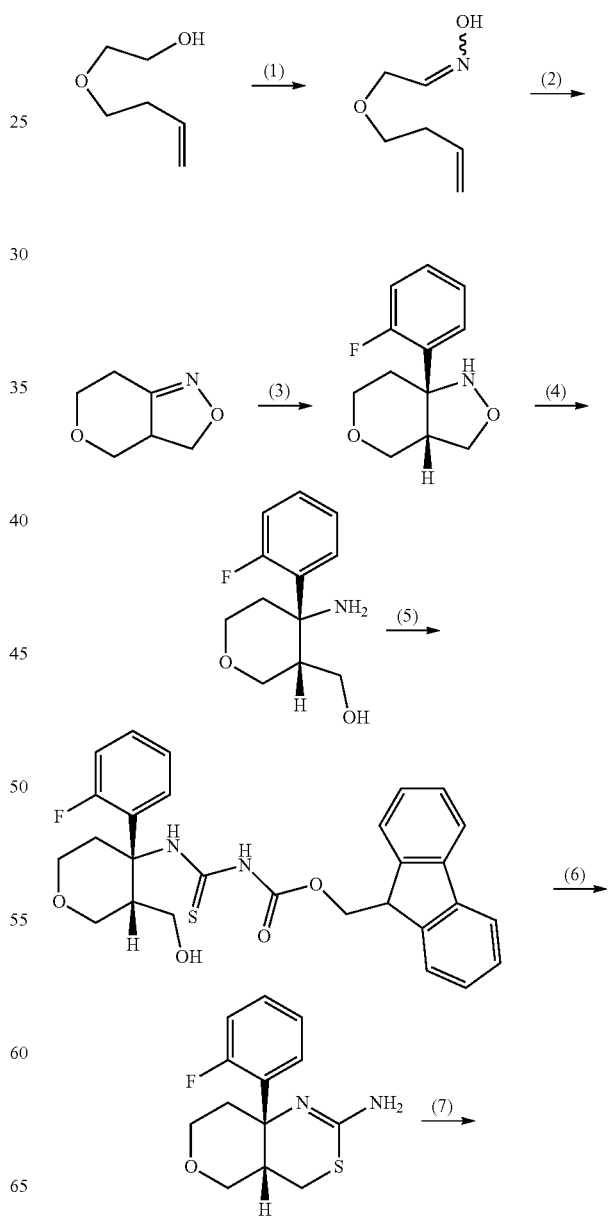

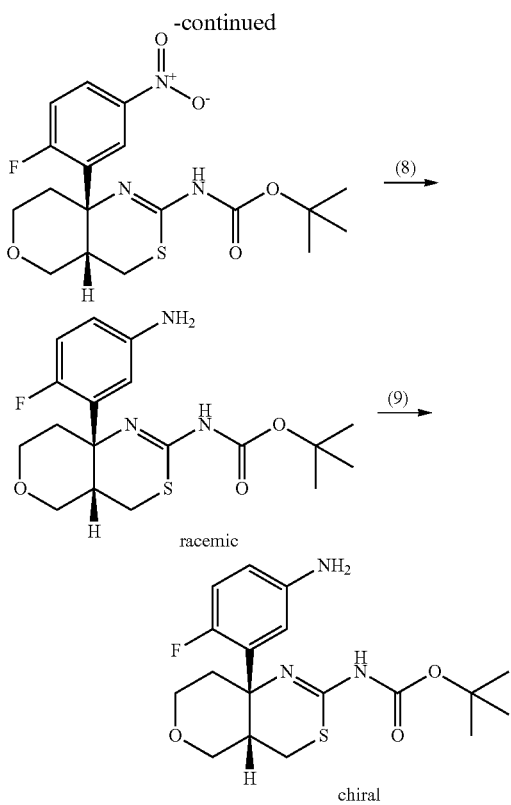

(1) Synthesis of 3-allyloxy-propionaldehyde oxime

A solution containing oxalyl chloride (5.45 mL) in dichloromethane (130 mL) was cooled to −78° C. under a nitrogen atmosphere. A solution containing dimethyl sulfoxide (4.85 mL) in dichloromethane (5 mL) was added dropwise to the reaction solution at the same temperature. After stirring at the same temperature for 10 minutes, a solution containing 3-allyloxy-propan-1-ol (4.99 g) in dichloromethane (5 mL) was added dropwise to the reaction solution. After stirring at the same temperature for one hour, triethylamine (20.4 mL) was added to the reaction solution. The cooling bath was removed. The reaction solution was warmed to room temperature and stirred at room temperature for one hour. Saturated aqueous ammonium chloride was added to the reaction solution, and the organic layer was separated. The organic layer was washed with saturated aqueous sodium chloride and then dried over anhydrous magnesium sulfate. The insoluble matter was separated by filtration and the filtrate was concentrated under reduced pressure. The residue was dissolved in ethanol (100 mL) and water (10 mL). Sodium acetate (12 g) and hydroxylamine sulfate (8.02 g) were added to the reaction solution at room temperature. The reaction solution was stirred at room temperature for 15 hours. Then, a saturated sodium chloride solution and ethyl acetate were added and the organic layer was separated. The organic layer was washed with saturated aqueous sodium chloride again. The organic layer was dried over anhydrous magnesium sulfate. The insoluble matter was separated by filtration and the filtrate was concentrated under reduced pressure. The residue was purified by silica gel column chromatography to obtain the title compound (5.5 g).

$^1$H-NMR (400 MHz, CDCl$_3$) δ (ppm): 2.47-2.52 (m, 1H), 2.65-2.70 (m, 1H), 3.58-3.62 (m, 2H), 3.98-4.01 (m, 2H), 5.17-5.22 (m, 1H), 5.24-5.31 (m, 1H), 5.85-5.96 (m, 1H), 6.86 (t, J=5.2 Hz, 0.5H), 7.50 (t, J=5.6 Hz, 0.5H).

(2) Synthesis of (±)-3a,4,6,7-tetrahydro-3H-pyrano[4,3-c]isoxazole

A 5% sodium hypochlorite solution (63.2 mL) was added to a solution containing the compound obtained in Preparation Example 8-(1) (5.5 g) in dichloromethane (200 mL) at room temperature, and the mixture was stirred at room temperature for four hours. Water and sodium bisulfite (10 g) were added to the reaction solution, followed by stirring at room temperature for 10 minutes. The organic layer was separated and washed with a saturated sodium chloride solution. The organic layer was dried over anhydrous magnesium sulfate. The insoluble matter was separated by filtration and the filtrate was concentrated. The residue was purified by silica gel column chromatography to obtain the title compound (3.33 g).

$^1$H-NMR (400 MHz, CDCl$_3$) δ (ppm): 2.47-2.56 (m, 1H), 2.73 (dd, J=2.8, 14.0 Hz, 1H), 3.23-3.47 (m, 3H), 3.73 (dd, J=2.4, 10.4 Hz, 1H), 4.26 (dd, J=2.4, 11.2 Hz, 1H), 4.34 (dd, J=6.8, 10.8 Hz, 1H), 4.47 (dd, J=8.0, 10.8 Hz, 1H).

(3) Synthesis of (±)-(3aS*, 7aS*)-7a-(2-fluorophenyl)-hexahydro-pyrano[4,3-c]isoxazole A solution of n-butyllithium in hexane (2.77 M; 18.9 mL) was added dropwise to a solution containing 2-bromofluorobenzene (9.61 g) in tetrahydrofuran/toluene (35 mL/115 mL) under a nitrogen atmosphere at −78° C. The reaction solution was stirred at the same temperature for one hour. A boron trifluoride-diethyl ether complex (6.6 mL) was added dropwise to a solution containing the compound obtained in Preparation Example 8-(2) (3.33 g) in toluene (235 mL) under a nitrogen atmosphere at −78° C. A previously prepared 2-fluorophenyllithium solution was added dropwise to the reaction solution at the same temperature. After stirring at the same temperature for one hour, aqueous ammonium chloride was added to the reaction solution, and the reaction solution was warmed to room temperature. Water and ethyl acetate were added to the reaction solution, and the organic layer was separated. The organic layer was washed with a saturated sodium chloride solution. The organic layer was dried over anhydrous magnesium sulfate, and the insoluble matter was separated by filtration. The filtrate was concentrated and the residue was purified by silica gel column chromatography to obtain the title compound (5.1 g).

$^1$H-NMR (400 MHz, CDCl$_3$) δ (ppm): 1.90-1.95 (m, 1H), 2.42-2.50 (m, 1H), 3.05-3.11 (m, 1H), 3.54-3.60 (m, 1H), 3.67-3.87 (m, 4H), 3.98 (dd, J=4.8, 12.0 Hz, 1H), 7.07 (dd, J=8.0, 12.0 Hz, 1H), 7.14-7.19 (m, 1H), 7.27-7.32 (m, 1H), 7.73-7.78 (m, 1H).

(4) Synthesis of (±)-[(3R*,4S*)-4-amino-4-(2-fluorophenyl)-tetrahydropyran-3-yl]methanol Zinc powder (19.1 g) was added to a solution containing the compound obtained in Preparation Example 8-(3) (5.1 g) in acetic acid (130 mL) at room temperature. The reaction solution was stirred at room temperature for 16 hours. The insoluble matter was separated by filtration through celite and the filtrate was concentrated. Ethyl acetate and a sodium bicarbonate solution were added to the residue, and the organic layer was separated. The organic layer was washed with saturated aqueous sodium chloride. The organic layers were further extracted from the aqueous layer with ethyl acetate four times. The organic layers were combined and dried over anhydrous magnesium sulfate. The insoluble matter was separated by filtration and the filtrate was concentrated under reduced pressure to obtain the title compound (5.1 g).

$^1$H-NMR (CDCl$_3$) δ (ppm): 1.45 (d, J=14.0 Hz, 1H), 2.52-2.58 (m, 1H), 2.62-2.70 (m, 1H), 3.54 (d, J=4.0 Hz, 2H), 3.89-3.96 (m, 4H), 7.07 (dd, J=8.0, 12.0 Hz, 1H), 7.15-7.19 (m, 1H), 7.26-7.31 (m, 1H), 7.57-7.61 (m, 1H).

(5) Synthesis of (±)-9H-fluoren-9-ylmethyl({[(3R*,4S*)-4-(2-fluorophenyl)-3-(hydroxymethyl)tetrahydro-2H-pyran-4-yl]amino}carbonothioyl)carbamate Fluorenylmethyloxycarbonyl isothiocyanate (7.02 g) was added to a solution containing the compound obtained in Preparation Example 8-(4) (5.1 g) in dichloromethane (100 mL), and the mixture was stirred at room temperature for two hours. The reaction solution was concentrated under reduced pressure. The residue was purified by silica gel column chromatography to obtain the title compound (10.03 g).

$^1$H-NMR (CDCl$_3$) δ (ppm): 1.64-1.66 (brm, 1H), 2.45-2.55 (brm, 1H), 2.59-2.67 (m, 1H), 3.49-3.52 (brm, 1H), 3.67-3.87 (m, 4H), 4.00-4.04 (m, 2H), 4.24-4.27 (m, 1H), 4.50-4.59 (m, 2H), 7.05 (ddd, J=1.2, 8.0, 12.8 Hz, 1H), 7.13-7.17 (m, 1H), 7.26-7.46 (m, 6H), 7.56-7.59 (m, 2H), 7.79 (d, J=8.0 Hz, 2H), 7.96 (brs, 1H), 10.6 (brs, 1H).

(6) Synthesis of (±)-(4aS*,8aS*)-8a-(2-fluorophenyl)-4a,7,8,8a-tetrahydro-4H,5H-6-oxa-3-thia-1-azanaphthalen-2-ylamine Concentrated hydrochloric acid (5 mL) was added to a solution containing the compound obtained in Preparation Example 8-(5) (10 g) in methanol (200 mL), and the reaction solution was heated under reflux for two hours. The reaction solution was cooled to room temperature and concentrated under reduced pressure. Ethyl acetate and a saturated sodium bicarbonate solution were added to the residue and the organic layer was separated. The organic layer was concentrated under reduced pressure. The residue was dissolved in acetonitrile (200 mL). Piperidine (20 mL) was added to the solution, followed by stirring at room temperature for two hours. The reaction solution was concentrated and the residue was purified by silica gel column chromatography to obtain the title compound (3.17 g).

$^1$H-NMR (CDCl$_3$) δ (ppm): 1.65 (d, J=13.2 Hz, 1H), 2.53 (dd, J=2.8, 12.8 Hz, 1H), 2.65-2.73 (m, 1H), 2.87 (dd, J=4.4, 12.4 Hz, 1H), 2.98-3.10 (m, 1H), 3.69-3.80 (m, 3H), 3.88 (dd, J=4.4, 10.8 Hz, 1H), 4.55 (brs, 2H), 7.04 (dd, J=8.0, 12.8 Hz, 1H), 7.09-7.13 (m, 1H), 7.21-7.32 (m, 2H).

(7) Synthesis of tert-butyl(±)-(4aS*,8aS*)-8a-(2-fluoro-5-nitrophenyl)-4a,7,8,8a-tetrahydro-4H,5H-6-oxa-3-thia-1-azanaphthalen-2-yl]carbamate Fuming nitric acid (682 μL) was added dropwise to a solution of the compound obtained in Preparation Example 8-(6) (2.08 g) in concentrated sulfuric acid (30 mL) under ice-cooling. After stirring the reaction solution at the same temperature for 30 minutes, the reaction solution was poured into ice water. The reaction mixture was made alkaline with a 5 N sodium hydroxide solution. Chloroform was added to the mixture, and the organic layer was separated. The organic layer was dried over anhydrous magnesium sulfate. The insoluble matter was separated by filtration and the filtrate was concentrated under reduced pressure. The residue was dissolved in tetrahydrofuran (120 mL). Triethylamine (6.6 mL) and di-tert-butyl dicarbonate (6.5 g) were added to the solution, and the mixture was stirred at room temperature for 17 hours. A saturated sodium chloride solution and ethyl acetate were added to the reaction solution, and the organic layer was separated. The organic layer was dried over anhydrous magnesium sulfate. The insoluble matter was separated by filtration and the filtrate was concentrated under reduced pressure. The residue was purified by silica gel column chromatography to obtain the title compound (4.7 g).

ESI-MS; m/z 412 [M$^+$+H].

$^1$H-NMR (CDCl$_3$) δ (ppm): 1.53 (s, 9H), 1.64-1.70 (m, 1H), 2.52-2.62 (m, 2H), 2.79 (dd, J=3.6, 13.2 Hz, 1H), 3.05-3.15 (brm, 1H), 3, 60-3, 93 (m, 4H), 7.22-7.28 (m, 1H), 8.18-8.22 (m, 2H).

(8) Synthesis of tert-butyl(±)-[(4aS*,8aS*)-8a-(5-amino-2-fluorophenyl)-4a,7,8,8a-tetrahydro-4H,5H-6-oxa-3-thia-1-azanaphthalen-2-yl]carbamate Iron powder (5.28 g) and saturated aqueous ammonium chloride (18.6 mL) were added to a solution of the compound obtained in Preparation Example 8-(7) (4.7 g) in ethanol (150 mL). The reaction solution was heated under reflux for 30 minutes and then iron powder (5.28 g) was added. The reaction solution was further heated under reflux for 30 minutes and then more iron powder (5.28 g) was added. The reaction solution was further heated under reflux for 30 minutes and then cooled to room temperature. The reaction solution was diluted with ethyl acetate and the insoluble matter was separated by filtration through celite. The filtrate was concentrated under reduced pressure. Ethyl acetate and saturated aqueous sodium chloride were added to the residue, and the organic layer was separated. The organic layer was dried over anhydrous magnesium sulfate, and the insoluble matter was separated by filtration. The filtrate was concentrated under reduced pressure to obtain the title compound (3.48 g).

ESI-MS; m/z 382 [M$^+$+H].

$^1$H-NMR (CDCl$_3$) δ (ppm): 1.53 (s, 9H), 1.55-1.66 (m, 1H), 2.48 (dd, J=2.8, 9.2 Hz, 1H), 2.72-2.81 (m, 1H), 2.92 (dd, J=4.0, 13.2 Hz, 1H), 3.09-3.13 (m, 1H), 3.66 (s, 2H), 3.71-3.94 (m, 4H), 6.53-6.59 (m, 2H), 6.88 (dd, J=8.0, 12.0 Hz, 1H).

(9) Synthesis of tert-butyl(−)-[(4aS*,8aS*)-8a-(5-amino-2-fluorophenyl)-4a,7,8,8a-tetrahydro-4H,5H-6-oxa-3-thia-1-azanaphthalen-2-yl]carbamate The compound obtained in Preparation Example 8-(8) (75 mg) was optically resolved by CHIRALPAK™ AD-H manufactured by Daicel Chemical Industries, Ltd. (2 cm×25 cm, mobile phase: hexane:ethanol=7:3, flow rate: 10 mL/min), and the components having a retention time of 31.8 to 38.3 minutes were collected. This operation was repeated to obtain the title compound (444 mg; >99% ee) from 1 g of the racemate.

ESI-MS; m/z 382 [M$^+$+H].

$^1$H-NMR (CDCl$_3$) δ (ppm): 1.53 (s, 9H), 1.55-1.66 (m, 1H), 2.48 (dd, J=2.8, 9.2 Hz, 1H), 2.72-2.81 (m, 1H), 2.92 (dd, J=4.0, 13.2 Hz, 1H), 3.09-3.13 (m, 1H), 3.66 (s, 2H), 3.71-3.94 (m, 4H), 6.53-6.59 (m, 2H), 6.88 (dd, J=8.0, 12.0 Hz, 1H).

Preparation Example 9

Synthesis of tert-butyl[(4aS*,7aS*)-7a-(5-amino-2-fluorophenyl)-4a,5,7,7a-tetrahydro-4H-furo[3,4-d][1,3]thiazin-2-yl]carbamate

[Formula 28]

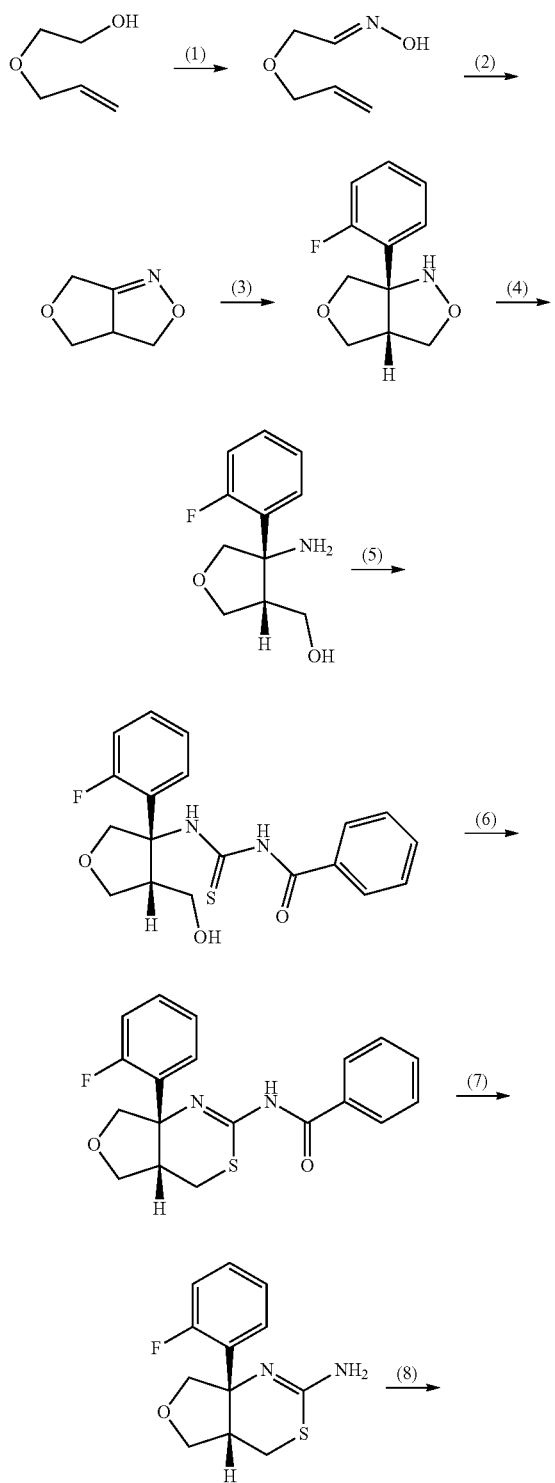

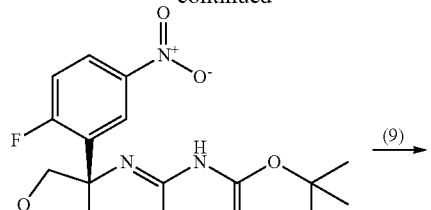

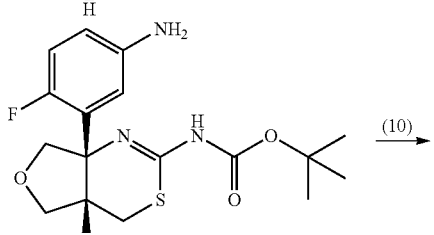

racemic

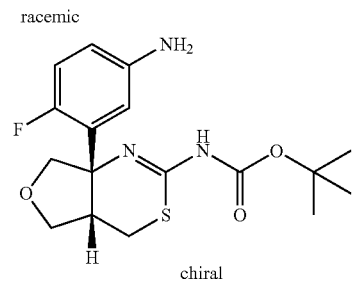

chiral (1) Synthesis of allyloxy-acetaldehyde oxime

A solution containing oxalyl chloride (27.3 mL) in dichloromethane (600 mL) was cooled to −78° C. under a nitrogen atmosphere. A solution containing dimethyl sulfoxide (24.3 mL) in dichloromethane (50 mL) was added dropwise to the reaction solution at the same temperature. After stirring at the same temperature for 10 minutes, a solution containing 2-allyloxyethanol (25 g) in dichloromethane (50 mL) was added dropwise to the reaction solution at the same temperature. After stirring at the same temperature for one hour, triethylamine (102 mL) was added to the reaction solution. The cooling bath was removed. The reaction solution was warmed to room temperature and stirred at room temperature for one hour. Saturated aqueous ammonium chloride was added to the reaction solution. The organic layer was separated and washed with saturated aqueous sodium chloride. The organic layer was dried over anhydrous magnesium sulfate, and the insoluble matter was separated by filtration. The filtrate was concentrated under reduced pressure. The residue was dissolved in ethanol (500 mL) and water (50 mL). Sodium acetate (60.2 g) and hydroxylamine sulfate (40.2 g) were added to the reaction solution at room temperature. The reaction solution was stirred at room temperature for 15 hours. Then, water and ethyl acetate were added and the organic layer was separated. The organic layer was washed with saturated aqueous sodium chloride and dried over anhydrous magnesium sulfate. The insoluble matter was separated by filtration and the filtrate was concentrated under reduced pressure. The residue was purified by silica gel column chromatography to obtain the title compound (13.2 g).

$^1$H-NMR (400 MHz, CDCl$_3$) δ (ppm): 4.00-4.04 (m, 2H), 4.09-4.11 (m, 1H), 4.35 (d, J=3.6 Hz, 1H), 5.21-5.25 (m, 1H), 5.27-5.35 (m, 1H), 5.85-5.95 (m, 1H), 6.92 (t, J=4.0 Hz, 0.5H), 7.51 (t, J=5.6 Hz, 0.5H).

(2) Synthesis of (±)-3a,4-dihydro-3H,6H-furo[3,4-c]isoxazole

A 5% sodium hypochlorite solution (170 mL) was added to a solution containing the compound obtained in Preparation Example 9-(1) (13.2 g) in dichloromethane (400 mL) at room temperature, and the mixture was stirred at room temperature for six hours. Water and sodium bisulfite (7.95 g) were added to the reaction solution, followed by stirring at room temperature for 10 minutes. Then, the organic layer was separated. The organic layer was dried over anhydrous magnesium sulfate. The insoluble matter was separated by filtration and the filtrate was concentrated under reduced pressure. The residue was purified by silica gel column chromatography to obtain the title compound (4.8 g).
$^1$H-NMR (400 MHz, CDCl$_3$) δ (ppm): 3.65 (dd, J=9.2, 8.0 Hz, 1H), 4.00 (dd, J=12.0, 8.0 Hz, 1H), 4.17-4.29 (m, 2H), 4.40-4.49 (m, 2H), 4.59 (dd, J=9.2, 8.0 Hz, 1H).

(3) Synthesis of (±)-(3aS*,6aS*)-6a-(2-fluorophenyl)tetrahydrofuro[3,4-c]isoxazole A 2.77 M solution of n-butyllithium in hexane (30.7 mL) was added dropwise to a solution containing 2-bromofluorobenzene (15.6 g) in tetrahydrofuran/toluene (50 mL/150 mL) under a nitrogen atmosphere at −78° C. The reaction solution was stirred at the same temperature for one hour. A boron trifluoride-diethyl ether complex (10.7 mL) was added dropwise to a solution containing the compound obtained in Preparation Example 9-(2) (4.8 g) in toluene (350 mL) under a nitrogen atmosphere at −78° C. Previously prepared 2-fluorophenyllithium was added dropwise to the reaction solution at the same temperature. After stirring at the same temperature for one hour, aqueous ammonium chloride was added to the reaction solution, and the reaction solution was warmed to room temperature. Water and ethyl acetate were added to the reaction solution, and the organic layer was separated. The organic layer was washed with a saturated sodium chloride solution. The organic layer was dried over anhydrous magnesium sulfate, and the insoluble matter was separated by filtration. The filtrate was concentrated under reduced pressure. The residue was purified by silica gel column chromatography to obtain the title compound (5.6 g).
$^1$H-NMR (400 MHz, CDCl$_3$) δ (ppm): 3.39-3.45 (m, 1H), 3.52-3.62 (brm, 1H), 3.84-3.92 (brm, 2H), 3.98 (brd, J=9.2 Hz, 1H), 4.16 (ddd, J=2.4, 6.4, 11.2 Hz, 1H), 4.50-4.58 (brm, 1H), 5.11 (brs, 1H), 7.06 (ddd, J=1.2, 8.4, 11.6 Hz, 1H), 7.16 (ddd, J=1.2, 7.6, 7.6 Hz, 1H), 7.25-7.31 (m, 1H), 7.84-7.95 (m, 1H).

(4) Synthesis of (±)-[(3R*,4S*)-4-amino-4-(2-fluorophenyl)tetrahydrofuran-3-yl]methanol Zinc (powder: 21 g) was added to a solution containing the compound obtained in Preparation Example 9-(3) (5.6 g) in acetic acid (140 mL) at room temperature. The reaction solution was stirred at room temperature for 16 hours. The insoluble matter was separated by filtration through celite and the filtrate was concentrated under reduced pressure. Ethyl acetate and a sodium bicarbonate solution were added to the residue, and the organic layer was separated. The organic layer was washed with saturated aqueous sodium chloride. The organic layers were further extracted from the aqueous layer with ethyl acetate three times. The organic layers were combined and dried over anhydrous magnesium sulfate. The insoluble matter was separated by filtration and the filtrate was concentrated under reduced pressure to obtain the title compound (5.46 g).
ESI-MS; m/z 212 [M$^+$+H].
$^1$H-NMR (CDCl$_3$) δ (ppm): 2.81-2.88 (m, 1H), 3.83 (dd, J=6.8, 12.0 Hz, 1H), 3.92 (dd, J=3.2, 8.8 Hz, 1H), 3, 94-4.00 (m, 2H), 4.07 (dd, J=8.4, 9.2 Hz, 1H), 4.14 (dd, J=1.2, 8.8 Hz, 1H), 7.09 (ddd, J=1.2, 8.0, 12.4 Hz, 1H), 7.16 (ddd, J=1.2, 7.6, 8.0 Hz, 1H), 7.26-7.32 (m, 1H), 7.53 (dt, J=2.0, 8.0 Hz, 1H).

(5) Synthesis of (±)-1-benzoyl-3-[(3S*,4R*)-3-(2-fluorophenyl)-4-hydroxymethyl-tetrahydrofuran-3-yl]thiourea The compound obtained in Preparation Example 9-(4) (2.5 g) was added to a solution of benzoyl isothiocyanate (2.13 g) in dichloromethane (75 mL), and the mixture was stirred at room temperature for three hours. The reaction solution was concentrated and the residue was purified by silica gel column chromatography to obtain the title compound (4.19 g).
ESI-MS; m/z 397 [M$^+$+Na].
$^1$H-NMR (CDCl$_3$) δ (ppm): 2.83 (dd, J=4.4, 6.8 Hz, 1H), 3.15-3.22 (m, 1H), 3.81 (dd, J=2.8, 8.8 Hz, 1H), 3.89-3.95 (m, 1H), 4.01-4.07 (m, 1H), 4.13-4.17 (m, 1H), 4.43 (dd, J=2.8, 9.6 Hz, 1H), 4, 69 (d, J=10.0 Hz, 1H), 7.04 (ddd, J=1.2, 8.0, 12.0 Hz, 1H), 7.18 (ddd, J=1.2, 8.0, 8.0 Hz, 1H), 7.24-7.33 (m, 1H), 7.52 (t, J=7.6 Hz, 2H), 7.64 (td, J=1.2, 8.0 Hz, 1H), 7.71 (td, J=1.6, 8.0 Hz, 1H), 7.86 (dd, J=1.6, 6.4 Hz, 1H), 8.90 (brs, 1H), 11.8 (brs, 1H).

(6) Synthesis of (±)-N-[(4aS*,7aS*)-7a-(2-fluorophenyl)-4a,5,7,7a-tetrahydro-4H-furo[3,4-d][1,3]thiazin-2-yl]benzamide Triphenylphosphine (7.08 g) was added to a solution of the compound obtained in Preparation Example 9-(5) (3.89 g) and carbon tetrabromide (8.95 g) in dichloromethane (100 mL) at room temperature. The reaction solution was cooled to 0° C., stirred for 20 minutes and then warmed to room temperature. The reaction solution was stirred at room temperature for 15 hours. Then, water was added to the reaction solution, and the organic layer was separated. The organic layer was dried over anhydrous magnesium sulfate, and the insoluble matter was separated by filtration. The filtrate was concentrated under reduced pressure and the residue was purified by silica gel column chromatography to obtain the title compound (1.93 g).
$^1$H-NMR (CDCl$_3$) δ (ppm): 2.90 (dd, J=4.8, 13.6 Hz, 1H), 3.23 (dd, J=4.0, 13.6 Hz, 1H), 3.39-3.46 (m, 1H), 4.06 (dd, J=2.8, 9.2 Hz, 1H), 4.22-4.25 (m, 2H), 4.44 (d, J=9.2 Hz, 1H), 7.13 (ddd, J=1.2, 8.4, 12.4 Hz, 1H), 7.21 (ddd, J=1.2, 7.6, 7.6 Hz, 1H), 7.33-7.52 (m, 5H), 8.15 (d, J=7.6 Hz, 2H).

(7) Synthesis of (±)-(4aS*,7aS*)-7a-(2-fluorophenyl)-4a,5,7,7a-tetrahydro-4H-furo[3,4-d][1,3]thiazin-2-ylamine A solution of the compound obtained in Preparation Example 9-(6) (2.08 g) and 1,8-diazabicyclo[5.4.0]undec-7-ene (1.6 mL) in methanol (20 mL) was heated under reflux for five hours. After cooling the reaction solution to room temperature, the solvent was evaporated under reduced pressure. The residue was subjected to silica gel chromatography. The resulting crude product was suspended in diethyl ether. The generated solid was collected by filtration to obtain the title compound (1.19 g).

ESI-MS; m/z 253 [M$^+$+H].

$^1$H-NMR (CDCl$_3$) δ (ppm): 2.83 (dd, J=5.2, 12.4 Hz, 1H), 2.99-3.08 (m, 2H), 3.82 (dd, J=2.0, 8.4 Hz, 1H), 4.05-4.15 (m, 2H), 4.44 (brs, 2H), 4.49 (d, J=8.8 Hz, 1H), 7.05 (ddd, J=1.6, 8.0, 12.0 Hz, 1H), 7.13 (ddd, J=1.2, 7.2, 8.0 Hz, 1H), 7.22-7.30 (m, 1H), 7.46 (dt, J=1.6, 8.0 Hz, 1H).

(8) Synthesis of tert-butyl(±)-[(4aS*,7aS*)-7a-(2-fluoro-5-nitrophenyl)-4a,5,7,7a-tetrahydro-4H-furo[3,4-d][1,3]thiazin-2-yl]carbamate Fuming nitric acid (293 μL) was added dropwise to a solution of the compound obtained in Preparation Example 9-(7) (1.19 g) in concentrated sulfuric acid (20 mL) under ice-cooling. The reaction solution was stirred at the same temperature for 30 minutes and then poured into ice water. The reaction mixture was neutralized with a 5 N sodium hydroxide solution. Chloroform was added to the mixture, and the organic layer was separated. The organic layer was dried over anhydrous magnesium sulfate, and the insoluble matter was separated by filtration. The filtrate was concentrated under reduced pressure and the residue was dissolved in tetrahydrofuran (50 mL). Triethylamine (2.62 mL) and di-tert-butyl dicarbonate (2.58 g) were added to the solution, and the mixture was stirred at room temperature for 18 hours. Water and ethyl acetate were added to the reaction solution, and the organic layer was separated. The organic layer was washed with a saturated sodium chloride solution and dried over anhydrous magnesium sulfate. The insoluble matter was separated by filtration and the filtrate was concentrated under reduced pressure. The residue was purified by silica gel column chromatography to obtain the title compound (1.68 g).

ESI-MS; m/z 398 [M$^+$+H].

$^1$H-NMR (CDCl$_3$) δ (ppm): 1.51 (s, 9H), 2.74-2.99 (brm, 2H), 3.15-3.44 (brm, 1H), 3.72-3.85 (brm, 1H), 4.17-4.19 (m, 2H), 4.37 (dd, J=8.4, 1.6 Hz, 1H), 7.21-7.29 (m, 1H), 8.19-8.24 (m, 1H), 8.35 (dd, J=7.2, 2.8 Hz, 1H).

(9) Synthesis of tert-butyl(±)-[(4aS*,7aS*)-7a-(5-amino-2-fluorophenyl)-4a,5,7,7a-tetrahydro-4H-furo[3,4-d][1,3]thiazin-2-yl]carbamate Iron powder (1.89 g) and saturated aqueous ammonium chloride (5 mL) were added to a solution of the compound obtained in Preparation Example 9-(8) (1.68 g) in ethanol (50 mL). The reaction solution was heated under reflux for 30 minutes and then cooled to room temperature. The reaction solution was diluted with ethyl acetate and the insoluble matter was separated by filtration through celite. The filtrate was concentrated under reduced pressure. Ethyl acetate and saturated aqueous sodium chloride were added to the residue and the organic layer was separated. The organic layer was dried over anhydrous magnesium sulfate, and the insoluble matter was separated by filtration. The filtrate was concentrated under reduced pressure to obtain the title compound (1.54 g).

ESI-MS; m/z 368 [M$^+$+H].

$^1$H-NMR (CDCl$_3$) δ (ppm): 1.50 (s, 9H), 2.75 (dd, J=4.4, 13.2 Hz, 1H), 3.01 (dd, J=3.2, 13.2 Hz, 1H), 3.25-3.30 (m, 1H), 3.62 (brs, 2H), 3.84 (d, J=7.6 Hz, 1H), 4.14-4.17 (m, 2H), 4.41 (dd, J=0.8, 9.2 Hz, 1H), 6.55-6.59 (m, 1H), 6.65 (dd, J=3.2, 6.4 Hz, 1H), 6.87 (dd, J=8.4, 12.4 Hz, 1H).

(10) Synthesis of tert-butyl(−)-[(4aS*,7aS*)-7a-(5-amino-2-fluorophenyl)-4a,5,7,7a-tetrahydro-4H-furo[3,4-d][1,3]thiazin-2-yl]carbamate The compound obtained in Preparation Example 9-(9) (50 mg) was optically resolved by CHIRALPAK™ AD-H manufactured by Daicel Chemical Industries, Ltd. (2 cm×25 cm, mobile phase: hexane:ethanol=7:3, flow rate: 10 mL/min), and the components having a retention time of 23.1 to 26.3 minutes were collected. This operation was repeated to obtain the title compound (220 mg; >99% ee) from 600 mg of the racemate.

ESI-MS; m/z 368 [M$^+$+H].

$^1$H-NMR (CDCl$_3$) δ (ppm): 1.50 (s, 9H), 2.75 (dd, J=4.4, 13.2 Hz, 1H), 3.01 (dd, J=3.2, 13.2 Hz, 1H), 3.25-3.30 (m, 1H), 3.62 (brs, 2H), 3.84 (d, J=7.6 Hz, 1H), 4.14-4.17 (m, 2H), 4.41 (dd, J=0.8, 9.2 Hz, 1H), 6.55-6.59 (m, 1H), 6.65 (dd, J=3.2, 6.4 Hz, 1H), 6.87 (dd, J=8.4, 12.4 Hz, 1H).

Preparation Example 10

Synthesis of (3aR*,5S*,6aS*)-6a-(2-fluorophenyl)-5-methoxy-hexahydrocyclopenta[c]isoxazole and (3aR*,5R*,6aS*)-6a-(2-fluorophenyl)-5-methoxy-hexahydrocyclopenta[c]isoxazole

[Formula 29]

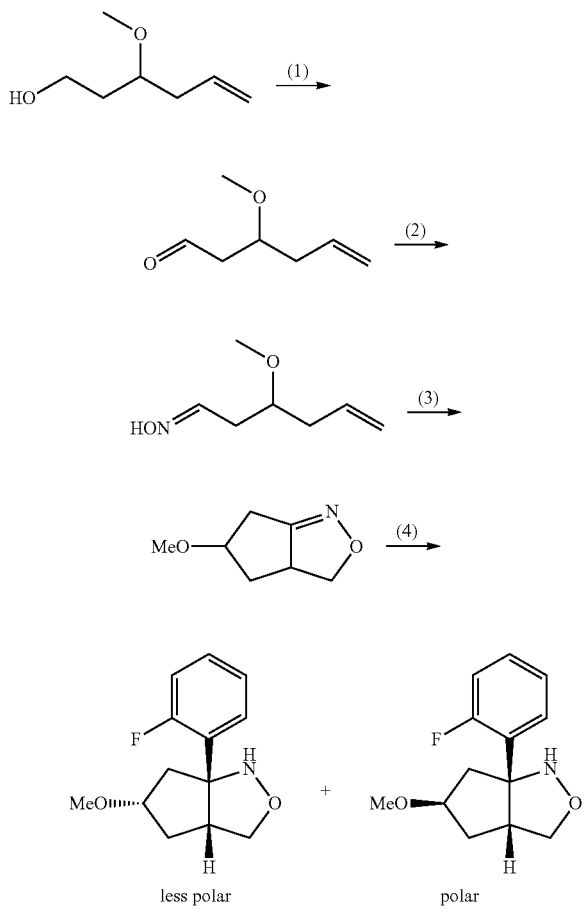

(1) Synthesis of 3-methoxy-5-hexenal

Dimethyl sulfoxide (0.612 mL) was added dropwise to a solution of oxalyl chloride (0.652 mL) in dichloromethane (15 mL) at −55° C., and the mixture was stirred at −70° C. for 10 minutes. A solution of 3-methoxy-5-hexenol (Tetrahedron, 61, 3183-3194 (2005)) (660 mg) in dichloromethane (5 mL) was added dropwise to the solution at −60° C., and the mixture was stirred at −60° C. for 15 minutes. Triethylamine (4.95 mL) was added dropwise to the solution at −60° C., and the reaction solution was stirred at −60° C. to room temperature for 30 minutes. The reaction solution was poured into water, followed by extraction with dichloromethane. The extract was washed with a saturated sodium chloride solution and then dried over anhydrous magnesium sulfate. The drying agent was removed by filtration and the filtrate was concentrated under reduced pressure to obtain the title compound containing dichloromethane and triethylamine (3.0 g).

$^1$H-NMR (400 MHz, CDCl$_3$) δ (ppm): 2.24-2.70 (m, 4H), 3.38 (s, 3H), 3.76-3.86 (m, 1H), 5.00-5.40 (m, 2H), 5.70-5.90 (m, 1H), 9.80 (t, J=1.6 Hz, 1H).

(2) Synthesis of 3-methoxy-5-hexenal oxime

A mixture of 3-methoxy-5-hexenal (3.0 g, contaminated with dichloromethane and triethylamine), hydroxylamine sulfate (990 mg) and sodium acetate (624 mg) in ethanol (6.5 mL)-water (0.65 mL) was stirred at room temperature for 12 hours. The reaction solution was poured into ice water, followed by extraction with ethyl acetate. The extract was washed with a saturated sodium chloride solution and then dried over anhydrous magnesium sulfate. The drying agent was removed by filtration and the filtrate was concentrated under reduced pressure. The resulting crude product was purified by silica gel column chromatography to obtain the title compound (500 mg).

$^1$H-NMR (400 MHz, CDCl$_3$) δ (ppm): 2.22-2.48 (m, 3H), 2.52-2.68 (m, 1H), 3.37 and 3.38 (s, total 3H), 3.40-3.54 (m, 1H), 5.05-5.20 (m, 2H), 5.72-5.90 (m, 1H), 6.86 and 7.48 (t, J=5.6 Hz, total 1H), 7.80 and 8.22 (brs, total 1H).

(3) Synthesis of 5-methoxy-3a,4,5,6-tetrahydro-3H-cyclopenta[c]isoxazole

A sodium hypochlorite solution (5% available chlorine, 9.36 mL) was added dropwise to a solution of 3-methoxy-5-hexenal oxime (450 mg) in dichloromethane (20 mL) at 0° C., and the mixture was stirred at 0° C. to room temperature for 1.5 hours. The reaction solution was poured into ice water, followed by extraction with dichloromethane. The extract was washed with a saturated sodium chloride solution and then dried over anhydrous magnesium sulfate. The drying agent was removed by filtration and the filtrate was concentrated under normal pressure. The resulting crude product was purified by silica gel column chromatography to obtain the less polar title compound (230 mg) and the more polar title compound (150 mg).

Low Polar Title Compound $^1$H-NMR (400 MHz, CDCl$_3$) δ (ppm): 1.54-1.68 (m, 1H), 2.20-2.30 (m, 1H), 2.46-2.56 (m, 1H), 2.72-2.84 (m, 1H), 3.30-3.34 (m, 3H), 3.72-3.80 (m, 1H), 3.92-4.06 (m, 1H), 4.26-4.32 (m, 1H), 4.54-4.61 (m, 1H).

More Polar Title Compound $^1$H-NMR (400 MHz, CDCl$_3$) δ (ppm): 1.45-1.60 (m, 1H), 2.40-2.55 (m, 2H), 2.83 (dd, J=8.4, 18.0, 1H), 3.35 (s, 3H), 3.55-3.70 (m, 1H), 3.75-3.85 (m, 1H), 4.20-4.33 (m, 1H), 4.50-4.60 (m, 1H).

(4) Synthesis of (3aR*,5S*,6aS*)-6a-(2-fluorophenyl)-5-methoxy-hexahydrocyclopenta[c]isoxazole and (3aR*,5R*,6aS*)-6a-(2-fluorophenyl)-5-methoxy-hexahydrocyclopenta[c]isoxazole

[Formula 30]

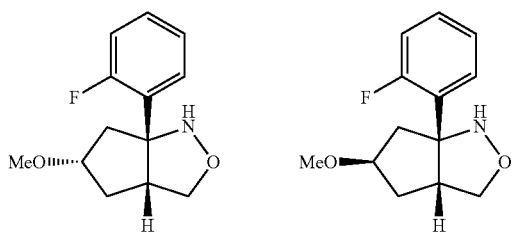 [SMILES: CO[C@H]1C[C@H]2CON[C@@]2(c2ccccc2F)C1 ; CO[C@@H]1C[C@H]2CON[C@@]2(c2ccccc2F)C1]

n-Butyllithium (2.77 M, 2.29 mL) was added dropwise to a solution of 2-bromofluorobenzene (1.22 g) in toluene (20 mL)-tetrahydrofuran (6 mL) at −78° C., and the mixture was stirred at the same temperature for one hour. A boron trifluoride-diethyl ether complex (0.797 mL) was added dropwise to a solution of 5-methoxy-3a,4,5,6-tetrahydro-3H-cyclopenta[c]isoxazole (427 mg, mixture of more polar and less polar compounds) in toluene (30 mL) at −78° C. A previously prepared 2-fluorophenyllithium solution was added dropwise to the solution at −78° C. to −60° C. The reaction solution was stirred at −78° C. for one hour. An ammonium chloride solution was added to the reaction solution at −78° C., followed by warming to room temperature over one hour. The reaction solution was extracted with ethyl acetate. The extract was washed with a saturated sodium chloride solution and then dried over anhydrous magnesium sulfate. The drying agent was removed by filtration and the filtrate was concentrated under reduced pressure. The resulting crude product was purified by silica gel column chromatography to obtain the less polar title compound (5S, 247 mg) and the more polar title compound (5R, 275 mg).

Less Polar Title Compound (5S)

$^1$H-NMR (400 MHz, CDCl$_3$) δ (ppm): 1.95-2.17 (m, 2H), 2.17-2.32 (m, 2H), 3.20-3.35 (m, 1H), 3.30 (s, 3H), 3.69 (t, J=8.0 Hz, 1H), 4.05-4.15 (m, 1H), 4.39 (t, J=8.0 Hz, 1H), 6.03 (s, 1H), 6.90-7.32 (m, 3H), 7.94 (t, J=8.0 Hz, 1H).

More Polar Title Compound (5R)

$^1$H-NMR (400 MHz, CDCl$_3$) δ (ppm): 2.00-2.26 (m, 3H), 2.34-2.44 (m, 1H), 3.26-3.38 (m, 1H), 3.34 (s, 3H), 3.69 (brs, 1H), 4.08-4.22 (m, 2H), 7.06 (dd, J=8.0, 12.0 Hz, 1H), 7.12 (t, J=8.0 Hz, 1H), 7.16-7.32 (m, 1H), 7.58-7.72 (m, 1H).

Preparation Example 11

Synthesis of tert-butyl[(4aR*,6S*,7aS*)-7a-(5-amino-2-fluorophenyl)-6-methoxy-4,4a,5,6,7,7a-hexahydrocyclopenta[d][1,3]thiazin-2-yl]carbamate ((+)-isomer and (−)-isomer)

[Formula 31]

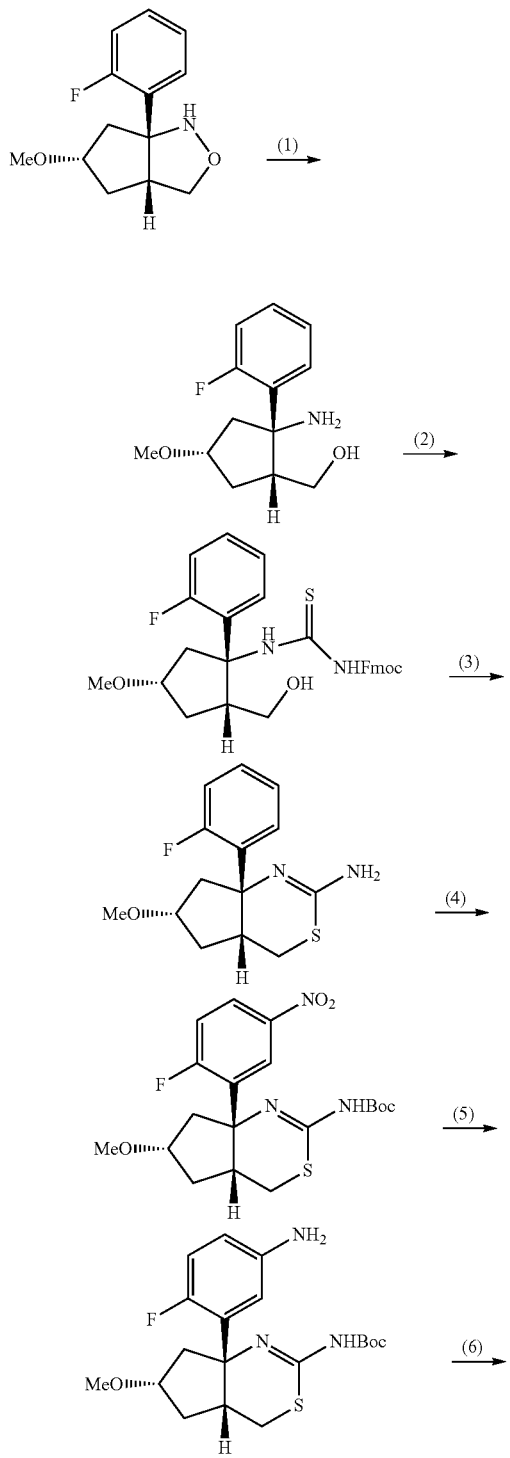

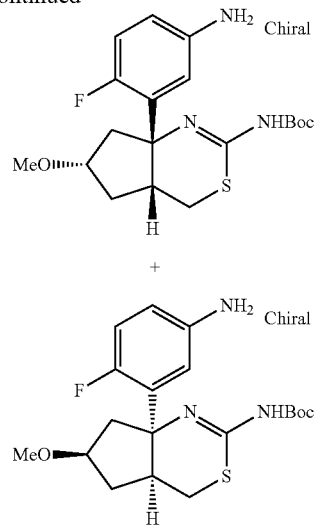

(1) Synthesis of [(1R*,2S*,4S*)-2-amino-2-(2-fluorophenyl)-4-methoxycyclopentyl]methanol Zinc (533 mg) was added to a solution of (3aR*,5S*,6aS*)-6a-(2-fluorophenyl)-5-methoxy-hexahydrocyclopenta[c]isoxazole (247 mg) in acetic acid (5 mL), and the mixture was stirred at room temperature for 12 hours. Zinc (500 mg) was added to the reaction solution, followed by stirring at room temperature for three hours. Zinc was removed by filtration and the filtrate was poured into a saturated sodium bicarbonate solution, followed by extraction with ethyl acetate. The extract was dried over anhydrous magnesium sulfate. The drying agent was removed by filtration and the filtrate was concentrated under reduced pressure to obtain the title compound (245 mg).

ESI-MS; m/z 240 [M$^+$+H].

(2) Synthesis of 9H-fluoren-9-ylmethyl ({[(1S*,2R*,4S*)-1-(2-fluorophenyl)-2-(hydroxymethyl)-4-methoxycyclopentyl]amino}carbonothioyl)carbamate A solution of [(1R*,2S*,4S*)-2-amino-2-(2-fluorophenyl)-4-methoxycyclopentanyl]methanol (225 mg) and fluorenylmethyloxycarbonyl isothiocyanate (316 mg) in dichloromethane (18 mL) was stirred at room temperature for three days. The reaction solution was purified by silica gel column chromatography to obtain the title compound (330 mg).

ESI-MS; m/z 543 [M$^+$+Na].

(3) Synthesis of [(4aR*,6S*,7aS*)-7a-(2-fluorophenyl)-6-methoxy-4,4a,5,6,7,7a-hexahydrocyclopenta[d][1,3]thiazin-2-yl]amine A solution of 9H-fluoren-9-ylmethyl({[(1S*,2R*,4S*)-1-(2-fluorophenyl)-2-(hydroxymethyl)-4-methoxycyclopentyl]amino}carbonothioyl)carbamate (330 mg) in methanol (20 mL)-concentrated hydrochloric acid (1 mL) was heated under reflux for three hours. The reaction solution was concentrated under reduced pressure. Acetonitrile (10 mL) and piperidine (1 mL) were added to the residue at room temperature, and the mixture was stirred at room temperature for one hour. The reaction solution was concentrated under reduced pressure. The resulting crude product was purified by NH-silica gel column chromatography to obtain the title compound (170 mg).

$^1$H-NMR (400 MHz, CDCl$_3$) δ (ppm): 1.98-2.10 (m, 2H), 2.14-2.24 (m, 1H), 2.58-2.68 (m, 1H), 2.77 (dd, J=4.8, 12.8 Hz, 1H), 2.91 (dd, J=3.2, 12.8 Hz, 1H), 2.98 (dd, J=8.4, 14.4 Hz, 1H), 3.33 (s, 3H), 4.10-4.22 (m, 1H), 7.01 (dd, J=8.0, 12.4 Hz, 1H), 7.09 (t, J=8.0 Hz, 1H), 7.17-7.35 (m, 2H).

(4) Synthesis of tert-butyl[(4aR*,6S*,7aS*)-7a-(2-fluoro-5-nitrophenyl)-6-methoxy-4,4a,5,6,7,7a-hexahydrocyclopenta[d][1,3]thiazin-2-yl]carbamate Fuming nitric acid (0.02 mL) was added to a solution of [(4aR*,6S*,7aS*)-7a-(2-fluorophenyl)-6-methoxy-4,4a,5,6,7,7a-hexahydrocyclopenta[d][1,3]thiazin-2-yl]amine (151 mg) in concentrated sulfuric acid (2 mL) at 0° C., and the mixture was stirred at 0° C. for 30 minutes. The reaction solution was poured into a 5 N sodium hydroxide solution-ice water, followed by extraction with ethyl acetate. The extract was washed with a saturated sodium chloride solution and then dried over anhydrous magnesium sulfate. The drying agent was removed by filtration and the filtrate was concentrated under reduced pressure. Triethylamine (0.301 mL) and di-tert-butyl dicarbonate (176 mg) were added to a solution of the resulting crude product in tetrahydrofuran (10 mL) at room temperature, and the mixture was stirred at room temperature for 12 hours. The reaction solution was poured into a saturated sodium bicarbonate solution, followed by extraction with ethyl acetate. The extract was washed with a saturated sodium chloride solution and then dried over anhydrous magnesium sulfate. The drying agent was removed by filtration and the filtrate was concentrated under reduced pressure. The resulting crude product was purified by silica gel column chromatography to obtain the title compound (118 mg).

$^1$H-NMR (400 MHz, CDCl$_3$) δ (ppm): 1.52 (s, 9H), 2.00-2.25 (m, 2H), 2.25-2.40 (m, 1H), 2.70-2.95 (m, 4H), 3.32 (s, 3H), 4.10-4.20 (m, 1H), 7.14-7.30 (m, 1H), 8.12-8.26 (m, 2H).

(5) Synthesis of tert-butyl[(4aR*,6S*,7aS*)-7a-(5-amino-2-fluorophenyl)-6-methoxy-4,4a,5,6,7,7a-hexahydrocyclopenta[d][1,3]thiazin-2-yl]carbamate A solution of tert-butyl[(4aR*,6S*,7aS*)-7a-(2-fluoro-5-nitrophenyl)-6-methoxy-4,4a,5,6,7,7a-hexahydrocyclopenta[d][1,3]thiazin-2-yl]carbamate (118 mg) and iron (133 mg) in ethanol (8 mL)-a saturated ammonium chloride solution (0.303 mL) was stirred at 87° C. for 30 minutes. The reaction solution was cooled to room temperature and then poured into water-ethyl acetate, followed by extraction with ethyl acetate. The extract was washed with a saturated sodium chloride solution and then dried over anhydrous magnesium sulfate. The drying agent was removed by filtration and the filtrate was concentrated under reduced pressure. The resulting crude product was purified by silica gel column chromatography to obtain the title compound (83 mg).

ESI-MS; m/z 396 [M$^+$+H].

(6) Synthesis of tert-butyl[(4aR*,6S*,7aS*)-7a-(5-amino-2-fluorophenyl)-6-methoxy-4,4a,5,6,7,7a-hexahydrocyclopenta[d][1,3]thiazin-2-yl]carbamate ((+)-isomer and (−)-isomer)

[Formula 32]

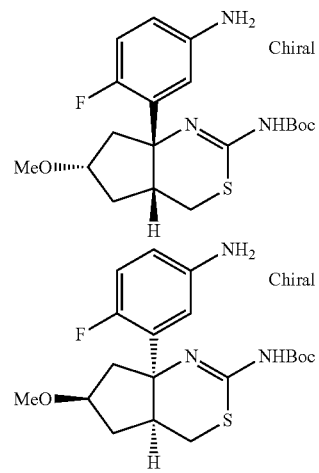

tert-Butyl(±)-[(4aR*,6S*,7aS*)-7a-(5-amino-2-fluorophenyl)-6-methoxy-4,4a,5,6,7,7a-hexahydrocyclopenta[d][1,3]thiazin-2-yl]carbamate (83 mg) was optically resolved by CHIRALPAK™ ADH manufactured by Daicel Chemical Industries, Ltd. (2 cm×25 cm, mobile phase: hexane:ethanol=8:2, flow rate: 10 mL/min). The components having a retention time of 14 to 17.5 minutes were collected to obtain the title (+)-isomer (44 mg; >99% ee). The components having a retention time of 17.5 to 23 minutes were collected to obtain the title (−)-isomer (45 mg; 95% ee). The property values of the (−)-compound are as shown below.
optical rotation (−)

$^1$H-NMR (400 MHz, CDCl$_3$) δ (ppm): 1.51 (s, 9H), 1.92-2.08 (m, 1H), 2.13 (ddd, J=6.4, 6.4, 12.0 Hz, 1H), 2.25-2.35 (m, 1H), 2.69 (dd, J=3.6, 13.2 Hz, 1H), 2.80-3.05 (m, 3H), 3.29 (s, 3H), 3.63 (brs, 2H), 4.10-4.20 (m, 1H), 6.54 (ddd, J=3.2, 3.6, 8.4 Hz, 1H), 6.59 (dd, J=3.2, 7.2 Hz, 1H), 6.84 (dd, J=8.4, 12.0 Hz, 1H).

Preparation Example 12

Synthesis of tert-butyl[(4aR*,6R*,7aS*)-7a-(5-amino-2-fluorophenyl)-6-methoxy-4,4a,5,6,7,7a-hexahydrocyclopenta[d][1,3]thiazin-2-yl]carbamate ((+)-isomer and (−)-isomer)

[Formula 33]

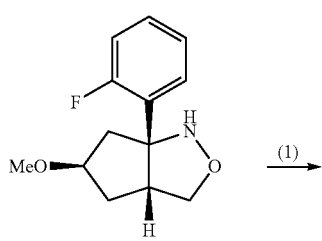

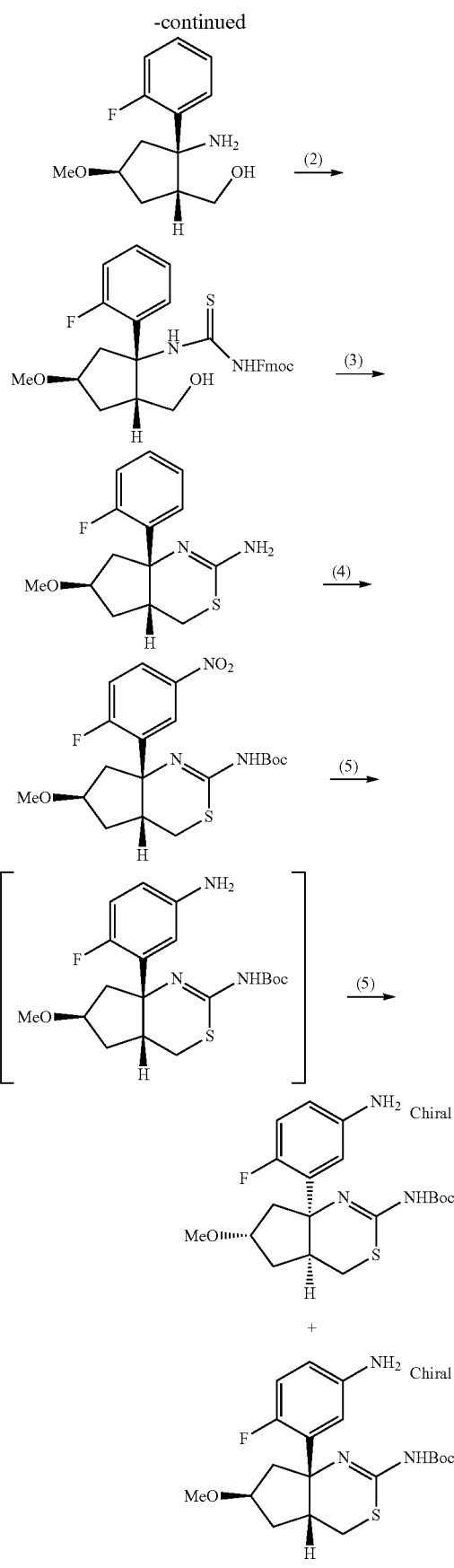

-continued (1) Synthesis of [(1R*,2S*,4R*)-2-amino-2-(2-fluorophenyl)-4-methoxycyclopentyl]methanol Zinc (533 mg) was added to a solution of (3aR*,5R*,6aS*)-6a-(2-fluorophenyl)-5-methoxy-hexahydrocyclopenta[c]isoxazole (275 mg) in acetic acid (5.57 mL), and the mixture was stirred at room temperature for 12 hours. More zinc (500 mg) was added to the reaction solution, followed by stirring at room temperature for three hours. Zinc was removed by filtration and the filtrate was poured into a saturated sodium bicarbonate solution, followed by extraction with ethyl acetate. The extract was dried over anhydrous magnesium sulfate. The drying agent was removed by filtration and the filtrate was concentrated under reduced pressure to obtain the title compound (270 mg).

ESI-MS; m/z 240 [M$^+$+H].

(2) Synthesis of 9H-fluoren-9-ylmethyl({[(1S*,2R*,4R*)-1-(2-fluorophenyl)-2-(hydroxymethyl)-4-methoxycyclopentyl]amino}carbonothioyl)carbamate A solution of [(1R*,2S*,4R*)-2-amino-2-(2-fluorophenyl)-4-methoxycyclopentyl]methanol (250 mg) and fluorenylmethyloxycarbonyl isothiocyanate (351 mg) in dichloromethane (20 mL) was stirred at room temperature for three days. The reaction solution was purified by silica gel column chromatography to obtain the title compound (340 mg).

ESI-MS; m/z 543 [M$^+$+Na].

(3) Synthesis of [(4aR*,6S*,7aS*)-7a-(2-fluorophenyl)-6-methoxy-4,4a,5,6,7,7a-hexahydrocyclopenta[d][1,3]thiazin-2-yl]amine A solution of 9H-fluoren-9-ylmethyl({[(1S*,2R*,4R*)-1-(2-fluorophenyl)-2-(hydroxymethyl)-4-methoxycyclopentyl]amino}carbonothioyl)carbamate (340 mg) in methanol (20 mL)-concentrated hydrochloric acid (1 mL) was heated under reflux for three hours. The reaction solution was concentrated under reduced pressure. Acetonitrile (10 mL) and piperidine (2 mL) were added to the residue at room temperature, and the mixture was stirred at room temperature for one hour. The reaction solution was concentrated under reduced pressure. The crude product was purified by NH-silica gel column chromatography to obtain the title compound (130 mg).

$^1$H-NMR (400 MHz, CDCl$_3$) δ (ppm): 1.87 (ddd, J=3.6, 9.2, 13.2 Hz, 1H), 2.20-2.38 (m, 2H), 2.64 (dd, J=6.8, 12.8 Hz, 1H), 2.73 (dd, J=3.6, 12.8 Hz, 1H), 2.95 (dd, J=3.6, 12.8 Hz, 1H), 3.05-3.15 (m, 1H), 3.33 (s, 3H), 3.87-4.00 (m, 1H), 7.02 (dd, J=7.6, 12.0 Hz, 1H), 7.09 (t, J=7.6 Hz, 1H), 7.17-7.33 (m, 2H).

(4) Synthesis of tert-butyl[(4aR*,6R*,7aS*)-7a-(2-fluoro-5-nitrophenyl)-6-methoxy-4,4a,5,6,7,7a-hexahydrocyclopenta[d][1,3]thiazin-2-yl]carbamate Fuming nitric acid (0.0193 mL) was added to a solution of (4aR*,6R*,7aS*)-7a-(2-fluorophenyl)-6-methoxy-4,4a,5,6,7,7a-hexahydrocyclopenta[d][1,3]thiazin-2-yl]amine (146 mg) in concentrated sulfuric acid (2 mL) at 0° C., and the mixture was stirred at 0° C. for 30 minutes. The reaction solution was poured into a 5 N sodium hydroxide solution-ice water, followed by extraction with ethyl acetate. The extract was washed with a saturated sodium chloride solution and then dried over anhydrous magnesium sulfate. The drying agent was removed by filtration and the filtrate was concentrated under reduced pressure. Triethylamine (0.291 mL) and di-tert-butyl dicarbonate (170 mg) were added to a solution of the resulting crude product in tetrahydrofuran (9.67 mL) at room temperature, and the mixture was stirred at room temperature for 12 hours. The reaction solution was poured into a saturated sodium bicarbonate solution, followed by extraction with ethyl acetate. The extract was washed with a saturated sodium chloride solution and then dried over anhydrous magnesium sulfate. The drying agent was removed by filtration and the filtrate was concentrated under reduced pressure. The resulting crude product was purified by silica gel column chromatography to obtain the title compound (198 mg).

$^1$H-NMR (400 MHz, CDCl$_3$) δ (ppm): 1.53 (s, 9H), 1.92-2.06 (m, 1H), 2.30-2.45 (m, 2H), 2.54 (dd, J=6.0, 12.8 Hz, 1H), 2.68-2.80 (m, 1H), 2.80-3.00 (m, 1H), 3.18-3.36 (m, 1H), 3.30 (s, 3H), 3.90-4.10 (m, 1H), 7.00-7.40 (m, 1H), 8.05-8.30 (m, 2H).

(5) Synthesis of tert-butyl[(4aR*,6R*,7aS*)-7a-(5-amino-2-fluorophenyl)-6-methoxy-4,4a,5,6,7,7a-hexahydrocyclopenta[d][1,3]thiazin-2-yl]carbamate ((+)-isomer and (−)-isomer)

[Formula 34]

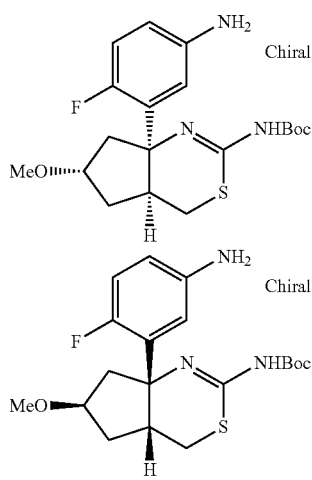

A solution of tert-butyl[(4aR*,6R*,7aS*)-7a-(2-fluoro-5-nitrophenyl)-6-methoxy-4,4a,5,6,7,7a-hexahydrocyclopenta[d][1,3]thiazin-2-yl]carbamate (198 mg) and iron (223 mg) in ethanol (13.4 mL)-a saturated ammonium chloride solution (0.508 mL) was stirred at 87° C. for 30 minutes. The reaction solution was poured into ethyl acetate-water at room temperature, followed by extraction with ethyl acetate. The extract was washed with a saturated sodium chloride solution and then dried over anhydrous magnesium sulfate. The drying agent was removed by filtration and the filtrate was concentrated under reduced pressure. The resulting crude product was purified by silica gel column chromatography to obtain the title (±)-mixture (118 mg).

This was optically resolved by CHIRALPAK™ ADH manufactured by Daicel Chemical Industries, Ltd. (2 cm×25 cm, mobile phase: hexane:ethanol ~5:5, flow rate: 10 mL/min). The components having a retention time of 8 to 11 minutes were collected to obtain the title (+)-isomer (52 mg; >95% ee). The components having a retention time of 17.5 to 23 minutes were collected to obtain the title (−)-isomer (52 mg; >95% ee). The property values of the (−)-isomer of the title compound are as shown below. optical rotation (−).

$^1$H-NMR (400 MHz, CDCl$_3$) δ (ppm): 1.52 (s, 9H), 1.90-2.02 (m, 1H), 2.26-2.44 (m, 2H), 2.65 (dd, J=6.0, 13.6 Hz, 1H), 2.70 (dd, J=3.6, 13.6 Hz, 1H), 3.03 (dd, J=3.6, 13.6 Hz, 1H), 3.20-3.36 (m, 1H), 3.32 (s, 3H), 3.62 (brs, 2H), 4.00-4.10 (m, 1H), 6.45-6.66 (m, 2H), 6.86 (dd, J=8.4, 12.0 Hz, 1H).

Preparation Example 13

Synthesis of 5-cyanopyridine-2-carboxylic acid

[Formula 35]

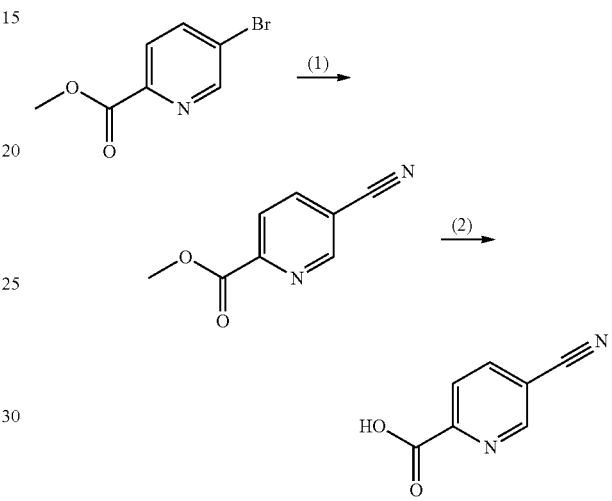

Synthesis of methyl 5-cyanopyridine-2-carboxylate

A mixture of methyl 5-bromopyridine-2-carboxylate (2.8 g) and copper cyanide (3.6 g) in NMP (30 mL) was heated with stirring at 170° C. for 1.5 hours. Water was added to the reaction solution at room temperature, and the insoluble matter was removed by filtration. The filtrate was extracted with ethyl acetate. The extract was washed with a saturated sodium chloride solution and then dried over anhydrous magnesium sulfate. The drying agent was removed by filtration and the filtrate was concentrated under reduced pressure. The resulting crude product was purified by silica gel column chromatography (ethyl acetate-heptane system) to obtain the title compound (920 mg).

$^1$H-NMR (400 MHz, CDCl$_3$) δ (ppm): 4.06 (s, 3H), 8.16 (dd, J=2.0, 8.0 Hz, 1H), 8.27 (d, J=8.0 Hz, 1H), 9.01 (d, J=2.0 Hz, 1H).

Synthesis of 5-cyanopyridine-2-carboxylic acid

A solution of the compound of Preparation Example 13-(1) (920 mg) and a 5 N sodium hydroxide solution (2.26 mL) in ethanol (30 mL) was stirred at room temperature for 10 minutes. 5 N hydrochloric acid (5.2 mL) was added to the reaction solution at room temperature, followed by extraction with ethyl acetate. The extract was dried over anhydrous magnesium sulfate. The drying agent was removed by filtration and the filtrate was concentrated under reduced pressure to obtain the title compound (800 mg).

$^1$H-NMR (400 MHz, DMSOd$_6$) δ (ppm): 8.18 (d, J=8.0 Hz, 1H), 8.51 (dd, J=2.0, 8.0 Hz, 1H), 9.12-9.18 (m, 1H).

Preparation Example 14

Synthesis of 5-difluoromethoxypyrazine-2-carboxylic acid

[Formula 36]

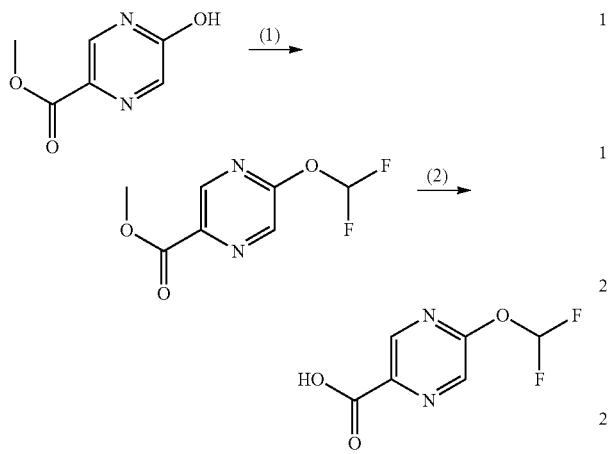

(1) Synthesis of methyl 5-difluoromethoxypyrazine-2-carbonxylate

Potassium carbonate (8.82 g) and sodium chlorodifluoroacetate (6.53 g) were added to a solution of a compound (CAS 13924-95-3) (3.3 g) in DMF (42.8 mL). The reaction solution was stirred at 100° C. for 30 minutes, and then saturated aqueous ammonium chloride was added, followed by extraction with ethyl acetate. The organic layer was washed with a saturated sodium bicarbonate solution and a saturated sodium chloride solution and then dried over magnesium sulfate. The drying agent was removed by filtration and then the solvent was evaporated under reduced pressure. The residue was purified by silica gel column chromatography to obtain the title compound (928 mg).

$^1$H-NMR (400 MHz, CDCl$_3$) δ (ppm): 4.04 (s, 3H), 7.49 (t, J=71.2 Hz, 1H), 8.47 (d, J=0.8 Hz, 1H), 8.92 (d, J=0.8 Hz, 1H).

(2) Synthesis of 5-difluoromethoxypyrazine-2-carboxylic acid

Water (1.54 mL) and a 5 N sodium hydroxide solution (492 mL) were added to a solution of the compound obtained in Preparation Example 14-(1) (250 mg) in THF (4.60 mL). The reaction solution was stirred at room temperature for five minutes and then a 2 N hydrochloric acid solution was added, followed by extraction with ethyl acetate. The organic layers were washed with a saturated sodium chloride solution and then dried over magnesium sulfate. The drying agent was removed by filtration and then the solvent was concentrated under reduced pressure to obtain the title compound (200 mg).

$^1$H-NMR (400 MHz, CDCl$_3$) δ (ppm): 7.51 (t, J=71.2 Hz, 1H), 8.39 (d, J=1.2 Hz, 1H), 9.04 (d, J=1.2 Hz, 1H).

Preparation Example 15

Synthesis of 5-fluoromethoxypyrazine-2-carboxylic acid

[Formula 37]

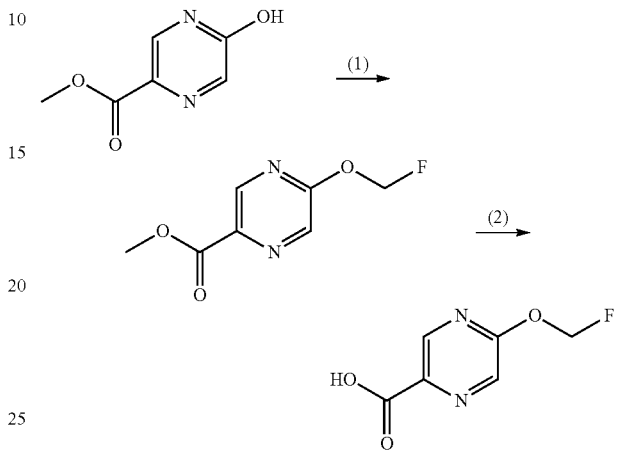

(1) Synthesis of methyl 5-fluoromethoxypyrazine-2-carboxylate

Fluoromethyl toluene-4-sulfonate (Journal of Labelled Compounds & Radiopharmaceuticals, 46 (6), 555-566; 2003) (344 mg) and cesium carbonate (824 mg) were added to a solution of methyl 5-hydroxypyrazine-2-carboxylate (130 mg) in N,N-dimethylformamide (2.0 mL). The reaction solution was stirred at 70° C. for five hours and 30 minutes and then cooled to room temperature. Water was added to the reaction solution, followed by extraction with ethyl acetate. The organic layer was concentrated under reduced pressure. The residue was purified by NH-silica gel column chromatography to obtain the title compound (18.0 mg).

$^1$H-NMR (400 MHz, CDCl$_3$) δ (ppm): 4.03 (s, 3H), 6.14 (d, J=51.2 Hz, 2H), 8.42 (d, J=1.2 Hz, 1H), 8.94 (d, J=1.2 Hz, 1H).

(2) Synthesis of 5-fluoromethoxypyrazine-2-carboxylic acid

Potassium trimethylsilanolate (18.6 mg) was added to a solution of methyl 5-fluoromethoxypyrazine-2-carboxylate obtained in Preparation Example 15-(1) (18.0 mg) in tetrahydrofuran (1.0 mL). The reaction solution was stirred at room temperature for one hour. Water and ethyl acetate were added to the reaction solution, and the aqueous layer was separated. The aqueous layer was made acidic with 1 M hydrochloric acid, followed by extraction with ethyl acetate. The organic layer was dried over anhydrous magnesium sulfate. The drying agent was removed by filtration and the filtrate was concentrated under reduced pressure to obtain a crude product of the title compound (10.2 mg). The compound was used for the next reaction without further purification.

$^1$H-NMR (400 MHz, CDCl$_3$) δ (ppm): 6.16 (d, J=50.8 Hz, 2H), 8.34 (d, J=1.4 Hz, 1H), 9.05 (d, J=1.4 Hz, 1H).

Preparation Example 16

Synthesis of 5-fluoromethoxypyridine-2-carboxylic acid

[Formula 38]

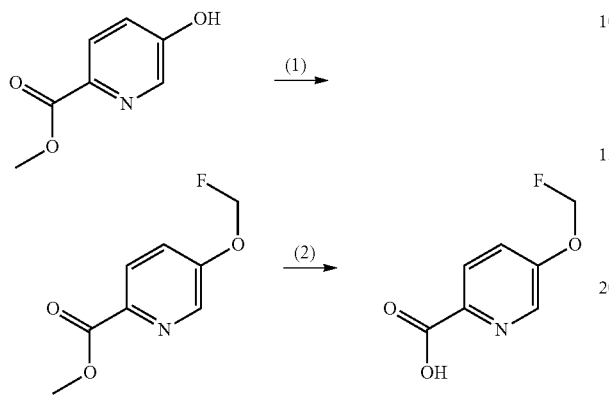

(1) Synthesis of methyl 5-fluoromethoxypyridine-2-carboxylate

A solution containing fluoromethyl toluene-4-sulfonate (233 mg) in DMF was added to a solution containing methyl 5-hydroxypyridine-2-carboxylate (100 mg) and cesium carbonate (532 mg) in DMF (5 mL). The reaction solution was stirred at 70° C. for three hours. The reaction solution was cooled to room temperature. Ethyl acetate and saturated aqueous ammonium chloride were added to the reaction solution, and the organic layer was separated. The organic layer was dried over anhydrous magnesium sulfate, and the insoluble matter was separated by filtration. The filtrate was concentrated and the residue was purified by silica gel column chromatography to obtain the title compound (51 mg).

$^1$H-NMR (CDCl$_3$) δ (ppm): 4.00 (s, 3H), 5.80 (d, J=45.1 Hz, 2H), 7.51 (ddd, J=0.8, 2.8, 8.8 Hz, 1H), 8.16 (d, J=0.4, 8.8 Hz, 1H), 8.54 (d, J=2.8 Hz, 1H).

(2) Synthesis of 5-fluoromethoxypyridine-2-carboxylic acid

N sodium hydroxide (81 μL) was added to a solution containing methyl 5-fluoromethoxypyridine-2-carboxylate (50 mg) in tetrahydrofuran/water (2 mL, 3/1), and the mixture was stirred at room temperature for 10 minutes. Water (1 mL) was added to the reaction solution, followed by further stirring for 20 minutes. The reaction solution was made acidic with 5 N hydrochloric acid. Ethyl acetate and a saturated sodium chloride solution were added to the reaction solution, and the organic layer was separated. The organic layer was dried over anhydrous magnesium sulfate, and the insoluble matter was separated by filtration. The filtrate was concentrated to obtain the title compound (22.6 mg).

$^1$H-NMR (CDCl$_3$) δ (ppm): 5.81 (d, J=53.2 Hz, 2H), 7.61 (ddd, J=0.8, 2.8, 8.8 Hz, 1H), 8.25 (d, J=0.8, 8.8 Hz, 1H), 8.42 (d, J=2.4 Hz, 1H).

Preparation Example 17

Synthesis of 5-difluoromethylpyrazine-2-carboxylic acid

[Formula 39]

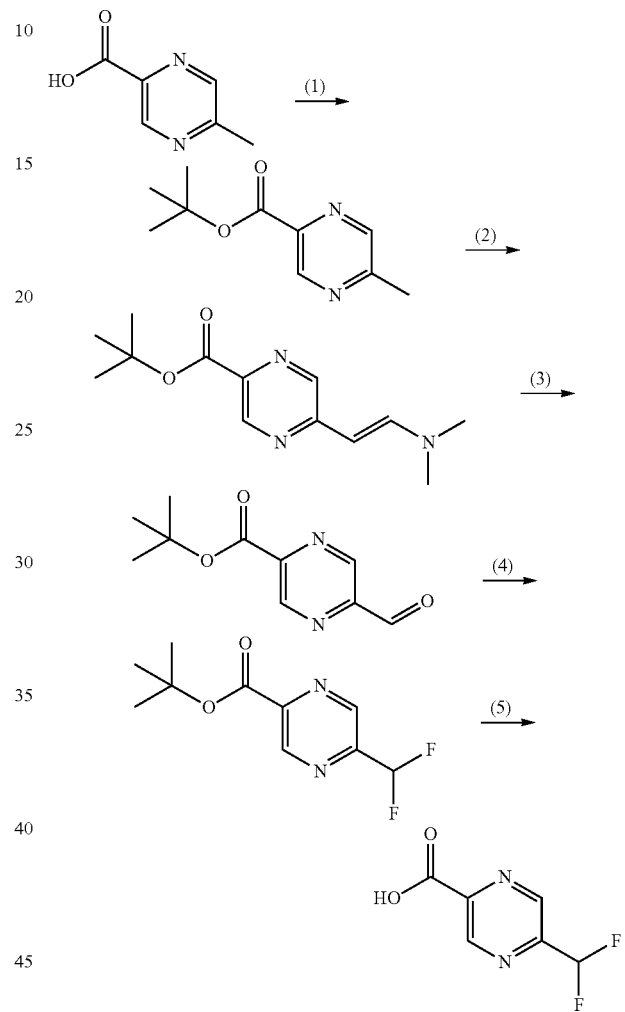

(1) Synthesis of t-butyl 5-methylpyrazine-2-carboxylate

A boron trifluoride-diethyl ether complex (91.7 μL) was added dropwise to a suspension of 2-methylpyrazine-5-carboxylic acid (1 g) and tert-butyl 2,2,2-trichloroacetimidate (4.75 g) in tetrahydrofuran (20 mL) under ice-cooling. The reaction solution was warmed to room temperature, followed by stirring for two hours. A saturated sodium chloride solution and ethyl acetate were added to the reaction solution, and the organic layer was separated. The organic layer was dried over anhydrous magnesium sulfate, and the insoluble matter was separated by filtration. The filtrate was concentrated and purified by silica gel column chromatography to obtain the title compound (1.4 g).

$^1$H-NMR (CDCl$_3$) δ (ppm): 1.65 (s, 9H), 2.65 (s, 3H), 8.57 (d, J=1.2 Hz, 1H), 9.10 (d, J=1.6 Hz, 1H).

(2) Synthesis of t-butyl 5-((E)-2-dimethylamino-vinyl)-pyrazine-2-carboxylate A mixture of t-butyl 5-methylpyrazine-2-carboxylate (1.35 g), N,N-dimethylformamide (25 mL) and N,N-dimethylformamide dimethylacetal (25 mL) was stirred at 130° C. for five hours. The reaction solution was cooled to room temperature and diluted with ethyl acetate. The mixture was washed with a saturated sodium chloride solution three times. The organic layer was dried over anhydrous magnesium sulfate, and the insoluble matter was separated by filtration. The filtrate was concentrated and the residue was purified by silica gel column chromatography to obtain the title compound (648 mg).

$^1$H-NMR (CDCl$_3$) δ (ppm): 1.63 (s, 9H), 3.00 (s, 6H), 5.16 (d, J=12.8 Hz, 1H), 7.72 (d, J=12.8 Hz, 1H), 8.16 (d, J=1.2 Hz, 1H), 8.81 (d, J=1.6 Hz, 1H).

(3) Synthesis of t-butyl 5-formylpyrazine-2-carboxylate

Sodium periodate (1.67 g) was added to a solution of t-butyl 5-((E)-2-dimethylamino-vinyl)-pyrazine-2-carboxylate (645 mg) in 50% tetrahydrofuran-water (26 mL), and the mixture was stirred at room temperature for four hours. A saturated sodium bicarbonate solution and ethyl acetate were added to the reaction solution, and the organic layer was separated. The organic layer was washed with a saturated sodium chloride solution and dried over anhydrous magnesium sulfate. The insoluble matter was separated by filtration and the filtrate was concentrated. The residue was purified by silica gel column chromatography to obtain the title compound (249 mg).

$^1$H-NMR (CDCl$_3$) δ (ppm): 1.68 (s, 9H), 9.25 (d, J=1.2 Hz, 1H), 9.36 (d, J=1.6 Hz, 1H), 10.2 (s, 1H).

(4) Synthesis of t-butyl 5-difluoromethylpyrazine-2-carboxylate

[Bis(2-methoxyethyl)amino]sulfur trifluoride (662 μL) was added dropwise to a solution of t-butyl 5-formylpyrazine-2-carboxylate (249 mg) in dichloromethane (12 mL) under a nitrogen atmosphere under ice-cooling. The reaction solution was stirred for two hours while gradually returning to room temperature. A saturated sodium bicarbonate solution and ethyl acetate were added to the reaction solution, and the organic layer was separated. The organic layer was washed with a saturated sodium chloride solution and dried over anhydrous magnesium sulfate. The insoluble matter was separated by filtration and the filtrate was concentrated. The residue was purified by silica gel column chromatography to obtain the title compound (175 mg).

$^1$H-NMR (CDCl$_3$) δ (ppm): 1.67 (s, 9H), 6.75 (t, J=54.4 Hz, 1H), 9.02 (d, J=0.8 Hz, 1H), 9.25 (d, J=0.8 Hz, 1H).

(5) Synthesis of 5-difluoromethylpyrazine-2-carboxylic acid

Trifluoroacetic acid (1 mL) was added to a solution of t-butyl 5-difluoromethylpyrazine-2-carboxylate (175 mg) in dichloromethane (1 mL), and the mixture was stirred at room temperature for five hours. Ether and 5 N sodium hydroxide were added to the reaction solution. The aqueous layer was separated and made acidic with 5 N hydrochloric acid. Ethyl acetate was added to the aqueous layer, and the organic layer was separated. The organic layer was dried over anhydrous magnesium sulfate, and the insoluble matter was separated by filtration. The filtrate was concentrated to obtain the title compound (100 mg).

$^1$H-NMR (CDCl$_3$) δ (ppm): 6.80 (t, J=54.4 Hz, 1H), 9.02 (s, 1H), 9.47 (s, 1H).

Preparation Example 18

Synthesis of tert-butyl(±)-{(4aR*,7aS*)-7a-[3-(2-fluoropyridin-3-yl)phenyl]-4,4a,5,6,7,7a-hexahydro-pyrrolo[3,4-d][1,3]thiazin-2-yl}carbamate

[Formula 40]

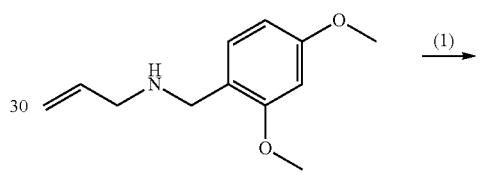

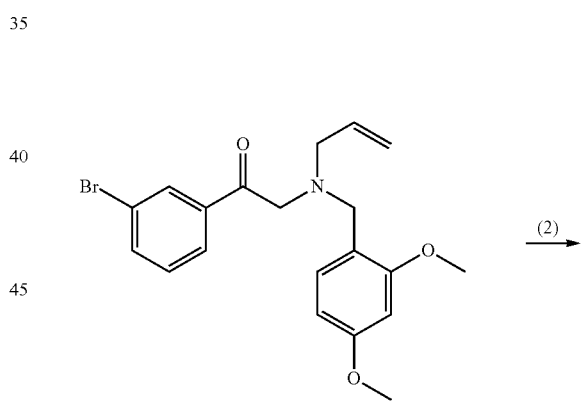

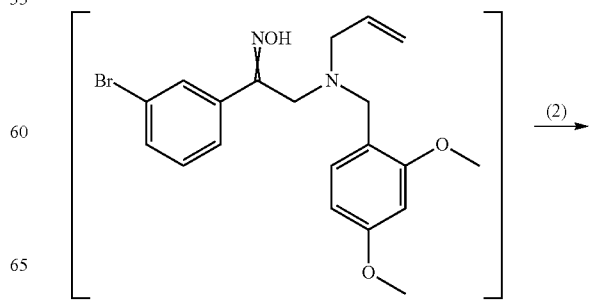

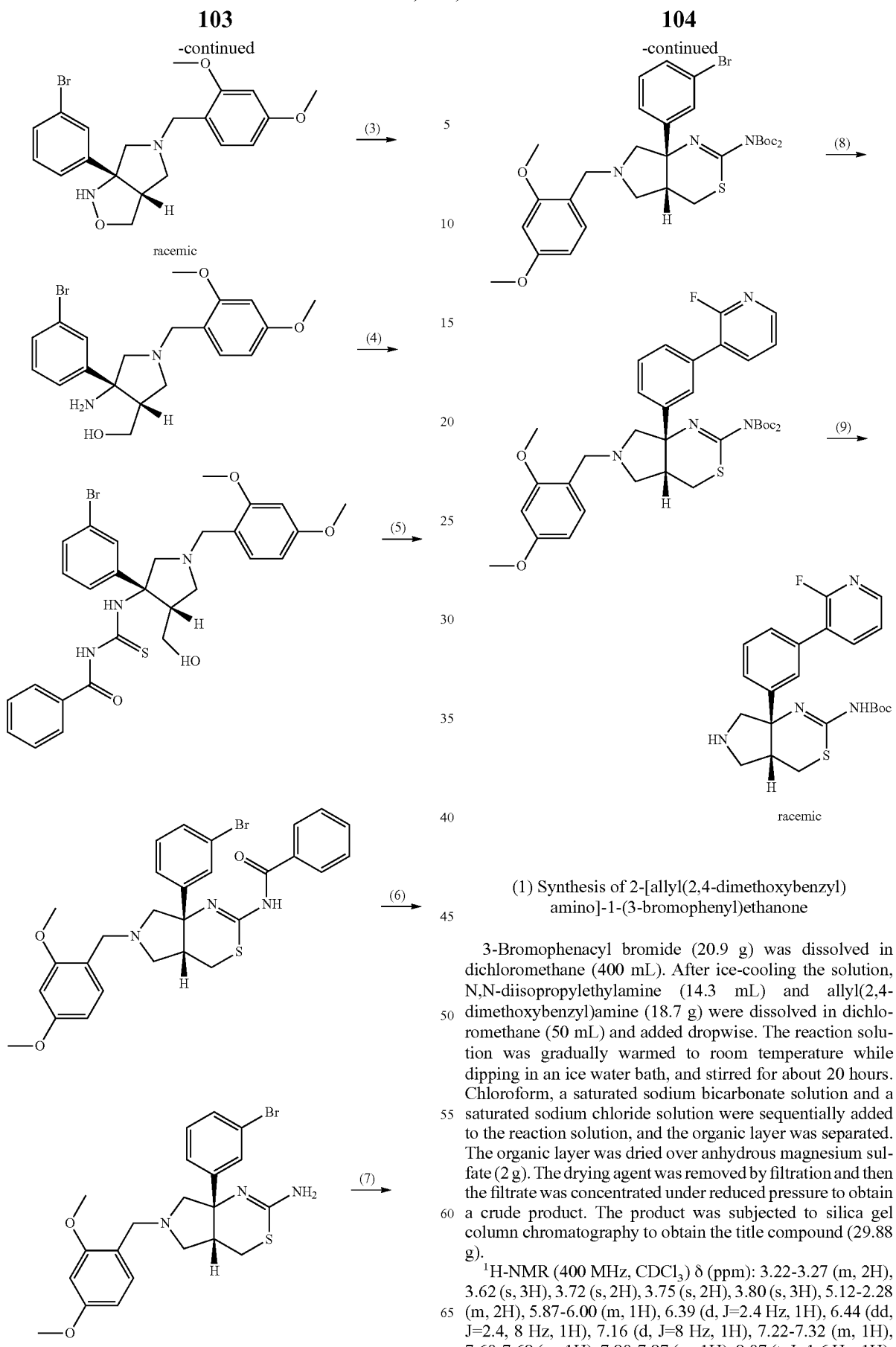

(1) Synthesis of 2-[allyl(2,4-dimethoxybenzyl)amino]-1-(3-bromophenyl)ethanone

3-Bromophenacyl bromide (20.9 g) was dissolved in dichloromethane (400 mL). After ice-cooling the solution, N,N-diisopropylethylamine (14.3 mL) and allyl(2,4-dimethoxybenzyl)amine (18.7 g) were dissolved in dichloromethane (50 mL) and added dropwise. The reaction solution was gradually warmed to room temperature while dipping in an ice water bath, and stirred for about 20 hours. Chloroform, a saturated sodium bicarbonate solution and a saturated sodium chloride solution were sequentially added to the reaction solution, and the organic layer was separated. The organic layer was dried over anhydrous magnesium sulfate (2 g). The drying agent was removed by filtration and then the filtrate was concentrated under reduced pressure to obtain a crude product. The product was subjected to silica gel column chromatography to obtain the title compound (29.88 g).
$^1$H-NMR (400 MHz, CDCl$_3$) δ (ppm): 3.22-3.27 (m, 2H), 3.62 (s, 3H), 3.72 (s, 2H), 3.75 (s, 2H), 3.80 (s, 3H), 5.12-2.28 (m, 2H), 5.87-6.00 (m, 1H), 6.39 (d, J=2.4 Hz, 1H), 6.44 (dd, J=2.4, 8 Hz, 1H), 7.16 (d, J=8 Hz, 1H), 7.22-7.32 (m, 1H), 7.60-7.68 (m, 1H), 7.80-7.87 (m, 1H), 8.07 (t, J=1.6 Hz, 1H).

(2) Synthesis of (3aS*,6aR*)-6a-(3-bromophenyl)-5-(2,4-dimethoxybenzyl)-hexahydropyrrolo[3,4-c]isoxazole The compound obtained in Preparation Example 18-(1) (29.8 g) was dissolved in ethanol (475 mL). Hydroxyamine hydrochloride (10.3 g) and sodium acetate (12.1 g) were added to the solution, and the mixture was heated with stirring at 90° C. After five hours, the reaction solution was cooled and then filtered. The filtrate was concentrated under reduced pressure. Ethyl acetate was added to the residue, and the mixture was sequentially washed with a saturated sodium bicarbonate solution and a saturated sodium chloride solution. The organic layer was dried over anhydrous magnesium sulfate (2 g). The drying agent was removed by filtration and then the filtrate was concentrated under reduced pressure to obtain an oxime compound (31.3 g). The oxime compound (31.3 g) was dissolved in toluene (600 mL). The solution was heated under reflux under a nitrogen atmosphere for eight hours. The reaction solution was to room temperature and then concentrated under reduced pressure. The residue was subjected to silica gel column chromatography to obtain the title compound (19 g).
$^1$H-NMR (400 MHz, CDCl$_3$) δ (ppm): 2.44 (brs, 1H), 2.65 (brs, 1H), 2.91 (brs, 1H), 2.97-3.14 (m, 2H), 3.50-3.62 (m, 1H), 3.66 (s, 2H), 3.79 (s, 3H), 3.81 (s, 3H), 4.47 (brs, 1H), 5.42 (brs, 1H), 6.44-6.50 (m, 2H), 7.15-7.22 (m, 2H), 7.33-7.40 (m, 1H), 7.42-7.49 (m, 1H), 7.69-7.74 (m, 1H).

(3) Synthesis of (±)-[(3S*,4R*)-4-amino-4-(3-bromophenyl)-1-(2,4-dimethoxybenzyl)pyrrolidin-3-yl]methanol The compound obtained in Preparation Example 18-(2) (19 g) was dissolved in acetic acid (230 mL). Zinc (30 g) was added to the solution, followed by stirring at room temperature. After 20 hours, the reaction solution was filtered through celite. The filtrate was concentrated under reduced pressure. A 5 N sodium hydroxide solution and chloroform were added to the residue, followed by filtration through celite. The filtrate was separated. The organic layer was dried over anhydrous magnesium sulfate. The drying agent was removed by filtration and the filtrate was concentrated under reduced pressure to obtain a residue. The residue was subjected to silica gel column chromatography to obtain the title compound (19.1 g).
ESI-MS; m/z 421 [M+H].
$^1$H-NMR (400 MHz, CDCl$_3$) δ (ppm): 2.44-2.53 (m, 1H), 2.68-2.77 (m, 3H), 2.97 (d, J=9.2 Hz, 1H), 3.62-3.82 (m, 4H), 3.81 (s, 3H), 3.82 (s, 3H) 6.44 (m, 2H), 7.18-7.29 (m, 2H), 7.34-7.40 (m, 1H), 7.46-7.53 (m, 1H), 7.71 (t, J=2.0 Hz, 1H).

(4) Synthesis of (±)-1-benzoyl-3-[(3R*,4S*)-3-(3-bromophenyl)-1-(2,4-dimethoxybenzyl)-4-hydroxylmethylpyrrolidin-3-yl]thiourea The compound obtained in Preparation Example 18-(3) (2.29 g) was dissolved in dichloromethane (50 mL). Benzoyl isothiocyanate (807 µL) was added to the solution, followed by stirring at room temperature. After 11 hours, the reaction solution was concentrated under reduced pressure. The residue was subjected to silica gel column chromatography to obtain the title compound (1.96 g).
$^1$H-NMR (400 MHz, CDCl$_3$) δ (ppm): 2.55 (t, J=8.4 Hz, 1H), 2.81-2.90 (m, 1H), 2.98-3.06 (m, 1H), 3.20 (d, J=10.4 Hz, 1H), 3.63-3.83 (m, 3H), 3.81 (s, 3H), 3.83 (s, 3H), 3.87-3.99 (m, 2H), 6.44-6.52 (m, 2H), 7.18 (t, J=8.0 Hz, 1H), 7.24-7.32 (m, 1H), 7.33-7.38 (m, 1H), 7.40-7.46 (m, 1H), 7.49-7.57 (m, 2H), 7.61-7.70 (m, 2H), 7.84-7.91 (m, 2H), 8.91 (s, 1H), 11.7 (s, 1H).

(5) Synthesis of (±)-N-[(4aR*,7aS*)-7a-(3-bromophenyl)-6-(2,4-dimethoxybenzyl)-4,4a,5,6,7,7a-hexahydropyrrolo[3,4-d][1,3]thiazin-2-yl]benzamide A solution of the compound obtained in Preparation Example 18-(4) (1.43 g) and pyridine (810 µL) in dichloromethane (55 mL) was cooled to −50° C. Trifluoromethanesulfonic anhydride (1.1 mL) was added dropwise to the solution, and the mixture was gradually warmed to 0° C. After one hour and 30 minutes, the reaction solution was cooled to −20° C., diluted with chloroform and washed with a saturated sodium bicarbonate solution. The organic layer was dried over anhydrous magnesium sulfate. The drying agent was removed by filtration. The filtrate was concentrated under reduced pressure to obtain a residue. The residue was subjected to silica gel column chromatography to obtain the title compound (1.30 g).
$^1$H-NMR (400 MHz, CDCl$_3$) δ (ppm): 2.73 (dd, J=4.4, 13.6 Hz, 1H), 2.90 (d, J=10.4 Hz, 1H), 2.92-3.18 (m, 4H), 3.38 (d, J=10.4 Hz, 1H), 3.70 (s, 2H), 3.77 (s, 3H), 3.81 (s, 3H), 6.40 (dd, J=2.4, 8.4 Hz, 1H), 6.44 (d, J=2.4 Hz, 1H), 7.18-7.30 (m, 2H), 7.40-7.54 (m, 5H), 7.68-7.72 (m, 1H), 8.17-8.26 (m, 2H).

(6) Synthesis of (±)-(4aR*,7aS*)-7a-(3-bromophenyl)-6-(2,4-dimethoxybenzyl)-4,4a,5,6,7,7a-hexahydropyrrolo[3,4-d][1,3]thiazin-2-ylamine 1,8-Diazabicyclo[5.4.0]undec-7-ene (684 µL) was added to a solution of the compound obtained in Preparation Example 18-(5) (1.3 g) in methanol (22 mL), and the mixture was heated under reflux. After four hours and 30 minutes, the reaction solution was left to cool and then concentrated under reduced pressure to obtain a residue. The residue was suspended in t-butyl methyl ether and collected by filtration to obtain the title compound (837 mg).
$^1$H-NMR (400 MHz, CDCl$_3$) δ (ppm): 2.52-2.68 (m, 3H), 2.72-2.80 (m, 1H), 2.92 (dd, J=4.0, 12.8 Hz, 1H), 3.06-3.14 (m, 1H), 3.39 (d, J=9.6 Hz, 1H), 3.64 (d, J=10 Hz, 2H), 3.81 (s, 3H), 3.83 (s, 3H), 4.48 (brs, 2H), 6.44-6.50 (m, 2H), 7.13-7.19 (m, 1H), 7.27-7.34 (m, 2H), 7.46-7.52 (m, 1H), 7.70-7.74 (m, 1H).

(7) Synthesis of (±)-di-t-butyl[(4aR*,7aS*)-7a-(3-bromophenyl)-6-(2,4-dimethoxybenzyl)-4,4a,5,6,7,7a-hexahydropyrrolo[3,4-d][1,3]thiazin-2-yl]imiodicarbonate The compound obtained in Preparation Example 18-(6) (1.14 g) was dissolved in THF (45 mL) and DMF (20 mL). Di-t-butyl dicarbonate (3.23 g) and 4-dimethylaminopyridine (2.11 g) were sequentially added to the solution, and then the mixture was stirred at room temperature. After about 17 hours, the reaction solution was concentrated under reduced pressure. Ethyl acetate and a saturated sodium bicarbonate solution were added to the residue, and the organic layer was separated. The organic layer was washed with a saturated sodium chloride solution and dried over anhydrous magnesium sulfate. The drying agent was removed by filtration and the filtrate was concentrated under reduced pressure to obtain a residue. The residue was subjected to silica gel chromatography to obtain the title compound (1.33 g).

$^1$H-NMR (400 MHz, CDCl$_3$) δ (ppm): 1.56 (s, 18H), 2.54 (d, J=10 Hz, 1H), 2.60-2.80 (m, 3H), 2.92-3.00 (m, 1H), 3.10-3.18 (m, 1H), 3.53-3.70 (m, 3H), 3.81 (s, 3H), 3.82 (s, 3H), 6.42-6.54 (m, 2H), 7.16-7.22 (m, 1H), 7.26-7.38 (m, 2H), 7.46-7.53 (m, 1H), 7.64 (t, J=2.0 Hz, 1H).

(8) Synthesis of (±)-di-t-butyl{(4aR*,7aS*)-6-(2,4-dimethoxybenzyl)-7a-[3-(2-fluoropyridin-3-yl)phenyl]-4,4a,5,6,7,7a-hexahydropyrrolo[3,4-d][1,3]thiazin-2-yl}imidodicarbonate The compound obtained in Preparation Example 18-(7) (1.33 g) was dissolved in THF (25 mL). 2-Fluoropyridine-3-boronic acid (848 mg), potassium fluoride (495 mg), Pd2DBA3 (172 mg) and Pd(t-Bu3P)2 (195 mg) were added to the solution, and the mixture was stirred under a nitrogen atmosphere at room temperature. After 3.5 hours, the reaction solution was diluted with ethyl acetate and filtered through NH silica gel (80 mL). This was further washed with ethyl acetate:heptane=1:1 (500 mL). The filtrate was concentrated under reduced pressure to obtain a residue. The residue was subjected to silica gel chromatography to obtain the title compound (1.15 g).

$^1$H-NMR (400 MHz, CDCl$_3$) δ (ppm): 1.52 (s, 18H), 2.63 (d, J=10.4 Hz, 1H), 2.68-2.87 (m, 3H), 3.00-3.07 (m, 1H), 3.13-3.20 (m, 1H), 3.60-3.69 (m, 3H), 3.78 (s, 3H), 3.81 (s, 3H), 6.40-6.52 (m, 2H), 7.22-7.29 (m, 1H), 7.29-7.36 (m, 1H), 7.38-7.50 (m, 2H), 7.53-7.59 (m, 1H), 7.72 (s, 1H), 7.87-7.94 (m, 1H), 8.16-8.22 (m, 1H).

(9) Synthesis of tert-butyl(±)-{(4aR*,7aS*)-7a-[3-(2-fluoropyridin-3-yl)phenyl]-4,4a,5,6,7,7a-hexahydropyrrolo[3,4-d][1,3]thiazin-2-yl}carbamate Triethylamine (387 μL) was added to a solution of the compound obtained in Preparation Example 18-(8) (411.00 mg) in dichloromethane (20.00 mL). The mixture was sufficiently cooled in an ice bath under a nitrogen atmosphere, and then trifluoroacetic anhydride (344 μL) was slowly added. After completion of the addition, the mixture was stirred for three hours and 30 minutes. The solvent was evaporated from the mixture under reduced pressure, and then the residue was dissolved in methanol (30 mL). 5 N potassium hydroxide aqueous solution (1.6 mL) was added thereto and the mixture was stirred at room temperature for two hours and 30 minutes. The reaction mixture was diluted with chloroform and then washed with a saturated sodium chloride solution. The resulting organic layer was dried over anhydrous sodium sulfate and concentrated under reduced pressure. The residue was purified by silica gel column chromatography to obtain the title compound (122 mg).

$^1$H-NMR (400 MHz, CDCl$_3$) δ (ppm): 1.58 (s, 9H), 2.73-2.78 (m, 1H), 2.91-2.95 (m, 1H), 3.10-3.15 (m, 1H), 3.24 (d, J=12.0 Hz, 1H), 3.34-3.45 (m, 2H), 3.53 (d, J=12.0 Hz, 1H), 7.28-7.32 (m, 1H), 7.42-7.46 (m, 1H), 7.50-7.54 (m, 3H), 7.85-7.89 (m, 1H), 8.22-8.24 (m, 1H)

Preparation Example 19

Synthesis of tert-butyl[(4aS,7R,8aS)-8a-(5-amino-2-fluorophenyl)-7-methoxymethyl-4a,7,8,8a-tetrahydro-4H,5H-6-oxa-3-thia-1-azanaphthalen-2-yl]carbamate

[Formula 41]

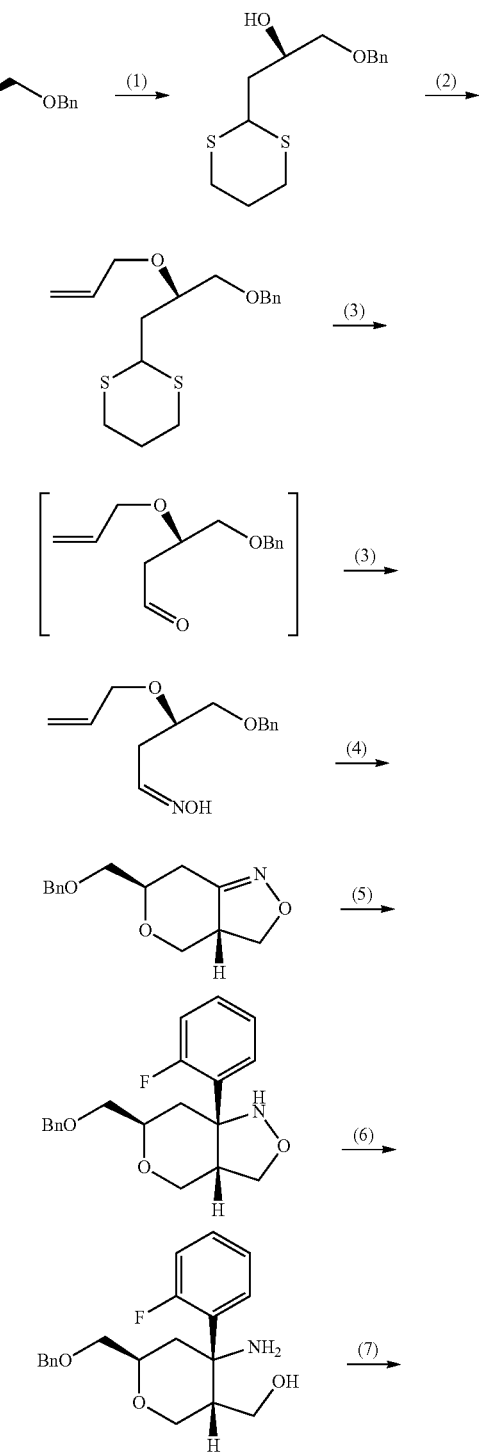

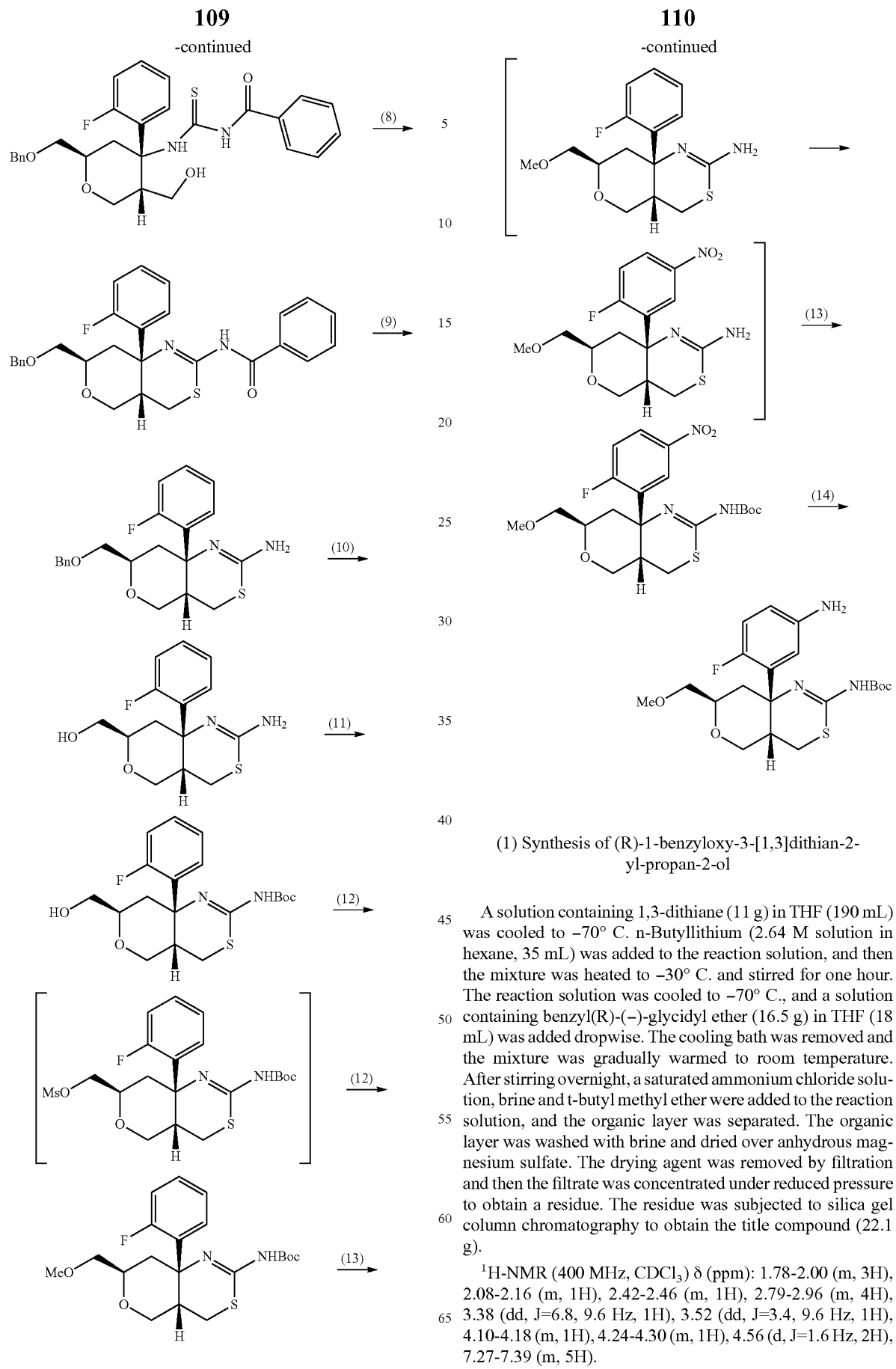

(1) Synthesis of (R)-1-benzyloxy-3-[1,3]dithian-2-yl-propan-2-ol

A solution containing 1,3-dithiane (11 g) in THF (190 mL) was cooled to −70° C. n-Butyllithium (2.64 M solution in hexane, 35 mL) was added to the reaction solution, and then the mixture was heated to −30° C. and stirred for one hour. The reaction solution was cooled to −70° C., and a solution containing benzyl(R)-(−)-glycidyl ether (16.5 g) in THF (18 mL) was added dropwise. The cooling bath was removed and the mixture was gradually warmed to room temperature. After stirring overnight, a saturated ammonium chloride solution, brine and t-butyl methyl ether were added to the reaction solution, and the organic layer was separated. The organic layer was washed with brine and dried over anhydrous magnesium sulfate. The drying agent was removed by filtration and then the filtrate was concentrated under reduced pressure to obtain a residue. The residue was subjected to silica gel column chromatography to obtain the title compound (22.1 g).

$^1$H-NMR (400 MHz, CDCl$_3$) δ (ppm): 1.78-2.00 (m, 3H), 2.08-2.16 (m, 1H), 2.42-2.46 (m, 1H), 2.79-2.96 (m, 4H), 3.38 (dd, J=6.8, 9.6 Hz, 1H), 3.52 (dd, J=3.4, 9.6 Hz, 1H), 4.10-4.18 (m, 1H), 4.24-4.30 (m, 1H), 4.56 (d, J=1.6 Hz, 2H), 7.27-7.39 (m, 5H).

(2) Synthesis of 2-((R)-2-allyloxy-3-benzyloxy-propyl)-[1,3]dithiane

A solution of (R)-1-benzyloxy-3-[1,3]dithian-2-yl-propan-2-ol (22.1 g) in THF (300 mL) was cooled to 0° C. 60% sodium hydride (4.35 g) was added, followed by stirring. After 12 minutes, allyl bromide (10 mL) was added and then the ice bath was removed. The mixture was further stirred at room temperature. After stirring overnight, the reaction solution was added to a mixture of ice and t-butyl methyl ether, and the organic layer was separated. The organic layer was washed with brine and then dried over anhydrous magnesium sulfate. The drying agent was removed by filtration and the filtrate was concentrated under reduced pressure to obtain a residue. The residue was subjected to silica gel chromatography to obtain the title compound (24.7 g).

$^1$H-NMR (400 MHz, CDCl$_3$) δ (ppm): 1.80-2.16 (m, 4H), 2.76-2.92 (m, 4H), 3.51 (dd, J=2, 4.8 Hz, 2H), 3.78-3.88 (m, 1H), 4.04-4.11 (m, 1H), 4.12-4.22 (m, 2H), 4.55 (d, J=5.6 Hz, 2H), 5.12-5.19 (m, 1H), 5.23-5.32 (m, 1H), 5.88-6.00 (m, 1H), 7.27-7.39 (m, 5H).

(3) Synthesis of (R)-3-allyloxy-4-benzyloxy-butyraldehyde oxime

Potassium carbonate (5.14 g) and methyl iodide (4.90 mL) were added to a mixed solution of 2-((R)-2-allyloxy-3-benzyloxy-propyl)-[1,3]dithiane (12 g) in acetonitrile (27 mL) and water (4.5 mL), and then the mixture was stirred at 40° C. After four hours, water (3 mL) and methyl iodide (2 mL) were added to the reaction solution. After further three hours, methyl iodide (1 mL) was added to the reaction solution. After stirring for eight hours in total, water and t-butyl methyl ether were added to the reaction solution, and the organic layer was separated. The organic layer was washed with brine. The organic layer was dried over anhydrous magnesium sulfate. The drying agent was removed by filtration and the filtrate was concentrated under reduced pressure to obtain crude (R)-3-allyloxy-4-benzyloxy-butyraldehyde (about 10 g). The crude product was used for the next reaction without further purification. Hydroxylamine hydrochloride (4.29 g) and sodium acetate (4.92 g) were sequentially added to a solution of ethanol (60 mL) and water (15 mL). The above aldehyde (10 g) was added to the mixture, followed by stirring for 20 hours. A saturated sodium bicarbonate solution and ethyl acetate were added to the reaction solution, and the organic layer was separated. The organic layer was sequentially washed with a saturated sodium bicarbonate solution and brine and dried over anhydrous magnesium sulfate. The drying agent was removed by filtration and then the filtrate was concentrated under reduced pressure to obtain a residue. The residue was subjected to silica gel column chromatography to obtain the title compound (5.74 g).

$^1$H-NMR (400 MHz, CDCl$_3$) δ (ppm): 2.41-2.55 (m, 1H), 2.59-2.74 (m, 1H), 3.47-3.60 (m, 2H), 3.68-3.82 (m, 1H), 4.02-4.19 (m, 2H), 4.52-4.58 (m, 2H), 5.14-5.20 (m, 1H), 5.23-5.32 (m, 1H), 5.84-5.98 (m, 1H), 6.87 (t, J=5.4 Hz, 0.5H) 7.24-7.40 (m, 5H), 7.48 (t, J=6.2 Hz, 0.5H).

(4) Synthesis of (3aS,6R)-6-benzyloxymethyl-3a,4,6,7-tetrahydro-3H-pyrano[4,3-c]isoxazole Sodium hypochlorite (5% aqueous solution, 42 mL) was added dropwise to a solution containing the oxime synthesized in the previous step (5.74 g) in dichloromethane (120 mL) at room temperature, followed by stirring for one hour. A sodium thiosulfate solution was added to the reaction solution, and the organic layer was separated. The organic layer was washed with brine and dried over anhydrous magnesium sulfate. The drying agent was removed by filtration and then the filtrate was concentrated under reduced pressure to obtain a residue. The residue was subjected to silica gel column chromatography to obtain the title compound (4.49 g).

$^1$H-NMR (400 MHz, CDCl$_3$) δ (ppm): 2.27-2.39 (m, 1H), 2.70-2.78 (m, 1H), 3.30-3.52 (m, 2H), 3.53-3.62 (m, 3H), 3.74 (dd, J=8.4, 10.4 Hz, 1H), 4.40 (dd, J=6.0, 10.0 Hz, 1H), 4.48 (dd, J=8.4, 10.0 Hz, 1H), 4.61 (s, 2H), 7.27-7.39 (m, 5H).

(5) Synthesis of (3aS,6R,7aS)-6-benzyloxymethyl-7a-(2-fluorophenyl)-hexahydropyrano[4,3-c]isoxazole THF (10 mL) and toluene (90 mL) were added to 2-bromofluorobenzene (4.14 mL) under a nitrogen atmosphere, and the mixture was cooled to −78° C. n-Butyllithium (2.64 M solution in hexane, 13.8 mL) was slowly added to the solution. After stirring at the same temperature for 10 minutes, a boron trifluoride-diethyl ether complex (4.57 mL) and a solution containing the isoxazole synthesized in the previous step (4.49 g) in toluene (10 mL) were sequentially added dropwise. The mixture was further stirred at the same temperature for four hours. A saturated ammonium chloride solution was added to the reaction solution, followed by warming to room temperature. Then, ethyl acetate and water were added and the organic layer was separated. The organic layer was washed with brine and then dried over anhydrous magnesium sulfate. The drying agent was removed by filtration and the filtrate was concentrated under reduced pressure. The residue was subjected to silica gel column chromatography and NH-silica gel column chromatography to obtain the title compound (5.73 g).

$^1$H-NMR (400 MHz, CDCl$_3$) δ (ppm): 1.81 (dd, J=3.2, 15.2 Hz, 1H), 2.28 (dd, J=12.4, 15.2 Hz, 1H), 3.07-3.16 (m, 1H), 3.40-3.85 (m, 6H), 4.08-4.19 (m, 1H), 4.58 (d, J=5.2 Hz, 2H), 5.94 (s, 1H), 7.00-7.08 (m, 1H), 7.10-7.17 (m, 1H), 7.22-7.39 (m, 6H), 7.83-7.92 (m, 1H).

(6) Synthesis of [(3R,4S,6R)-4-amino-6-benzyloxymethyl-4-(2-fluorophenyl)-tetrahydropyran-3-yl]methanol The isoxazole synthesized in the previous step (5.73 g) was dissolved in acetic acid (70 mL). Zinc (11 g) was added to the solution, followed by stirring at room temperature. After 15 hours, the reaction solution was filtered through celite and washed with methanol. The filtrate was concentrated under reduced pressure. A 2 N sodium hydroxide solution and chloroform were added to the residue, and the organic layer was separated. The organic layer was dried over anhydrous magnesium sulfate. The drying agent was removed by filtration and the filtrate was concentrated under reduced pressure to obtain the title compound (6.08 g). The compound was used for the next reaction without further purification.

ESI-MS; m/z 346 [M$^+$+H].

$^1$H-NMR (400 MHz, CDCl$_3$) δ (ppm): 1.44 (dd, J=2.4, 13.6 Hz, 1H), 2.37 (dd, J=11.6, 13.6 Hz, 1H), 2.49-2.58 (m, 1H), 3.41-3.59 (m, 4H), 3.99-4.16 (m, 3H), 4.59 (d, J=10.0 Hz, 2H), 7.01-7.09 (m, 1H), 7.14-7.20 (m, 1H), 7.24-7.36 (m, 6H), 7.57-7.63 (m, 1H).

(7) Synthesis of 1-benzoyl-3-[(2R,4S,5R)-2-benzyloxymethyl-4-(2-fluorophenyl)-5-hydroxymethyl-tetrahydropyran-4-yl]thiourea The amine synthesized in the previous step (6.08 g) was dissolved in dichloromethane (60 mL). Benzoyl isothiocyanate (2.58 mL) was added to the solution, followed by stirring at room temperature. After 15 hours, the reaction solution was concentrated under reduced pressure. The residue was subjected to silica gel column chromatography to obtain the title compound (7.83 g).

ESI-MS; m/z 509 [M$^+$+H], 531 [M$^+$+Na].

$^1$H-NMR (400 MHz, CDCl$_3$) δ (ppm): 2.25-2.50 (m, 1H), 3.50-3.90 (m, 5H), 3.90-4.05 (m, 1H), 4.10-4.30 (m, 2H), 4.61 (d, J=2.4 Hz, 2H), 7.02-7.10 (m, 1H), 7.13-7.20 (m, 1H), 7.24-7.44 (m, 7H), 7.50-7.57 (m, 2H), 7.61-7.68 (m, 1H), 7.85-7.91 (m, 2H), 8.90 (s, 1H), 11.7 (s, 1H).

(8) Synthesis of N-[(4aS,7R,8aS)-7-benzyloxymethyl-8a-(2-fluorophenyl)-4a,7,8,8a-tetrahydro-4H,5H-6-oxa-3-thia-1-azanaphthalen-2-yl]benzamide The thiourea synthesized in the previous step (7.83 g) was dissolved in methanol (100 mL) and concentrated hydrochloric acid (3 mL). The solution was heated under reflux at 95° C. After four hours, the reaction solution was left to cool and then concentrated under reduced pressure. Chloroform, a 5 N sodium hydroxide solution and brine were added to the residue, and the organic layer was separated. The organic layer was dried over anhydrous magnesium sulfate. The drying agent was removed by filtration and the filtrate was concentrated under reduced pressure to obtain the title compound (10 g). The compound was used for the next reaction without further purification.

ESI-MS; m/z 491 [M$^+$+H].

(9) Synthesis of (4aS,7R,8aS)-7-benzyloxymethyl-8a-(2-fluorophenyl)-4a,7,8,8a-tetrahydro-4H,5H-6-oxa-3-thia-1-azanaphthalen-2-ylamine The compound obtained in Preparation Example 19-(8) (10 g) was dissolved in methanol (60 mL). DBU (5 mL) was added to the solution, and the mixture was heated under reflux at 95° C. After five hours, the reaction solution was left to cool and concentrated under reduced pressure. Ethyl acetate, a saturated sodium bicarbonate solution and brine were added to the residue, and the organic layer was separated. The organic layer was dried over anhydrous magnesium sulfate. The drying agent was removed by filtration and the filtrate was concentrated under reduced pressure. The residue was subjected to silica gel chromatography to obtain the title compound (6.42 g).

ESI-MS; m/z 387 [M$^+$+H].

$^1$H-NMR (400 MHz, CDCl$_3$) δ (ppm): 1.67 (dd, J=2.0, 12.8 Hz, 1H), 2.36-2.46 (m, 1H), 2.52-2.60 (m, 1H), 2.87 (dd, J=4.4, 12.4 Hz, 1H), 2.94-3.02 (m, 1H), 3.42-3.58 (m, 2H), 3.79-3.99 (m, 3H), 4.40-4.70 (m, 4H), 6.99-7.07 (m, 1H), 7.07-7.13 (m, 1H), 7.20-7.36 (m, 7H).

(10) Synthesis of [(4aS,7R,8aS)-2-amino-8a-(2-fluorophenyl)-4a,7,8,8a-tetrahydro-4H,5H-6-oxa-3-thia-1-azanaphthalen-7-yl]methanol Concentrated hydrochloric acid (35 mL) was added to the compound obtained in Preparation Example 19-(9) (6.42 g), and the mixture was heated under reflux at 125° C. After two hours, the reaction solution was left to cool. t-Butyl methyl ether was added and the organic layer was separated. Chloroform and a 5 N sodium hydroxide solution were added to the aqueous layer, and the organic layer was separated. The organic layers were dried over anhydrous magnesium sulfate. The drying agent was removed by filtration and the filtrate was concentrated under reduced pressure to obtain the title compound (4.16 g).

ESI-MS; m/z 297 [M$^+$+H].

$^1$H-NMR (400 MHz, CDCl$_3$) δ (ppm): 1.64 (dd, J=2.0, 12.8 Hz, 1H), 2.34-2.44 (m, 1H), 2.53-2.62 (m, 1H), 2.85-2.93 (m, 1H), 2.93-3.03 (m, 1H), 3.54-3.69 (m, 2H), 3.78-3.91 (m, 3H), 4.55 (brs, 2H), 6.99-7.07 (m, 1H), 7.08-7.15 (m, 1H), 7.20-7.32 (m, 2H).

(11) Synthesis of tert-butyl[(4aS,7R,8aS)-8a-(2-fluorophenyl)-7-hydroxymethyl-4a,7,8,8a-tetrahydro-4H,5H-6-oxa-3-thia-1-azanaphthalen-2-yl]carbamate THF (100 mL), methanol (50 mL) and triethylamine (2.80 mL) were added to the compound obtained in Preparation Example 19-(10) (3.8 g). Di-t-butyl dicarbonate (3.7 g) was added to the reaction mixture, followed by stirring. After stirring overnight, the reaction solution was concentrated under reduced pressure to obtain a residue. The residue was subjected to column chromatography and precipitated using ether to obtain the title compound (5.35 g).

ESI-MS; m/z 397 [M$^+$+H].

$^1$H-NMR (400 MHz, CDCl$_3$) δ (ppm): 1.53 (s, 9H), 1.63 (dd, J=2.0, 14.0 Hz, 1H), 1.98 (brs, 1H), 2.46-2.58 (m, 2H), 2.86 (dd, J=4.4, 13.2 Hz, 1H), 3.04-3.16 (m, 1H), 3.54-3.74 (m, 2H), 3.76-3.89 (m, 1H), 3.96 (d, J=7.6 Hz, 2H), 7.04-7.12 (m, 1H), 7.14-7.21 (m, 1H), 7.21-7.36 (m, 2H).

(12) Synthesis of tert-butyl[(4aS,7R,8aS)-8a-(2-fluorophenyl)-7-methoxymethyl-4a,7,8,8a-tetrahydro-4H,5H-6-oxa-3-thia-1-azanaphthalen-2-yl]carbamate A solution of the compound obtained in Preparation Example 19-(11) (613 mg) in dichloromethane (15 mL) was ice-cooled. Triethylamine (432 μL) and methanesulfonyl chloride (144 μL) were added to the solution. The reaction solution was stirred at the same temperature for one hour. Then, dichloromethane and a saturated sodium bicarbonate solution were added to the reaction solution, and the organic layer was separated. The organic layer was dried over anhydrous magnesium sulfate. The drying agent was removed by filtration and then the filtrate was concentrated under reduced pressure to obtain a mesyl compound. The mesyl compound was dissolved in methanol (10 mL), followed by ice-cooling. Sodium methoxide (28% solution in methanol, 1.7 mL) was added to the solution, and the mixture was stirred at room temperature. After one hour, the reaction solution was heated to 70° C. After about three hours, sodium methoxide (28% solution in methanol, 5 mL) was further added and the mixture was further stirred for four hours. The reaction solution was left to cool. Then, chloroform and a saturated sodium bicarbonate solution were added and the organic layer was separated. The organic layer was washed with brine. The organic layer was dried over anhydrous magnesium sulfate. The drying agent was removed by filtration and then the filtrate was concentrated under reduced pressure to obtain a residue. The residue was subjected to silica gel chromatography to obtain the title compound (262 mg).

ESI-MS; m/z 411 [M$^+$+H].

$^1$H-NMR (400 MHz, CDCl$_3$) δ (ppm): 1.53 (s, 9H), 1.67 (dd, J=2.0, 13.6 Hz, 1H), 1.98 (brs, 1H), 2.46-2.56 (m, 2H), 2.81-2.90 (m, 1H), 3.07-3.16 (m, 1H), 3.40 (s, 3H), 3.40-3.52 (m, 2H), 3.86-4.01 (m, 3H), 7.04-7.12 (m, 1H), 7.14-7.21 (m, 1H), 7.25-7.36 (m, 2H).

(13) Synthesis of tert-butyl[(4aS,7R,8aS)-8a-(2-fluoro-5-nitrophenyl)-7-methoxymethyl-4a,7,8,8a-tetrahydro-4H,5H-6-oxa-3-thia-1-azanaphthalen-2-yl]carbamate The compound obtained in Preparation Example 19-(12) (262 mg) was dissolved in dichloromethane (3 mL), followed by ice-cooling. TFA (1 mL) was added thereto, followed by stirring at room temperature. After four hours, the reaction solution was concentrated under reduced pressure to obtain a residue. TFA (1 mL) was added to the residue, followed by ice-cooling. Concentrated sulfuric acid (0.5 mL) was added to the solution. Then, fuming nitric acid (37 μL) was added and the mixture was stirred for one hour. The reaction solution was poured into water. Chloroform and a 5 N sodium hydroxide solution were carefully added and the organic layer was separated. The organic layer was dried over anhydrous magnesium sulfate. The drying agent was removed by filtration and the filtrate was concentrated under reduced pressure to obtain a residue. The residue (239 mg) was dissolved in THF (3 mL) and methanol (1 mL), and then triethylamine (200 μL) was added. Di-t-butyl dicarbonate (215 mg) was dissolved in THF (2 mL), and the solution was added to the above solution. After 18 hours, the reaction solution was concentrated under reduced pressure to obtain a residue. The residue was subjected to column chromatography to obtain the title compound (256 mg).

ESI-MS; m/z 456 [M$^+$+H].

$^1$H-NMR (400 MHz, CDCl$_3$) δ (ppm): 1.54 (s, 9H), 1.66-1.73 (m, 1H), 2.26-2.42 (m, 1H), 2.56 (dd, J=2.8, 13.2 Hz, 1H), 2.74-2.84 (m, 1H), 3.00-3.12 (m, 1H), 3.39 (s, 3H), 3.36-3.50 (m, 2H), 3.72-4.02 (m, 3H), 7.18-7.32 (m, 1H), 8.12-8.24 (m, 2H).

(14) Synthesis of tert-butyl[(4aS,7R,8aS)-8a-(5-amino-2-fluorophenyl)-7-methoxymethyl-4a,7,8,8a-tetrahydro-4H,5H-6-oxa-3-thia-1-azanaphthalen-2-yl]carbamate The compound obtained in Preparation Example 19-(13) (255 mg) was dissolved in ethanol (9 mL). A saturated ammonium chloride solution (0.9 mL) and iron powder (440 mg) were added thereto, and the mixture was heated at 90° C. for 40 minutes. The reaction solution was left to cool and filtered through celite. Ethyl acetate and a sodium bicarbonate solution were added to the filtrate, and the organic layer was separated. The organic layer was dried over anhydrous magnesium sulfate. The drying agent was removed by filtration and the filtrate was concentrated under reduced pressure to obtain a residue. The residue was subjected to silica gel column chromatography and further precipitated using t-butyl methyl ether and hexane to obtain the title compound (151 mg).

ESI-MS; m/z 426 [M$^+$+H].

$^1$H-NMR (400 MHz, CDCl$_3$) δ (ppm): 1.53 (s, 9H), 1.63 (dd, J=2.0, 14.0 Hz, 1H), 2.44-2.55 (m, 2H), 2.92 (dd, J 4.0, 13.2 Hz, 1H), 3.04-3.13 (m, 1H), 3.39 (s, 3H), 3.38-3.49 (m, 2H), 3.64 (brs, 2H), 3.86-4.00 (m, 3H), 6.50-6.60 (m, 2H), 6.87 (dd, J=8.4, 12.0 Hz, 1H).

Preparation Example 20

Synthesis of tert-butyl[(4aS,7R,8aS)-8a-(5-amino-2-fluorophenyl)-7-fluoromethyl-4a,7,8,8a-tetrahydro-4H,5H-6-oxa-3-thia-1-azanaphthalen-2-yl]carbamate

[Formula 42]

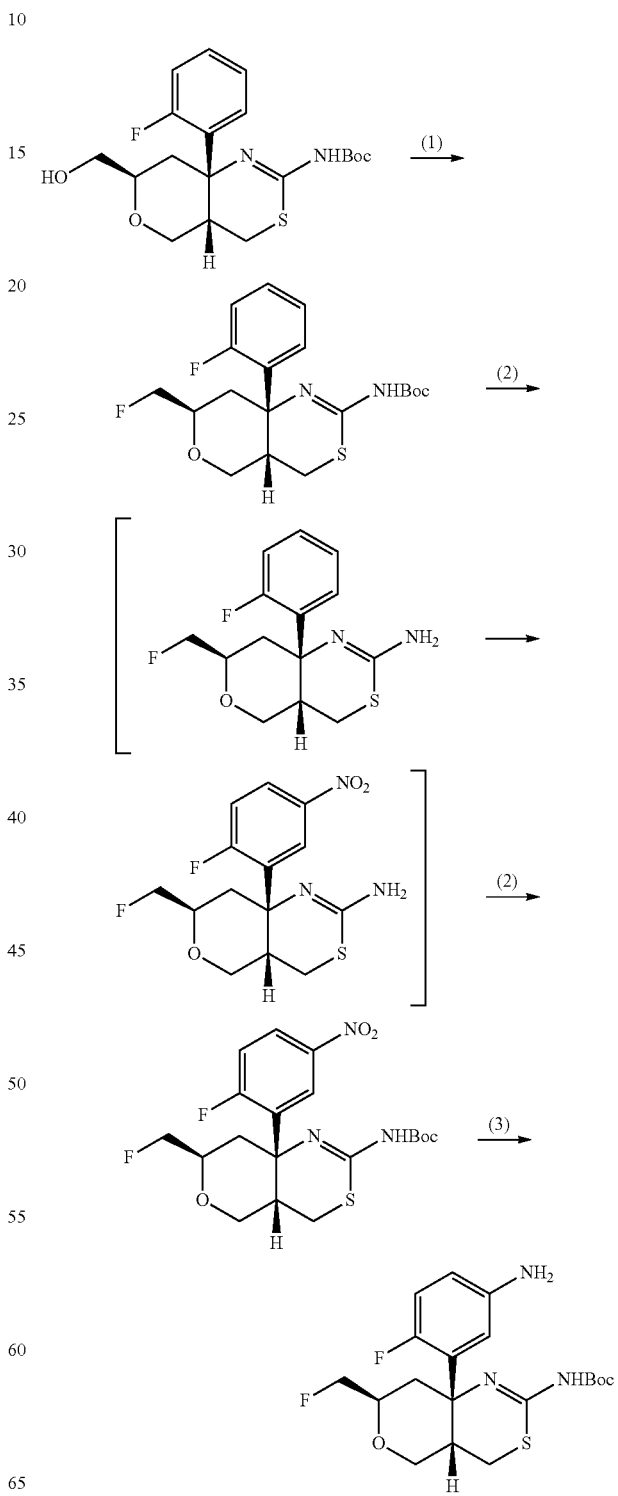

(1) Synthesis of tert-butyl[(4aS,7R,8aS)-7-fluoromethyl-8a-(2-fluorophenyl)-4a,7,8,8a-tetrahydro-4H,5H-6-oxa-3-thia-1-azanaphthalen-2-yl]carbamate Perfluorobutanesulfonyl fluoride (990 μL), triethylamine trihydrofluoride (842 μL) and triethylamine (2.2 mL) were sequentially added to a mixture of the compound obtained in Preparation Example 19-(11) (1 g) in acetonitrile (15 mL) and THF (4 mL), followed by stirring at room temperature. After about 22 hours, a saturated sodium bicarbonate solution was added to the reaction solution. The organic layer was extracted from chloroform and washed with brine. The organic layer was dried over anhydrous magnesium sulfate. The drying agent was removed by filtration and then the filtrate was concentrated under reduced pressure to obtain a residue. The residue was subjected to silica gel chromatography to obtain the title compound (307 mg).

ESI-MS; m/z 399 [M$^+$+H].

$^1$H-NMR (400 MHz, CDCl$_3$) δ (ppm): 1.53 (s, 9H), 1.69 (dd, J=2.0, 13.6 Hz, 1H), 2.48-2.60 (m, 2H), 2.85 (dd, J=4.4, 13.2 Hz, 1H), 3.04-3.18 (m, 1H), 3.85-4.08 (m, 3H), 4.32-4.44 (m, 1H), 4.45-4.56 (m, 1H), 7.05-7.14 (m, 1H), 7.14-7.21 (m, 1H), 7.24-7.37 (m, 2H).

(2) Synthesis of tert-butyl[(4aS,7R,8aS)-7-fluoromethyl-8a-(2-fluoro-5-nitrophenyl)-4a,7,8,8a-tetrahydro-4H,5H-6-oxa-3-thia-1-azanaphthalen-2-yl]carbamate The compound obtained in Preparation Example 20-(1) (307 mg) was dissolved in dichloromethane (3 mL), followed by ice-cooling. TFA (1 mL) was added thereto, followed by stirring at room temperature. After four hours, the reaction solution was concentrated under reduced pressure to obtain a residue. TFA (1 mL) was added to the resulting residue, followed by ice-cooling. Concentrated sulfuric acid (0.5 mL) was added to the solution. Then, fuming nitric acid (42 μL) was added and the mixture was stirred for one hour. The reaction solution was poured into water. Chloroform and a 5 N sodium hydroxide solution were carefully added and the organic layer was separated. The organic layer was dried over anhydrous magnesium sulfate. The drying agent was removed by filtration and the filtrate was concentrated under reduced pressure to obtain a residue (260 mg). The residue (260 mg) was dissolved in THF (3 mL) and methanol (1 mL), and then triethylamine (200 μL) was added. Di-t-butyl dicarbonate (285 mg) was dissolved in THF (2 mL), and the solution was added to the above solution. After 18 hours, ethyl acetate and a saturated sodium bicarbonate solution were added to the reaction solution, and the organic layer was separated. The organic layer was dried over anhydrous magnesium sulfate. The drying agent was removed by filtration and the filtrate was concentrated under reduced pressure to obtain a residue. The residue was subjected to column chromatography to obtain the title compound (292 mg). ESI-MS; m/z 444 [M$^+$+H].

$^1$H-NMR (400 MHz, CDCl$_3$) δ (ppm): 1.54 (s, 9H), 1.66-1.74 (m, 1H), 2.27-2.48 (m, 1H), 2.57 (dd, J=2.8, 13.6 Hz, 1H), 2.72-2.88 (m, 1H), 2.98-3.16 (m, 1H), 3.76-4.04 (m, 3H), 4.30-4.56 (m, 2H), 4.45-4.56 (m, 1H), 7.18-7.29 (m, 1H), 8.12-8.25 (m, 2H).

(3) Synthesis of tert-butyl[(4aS,7R,8aS)-8a-(5-amino-2-fluorophenyl)-7-fluoromethyl-4a,7,8,8a-tetrahydro-4H,5H-6-oxa-3-thia-1-azanaphthalen-2-yl]carbamate The compound obtained in Preparation Example 20-(2) (290 mg) was dissolved in ethanol (10 mL). A saturated ammonium chloride solution (1 mL) and iron powder (490 mg) were added thereto, and the mixture was heated at 90° C. for 40 minutes. The reaction solution was left to cool and filtered through celite. Ethyl acetate and a sodium bicarbonate solution were added to the filtrate, and the organic layer was separated. The organic layer was dried over anhydrous magnesium sulfate. The drying agent was removed by filtration and the filtrate was concentrated under reduced pressure to obtain a residue. The residue was subjected to column chromatography to obtain the title compound (186 mg). ESI-MS; m/z 414 [M$^+$+H].

$^1$H-NMR (400 MHz, CDCl$_3$) δ (ppm): 1.53 (s, 9H), 1.58-1.72 (m, 1H), 2.47-2.60 (m, 2H), 2.93 (dd, J=4.0, 13.2 Hz, 1H), 3.03-3.12 (m, 1H), 3.65 (brs, 2H), 3.87-4.03 (m, 3H), 4.33-4.43 (m, 1H), 4.44-4.54 (m, 1H), 6.48-6.60 (m, 2H), 6.83-6.92 (m, 1H).

Preparation Example 21

Synthesis of tert-butyl(-)-[(4aS*,5R*,7aS*)-7a-(5-amino-2-fluorophenyl)-5-ethyl-4a,5,7,7a-tetrahydro-4H-furo[3,4-d][1,3]thiazin-2-yl]carbamate

[Formula 43]

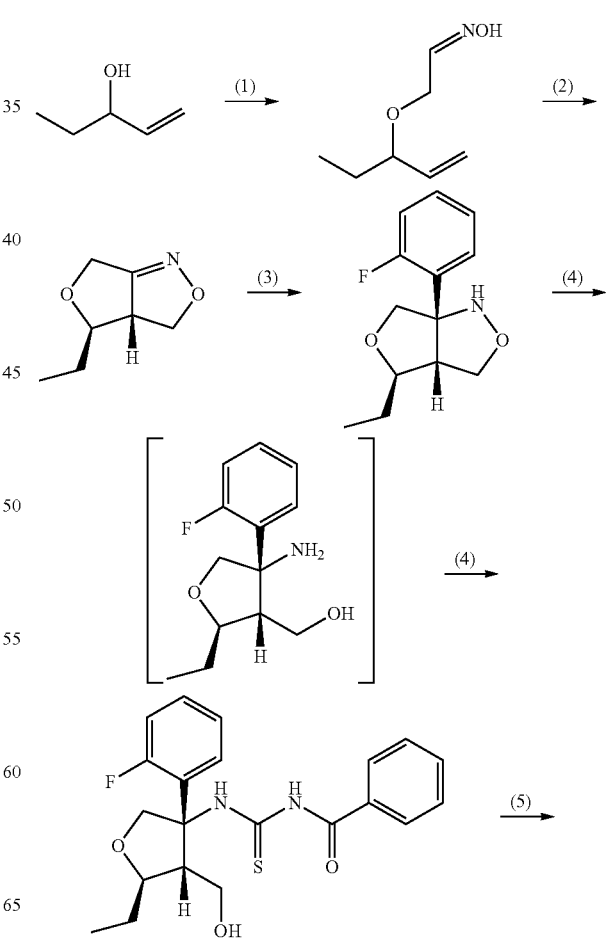

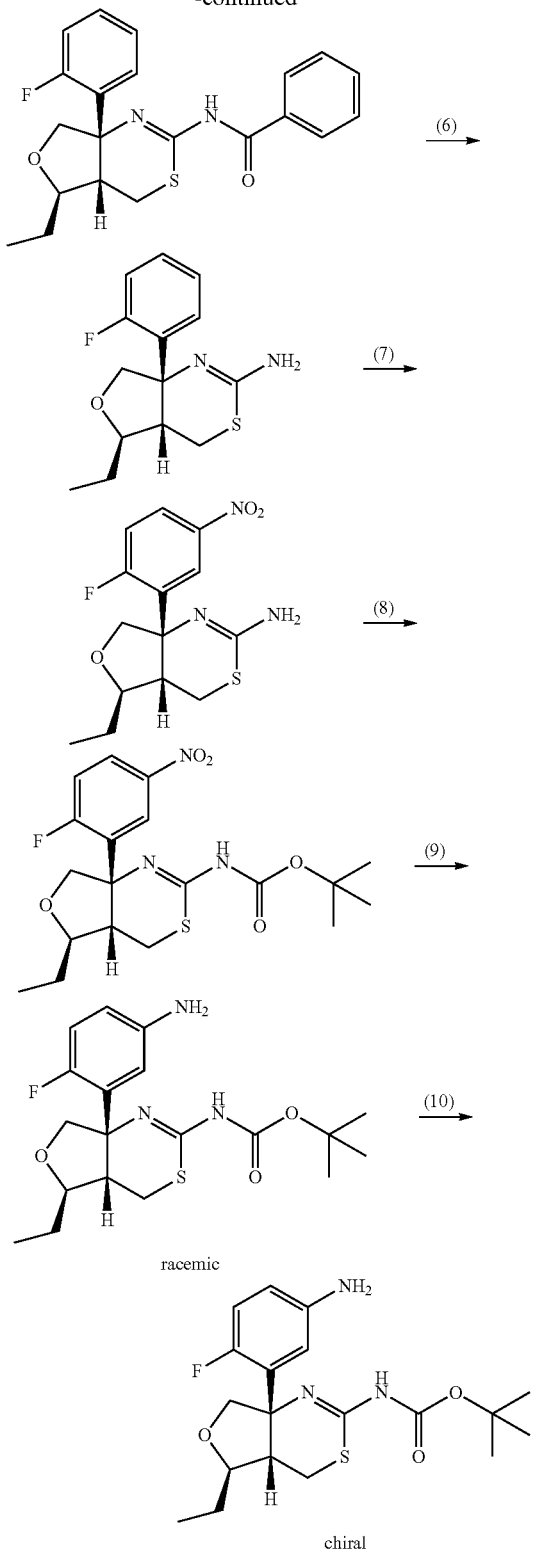

racemic chiral (1) Synthesis of (1-ethylallyloxy)acetaldehyde oxime

A solution of 1-penten-3-ol (15.0 mL) in N-methyl-2-pyrrolidone (292 mL) was cooled to 0° C. under a nitrogen atmosphere. Sodium hydride (60%, 6.42 g) and bromoacetaldehyde diethyl acetal (31.6 g) were added to the reaction solution at the same temperature, and the mixture was stirred at 80° C. for 30 minutes. A saturated ammonium chloride solution was added to the reaction solution at 0° C., followed by extraction with ethyl acetate. The organic layer was washed with saturated sodium bicarbonate and saturated aqueous sodium chloride and then dried over anhydrous magnesium sulfate. The insoluble matter was separated by filtration and the filtrate was concentrated under reduced pressure. The residue was dissolved in heptane. The solution was filtered through silica gel using 30% ethyl acetate/heptane and concentrated under reduced pressure. Formic acid (100 mL), hydroxylamine hydrochloride (15.2 g) and sodium acetate (24.0 g) were added to the residue, and the mixture was stirred at room temperature for two days. Ethyl acetate and a saturated sodium chloride solution were added to the reaction solution, and the organic layer was separated. The organic layer was washed with saturated aqueous sodium chloride and then dried over anhydrous magnesium sulfate. The insoluble matter was separated by filtration and the filtrate was concentrated under reduced pressure. The residue was purified by silica gel column chromatography to obtain the title compound (4.30 g).

$^1$H-NMR (400 MHz, CDCl$_3$) δ (ppm): 0.88-0.92 (m, 3H), 1.55-1.63 (m, 2H) 3.59-4.36 (m, 3H), 5.19-5.24 (m, 2H), 5.61-5.68 (m, 1H), 6.90-6.92 (m, 0.5H), 7.48-7.50 (m, 0.5H).

(2) Synthesis of (3aR*,4R*)-4-ethyl-3a,4-dihydro-3H,6H-furo[3,4-c]isoxazole

A 5% sodium hypochlorite solution (53.6 g) was added to a solution containing the compound obtained in Preparation Example 21-(1) (4.30 g) in dichloromethane (95.7 mL) at 0° C., and the mixture was stirred at 0° C. for 30 minutes. A sodium bisulfite solution was added to the reaction solution at the same temperature. The organic layer was separated and dried over anhydrous magnesium sulfate. The insoluble matter was separated by filtration and the filtrate was concentrated. The residue was purified by silica gel column chromatography to obtain the title compound (2.02 g).

$^1$H-NMR (400 MHz, CDCl$_3$) δ (ppm): 0.92 (t, J=7.2 Hz, 3H), 1.56-1.83 (m, 2H), 3.74-3.78 (m, 2H), 3.97-4.02 (m, 1H), 4.44-4.57 (m, 3H).

(3) Synthesis of (3aR*,4R*,6aS*)-4-ethyl-6a-(2-fluorophenyl)tetrahydrofuro[3,4-c]isoxazole A solution of n-butyllithium in hexane (2.60 M; 12.2 mL) was added dropwise to a solution containing 2-bromofluorobenzene (3.62 mL) in tetrahydrofuran/toluene (5.80 mL/58.0 mL) under a nitrogen atmosphere at −78° C. The reaction solution was stirred at the same temperature for 10 minutes. A boron trifluoride-diethyl ether complex (3.92 mL) and a solution containing the compound obtained in Preparation Example 21-(2) (2.02 g) in toluene (20 mL) were added dropwise to the reaction solution sequentially at the same temperature. After stirring at the same temperature for 40 minutes, aqueous ammonium chloride was added to the reaction solution, followed by warming to room temperature. Water and ethyl acetate were added to the reaction solution, and the organic layer was separated. The organic layer was washed with a saturated sodium chloride solution. The organic layer was dried over anhydrous magnesium sulfate, and the insoluble matter was separated by filtration. The filtrate was concentrated and the residue was purified by silica gel column chromatography to obtain the title compound (3.39 g).

ESI-MS; m/z 238 [M$^+$+H].

(4) Synthesis of 1-benzoyl-3-[(3S*,4R*,5R*)-5-ethyl-3-(2-fluorophenyl)-4-hydroxymethyl-tetrahydrofuran-3-yl]thiourea Zinc powder (9.35 g) was added to a solution containing the compound obtained in Preparation Example 21-(3) (3.39 g) in acetic acid (59.8 mL) at room temperature. The reaction solution was stirred at room temperature for 18 hours. The insoluble matter was separated by filtration through celite and the filtrate was concentrated. Ethyl acetate and a sodium bicarbonate solution were added to the residue, and the organic layer was separated. The organic layer was washed with saturated aqueous sodium chloride and dried over anhydrous magnesium sulfate. The insoluble matter was separated by filtration and the filtrate was concentrated under reduced pressure. Benzoyl isothiocyanate (2.12 mL) was added to a solution containing the residue in dichloromethane (43.2 mL), and the mixture was stirred at room temperature for 10 minutes. The reaction solution was concentrated under reduced pressure. The residue was purified by silica gel column chromatography to obtain the title compound (3.83 g).

$^1$H-NMR (400 MHz, CDCl$_3$) δ (ppm): 1.02 (t, J=8.0 Hz, 3H), 1.57-1.61 (m, 2H), 2.72-2.74 (m, 1H), 2.95-2.97 (m, 1H), 3.83-3.99 (m, 2H), 4.40-4.43 (m, 1H), 4.60-4.63 (m, 1H), 7.02-7.04 (m, 1H), 7.16-7.19 (m, 1H), 7.26-7.28 (m, 1H), 7.50-7.54 (m, 2H), 7.62-7.64 (m, 1H), 7.73-7.74 (m, 1H), 7.85-7.88 (m, 2H), 8.87 (br, 1H).

(5) Synthesis of N-[(4aS*,5R*,7aS*)-5-ethyl-7a-(2-fluorophenyl)-4a,5,7,7a-tetrahydro-4H-furo[3,4-d][1,3]thiazin-2-yl]benzamide Pyridine (2.15 mL) and trifluoromethanesulfonic anhydride (3.20 mL) were added to a solution of the compound obtained in Preparation Example 21-(4) (4.11 g) in dichloromethane (18.0 mL) at 0° C., and the mixture was stirred at the same temperature for 10 minutes. A saturated sodium bicarbonate solution was added to the reaction solution, followed by extraction with ethyl acetate. The organic layer was dried over anhydrous magnesium sulfate, and the insoluble matter was separated by filtration. The filtrate was concentrated under reduced pressure and the residue was purified by silica gel column chromatography to obtain the title compound (3.53 g). ESI-MS; m/z 385 [M$^+$+H].

(6) Synthesis of (4aS*,5R*,7aS*)-5-ethyl-7a-(2-fluorophenyl)-4a,5,7,7a-tetrahydro-4H-furo[3,4-d][1,3]thiazin-2-ylamine A solution of the compound obtained in Preparation Example 21-(5) (3.53 g) and sodium methoxide (28% solution in methanol; 3.67 mL) in methanol (23.4 mL) was heated under reflux for 2.5 hours. After cooling the reaction solution to room temperature, the solvent was evaporated under reduced pressure. The residue was purified by silica gel chromatography to obtain the title compound (1.21 g). ESI-MS; m/z 281 [M$^+$+H].

$^1$H-NMR (400 MHz, CDCl$_3$) δ (ppm): 1.06 (t, J=7.6 Hz, 3H), 1.62-1.73 (m, 2H), 2.62-2.75 (m, 2H), 3.05-3.09 (m, 1H), 3.79-3.81 (m, 1H), 4.10-4.19 (m, 1H), 4.57-4.59 (m, 1H), 7.01-7.24 (m, 3H), 7.40-7.44 (m, 1H).

(7) Synthesis of (4aS*,5R*,7aS*)-5-ethyl-7a-(2-fluoro-5-nitrophenyl)-4a,5,7,7a-tetrahydro-4H-furo[3,4-d][1,3]thiazin-2-ylamine Fuming nitric acid (215 μL) was added dropwise to a solution of the compound obtained in Preparation Example 21-(6) (1.21 g) in concentrated sulfuric acid (21.6 mL) under ice-cooling. The reaction solution was stirred at the same temperature for 30 minutes and then poured into ice water. The reaction mixture was neutralized with a 5 N sodium hydroxide solution. The mixture was extracted with ethyl acetate twice. The organic layers were dried over anhydrous magnesium sulfate, and the insoluble matter was separated by filtration. The filtrate was concentrated under reduced pressure to obtain the title compound (1.41 g).

ESI-MS; m/z 326 [M$^+$+H].

(8) Synthesis of tert-butyl[(4aS*,5R*,7aS*)-5-ethyl-7a-(2-fluoro-5-nitrophenyl)-4a,5,7,7a-tetrahydro-4H-furo[3,4-d][1,3]thiazin-2-yl]carbamate The compound obtained in Preparation Example 21-(7) (1.34 g) was dissolved in dichloromethane (20.4 mL). Triethylamine (2.41 mL) and di-tert-butyl dicarbonate (1.88 g) were added to the solution, and the mixture was stirred at room temperature for 10 minutes. The reaction solution was concentrated under reduced pressure and the residue was purified by silica gel column chromatography to obtain the title compound (1.41 g).

$^1$H-NMR (400 MHz, CDCl$_3$) δ (ppm): 1.06 (t, J=7.6 Hz, 3H), 1.52 (s, 9H), 1.52-1.65 (m, 2H), 2.66-2.70 (m, 2H), 2.91-2.93 (m, 1H), 3.78-3.79 (m, 1H), 4.25-4.26 (m, 1H), 4.46-4.48 (m, 1H), 7.20-7.22 (m, 1H), 8.21-8.29 (m, 2H).

(9) Synthesis of tert-butyl[(4aS*,5R*,7aS*)-7a-(5-amino-2-fluorophenyl)-5-ethyl-4a,5,7,7a-tetrahydro-4H-furo[3,4-d][1,3]thiazin-2-yl]carbamate A saturated ammonium chloride solution (3.1 mL) and iron powder (1.48 g) were added to a solution of the compound obtained in Preparation Example 21-(8) (1.41 g) in ethanol (33.1 mL). The reaction solution was heated under reflux for 30 minutes and then cooled to room temperature. The reaction solution was diluted with ethyl acetate and the insoluble matter was separated by filtration through celite. Ethyl acetate and water were added to the filtrate, and the organic layer was separated. The organic layer was dried over anhydrous magnesium sulfate, and the insoluble matter was separated by filtration. The filtrate was concentrated under reduced pressure to obtain the title compound (920 mg).

$^1$H-NMR (400 MHz, CDCl$_3$) δ (ppm): 1.06 (t, J=7.6 Hz, 3H), 1.46-1.71 (m, 2H), 1.49 (s, 9H), 2.63-2.67 (m, 1H), 2.84-2.85 (m, 1H), 3.07-3.09 (m, 1H), 3.62 (br, 2H), 3.81-3.83 (m, 1H), 4.27-4.28 (m, 1H), 4.49-4.51 (m, 1H), 6.55-6.63 (m, 2H), 6.84-6.89 (m, 1H).

(10) Synthesis of tert-butyl(−)-[(4aS*,5R*,7aS*)-7a-(5-amino-2-fluorophenyl)-5-ethyl-4a,5,7,7a-tetrahydro-4H-furo[3,4-d][1,3]thiazin-2-yl]carbamate The compound obtained in Preparation Example 21-(9) (50 mg) was optically resolved by CHIRALPAK™ OJ-H manufactured by Daicel Chemical Industries, Ltd. (2 cm×25 cm, mobile phase: hexane:ethanol=1:1, flow rate: 10 mL/min), and the components having a retention time of 19 to 25 minutes were collected. This operation was repeated to obtain the title compound (365 mg; >99% ee) from 920 mg of the racemate.

Preparation Example 22

Synthesis of tert-butyl(−)-[(4aS*,5R*,7aS*)-7a-(5-amino-2-fluorophenyl)-5-methyl-4a,5,7,7a-tetrahydro-4H-furo[3,4-d][1,3]thiazin-2-yl]carbamate

[Formula 44]

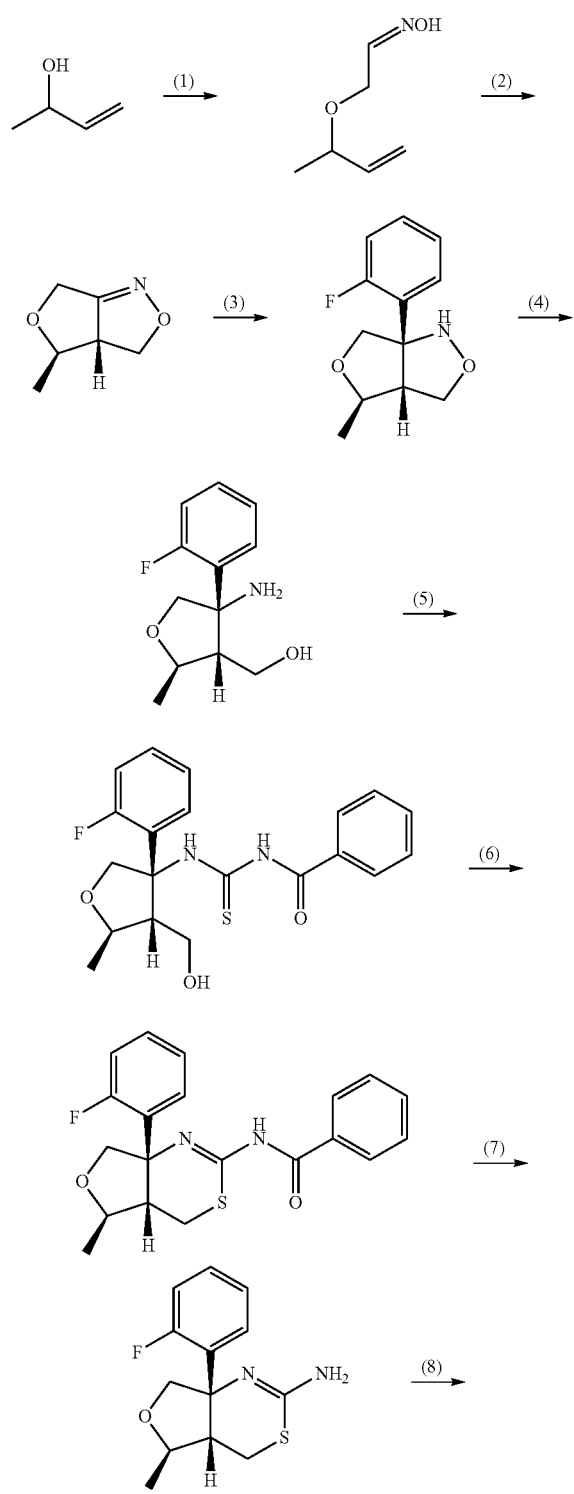

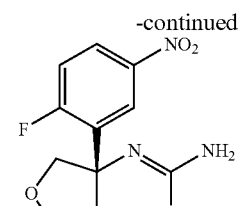

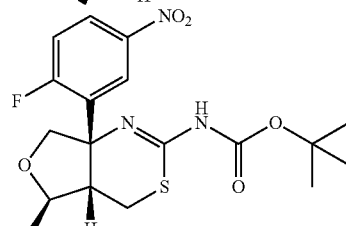

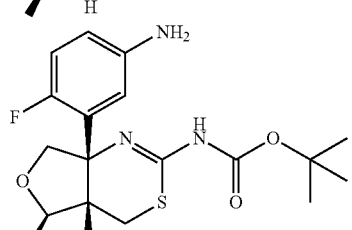

racemic

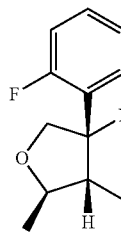

chiral (1) Synthesis of (1-methylallyloxy)acetaldehyde oxime

A solution of 3-buten-2-ol (5.00 g) in N-methyl-2-pyrrolidone (70.0 mL) was cooled to 0° C. under a nitrogen atmosphere. Sodium hydride (60%, 3.33 g) and bromoacetaldehyde diethyl acetal (15.0 g) were added to the reaction solution at the same temperature, and the mixture was stirred at 60° C. for 30 minutes. A saturated ammonium chloride solution was added to the reaction solution at 0° C., followed by extraction with ethyl acetate. The organic layer was washed with saturated sodium bicarbonate and saturated aqueous sodium chloride and then dried over anhydrous magnesium sulfate. The insoluble matter was separated by filtration and the filtrate was concentrated under reduced pressure. The residue was dissolved in heptane. The solution was filtered through silica gel and concentrated under reduced pressure. Formic acid (30.0 mL) and water (10.0 mL) were added to the residue, and the mixture was stirred at room temperature for 30 minutes. Hydroxylamine hydrochloride (5.78 g) and sodium acetate (11.4 g) were added to the reaction solution at the same temperature, and the mixture was stirred at room temperature for five days. Ethyl acetate and a saturated sodium chloride solution were added to the reaction solution, and the organic layer was separated. The organic layer was washed with saturated aqueous sodium chloride and then dried over anhydrous magnesium sulfate. The insoluble matter was separated by filtration and the filtrate was concentrated under reduced pressure. The residue was purified by silica gel column chromatography to obtain the title compound (2.29 g).

$^1$H-NMR (400 MHz, CDCl$_3$) δ (ppm): 1.26-1.29 (m, 3H), 3.85-4.36 (m, 3H), 5.17-5.24 (m, 2H), 5.68-5.77 (m, 1H), 6.90 (t, J=3.6 Hz, 0.5H), 7.49 (t, J=6.0 Hz, 0.5H).

(2) Synthesis of (3aR*,4R*)-4-methyl-3a,4-dihydro-3H,6H-furo[3,4-c]isoxazole

A 5% sodium hypochlorite solution (87.1 g) was added dropwise to a solution containing the compound obtained in Preparation Example 22-(1) (7.55 g) in dichloromethane (168 mL) at 0° C., and the mixture was stirred at 0° C. for 30 minutes. A sodium bisulfite solution was added to the reaction solution at the same temperature. The organic layer was separated and dried over anhydrous magnesium sulfate. The insoluble matter was separated by filtration and the filtrate was concentrated. The residue was purified by silica gel column chromatography to obtain the title compound (3.95 g).

$^1$H-NMR (400 MHz, CDCl$_3$) δ (ppm): 1.37 (d, J=5.6 Hz, 3H), 3.75-3.80 (m, 2H), 3.90-4.00 (m, 1H), 4.40-4.57 (m, 3H).

(3) Synthesis of (3aR*,4R*,6aS*)-6a-(2-fluorophenyl)-4-methyltetrahydrofuro[3,4-c]isoxazole A solution of n-butyllithium in hexane (2.60 M; 6.05 mL) was added dropwise to a solution containing 2-bromofluorobenzene (1.79 mL) in tetrahydrofuran/toluene (2.88 mL/28.8 mL) under a nitrogen atmosphere at −78° C. The reaction solution was stirred at the same temperature for 10 minutes. A boron trifluoride-diethyl ether complex (1.94 mL) and a solution containing the compound obtained in Preparation Example 22-(2) (1.00 g) in toluene (10 mL) were added dropwise to the reaction solution sequentially at the same temperature. After stirring at the same temperature for one hour, aqueous ammonium chloride was added to the reaction solution, and the reaction solution was warmed to room temperature. Water and ethyl acetate were added to the reaction solution, and the organic layer was separated. The organic layer was washed with a saturated sodium chloride solution. The organic layer was dried over anhydrous magnesium sulfate, and the insoluble matter was separated by filtration. The filtrate was concentrated and the residue was purified by silica gel column chromatography to obtain the title compound (1.60 g). ESI-MS; m/z 224 [M$^+$+H].

(4) Synthesis of [(2R*,3R*,4S*)-4-amino-4-(2-fluorophenyl)-2-methyl-tetrahydrofuran-3-yl]methanol Zinc powder (4.69 g) was added to a solution containing the compound obtained in Preparation Example 22-(3) (1.60 g) in acetic acid (30.0 mL) at room temperature. The reaction solution was stirred at room temperature for 17 hours. The insoluble matter was separated by filtration through celite and the filtrate was concentrated. Ethyl acetate and a sodium bicarbonate solution were added to the residue, and the organic layer was separated. The organic layer was washed with saturated aqueous sodium chloride and dried over anhydrous magnesium sulfate. The insoluble matter was separated by filtration and the filtrate was concentrated under reduced pressure to obtain the title compound (1.57 g).

$^1$H-NMR (400 MHz, CDCl$_3$) δ (ppm): 1.32 (d, J=6.4 Hz, 1H), 2.20-2.22 (m, 1H), 3.76-3.86 (m, 2H), 4.04-4.10 (m, 1H), 4.31-4.38 (m, 2H), 7.06-7.26 (m, 3H), 7.45-7.49 (m, 1H).

(5) Synthesis of 1-benzoyl-3-[(3S*,4R*,5R*)-3-(2-fluorophenyl)-4-hydroxymethyl)-5-methyl-tetrahydrofuran-3-yl]thiourea Benzoyl isothiocyanate (1.25 g) was added to a solution containing the compound obtained in Preparation Example 22-(4) (1.57 g) in dichloromethane (21.0 mL), and the mixture was stirred at room temperature for 10 minutes. The reaction solution was concentrated under reduced pressure. The residue was purified by silica gel column chromatography to obtain the title compound (1.43 g).

ESI-MS; m/z 389 [M$^+$+H].

$^1$H-NMR (400 MHz, CDCl$_3$) δ (ppm): 1.37 (d, J=6.0 Hz, 1H), 2.61-2.62 (m, 2H), 2.85-2.86 (m, 1H), 3.95-4.07 (m, 2H), 4.41-4.44 (m, 1H), 4.68 (d, J=10 Hz, 1H), 7.00-7.30 (m, 3H), 7.52 (t, J=8.0 Hz, 2H), 7.62-7.72 (m, 2H), 7.85-7.87 (m, 2H), 8.88 (br, 1H).

(6) Synthesis of N-[(4aS*,5R*,7aS*)-7a-(2-fluorophenyl)-5-methyl-4a,5,7,7a-tetrahydro-4H-furo[3,4-d][1,3]thiazin-2-yl]benzamide Trifluoromethanesulfonic anhydride (1.55 mL) was added to a solution of the compound obtained in Preparation Example 22-(5) (1.43 g) in pyridine (7.0 mL) at 0° C., and the mixture was stirred at the same temperature for 10 minutes. A saturated sodium bicarbonate solution was added to the reaction solution, followed by extraction with ethyl acetate. The organic layer was dried over anhydrous magnesium sulfate, and the insoluble matter was separated by filtration. The filtrate was concentrated under reduced pressure and the residue was purified by silica gel column chromatography to obtain the title compound (780 mg).

ESI-MS; m/z 371 [M$^+$+H].

(7) Synthesis of (4aS*,5R*,7aS*)-7a-(2-fluorophenyl)-5-methyl-4a,5,7,7a-tetrahydro-4H-furo[3,4-d][1,3]thiazin-2-ylamine A solution of the compound obtained in Preparation Example 22-(6) (3.02 g) and sodium methoxide (28% solution in methanol; 3.14 mL) in methanol (20 mL) was heated under reflux for 2.5 hours. After cooling the reaction solution to room temperature, the solvent was evaporated under reduced pressure. The residue was purified by silica gel chromatography to obtain the title compound (980 mg). ESI-MS; m/z 267 [M$^+$+H].

(8) Synthesis of (4aS*,5R*,7aS*)-7a-(2-fluoro-5-nitrophenyl)-5-methyl-4a,5,7,7a-tetrahydro-4H-furo[3,4-d][1,3]thiazin-2-ylamine Fuming nitric acid (199 μL) was added dropwise to a solution of the compound obtained in Preparation Example 22-(7) (980 mg) in concentrated sulfuric acid (36.6 mL) under ice-cooling. The reaction solution was stirred at the same temperature for 30 minutes and then poured into ice water. The reaction mixture was neutralized with a 5 N sodium hydroxide solution. The mixture was extracted with ethyl acetate twice. The organic layers were dried over anhydrous magnesium sulfate, and the insoluble matter was separated by filtration. The filtrate was concentrated under reduced pressure to obtain the title compound (1.02 g).
ESI-MS; m/z 312 [M++H].

(9) Synthesis of tert-butyl[(4aS*,5R*,7aS*)-7a-(2-fluoro-5-nitrophenyl)-5-methyl-4a,5,7,7a-tetrahydro-4H-furo[3,4-d][1,3]thiazin-2-yl]carbamate The compound obtained in Preparation Example 22-(8) (1.02 g) was dissolved in dichloromethane (15.5 mL). Triethylamine (1.83 mL) and di-tert-butyl dicarbonate (1.43 g) were added to the solution, and the mixture was stirred at room temperature for 14 hours. The reaction solution was concentrated under reduced pressure and the residue was purified by silica gel column chromatography to obtain the title compound (1.68 g).
ESI-MS; m/z 412 [M++H].

(10) Synthesis of tert-butyl[(4aS*,5R*,7aS*)-7a-(5-amino-2-fluorophenyl)-5-methyl-4a,5,7,7a-tetrahydro-4H-furo[3,4-d][1,3]thiazin-2-yl]carbamate A saturated ammonium chloride solution (2.7 mL) and iron powder (1.25 g) were added to a solution of the compound obtained in Preparation Example 22-(9) (1.15 g) in ethanol (27 mL). The reaction solution was heated under reflux for 30 minutes and then cooled to room temperature. The reaction solution was diluted with ethyl acetate and the insoluble matter was separated by filtration through celite. Ethyl acetate and water were added to the filtrate, and the organic layer was separated. The organic layer was dried over anhydrous magnesium sulfate, and the insoluble matter was separated by filtration. The filtrate was concentrated under reduced pressure to obtain the title compound (1.01 g).
$^1$H-NMR (400 MHz, CDCl$_3$) δ (ppm): 1.39-1.50 (m, 3H), 1.50 (s, 9H), 2.64-2.74 (m, 2H), 3.08-3.12 (m, 1H), 3.61 (br, 2H), 3.82-3.84 (m, 1H), 4.43-4.56 (m, 2H), 6.58-6.60 (m, 2H), 6.84-6.89 (m, 1H).

(11) Synthesis of tert-butyl(−)-[(4aS*,5R*,7aS*)-7a-(5-amino-2-fluorophenyl)-5-methyl-4a,5,7,7a-tetrahydro-4H-furo[3,4-d][1,3]thiazin-2-yl]carbamate The compound obtained in Preparation Example 22-(10) (50 mg) was optically resolved by CHIRALPAK™ OJ-H manufactured by Daicel Chemical Industries, Ltd.
(2 cm×25 cm, mobile phase: hexane:ethanol=9:1, flow rate: 10 mL/min), and the components having a retention time of 19 to 30 minutes were collected. This operation was repeated to obtain the title compound (363 mg; >99% ee) from 1.01 g of the racemate.
$^1$H-NMR (400 MHz, CDCl$_3$) δ (ppm): 1.38 (d, J=6.0 Hz, 3H), 2.64-2.68 (m, 1H), 2.73-2.75 (m, 1H), 3.08-3.12 (m, 1H), 3.62 (br, 2H), 3.82-3.85 (m, 1H), 4.42-4.45 (m, 1H), 4.54-4.56 (m, 1H), 6.55-6.62 (m, 2H), 6.84-6.89 (m, 1H).

Preparation Example 23

[Formula 45]

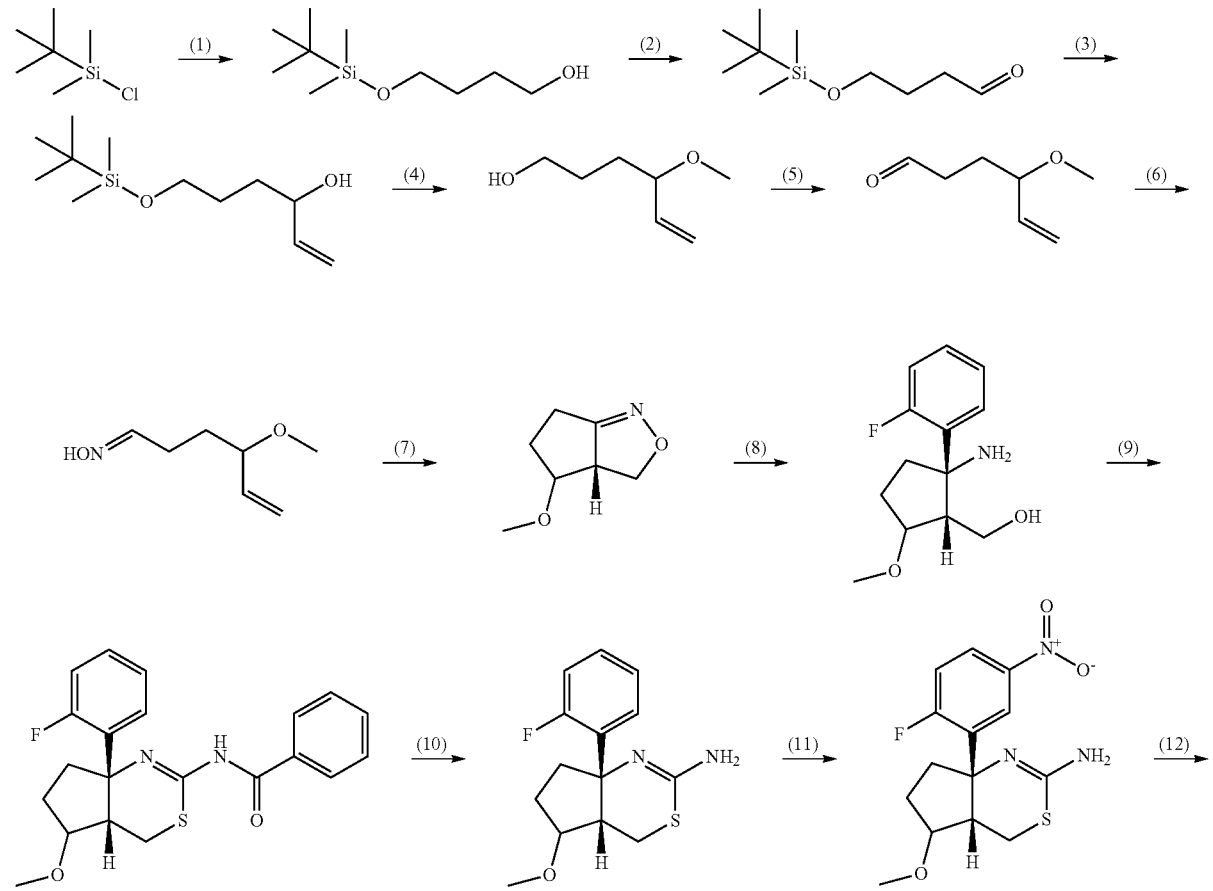

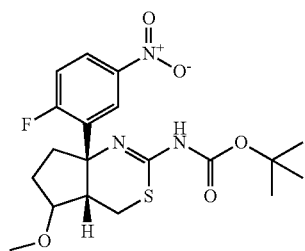
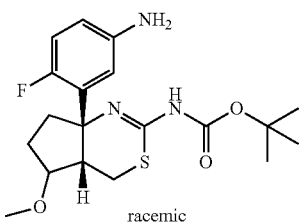
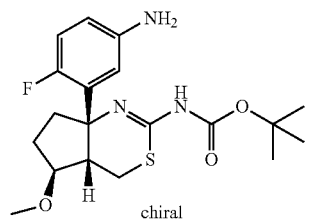

racemic chiral

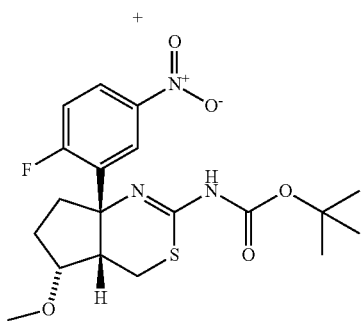
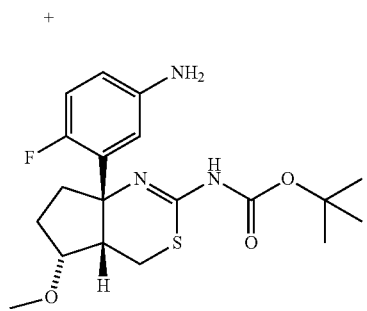

(1) Synthesis of 4-(tert-butyldimethylsilanyloxy)butan-1-ol

Imidazole (6.77 g) was added to a solution containing 1,4-butanediol (58.8 mL) in DMF (60.0 mL) at room temperature. A solution of tert-butyldimethylsilyl chloride (10.0 g) in dichloromethane (5.0 mL) was added dropwise, and the mixture was stirred at the same temperature for three hours. Diethyl ether and water were added to the reaction solution. The organic layer was separated, washed with water and a saturated sodium chloride solution and then dried over anhydrous magnesium sulfate. The insoluble matter was separated by filtration and the filtrate was concentrated to obtain the title compound (13.4 g).

$^1$H-NMR (400 MHz, CDCl$_3$) δ (ppm): 0.07 (s, 6H), 0.90 (s, 9H), 1.62-1.68 (m, 4H), 3.64-3.69 (m, 4H).

(2) Synthesis of 4-(tert-butyldimethylsilanyloxy)butyraldehyde

Dimethyl sulfoxide (23.1 mL), N,N-diisopropylethylamine (45.4 mL) and a sulfur trioxide-pyridine complex (36.3 g) were added to a solution containing the compound obtained in Preparation Example 23-(1) (13.3 g) in dichloromethane (162 mL) at 0° C., and the mixture was stirred at the same temperature for 20 minutes. A saturated sodium bicarbonate solution was added to the reaction solution at the same temperature. The organic layer was separated and dried over anhydrous magnesium sulfate. The insoluble matter was separated by filtration and the filtrate was concentrated. Diethyl ether and a 2 N hydrochloric acid solution were added to the residue. The organic layer was separated, washed with a saturated sodium bicarbonate solution and then dried over anhydrous magnesium sulfate. The insoluble matter was separated by filtration through silica gel and the filtrate was concentrated to obtain the title compound (12.0 g).

$^1$H-NMR (400 MHz, CDCl$_3$) δ (ppm): 0.05 (s, 6H), 0.89 (s, 9H), 1.83-1.89 (m, 2H), 2.49-2.62 (m, 2H), 3.64-3.67 (m, 2H), 9.79 (t, J=1.6 Hz, 1H).

(3) Synthesis of 6-(tert-butyldimethylsilanyloxy)-hex-1-en-3-ol

A solution of vinylmagnesium chloride in THF (1.38 M, 51.6 mL) was added dropwise to a solution containing the compound obtained in Preparation Example 23-(2) (12.0 g) in THF (138 mL) at −78° C., and the mixture was stirred at 0° C. for 10 minutes. A saturated ammonium chloride solution was added to the reaction solution at the same temperature, followed by addition of ethyl acetate and a 2 N hydrochloric acid solution. The organic layer was separated, washed with a saturated sodium bicarbonate solution and then dried over anhydrous magnesium sulfate. The insoluble matter was separated by filtration through silica gel and the filtrate was concentrated to obtain the title compound (13.5 g).

$^1$H-NMR (400 MHz, CDCl$_3$) δ (ppm): 0.07 (s, 6H), 0.90 (s, 9H), 1.63-1.66 (m, 4H), 3.65-3.68 (m, 2H), 4.15-4.17 (m, 1H), 5.09-5.11 (m, 1H), 5.22-5.27 (m, 1H), 5.85-5.87 (m, 1H).

(4) Synthesis of 4-methoxy-hex-5-en-1-ol

Methyl iodide (10.9 mL) and sodium hydride (60%, 2.34 g) were added to a solution containing the compound obtained in Preparation Example 23-(3) (13.5 g) in N-methyl-2-pyrrolidone (146 mL) at 0° C., and the mixture was stirred at 60° C. for 30 minutes. A saturated ammonium chloride aqueous solution and diethyl ether were added to the reaction solution at 0° C. The organic layer was separated, washed with a saturated sodium bicarbonate solution and a saturated sodium chloride solution and then dried over anhydrous magnesium sulfate. The insoluble matter was separated by filtration through silica gel and the filtrate was concentrated to obtain a residue. Acetyl chloride (15 mL) was added dropwise to methanol (135 mL) at 0° C., and the mixture was added to the above residue. The reaction solution was concentrated and the resulting residue was purified by silica gel column chromatography to obtain the title compound (5.52 g).

$^1$H-NMR (400 MHz, CDCl$_3$) δ (ppm): 1.64-1.68 (m, 4H), 3.29 (s, 3H), 3.55-3.65 (m, 3H), 5.18-5.23 (m, 2H), 5.63-5.72 (m, 1H).

(5) Synthesis of 4-methoxy-hex-5-enal

Dimethyl sulfoxide (12.0 mL), N,N-diisopropylethylamine (29.5 mL) and a sulfur trioxide-pyridine complex (20.2 g) were added to a solution containing the compound obtained in Preparation Example 23-(4) (5.52 g) in dichloromethane (84.8 mL) at 0° C., and the mixture was stirred at the same temperature for 20 minutes. A saturated sodium bicarbonate solution was added to the reaction solution at the same temperature. The organic layer was separated and dried over anhydrous magnesium sulfate. The insoluble matter was separated by filtration and the filtrate was concentrated. Diethyl ether and a 2 N hydrochloric acid solution were added to the residue. The organic layer was separated, washed with a saturated sodium bicarbonate solution and then dried over anhydrous magnesium sulfate. The insoluble matter was separated by filtration and the filtrate was concentrated to obtain the title compound (3.85 g).

$^1$H-NMR (400 MHz, CDCl$_3$) δ (ppm): 1.84-1.91 (m, 2H), 2.50-2.53 (m, 2H), 3.26 (s, 3H), 3.54-3.57 (m, 1H), 5.20-5.25 (m, 2H), 5.61-5.70 (m, 1H), 9.76 (t, J=1.6 Hz, 1H).

(6) Synthesis of 4-methoxy-hex-5-enal oxime

Sodium acetate (4.92 g) and hydroxylamine hydrochloride (3.13 g) were added to a solution containing the compound obtained in Preparation Example 23-(5) (3.85 g) in methanol (60.0 mL) at room temperature, and the mixture was stirred at the same temperature for three hours. Ethyl acetate and a saturated sodium bicarbonate solution were added to the reaction solution. The organic layer was separated, washed with a saturated sodium chloride solution and then dried over anhydrous magnesium sulfate. The insoluble matter was separated by filtration and the filtrate was concentrated to obtain the title compound (3.40 g).

$^1$H-NMR (400 MHz, CDCl$_3$) δ (ppm): 1.75-1.82 (m, 2H), 2.26-2.31 (m, 1H), 2.42-2.48 (m, 1H), 3.27-3.29 (m, 3H), 3.52-3.58 (m, 1H), 5.20-5.25 (m, 2H), 5.61-5.71 (m, 1H), 6.75 (t, J=5.6 Hz, 0.5H), 7.43 (t, J=5.2 Hz, 0.5H).

(7) Synthesis of 4-methoxy-3a,4,5,6-tetrahydro-3H-cyclopenta[c]isoxazole

The title compound (1.30 g) was obtained from the compound obtained in Preparation Example 23-(6) (3.40 g) according to Preparation Example 22-(2).

$^1$H-NMR (400 MHz, CDCl$_3$) δ (ppm): 2.18-2.70 (m, 5H), 3.26-3.28 (m, 3H), 3.42-3.79 (m, 1H), 3.96-4.20 (m, 1H), 4.35-4.68 (m, 1H).

(8) Synthesis of [2-amino-2-(2-fluorophenyl)-5-methoxy-cyclopentyl]methanol

A solution of n-butyllithium in hexane (2.60 M; 7.07 mL) was added dropwise to a solution containing 2-bromofluorobenzene (2.09 mL) in tetrahydrofuran/toluene (3.36 mL/33.6 mL) under a nitrogen atmosphere at −78° C. The reaction solution was stirred at the same temperature for 10 minutes. A boron trifluoride-diethyl ether complex (2.27 mL) and a solution containing the compound obtained in Preparation Example 23-(7) (1.30 g) in toluene (10 mL) were added dropwise to the reaction solution at the same temperature. After stirring at the same temperature for 40 minutes, aqueous ammonium chloride was added to the reaction solution, followed by warming to room temperature. Water and ethyl acetate were added to the reaction solution, and the organic layer was separated. The organic layer was washed with a saturated sodium chloride solution. The organic layer was dried over anhydrous magnesium sulfate, and the insoluble matter was separated by filtration. The filtrate was concentrated and the residue was dissolved in ethyl acetate-heptane. The solution was filtered through silica gel and concentrated. Acetic acid (31.0 mL) and zinc powder (5.02 g) were added at room temperature. The reaction solution was stirred at room temperature for four hours. The insoluble matter was separated by filtration through celite and the filtrate was concentrated. Ethyl acetate and a sodium bicarbonate solution were added to the residue, and the organic layer was separated. The organic layer was washed with saturated aqueous sodium chloride and dried over anhydrous magnesium sulfate. The insoluble matter was separated by filtration and the filtrate was concentrated under reduced pressure to obtain the title compound (1.41 g).

ESI-MS; m/z 240 [M$^+$+H].

(9) Synthesis of N-[7a-(2-fluorophenyl)-5-methoxy-4,4a,5,6,7,7a-hexahydro-cyclopenta[d][1,3]thiazin-2-yl]benzamide Benzoyl isothiocyanate (0.871 mL) was added to a solution containing the compound obtained in Preparation Example 23-(8) (1.41 g) in dichloromethane (19.6 mL), and the mixture was stirred at room temperature for 10 minutes. The reaction solution was concentrated under reduced pressure and the residue was dissolved in ethyl acetate-heptane. The solution was filtered through silica gel and concentrated. Dichloromethane (24.0 mL), pyridine (1.16 mL) and trifluoromethanesulfonic anhydride (2.20 mL) were added at −78° C., and the mixture was stirred at the same temperature for 30 minutes. A saturated sodium bicarbonate solution was added to the reaction solution, followed by extraction with dichloromethane. The organic layer was dried over anhydrous magnesium sulfate, and the insoluble matter was separated by filtration. The filtrate was concentrated under reduced pressure and the residue was purified by silica gel column chromatography to obtain the title compound (1.71 g).

ESI-MS; m/z 385 [M$^+$+H].

(10) Synthesis of 7a-(2-fluorophenyl)-5-methoxy-4,4a,5,6,7,7a-hexahydro-cyclopenta[d][1,3]thiazin-2-ylamine The title compound (681 mg) was obtained from the compound obtained in Preparation Example 23-(9) (1.71 g) according to the method of Preparation Example 22-(7).

ESI-MS; m/z 281 [M$^+$+H].

(11) Synthesis of 7a-(2-fluoro-5-nitrophenyl)-5-methoxy-4,4a,5,6,7,7a-hexahydro-cyclopenta[d][1,3]thiazin-2-ylamine The title compound (506 mg) was obtained from the compound obtained in Preparation Example 23-(10) (681 mg) according to the method of Preparation Example 22-(8).

ESI-MS; m/z 326 [M$^+$+H].

(12) Synthesis of tert-butyl[(4aS*,5S*,7aS*)-7a-(2-fluoro-5-nitrophenyl)-5-methoxy-4,4a,5,6,7,7a-hexahydro-cyclopenta[d][1,3]thiazin-2-yl]carbamate and tert-butyl[(4aS*,5R*,7aS*)-7a-(2-fluoro-5-nitrophenyl)-5-methoxy-4,4a,5,6,7,7a-hexahydro-cyclopenta[d][1,3]thiazin-2-yl]carbamate The more polar title compound (283 mg) and the less polar title compound (135 mg) were obtained from the compound obtained in Preparation Example 23-(11) (506 mg) according to the method of Preparation Example 22-(9).

More polar title compound (tert-butyl[(4aS*,5S*,7aS*)-7a-(2-fluoro-5-nitrophenyl)-5-methoxy-4,4a,5,6,7,7a-hexahydro-cyclopenta[d][1,3]thiazin-2-yl]carbamate)

¹H-NMR (400 MHz, CDCl₃) δ (ppm): 1.53 (s, 9H), 1.87-2.10 (m, 5H), 2.66-2.90 (m, 2H), 3.41 (s, 3H), 4.10-4.15 (m, 1H), 7.20-7.26 (m, 1H), 8.18-8.21 (m, 2H).

Less polar title compound (tert-butyl[(4aS*,5R*,7aS*)-7a-(2-fluoro-5-nitrophenyl)-5-methoxy-4,4a,5,6,7,7a-hexahydro-cyclopenta[d][1,3]thiazin-2-yl]carbamate)

¹H-NMR (400 MHz, CDCl₃) δ (ppm): 1.50 (s, 9H), 1.81-2.45 (m, 5H), 2.88-3.01 (m, 2H), 3.41 (s, 3H), 4.11-4.13 (m, 1H), 7.20-7.26 (m, 1H), 8.19-8.28 (m, 2H).

(13) Synthesis of tert-butyl[(4aS*,5S*,7aS*)-7a-(5-amino-2-fluorophenyl)-5-methoxy-4,4a,5,6,7,7a-hexahydro-cyclopenta[d][1,3]thiazin-2-yl]carbamate The title compound (244 mg) was obtained from the more polar compound obtained in Preparation Example 23-(12) (283 mg) according to the method of Preparation Example 22-(10).

¹H-NMR (400 MHz, CDCl₃) δ (ppm): 1.51 (s, 9H), 1.52-2.15 (m, 5H), 2.75-3.00 (m, 2H), 3.40 (s, 3H), 4.10-4.15 (m, 1H), 6.54-6.57 (m, 2H), 6.83-6.86 (m, 1H).

(14) Synthesis of tert-butyl[(4aS*,5R*,7aS*)-7a-(5-amino-2-fluorophenyl)-5-methoxy-4,4a,5,6,7,7a-hexahydro-cyclopenta[d][1,3]thiazin-2-yl]carbamate The title compound (79.0 mg) was obtained from the less polar compound obtained in Preparation Example 23-(12) (100 mg) according to the method of Preparation Example 22-(10).

¹H-NMR (400 MHz, CDCl₃) δ (ppm): 1.49 (s, 9H), 1.57-2.20 (m, 4H), 2.45-2.49 (m, 1H), 2.86-3.03 (m, 3H), 3.32 (s, 3H), 3.98-4.00 (m, 1H), 6.54-6.55 (m, 2H), 6.83-6.88 (m, 1H).

(15) Synthesis of tert-butyl[(4aS*,5S*,7aS*)-7a-(5-amino-2-fluorophenyl)-5-methoxy-4,4a,5,6,7,7a-hexahydro-cyclopenta[d][1,3]thiazin-2-yl]carbamate The compound obtained in Preparation Example 23-(13) (50 mg) was optically resolved by CHIRALPAK™ OJ-H manufactured by Daicel Chemical Industries, Ltd. (2 cm×25 cm, mobile phase: hexane:ethanol=1:1→0:1 (gradient, 30 min), flow rate: 10 mL/min), and the components having a retention time of 14 to 20 minutes were collected. This operation was repeated to obtain the title compound (89 mg; >99% ee) from 244 mg of the racemate.

Preparation Example 24 tert-Butyl[(4aS,5S,7aS)-7a-(5-amino-2-fluorophenyl)-5-methoxymethyl-4,5,7,7a-tetrahydro-4H-furo[3,4-d][1,3]thiazin-2-yl]carbamate

[Formula 46]

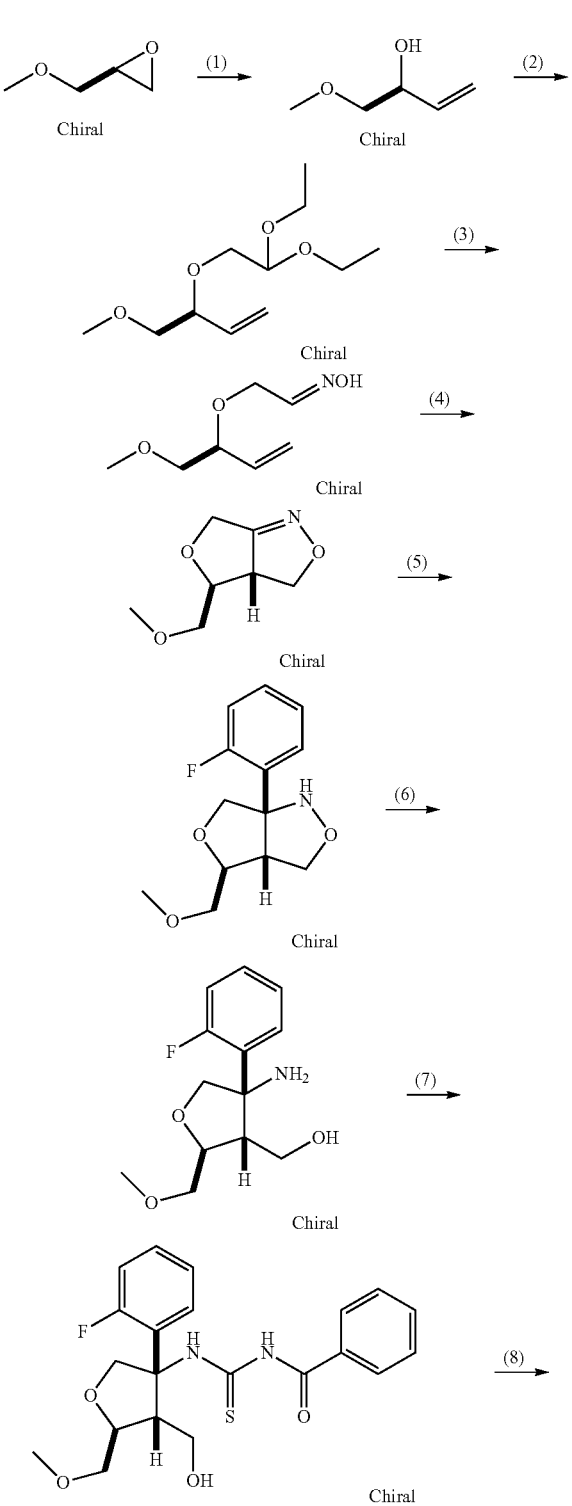

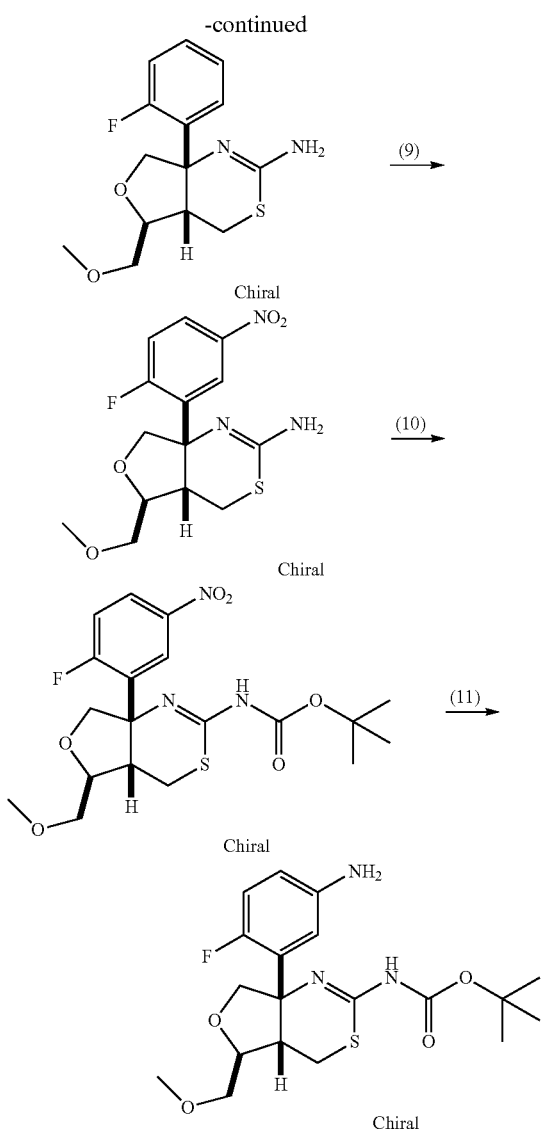

(1) Synthesis of (S)-1-methoxy-but-3-en-2-ol

A solution of trimethylsulfonium iodide (50.0 g) in toluene (200 mL) was heated under reflux using a Dean-Stark trap for one hour and concentrated. The residue was dissolved in THF (444 mL), and a solution of n-BuLi in hexane (2.6 M; 94.0 mL) was added dropwise at −15° C. After stirring at the same temperature for 30 minutes, (S)-glycidyl methyl ether (7.31 mL) was added dropwise and the mixture was stirred at room temperature for 14 hours. Water was added to the reaction solution at 0° C., followed by extraction with diethyl ether. The organic layer was dried over anhydrous magnesium sulfate, and the insoluble matter was separated by filtration. The filtrate was concentrated under reduced pressure. The residue was purified by silica gel chromatography to obtain the title compound (3.30 g).

(2) Synthesis of (S)-3-(2,2-diethoxy-ethoxy)-4-methoxy-but-1-ene

A solution of the compound obtained in Preparation Example 24-(1) (5.00 g) in N-methyl-2-pyrrolidone (98.0 mL) was cooled to 0° C. Sodium hydride (60%, 2.16 g) and bromoacetaldehyde diethyl acetal (8.86 g) were added to the reaction solution at the same temperature, and the mixture was stirred at 100° C. for two hours. A saturated ammonium chloride solution was added to the reaction solution at 0° C., followed by extraction with ethyl acetate. The organic layer was washed with saturated sodium bicarbonate and saturated aqueous sodium chloride and then dried over anhydrous magnesium sulfate. The insoluble matter was separated by filtration and the filtrate was concentrated under reduced pressure. The residue was purified by silica gel chromatography to obtain the title compound (5.82 g).
$^1$H-NMR (400 MHz, CDCl$_3$) δ (ppm): 1.91-1.26 (m, 6H), 3.37 (s, 3H), 3.38-4.00 (m, 5H), 4.63-4.67 (m, 1H), 5.25-5.35 (m, 2H), 5.70-5.74 (m, 1H).

(3) Synthesis of ((S)-1-methoxymethyl-allyloxy)-acetaldehyde oxime

Formic acid (35.1 mL), hydroxylamine hydrochloride (2.83 g) and sodium acetate (4.46 g) were added to the compound obtained in Preparation Example 24-(2) (5.82 g), and the mixture was stirred at room temperature for 30 minutes. Ethyl acetate and a saturated sodium chloride solution were added to the reaction solution, and the organic layer was separated. The organic layer was washed with saturated aqueous sodium chloride and then dried over anhydrous magnesium sulfate. The insoluble matter was separated by filtration and the filtrate was concentrated under reduced pressure. The residue was purified by silica gel column chromatography to obtain the title compound (2.00 g).
$^1$H-NMR (400 MHz, CDCl$_3$) δ (ppm): 3.34-3.51 (m, 4H), 3.93-4.23 (m, 3H), 4.33-4.46 (m, 1H), 5.31-5.38 (m, 2H), 5.69-5.78 (m, 1H), 6.98 (t, J=3.6 Hz, 0.5H), 7.53 (t, J=4.8 Hz, 0.5H).

(4) Synthesis of (3aR,4S)-4-methoxymethyl-3a,4-dihydro-3H,6H-furo[3,4-c]isoxazole The title compound (870 mg) was obtained from the compound obtained in Preparation Example 24-(3) (2.00 g) according to Preparation Example 22-(2).
$^1$H-NMR (400 MHz, CDCl$_3$) δ (ppm): 3.38-3.55 (m, 4H), 3.41 (s, 3H), 3.97-4.13 (m, 2H), 4.48-4.58 (m, 2H).

(5) Synthesis of (3aR,4S,6aS)-6a-(2-fluorophenyl)-4-methoxymethyltetrahydrofuro[3,4-c]isoxazole The title compound (940 mg) was obtained from the compound obtained in Preparation Example 24-(4) (870 mg) according to Preparation Example 22-(3).
ESI-MS; m/z 254 [M$^+$+H].

(6) Synthesis of [(2S,3R,4S)-4-amino-4-(2-fluorophenyl)-2-methoxymethyltetrahydrofuran-3-yl]methanol The title compound (850 mg) was obtained from the compound obtained in Preparation Example 24-(5) (940 mg) according to Preparation Example 22-(4). ESI-MS; m/z 256 [M$^+$+H].

(7) Synthesis of 1-benzoyl-3-[(3S,4R,5S)-3-(2-fluorophenyl)-4-hydroxymethyl-5-methoxymethyl-tetrahydrofuran-3-yl]thiourea The title compound (1.22 g) was obtained from the compound obtained in Preparation Example 24-(6) (850 mg) according to Preparation Example 22-(5). ESI-MS; m/z 441 [M$^+$+Na].

(8) Synthesis of (4aS,5S,7aS)-7a-(2-fluorophenyl)-5-methoxymethyl-4a,5,7,7a-tetrahydro-4H-furo[3,4-d][1,3]thiazin-2-ylamine Pyridine (0.66 mL) and trifluoromethanesulfonic anhydride (0.983 mL) were added to a solution of the compound obtained in Preparation Example 24-(7) (1.22 g) in dichloromethane (5.80 mL) at −78° C., and the mixture was stirred at 0° C. for 10 minutes. A saturated sodium bicarbonate solution was added to the reaction solution, followed by extraction with dichloromethane. The organic layer was dried over anhydrous magnesium sulfate, and the insoluble matter was separated by filtration. The filtrate was concentrated under reduced pressure. The residue was filtered through silica gel using ethyl acetate and heptane and concentrated under reduced pressure. A solution of sodium methoxide (28% solution in methanol; 1.08 mL) in methanol (7.00 mL) was added to the residue, followed by heating under reflux for 2.5 hours. After cooling the reaction solution to room temperature, the solvent was evaporated under reduced pressure. The residue was purified by silica gel chromatography to obtain the title compound (231 mg). ESI-MS; m/z 297 [M$^+$+H].

(9) Synthesis of (4aS,5S,7aS)-7a-(2-fluoro-5-nitrophenyl)-5-methoxymethyl-4a,5,7,7a-tetrahydro-4H-furo[3,4-d][1,3]thiazin-2-ylamine The title compound (211 mg) was obtained from the compound obtained in Preparation Example 24-(8) (231 mg) according to Preparation Example 22-(8). ESI-MS; m/z 342 [M$^+$+H].

(10) Synthesis of tert-butyl[(4aS,5S,7aS)-7a-(2-fluoro-5-nitrophenyl)-5-methoxymethyl-4,5,7,7a-tetrahydro-4H-furo[3,4-d][1,3]thiazin-2-yl]carbamate The title compound (144 mg) was obtained from the compound obtained in Preparation Example 24-(9) (211 mg) according to Preparation Example 22-(9).
$^1$H-NMR (400 MHz, CDCl$_3$) δ (ppm): 1.52 (s, 9H), 2.68-2.77 (m, 1H), 2.88-2.93 (m, 2H), 3.39 (s, 3H), 3.44-3.62 (m, 2H), 3.97-3.99 (m, 1H), 4.46-4.52 (m, 2H), 7.14-7.17 (m, 1H), 8.21-8.30 (m, 2H).

(11) tert-Butyl[(4aS,5S,7aS)-7a-(5-amino-2-fluorophenyl)-5-methoxymethyl-4,5,7,7a-tetrahydro-4H-furo[3,4-d][1,3]thiazin-2-yl]carbamate The title compound (86 mg) was obtained from the compound obtained in Preparation Example 24-(10) (114 mg) according to Preparation Example 22-(10).
$^1$H-NMR (400 MHz, CDCl$_3$) δ (ppm): 1.50 (s, 9H), 2.72-2.76 (m, 1H), 3.12-3.13 (m, 2H), 3.56 (s, 3H), 3.58-3.65 (m, 2H), 3.81-3.82 (m, 1H), 4.49-4.51 (m, 2H), 6.56-6.63 (m, 2H), 6.84-6.89 (m, 1H).

Preparation Example 25

Synthesis of tert-butyl[(4aS,5S,7aS)-7a-(5-amino-2-fluorophenyl)-5-fluoromethyl-4a,5,7,7a-tetrahydro-4H-furo[3,4-d][1,3]thiazin-2-yl]carbamate

[Formula 47]

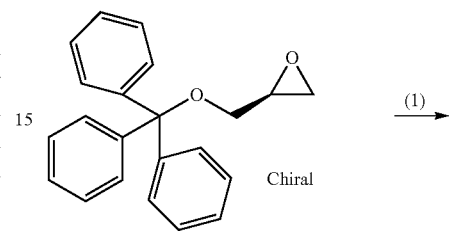

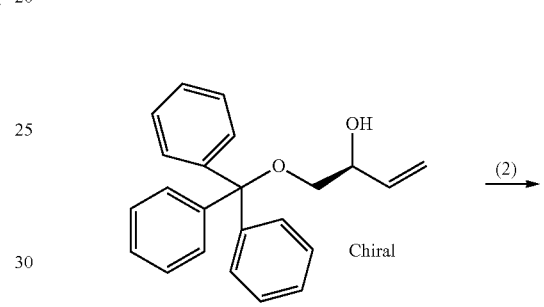

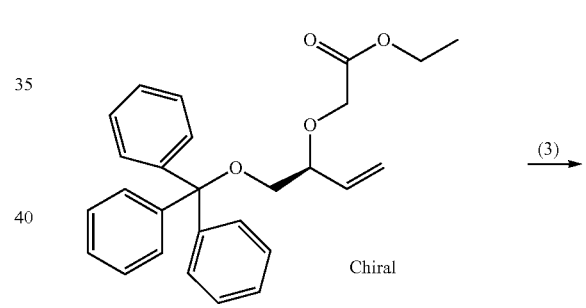

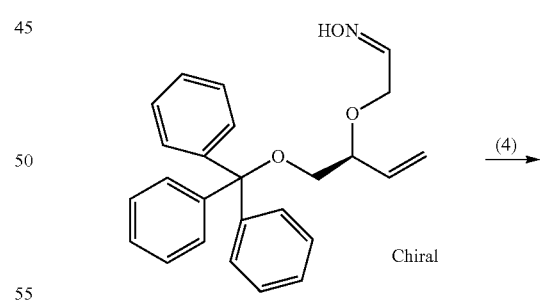

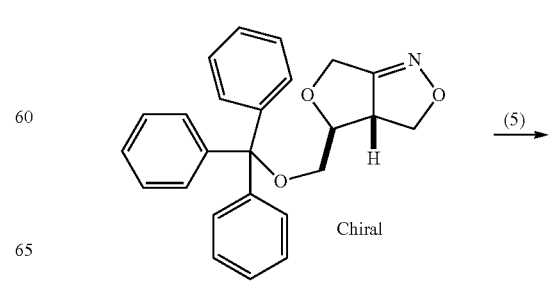

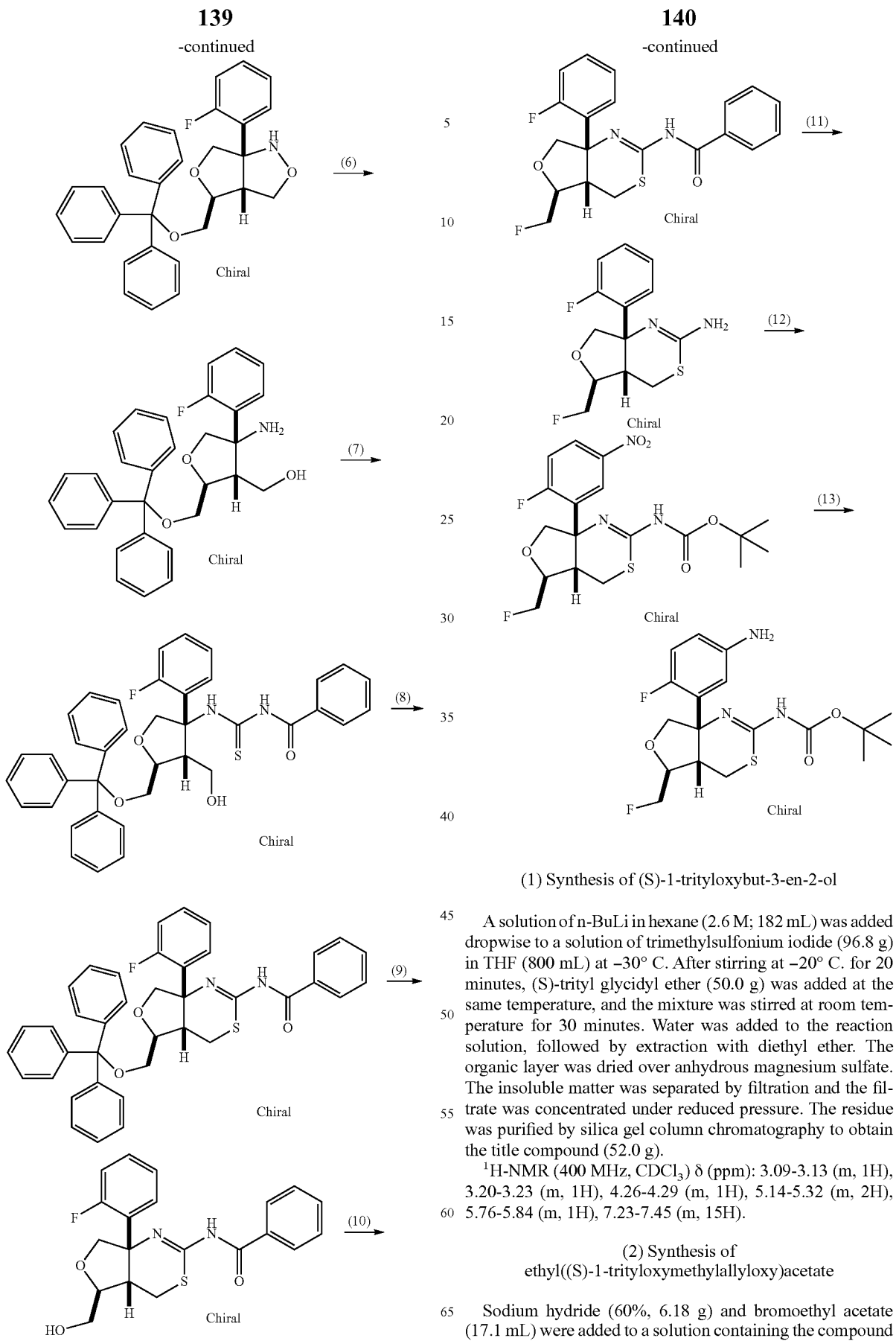

(1) Synthesis of (S)-1-trityloxybut-3-en-2-ol

A solution of n-BuLi in hexane (2.6 M; 182 mL) was added dropwise to a solution of trimethylsulfonium iodide (96.8 g) in THF (800 mL) at −30° C. After stirring at −20° C. for 20 minutes, (S)-trityl glycidyl ether (50.0 g) was added at the same temperature, and the mixture was stirred at room temperature for 30 minutes. Water was added to the reaction solution, followed by extraction with diethyl ether. The organic layer was dried over anhydrous magnesium sulfate. The insoluble matter was separated by filtration and the filtrate was concentrated under reduced pressure. The residue was purified by silica gel column chromatography to obtain the title compound (52.0 g).

$^1$H-NMR (400 MHz, CDCl$_3$) δ (ppm): 3.09-3.13 (m, 1H), 3.20-3.23 (m, 1H), 4.26-4.29 (m, 1H), 5.14-5.32 (m, 2H), 5.76-5.84 (m, 1H), 7.23-7.45 (m, 15H).

(2) Synthesis of ethyl((S)-1-trityloxymethylallyloxy)acetate

Sodium hydride (60%, 6.18 g) and bromoethyl acetate (17.1 mL) were added to a solution containing the compound obtained in Preparation Example 25-(1) (25.5 g) in N-methyl- 2-pyrrolidone (210 mL) at 0° C. The mixture was stirred at 50° C. for 18 hours and stirred at 100° C. for one hour. A saturated ammonium chloride solution was added to the reaction solution at 0° C., followed by extraction with diethyl ether. The organic layer was dried over anhydrous magnesium sulfate. The insoluble matter was separated by filtration and the filtrate was concentrated. The residue was purified by silica gel column chromatography to obtain the title compound (15.5 g).

$^1$H-NMR (400 MHz, CDCl$_3$) δ (ppm): 1.32 (t, J=7.2 Hz, 3H), 3.13-3.17 (m, 1H), 3.31-3.35 (m, 1H), 3.98-4.27 (m, 5H), 5.28-5.33 (m, 2H), 5.74-5.76 (m, 1H), 7.20-7.47 (m, 15H).

(3) Synthesis of ((S)-1-trityloxymethylallyloxy)acetaldehyde oxime

A solution of diisobutylaluminum hydride in toluene (1.0 M; 55.2 mL) was added dropwise to a solution containing the compound obtained in Preparation Example 25-(2) (15.5 g) in dichloromethane (74.0 mL) at −78° C. The mixture was stirred at the same temperature for 30 minutes. A 2 N hydrochloric acid solution was added to the reaction solution, followed by extraction with dichloromethane. The organic layer was washed with a saturated sodium bicarbonate solution and dried over anhydrous magnesium sulfate. The insoluble matter was separated by filtration and the filtrate was concentrated. Methanol (70.0 mL), sodium acetate (6.04 g) and hydroxylamine hydrochloride (3.84 g) were added to the residue at room temperature, and the mixture was stirred at the same temperature for 15 minutes. Ethyl acetate and water were added to the reaction solution, and the organic layer was separated and dried over anhydrous magnesium sulfate. The insoluble matter was separated by filtration and the filtrate was concentrated. The residue was purified by silica gel column chromatography to obtain the title compound (11.3 g).

$^1$H-NMR (400 MHz, CDCl$_3$) δ (ppm): 3.08-3.12 (m, 1H), 3.24-3.26 (m, 1H), 3.81-4.42 (m, 4H), 5.23-5.30 (m, 2H), 5.70-5.72 (m, 1H), 6.95-6.96 (m, 0.5H), 7.21-7.47 (m, 15H), 7.52-7.53 (m, 0.5H).

(4) Synthesis of (3aR,4S)-4-trityloxymethyl-3a,4-dihydro-3H,6H-furo[3,4-c]isoxazole A 5% sodium hypochlorite solution (52.2 mL) was added dropwise to a solution containing the compound obtained in Preparation Example 25-(3) (11.3 g) in dichloromethane (100 mL) at 0° C., and the mixture was stirred at 0° C. for 30 minutes. A sodium bisulfite solution was added to the reaction solution at the same temperature. The organic layer was separated and dried over anhydrous magnesium sulfate. The insoluble matter was separated by filtration and the filtrate was concentrated. The residue was purified by silica gel column chromatography to obtain the title compound (5.20 g).

$^1$H-NMR (400 MHz, CDCl$_3$) δ (ppm): 3.21-3.35 (m, 1H), 3.37-3.40 (m, 1H), 3.93-4.07 (m, 3H), 4.47-4.57 (m, 3H), 7.23-7.42 (m, 15H).

(5) Synthesis of (3aR,4S,6aS)-6a-(2-fluorophenyl)-4-trityloxymethyltetrahydrofuro[3,4-c]isoxazole A solution of n-butyllithium in hexane (2.60 M; 10.4 mL) was added dropwise to a solution containing 2-bromofluorobenzene (2.93 mL) in tetrahydrofuran/toluene (10.8 mL/108 mL) under a nitrogen atmosphere at −78° C. The reaction solution was stirred at the same temperature for 10 minutes. A boron trifluoride-diethyl ether complex (3.33 mL) and a solution containing the compound obtained in Preparation Example 25-(4) (5.20 g) in toluene (50 mL) were added dropwise to the reaction solution sequentially at the same temperature. After stirring at the same temperature for 40 minutes, aqueous ammonium chloride was added to the reaction solution, followed by warming to room temperature. Water and ethyl acetate were added to the reaction solution, and the organic layer was separated. The organic layer was washed with a saturated sodium chloride solution. The organic layer was dried over anhydrous magnesium sulfate, and the insoluble matter was separated by filtration. The filtrate was concentrated and the residue was purified by silica gel column chromatography to obtain the title compound (6.23 g).

$^1$H-NMR (400 MHz, CDCl$_3$) δ (ppm): 3.24-3.49 (m, 3H), 3.91-3.98 (m, 2H), 4.07-4.35 (m, 3H), 7.00-7.62 (m, 19H).

(6) Synthesis of [(2S,3R,4S)-4-amino-4-(2-fluorophenyl)-2-trityloxymethyl-tetrahydrofuran-3-yl]methanol Zinc powder (8.44 g) was added to a solution containing the compound obtained in Preparation Example 25-(5) (6.22 g) in acetic acid (50.0 mL) at room temperature. The reaction solution was stirred at room temperature for 18 hours. The insoluble matter was separated by filtration through celite and the filtrate was concentrated. Ethyl acetate and a sodium bicarbonate solution were added to the residue, and the organic layer was separated. The organic layer was washed with saturated aqueous sodium chloride and dried over anhydrous magnesium sulfate. The insoluble matter was separated by filtration and the filtrate was concentrated under reduced pressure. The residue was purified by column silica gel chromatography to obtain the title compound (4.10 g).

$^1$H-NMR (400 MHz, CDCl$_3$) δ (ppm): 2.63-2.65 (m, 1H), 3.24-3.31 (m, 2H), 3.61-3.65 (m, 1H), 3.92-3.97 (m, 2H), 4.15-4.26 (m, 1H), 4.37-4.41 (m, 1H), 7.00-7.52 (m, 19H).

(7) Synthesis of 1-benzo 1-3-[(3S,4R,5S)-3-(2-fluorophenyl)-4-hydroxymethyl-5-trityloxymethyl-tetrahydrofuran-3-yl]thiourea Benzoyl isothiocyanate (1.37 mL) was added to a solution containing the compound obtained in Preparation Example 25-(6) (4.10 g) in dichloromethane (16.0 mL), and the mixture was stirred at room temperature for 10 minutes. The reaction solution was concentrated under reduced pressure. The residue was purified by silica gel column chromatography to obtain the title compound (4.32 g).

$^1$H-NMR (400 MHz, CDCl$_3$) δ (ppm): 3.19-3.36 (m, 3H), 3.79-4.05 (m, 3H), 4.57-4.58 (m, 2H), 7.03-7.89 (m, 24H), 8.89 (br, 1H).

(8) Synthesis of N-[(4aS,5S,7aS)-7a-(2-fluorophenyl)-5-trityloxy-4,5,7,7a-tetrahydro-4H-furo[3,4-d][1,3]thiazin-2-yl]benzamide Pyridine (2.01 mL) and trifluoromethanesulfonic anhydride (2.25 mL) were added to a solution of the compound obtained in Preparation Example 25-(7) (4.32 g) in dichloromethane (27.7 mL) at 0° C., and the mixture was stirred at the same temperature for 20 minutes. A saturated sodium bicarbonate solution was added to the reaction solution, followed by extraction with dichloromethane. The organic layer was dried over anhydrous magnesium sulfate, and the insoluble matter was separated by filtration. The filtrate was concentrated under reduced pressure and the residue was purified by silica gel column chromatography to obtain the title compound (3.52 g).

$^1$H-NMR (400 MHz, CDCl$_3$) δ (ppm): 2.65-2.69 (m, 1H), 3.15-3.19 (m, 1H), 3.32-3.47 (m, 3H), 4.08-4.10 (m, 1H), 4.55-4.58 (m, 2H), 7.11-7.52 (m, 22H), 8.15-8.17 (m, 2H).

(9) Synthesis of N-[(4aS,5S,7aS)-7a-(2-fluorophenyl)-5-hydroxymethyl-4,5,7,7a-tetrahydro-4H-furo[3,4-d][1,3]thiazin-2-yl]benzamide Formic acid (15.0 mL) and diethyl ether (15.0 mL) were added to the compound obtained in Preparation Example 25-(8) (3.52 g) at room temperature, and the mixture was stirred at the same temperature for eight hours. The reaction solution was concentrated under reduced pressure. Formic acid (20 mL) was added at room temperature, and the mixture was stirred at the same temperature for 15 hours. The reaction solution was concentrated under reduced pressure. A solution of triethylamine in methanol (10%; 20.0 mL) was added at room temperature, followed by heating under reflux for 30 minutes. The reaction solution was concentrated. Ethyl acetate and brine were added, and the organic layer was separated and dried over anhydrous magnesium sulfate. The insoluble matter was separated by filtration. The filtrate was concentrated under reduced pressure and the residue was purified by silica gel column chromatography to obtain the title compound (1.72 g).

$^1$H-NMR (400 MHz, CDCl$_3$) δ (ppm): 2.80-2.84 (m, 1H), 3.25-3.29 (m, 1H), 3.40-3.44 (m, 1H), 3.73-3.77 (m, 1H), 3.94-3.98 (m, 1H), 4.08-4.11 (m, 1H), 4.13-4.57 (m, 2H), 7.12-7.53 (m, 7H), 8.14-8.16 (m, 2H).

(10) Synthesis of N-[(4aS,5S,7aS)-5-fluoromethyl-7a-(2-fluorophenyl)-4,5,7,7a-tetrahydro-4H-furo[3,4-d][1,3]thiazin-2-yl]benzamide Triethylamine (3.52 mL), triethylamine trihydrofluoride (1.37 mL) and perfluorobutanesulfonyl fluoride (1.45 mL) were added to a solution of the compound obtained in Preparation Example 25-(9) (1.62 g) in acetonitrile (16.2 mL) at 0° C., and the mixture was stirred at room temperature for 20 minutes. The reaction solution was purified by silica gel column chromatography to obtain the title compound (920 mg).

$^1$H-NMR (400 MHz, CDCl$_3$) δ (ppm): 2.81-2.85 (m, 1H), 3.28-3.31 (m, 1H), 3.41-3.43 (m, 1H), 4.05-4.07 (m, 1H), 4.55-4.74 (m, 4H), 7.12-7.54 (m, 7H), 8.12-8.14 (m, 2H).

(11) Synthesis of (4aS,5S,7aS)-5-fluoromethyl-7a-(2-fluorophenyl)-4a,5,7,7a-tetrahydro-4H-furo[3,4-d][1,3]thiazin-2-ylamine A solution of the compound obtained in Preparation Example 25-(10) (970 mg) and sodium methoxide (28% solution in methanol; 0.965 mL) in methanol (6.43 mL) was heated under reflux for 14 hours. After cooling the reaction solution to room temperature, the solvent was evaporated under reduced pressure. The residue was purified by silica gel chromatography to obtain the title compound (310 mg).

$^1$H-NMR (400 MHz, CDCl$_3$) δ (ppm): 2.76-2.80 (m, 1H), 3.00-3.04 (m, 1H), 3.09-3.13 (m, 1H), 3.85-3.88 (m, 1H), 4.47-4.63 (m, 4H), 7.00-7.16 (m, 2H), 7.27-7.44 (m, 2H).

(12) Synthesis of tert-butyl[(4aS,5S,7aS)-5-fluoromethyl-7a-(2-fluoro-5-nitrophenyl)-4a,5,7,7a-tetrahydro-4H-furo[3,4-d][1,3]thiazin-2-yl]carbamate Fuming nitric acid (55 μL) was added dropwise to a solution of the compound obtained in Preparation Example 25-(11) (310 mg) in concentrated sulfuric acid (5.53 mL) under ice-cooling. The reaction solution was stirred at the same temperature for 10 minutes and then poured into ice water. The reaction mixture was neutralized with a 5 N sodium hydroxide solution. The mixture was extracted with ethyl acetate twice. The organic layers were dried over anhydrous magnesium sulfate, and the insoluble matter was separated by filtration. The filtrate was concentrated under reduced pressure and the residue was dissolved in dichloromethane (5.40 mL). Triethylamine (0.602 mL) and di-tert-butyl dicarbonate (471 mg) were added to the solution. The reaction solution was concentrated under reduced pressure, and the residue was purified by silica gel column chromatography to obtain the title compound (419 mg).

$^1$H-NMR (400 MHz, CDCl$_3$) δ (ppm): 1.56 (s, 9H), 2.70-2.74 (m, 1H), 2.96-2.99 (m, 1H), 3.18-3.19 (m, 1H), 3.84-3.85 (m, 1H), 4.47-4.70 (m, 4H), 7.22-7.24 (m, 1H), 8.20-8.31 (m, 2H).

(13) Synthesis of tert-butyl[(4aS,5S,7aS)-7a-(5-amino-2-fluorophenyl)-5-fluoromethyl-4a,5,7,7a-tetrahydro-4H-furo[3,4-d][1,3]thiazin-2-yl]carbamate A saturated ammonium chloride solution (1.0 mL) and iron powder (436 mg) were added to a solution of the compound obtained in Preparation Example 25-(12) (419 mg) in ethanol (10 mL). The reaction solution was heated under reflux for 30 minutes and then cooled to room temperature. The reaction solution was diluted with ethyl acetate and the insoluble matter was separated by filtration through celite. Ethyl acetate and water were added to the filtrate, and the organic layer was separated. The organic layer was dried over anhydrous magnesium sulfate, and the insoluble matter was separated by filtration. The filtrate was concentrated under reduced pressure to obtain the title compound (291 mg).

$^1$H-NMR (400 MHz, CDCl$_3$) δ (ppm): 1.51 (s, 9H), 3.10-3.21 (m, 2H), 3.62 (br, 1H), 3.85-3.86 (m, 1H), 4.15-4.66 (m, 4H), 6.56-6.62 (m, 2H), 6.85-6.92 (m, 1H).

Preparation Example 26

Synthesis of 3-ethoxy-5-hexen-1-ol

[Formula 48]

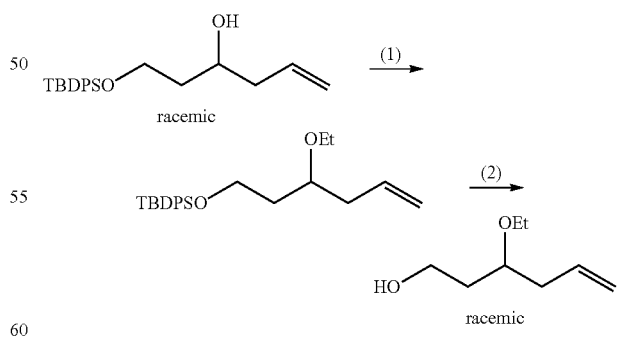

(1) Synthesis of tert-butyl-(3-ethoxy-5-hexenyloxy)diphenylsilane

A solution of 1-(tert-butyl-diphenylsilanyloxy)-5-hexen-3-ol (Tetrahedron, 57, 4023-4034 (2001)) (5.0 g) and ethyl iodide (2.03 mL) in THF (10 mL) was added dropwise to a suspension of sodium hydride (60%, 1.85 g) in THF (40 mL) at 50° C. over 10 minutes. The reaction solution was stirred at 50° C. for one hour. Ethyl iodide (6.0 mL) was added to the solution at 50° C., and the mixture was stirred at 60° C. for 1.5 hours. The reaction solution was returned to room temperature and poured into ice water, followed by extraction with ethyl acetate. The extract was washed with a saturated sodium chloride solution and then dried over anhydrous magnesium sulfate. The drying agent was removed by filtration and the filtrate was concentrated under reduced pressure. The resulting crude product was purified by silica gel column chromatography to obtain the title compound (4.1 g).

$^1$H-NMR (400 MHz, CDCl$_3$) δ (ppm): 1.05 (s, 9H), 1.14 (t, J=7.2 Hz, 3H) 1.66-1.80 (m, 2H), 2.22-2.30 (m, 2H), 3.36-3.86 (m, 5H), 5.00-5.10 (m, 2H), 5.74-5.88 (m, 1H), 7.30-7.46 (m, 6H), 7.60-7.74 (m, 4H).

(2) Synthesis of 3-ethoxy-5-hexen-1-ol

Tetrabutylammonium fluoride (1 M solution in THF, 13 mL) was added to a solution of tert-butyl-(3-ethoxy-5-hexenyloxy)diphenylsilane (4.1 g) in THF (40 mL) at room temperature, followed by stirring for one hour. The reaction solution was concentrated. The resulting crude product was purified by silica gel column chromatography to obtain the title compound (1.1 g).

$^1$H-NMR (400 MHz, CDCl$_3$) δ (ppm): 1.20 (t, J=7.2 Hz, 3H) 1.68-1.82 (m, 2H), 2.22-2.44 (m, 2H), 2.70 (s, 1H), 3.36-3.88 (m, 5H), 5.00-5.16 (m, 2H), 5.70-5.90 (m, 1H).

Preparation Example 27

Synthesis of (3aR*,5S*,6aS*)-5-ethoxy-6a-(2-fluorophenyl)hexahydrocyclopenta[c]isoxazole and (3aR*,5R*,6aS*)-5-ethoxy-6a-(2-fluorophenyl)hexahydrocyclopenta[c]isoxazole

[Formula 49]

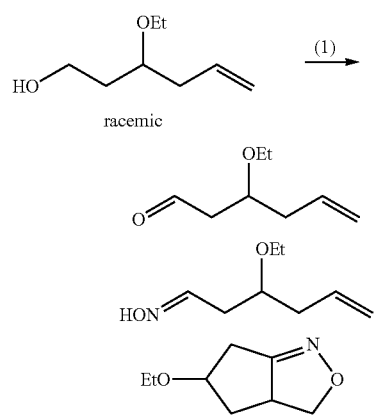

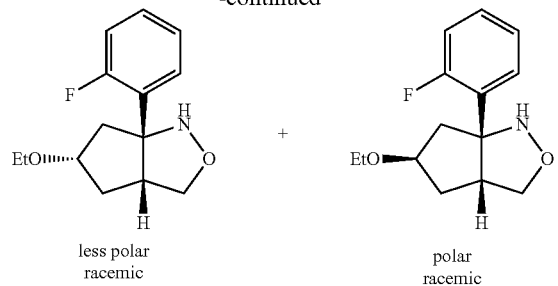

less polar racemic + polar racemic

The less polar title compound and the more polar title compound were obtained by treating 3-ethoxy-5-hexen-1-ol according to the method of Preparation Example 10-(1) to (4).

Less polar title compound ((3aR*,5S*,6aS*)-5-ethoxy-6a-(2-fluorophenyl)hexahydrocyclopenta[c]isoxazole)

ESI-MS; m/z 252 [M$^+$+H].

More polar title compound ((3aR*,5R*,6aS*)-5-ethoxy-6a-(2-fluorophenyl)hexahydrocyclopenta[c]isoxazole)

ESI-MS; m/z 252 [M$^+$+H].

Preparation Example 28

Synthesis of tert-butyl[(4aR*,6R*,7aS*)-7a-(5-amino-2-fluorophenyl)-6-ethoxy-4,4a,5,6,7,7a-hexahydrocyclopenta[d][1,3]thiazin-2-yl]carbamate ((+)-isomer and (−)-isomer)

[Formula 50]

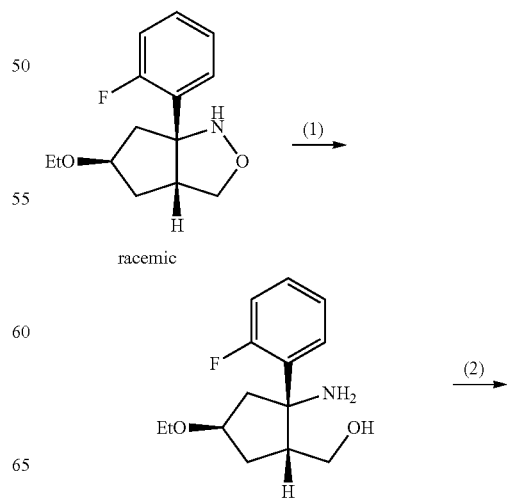

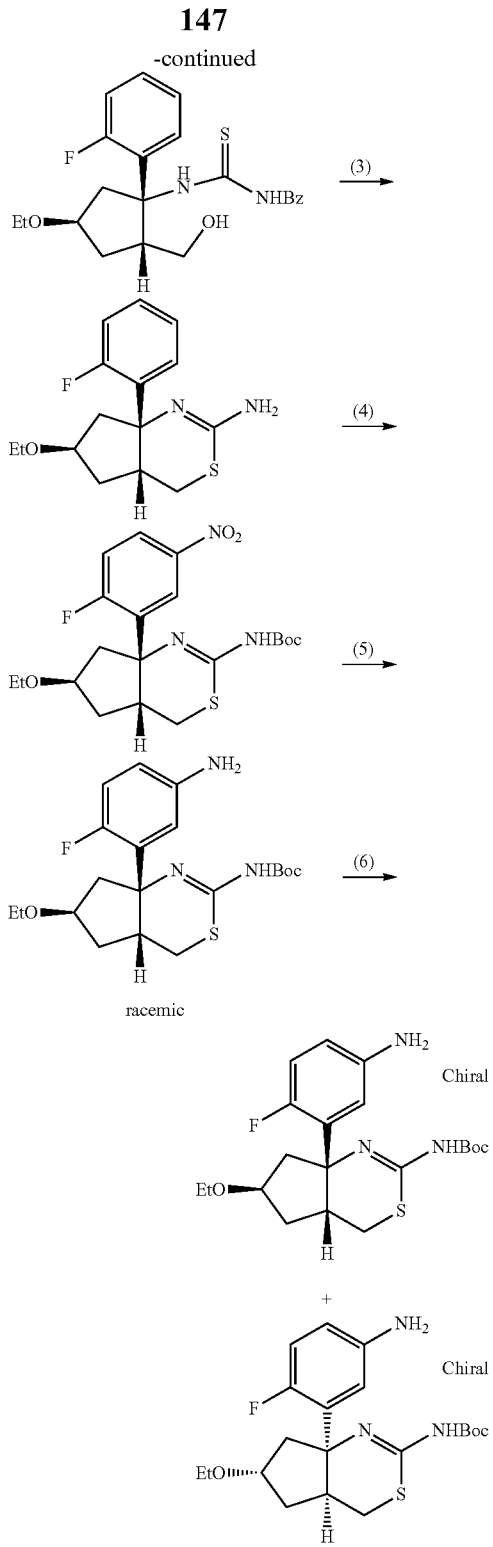

(1) Synthesis of [(1R*,2S*,4R*)-2-amino-4-ethoxy-2-(2-fluorophenyl)cyclopentyl]methanol Zinc (3.68 g) was added to a solution of (3aR*,5R*,6aS*)-5-ethoxy-6a-(2-fluorophenyl)hexahydrocyclopenta[c]isoxazole (540 mg) in acetic acid (15 mL), and the mixture was stirred at room temperature for two hours. A saturated sodium bicarbonate solution and ethyl acetate were added to the reaction solution, and zinc was removed by filtration. The filtrate was extracted with ethyl acetate. The extract was dried over anhydrous magnesium sulfate. The drying agent was removed by filtration and the filtrate was concentrated under reduced pressure to obtain the title compound (540 mg).

ESI-MS; m/z 254 [M$^+$+H].

(2) Synthesis of N-({[(1S*,2R*,4R*)-4-ethoxy-1-(2-fluorophenyl)-2-(hydroxymethyl)cyclopentyl]amino}carbonothioyl)benzamide Benzoyl isothiocyanate (0.345 mL) was added to a solution of the amine synthesized in the previous step (540 mg) in dichloromethane (9 mL), and the mixture was stirred at room temperature for 12 hours. The reaction solution was concentrated under reduced pressure. The residue was purified by silica gel column chromatography to obtain the title compound (180 mg). ESI-MS; m/z 439 [M$^+$+Na].

(3) Synthesis of (4aR*,6S*,7aS*)-6-ethoxy-7a-(2-fluorophenyl)-4,4a,5,6,7,7a-hexahydrocyclopenta[d][1,3]thiazin-2-yl]amine A solution of the thiourea obtained in the previous step (180 mg) in methanol (20 mL)-concentrated hydrochloric acid (0.7 mL) was heated under reflux for three hours. The reaction solution was returned to room temperature and then poured into a cooled sodium bicarbonate solution, followed by extraction with ethyl acetate. The extract was dried over anhydrous magnesium sulfate. The drying agent was removed by filtration and the filtrate was concentrated under reduced pressure. The resulting crude product was purified by silica gel column chromatography to obtain a cyclized compound (94 mg). DBU (0.2 mL) was added to a solution of the cyclized compound in methanol (10 mL), followed by heating under reflux for four hours. The reaction solution was concentrated under reduced pressure. The crude product was purified by silica gel column chromatography to obtain the title compound (69 mg). ESI-MS; m/z 295 [M$^+$+H].

(4)-(6) Synthesis of tert-butyl[(4aR*,6R*,7aS*)-7a-(5-amino-2-fluorophenyl)-6-ethoxy-4,4a,5,6,7,7a-hexahydrocyclopenta[d][1,3]thiazin-2-yl]carbamate ((+)-isomer and (−)-isomer)

The title (−)-compound was obtained by treating the cyclized compound obtained in the previous step according to the method of Steps (4) to (5) of Preparation Example 12. Optical resolution was performed using CHIRALPAK™ ADH manufactured by Daicel Chemical Industries, Ltd. (2 cm×25 cm, mobile phase: hexane:ethanol=8:2, flow rate: 10 mL/min). The components having a retention time of 7 to 10 minutes were collected to obtain the title (+)-isomer. The components having a retention time of 16 to 19 minutes were collected to obtain the title (−)-isomer. The (−)-isomer was used for synthesis of the chiral compound in the Example.

The property values of the (−)-isomer are as follows.

optical rotation (−)

ESI-MS; m/z 410 [M$^+$+H].

$^1$H-NMR (400 MHz, CDCl$_3$) δ (ppm): 1.21 (t, J=7.2 Hz, 3H), 1.52 (s, 9H), 1.90-2.05 (m, 1H), 2.25-2.45 (m, 2H), 2.60-2.75 (m, 2H), 3.03 (dd, J=3.6, 13.6 Hz, 1H), 3.25-3.35 (m, 1H), 3.46 (q, J=7.2 Hz, 2H), 3.62 (brs, 2H), 4.10-4.20 (m, 1H), 6.51-6.58 (m, 2H), 6.86 (dd, J=8.0, 12.0 Hz, 1H).

Preparation Example 29

Synthesis of tert-butyl(±)-[(4aR*,6S*,7aS*)-7a-(5-amino-2-fluorophenyl)-6-ethoxy-4,4a,5,6,7,7a-hexahydrocyclopenta[d][1,3]thiazin-2-yl]carbamate

[Formula 51]

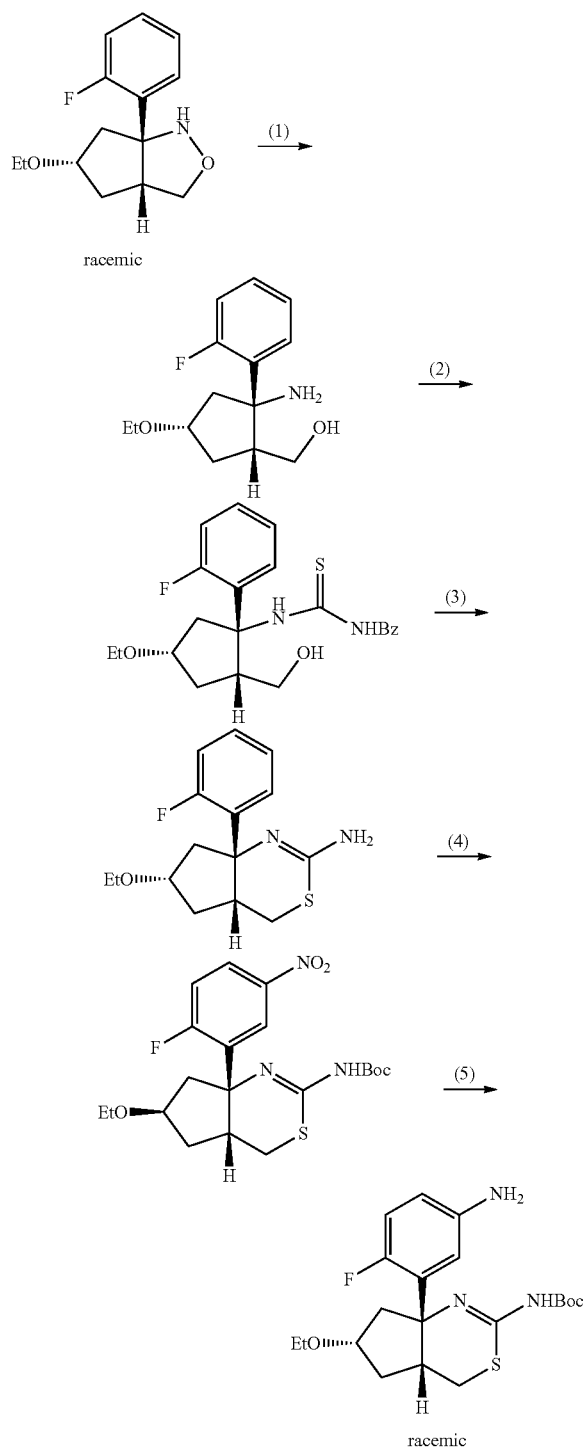

The title compound was obtained by treating (3aR*,5S*,6aS*)-5-ethoxy-6a-(2-fluorophenyl)hexahydrocyclopenta[c]isoxazole obtained in Preparation Example 27 according to the method of Preparation Example 28-(1) to (3) and Preparation Example 11-(4) to (5).

ESI-MS; m/z 410 [M$^+$+H].

Preparation Example 30

Synthesis of tert-butyl(−)-[(4aR*,6R*,7aS*)-7a-(5-amino-2-fluorophenyl)-6-butoxy-4,4a,5,6,7,7a-hexahydrocyclopenta[d][1,3]thiazin-2-yl]carbamate

[Formula 52]

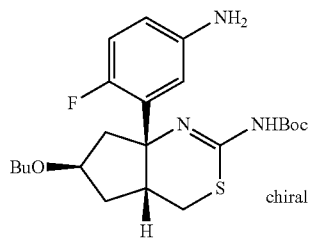

The title compound was obtained by treating 1-(tert-butyl-diphenylsilanyloxy)-5-hexen-3-ol and iodobutane according to the method of Preparation Examples 26 to 29.

$^1$H-NMR (400 MHz, CDCl$_3$) δ (ppm): 0.92 (t, J=7.2 Hz, 3H), 1.32-1.42 (m, 2H), 1.52 (s, 9H), 1.48-1.60 (m, 2H), 1.85-2.05 (m, 1H), 2.20-2.45 (m, 2H), 2.55-2.75 (m, 2H), 3.03 (d, J=13.2 Hz, 1H), 3.20-3.45 (m, 3H), 3.62 (s, 2H), 4.05-4.20 (m, 1H), 6.50-6.60 (m, 2H), 6.80-6.95 (m, 1H).

ESI-MS m/z 438 [M$^+$+H]

Preparation Example 31

Synthesis of tert-butyl(±)-[(4aR*,6S*,7aS*)-7a-(5-amino-2-fluorophenyl)-6-butoxy-4,4a,5,6,7,7a-hexahydrocyclopenta[d][1,3]thiazin-2-yl]carbamate

[Formula 53]

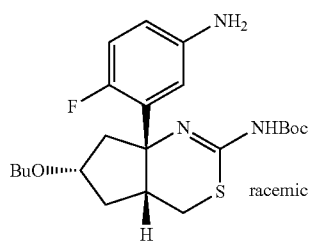

The title compound was obtained by treating 1-(tert-butyl-diphenylsilanyloxy)-5-hexen-3-ol and iodobutane according to the method of Preparation Examples 26 to 29.

ESI-MS m/z 438 [M$^+$+H]

Preparation Example 32

Synthesis of (3aR*,5S*,6aS*)-6a-(2-fluorophenyl)-5-(3,4-difluorobenzyl)oxy-hexahydrocyclopenta[c]isoxazole and (3aR*,5R*,6aS*)-6a-(2-fluorophenyl)-5-(3,4-difluorobenzyl)oxy-hexahydrocyclopenta[c]isoxazole

[Formula 54]

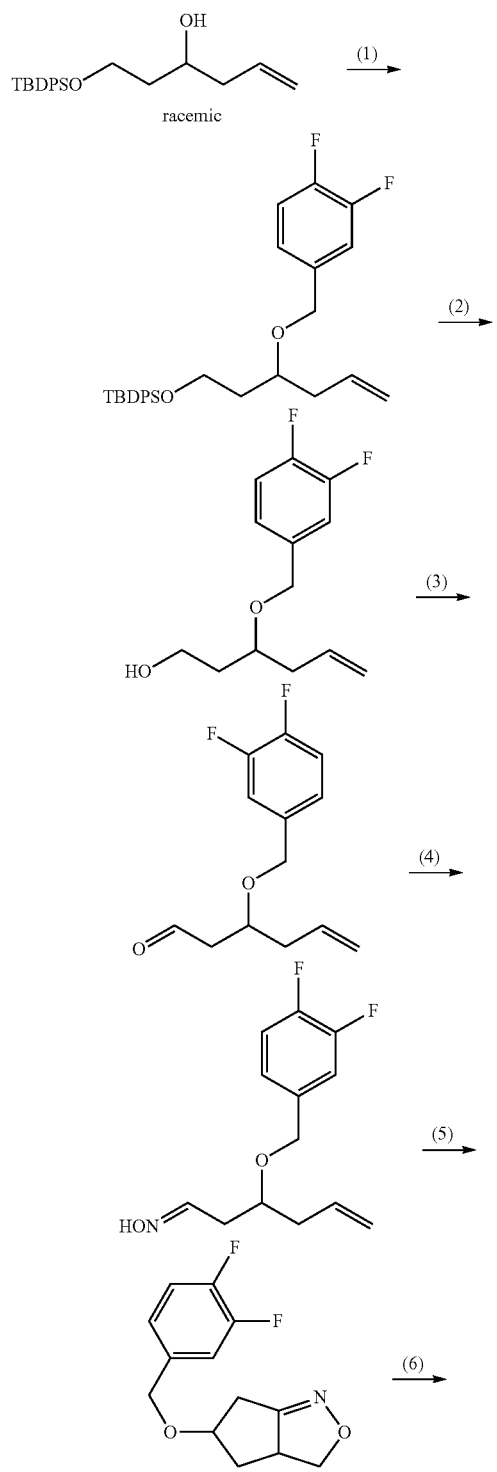

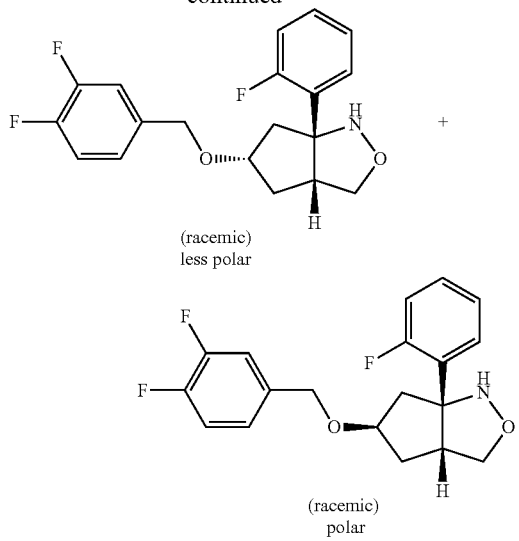

The title compound was obtained by treating 1-(tert-butyldiphenylsilanyloxy)-5-hexen-3-ol and 3,4-difluorobenzyl bromide according to the method of Preparation Example 26-(1) to (2) and Preparation Example 10-(1) to (4).

Less polar title compound ((3aR*,5S*,6aS*)-6a-(2-fluorophenyl)-5-(3,4-difluorobenzyl)oxy-hexahydrocyclopenta[c]isoxazole)

$^1$H-NMR (400 MHz, CDCl$_3$) δ (ppm): 2.00-2.20 (m, 2H), 2.20-2.40 (m, 2H), 3.02 (brs, 1H), 3.31 (q, J=7.6 Hz, 1H), 3.73 (t, J=7.6 Hz, 1H), 4.30 (s, 1H), 4.30-4.55 (m, 2H), 4.39 (t, J=8.0 Hz, 1H), 6.03 (s, 1H), 6.90-8.00 (m, 7H).

More polar title compound ((3aR*,5R*,6aS*)-6a-(2-fluorophenyl)-5-(3,4-difluorobenzyl)oxy-hexahydrocyclopenta[c]isoxazole)

$^1$H-NMR (400 MHz, CDCl$_3$) δ (ppm): 2.00-2.28 (m, 2H), 2.32 (dd, J=8.8, 13.6 Hz, 1H), 2.41 (dd, J=5.6, 13.6 Hz, 1H), 3.30-3.45 (m, 1H), 3.73 (brs, 1H), 4.13 (brs, 1H), 4.25-4.40 (m, 1H), 4.44 (s, 2H), 6.94-7.32 (m, 6H), 7.56-7.66 (m, 1H).

Preparation Example 33

Synthesis of tert-butyl[(4aR*,6S*,7aS*)-7a-(2-fluorophenyl)-6-hydroxy-4,4a,5,6,7,7a-hexahydrocyclopenta[d][1,3]thiazin-2-yl]carbamate

[Formula 55]

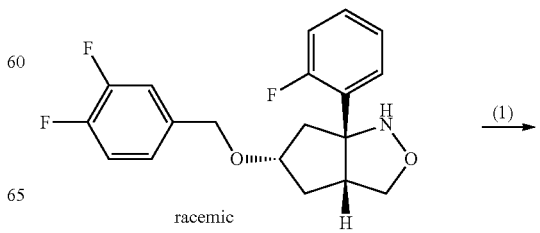

153
-continued

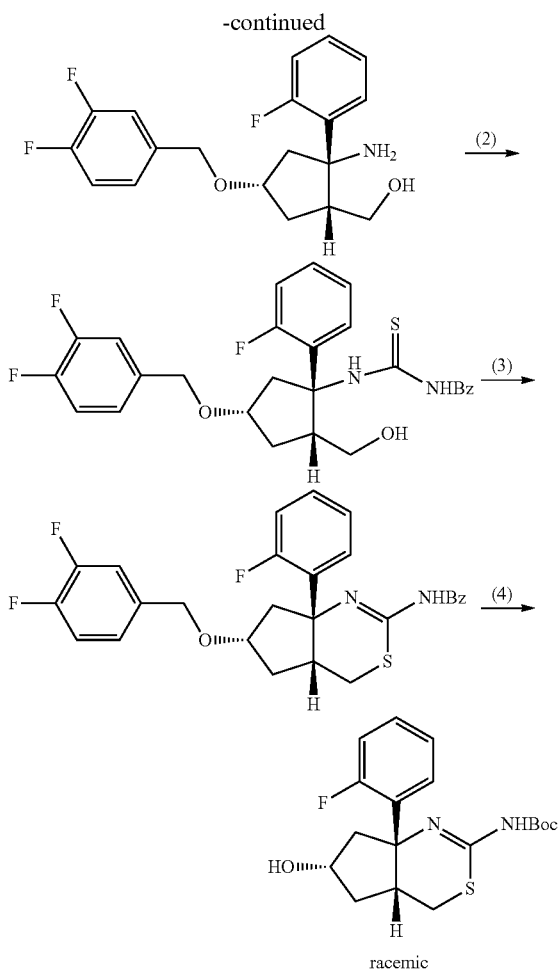

(1) Synthesis of [(1R*,2S*,4S*)-2-amino-2-(2-fluorophenyl)-4-(3,4-difluorobenzyloxy)cyclopentyl]methanol Zinc (3.0 g) was added to a solution of (3aR*,5S*,6aS*)-6a-(2-fluorophenyl)-5-(3,4-difluorobenzyloxy)-hexahydrocyclopenta[c]isoxazole (620 mg) in acetic acid (25 mL), and the mixture was stirred at room temperature for two hours. A saturated sodium bicarbonate solution and ethyl acetate were added to the reaction solution, and zinc was removed by filtration. The filtrate was extracted with ethyl acetate. The extract was dried over anhydrous magnesium sulfate. The drying agent was removed by filtration and the filtrate was concentrated under reduced pressure to obtain the title compound (630 mg).
ESI-MS; m/z 352 [M⁺+H].

(2) Synthesis of N-({[(1S*,2R*,4S*)-1-(2-fluorophenyl)-2-(hydroxymethyl)-4-(3,4-difluorobenzyloxy)cyclopentyl]amino}carbonothioyl)benzamide Benzoyl isothiocyanate (0.362 mL) was added to a solution of the amine synthesized in the previous step (630 mg) in dichloromethane (20 mL), and the mixture was stirred at room temperature for 12 hours. The reaction solution was purified by silica gel column chromatography to obtain the title compound (550 mg). ESI-MS; m/z 537 [M⁺+Na].

154

(3) Synthesis of N-((4aR*,6S*,7aS*)-7a-(2-fluorophenyl)-6-(3,4-difluorobenzyloxy)-4,4a,5,6,7,7a-hexahydrocyclopenta[d][1,3]thiazin-2-yl)benzamide Concentrated hydrochloric acid (1.7 mL) was added to a solution of the thiourea synthesized in the previous step (550 mg) in methanol (50 mL), and the mixture was heated under reflux for three hours. The reaction solution was left to cool and then poured into an ice-cooled sodium bicarbonate solution, followed by extraction with ethyl acetate. The extract was washed with brine and dried over anhydrous magnesium sulfate. The drying agent was removed by filtration and the filtrate was concentrated under reduced pressure. The residue was purified by silica gel column chromatography to obtain the title compound (480 mg).
ESI-MS; m/z 497 [M⁺+H].

(4) Synthesis of tert-butyl[(4aR*,6S*,7aS*)-7a-(2-fluorophenyl)-6-hydroxy-4,4a,5,6,7,7a-hexahydrocyclopenta[d][1,3]thiazin-2-yl]carbamate A solution of the amide compound obtained in the previous step (135 mg) in concentrated hydrochloric acid (20 mL) was heated under reflux for four hours. The reaction solution was returned to room temperature and poured into an ice-cooled sodium bicarbonate solution, followed by extraction with ethyl acetate. The extract was washed with brine and dried over anhydrous magnesium sulfate. The drying agent was removed by filtration and the filtrate was concentrated under reduced pressure. The residue was dissolved in THF (3.3 mL). Triethylamine (0.0525 mL) and di-tert-butyl dicarbonate (49.3 mg) were added and the reaction solution was stirred at room temperature for two hours. The reaction solution was poured into a saturated sodium bicarbonate solution, followed by extraction with ethyl acetate. The extract was washed with brine and dried over anhydrous magnesium sulfate. The drying agent was removed by filtration and the filtrate was concentrated under reduced pressure. The residue was purified by silica gel column chromatography to obtain the title compound (64 mg).
ESI-MS; m/z 367 [M⁺+H].

Preparation Example 34

Synthesis of tert-butyl[(4aR*,6R*,7aS*)-7a-(5-amino-2-fluorophenyl)-6-fluoro-4,4a,5,6,7,7a-hexahydrocyclopenta[d][1,3]thiazin-2-yl]carbamate ((+)-isomer and (−)-isomer)

[Formula 56]

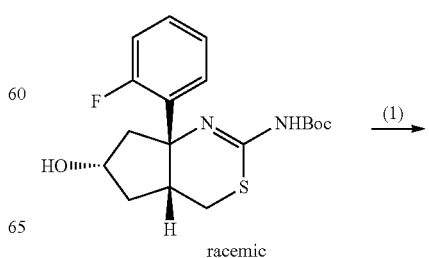

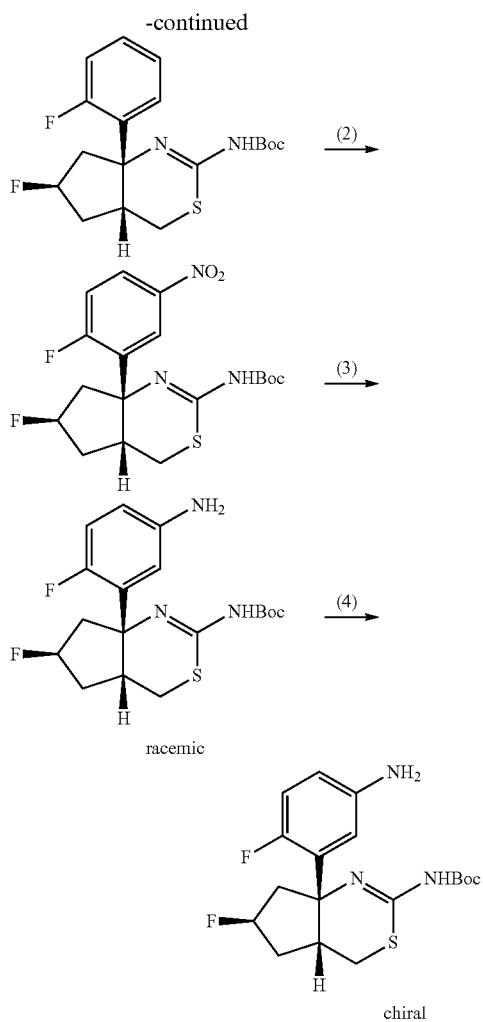

(1) Synthesis of tert-butyl[(4aR*,6R*,7aS*)-7a-(2-fluorophenyl)-6-fluoro-4,4a,5,6,7,7a-hexahydrocyclopenta[d][1,3]thiazin-2-yl]carbamate

[Bis(2-methoxyethyl)amino]sulfur trifluoride (0.0564 mL) was added to a solution of tert-butyl [(4aR*,6S*,7aS*)-7a-(2-fluorophenyl)-6-hydroxy-4,4a,5,6,7,7a-hexahydrocyclopenta[d][1,3]thiazin-2-yl]carbamate (51 mg) in dichloromethane (2 mL) at 0° C., and the mixture was stirred at 0° C. for 1.5 hours. Water was added to the reaction solution, followed by extraction with ethyl acetate. The extract was washed with brine and then dried over anhydrous magnesium sulfate. The title compound (51 mg) was obtained by removal of the drying agent and concentration under reduced pressure.
ESI-MS; m/z 369 [M$^+$+H].

(2) Synthesis of tert-butyl[(4aR*,6R*,7aS*)-7a-(2-fluoro-5-nitrophenyl)-6-fluoro-4,4a,5,6,7,7a-hexahydrocyclopenta[d][1,3]thiazin-2-yl]carbamate TFA (1.0 mL) was added to a solution of the tert-butyl ester obtained in the previous step (51 mg) in dichloromethane (2.0 mL) at room temperature, and the reaction solution was stirred at room temperature for one hour. The reaction solution was poured into a cooled sodium bicarbonate solution, followed by extraction with ethyl acetate. The extract was washed with brine and then dried over anhydrous magnesium sulfate. The drying agent was removed, followed by concentration under reduced pressure. The residue was purified by silica gel column chromatography to obtain an amine compound (34 mg). Fuming nitric acid (4.48 µL) was added to a solution of the amine compound (34 mg) in concentrated sulfuric acid (1.5 mL) at 0° C., and the mixture was stirred at 0° C. for 30 minutes. The reaction solution was poured into a 5 N sodium hydroxide solution-ice water, followed by extraction with ethyl acetate. The extract was washed with a saturated sodium chloride solution and then dried over anhydrous magnesium sulfate. The drying agent was removed by filtration and the filtrate was concentrated under reduced pressure. Triethylamine (44.2 µL) and di-tert-butyl dicarbonate (41.6 mg) were added to a solution of the resulting crude product in THF (5 mL) at room temperature, and the mixture was stirred at room temperature for 12 hours. The reaction solution was poured into a saturated sodium bicarbonate solution, followed by extraction with ethyl acetate. The extract was washed with a saturated sodium chloride solution and then dried over anhydrous magnesium sulfate. The drying agent was removed by filtration and the filtrate was concentrated under reduced pressure. The resulting crude product was purified by silica gel column chromatography to obtain the title compound (27 mg). ESI-MS; m/z 414 [M$^+$+H].

(3) Synthesis of tert-butyl[(4aR*,6R*,7aS*)-7a-(5-amino-2-fluorophenyl)-6-fluoro-4,4a,5,6,7,7a-hexahydrocyclopenta[d][1,3]thiazin-2-yl]carbamate A solution of the nitro compound obtained in the previous step (27 mg) and iron (60 mg) in ethanol (1.25 mL) and a saturated ammonium chloride solution (0.1 mL) was stirred at 87° C. for 30 minutes. After returning the reaction solution to room temperature, iron was removed by filtration. The filtrate was poured into water-ethyl acetate, followed by extraction with ethyl acetate. The extract was washed with a saturated sodium chloride solution and then dried over anhydrous magnesium sulfate. The drying agent was removed by filtration and then the filtrate was concentrated under reduced pressure to obtain the title compound (23 mg).
ESI-MS; m/z 384 [M$^+$+H].

(4) Synthesis of tert-butyl[(4aR*,6R*,7aS*)-7a-(5-amino-2-fluorophenyl)-6-fluoro-4,4a,5,6,7,7a-hexahydrocyclopenta[d][1,3]thiazin-2-yl]carbamate ((+)-isomer and (−)-isomer)

tert-Butyl(±)-[(4aR*,6R*,7aS*)-7a-(5-amino-2-fluorophenyl)-6-methoxy-4,4a,5,6,7,7a-hexahydrocyclopenta[d][1,3]thiazin-2-yl]carbamate (46 mg) was optically resolved by CHIRALPAK™ ADH manufactured by Daicel Chemical Industries, Ltd. (2 cm×25 cm, mobile phase: hexane:ethanol=8:2, flow rate: 10 mL/min). 15 mg of the components having a retention time of 15 to 20 minutes were obtained. 11 mg of the components having a retention time of 28 to 33 minutes were also obtained.

The compound obtained from the components having a retention time of 28 to 33 minutes was used for synthesis of the chiral compound in the Example.

$^1$H-NMR (400 MHz, CDCl$_3$) δ (ppm): 1.51 (s, 9H), 2.10-2.30 (m, 1H), 2.30-2.55 (m, 2H), 2.73 (d, J=13.2 Hz, 1H), 2.92 (dd, J=14.4, 32.4 Hz, 1H), 3.05 (d, J=13.2 Hz, 1H), 3.33 (brs, 1H), 3.63 (brs, 2H), 5.02-5.45 (m, 1H), 6.45-6.60 (m, 2H), 6.80-6.95 (m, 1H).

Preparation Example 35

Synthesis of tert-butyl[(4aR*,6R*,7aS*)-7a-(2-fluorophenyl)-6-hydroxy-4,4a,5,6,7,7a-hexahydrocyclopenta[d][1,3]thiazin-2-yl]carbamate

[Formula 57]

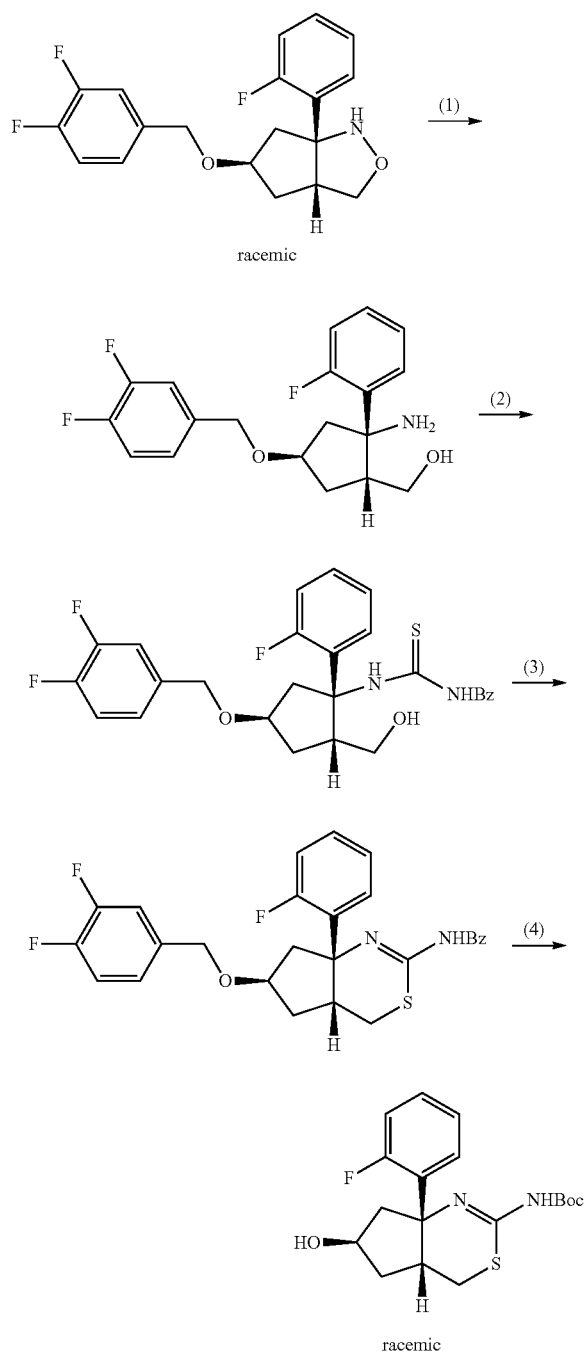

The title compound was obtained by treating (3aR*,5R*,6aS*)-6a-(2-fluorophenyl)-5-(3,4-difluorobenzyloxy)-hexahydrocyclopenta[c]isoxazole according to the method of Preparation Example 33. ESI-MS; m/z 367 [M$^+$+H].

Preparation Example 36

Synthesis of tert-butyl(−)-[(4aR*,6S*,7aS*)-7a-(5-amino-2-fluorophenyl)-6-fluoro-4,4a,5,6,7,7a-hexahydrocyclopenta[d][1,3]thiazin-2-yl]carbamate

[Formula 58]

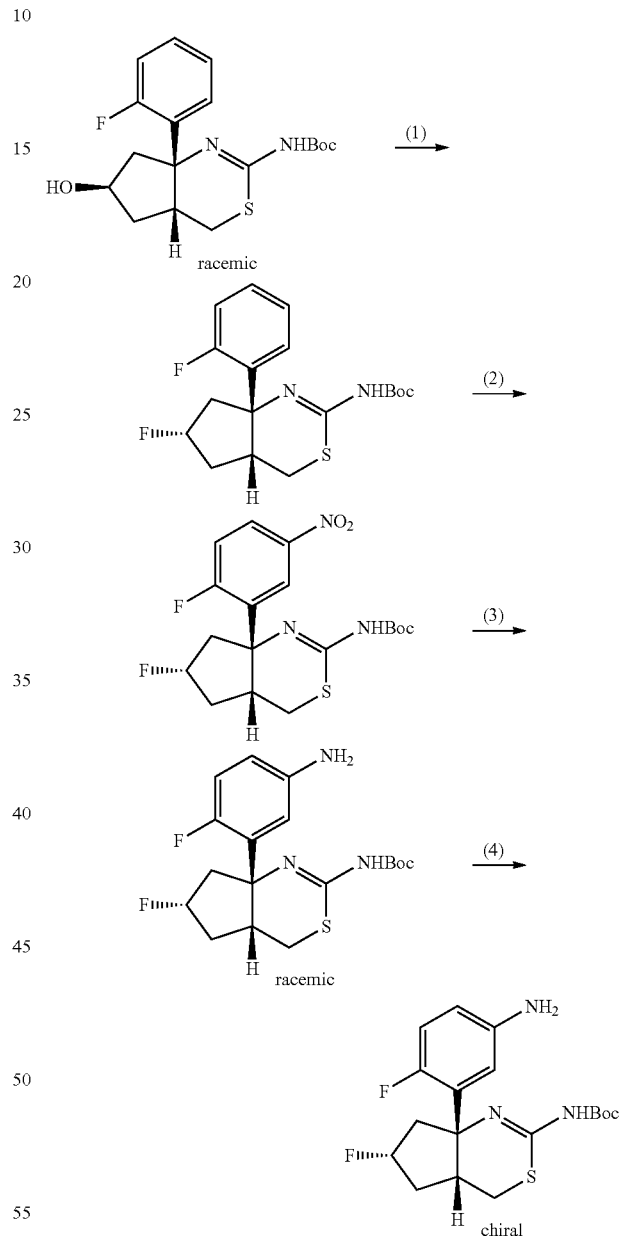

The title compound was obtained by treating tert-butyl [(4aR*,6R*,7aS*)-7a-(2-fluorophenyl)-6-hydroxy-4,4a,5,6,7,7a-hexahydrocyclopenta[d][1,3]thiazin-2-yl]carbamate according to the method of Preparation Example 34. Optical resolution was performed using CHIRALPAK™ ADH manufactured by Daicel Chemical Industries, Ltd. (2 cm×25 cm, mobile phase: hexane:ethanol=7:3, flow rate: 10 mL/min). The components having a retention time of 18 to 23 minutes were collected to obtain the title (−)-isomer.

The property values of the (−)-isomer are as follows.

optical rotation (−)

$^1$H-NMR (400 MHz, CDCl$_3$) δ (ppm): 1.51 (s, 9H), 2.10-2.60 (m, 3H), 2.70 (d, J=12.0 Hz, 1H), 2.75-3.10 (m, 3H), 3.64 (brs, 2H), 5.20-5.50 (m, 1H), 6.45-6.65 (m, 2H), 6.75-6.90 (m, 1H).

Preparation Example 37

Synthesis of tert-butyl[(4aR*,7aS*)-7a-(5-amino-2-fluorophenyl)-6,6-difluoro-4,4a,5,6,7,7a-hexahydro-cyclopenta[d][1,3]thiazin-2-yl]carbamate

[Formula 59]

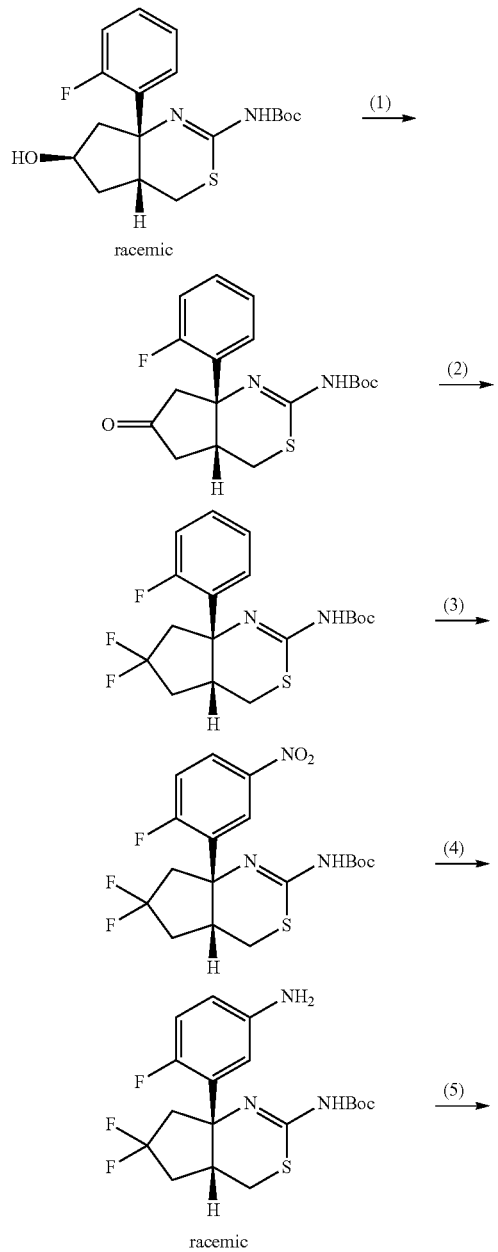

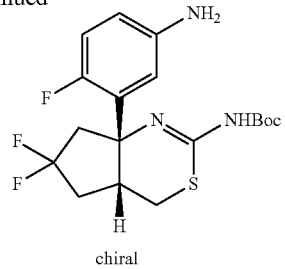

(1) Synthesis of tert-butyl[(4aR*,7aS*)-7a-(2-fluorophenyl)-4a,5,7,7a-tetrahydro-4H-cyclopenta[d][1,3]thiazin-6-on-2-yl]carbamate Dimethyl sulfoxide (0.014 mL) was added dropwise to a solution of oxalyl chloride (0.0169 mL) in dichloromethane (5 mL) at −55° C., and the mixture was stirred at −70° C. for 10 minutes. A solution of the alcohol obtained in Preparation Example 33 (48 mg) in dichloromethane (5 mL) was added dropwise to the solution at −60° C., and the mixture was stirred at −60° C. for 15 minutes. Triethylamine (0.128 mL) was added dropwise to the solution at −60° C., and the reaction solution was stirred at −60° C. to room temperature for 30 minutes. The reaction solution was poured into water, followed by extraction with ethyl acetate. The extract was washed with a saturated sodium chloride solution and then dried over anhydrous magnesium sulfate. The drying agent was removed by filtration and the filtrate was concentrated under reduced pressure. The residue was purified by silica gel column chromatography to obtain the title compound (28 mg).

ESI-MS; m/z 365 [M$^+$+H].

(2) Synthesis of tert-butyl[(4aR*,7aS*)-7a-(2-fluorophenyl)-6,6-difluoro-4,4a,5,6,7,7a-hexahydrocyclopenta[d][1,3]thiazin-2-yl]carbamate

[Bis(2-methoxyethyl)amino]sulfur trifluoride (1.42 mL) was added to a solution of the ketone compound obtained in the previous step (281 mg) in dichloromethane (3 mL) at room temperature, and the mixture was stirred at room temperature for 12 hours. Ice water was added to the reaction solution, followed by extraction with ethyl acetate. The extract was washed with brine and then dried over anhydrous magnesium sulfate. The drying agent was removed, followed by concentration under reduced pressure. The residue was purified by silica gel column chromatography to obtain the title compound (50 mg). ESI-MS; m/z 387 [M$^+$+H].

(3)-(5) Synthesis of tert-butyl[(4aR*,7aS*)-7a-(5-amino-2-fluorophenyl)-6,6-difluoro-4,4a,5,6,7,7a-hexahydrocyclopenta[d][1,3]thiazin-2-yl]carbamate The title compound was obtained by treating the difluoro compound obtained in Preparation Example 37-(2) according to the method of Preparation Example 34-(2) to (4). Optical resolution was performed using CHIRALPAK™ ADH manufactured by Daicel Chemical Industries, Ltd. (2 cm×25 cm, mobile phase: hexane:ethanol=7:3, flow rate: 10 mL/min).

The compound obtained from the components having a retention time of 18.5 to 21 minutes was used for synthesis of the chiral compound in the Example.

$^1$H-NMR (400 MHz, CDCl$_3$) δ (ppm): 1.52 (s, 9H), 2.30-2.76 (m, 4H), 2.98 (d, J=13.2 Hz, 1H), 3.10-3.30 (m, 2H), 3.63 (brs, 2H), 6.50 (dd, J=2.8, 7.2 Hz, 1H), 6.53-6.63 (m, 1H), 6.87 (dd, J=8.4, 12.0 Hz, 1H).

Preparation Example 38

Synthesis of di-tert-butyl[(4aR*,7aS*)-7a-(5-amino-2-fluorophenyl)-4,4a,5,6,7,7a-hexahydrocyclopenta[d][1,3]thiazin-2-yl]imidodicarbonate

[Formula 60]

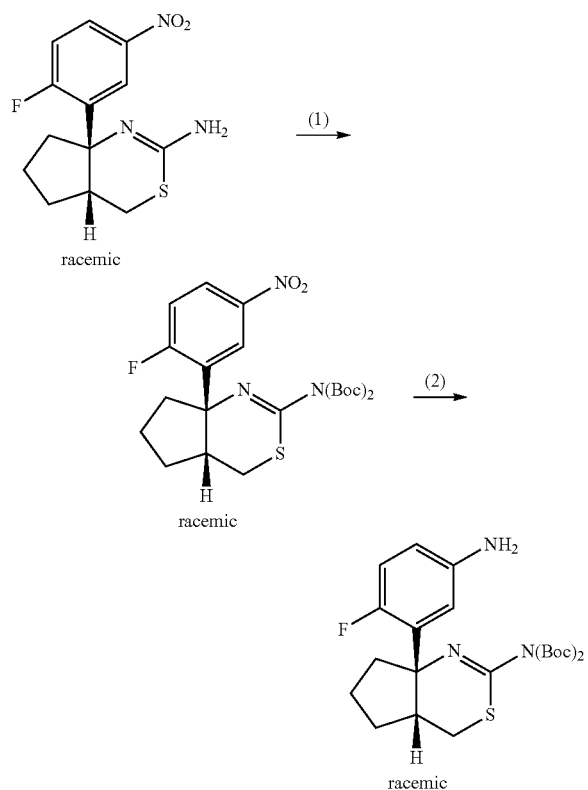

(1) Synthesis of di-tert-butyl[(4aR*,7aS*)-7a-(2-fluoro-5-nitrophenyl)-4,4a,5,6,7,7a-hexahydrocyclopenta[d][1,3]thiazin-2-yl]imidodicarbonate N,N-Dimethylaminopyridine (721 mg) and di-tert-butyl dicarbonate (1.03 g) were added to a solution of [(4aR*,7aS*)-7a-(2-fluoro-5-nitrophenyl)-4,4a,5,6,7,7a-hexahydrocyclopenta[d][1,3]thiazin-2-yl]amine obtained in Preparation Example 3-(6) (350 mg) in dichloromethane (10 mL), and the mixture was stirred at room temperature for 12 hours. The reaction solution was poured into water, followed by extraction with ethyl acetate. The extract was washed with brine and then dried over anhydrous magnesium sulfate. The drying agent was removed, followed by concentration under reduced pressure. The residue was purified by silica gel column chromatography to obtain the title compound (580 mg). ESI-MS; m/z 496 [M$^+$+H].

(2) Synthesis of di-tert-butyl[(4aR*,7aS*)-7a-(5-amino-2-fluorophenyl)-4,4a,5,6,7,7a-hexahydrocyclopenta[d][1,3]thiazin-2-yl]imidodicarbonate A solution of the diimide compound obtained in the previous step (630 mg) and iron (945 mg) in ethanol (10 mL) and a saturated ammonium chloride solution (1 mL) was stirred at 87° C. for 30 minutes. After cooling the reaction solution to room temperature, the reaction solution was poured into ethyl acetate and the insoluble matter was removed by filtration. The filtrate was concentrated under reduced pressure. The residue was purified by silica gel column chromatography to obtain the title compound (380 mg). ESI-MS; m/z 466 [M$^+$+H].

Preparation Example 39

Synthesis of 5-cyclopropylethynyl-pyridine-2-carboxylic acid

[Formula 61]

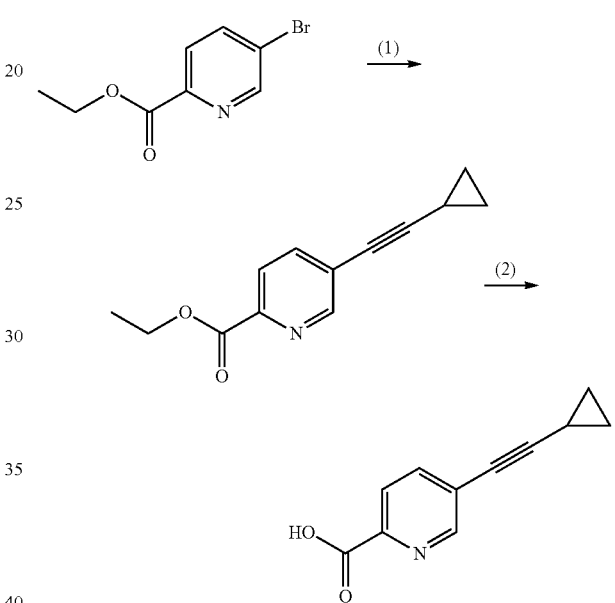

(1) Synthesis of ethyl 5-cyclopropylethynyl-pyridine-2-carboxylate

Cyclopropylacetylene (73.7 μL), copper iodide (3.16 mg) and tetrakis(triphenylphosphine)palladium (9.59 mg) were added to a solution of ethyl 5-bromopyridine-2-carboxylate (95.5 mg) in diisopropylamine (2 mL) at room temperature, and the mixture was stirred at room temperature for 17 hours and five minutes. The reaction solution was concentrated under reduced pressure. The residue was purified by NH-silica gel column chromatography to obtain the title compound (19.4 mg).

$^1$H-NMR (400 MHz, CDCl$_3$) δ (ppm): 0.86-0.90 (m, 2H), 0.91-0.97 (m, 2H), 1.44 (t, J=7.2 Hz, 3H), 1.47-1.54 (m, 1H), 4.47 (q, J=7.2 Hz, 2H), 7.77 (dd, J=8.0, 2.0 Hz, 1H), 8.04 (dd, J=8.0, 0.8 Hz, 1H), 8.70 (dd, J=2.0, 0.8 Hz, 1H).

(2) Synthesis of 5-cyclopropylethynyl-pyridine-2-carboxylic acid

A 5 M sodium hydroxide solution (36.6 μL) was added to a solution of the compound obtained in the previous step (19.4 mg) in ethanol (500 μL), and the mixture was stirred at room temperature for 40 minutes. M hydrochloric acid (36.6 μL) was added to the reaction solution, followed by extraction

Preparation Example 40

Synthesis of 5-thiazol-2-yl-pyridine-2-carboxylic acid

[Formula 62]

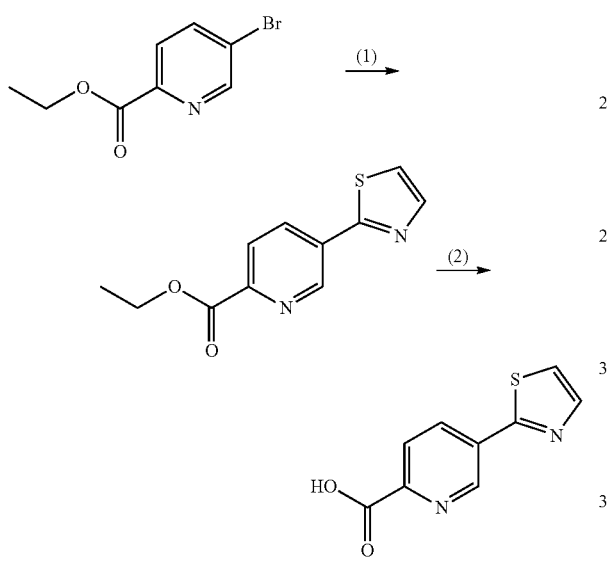

(1) Synthesis of ethyl 5-thiazol-2-yl-pyridine-2-carboxylate

2-Tributylstanylthiazole (325 mg) and bis(tri-tert-butylphosphine)palladium (0) (25 mg) were added to a solution of ethyl 5-bromopyridine-2-carboxylate (100 mg) in 1,4-dioxane (2 mL). After replacement with nitrogen, the mixture was stirred at 100° C. for eight hours. The reaction solution was returned to room temperature and the solvent was evaporated under reduced pressure to obtain the title compound (10 mg).

$^1$H-NMR (400 MHz, CDCl$_3$) δ (ppm): 1.47 (t, J=7.2 Hz, 3H), 4.52 (q, J=7.2, 2H), 7.50 (d, J=3.2 Hz, 1H), 7.99 (d, J=3.2 Hz, 1H), 8.22 (dd, J=0.8, 8.4 Hz, 1H), 8.39 (dd, J=2.2, 8.4 Hz, 1H), 9.31 (dd, J=0.8, 2.2 Hz, 1H).

(2) Synthesis of 5-thiazol-2-yl-pyridine-2-carboxylic acid

A 5 M sodium hydroxide solution (17.1 μL) was added to a solution of the compound obtained in the previous step (10 mg) in ethanol (250 μL) at room temperature, followed by stirring for 35 minutes. 5 M hydrochloric acid (17.1 μL) was added to the reaction solution, followed by extraction with ethyl acetate. The organic layer was dried over anhydrous magnesium sulfate, and the drying agent was filtered off. The filtrate was concentrated under reduced pressure to obtain the title compound (8.6 mg).

$^1$H-NMR (400 MHz, CDCl$_3$) δ (ppm): 7.54 (d, J=3.2 Hz, 1H), 8.02 (d, J=3.2 Hz, 1H), 8.30-8.34 (m, 1H), 8.46-8.51 (m, 1H), 9.22-9.24 (m, 1H).

Preparation Example 41

Synthesis of 5-cyclopropyl-pyridine-2-carboxylic acid

[Formula 63]

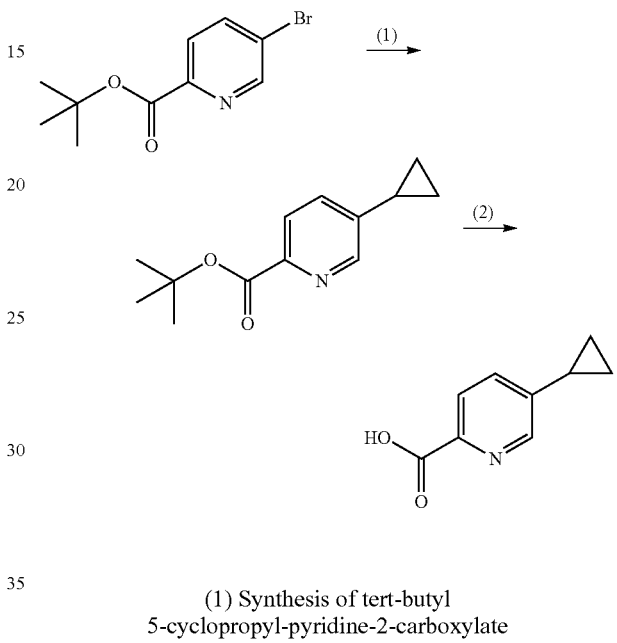

(1) Synthesis of tert-butyl 5-cyclopropyl-pyridine-2-carboxylate

Cyclopropylboronic acid (43.2 mg), tricyclohexylphosphine (10.9 mg), palladium acetate (4.34 mg) and potassium phosphate (288 mg) were added to a mixed solution of tert-butyl 5-bromopyridine-2-carboxylate (100 mg) in toluene (2 mL) and water (100 μL), and the mixture was stirred at 100° C. for nine hours and 30 minutes. After returning to room temperature, water was added to the reaction solution. After extraction with ethyl acetate, the organic layer was concentrated under reduced pressure. The residue was purified by silica gel column chromatography to obtain the title compound (11.6 mg).

$^1$H-NMR (400 MHz, CDCl$_3$) δ (ppm): 0.76-0.82 (m, 2H), 1.08-1.14 (m, 2H), 1.63 (s, 9H), 1.91-2.00 (m, 1H), 7.36 (dd, J=8.4, 2.4 Hz, 1H), 7.93 (d, J=8.4 Hz, 1H), 8.51 (d, J=2.4 Hz, 1H).

(2) Synthesis of 5-cyclopropyl-pyridine-2-carboxylic acid

A mixed solution of the compound obtained in the previous step (11.6 mg) in trifluoroacetic acid (333 μL) and dichloromethane (666 μL) was allowed to stand at room temperature for two hours and 20 minutes. The reaction solution was concentrated under reduced pressure to obtain the title compound (16.6 mg).

$^1$H-NMR (400 MHz, CDCl$_3$) δ (ppm): 0.95-1.03 (m, 2H), 1.31-1.41 (m, 2H), 2.08-2.20 (m, 1H), 7.94 (brd, J=8.0 Hz, 1H), 8.33 (brd, J=8.0 Hz, 1H), 8.65 (brs, 1H).

---

(continued from previous page)

with ethyl acetate. The organic layer was dried over anhydrous magnesium sulfate, and the drying agent was filtered off. The filtrate was concentrated under reduced pressure to obtain the title compound (18.7 mg).

$^1$H-NMR (400 MHz, CDCl$_3$) δ (ppm): 0.87-0.92 (m, 2H), 0.94-1.00 (m, 2H), 1.48-1.55 (m, 1H), 7.86 (dd, J=8.0, 2.0 Hz, 1H), 8.13 (dd, J=8.0, 1.1 Hz, 1H), 8.56 (dd, J=2.0, 1.1 Hz, 1H).

Preparation Example 42

Synthesis of 5-methylsulfanyl-pyrazine-2-carboxylic acid

[Formula 64]

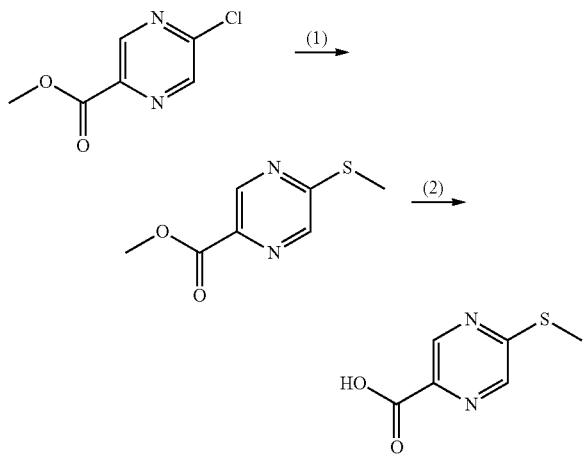

(1) Synthesis of methyl 5-methylsulfanyl-pyrazine-2-carboxylate

Sodium methanethiolate (44.6 mg) was added to a solution of methyl 5-chloropyrazine-2-carboxylate (87 mg) in hexamethylphosphorous triamide (1 mL) at room temperature, followed by stirring for 13 hours and 30 minutes. Water was added to the reaction solution, followed by extraction with ethyl acetate. The organic layer was concentrated under reduced pressure. The residue was purified by NH-silica gel column chromatography to obtain the title compound (6.8 mg).

$^1$H-NMR (400 MHz, CDCl$_3$) δ (ppm): 2.63 (s, 3H), 4.02 (s, 3H), 8.53 (d, J=1.4 Hz, 1H), 9.07 (d, J=1.4 Hz, 1H).

(2) Synthesis of 5-methylsulfanyl-pyrazine-2-carboxylic acid

Potassium trimethylsilanolate (6.15 mg) was added to a solution of the compound obtained in the previous step (6.8 mg) in tetrahydrofuran (500 μL) at room temperature, followed by stirring for one hour. Water and ethyl acetate were added to the reaction solution, and the aqueous layer was separated. 1 M hydrochloric acid was added to the aqueous layer, followed by extraction with ethyl acetate. The organic layer was dried over anhydrous magnesium sulfate, and the drying agent was filtered off. The filtrate was concentrated under reduced pressure to obtain the title compound (6.6 mg).

$^1$H-NMR (400 MHz, CDCl$_3$) δ (ppm): 2.67 (s, 3H), 8.49 (brs, 1H), 9.17 (brs, 1H).

Preparation Example 43

Synthesis of 5-(3-methoxy-propyn-1-yl)-pyridine-2-carboxylic acid

[Formula 65]

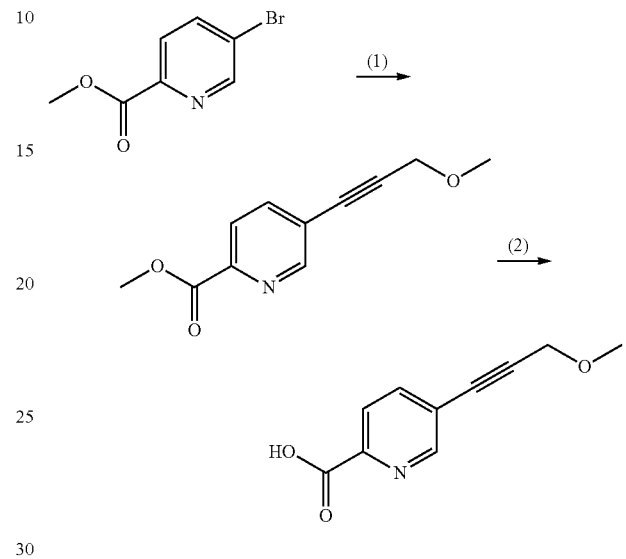

(1) Synthesis of methyl 5-(3-methoxy-propyn-1-yl)-pyridine-2-carboxylate

Bis(triphenylphosphine)palladium (II) chloride (82.4 mg), copper iodide (22.3 mg), methyl propargyl ether (828 μL) and triethylamine (1.9 mL) were added to a solution of methyl 5-bromo-pyridine-2-carboxylate (423 mg) in tetrahydrofuran (10.6 mL), and the mixture was stirred at room temperature for 19 hours and 50 minutes. The reaction solution was concentrated under reduced pressure and water was added to the residue. After extraction with ethyl acetate, the organic layer was washed with brine and the solvent was evaporated under reduced pressure. The residue was purified by silica gel column chromatography to obtain the title compound (88.1 mg).

$^1$H-NMR (400 MHz, CDCl$_3$) δ (ppm): 3.47 (s, 3H), 4.02 (s, 3H), 4.36 (s, 2H), 7.88 (dd, J=8.0, 2.0 Hz, 1H), 8.10 (dd, J=8.0, 0.8 Hz, 1H), 8.78 (dd, J=2.0, 0.8 Hz, 1H).

(2) Synthesis of 5-(3-methoxy-propyn-1-yl)-pyridine-2-carboxylic acid

Potassium trimethylsilylsilanolate (26.9 mg) was added to a solution of the compound obtained in the previous step (33 mg) in tetrahydrofuran (1 mL), and the mixture was stirred at room temperature for one hour and 20 minutes. The reaction solution was concentrated under reduced pressure. Water and diethyl ether were added to the residue, and the aqueous layer was separated. 1 M hydrochloric acid was added to the aqueous layer, followed by extraction with ethyl acetate. The organic layer was dried over anhydrous magnesium sulfate, and the drying agent was filtered off. The filtrate was concentrated under reduced pressure to obtain the title compound (25.4 mg).

$^1$H-NMR (400 MHz, CDCl$_3$) δ (ppm): 3.48 (s, 3H), 4.37 (s, 2H), 7.97 (dd, J=8.0, 1.8 Hz, 1H), 8.19 (dd, J=8.0, 0.8 Hz, 1H), 8.66 (dd, J=1.8, 0.8 Hz, 1H).

Preparation Example 44
Synthesis of tert-butyl(−)-[(4aS*,5S*,8aS*)-8a-(5-amino-2-fluorophenyl)-5-fluoromethyl-4a,7,8,8a-tetrahydro-4H,5H-6-oxa-3-thia-1-azanaphthalen-2-yl]carbamate
[Formula 66]
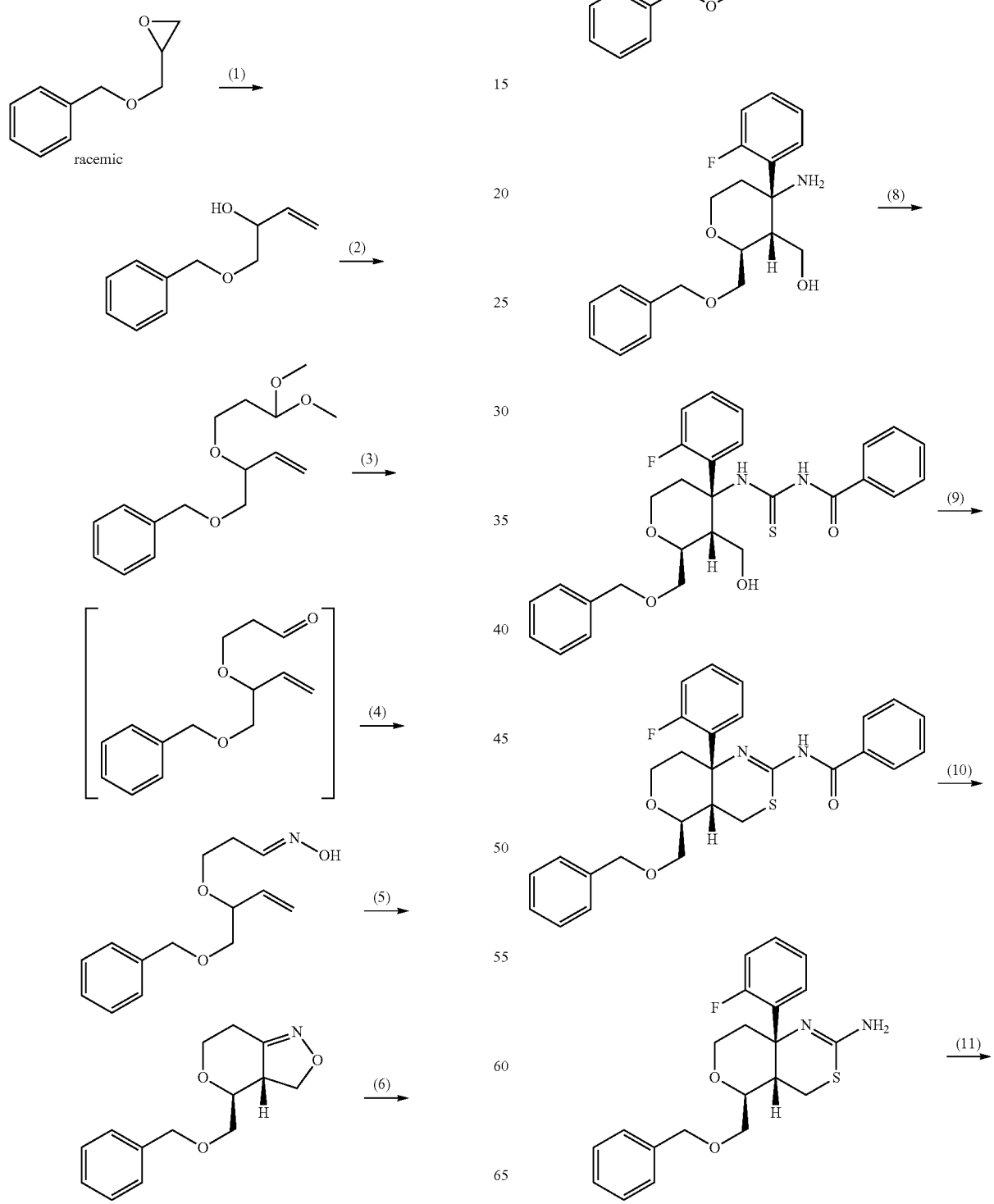

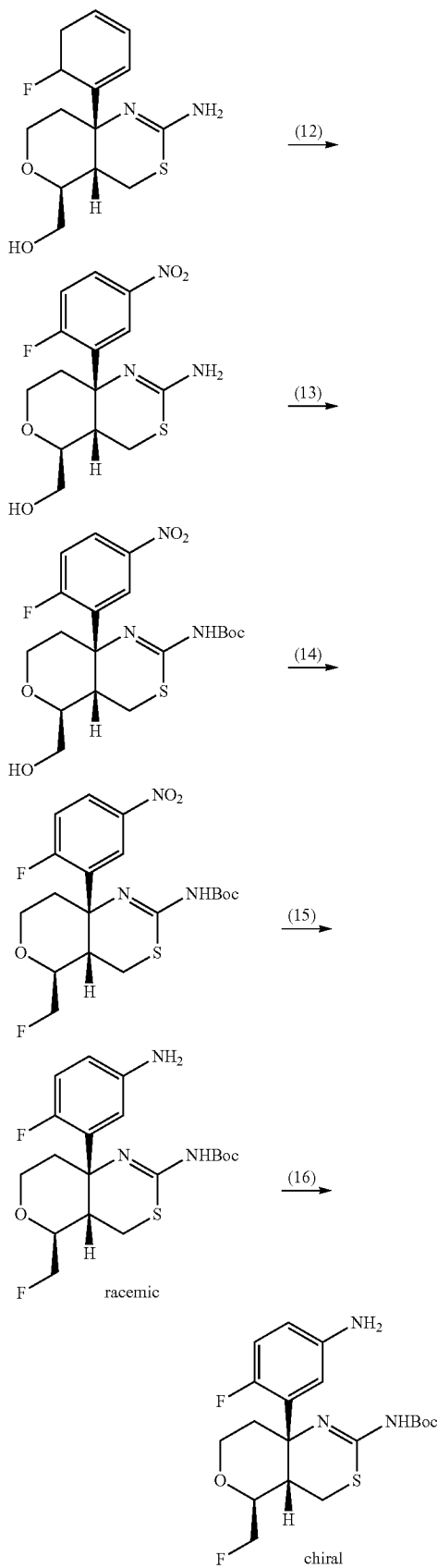 [SMILES: NC1=N[C@@]2(C3=CC=CCC3F)CCO[C@H](CO)[C@H]2CS1 ; NC1=N[C@@]2(c3cc([N+](=O)[O-])ccc3F)CCO[C@H](CO)[C@H]2CS1 ; CC(C)(C)OC(=O)NC1=N[C@@]2(c3cc([N+](=O)[O-])ccc3F)CCO[C@H](CO)[C@H]2CS1 ; CC(C)(C)OC(=O)NC1=N[C@@]2(c3cc([N+](=O)[O-])ccc3F)CCO[C@H](CF)[C@H]2CS1 ; CC(C)(C)OC(=O)NC1=N[C@@]2(c3cc(N)ccc3F)CCO[C@H](CF)[C@H]2CS1 ; CC(C)(C)OC(=O)NC1=N[C@@]2(c3cc(N)ccc3F)CCO[C@H](CF)[C@H]2CS1]

(1) Synthesis of 1-benzyloxy-3-buten-2-ol

A 2.64 M solution of n-butyllithium in hexane (35.7 mL) was added to a solution of trimethylsulfonium iodide (19.9 g) in tetrahydrofuran (300 mL) at −25° C. The mixture was stirred at the same temperature for 30 minutes. Benzyl glycidyl ether (5.00 mL) was added to the reaction solution at the same temperature, and then the mixture was warmed to room temperature over two hours and 50 minutes. Water was added to the reaction solution, followed by extraction with diethyl ether. The organic layer was dried over anhydrous magnesium sulfate. The drying agent was filtered off and the filtrate was concentrated under reduced pressure. The residue was purified by silica gel column chromatography to obtain the title compound (6.98 g).

$^1$H-NMR (400 MHz, CDCl$_3$) δ (ppm): 2.44 (d, J=3.6 Hz, 1H), 3.38 (dd, J=9.6, 8.0 Hz, 1H), 3.55 (dd, J=9.6, 3.0 Hz, 1H), 4.32-4.40 (m, 1H), 4.58 (s, 2H), 5.18-5.23 (m, 1H), 5.33-5.40 (m, 1H), 5.79-5.89 (m, 1H), 7.28-7.40 (m, 5H).

In the present Preparation Example 44-(2) to (8), synthesis was performed according to Preparation Example 22-(1) to (5). However, 3-bromopropionaldehyde dimethyl acetal was used instead of bromoacetaldehyde diethyl acetal.

In the present Preparation Example 44-(9) to (11), synthesis was performed according to Preparation Example 19-(8) to (10).

(12) Synthesis of [(4aS*,5S*,8aS*)-2-amino-8a-(2-fluoro-5-nitrophenyl)-4a,7,8,8a-tetrahydro-4H,5H-6-oxa-3-thia-1-azanaphthalen-5-yl]methanol Fuming nitric acid (121 µL) was added to a mixed solution of the compound obtained in the previous step (720 mg) in trifluoroacetic acid (12 mL) and sulfuric acid (6 mL) at 0° C., followed by stirring for one hour. The reaction solution was poured into ice and a 2 M sodium hydroxide solution was added at 0° C. After extraction with ethyl acetate, the organic layer was dried over anhydrous magnesium sulfate. The drying agent was filtered off and the filtrate was concentrated under reduced pressure to obtain the title compound (908 mg).

$^1$H-NMR (400 MHz, CDCl$_3$) δ (ppm): 1.68-1.77 (m, 1H), 2.56-2.67 (m, 1H), 2.73-2.79 (m, 2H), 2.90-3.00 (m, 1H), 3.67-3.75 (m, 1H), 3.77-3.92 (m, 3H), 3.93-4.00 (m, 1H), 7.19-7.26 (m, 1H), 8.16-8.22 (m, 1H), 8.24-8.28 (m, 1H).

(13) Synthesis of tert-butyl[(4aS*,5S*,8aS*)-8a-(2-fluoro-5-nitrophenyl)-5-hydroxymethyl-4a,7,8,8a-tetrahydro-4H,5H-6-oxa-3-thia-1-azanaphthalen-2-yl]carbamate Di-tert-butyl dicarbonate (1.16 g) and triethylamine (1.48 mL) were added to a solution of the compound obtained in the previous step (908 mg) in tetrahydrofuran (30 mL), and the mixture was stirred at room temperature for five hours and 30 minutes. The reaction solution was concentrated under reduced pressure. The residue was purified by silica gel column chromatography to obtain the title compound (454 mg).

$^1$H-NMR (400 MHz, CDCl$_3$) δ (ppm): 1.54 (s, 9H), 1.63-1.71 (m, 1H), 2.55-2.77 (m, 3H), 2.97-3.08 (m, 1H), 3.67-4.02 (m, 5H), 7.21-7.27 (m, 1H), 8.14-8.24 (m, 2H).

(14) Synthesis of tert-butyl[(4aS*,5S*,8aS*)-5-fluoromethyl-8a-(2-fluoro-5-nitrophenyl)-4a,7,8,8a-tetrahydro-4H,5H-6-oxa-3-thia-1-azanaphthalen-2-yl]carbamate

[Bis(2-methoxyethyl)amino]sulfur trifluoride (500 µL) was added to a solution of the compound obtained in the previous step (398 mg) in dichloromethane (20 mL) at −78° C., and the mixture was stirred at the same temperature for 30 minutes. Thereafter, the reaction solution was stirred at 0° C. for 30 minutes and at room temperature for four hours. A saturated sodium bicarbonate solution was added to the reaction solution, followed by extraction with chloroform. The organic layer was concentrated under reduced pressure. The residue was purified by silica gel column chromatography to obtain the title compound (414 mg).

$^1$H-NMR (400 MHz, CDCl$_3$) δ (ppm): 1.55 (s, 9H), 1.62-1.71 (m, 1H), 2.56-2.80 (m, 3H), 3.05-3.16 (m, 1H), 3.64-4.03 (m, 3H), 4.55-4.75 (m, 2H), 7.22-7.28 (m, 1H), 8.15-8.24 (m, 2H).

In the present Preparation Example 44-(15), synthesis was performed according to Preparation Example 20-(3).

(16) Synthesis of tert-butyl(−)-[(4aS*,5S*,8aS*)-8a-(5-amino-2-fluorophenyl)-5-fluoromethyl-4a,7,8,8a-tetrahydro-4H,5H-6-oxa-3-thia-1-azanaphthalen-2-yl]carbamate The compound obtained in the previous step (33 mg) was optically resolved by CHIRALPAK™ AD-H manufactured by Daicel Chemical Industries, Ltd. (2 cm×25 cm, mobile phase: hexane:ethanol=7:3, flow rate: 8 mL/min), and the component having a retention time of 20 to 27 minutes was collected. This operation was repeated to obtain the title compound (174 mg; >99% ee) from 364 mg of the racemate.

$^1$H-NMR (400 MHz, CDCl$_3$) δ (ppm): 1.53 (s, 9H), 1.58-1.66 (m, 1H), 2.62-2.69 (m, 1H), 2.75-2.86 (m, 1H), 2.89-2.96 (m, 1H), 3.08-3.15 (m, 1H), 3.66 (brs, 2H), 3.78-4.04 (m, 3H), 4.65 (dd, J=47.6, 2.8 Hz, 2H), 6.52-6.61 (m, 2H), 6.85-6.93 (m, 1H).

Preparation Example 45

Synthesis of tert-butyl[(4aS*,8aS*)-8a-(5-amino-2-trifluoromethoxyphenyl)-4a,7,8,8a-tetrahydro-4H,5H-6-oxa-3-thia-1-azanaphthalen-2-yl]carbamate

[Formula 67]

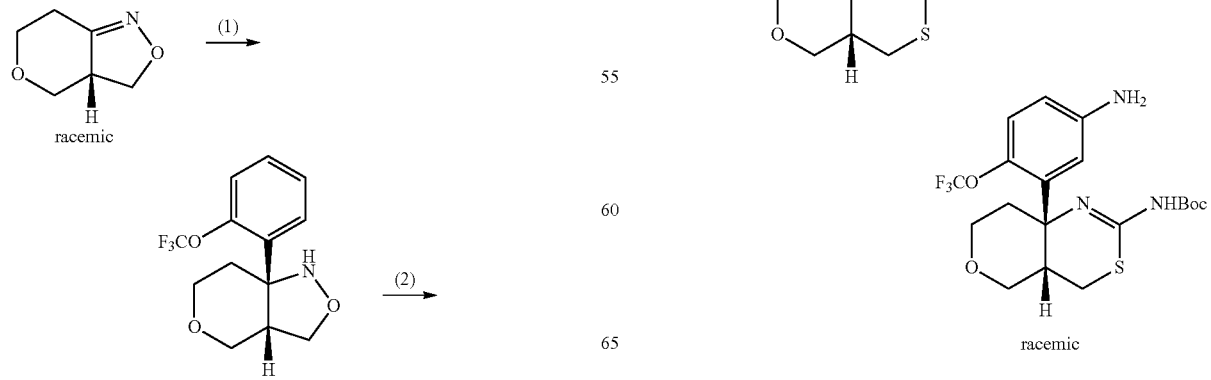

In the present Preparation Example 45, the compound obtained in Preparation Example 8-(2) was used as a starting material.

In the present Preparation Example 45-(1) to (3), synthesis was performed according to Preparation Example 22-(3) to (5). However, 1-bromo-2-trifluoromethoxybenzene was used instead of 2-bromofluorobenzene.

(4) Synthesis of N-[(4aS*,8aS*)-8a-(2-trifluoromethoxyphenyl)-4a,7,8,8a-tetrahydro-4H,5H-6-oxa-3-thia-1-azanaphthalen-2-yl]benzamide Carbon tetrabromide (542 mg) and triphenylphosphine (429 mg) were added to a solution of the compound obtained in the previous step (286 mg) in dichloromethane (6.41 mL) at room temperature, followed by stirring for four hours. The reaction solution was concentrated under reduced pressure. The residue was purified by silica gel column chromatography to obtain the title compound (52.4 mg).

¹H-NMR (400 MHz, CDCl₃) δ (ppm): 1.65-1.75 (m, 1H), 2.55-2.64 (m, 1H), 2.77-2.95 (m, 2H), 3.25-3.35 (m, 1H), 3.80-4.03 (m, 4H), 7.27-7.55 (m, 7H), 8.22-8.27 (m, 2H).

(5)-(8) Synthesis of tert-butyl[(4aS*,8aS*)-8a-(5-amino-2-trifluoromethoxyphenyl)-4a,7,8,8a-tetrahydro-4H,5H-6-oxa-3-thia-1-azanaphthalen-2-yl]carbamate The title compound was obtained by synthesis in the present Preparation Example 45-(5) according to Preparation Example 19-(9) and synthesis in the present Preparation Example 45-(6), (7) and (8) according to Preparation Example 22-(8), (9) and (10).

¹H-NMR (400 MHz, CDCl₃) δ (ppm): 1.54 (s, 9H), 1.54-1.62 (m, 1H), 2.45-2.53 (m, 1H), 2.67-2.80 (m, 1H), 2.83-2.92 (m, 1H), 3.09-3.18 (m, 1H), 3.69-3.96 (m, 6H), 6.58-6.64 (m, 2H), 7.09-7.14 (m, 1H).

Preparation Example 46

Synthesis of tert-butyl(-)-[(6S*,7S*,7aS*)-7a-(5-amino-2-fluorophenyl)-7-methyl-4a,5,7,7a-tetrahydro-4H-furo[3,4-d][1,3]thiazin-2-yl]carbamate

[Formula 68]

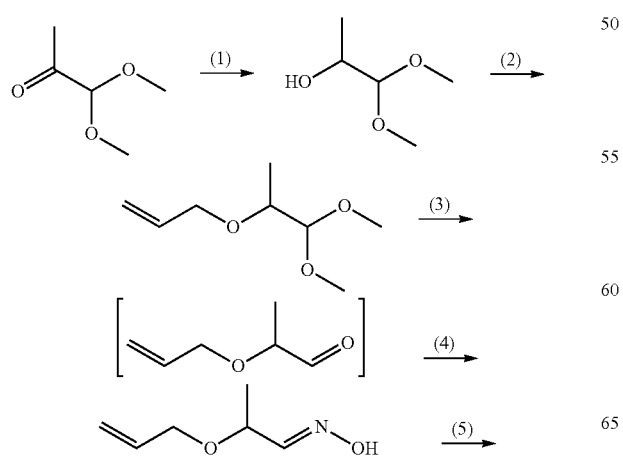

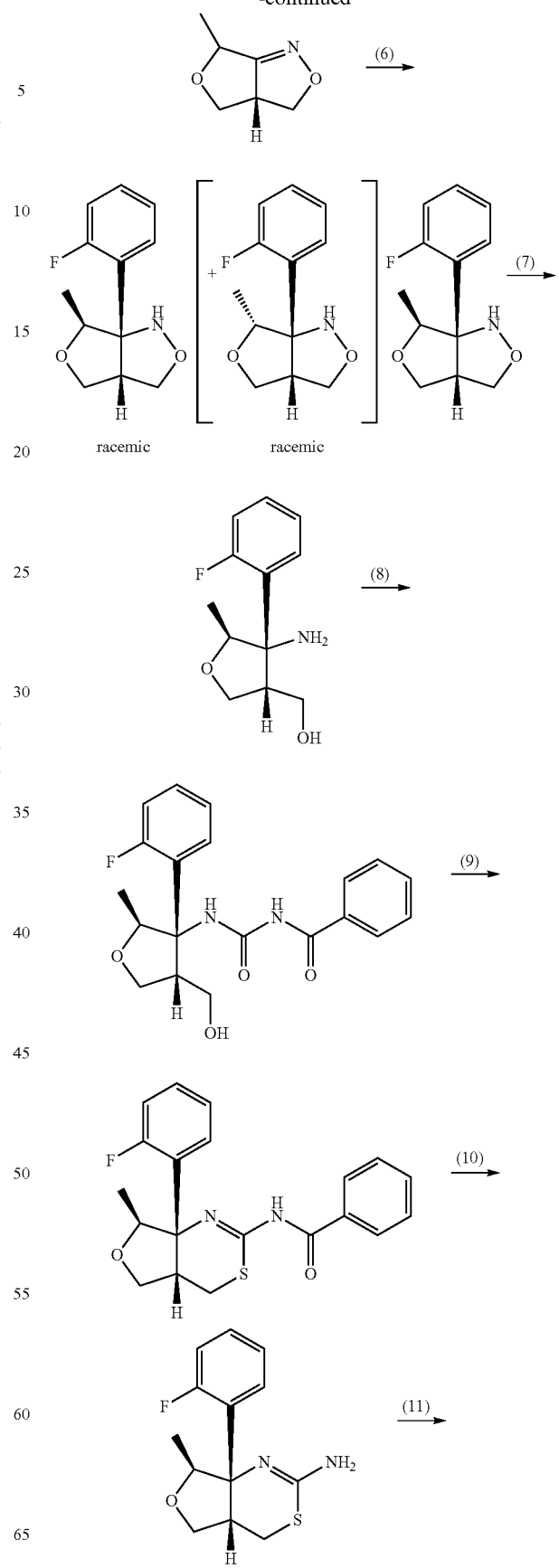

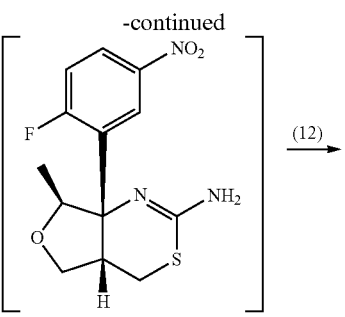
(12) →

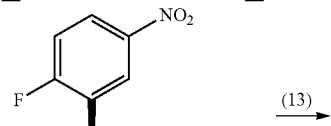
(13) →

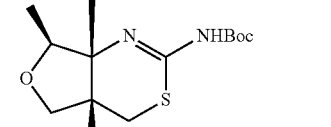
(14) → racemic

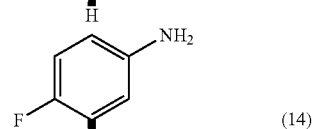

chiral (1) Synthesis of 1,1-dimethoxy-propan-2-ol

Sodium borohydride was added to a mixed solution of pyruvic aldehyde dimethyl acetal (10 mL) in methanol (50 mL) and tetrahydrofuran (50 mL) at 0° C., followed by stirring for 10 minutes. The reaction solution was warmed to room temperature and stirred for one hour and 20 minutes. A saturated ammonium chloride solution was added to the reaction solution. After extraction with diethyl ether, the organic layer was dried over anhydrous magnesium sulfate. The drying agent was filtered off and the filtrate was concentrated under reduced pressure to obtain the title compound (9.86 g).

$^1$H-NMR (400 MHz, CDCl$_3$) δ (ppm): 1.20 (d, J=6.4 Hz, 3H), 2.17 (brd, J=3.2 Hz, 1H), 3.44 (s, 3H), 3.46 (s, 3H), 3.72-3.80 (m, 1H), 4.08 (d, J=6.4 Hz, 1H).

(2) Synthesis of 3-(2,2-dimethoxy-1-methyl-ethoxy)-propene

60% sodium hydride (992 mg) was added to a solution of 1,1-dimethoxy-propan-2-ol (2.49 g) in dimethylformamide (50 mL) at 0° C., followed by stirring for 15 minutes. Allyl bromide (1.96 mL) was added at the same temperature, followed by stirring for 15 minutes. Ice was added to the reaction solution, followed by extraction with ethyl acetate. The organic layer was concentrated under reduced pressure. The residue was purified by silica gel column chromatography to obtain the title compound (3.46 g).

$^1$H-NMR (400 MHz, CDCl$_3$) δ (ppm): 1.16 (d, J=6.5 Hz, 3H), 3.43 (s, 3H), 3.45 (s, 3H), 3.48-3.54 (m, 1H), 4.03-4.14 (m, 2H), 4.18 (d, J=5.2 Hz, 1H), 5.14-5.19 (m, 1H), 5.25-5.32 (m, 1H), 5.87-5.98 (m, 1H).

In the present Preparation Example 46-(3) and (4), synthesis was performed according to Preparation Example 24-(3).

In the present Preparation Example 46-(5) to (9), synthesis was performed according to Preparation Example 22-(2) to (6).

In the present Preparation Example 46-(10), synthesis was performed according to Preparation Example 19-(9).

In the present Preparation Example 46-(11), (12) and (13), synthesis was performed according to Preparation Example 22-(8), (9) and (10).

(14) Synthesis of tert-butyl(−)-[(6S*,7S*,7aS*)-7a-(5-amino-2-fluorophenyl)-7-methyl-4a,5,7,7a-tetrahydro-4H-furo[3,4-d][1,3]thiazin-2-yl]carbamate The compound obtained in the previous step (12 mg) was optically resolved by CHIRALPAK™ AD-H manufactured by Daicel Chemical Industries, Ltd. (2 cm×25 cm, mobile phase: hexane:ethanol=8:2, flow rate: 10 mL/min), and the component having a retention time of 16 to 21 minutes was collected. This operation was repeated to obtain the title compound (112 mg; >99% ee) from 240 mg of the racemate.

$^1$H-NMR (400 MHz, CDCl$_3$) δ (ppm): 0.96 (d, J=6.0 Hz, 3H), 1.49 (s, 9H), 2.81-2.90 (m, 1H), 3.30-3.40 (m, 1H), 3.43-3.52 (m, 1H), 3.61 (brs, 2H), 4.10-4.19 (m, 1H), 4.20-4.38 (m, 2H), 6.56-6.64 (m, 2H), 6.87-6.94 (m, 1H).

Preparation Example 47

Synthesis of tert-butyl(−)-[(6R*,7S*,7aS*)-7a-(5-amino-2-fluorophenyl)-7-methyl-4a,5,7,7a-tetrahydro-4H-furo[3,4-d][1,3]thiazin-2-yl]carbamate

[Formula 69]

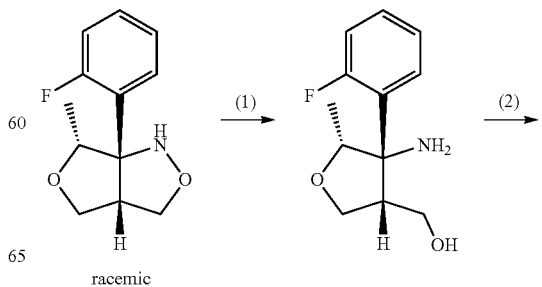

racemic

-continued

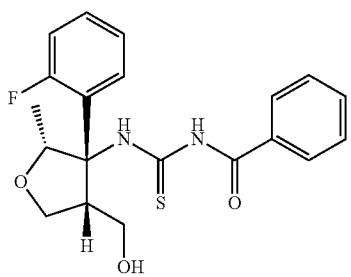

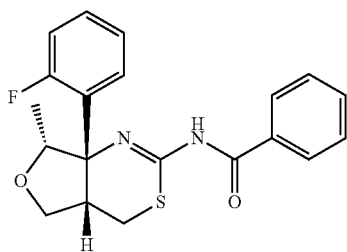

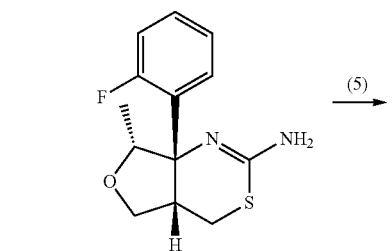

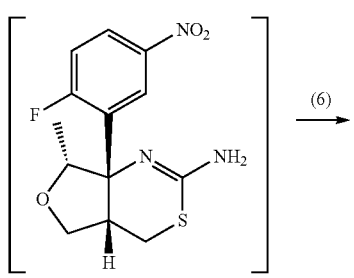

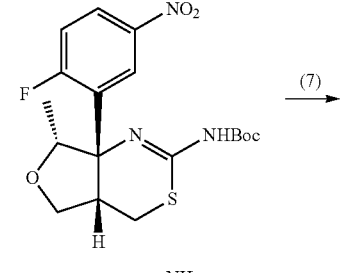

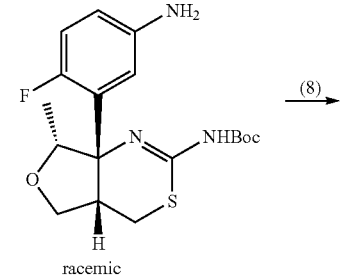
racemic

-continued

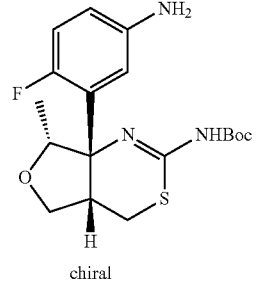
chiral (1)-(8) Synthesis of tert-butyl(−)-[(6R*,7S*,7aS*)-7a-(5-amino-2-fluorophenyl)-7-methyl-4a,5,7,7a-tetrahydro-4H-furo[3,4-d][1,3]thiazin-2-yl]carbamate In the present Preparation Example, (3S*,3aS*,5R*)-6a-(2-fluorophenyl)-6-methyltetrahydrofuro[3,4-c]isoxazole obtained in Preparation Example 46-(6) was used as a starting material.

The title compound was obtained by synthesis in the present Preparation Example 47-(1) to (8) according to Preparation Example 46-(7) to (14).

$^1$H-NMR (400 MHz, CDCl$_3$) δ (ppm): 1.14 (brd, J=6.4 Hz, 3H), 1.52 (s, 9H), 2.62-2.70 (m, 1H), 3.03-3.15 (m, 1H), 3.46-3.60 (m, 1H), 3.64 (brs, 2H), 4.10-4.23 (m, 2H), 4.56-4.65 (m, 1H), 6.55-6.62 (m, 1H), 6.63-6.67 (m, 1H), 6.83-6.90 (m, 1H).

Preparation Example 48

Synthesis of tert-butyl(−)-[(4aS*,5R*,8aS*)-8a-(5-amino-2-fluorophenyl)-5-methyl-4a,7,8,8a-tetrahydro-4H,5H-6-oxa-3-thia-1-azanaphthalen-2-yl]carbamate

[Formula 70]

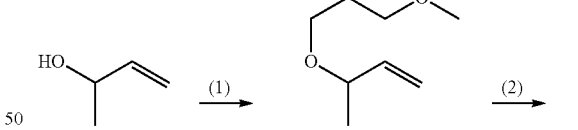

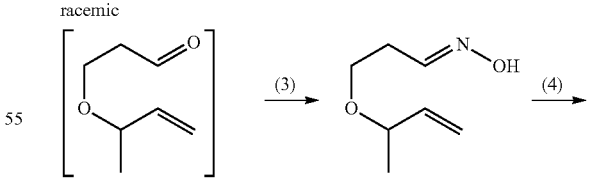

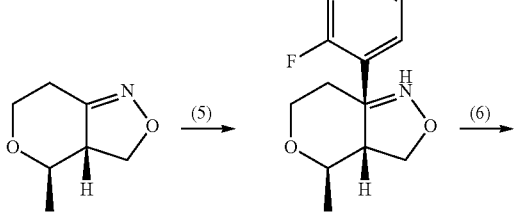

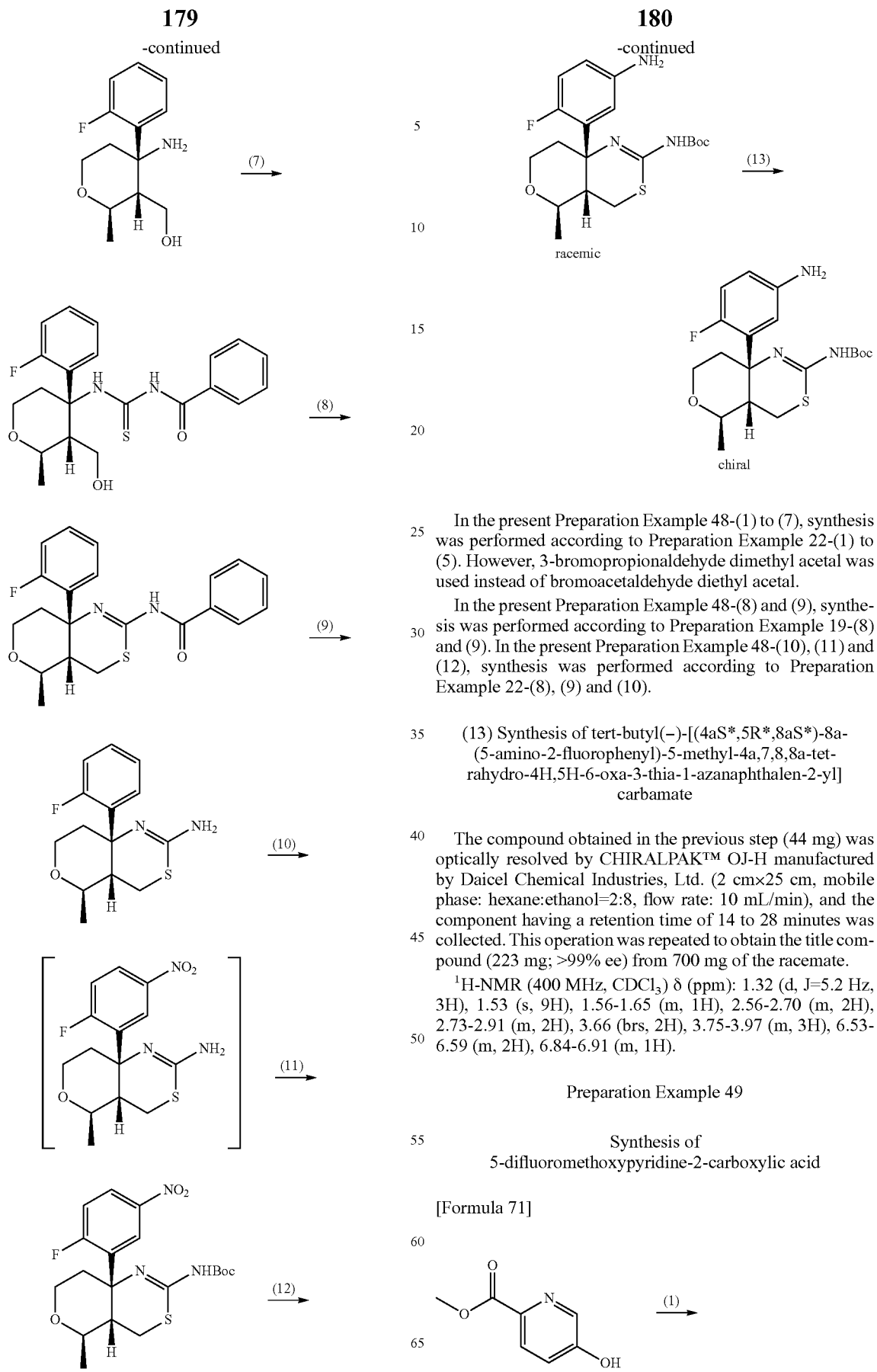

In the present Preparation Example 48-(1) to (7), synthesis was performed according to Preparation Example 22-(1) to (5). However, 3-bromopropionaldehyde dimethyl acetal was used instead of bromoacetaldehyde diethyl acetal.

In the present Preparation Example 48-(8) and (9), synthesis was performed according to Preparation Example 19-(8) and (9). In the present Preparation Example 48-(10), (11) and (12), synthesis was performed according to Preparation Example 22-(8), (9) and (10).

(13) Synthesis of tert-butyl(−)-[(4aS*,5R*,8aS*)-8a-(5-amino-2-fluorophenyl)-5-methyl-4a,7,8,8a-tetrahydro-4H,5H-6-oxa-3-thia-1-azanaphthalen-2-yl]carbamate The compound obtained in the previous step (44 mg) was optically resolved by CHIRALPAK™ OJ-H manufactured by Daicel Chemical Industries, Ltd. (2 cm×25 cm, mobile phase: hexane:ethanol=2:8, flow rate: 10 mL/min), and the component having a retention time of 14 to 28 minutes was collected. This operation was repeated to obtain the title compound (223 mg; >99% ee) from 700 mg of the racemate.

$^1$H-NMR (400 MHz, CDCl$_3$) δ (ppm): 1.32 (d, J=5.2 Hz, 3H), 1.53 (s, 9H), 1.56-1.65 (m, 1H), 2.56-2.70 (m, 2H), 2.73-2.91 (m, 2H), 3.66 (brs, 2H), 3.75-3.97 (m, 3H), 6.53-6.59 (m, 2H), 6.84-6.91 (m, 1H).

Preparation Example 49

Synthesis of 5-difluoromethoxypyridine-2-carboxylic acid

[Formula 71]

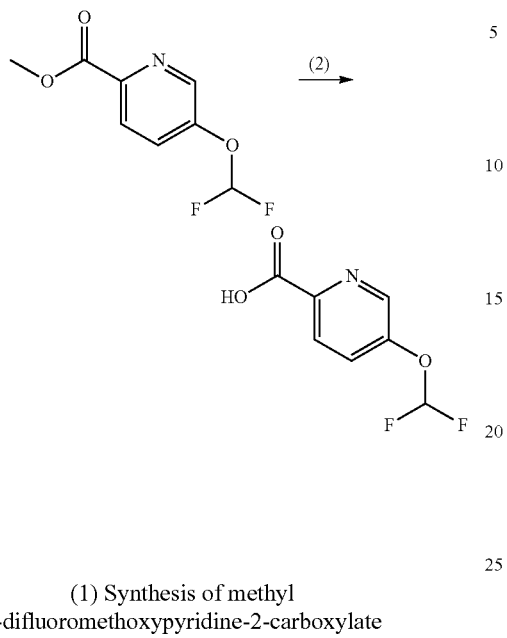

(1) Synthesis of methyl 5-difluoromethoxypyridine-2-carboxylate

Cesium carbonate (7.45 g) and 2-chloro-2,2-difluoroacetophenone (5.75 g) were added to a solution of methyl 5-hydroxypyridine-2-carboxylate (2.5 g) in DMF, and the mixture was stirred at 100° C. for three hours. The reaction solution was returned to room temperature. Aqueous ammonium chloride and ethyl acetate were added and the organic layer was separated. The organic layer was washed with saturated aqueous sodium chloride and dried over anhydrous magnesium sulfate. The organic layer was concentrated under reduced pressure. The residue was purified by silica gel column chromatography to obtain the title compound (760 mg).

$^1$H-NMR (400 MHz, CDCl$_3$) δ (ppm): 4.02 (s, 3H), 6.64 (t, J=72.0 Hz, 1H), 7.62 (dd, J=2.8, 8.8 Hz, 1H), 8.18 (d, J=9.2 Hz, 1H), 8.58 (d, J=2.8 Hz, 1H).

(2) Synthesis of 5-difluoromethoxypyridine-2-carboxylic acid

A 2 N sodium hydroxide solution (3.74 mL) was added to a solution of methyl 5-difluoromethoxypyridine-2-carboxylate obtained in Preparation Example 49-(1) (760 mg) in methanol (15 mL), and the mixture was stirred at room temperature for 30 minutes. The reaction solution was made acidic with hydrochloric acid. Saturated aqueous sodium chloride and ethyl acetate were added to the reaction solution, and the organic layer was separated. The organic layer was dried over anhydrous magnesium sulfate. The solvent was evaporated under reduced pressure to obtain the title compound (482 mg).

$^1$H-NMR (400 MHz, CDCl$_3$) δ (ppm): 6.67 (t, J=71.6 Hz, 1H), 7.72 (dd, J=2.0, 8.4 Hz, 1H), 8.28 (d, J=8.8 Hz, 1H), 8.50 (d, J=2.0 Hz, 1H).

Preparation Example 50

Synthesis of 5-(2,2,2-trifluoroethoxy)pyrazine-2-carboxylic acid

[Formula 72]

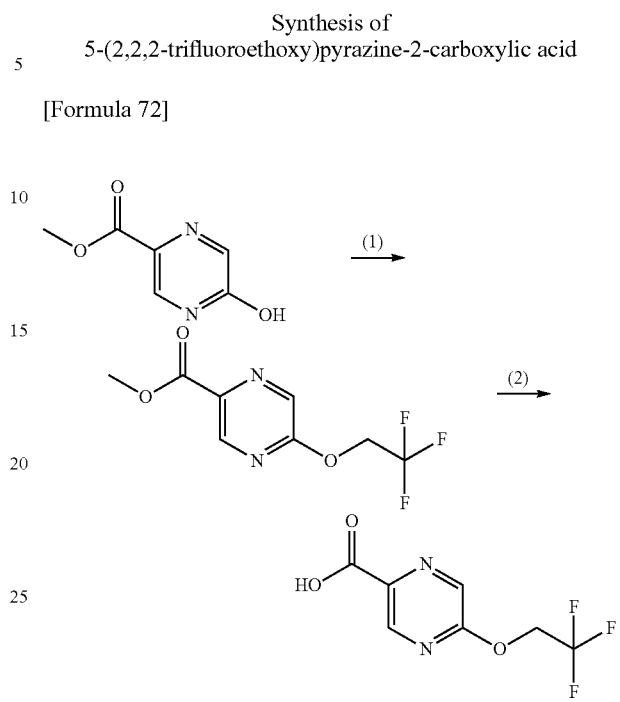

(1) Synthesis of methyl 5-(2,2,2-trifluoroethoxy)pyrazine-2-carboxylate

Cesium carbonate (2.96 g) and 2,2,2-trifluoroethyl trifluoromethanesulfonate (1.57 g) were added to a solution of methyl 5-hydroxypyrazine-2-carboxylate (700 mg) in DMF (20 mL), and the mixture was stirred at room temperature for 20 hours. Aqueous ammonium chloride and ethyl acetate were added to the reaction solution, and the organic layer was separated. The organic layer was washed with saturated aqueous sodium chloride and dried over anhydrous magnesium sulfate. The organic layer was concentrated under reduced pressure. The residue was purified by silica gel chromatography to obtain the title compound (197 mg).

$^1$H-NMR (400 MHz, CDCl$_3$) δ (ppm): 4.02 (s, 3H), 4.85 (q, J=8.0 Hz, 2H), 8.44 (d, J=1.2 Hz, 1H), 8.88 (d, J=1.2 Hz, 1H).

(2) Synthesis of 5-(2,2,2-trifluoroethoxy)pyrazine-2-carboxylic acid

A 5 N sodium hydroxide solution (3 mL) and ethanol (3 mL) were added to a solution of methyl 5-(2,2,2-trifluoroethoxy)pyrazine-2-carboxylate obtained in Preparation Example 50-(1) (197 mg) in THF (5 mL), and the mixture was heated under reflux for 15 minutes. After returning to room temperature, water and ethyl acetate were added and the aqueous layer was separated. The aqueous layer was adjusted to pH 1 with hydrochloric acid, and ethyl acetate was added to the aqueous layer. The organic layer was separated and dried over anhydrous magnesium sulfate. The organic layer was concentrated under reduced pressure to obtain the title compound (87 mg).

$^1$H-NMR (400 MHz, CDCl$_3$) δ (ppm): 4.88 (q, J=8.4 Hz, 2H), 8.37 (d, J=1.2 Hz, 1H), 8.99 (d, J=1.2 Hz, 1H).

Preparation Example 51

Synthesis of
5-(2,2-difluoroethoxy)-pyrazine-2-carboxylic acid

[Formula 73]

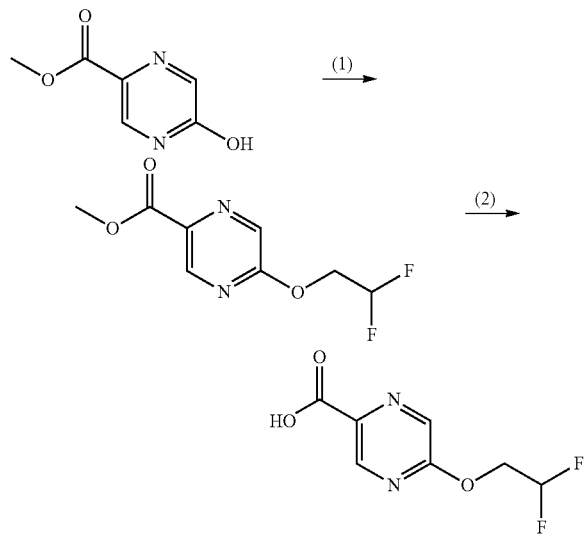

(1) Synthesis of methyl 5-(2,2-difluoroethoxy)pyrazine-2-carboxylate

Cesium carbonate (2.12 g) and 2-bromo-1,1-difluoroethane (939 mg) were added to a solution of methyl 5-hydroxy-pyrazine-2-carboxylate (500 mg) in DMF (20 mL), and the mixture was stirred at 80° C. for four hours. The reaction solution was returned to room temperature. Saturated aqueous sodium chloride and ethyl acetate were added and the organic layer was separated. The organic layer was dried over anhydrous magnesium sulfate. The organic layer was concentrated under reduced pressure. The residue was purified by silica gel column chromatography to obtain the title compound (145 mg).

$^1$H-NMR (400 MHz, CDCl$_3$) δ (ppm): 4.02 (s, 3H), 4.64 (dt, J=4.0, 13.2 Hz, 2H), 6.15 (tt, J=4.0, 54.8 Hz, 1H), 8.39 (d, J=1.2 Hz, 1H), 8.88 (d, J=1.2 Hz, 1H).

(2) Synthesis of 5-(2,2-difluoroethoxy)pyrazine-2-carboxylic acid

A 5 N sodium hydroxide solution (266 μL) was added to a solution of methyl 5-(2,2-difluoroethoxy)pyrazine-2-carboxylate obtained in Preparation Example 51-(1) (145 mg) in ethanol (4 mL), and the mixture was stirred at room temperature for one hour. 5 N hydrochloric acid was added to the reaction solution to prepare an acidic solution. Ethyl acetate and brine were added to the reaction solution, and the organic layer was separated. The organic layer was dried over anhydrous magnesium sulfate. The organic layer was concentrated under reduced pressure to obtain the title compound (92 mg).

$^1$H-NMR (400 MHz, CDCl$_3$) δ (ppm): 4.68 (dt, J=4.0, 13.2 Hz, 2H), 6.16 (tt, J=4.0, 54.8 Hz, 1H), 8.34 (s, 1H), 8.99 (d, J=0.8 Hz, 1H).

Preparation Example 52

Synthesis of
5-(2,2-difluoroethoxy)pyridine-2-carboxylic acid

[Formula 74]

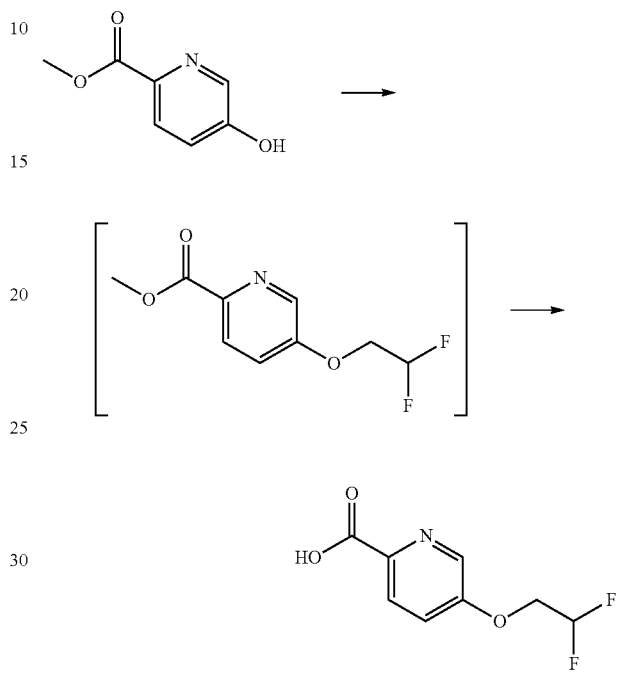

Cesium carbonate (423 mg) and 2-bromo-1,1-difluoroethane (189 mg) were added to a solution of methyl 5-hydroxy-pyridine-2-carboxylate (100 mg) in DMF (4 mL), and the mixture was stirred at room temperature for 20 hours. Saturated aqueous sodium chloride and ethyl acetate were added to the reaction solution, and the organic layer was separated. The organic layer was dried over anhydrous magnesium sulfate. The organic layer was concentrated under reduced pressure. The residue was purified by silica gel column chromatography to obtain the title intermediate. A 5 N sodium hydroxide solution (262 μL) was added to a solution of the resulting intermediate in ethanol (5 mL). The reaction solution was stirred at room temperature for 30 minutes. The reaction solution was made acidic with 5 N hydrochloric acid (1 mL). Saturated aqueous sodium chloride and ethyl acetate were added to the reaction solution, and the organic layer was separated. The organic layer was dried over anhydrous magnesium sulfate. The organic layer was concentrated under reduced pressure to obtain the title compound (22.4 mg).

$^1$H-NMR (400 MHz, CDCl$_3$) δ (ppm): 4.33 (dt, J=4.0, 12.8 Hz, 2H), 6.15 (tt, J=4.0, 54.8 Hz, 1H), 7.42 (dd, J=2.8, 8.4 Hz, 1H), 8.22 (d, J=8.8 Hz, 1H), 8.34 (s, 1H).

Preparation Example 53

Synthesis of 5-(2-fluoroethoxy)pyrazine-2-carboxylic acid

[Formula 75]

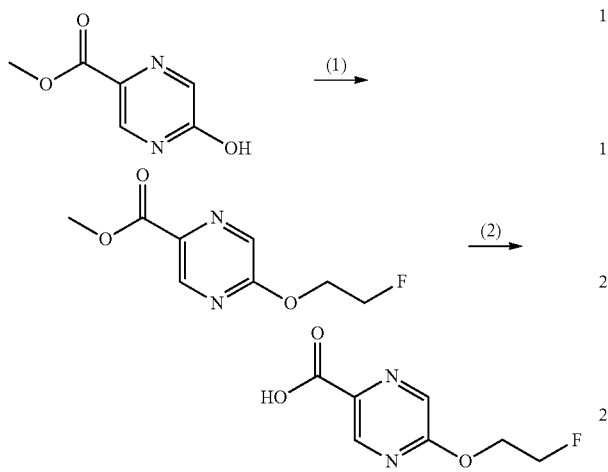

(1) Synthesis of methyl 5-(2-fluoroethoxy)pyrazine-2-carboxylate

Cesium carbonate (6.34 g) and 1-iodo-2-fluoroethane (2.26 g) were added to a solution of methyl 5-hydroxypyrazine-2-carboxylate (1 g) in DMF (30 mL), and the mixture was stirred at room temperature for 20 hours. Aqueous ammonium chloride and ethyl acetate were added to the reaction solution, and the organic layer was separated. The organic layer was washed with saturated aqueous sodium chloride and then dried over anhydrous magnesium sulfate. The organic layer was concentrated under reduced pressure. The residue was purified by silica gel column chromatography to obtain the title compound (200 mg).

$^1$H-NMR (400 MHz, CDCl$_3$) δ (ppm): 4.00 (s, 3H), 4.63-4.86 (m, 4H), 8.36 (d, J=1.2 Hz, 1H), 8.87 (d, J=1.6 Hz, 1H).

(2) Synthesis of 5-(2-fluoroethoxy)pyrazine-2-carboxylic acid

A 5 N sodium hydroxide solution (400 μL) was added to a solution of methyl 5-(2-fluoroethoxy)pyrazine-2-carboxylate obtained in Preparation Example 53-(1) (200 mg) in ethanol (4 mL). Water was added until the reaction solution became a complete solution, followed by stirring at room temperature for 10 minutes. The reaction solution was made acidic with 5 N hydrochloric acid. Saturated aqueous sodium chloride and ethyl acetate were added to the reaction solution, and the organic layer was separated. The organic layer was dried over anhydrous magnesium sulfate. The organic layer was concentrated under reduced pressure to obtain the title compound (150 mg).

$^1$H-NMR (400 MHz, CDCl$_3$) δ (ppm): 4.67-4.87 (m, 4H), 8.27 (d, J=1.2 Hz, 1H), 8.97 (d, J=1.2 Hz, 1H).

Preparation Example 54

Synthesis of (±)-(4aR*,7aS*)-7a-(5-bromo-2-fluorophenyl)-4,4a,5,6,7,7a-hexahydrocyclopenta[d][1,3]thiazin-2-ylamine

[Formula 76]

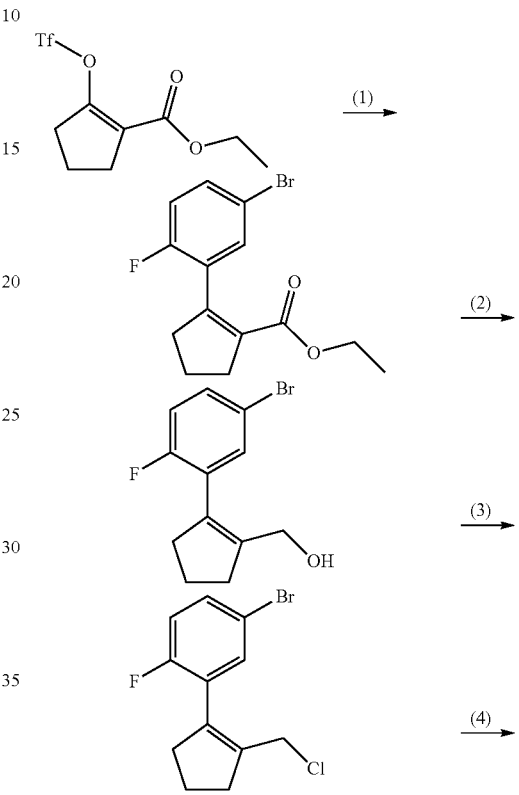

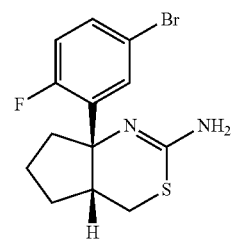

(1)-(4) Synthesis of (±)-(4aR*,7aS*)-7a-(5-bromo-2-fluorophenyl)-4,4a,5,6,7,7a-hexahydrocyclopenta[d][1,3]thiazin-2-ylamine The title compound (4.03 g) was obtained from the compound obtained in Preparation Example 3-(1) (10 g) according to Preparation Example 3, using 5-bromo-2-fluorophenylboronic acid in the above Step (2) and using lithium borohydride with heating under reflux instead of lithium aluminum hydride in Step (3).

ESI-MS; m/z 331 [M$^+$+H].

Preparation Example 55

Synthesis of (±)-di-tert-butyl[(4aR*,7aS*)-7a-(3-amino-5-fluorophenyl)-4,4a,5,6,7,7a-hexahydrocyclopenta[d][1,3]thiazin-2-yl]imidodicarbonate

[Formula 77]

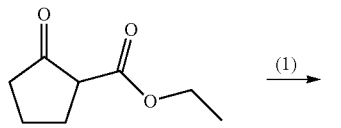

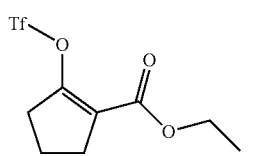

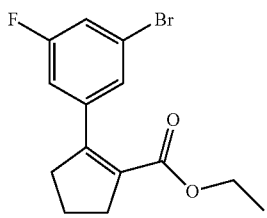



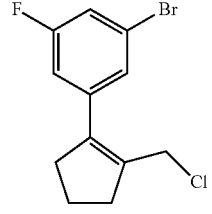

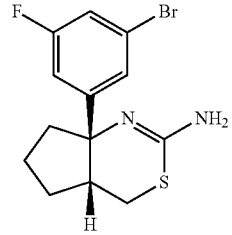

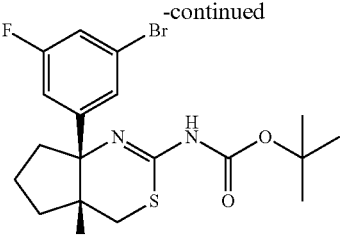

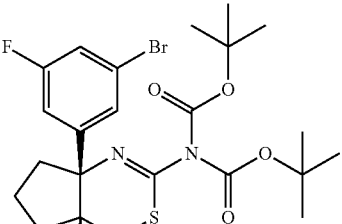

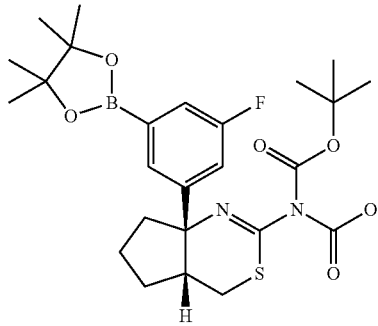

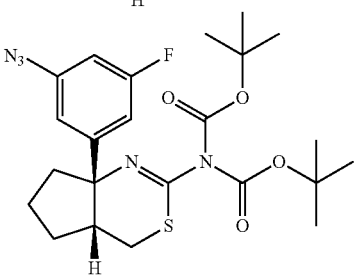

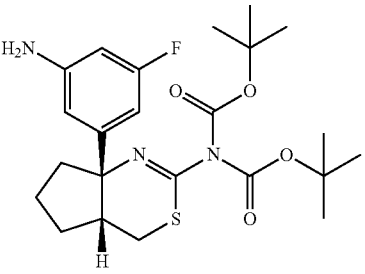

(1)-(2) Synthesis of ethyl 2-(3-bromo-5-fluorophenyl)-cyclopent-1-enecarboxylate The title compound (12.9 g) was obtained from ethyl 2-oxocyclopentanecarboxylate (6.8 g) according to Preparation Example 3.
ESI-MS; m/z 313 [M$^+$+H].

(3) Synthesis of 2-(3-bromo-5-fluorophenyl)-cyclopent-1-enecarboxylic acid

A 5 N sodium hydroxide solution (16.5 mL) was added to a solution of the compound obtained in Preparation Example 55-(2) (12.9 g) in ethanol (130 mL), and the mixture was stirred at room temperature for 16 hours. Ethanol was evaporated under reduced pressure. Water (100 mL) and ether (150 mL) were added to the residue, and the aqueous layer was separated. The aqueous layer was made acidic with 5 N hydrochloric acid, and ethyl acetate was added to the aqueous layer. The organic layer was separated and dried over anhydrous magnesium sulfate. The organic layer was concentrated under reduced pressure. The resulting solid was washed with heptane (150 mL) to obtain the title compound (10.58 g).

$^1$H-NMR (CDCl$_3$) δ (ppm): 1.96-2.05 (m, 2H), 2.80-2.85 (m, 4H), 6.96-7.00 (m, 1H), 7.15-7.18 (m, 1H), 7.22-7.24 (m, 1H).

(4) Synthesis of [2-(3-bromo-5-fluorophenyl)cyclopent-1-enyl]methanol

Isobutyl chloroformate (5.08 mL) was added dropwise to a solution of the compound obtained in Preparation Example 55-(3) (10.6 g) and triethylamine (5.41 mL) in tetrahydrofuran (230 mL) under a nitrogen atmosphere at −20° C. The reaction solution was stirred at the same temperature for 30 minutes, and then the resulting insoluble matter was separated by filtration through celite. The filtrate was added dropwise to a solution of sodium borohydride in water (2.81 g/162 mL) at 0 to −10° C. The mixture was stirred at the same temperature for two hours and then warmed to room temperature. The reaction solution was stirred at room temperature for 3 hours. Ethyl acetate and saturated aqueous sodium chloride were added to the reaction solution, and the organic layer was separated. The organic layer was dried over anhydrous magnesium sulfate. The organic layer was concentrated under reduced pressure. The residue was purified by silica gel column chromatography to obtain the title compound (9.3 g).

$^1$H-NMR (CDCl$_3$) δ (ppm): 1.93-2.05 (m, 2H), 2.66-2.76 (m, 4H), 4.30 (d, J=2.8 Hz, 2H), 6.89-6.92 (m, 1H), 7.11-7.19 (m, 2H).

(5)-(6) Synthesis of (±)-(4aR*,7aS*)-7a-(3-bromo-5-fluorophenyl)-4,4a,5,6,7,7a-hexahydrocyclopenta[d][1,3]thiazin-2-ylamine The title compound (12.2 g) was obtained from the compound obtained in Preparation Example 55-(4) (9.3 g) according to Preparation Example 3.

ESI-MS; m/z 331 [M$^+$+H].

(7) Synthesis of tert-butyl(±)-[(4aR*,7aS*)-7a-(3-bromo-5-fluorophenyl)-4,4a,5,6,7,7a-hexahydrocyclopenta[d][1,3]thiazin-2-yl]carbamate Triethylamine (1.11 mL) and di-tert-butyl dicarbonate (1.16 g) were added to a solution of the compound obtained in Preparation Example 55-(6) (1 g) in tetrahydrofuran (30 mL), and the mixture was stirred at room temperature for 14 hours. Water and ethyl acetate were added to the reaction solution, and the organic layer was separated. The organic layer was washed with saturated aqueous sodium chloride and dried over anhydrous magnesium sulfate. The organic layer was concentrated under reduced pressure. The residue was purified by silica gel column chromatography to obtain the title compound (1.03 g).

ESI-MS; m/z 431 [M$^+$+H].

(8) Synthesis of (±)-di-tert-butyl[(4aR*,7aS*)-7a-(3-bromo-5-fluorophenyl)-4,4a,5,6,7,7a-hexahydrocyclopenta[d][1,3]thiazin-2-yl]imidodicarbonate 4-Dimethylaminopyridine (880 mg) and di-tert-butyl dicarbonate (1.05 g) were added to a solution of the compound obtained in Preparation Example 55-(7) (1.03 g) in acetonitrile (20 mL). The reaction solution was stirred at room temperature for two hours. Ethyl acetate and saturated aqueous sodium chloride were added to the reaction solution, and the organic layer was separated. The organic layer was washed with brine again and dried over anhydrous magnesium sulfate. The organic layer was concentrated under reduced pressure. The residue was purified by silica gel column chromatography to obtain the title compound (1.12 g).

ESI-MS; m/z 531 [M$^+$+H].

(9) Synthesis of (±)-di-tert-butyl {(4aR*,7aS*)-7a-[3-fluoro-5-(4,4,5,5-tetramethyl-1,3,2-dioxaboran-2-yl)phenyl]-4,4a,5,6,7,7a-hexahydrocyclopenta[d][1,3]thiazin-2-yl}imidodicarbonate A solution of the compound obtained in Preparation Example 55-(8) (635 mg), bis(pinacolato)diborane (3.04 g), potassium acetate (471 mg) and 1,1'-bis(diphenylphosphino)ferrocene dichloropalladium (II) (87.5 mg) in DMF (12 mL) was stirred under a nitrogen atmosphere at 80° C. for five hours. The reaction solution was returned to room temperature. Ethyl acetate and saturated aqueous sodium chloride were added to the reaction solution, and the organic layer was separated. The organic layer was washed with saturated aqueous sodium chloride again. The organic layer was dried over anhydrous magnesium sulfate. The organic layer was concentrated under reduced pressure. The residue was purified by silica gel column chromatography to obtain the title compound (692 mg).

ESI-MS; m/z 577 [M$^+$+H].

(10) Synthesis of (±)-di-tert-butyl[(4aR*,7aS*)-7a-(3-azido-5-fluorophenyl)-4,4a,5,6,7,7a-hexahydrocyclopenta[d][1,3]thiazin-2-yl]imidodicarbonate A solution of the compound obtained in Preparation Example 55-(9) (695 mg), sodium azide (118 mg) and copper (II) acetate (44 mg) in methanol (15 mL) was stirred at room temperature for 72 hours. Water and ethyl acetate were added to the reaction solution, and the organic layer was separated. The organic layer was washed with saturated aqueous sodium chloride twice. The organic layer was dried over anhydrous magnesium sulfate. The organic layer was concentrated under reduced pressure. The residue was purified by silica gel column chromatography to obtain the title compound (370 mg).

ESI-MS; m/z 492 [M$^+$+H].

(11) Synthesis of (±)-di-tert-butyl[(4aR*,7aS*)-7a-(3-amino-5-fluorophenyl)-4,4a,5,6,7,7a-hexahydrocyclopenta[d][1,3]thiazin-2-yl]imidodicarbonate Water (2 mL) and triphenylphosphine (257 mg) were added to a solution of the compound obtained in Preparation Example 55-(10) (370 mg) in tetrahydrofuran (8 mL), and the mixture was stirred at 60° C. for three hours. The reaction solution was further heated under reflux for 40 hours. The reaction solution was returned to room temperature. Ethyl acetate and saturated aqueous sodium chloride were added to the reaction solution, and the organic layer was separated. The organic layer was dried over anhydrous magnesium sulfate. The organic layer was concentrated under reduced pressure. The residue was purified by silica gel column chromatography to obtain the title compound (103 mg).

ESI-MS; m/z 466 [M$^+$+H].

Preparation Example 56
Synthesis of tert-butyl(−)-[(4aS*,8aR*)-8a-(5-amino-2-fluorophenyl)-4,4a,7,8,8a-tetrahydro-4H,5H-6-oxa-3-thia-1-azanaphthalen-2-yl]carbamate
[Formula 78]
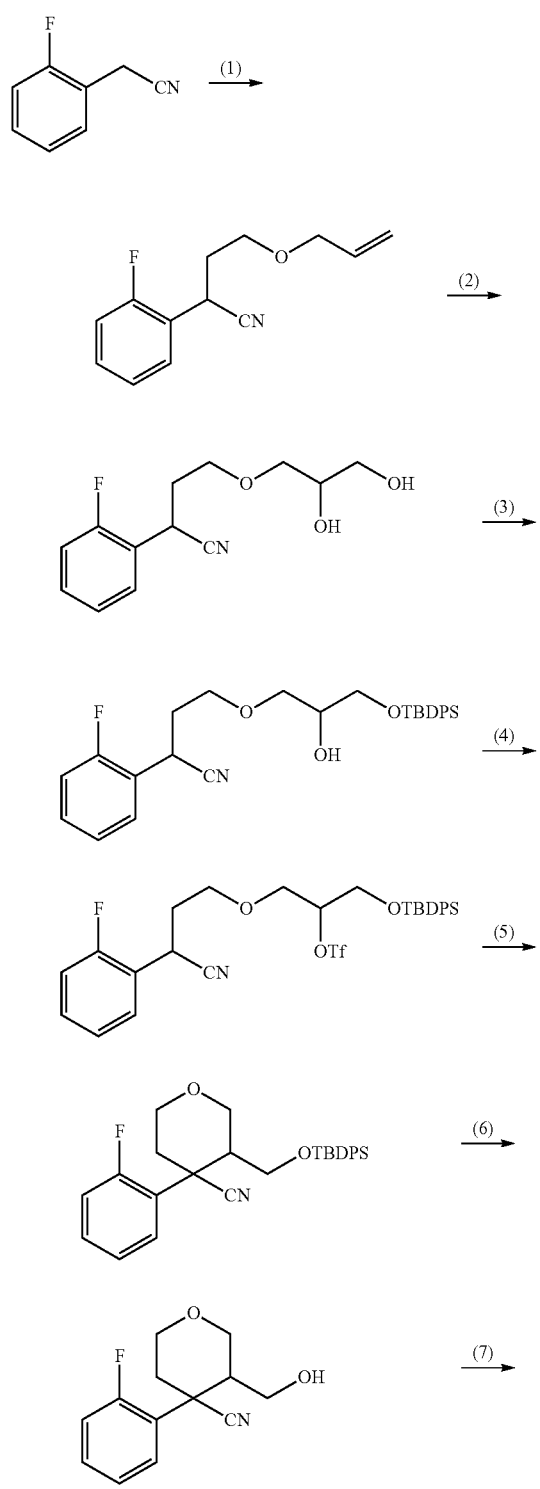
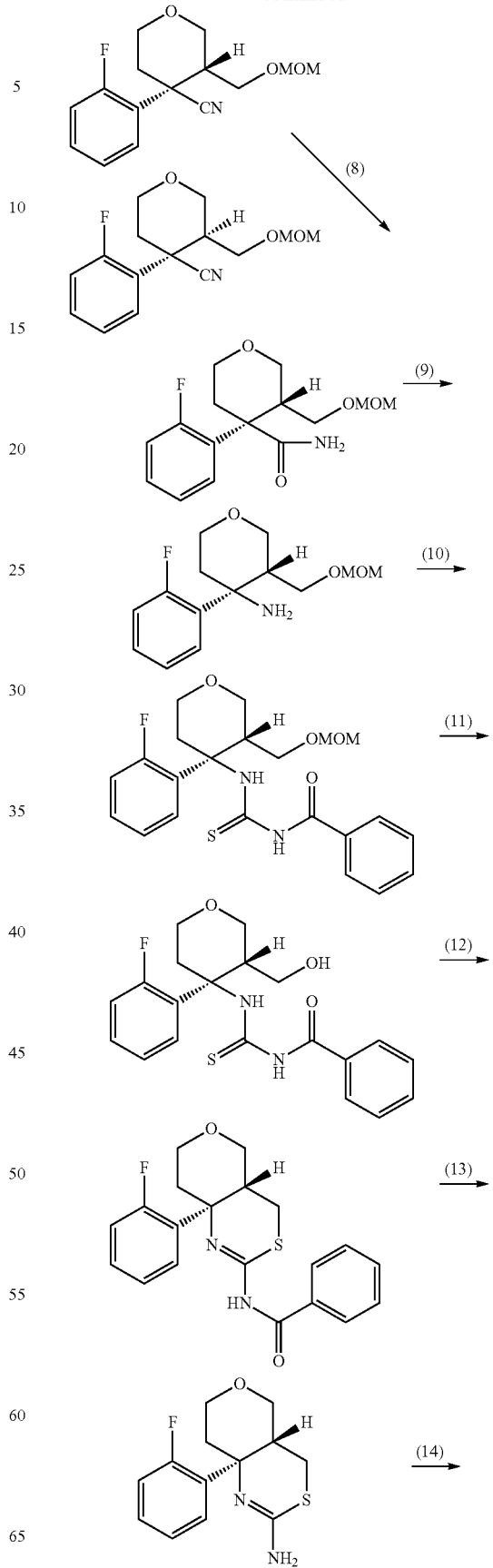

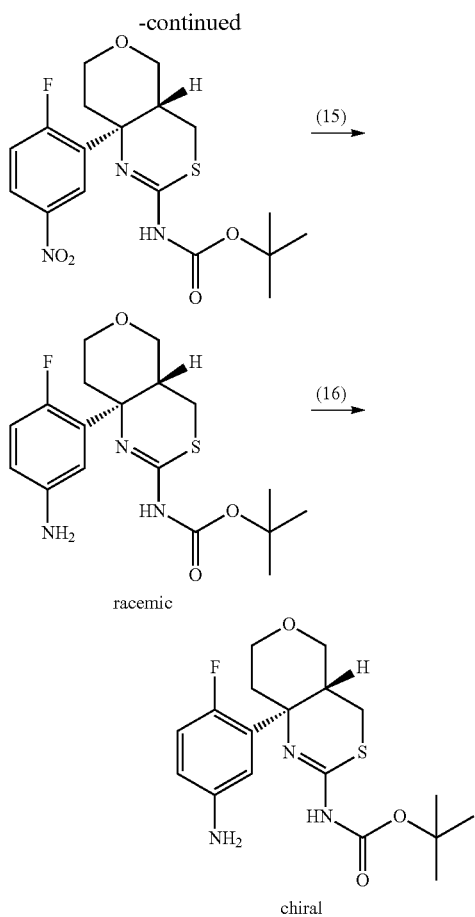

racemic chiral (1) Synthesis of 4-allyloxy-2-(2-fluorophenyl)butyronitrile

Piotassium tert-butoxide (9.93 g) was added to a solution of 2-fluorophenylacetonitrile (10 g), toluene-4-sulfonic acid 2-allyloxyethyl ester (19 g) and 18-crown-6 (3.91 g) in tetrahydrofuran (400 mL) under ice-cooling. The reaction solution was stirred at the same temperature for 10 minutes. The reaction solution was warmed to room temperature and further stirred for four hours. Aqueous ammonium chloride and ethyl acetate were added to the reaction solution, and the organic layer was separated. The organic layer was washed with saturated aqueous sodium chloride. The organic layer was dried over anhydrous magnesium sulfate. The organic layer was concentrated under reduced pressure. The residue was purified by silica gel column chromatography to obtain the title compound (10.9 g).

$^1$H-NMR (400 MHz, CDCl$_3$) δ (ppm): 2.18 (q, J=6.4 Hz, 2H), 3.46-3.52 (m, 1H), 3.60-3.66 (m, 1H), 3.99 (d, J=6.4 Hz, 2H), 4.35 (t, J=7.2 Hz, 1H), 5.21-5.87 (m, 2H), 5.86-5.96 (m, 1H), 7.07-7.12 (m, 1H), 7.16-7.20 (m, 1H), 7.30-7.35 (m, 1H), 7.42-7.47 (m, 1H).

(2) Synthesis of 4-(2,3-dihydroxy-propoxy)-2-(2-fluorophenyl)-butyronitrile

Osmium tetroxide (2.5 wt % solution in tert-butyl alcohol, 15.6 mL) was added to a solution of the compound obtained in Preparation Example 56-(1) (10.9 g) and 4-methylmorpholine-4-oxide (8.75 g) in acetone/water (2/1, 390 mL) under ice-cooling. The reaction solution was warmed to room temperature and stirred for 15 hours. Sodium bisulfite (5.18 g) was added to the reaction solution, and the mixture was stirred at the same temperature for 20 minutes. Ethyl acetate and saturated aqueous sodium chloride were added to the reaction solution, and the organic layer was separated. The organic layer was dried over anhydrous magnesium sulfate. The organic layer was concentrated under reduced pressure. The residue was purified by silica gel column chromatography to obtain the title compound (10.5 g).

$^1$H-NMR (400 MHz, CDCl$_3$) δ (ppm): 1.99-2.02 (m, 1H), 2.17-2.22 (m, 2H), 2.53-2.57 (m, 1H), 3.50-3.59 (m, 3H), 3.61-3.76 (m, 3H), 3.87-3.91 (m, 1H), 4.32 (t, J=6.4 Hz, 1H), 7.08-7.13 (m, 1H), 7.18-7.23 (m, 1H), 7.32-7.38 (m, 1H), 7.45-7.50 (m, 1H).

(3) Synthesis of 4-[3-(tert-butyldiphenylsilanyloxy)-2-hydroxypropoxy]-2-(2-fluorophenyl)butyronitrile Imidazole (7.05 g) and tert-butyldiphenylchlorosilane (12.3 mL) are added to a solution of the compound obtained in Preparation Example 56-(2) (10.5 g) in DMF (125 mL) under ice-cooling. The reaction solution was warmed to room temperature and stirred at room temperature for 18 hours. Saturated aqueous sodium chloride and ethyl acetate were added to the reaction solution, and the organic layer was separated. The organic layer was washed with saturated aqueous sodium chloride again. The organic layer was dried over anhydrous magnesium sulfate, and the organic layer was concentrated under reduced pressure. The residue was purified by silica gel column chromatography to obtain the title compound (16.4 g).

$^1$H-NMR (400 MHz, CDCl$_3$) δ (ppm): 1.07 (s, 9H), 2.11-2.18 (m, 2H), 2.47-2.49 (m, 1H), 3.45-3.55 (m, 3H), 3.59-3.64 (m, 1H), 3.69-3.71 (m, 2H), 3.88-3.91 (m, 1H), 4.21-4.26 (m, 1H), 7.05-7.10 (m, 1H), 7.14-7.19 (m, 1H), 7.29-7.35 (m, 1H), 7.36-7.45 (m, 7H), 7.64-7.68 (m, 4H).

(4) Synthesis of 1-(tert-butyl-diphenyl-silanyloxymethyl)-2-[3-cyano-3-(2-fluorophenyl)-propoxy]ethyl trifluoromethanesulfonate A solution of the compound obtained in Preparation Example 56-(3) (16.4 g) and N,N-diisodiisopropylethylamine (17.4 mL) in dichloromethane (330 mL) was cooled to −78° C. under a nitrogen atmosphere. Trifluoromethanesulfonic anhydride (8.28 mL) was added dropwise to the reaction solution at the same temperature. The reaction solution was stirred for six hours while gradually warming to room temperature. Aqueous ammonium chloride was added to the reaction solution, and the organic layer was separated. The organic layer was washed with saturated aqueous sodium chloride and dried over anhydrous magnesium sulfate. The organic layer was concentrated and the residue was purified by column chromatography to obtain the title compound (15.1 g).

$^1$H-NMR (400 MHz, CDCl$_3$) δ (ppm): 1.07 (s, 9H), 2.12-2.17 (m, 2H), 3.48-3.53 (m, 1H), 3.62-3.80 (m, 3H), 3.85-3.87 (m, 2H), 4.23-4.28 (m, 1H), 5.01-5.04 (m, 1H), 7.06-7.11 (m, 1H), 7.15-7.19 (m, 1H), 7.29-7.34 (m, 1H), 7.37-7.48 (m, 6H), 7.52-7.67 (m, 4H), 7.67-7.73 (m, 1H).

(5) Synthesis of 3-(tert-butyldiphenylsilanyloxymethyl)-4-(2-fluorophenyl)-tetrahydropyran-4-carbonitrile Potassium tert-butoxide (2.98 g) was added to a solution of the compound obtained in Preparation Example 56-(4) (15.1 g) and 18-crown-6 (1.28 g) in tetrahydrofuran (250 mL) under ice-cooling. The reaction solution was stirred at the same temperature for one hour. Aqueous ammonium chloride and ethyl acetate were added to the reaction solution, and the organic layer was separated. The organic layer was washed with saturated aqueous sodium chloride and dried over anhydrous magnesium sulfate. The organic layer was concentrated under reduced pressure and the residue was purified by silica gel column chromatography to obtain the title compound (11.1 g).
ESI-MS; m/z 496 [M$^+$+Na].

(6) Synthesis of 4-(2-fluorophenyl)-3-hydroxymethyl-tetrahydropyran-4-carbonitrile Tetrabutylammonium fluoride (1 M solution in tetrahydrofuran, 46.9 mL) was added dropwise to a solution of the compound obtained in Preparation Example 56-(5) (11.1 g) in tetrahydrofuran (240 mL). The reaction solution was stirred at room temperature for 12 hours. The reaction solution was concentrated and ethyl acetate and saturated aqueous sodium chloride were added to the residue. The organic layer was separated and dried over anhydrous magnesium sulfate. The organic layer was concentrated under reduced pressure and the residue was purified by silica gel column chromatography to obtain the title compound (4.0 g).
ESI-MS; m/z 236 [M$^+$+H].

(7) Synthesis of (±)-(3R*,4S*)-4-(2-fluorophenyl)-3-methoxymethoxymethyl-tetrahydropyran-4-carbonitrile N,N-Diisopropylethylamine (14.8 mL) and chloromethyl methyl ether (3.87 mL) were added to the compound obtained in Preparation Example 56-(6) (4 g) in dichloromethane (100 mL). The reaction solution was stirred at room temperature for 16 hours. Water and chloroform were added to the reaction solution, and the organic layer was separated. The organic layer was dried over anhydrous magnesium sulfate. The organic layer was concentrated and the residue was purified by silica gel column chromatography to obtain the title compound (1.65 g).
$^1$H-NMR (400 MHz, CDCl$_3$) δ (ppm): 2.00 (d, J=11.6 Hz, 1H), 2.38-2.46 (m, 1H), 2, 72 (d, J=8.8 Hz, 1H), 2.93 (dd, J=4.0, 9.6 Hz, 1H), 3.19 (s, 3H), 3.62 (t, J=9.6 Hz, 1H), 3.99-4.06 (m, 2H), 4.17 (d, J=12.0 Hz, 2H), 4.37-4.43 (m, 2H), 7.14-7.21 (m, 3H), 7.36-7.41 (m, 1H).

(8) Synthesis of (±)-(3R*,4S*)-4-(2-fluorophenyl)-3-methoxymethoxymethyl-tetrahydropyran-4-carboxamide Potassium hydroxide (1.33 g) was added to a solution of the compound obtained in Preparation Example 56-(7) (1.65 g) in tert-butyl alcohol (35 mL). The reaction solution was heated under reflux for six hours. The reaction solution was cooled to room temperature. Ethyl acetate and saturated aqueous sodium chloride were added to the reaction solution, and the organic layer was separated. The organic layer was washed with saturated aqueous sodium chloride again. The organic layer was dried over anhydrous magnesium sulfate and concentrated under reduced pressure. The residue was purified by silica gel column chromatography to obtain the title compound (1.37 g).
$^1$H-NMR (400 MHz, CDCl$_3$) δ (ppm): 2.18-2.32 (m, 2H), 2.86-2.90 (m, 1H), 3.02 (dd, J=3.2, 9.6 Hz, 1H), 3.23 (s, 3H), 3.58-3.72 (m, 2H), 3.99-4.15 (m, 3H), 4.44-4.48 (m, 2H), 5.30-5.55 (m, 2H), 7.04-7.10 (m, 1H), 7.16-7.20 (m, 1H), 7.29-7.35 (m, 2H).

(9) Synthesis of (±)-(3R*,4S*)-4-(2-fluorophenyl)-3-methoxymethoxymethyl-tetrahydropyran-4-ylamine

[Bis(trifluoroacetoxy)iodo]benzene (2.36 g) was added to a solution of the compound obtained in Preparation Example 56-(8) (1.37 g) in acetonitrile/water (35 mL/15 mL). The reaction solution was stirred at room temperature for 18 hours. The reaction solution was concentrated under reduced pressure. 5 N sodium hydroxide and chloroform were added to the residue, and the organic layer was separated. The organic layer was dried over anhydrous magnesium sulfate. The organic layer was concentrated under reduced pressure. The residue was purified by silica gel column chromatography to obtain the title compound (619 mg). ESI-MS; m/z 270 [M$^+$+H].

(10) Synthesis of (±)-1-benzoyl-3-[(3R*,4S*)-4-(2-fluorophenyl)-3-methoxymethoxymethyl-tetrahydropyran-4-yl]thiourea Benzoyl isocyanate (412 mg) was added to a solution of the compound obtained in Preparation Example 56-(9) (619 mg) in dichloromethane (15 mL). The reaction solution was stirred at room temperature for 15 hours. The reaction solution was concentrated and the residue was purified by NH-silica gel column chromatography to obtain the title compound (956 mg).
$^1$H-NMR (400 MHz, CDCl$_3$) δ (ppm): 2.24-2.33 (m, 1H), 2.58 (d, J=9.2 Hz, 1H), 2.99-3.03 (m, 1H), 3.21 (s, 3H), 3.55 (dd, J=1.6, 14.0 Hz, 1H), 3.71-3.84 (m, 2H), 3.98-4.08 (m, 2H), 4.19 (d, J=12.4 Hz, 1H), 4.41-4.45 (m, 2H), 6.99-7.06 (m, 1H), 7.14-7.18 (m, 1H), 7.26-7.38 (m, 2H), 7.52 (t, J=7.2 Hz, 2H), 7.63 (tt, J=2.0, 7.2 Hz, 1H), 7.84-7.87 (m, 2H), 8.76 (s, 1H), 11.7 (s, 1H).

(11) Synthesis of (±)-1-benzoyl-3-[(3S*,4S*)-4-(2-fluorophenyl)-3-hydroxymethyl-tetrahydropyran-4-yl]thiourea Concentrated hydrochloric acid (1 mL) was added to a solution of the compound obtained in Preparation Example 56-(10) (956 mg) in methanol (20 mL). The reaction solution was heated under reflux for four hours. The reaction solution was concentrated under reduced pressure. Ethyl acetate and aqueous sodium bicarbonate were added to the residue, and the organic layer was separated. The organic layer was washed with saturated aqueous sodium chloride. The organic layer was dried over anhydrous magnesium sulfate. The organic layer was concentrated under reduced pressure. The residue was purified by silica gel column chromatography to obtain the title compound (465 mg).
ESI-MS; m/z 411 [M$^+$+Na].

(12)-(15) Synthesis of tert-butyl(±)-[(4aR*,8aS*)-8a-(5-amino-2-fluorophenyl)-4a,7,8,8a-tetrahydro-4H, 5H-6-oxa-3-thia-1-azanaphthalen-2-yl]carbamate The title compound (58 mg) was obtained from the compound obtained in Preparation Example 56-(11) (465 mg) according to Preparation Example 9. ESI-MS; m/z 382 [M$^+$+H].

197

(16) Synthesis of tert-butyl(−)-[(4aR*,8aS*)-8a-(5-amino-2-fluorophenyl)-4a,7,8,8a-tetrahydro-4H,5H-6-oxa-3-thia-1-azanaphthalen-2-yl]carbamate The compound obtained in Preparation Example 56-(15) (19 mg) was optically resolved by CHIRALPAK™ AD-H manufactured by Daicel Chemical Industries, Ltd. (2 cm×25 cm, mobile phase: hexane:ethanol=7:3, flow rate: 10 mL/min), and the component having a retention time of 15.3 to 18.3 minutes was collected. This operation was repeated to obtain the title compound (23 mg; >99% ee) from 58 mg of the racemate. ESI-MS; m/z 382 [M$^+$+H].

Preparation Example 57

Synthesis of tert-butyl(−)-[(4aR*,7S*,8aS*)-8a-(5-amino-2-fluorophenyl)-7-methoxy-4a,5,6,7,8,8a-hydro-4H-benzo[d][1,3]thiazin-2-yl]carbamate

[Formula 79]

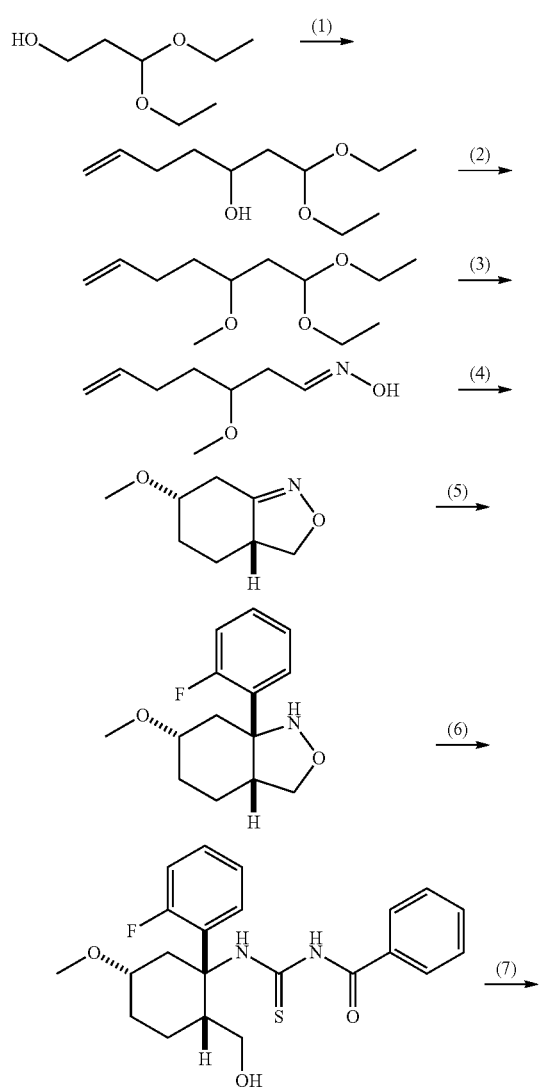

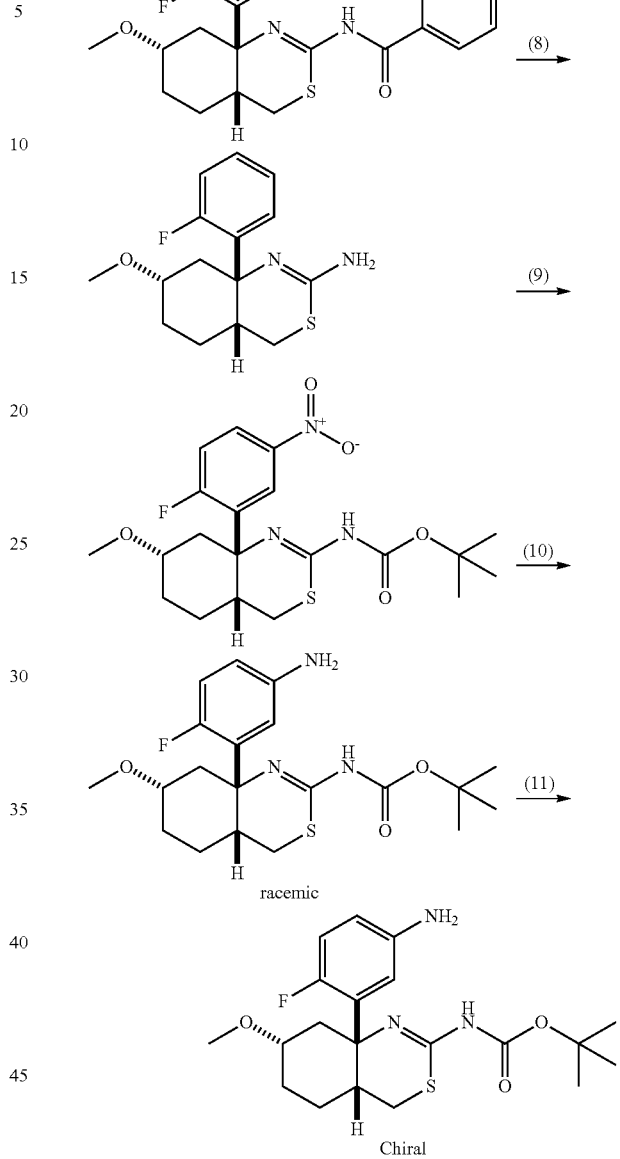

198

(1) Synthesis of 1,1-diethoxyhept-6-en-3-ol

A solution of oxalyl chloride (4.07 mL, specific gravity: 1.455 g/cm$^3$) in dichloromethane (200 mL) was cooled to −78° C. under a nitrogen atmosphere. Then, a solution of DMSO (6.62 mL, specific gravity: 1.101 g/cm$^3$) in dichloromethane (50 mL) was slowly added so that the internal temperature did not exceed −60° C. After stirring for 15 minutes, a solution of 3,3-diethoxy-1-propanol in dichloromethane (50 mL) was slowly added so that the internal temperature did not exceed −65° C. After stirring further for one hour and 45 minutes, TEA (25.9 mL) was slowly added. The mixture was further stirred for 30 minutes after the addition. After warming to room temperature, a saturated ammonium chloride solution was added, followed by further stirring. The aqueous layer was separated and then the organic layer was washed with a saturated ammonium chloride solution. The resulting organic layer was dried over anhydrous magnesium sulfate. The drying agent was removed by filtration and the filtrate was concentrated under reduced pressure. The resulting residue was suspended in diethyl ether, and the solid was removed by filtration. The resulting filtrate was concentrated under reduced pressure. THF (60 mL) was added to the resulting residue, and the mixture was sufficiently cooled in an ice bath under a nitrogen atmosphere. A solution of 3-butenylmagnesium bromide in THF (0.5 M, 100 mL) was added thereto so that the internal temperature did not exceed 10° C. After completion of the addition, the mixture was stirred for 13 hours and 30 minutes while gradually warming to room temperature. Water was slowly added to the reaction system, followed by stirring for a while. Then, ethyl acetate and a saturated ammonium chloride solution were added, followed by further stirring. The aqueous layer was separated and then the resulting organic layer was sequentially washed with a saturated ammonium chloride solution, water and brine. The resulting organic layer was dried over anhydrous magnesium sulfate and concentrated under reduced pressure. Then, the residue was purified by NH-silica gel column chromatography to obtain the title compound (3.71 g).

$^1$H-NMR (400 MHz, CDCl$_3$) δ (ppm): 1.19-1.25 (m, 6H), 1.50-1.64 (m, 2H), 1.77-1.79 (m, 2H), 2.10-2.24 (m, 2H), 3.18 (s, 1H), 3.49-3.58 (m, 2H), 3.62-3.78 (m, 2H), 3.83 (bs, 1H), 4.69-4.71 (m, 1H), 4.95-5.06 (m, 2H), 5.79-5.89 (m, 1H)

(2) Synthesis of 7,7-diethoxy-5-methoxyhept-1-ene

DMF (30 mL) was added to 1,1-diethoxy-hept-6-en-3-ol obtained in Preparation Example 57-(1) (3.07 g), and the mixture was cooled in an ice bath under a nitrogen atmosphere. Then, sodium hydride (60% 699 mg) was added, followed by stirring for 10 minutes. Methyl iodide (1.8 mL, specific gravity: 2.28 g/cm$^3$) was added, followed by stirring for one hour and 50 minutes. Then, the mixture was warmed to room temperature and further stirred for one hour and 30 minutes. Sodium hydride (600, 300 mg) and methyl iodide (0.9 mL, specific gravity: 2.28 g/cm$^3$) were further added, followed by stirring for two hours and 30 minutes. Then, water and a saturated ammonium chloride solution were slowly added, followed by stirring for a while. After extraction with ethyl acetate, the organic layer was sequentially washed with a saturated ammonium chloride solution, water and brine. The resulting organic layer was dried over anhydrous magnesium sulfate. The drying agent was removed by filtration and then the filtrate was concentrated under reduced pressure. The resulting residue was purified by silica gel column chromatography to obtain the title compound (2.98 g).

$^1$H-NMR (400 MHz, CDCl$_3$) δ (ppm): 1.19-1.23 (m, 6H), 1.56-1.63 (m, 2H), 1.70-1.84 (m, 2H), 2.08-2.14 (m, 2H), 3.31-3.37 (m, 4H), 3.46-3.56 (m, 2H), 3.62-3.71 (m, 2H), 4.66 (dd, J=4.4, 8.0 Hz, 1H), 4.94-5.06 (m, 2H), 5.76-5.88 (m, 1H)

(3) Synthesis of 3-methoxyhept-6-enal oxime

A 80% formic acid solution (30 mL) was added to 7,7-diethoxy-5-methoxyhept-1-ene obtained in Preparation Example 57-(2) (2.98 g), and the mixture was stirred at room temperature for 10 minutes. After further adding a 75% ethanol solution (64 mL), sodium acetate (3.75 g) and hydroxylamine hydrochloride (1.92 g) were added, followed by further stirring for one hour and 20 minutes. The solvent was concentrated to about 40 mL under reduced pressure, followed by extraction with ethyl acetate. The resulting organic layer was sequentially washed with a saturated sodium bicarbonate solution (three times), water and brine. The resulting organic layer was dried over anhydrous magnesium sulfate. The drying agent was removed by filtration and then the filtrate was concentrated under reduced pressure. The resulting residue was purified by silica gel column chromatography to obtain the title compound (1.95 g).

$^1$H-NMR (400 MHz, CDCl$_3$) δ (ppm): 1.51-1.74 (m, 2H), 2.08-2.16 (m, 2H), 2.35-2.68 (m, 2H), 3.36 (s, 3H), 3.38-3.46 (m, 1H), 4.96-5.08 (m, 2H), 5.76-5.86 (m, 1H), 6.84-6.86 and 7.47-7.49 (m, total 1H), 7.56 and 7.97 (br, total 1H)

(4) Synthesis of (±)-(3aR*,6S*)-6-methoxy-3,3a,4,5,6,7-hexahydrobenz[c]isoxazole A sodium hypochlorite solution (5%, 18.5 mL) was added to a solution of 3-methoxyhept-6-enal oxime obtained in Preparation Example 57-(3) (1.95 g) in dichloromethane, and the mixture was stirred at room temperature for one hour and 10 minutes. The excess of sodium hypochlorite was decomposed with sodium thiosulfate, followed by extraction with chloroform three times. The resulting organic layers were dried over anhydrous magnesium sulfate. The drying agent was removed by filtration and then the filtrate was concentrated under reduced pressure. The resulting residue was purified by silica gel column chromatography to obtain the title compound (796 mg).

$^1$H-NMR (400 MHz, CDCl$_3$) δ (ppm): 1.54 (ddt, J=2.0, 3.6, 14.0, 1H), 1.68-1.79 (m, 1H), 1.90-1.97 (m, 1H), 2.05-2.13 (m, 1H), 2.20 (ddd, J=1.6, 7.6, 11.2 Hz, 1H), 3.04 (td, J=2.4, 14.8 Hz, 1H), 3.13-3.21 (m, 1H), 3.32 (s, 3H), 3.78 (t, J=2.4 Hz, 1H), 3.79 (dd, J=8.0, 11.2 Hz, 1H), 4.53 (dd, J=7.6, 10.0 Hz, 1H)

(5) Synthesis of (±)-(3aR*,6S*,7aS*)-7a-(2-fluorophenyl)-6-methoxyoctahydrobenz[c]isoxazole THF (3 mL) and toluene (20 mL) were added to 2-bromofluorobenzene (1.23 mL, specific gravity: 1.614 g/cm$^3$) under a nitrogen atmosphere, and the mixture was cooled to −78° C. A solution of n-butyllithium in hexane (3.9 mL, 2.63 M) was slowly added so that the internal temperature was maintained at −60° C. or less. After completion of the addition, the mixture was stirred for 10 minutes. After slowly adding a boron trifluoride-diethyl ether complex (1.29 mL), a solution of (±)-(3aR*,6S*)-6-methoxy-3,3a,4,5,6,7-hexahydrobenz[c]isoxazole obtained in Preparation Example 57-(4) (796 mg) in toluene (10 mL) was slowly added so that the internal temperature was maintained at −60° C. or less. After completion of the addition, the mixture was stirred for one hour and 50 minutes. A saturated ammonium chloride solution was added, followed by warming to room temperature. Ethyl acetate and water were added, followed by further stirring. The aqueous layer was separated and then the organic layer was sequentially washed with a saturated ammonium chloride solution, water and brine. The resulting organic layer was dried over anhydrous magnesium sulfate. The drying agent was removed by filtration and then the filtrate was concentrated under reduced pressure. The resulting residue was purified by silica gel column chromatography to obtain the title compound (711 mg).

ESI-MS; m/z 252 [M+H]

(6) Synthesis of (±)-1-benzoyl-3-[(1S*,2R*,5S*)-1-(2-fluorophenyl)-2-hydroxymethyl-5-methoxycyclohexyl]thiourea (±)-(3aR*,6S*,7aS*)-7a-(2-Fluorophenyl)-6-methoxyoctahydrobenz[c]isoxazole obtained in Preparation Example 57-(5) (872 mg) was dissolved in acetic acid (20 mL). Then, zinc powder (2.27 g) was added and the mixture was stirred at room temperature for 14 hours and 10 minutes. The solid was removed by filtration through celite, and then the celite was washed with ethyl acetate. The resulting filtrate was concentrated under reduced pressure. The residue was dissolved in ethyl acetate. Then, a saturated sodium bicarbonate solution was added, followed by vigorous stirring. The organic layer was separated and then the aqueous layer was extracted again with ethyl acetate twice. The combined organic layers were dried over anhydrous magnesium sulfate. The solid was removed by filtration and the filtrate was concentrated under reduced pressure. The resulting residue was dissolved in dichloromethane (7 mL). Then, benzoyl isothiocyanate (524 µL, specific gravity: 1.21 g/cm$^3$) was added and the mixture was stirred at room temperature for 16 hours and 30 minutes. The reaction solution was concentrated under reduced pressure and then purified by silica gel column chromatography to obtain the title compound (453 mg).

$^1$H-NMR (400 MHz, CDCl$_3$) δ (ppm): 1.67-1.76 (m, 2H), 2.05 (br, 3H), 2.26 (br, 2H), 2.63 (br, 1H), 3.39 (s, 3H), 3.57 (br, 1H), 3.67 (br, 1H), 3.78 (br, 1H), 6.99-7.04 (m, 1H), 7.13 (s, 1H), 7.51-7.62 (m, 4H), 7.87-7.88 (m, 2H), 8.83 (s, 1H), 11.60 (s, 1H)

(7) Synthesis of (±)-N-[(4aR*,7S*,8aS*)-8a-(2-fluorophenyl)-7-methoxy-4a,5,6,7,8,8a-hexahydro-4H-benzo[d][1,3]thiazin-2-yl]benzamide Dichloromethane (20 mL) and pyridine (264 µL, specific gravity: 0.978 g/cm$^3$) were added to (±)-1-benzoyl-3-[(1S*,2R*,5S*)-1-(2-fluorophenyl)-2-hydroxymethyl-5-methoxycyclohexyl]thiourea obtained in Preparation Example 57-(6) (453 mg) according to the method of Preparation Example 18-(5). The mixture was cooled to −78° C. under a nitrogen atmosphere and stirred for 15 minutes. Trifluoromethanesulfonic anhydride (358 µL, specific gravity: 1.72 g/cm$^3$) was slowly added to the reaction solution. After completion of the addition, the mixture was stirred for 15 minutes and then further stirred for one hour while warming to 0° C. After adding ethyl acetate, a saturated sodium bicarbonate solution was added, followed by extraction with ethyl acetate. The organic layer was sequentially washed with water and brine and dried over anhydrous magnesium sulfate. The solid was removed by filtration. After concentration under reduced pressure, the residue was purified by silica gel column chromatography to obtain the title compound (268 mg).

ESI-MS; m/z 399 [M+H]

$^1$H-NMR (400 MHz, CDCl$_3$) δ (ppm): 1.50-1.52 (m, 1H), 1.72 (tt, J=3.2, 13.6 Hz, 1H), 2.18-2.30 (m, 3H), 2.43 (dd, J=3.6, 15.2 Hz, 1H), 2.61 (dd, J=2.8, 12.8 Hz, 1H), 2.90 (dd, J=4.0, 12.8 Hz, 1H), 2.95-3.01 (m, 1H), 3.35 (s, 3H), 3.63 (t, J=2.8 Hz, 1H), 7.07 (ddd, J=1.2, 8.0, 12.8 Hz, 1H), 7.15 (dt, J=1.2, 8.0 Hz, 1H), 7.28-7.33 (m, 1H), 7.38-7.43 (m, 3H), 7.45-7.49 (m, 1H), 8.26 (dd, J=1.6, 8.4 Hz, 2H)

(8) Synthesis of (±)-(4aR*,7S*,8aS*)-8a-(2-fluorophenyl)-7-methoxy-4a,5,6,7,8,8a-hexahydro-4H-benzo[d][1,3]thiazin-2-ylamine (±)-N-[(4aR*,7S*,8aS*)-8a-(2-Fluorophenyl)-7-methoxy-4a,5,6,7,8,8a-hexahydro-4H-benzo[d][1,3]thiazin-2-yl]benzamide obtained in Preparation Example 57-(7) (268 mg) was dissolved in methanol (8 mL). Then, DBU (202 µL, specific gravity: 1.018 g/cm$^3$) was added, and the mixture was stirred with heating under reflux for four hours and 15 minutes. Then, the reaction solution was stirred at 64° C. for 13 hours and 30 minutes. Thereafter, the reaction solution was stirred with heating under reflux for nine hours and 30 minutes. The reaction solution was left to cool to room temperature and then concentrated under reduced pressure. The residue was purified by NH-silica gel column chromatography to obtain the title compound (150 mg).

$^1$H-NMR (400 MHz, CDCl$_3$) δ (ppm): 1.37-1.40 (m, 1H), 1.66-1.73 (m, 1H), 2.05-2.19 (m, 3H), 2.35-2.39 (m, 1H), 2.58-2.60 (m, 1H), 2.72-2.75 (m, 1H), 2.81-2.90 (m, 1H), 3.34 (s, 3H), 3.61 (br, 1H), 6.98-7.03 (m, 1H), 7.09-7.12 (m, 1H), 7.20-7.23 (m, 1H), 7.38 (br, 1H)

(9) Synthesis of tert-butyl(±)-[(4aR*,7S*,8aS*)-8a-(2-fluoro-5-nitrophenyl)-7-methoxy-4a,5,6,7,8,8a-hexahydro-4H-benzo[d][1,3]thiazin-2-yl]carbamate TFA (1 mL) and concentrated sulfuric acid (0.5 mL) were added to (±)-(4aR*,7S*,8aS*)-8a-(2-fluorophenyl)-7-methoxy-4a,5,6,7,8,8a-hexahydro-4H-benzo[d][1,3]thiazin-2-ylamine obtained in Preparation Example 57-(8) (150 mg). The mixture was sufficiently cooled in an ice bath and then fuming nitric acid (27.3 µL) was slowly added. After completion of the addition, the mixture was stirred for 15 minutes. The reaction solution was diluted with dichloromethane and then slowly poured into crushed ice. A 5 N sodium hydroxide solution was added until the reaction solution was made alkaline, followed by extraction with dichloromethane three times. The resulting organic layers were dried over anhydrous magnesium sulfate, and the solid was removed by filtration. The filtrate was concentrated under reduced pressure. Then, THF (2.5 mL), water (2.5 mL) and di-tert-butyl dicarbonate (170 mg) were added to the residue at room temperature, and the mixture was stirred at room temperature for two hours. Ethyl acetate and water were added and then the aqueous layer was separated. The organic layer was sequentially washed with a saturated ammonium chloride solution, water and brine. The resulting organic layer was dried over anhydrous magnesium sulfate, and the solid was removed by filtration. The filtrate was concentrated under reduced pressure and then purified by silica gel column chromatography to obtain the title compound (138 mg).

ESI-MS; m/z 440 [M+H]

(10) Synthesis of tert-butyl(±)-[(4aR*,7S*,8aS*)-8a-(5-amino-2-fluorophenyl)-7-methoxy-4a,5,6,7,8,8a-hexahydro-4H-benzo[d][1,3]thiazin-2-yl]carbamate Ethanol (5 mL), a saturated ammonium chloride solution (0.5 mL) and iron powder (175 mg) were added to tert-butyl (±)-[(4aR*,7S*,8aS*)-8a-(2-fluoro-5-nitrophenyl)-7-methoxy-4a,5,6,7,8,8a-hexahydro-4H-benzo[d][1,3]thiazin-2-yl]carbamate obtained in Preparation Example 57-(9) (138 mg), and the mixture was stirred with heating under reflux for 30 minutes. The reaction solution was cooled to room temperature, and then the solid was removed by filtration through celite. The filtrate was concentrated under reduced pressure. Then, the residue was suspended in dichloromethane, and the solid was removed by filtration. The filtrate was concentrated under reduced pressure and then purified by silica gel column chromatography to obtain the title compound (98 mg).

$^1$H-NMR (400 MHz, CDCl$_3$) δ (ppm): 1.42-1.49 (m, 1H), 1.53 (s, 9H), 1.66-1.70 (m, 1H), 2.06-2.10 (m, 1H), 2.14-2.19

(m, 2H), 2.38 (dd, J=3.6, 15.2 Hz, 1H), 2.49-2.54 (m, 1H), 2.84-2.90 (m, 2H), 3.31 (s, 3H), 3.58-3.60 (m, 1H), 3.66 (br, 2H), 6.52-6.56 (m, 1H), 6.62 (dd, J=2.8, 6.8 Hz, 1H), 6.84 (dd, J=8.4, 12.4 Hz, 1H)

(11) Synthesis of tert-butyl(−)-[(4aR*,7S*,8aS*)-8a-(5-amino-2-fluorophenyl)-7-methoxy-4a,5,6,7,8,8a-hexahydro-4H-benzo[d][1,3]thiazin-2-yl]carbamate tert-Butyl(±)-[(4aR*,7S*,8aS*)-8a-(5-amino-2-fluorophenyl)-7-methoxy-4a,5,6,7,8,8a-hexahydro-4H-benzo[d][1,3]thiazin-2-yl]carbamate obtained in Preparation Example 57-(10) was optically resolved by CHIRALPAK™ AD-H manufactured by Daicel Chemical Industries, Ltd. (2 cm×25 cm, mobile phase: hexane:ethanol=85:15, flow rate: 20 mL/min, charged with a solution of about 10 mg in 0.5 mL of ethanol for one cycle). The component having a retention time of 18.1 to 21.2 minutes was collected to obtain the title compound (41 mg, >99% ee, optical rotation (−)).

$^1$H-NMR (400 MHz, CDCl$_3$) δ (ppm): 1.43-1.46 (m, 1H), 1.53 (s, 9H), 1.67-1.70 (m, 1H), 2.06-2.18 (m, 3H), 2.36-2.39 (m, 1H), 2.50-2.53 (m, 1H), 2.86-2.89 (m, 2H), 3.31 (s, 3H), 3.58 (br, 1H), 3.67 (br, 2H), 6.53-6.55 (m, 1H), 6.60-6.62 (m, 1H), 6.81-6.86 (m, 1H)

Preparation Example 58

Synthesis of tert-butyl(−)-[(4aR*,7R*,8aS*)-8a-(5-amino-2-fluorophenyl)-7-methoxy-4a,5,6,7,8,8a-hydro-4H-benzo[d][1,3]thiazin-2-yl]carbamate

[Formula 80]

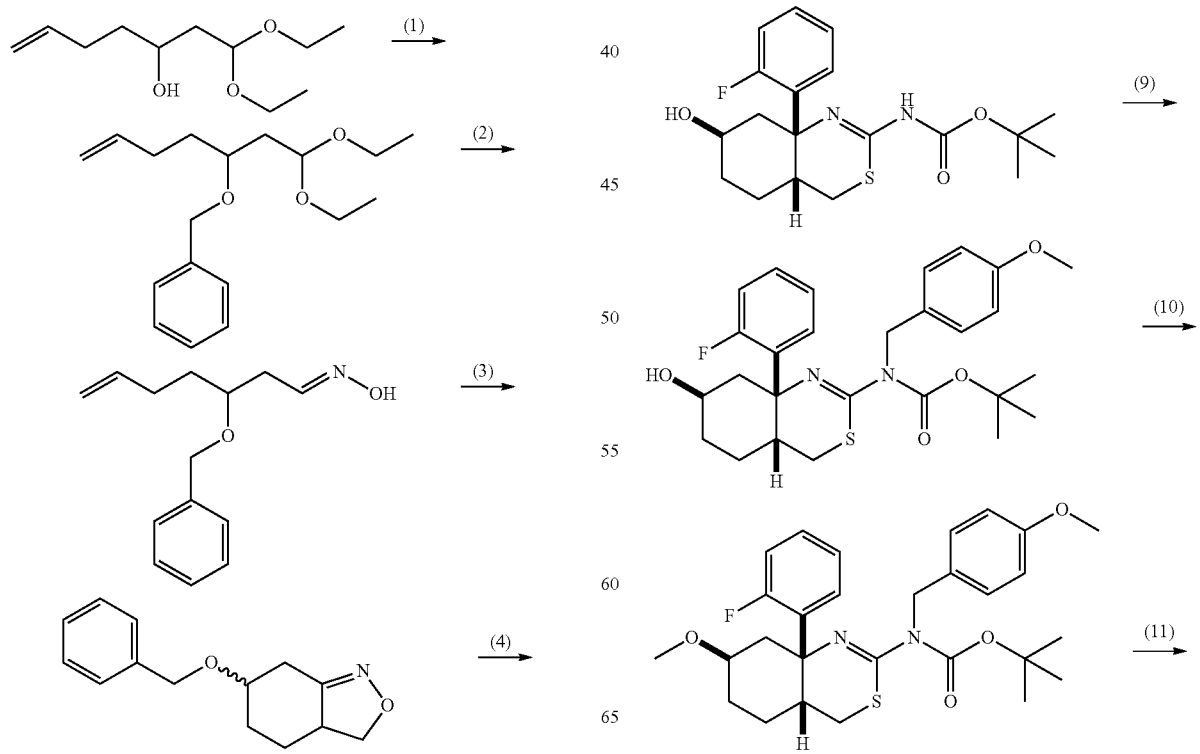

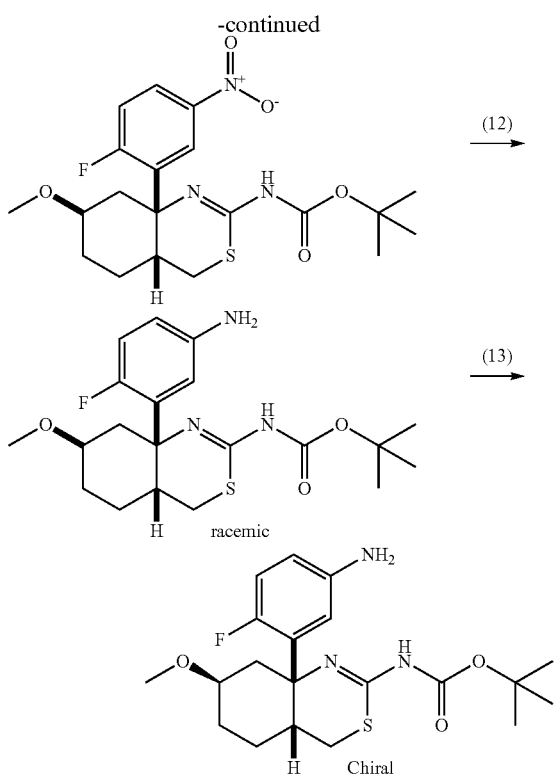

(1) Synthesis of [1-(2,2-diethoxyethyl)pent-4-enyloxymethyl]benzene

DMF (40 mL) and benzyl bromide (2.4 mL, specific gravity: 1.44 g/cm³) were added to 1,1-diethoxyhept-6-en-3-ol obtained in Preparation Example 57-(1) (3.71 g), and the mixture was cooled in an ice bath under a nitrogen atmosphere. Then, sodium hydride (60%, 883 mg) was added, followed by stirring for 60 minutes. Benzyl bromide (1.09 mL) was further added, followed by stirring for one hour. Sodium hydride (60%, 116 mg) was further added, and the mixture was stirred for one hour and 50 minutes while gradually warming to room temperature. Tetrabutylammonium iodide (680 mg) was further added, followed by stirring for one hour and 10 minutes. Water and a saturated ammonium chloride solution were slowly added. After stirring for a while, the aqueous layer was separated. The organic layer was sequentially washed with a saturated ammonium chloride solution, water and brine. The resulting organic layer was dried over anhydrous magnesium sulfate. The drying agent was removed by filtration and then the filtrate was concentrated under reduced pressure. The resulting residue was purified by silica gel column chromatography to obtain the title compound (4.06 g).

¹H-NMR (400 MHz, CDCl₃) δ (ppm): 1.19 (dt, J=4.4, 7.2 Hz, 6H), 1.63-1.70 (m, 2H), 1.76-1.93 (m, 2H), 2.11-2.17 (m, 2H), 3.39-3.54 (m, 2H), 3.56-3.69 (m, 3H), 4.46-4.56 (m, 2H), 4.68 (dd, J=4.0, 7.2 Hz, 1H), 4.95-4.97 (m, 1H), 4.99-5.05 (m, 1H), 5.82 (tdd, J=6.8, 10.0, 16.8 Hz, 1H), 7.25-7.32 (m, 1H), 7.32-7.36 (m, 4H)

(2) Synthesis of 3-benzyloxyhept-6-enal oxime

The title compound (3.53 g) was obtained from [1-(2,2-diethoxyethyl)-pent-4-enyloxymethyl]benzene obtained in Preparation Example 58-(1) (3.71 g) according to the method of Preparation Example 57-(3) without purification by silica gel column chromatography.

¹H-NMR (400 MHz, CDCl₃) δ (ppm): 1.59-1.81 (m, 2H), 2.11-2.23 (m, 2H), 2.42-2.51 (m, 1H), 2.65-2.68 (m, 1H), 3.64 (td, J=6.0, 18.4 Hz, 1H), 4.50-4.58 (m, 2H), 4.95-5.04 (m, 2H), 5.73-5.85 (m, 1H), 6.86-6.89 and 7.48-7.51 (m, total 1H), 7.17 and 7.53 (br, total 1H), 7.29 (br, 1H), 7.34 (s, 4H)

(3) Synthesis of 6-benzyloxy-3,3a,4,5,6,7-hexahydrobenz[c]isoxazole

The title compound (2.91 g) was obtained from 3-benzyloxyhept-6-enal oxime obtained in Preparation Example 58-(2) (3.53 g) according to the method of Preparation Example 57-(4).

ESI-MS; m/z 232 [M+H]

(4) Synthesis of (±)-(3aR*,6R*,7aS*)-6-benzyloxy-7a-(2-fluorophenyl)octahydrobenz[c]isoxazole The title compound (1.69 g) was obtained from 6-benzyloxy-3,3a,4,5,6,7-hexahydrobenz[c]isoxazole obtained in Preparation Example 58-(3) (2.91 g) according to the method of Preparation Example 57-(5).

¹H-NMR (400 MHz, CDCl₃) δ (ppm): 1.38-1.49 (m, 1H), 1.59-1.69 (m, 1H), 1.98-2.05 (m, 1H), 2.12-2.17 (m, 1H), 2.22-2.35 (m, 2H), 2.90-2.96 (m, 1H), 3.50-3.58 (m, 2H), 3.67 (d, J=6.8 Hz, 1H), 4.52 (s, 2H), 5.77 (br, 1H), 7.03 (ddd, J=1.6, 8.0, 12.4 Hz, 1H), 7.13 (dt, J=1.2, 7.6 Hz, 1H), 7.22-7.35 (m, 6H), 7.82 (dt, J=1.6, 8.0 Hz, 1H)

(5) Synthesis of (±)-1-benzoyl-3-[(1S*,2R*,5R*)-5-benzyloxy-1-(2-fluorophenyl)-2-hydroxymethylcyclohexyl]thiourea The title compound (2.26 g) was obtained from (±)-(3aR*,6R*,7aS*)-6-benzyloxy-7a-(2-fluorophenyl)octahydrobenz[c]isoxazole obtained in Preparation Example 58-(4) (1.69 g) according to the method of Preparation Example 57-(6).

¹H-NMR (400 MHz, CDCl₃) δ (ppm): 1.70-1.76 (m, 1H), 1.83-1.87 (m, 1H), 2.14-2.25 (m, 3H), 2.42-2.45 (m, 2H), 3.66 (br, 2H), 3.84 (br, 1H), 4.49-4.64 (m, 2H), 6.94-7.14 (m, 5H), 7.22-7.28 (m, 1H), 7.29-7.32 (m, 2H), 7.40-7.49 (m, 3H), 7.55-7.60 (m, 3H), 8.57 (br, 1H), 11.57 (br, 1H)

(6) Synthesis of (±)-N-[(4aR*,7R*,8aS*)-7-benzyloxy-8a-(2-fluorophenyl)-4a,5,6,7,8,8a-hexahydro-4H-benzo[d][1,3]thiazin-2-yl]benzamide The title compound (1.81 g) was obtained from (±)-1-benzoyl-3-[(1S*,2R*,5R*)-5-benzyloxy-1-(2-fluorophenyl)-2-hydroxymethylcyclohexyl]thiourea obtained in Preparation Example 58-(5) (2.26 g) according to the method of Preparation Example 57-(7).

ESI-MS; m/z 475 [M+H]

¹H-NMR (400 MHz, CDCl₃) δ (ppm): 1.59-1.69 (m, 1H), 1.78-1.85 (m, 1H), 1.97-2.10 (m, 1H), 2.27-2.32 (m, 2H), 2.41-2.47 (m, 1H), 2.62 (dd, J=2.8, 12.8 Hz, 1H), 2.90-3.00 (m, 2H), 3.78-3.86 (m, 1H), 4.58 (s, 2H), 7.07-7.13 (m, 1H), 7.14-7.18 (m, 1H), 7.24-7.28 (m, 1H), 7.30-7.36 (m, 6H), 7.42-7.46 (m, 2H), 7.49-7.54 (m, 1H) 8.24-8.27 (m, 2H)

(7) Synthesis of (±)-(4aR*,7R*,8aS*)-7-benzyloxy-8a-(2-fluorophenyl)-4a,5,6,7,8,8a-hexahydro-4H-benzo[d][1,3]thiazin-2-ylamine (±)-N-[(4aR*,7R*,8aS*)-7-Benzyloxy-8a-(2-fluorophenyl)-4a,5,6,7,8,8a-hexahydro-4H-benzo[d][1,3]thiazin-2-yl]

benzamide obtained in Preparation Example 58-(6) (1.81 g) was dissolved in methanol (60 mL). Then, DBU (1.14 mL, specific gravity: 1.018 g/cm$^3$) was added, and the mixture was stirred with heating under reflux for three hours. Then, the reaction solution was stirred at 64° C. for 14 hours. The reaction solution was left to cool to room temperature and then concentrated under reduced pressure. The residue was purified by NH-silica gel column chromatography to obtain the title compound (1.20 g).

$^1$H-NMR (400 MHz, CDCl$_3$) δ (ppm): 1.53-1.63 (m, 2H), 1.76-1.88 (m, 1H), 2.18-2.22 (m, 1H), 2.26-2.30 (m, 2H), 2.58 (dd, J=2.8, 12.0 Hz, 1H), 2.68-2.74 (m, 1H), 2.85 (dd, J=4.0, 12.0 Hz, 1H), 3.63-3.71 (m, 1H), 4.42 (br, 2H), 4.52-4.59 (m, 2H), 7.00-7.05 (m, 1H), 7.10 (dt, J=1.2, 7.6 Hz, 1H), 7.20-7.27 (m, 3H), 7.29-7.34 (m, 4H)

(8) Synthesis of tert-butyl(±)-[(4aR*,7R*,8aS*)-8a-(2-fluorophenyl)-7-hydroxy-4a,5,6,7,8,8a-hexahydro-4H-benzo[d][1,3]thiazin-2-yl]carbamate (±)-(4aR*,7R*,8aS*)-7-Benzyloxy-8a-(2-fluorophenyl)-4a,5,6,7,8,8a-hexahydro-4H-benzo[d][1,3]thiazin-2-ylamine obtained in Preparation Example 58-(7) (1.2 g) was stirred in concentrated hydrochloric acid (120 mL) with heating under reflux for three hours and 10 minutes. The reaction solution was cooled to room temperature, and the solvent was concentrated under reduced pressure. Then, a 1 N sodium hydroxide solution (16.2 mL), THF (16 mL) and di-tert-butyl dicarbonate (1.06 g) were added to the residue, and the mixture was stirred at room temperature. After one hour and 30 minutes, di-tert-butyl dicarbonate (15 g) was further added, followed by stirring for 12 hours and 30 minutes. Ethyl acetate and water were added to the reaction solution, followed by further stirring. Then, the aqueous layer was separated. The organic layer was sequentially washed with a saturated ammonium chloride solution, water and brine. The resulting organic layer was dried over anhydrous magnesium sulfate, and the solid was removed by filtration. The filtrate was concentrated under reduced pressure and then purified by silica gel column chromatography to obtain the title compound (1.31 g).

$^1$H-NMR (400 MHz, CDCl$_3$) δ (ppm): 1.53 (s, 9H), 1.55-1.65 (m, 1H), 1.71-1.76 (m, 1H), 1.96-2.20 (m, 3H), 2.32-2.38 (m, 1H), 2.52-2.54 (m, 1H), 2.79-2.87 (m, 2H), 3.95-4.00 (m, 1H), 7.08 (ddd, J=1.2, 8.0, 12.8 Hz, 1H), 7.16-7.20 (m, 1H), 7.24-7.27 (m, 1H), 7.28-7.34 (m, 1H)

(9) Synthesis of tert-butyl(±)-[(4aR*,7R*,8aS*)-8a-(2-fluorophenyl)-7-hydroxy-4a,5,6,7,8,8a-hexahydro-4H-benzo[d][1,3]thiazin-2-yl]-(4-methoxybenzyl)carbamate tert-Butyl (±)-[(4aR*,7R*,8aS*)-8a-(2-fluorophenyl)-7-hydroxy-4a,5,6,7,8,8a-hexahydro-4H-benzo[d][1,3]thiazin-2-yl]carbamate obtained in Preparation Example 58-(8) (500 mg) was dissolved in DMF (10 mL), and the mixture was cooled in an ice bath under a nitrogen atmosphere. p-Methoxybenzyl chloride (161 μL, specific gravity: 1.154 g/cm$^3$) and potassium carbonate (247 mg) were added thereto, followed by stirring for one hour. Thereafter, the reaction solution was warmed to room temperature and stirred for 19 hours. Ethyl acetate and water were added to the reaction solution, followed by further stirring. Then, the aqueous layer was separated. The organic layer was sequentially washed with a saturated ammonium chloride solution, water and brine. The resulting organic layer was dried over anhydrous magnesium sulfate, and the solid was removed by filtration. The filtrate was concentrated under reduced pressure and then purified by silica gel column chromatography to obtain the title compound (541 mg).

ESI-MS; m/z 501 [M+H]

(10) Synthesis of tert-butyl(±)-[(4aR*,7R*,8aS*)-8a-(2-fluorophenyl)-7-methoxy-4a,5,6,7,8,8a-hexahydro-4H-benzo[d][1,3]thiazin-2-yl]-(4-methoxybenzyl)carbamate tert-Butyl (±)-[(4aR*,7R*,8aS*)-8a-(2-fluorophenyl)-7-hydroxy-4a,5,6,7,8,8a-hexahydro-4H-benzo[d][1,3]thiazin-2-yl]-(4-methoxybenzyl)carbamate obtained in Preparation Example 58-(9) (541 mg) was dissolved in DMF (5 mL). Methyl iodide (113 μL, specific gravity: 2.28 g/cm$^3$) was added and then the mixture was cooled in an ice bath under a nitrogen atmosphere. Sodium hydride (60%, 55 mg) was added, followed by stirring for one hour and 45 minutes. Thereafter, methyl iodide (113 μL, specific gravity: 2.28 g/cm$^3$) and sodium hydride (60%, 55 mg) were added, and the mixture was warmed to room temperature and stirred for one hour and 45 minutes. Thereafter, methyl iodide (113 μL, specific gravity: 2.28 g/cm$^3$) was further added, followed by stirring for 13 hours. Ethyl acetate and water were added to the reaction solution, followed by further stirring. Then, the aqueous layer was separated. The organic layer was sequentially washed with a saturated ammonium chloride solution, water and brine. The resulting organic layer was dried over anhydrous magnesium sulfate, and the solid was removed by filtration. The filtrate was concentrated under reduced pressure and then purified by silica gel column chromatography to obtain the title compound (409 mg).

$^1$H-NMR (400 MHz, CDCl$_3$) δ (ppm): 1.32-1.42 (m, 1H) 1.47-1.52 (m, 2H), 1.53 (s, 9H), 1.95-1.99 (m, 1H), 2.10-2.16 (m, 1H), 2.26-2.31 (m, 1H), 2.47 (dd, J=2.8, 12.4 Hz, 1H), 2.59-2.64 (m, 1H), 2.77 (dd, J=4.0, 12.4 Hz, 1H), 2.96-3.04 (m, 1H), 3.26 (s, 3H), 3.80 (s, 3H), 4.92-5.04 (m, 2H), 6.85-6.88 (m, 2H), 6.96-7.05 (m, 3H), 7.18-7.23 (m, 1H), 7.31-7.34 (m, 2H)

(11) Synthesis of tert-butyl(±)-[(4aR*,7R*,8aS*)-8a-(2-fluoro-5-nitrophenyl)-7-methoxy-4a,5,6,7,8,8a-hexahydro-4H-benzo[d][1,3]thiazin-2-yl]carbamate The title compound (283 mg) was obtained from tert-butyl (±)-[(4aR*,7R*,8aS*)-8a-(2-fluorophenyl)-7-methoxy-4a,5,6,7,8,8a-hexahydro-4H-benzo[d][1,3]thiazin-2-yl]-(4-methoxybenzyl)carbamate obtained in Preparation Example 58-(10) (409 mg) according to the method of Preparation Example 57-(9) using 82.1 μL of fuming nitric acid (specific gravity: 1.52 g/cm$^3$, 2.6 equivalents with respect to the raw material).

$^1$H-NMR (400 MHz, CDCl$_3$) δ (ppm): 1.38-1.52 (m, 2H), 1.54 (s, 9H), 1.70-1.74 (m, 1H), 1.89-1.92 (m, 1H), 2.08-2.24 (m, 3H), 2.56-2.60 (m, 1H), 2.74-2.81 (m, 2H), 3.35-3.39 (m, 4H), 7.20-7.25 (m, 1H), 8.12-8.21 (m, 2H)

(12) Synthesis of tert-butyl(±)-[(4aR*,7R*,8aS*)-8a-(5-amino-2-fluorophenyl)-7-methoxy-4a,5,6,7,8,8a-hexahydro-4H-benzo[d][1,3]thiazin-2-yl]carbamate The title compound (221 mg) was obtained from tert-butyl (±)-[(4aR*,7R*,8aS*)-8a-(2-fluoro-5-nitrophenyl)-7-methoxy-4a,5,6,7,8,8a-hexahydro-4H-benzo[d][1,3]thiazin-2-yl]carbamate obtained in Preparation Example 58-(11) (283 mg)

according to the method of Preparation Example 57-(10) where purification was performed by NH-silica gel column chromatography.

$^1$H-NMR (400 MHz, CDCl$_3$) δ (ppm): 1.30-1.49 (m, 1H), 1.53 (s, 9H), 1.70-1.77 (m, 1H), 1.89-1.99 (m, 1H), 2.09-2.12 (m, 1H), 2.23-2.29 (m, 2H), 2.52 (dd, J=2.4, 12.8 Hz, 1H), 2.81-2.91 (m, 2H), 3.36 (s, 3H), 3.42-3.47 (m, 1H), 3.65 (br, 2H), 6.49-6.57 (m, 2H), 6.83-6.88 (m, 1H)

(13) Synthesis of tert-butyl (−)-[(4aR*,7R*,8aS*)-8a-(5-amino-2-fluorophenyl)-7-methoxy-4a,5,6,7,8,8a-hexahydro-4H-benzo[d][1,3]thiazin-2-yl]carbamate tert-Butyl (±)-[(4aR*,7R*,8aS*)-8a-(5-amino-2-fluorophenyl)-7-methoxy-4a,5,6,7,8,8a-hexahydro-4H-benzo[d][1,3]thiazin-2-yl]carbamate obtained in Preparation Example 58-(12) (221 mg) was optically resolved by CHIRALPAK™ AD-H manufactured by Daicel Chemical Industries, Ltd. (2 cm×25 cm, mobile phase: hexane:ethanol=70:30, flow rate: 10 mL/min, charged with a solution of about 35 mg in 1 mL of ethanol for one cycle). The component having a retention time of 17.8 to 23.7 minutes was collected to obtain the title compound (93 mg, >99% ee, optical rotation (−)).

$^1$H-NMR (400 MHz, CDCl$_3$) δ (ppm): 1.46-1.49 (m, 1H), 1.54 (s, 9H), 1.71-1.75 (m, 1H), 1.89-1.99 (m, 1H), 2.09-2.12 (m, 1H), 2.23-2.29 (m, 2H), 2.50-2.53 (m, 1H), 2.81-2.91 (m, 2H), 3.36 (s, 3H), 3.44-3.49 (m, 1H), 3.65 (br, 2H), 6.49-6.52 (m, 1H), 6.53-6.57 (m, 1H), 6.83-6.88 (m, 1H)

Preparation Example 59

Synthesis of (±)-N-[(4aR*,6S*,8aS*)-8a-(2-fluorophenyl)-6-methoxy-4a,5,6,7,8,8a-hexahydro-4H-benzo[d][1,3]thiazin-2-yl]benzamide and (±)-N-[(4aR*,6R*,8aS*)-8a-(2-fluorophenyl)-6-methoxy-4a,5,6,7,8,8a-hexahydro-4H-benzo[d][1,3]thiazin-2-yl]benzamide

[Formula 81]

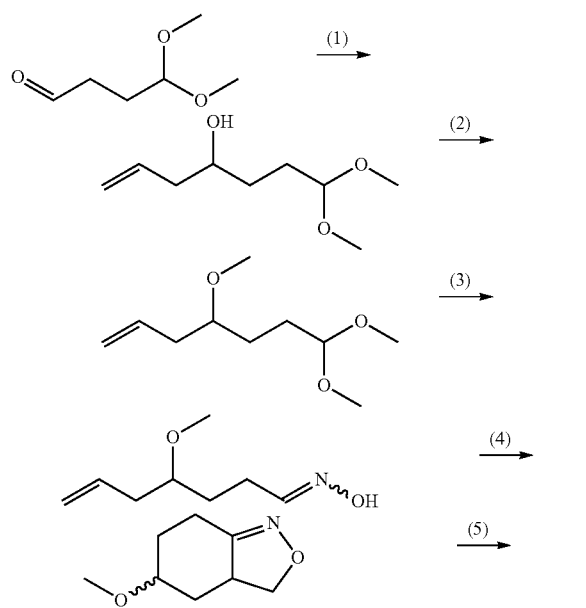

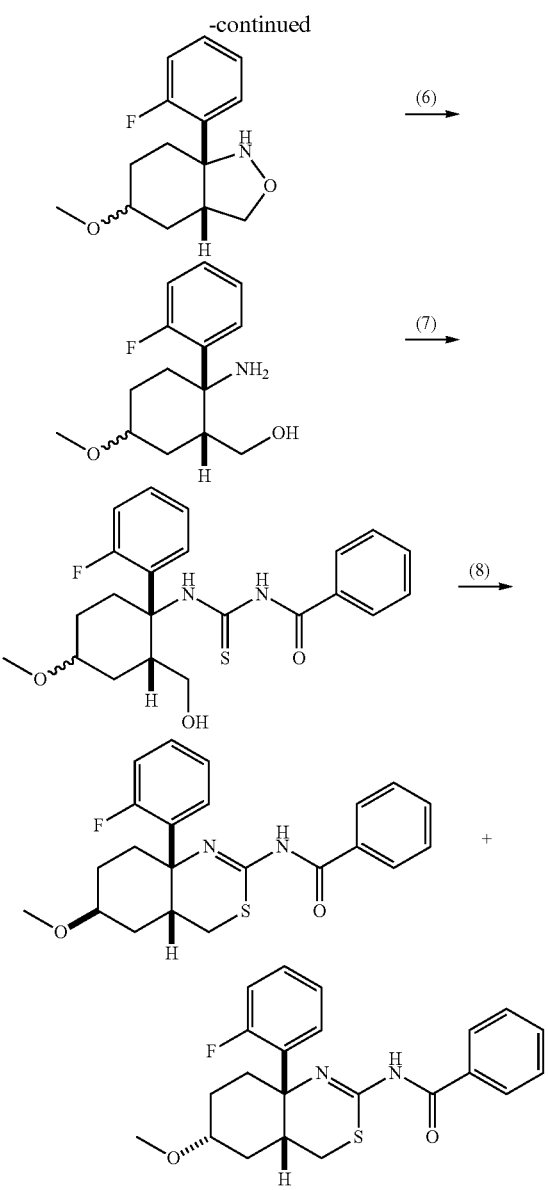

(1) Synthesis of 7,7-dimethoxyhept-1-en-4-ol 4,4-Dimethoxybutyraldehyde (Org. Biomol. Chem. 4 (2006) 2158) (5.47 g) was dissolved in THF (55 mL), and the solution was cooled in an ice bath under a nitrogen atmosphere. Then, a solution of allylmagnesium chloride in THF (62.1 mL, 1 M) was slowly added. After completion of the addition, the mixture was stirred for three hours. After slowly adding water, ethyl acetate and a saturated ammonium chloride solution were added, followed by further stirring. The aqueous layer was separated and then the organic layer was sequentially washed with a saturated ammonium chloride solution, water and brine. The resulting organic layer was dried over anhydrous magnesium sulfate, and the solid was removed by filtration. The filtrate was concentrated under reduced pressure and then purified by silica gel column chromatography to obtain the title compound (5.55 g).

$^1$H-NMR (400 MHz, CDCl$_3$) δ (ppm): 1.44-1.62 (m, 2H), 1.67-1.86 (m, 2H), 2.09 (d, J=3.6, 1H), 2.14-2.23 (m, 1H), 2.24-2.32 (m, 1H), 3.34 (s, 6H), 3.63-3.69 (m, 1H), 4.38-4.41 (m, 1H), 5.11 (d, J=1.2 Hz, 1H), 5.13-5.16 (m, 1H), 5.78-5.89 (m, 1H)

(2) Synthesis of 4,7,7-trimethoxyhept-1-ene 7,7-Dimethoxyhept-1-en-4-ol obtained in Preparation Example 59-(1) (6.16 g) was dissolved in 1-methyl-2-pyrrolidinone (60 mL), and the solution was cooled in an ice bath under a nitrogen atmosphere. Then, sodium hydride (60%, 2.12 g) was added, followed by stirring for 10 minutes. Methyl iodide (6.61 g, 2.28 g/cm$^3$) was further added and the mixture was further stirred for two hours and 10 minutes. After slowly adding water, ethyl acetate was added, followed by further stirring. The aqueous layer was separated and then the organic layer was sequentially washed with a saturated ammonium chloride solution, water and brine. The resulting organic layer was dried over anhydrous magnesium sulfate, and the solid was removed by filtration. The filtrate was concentrated under reduced pressure and then purified by silica gel column chromatography to obtain the title compound (5.83 g).
$^1$H-NMR (400 MHz, CDCl$_3$) δ (ppm): 1.47-1.76 (m, 4H), 2.20-2.33 (m, 2H), 3.20-3.26 (m, 1H), 3.32 (s, 6H), 3.34 (s, 3H), 4.36 (t, J=5.6 Hz, 1H), 5.05-5.10 (m, 2H), 5.76-5.86 (m, 1H)

(3) Synthesis of 4-methoxyhept-6-enal oxime

The title compound (4.61 g) was obtained from 4,7,7-trimethoxyhept-1-ene obtained in Preparation Example 59-(2) (5.83 g) according to the method of Preparation Example 57-(3) without purification by silica gel column chromatography.
$^1$H-NMR (400 MHz, CDCl$_3$) δ (ppm): 1.62-1.73 (m, 2H), 2.21-2.36 (m, 3H), 2.46 (dt, J=5.6, 8.0 Hz, 1H), 3.21-3.28 (m, 1H), 3.36 (d, J=3.6 Hz, 3H), 5.06-5.13 (m, 2H), 5.70-5.86 (m, 1H), 6.74-6.77 and 7.43-7.46 (m, total 1H), 7.44 and 7.82 (br, total 1H)

(4) Synthesis of 5-methoxy-3,3a,4,5,6,7-hexahydrobenz[c]isoxazole

The title compound (3.95 g) was obtained from 4-methoxyhept-6-enal oxime obtained in Preparation Example 59-(3) (4.61 g) according to the method of Preparation Example 57-(4).
ESI-MS; m/z 156 [M+H]

(5) Synthesis of (±)-(3aR*,7aS*)-7a-(2-fluorophenyl)-5-methoxyoctahydrobenz[c]isoxazole The title compound (5.60 g) was obtained from 5-methoxy-3,3a,4,5,6,7-hexahydrobenz[c]isoxazole obtained in Preparation Example 59-(4) (3.95 g) according to the method of Preparation Example 57-(5).
ESI-MS; m/z 252 [M+H]

(6) Synthesis of (±)-[(1R*,2S*)-2-amino-2-(2-fluorophenyl)-5-methoxycyclohexyl]methanol (±)-(3aR*,7aS*)-7a-(2-Fluorophenyl)-5-methoxyoctahydrobenz[c]isoxazole obtained in Preparation Example 59-(5) (5.60 g) was dissolved in acetic acid (128 mL). Then, zinc powder (14.1 g) was added and the mixture was stirred at room temperature for eight hours. The solid was removed by filtration through celite, and then the celite was washed with ethyl acetate. The resulting filtrate was concentrated under reduced pressure. The residue was dissolved in ethyl acetate. Then, a saturated sodium bicarbonate solution was added, followed by vigorous stirring. The organic layer was separated and then the aqueous layer was extracted again with ethyl acetate twice. The combined organic layers were dried over anhydrous magnesium sulfate. The solid was removed by filtration and the filtrate was concentrated under reduced pressure to obtain the title compound (5.49 g). ESI-MS; m/z 254 [M+H]

(7) Synthesis of (±)-1-benzoyl-3-[(1S*,2R*)-1-(2-fluorophenyl)-2-hydroxymethyl-4-methoxycyclohexyl]thiourea (±)-[(1R*,2S*)-2-Amino-2-(2-fluorophenyl)-5-methoxycyclohexyl]methanol obtained in Preparation Example 59-(6) (5.49 g) was dissolved in dichloromethane (22 mL). Then, benzoyl isothiocyanate (3.04 mL, specific gravity: 1.21 g/cm$^3$) was added and the mixture was stirred at room temperature for 16 hours and 30 minutes. The reaction solution was concentrated under reduced pressure and then purified by silica gel column chromatography to obtain the title compound (7.16 g).
$^1$H-NMR (400 MHz, CDCl$_3$) δ (ppm): 1.51-1.70 (m, 3H), 1.84-2.19 (m, 2H), 2.27-2.30 (m, 1H), 2.57 (br, 1H), 3.39-3.42 (m, 3H), 3.56 (br, 2H), 3.67 (br, 1H), 7.04-7.15 (m, 2H), 7.43-7.63 (m, 5H), 7.88 (s, 2H), 8.90 (br, 1H), 11.53 (br, 1H)

(8) Synthesis of (±)-N-[(4aR*,6S*,8aS*)-8a-(2-fluorophenyl)-6-methoxy-4a,5,6,7,8,8a-hexahydro-4H-benzo[d][1,3]thiazin-2-yl]benzamide and (±)-N-[(4aR*,6R*,8aS*)-8a-(2-fluorophenyl)-6-methoxy-4a,5,6,7,8,8a-hexahydro-4H-benzo[d][1,3]thiazin-2-yl]benzamide The title compounds (±)-N-[(4aR*,6S*,8aS*)-8a-(2-fluorophenyl)-6-methoxy-4a,5,6,7,8,8a-hexahydro-4H-benzo[d][1,3]thiazin-2-yl]benzamide (3.11 g) and (±)-N-[(4aR*,6R*,8aS*)-8a-(2-fluorophenyl)-6-methoxy-4a,5,6,7,8,8a-hexahydro-4H-benzo[d][1,3]thiazin-2-yl]benzamide (1.65 g) were obtained from (±)-1-benzoyl-3-[(1S*,2R*)-1-(2-fluorophenyl)-2-hydroxymethyl-4-methoxycyclohexyl]thiourea obtained in Preparation Example 59-(7) (7.16 g) according to the method of Preparation Example 57-(7).

(±)-N-[(4aR*,6S*,8aS*)-8a-(2-Fluorophenyl)-6-methoxy-4a,5,6,7,8,8a-hexahydro-4H-benzo[d][1,3]thiazin-2-yl]benzamide ESI-MS; m/z 399 [M+H]
$^1$H-NMR (400 MHz, CDCl$_3$) δ (ppm): 1.64 (d, J=14.8 Hz, 1H), 1.77-1.85 (m, 1H), 1.89-1.94 (m, 1H), 1.99-2.08 (m, 2H), 2.54 (dd, J=2.8, 12.8 Hz, 1H), 2.75 (dt, J=4.0, 13.6 Hz, 1H), 2.97 (dd, J=4.0, 12.8 Hz, 1H), 3.30-3.38 (m, 1H), 3.40 (s, 3H), 3.68 (t, J=2.4 Hz, 1H), 7.09 (ddd, J=1.2, 8.0, 12.4 Hz, 1H), 7.14 (dt, J=1.6, 7.6 Hz, 1H), 7.28-7.35 (m, 2H), 7.41-7.45 (m, 2H), 7.48-7.52 (m, 1H), 8.24-8.27 (m, 2H)

(±)-N-[(4aR*,6R*,8aS*)-8a-(2-Fluorophenyl)-6-methoxy-4a,5,6,7,8,8a-hexahydro-4H-benzo[d][1,3]thiazin-2-yl]benzamide ESI-MS; m/z 399 [M+H]
$^1$H-NMR (400 MHz, CDCl$_3$) δ (ppm): 1.63-1.74 (m, 1H), 1.89-1.95 (m, 2H), 2.05-2.13 (m, 2H), 2.46 (dt, J=3.6, 14.4 Hz, 1H), 2.60 (dd, J=2.8, 12.8 Hz, 1H), 2.93 (dd, J=4.0, 12.8

Hz, 1H), 2.98-3.04 (m, 1H), 3.40 (s, 3H), 3.47-3.54 (m, 1H), 7.09 (ddd, J=1.2, 8.0, 12.8 Hz, 1H), 7.16 (dt, J=1.6, 7.6 Hz, 1H), 7.29-7.38 (m, 2H), 7.41-7.45 (m, 2H), 7.48-7.52 (m, 1H), 8.22-8.25 (m, 2H)

Preparation Example 60

Synthesis of tert-butyl (−)-[(4aR*,6S*,8aS*)-8a-(5-amino-2-fluorophenyl)-6-methoxy-4a,5,6,7,8,8a-hexahydro-4H-benzo[d][1,3]thiazin-2-yl]carbamate

[Formula 82]

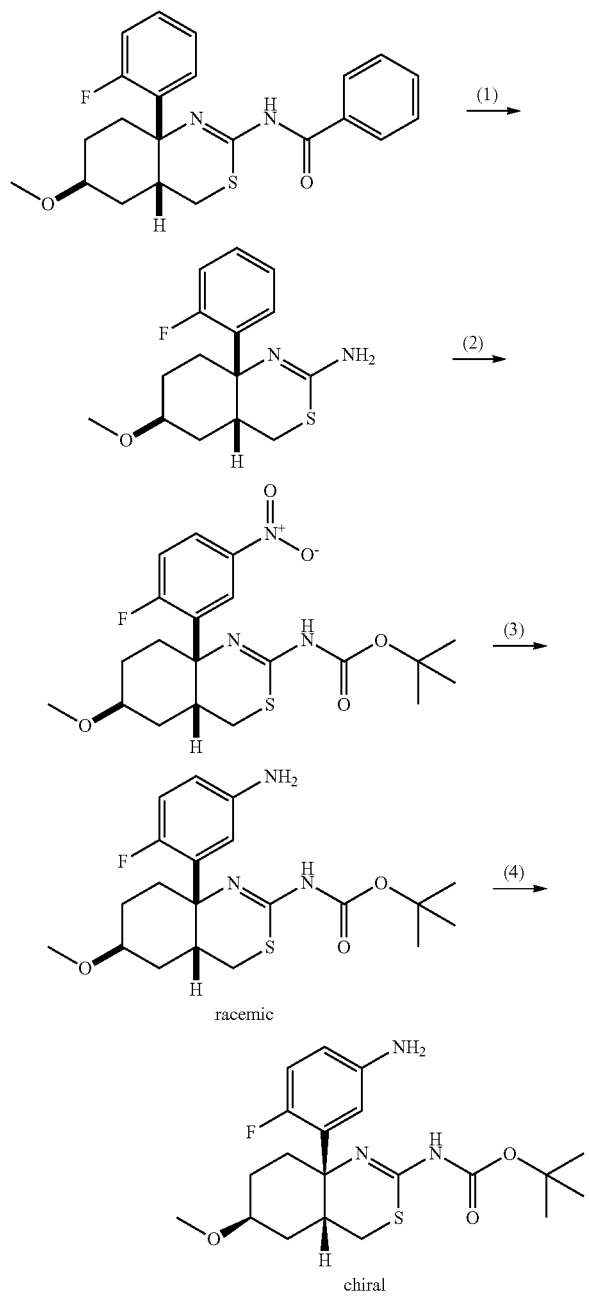

(1) Synthesis of (±)-(4aR*,6S*,8aS*)-8a-(2-fluorophenyl)-6-methoxy-4a,5,6,7,8,8a-hexahydro-4H-benzo[d][1,3]thiazin-2-ylamine (±)-N-[(4aR*,6S*,8aS*)-8a-(2-Fluorophenyl)-6-methoxy-4a,5,6,7,8,8a-hexahydro-4H-benzo[d][1,3]thiazin-2-yl]benzamide obtained in Preparation Example 59-(8) (3.11 g) was dissolved in methanol (100 mL). Then, DBU (2.34 mL, specific gravity: 1.018 g/cm$^3$) was added, and the mixture was stirred with heating under reflux for two hours and 15 minutes. Then, the reaction solution was stirred at 64° C. for 13 hours and 30 minutes. The reaction solution was left to cool to room temperature and then concentrated under reduced pressure. The residue was purified by NH-silica gel column chromatography to obtain the title compound (1.96 g).
$^1$H-NMR (400 MHz, CDCl$_3$) δ (ppm): 1.53 (td, J=3.6, 13.2 Hz, 1H), 1.66-1.75 (m, 2H), 1.81-1.91 (m, 2H), 2.49 (dd, J=2.8, 12.4 Hz, 1H), 2.61 (dt, J=4.0, 13.2 Hz, 1H), 2.90 (dd, J=4.4, 12.0 Hz, 1H), 3.09 (qd, J=3.6, 12.4 Hz, 1H), 3.39 (s, 3H), 3.60 (t, J=2.8 Hz, 1H), 7.02 (ddd, J=1.6, 8.0, 12.8 Hz, 1H), 7.06-7.10 (m, 1H), 7.18-7.24 (m, 1H), 7.25-7.29 (m, 1H)

(2) Synthesis of tert-butyl(±)-[(4aR*,6S*,8aS*)-8a-(2-fluoro-5-nitrophenyl)-6-methoxy-4a,5,6,7,8,8a-hexahydro-4H-benzo[d][1,3]thiazin-2-yl]carbamate The title compound (1.37 g) was obtained from (±)-(4aR*,6S*,8aS*)-8a-(2-fluorophenyl)-6-methoxy-4a,5,6,7,8,8a-hexahydro-4H-benzo[d][1,3]thiazin-2-ylamine obtained in Preparation Example 60-(1) (1 g) according to the method of Preparation Example 57-(9).
$^1$H-NMR (400 MHz, CDCl$_3$) δ (ppm): 1.42-1.55 (m, 1H), 1.54 (s, 9H), 1.66-1.73 (m, 1H), 1.85-2.00 (m, 3H), 2.49-2.61 (m, 2H), 2.83-2.87 (m, 1H), 3.21-3.25 (m, 1H), 3.39 (s, 3H), 3.66 (br, 1H), 7.21-7.25 (m, 1H), 8.19-8.21 (m, 2H)

(3) Synthesis of tert-butyl(±)-[(4aR*,6S*,8aS*)-8a-(5-amino-2-fluorophenyl)-6-methoxy-4a,5,6,7,8,8a-hexahydro-4H-benzo[d][1,3]thiazin-2-yl]carbamate The title compound (1.21 g) was obtained from tert-butyl (±)-[(4aR*,6S*,8aS*)-8a-(2-fluoro-5-nitrophenyl)-6-methoxy-4a,5,6,7,8,8a-hexahydro-4H-benzo[d][1,3]thiazin-2-yl]carbamate obtained in Preparation Example 60-(2) (2.56 g) according to the method of Preparation Example 57-(10). ESI-MS; m/z 410 [M+H]

(4) Synthesis of tert-butyl (−)-[(4aR*,6S*,8aS*)-8a-(5-amino-2-fluorophenyl)-6-methoxy-4a,5,6,7,8,8a-hexahydro-4H-benzo[d][1,3]thiazin-2-yl]carbamate tert-Butyl (±)-[(4aR*,6S*,8aS*)-8a-(5-amino-2-fluorophenyl)-6-methoxy-4a,5,6,7,8,8a-hexahydro-4H-benzo[d][1,3]thiazin-2-yl]carbamate obtained in Preparation Example 60-(3) was optically resolved by CHIRALPAK™ AD-H manufactured by Daicel Chemical Industries, Ltd. (2 cm×25 cm, mobile phase: hexane:ethanol=70:30, flow rate: 10 mL/min, charged with a solution of about 50 mg in 2 mL of ethanol for one cycle). The component having a retention time of 15.7 to 20.5 minutes was collected to obtain the title compound (502 mg, >99% ee, optical rotation (−)).
$^1$H-NMR (400 MHz, CDCl$_3$) δ (ppm): 1.48-1.54 (m, 2H), 1.53 (s, 9H), 1.66-1.75 (m, 1H), 1.82-1.88 (m, 1H), 1.91-2.00 (m, 2H), 2.41-2.45 (m, 1H), 2.66-2.74 (m, 1H), 2.94 (dd, J=4.0, 12.0 Hz, 1H), 3.19-3.25 (m, 1H), 3.38 (s, 3H), 3.64-3.65 (m, 2H), 6.52-6.57 (m, 2H), 6.83-6.88 (m, 1H)

Preparation Example 61

Synthesis of tert-butyl (−)-[(4aR*,6R*,8aS*)-8a-(5-amino-2-fluorophenyl)-6-methoxy-4a,5,6,7,8,8a-hexahydro-4H-benzo[d][1,3]thiazin-2-yl]carbamate

[Formula 83]

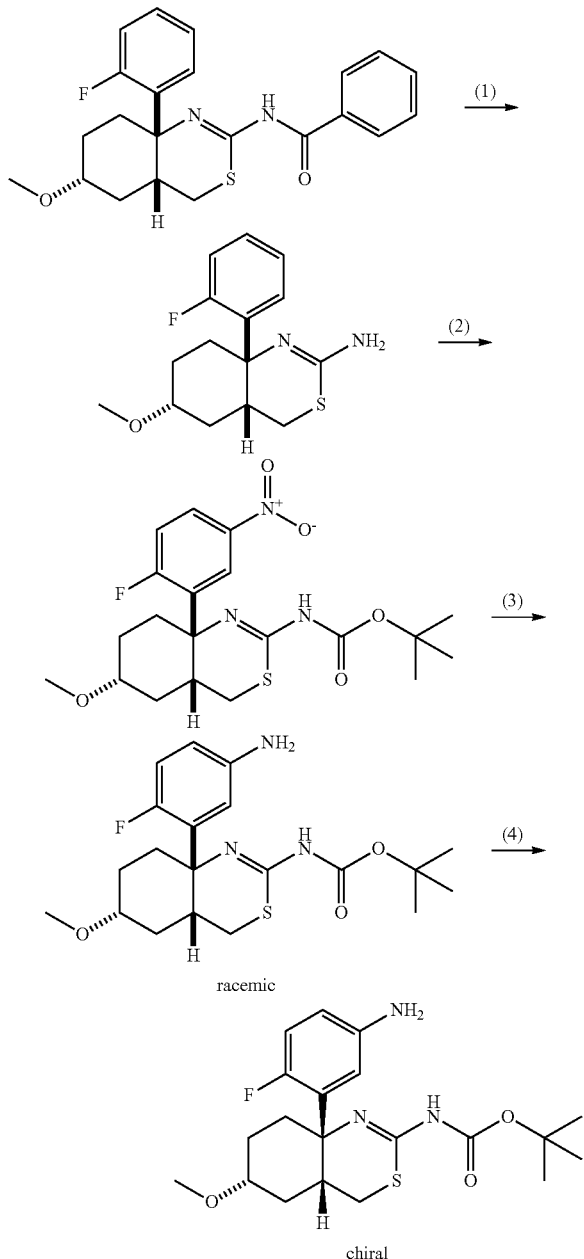

(1) Synthesis of (±)-(4aR*,6R*,8aS*)-8a-(2-fluorophenyl)-6-methoxy-4a,5,6,7,8,8a-hexahydro-4H-benzo[d][1,3]thiazin-2-ylamine (±)-N-[(4aR*,6R*,8aS*)-8a-(2-Fluorophenyl)-6-methoxy-4a,5,6,7,8,8a-hexahydro-4H-benzo[d][1,3]thiazin-2-yl]benzamide obtained in Preparation Example 59-(8) (1.65 g) was dissolved in methanol (60 mL). Then, DBU (1.24 mL, specific gravity: 1.018 g/cm³) was added, and the mixture was stirred with heating under reflux for 13 hours and 30 minutes. The reaction solution was left to cool to room temperature and then concentrated under reduced pressure. The residue was purified by NH-silica gel column chromatography to obtain the title compound (1.16 g).

¹H-NMR (400 MHz, CDCl₃) δ (ppm): 1.52-1.74 (m, 2H), 1.80-1.90 (m, 2H), 1.94-2.01 (m, 1H), 2.27-2.35 (m, 1H), 2.56 (dd, J=2.8, 12.0 Hz, 1H), 2.71-2.77 (m, 1H), 2.87 (dd, J=4.0, 12.0 Hz, 1H), 3.36-3.49 (m, 4H), 4.46 (br, 2H), 7.01 (ddd, J=1.2, 8.0, 12.8 Hz, 1H), 7.10 (ddd, J=1.2, 7.2, 7.6 Hz, 1H), 7.19-7.25 (m, 1H), 7.26-7.31 (m, 1H)

(2) Synthesis of tert-butyl(±)-[(4aR*,6R*,8aS*)-8a-(2-fluoro-5-nitrophenyl)-6-methoxy-4a,5,6,7,8,8a-hexahydro-4H-benzo[d][1,3]thiazin-2-yl]carbamate The title compound (1.27 g) was obtained from (±)-(4aR*,6R*,8aS*)-8a-(2-fluorophenyl)-6-methoxy-4a,5,6,7,8,8a-hexahydro-4H-benzo[d][1,3]thiazin-2-ylamine obtained in Preparation Example 61-(1) (1.16 g) according to the method of Preparation Example 57-(9).

¹H-NMR (400 MHz, CDCl₃) δ (ppm): 1.46-1.55 (m, 1H), 1.54 (s, 9H), 1.77-1.87 (m, 2H), 1.99-2.08 (m, 2H), 2.21-2.27 (m, 1H), 2.54-2.58 (m, 1H), 2.76-2.80 (m, 1H), 2.86-2.90 (m, 1H), 3.39-3.49 (m, 4H), 7.20-7.28 (m, 1H), 8.18-8.21 (m, 2H)

(3) Synthesis of tert-butyl(±)-[(4aR*,6R*,8aS*)-8a-(5-amino-2-fluorophenyl)-6-methoxy-4a,5,6,7,8,8a-hexahydro-4H-benzo[d][1,3]thiazin-2-yl]carbamate The title compound (838 mg) was obtained from tert-butyl (±)-[(4aR*,6R*,8aS*)-8a-(2-fluoro-5-nitrophenyl)-6-methoxy-4a,5,6,7,8,8a-hexahydro-4H-benzo[d][1, 3]thiazin-2-yl]carbamate obtained in Preparation Example 61-(2) (1.27 g) according to the method of Preparation Example 57-(10).

¹H-NMR (400 MHz, CDCl₃) δ (ppm): 1.46-1.54 (m, 1H), 1.53 (s, 9H), 1.77-1.86 (m, 2H), 1.98-2.07 (m, 2H), 2.41 (dt, J=4.0, 6.4 Hz, 1H), 2.47-2.52 (m, 1H), 2.87-2.93 (m, 2H), 3.38-3.49 (m, 4H), 3.65 (br, 2H) 6.53-6.57 (m, 2H), 6.82-6.87 (m, 1H)

HPLC (CHIRALPAK™ AD-H manufactured by Daicel Chemical Industries, Ltd., 2 cm×25 cm, mobile phase: hexane:ethanol=70:30, flow rate: 1 mL/min): 3.1 minutes (optical rotation (+)), 4.3 minutes (optical rotation (−))

(4) Synthesis of tert-butyl (−)-[(4aR*,6R*,8aS*)-8a-(5-amino-2-fluorophenyl)-6-methoxy-4a,5,6,7,8,8a-hexahydro-4H-benzo[d][1,3]thiazin-2-yl]carbamate tert-Butyl (±)-[(4aR*,6R*,8aS*)-8a-(5-amino-2-fluorophenyl)-6-methoxy-4a,5,6,7,8,8a-hexahydro-4H-benzo[d][1,3]thiazin-2-yl]carbamate obtained in Preparation Example 58-(12) (838 mg) was optically resolved by CHIRALPAK™ AD-H manufactured by Daicel Chemical Industries, Ltd. (2 cm×25 cm, mobile phase: hexane:ethanol=50:50, flow rate: 10 mL/min, charged with a solution of about 16 mg in 2 mL of ethanol for one cycle). The component having a longer retention time among the two main components was collected to obtain the title compound (335 mg, >99% ee, optical rotation (−)).

HPLC (CHIRALPAK™ AD-H manufactured by Daicel Chemical Industries, Ltd., 2 cm×25 cm, mobile phase: hexane:ethanol=70:30, flow rate: 1 mL/min): 4.3 minutes ¹H-NMR (400 MHz, CDCl₃) δ (ppm): 1.44-1.54 (m, 1H), 1.53 (s, 9H), 1.80-1.86 (m, 2H), 1.98-2.07 (m, 2H), 2.37-2.45

(m, 1H), 2.48-2.51 (m, 1H), 2.87-2.92 (m, 2H), 3.41 (s, 3H), 3.45-3.49 (m, 1H), 3.65 (br, 2H), 6.53-6.55 (m, 2H), 6.82-6.87 (m, 1H)

Preparation Example 62

Synthesis of (±)-(3aR*,5S*,7aS*)-5-benzyloxy-7a-(2-fluorophenyl)-octahydrobenz[c]isoxazole and (±)-(3aR*,5R*,7aS*)-5-benzyloxy-7a-(2-fluorophenyl)-octahydrobenz[c]isoxazole

[Formula 84]

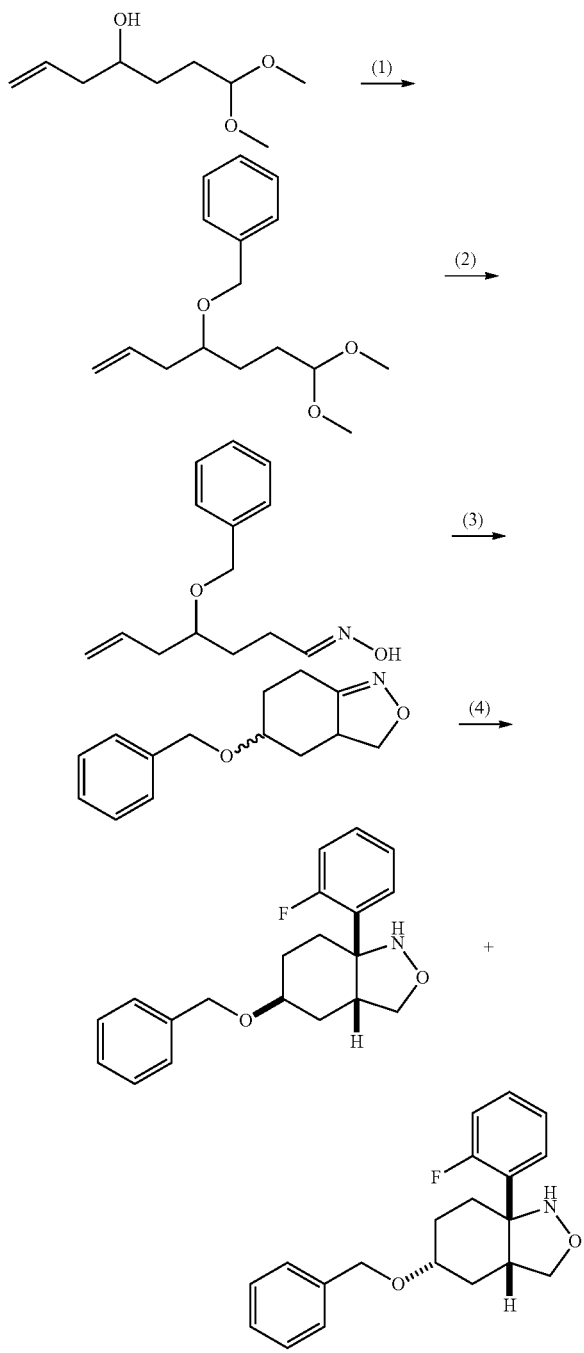

(1) Synthesis of [1-(3,3-dimethoxypropyl)-but-3-enyloxymethyl]benzene 7,7-Dimethoxyhept-1-en-4-ol obtained in Preparation Example 59-(1) (5.47 g) was dissolved in 1-methyl-2-pyrrolidinone (35 mL). Benzyl bromide (3.12 mL, specific gravity: 1.44 g/cm³) was added and the mixture was sufficiently cooled in an ice bath under a nitrogen atmosphere. Sodium hydride (60%, 2.12 g) was added, followed by stirring for one hour and 30 minutes. Water and saturated ammonium chloride were slowly added and then ethyl acetate was added, followed by further stirring. The aqueous layer was separated and then the organic layer was sequentially washed with a saturated ammonium chloride solution, water and brine. The resulting organic layer was dried over anhydrous magnesium sulfate, and the solid was removed by filtration. The filtrate was concentrated under reduced pressure and then purified by silica gel column chromatography to obtain the title compound (4.14 g).
$^1$H-NMR (400 MHz, CDCl$_3$) δ (ppm): 1.55-1.68 (m, 3H), 1.73-1.81 (m, 1H), 2.27-2.41 (m, 2H), 3.30 (d, J=2.0 Hz, 6H), 3.44-3.50 (m, 1H), 4.33-4.37 (m, 1H), 4.47-4.59 (m, 2H), 5.05-5.12 (m, 2H), 5.79-5.90 (m, 1H), 7.28-7.34 (m, 5H)

(2) Synthesis of 4-benzyloxyhept-6-enal oxime

The title compound (6.42 g) was obtained from [1-(3,3-dimethoxypropyl)-but-3-enyloxymethyl]benzene obtained in Preparation Example 62-(1) (7.78 g) according to the method of Preparation Example 57-(3) without purification by silica gel column chromatography.
$^1$H-NMR (400 MHz, CDCl$_3$) δ (ppm): 1.70-1.75 (m, 2H), 2.22-2.43 (m, 3H), 2.46-2.51 (m, 1H), 3.45-3.52 (m, 1H), 4.46-4.50 (m, 1H), 4.58-4.61 (m, 1H), 5.06-5.14 (m, 2H), 5.78-5.89 (m, 1H), 6.71-6.74 and 7.41-7.44 (m, total 1H), 7.16 and 7.53 (br, total 1H), 7.26-7.32 (m, 1H), 7.34-7.35 (m, 4H)

(3) Synthesis of 5-benzyloxy-3,3a,4,5,6,7-hexahydro-benz[c]isoxazole

The title compound (5.66 g) was obtained from 4-benzyloxyhept-6-enal oxime obtained in Preparation Example 62-(2) (6.42 g) according to the method of Preparation Example 57-(4).
ESI-MS; m/z 232 [M+H]

(4) Synthesis of (±)-(3aR*,5S*,7aS*)-5-benzyloxy-7a-(2-fluorophenyl)-octahydrobenz[c]isoxazole and (±)-(3aR*,5R*,7aS*)-5-benzyloxy-7a-(2-fluorophenyl)-octahydrobenz[c]isoxazole The title compounds (±)-(3aR*,5S*,7aS*)-5-benzyloxy-7a-(2-fluorophenyl)-octahydrobenz[c]isoxazole (5.04 g) and (±)-(3aR*,5R*,7aS*)-5-benzyloxy-7a-(2-fluorophenyl)-octahydrobenz[c]isoxazole (2.49 g) were obtained from 5-benzyloxy-3,3a,4,5,6,7-hexahydro-benz[c]isoxazole obtained in Preparation Example 62-(3) (5.66 g) according to the method of Preparation Example 57-(5).
(±)-(3aR*,5S*,7aS*)-5-Benzyloxy-7a-(2-fluorophenyl)-octahydrobenz[c]isoxazole
$^1$H-NMR (400 MHz, CDCl$_3$) δ (ppm): 1.63 (br, 2H), 1.76-1.80 (m, 1H), 1.87 (br, 1H), 2.10-2.15 (m, 1H), 2.58-2.64 (m, 1H), 3.21 (br, 1H), 3.66 (br, 2H), 3.81 (br, 1H), 4.56-4.63 (m, 2H), 5.95 (br, 1H), 7.02-7.07 (m, 1H), 7.11-7.15 (m, 1H), 7.23-7.31 (m, 2H), 7.35-7.43 (m, 4H), 7.82 (br, 1H)

(±)-(3aR*,5R*,7aS*)-5-Benzyloxy-7a-(2-fluorophenyl)-octahydrobenz[c]isoxazole

¹H-NMR (400 MHz, CDCl₃) δ (ppm): 1.40-1.54 (m, 2H), 1.99-2.05 (m, 1H), 2.07-2.13 (m, 1H), 2.18-2.25 (m, 1H), 2.28-2.36 (m, 1H), 2.99-3.05 (m, 1H), 3.53-3.56 (m, 1H), 3.64-3.74 (m, 2H), 4.61 (d, J=1.6 Hz, 2H), 6.00 (br, 1H), 7.01 (ddd, J=1.2, 8.4, 12.4 Hz, 1H), 7.13 (dt, J=1.2, 7.6 Hz, 1H), 7.21-7.27 (m, 1H), 7.28-7.33 (m, 1H), 7.36-7.37 (m, 4H), 7.87 (dt, J=1.6, 8.0 Hz, 1H)

Preparation Example 63

Synthesis of tert-butyl (−)-[(4aR*,6R*,8aS*)-8a-(5-amino-2-fluorophenyl)-6-fluoro-4a,5,6,7,8,8a-hexahydro-4H-benzo[d][1,3]thiazin-2-yl]carbamate

[Formula 85]

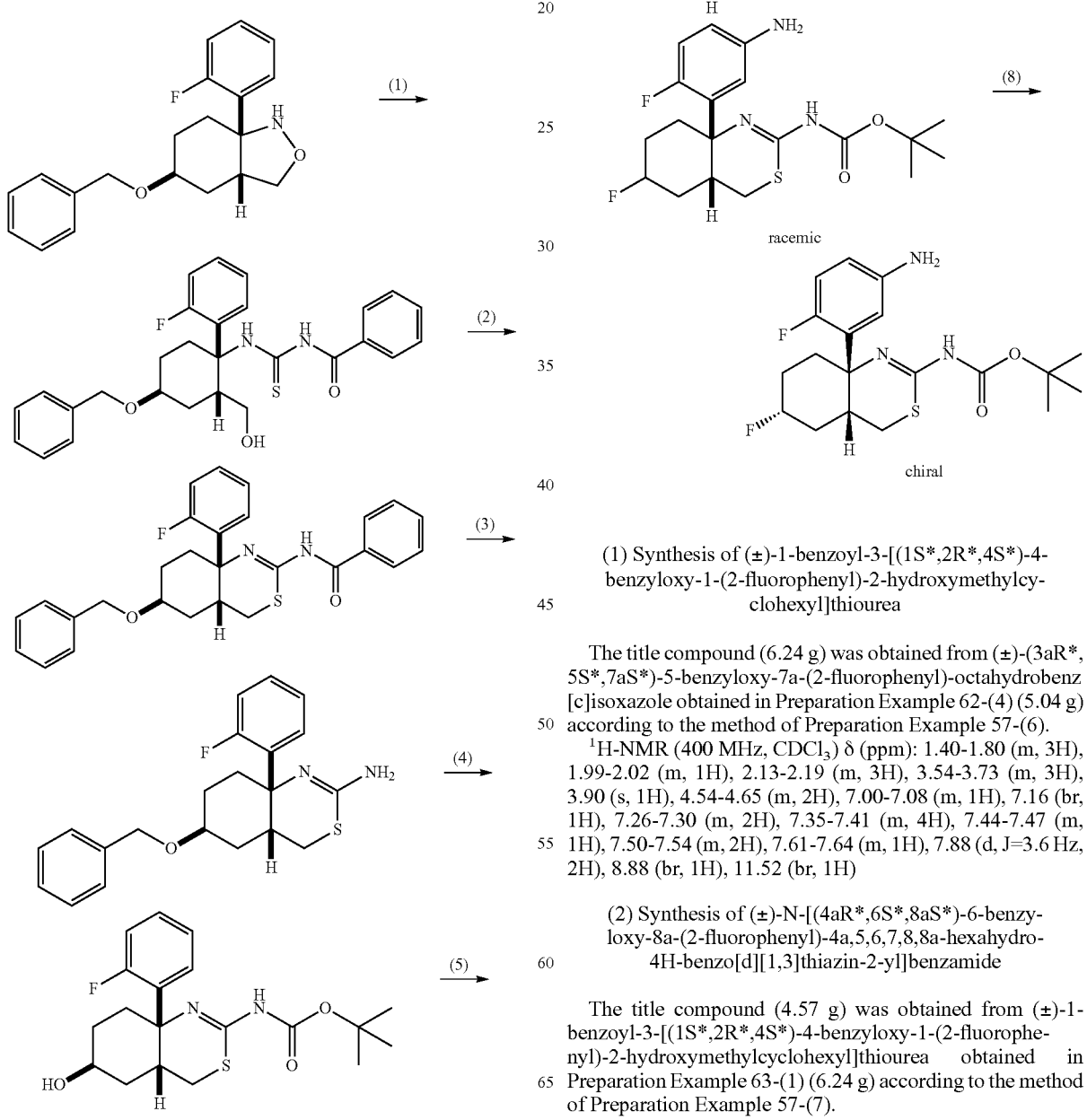

(1) Synthesis of (±)-1-benzoyl-3-[(1S*,2R*,4S*)-4-benzyloxy-1-(2-fluorophenyl)-2-hydroxymethylcyclohexyl]thiourea The title compound (6.24 g) was obtained from (±)-(3aR*,5S*,7aS*)-5-benzyloxy-7a-(2-fluorophenyl)-octahydrobenz[c]isoxazole obtained in Preparation Example 62-(4) (5.04 g) according to the method of Preparation Example 57-(6).
¹H-NMR (400 MHz, CDCl₃) δ (ppm): 1.40-1.80 (m, 3H), 1.99-2.02 (m, 1H), 2.13-2.19 (m, 3H), 3.54-3.73 (m, 3H), 3.90 (s, 1H), 4.54-4.65 (m, 2H), 7.00-7.08 (m, 1H), 7.16 (br, 1H), 7.26-7.30 (m, 2H), 7.35-7.41 (m, 4H), 7.44-7.47 (m, 1H), 7.50-7.54 (m, 2H), 7.61-7.64 (m, 1H), 7.88 (d, J=3.6 Hz, 2H), 8.88 (br, 1H), 11.52 (br, 1H)

(2) Synthesis of (±)-N-[(4aR*,6S*,8aS*)-6-benzyloxy-8a-(2-fluorophenyl)-4a,5,6,7,8,8a-hexahydro-4H-benzo[d][1,3]thiazin-2-yl]benzamide The title compound (4.57 g) was obtained from (±)-1-benzoyl-3-[(1S*,2R*,4S*)-4-benzyloxy-1-(2-fluorophenyl)-2-hydroxymethylcyclohexyl]thiourea obtained in Preparation Example 63-(1) (6.24 g) according to the method of Preparation Example 57-(7).
ESI-MS; m/z 475 [M+H]

¹H-NMR (400 MHz, CDCl₃) δ (ppm): 1.68 (d, J=14.4 Hz, 1H), 1.81-1.89 (m, 1H), 1.93-1.97 (m, 1H), 2.03-2.10 (m, 2H), 2.52 (dd, J=3.2, 12.8 Hz, 1H), 2.85-2.93 (m, 1H), 2.97 (dd, J=4.0, 12.8 Hz, 1H), 3.43-3.49 (m, 1H), 3.92 (s, 1H), 4.54-4.66 (m, 2H), 7.09-7.17 (m, 2H), 7.28-7.45 (m, 9H), 7.48-7.52 (m, 1H), 8.24-8.27 (m, 2H), 12.32 (br, 1H)

(3) Synthesis of (±)-(4aR*,6S*,8aS*)-6-benzyloxy-8a-(2-fluorophenyl)-4a,5,6,7,8,8a-hexahydro-4H-benzo[d][1,3]thiazin-2-ylamine The title compound (3.96 g, purity from ¹H-NMR: about 90%) was obtained from (±)-N-[(4aR*,6S*,8aS*)-6-benzyloxy-8a-(2-fluorophenyl)-4a,5,6,7,8,8a-hexahydro-4H-benzo[d][1,3]thiazin-2-yl]benzamide obtained in Preparation Example 63-(2) (4.58 g) according to the method of Preparation Example 61-(1).

ESI-MS; m/z 371 [M+H]

¹H-NMR (400 MHz, CDCl₃) δ (ppm): 1.54-1.72 (m, 1H), 1.74-1.83 (m, 2H), 1.84-1.88 (m, 1H), 1.90-1.97 (m, 1H), 2.48 (dd, J=2.8, 12.0 Hz, 1H), 2.76 (dt, J=3.6, 13.2 Hz, 1H), 2.87-2.91 (m, 1H), 3.18-3.24 (m, 1H), 3.84 (t, J=2.8 Hz, 1H), 4.54 (br, 2H), 4.51-4.66 (m, 2H), 7.04 (ddd, J=1.2, 8.0, 12.4 Hz, 1H), 7.09 (dt, J=1.6, 7.6 Hz, 1H), 7.19-7.25 (m, 1H), 7.26-7.31 (m, 2H), 7.35-7.39 (m, 2H), 7.43-7.45 (m, 2H)

(4) Synthesis of tert-butyl(±)-[(4aR*,6S*,8aS*)-8a-(2-fluorophenyl)-6-hydroxy-4a,5,6,7,8,8a-hexahydro-4H-benzo[d][1,3]thiazin-2-yl]carbamate The title compound (3.58 g) was obtained from (±)-(4aR*,6S*,8aS*)-6-benzyloxy-8a-(2-fluorophenyl)-4a,5,6,7,8,8a-hexahydro-4H-benzo[d][1,3]thiazin-2-ylamine obtained in Preparation Example 63-(3) (3.96 g, purity from ¹H-NMR: about 90%) according to the method of Preparation Example 58-(8).

¹H-NMR (400 MHz, CDCl₃) δ (ppm): 1.54-1.68 (m, 1H), 1.71-1.79 (m, 2H), 1.87-1.96 (m, 1H), 2.07-2.15 (m, 1H), 2.45 (dd, J=2.8, 10.0 Hz, 1H), 2.82-2.91 (m, 2H), 3.31-3.45 (m, 2H), 4.29-4.33 (m, 1H), 7.06-7.11 (m, 1H), 7.15-7.19 (m, 1H), 7.29-7.34 (m, 2H)

(5) Synthesis of tert-butyl(±)-[(4aR*,6R*,8aS*)-6-fluoro-8a-(2-fluorophenyl)-4a,5,6,7,8,8a-hexahydro-4H-benzo[d][1,3]thiazin-2-yl]carbamate tert-Butyl (±)-[(4aR*,6S*,8aS*)-8a-(2-fluorophenyl)-6-hydroxy-4a,5,6,7,8,8a-hexahydro-4H-benzo[d][1,3]thiazin-2-yl]carbamate obtained in Preparation Example 63-(4) (1.5 g) was dissolved in THF. Then, perfluorobutanesulfonyl fluoride (1.36 mL, specific gravity: 1.682 g/cm³), a triethylamine-trihydrofluoric acid complex (1.23 mL, specific gravity: 0.989 g/cm³) and triethylamine (3.15 mL, specific gravity: 0.73 g/cm³) were sequentially added at room temperature. After completion of the addition, the mixture was stirred for 16 hours. The mixture was heated to 50° C. and further stirred for 24 hours. Perfluorobutanesulfonyl fluoride (0.68 mL), a triethylamine-trihydrofluoric acid complex (0.62 mL) and triethylamine (1.58 mL) were further sequentially added to the mixture, followed by further stirring with heating under reflux for eight hours. The reaction solution was cooled to room temperature and concentrated under reduced pressure. Then, the residue was purified by silica gel column chromatography to obtain the title compound (106 mg).

¹H-NMR (400 MHz, CDCl₃) δ (ppm): 1.53 (s, 9H), 1.84-1.89 (m, 2H), 2.06-2.13 (m, 3H), 2.39-2.47 (m, 1H), 2.52 (dd, J=3.2, 12.8 Hz, 1H), 2.80-2.85 (m, 1H), 2.89-2.97 (m, 1H), 4.69-4.90 (m, 1H), 7.04-7.11 (m, 1H), 7.15-7.20 (m, 1H), 7.27-7.34 (m, 2H)

(6) Synthesis of tert-butyl(±)-[(4aR*,6R*,8aS*)-6-fluoro-8a-(2-fluoro-5-nitrophenyl)-4a,5,6,7,8,8a-hexahydro-4H-benzo[d][1,3]thiazin-2-yl]carbamate The title compound (406 mg) was obtained from tert-butyl (±)-[(4aR*,6R*,8aS*)-6-fluoro-8a-(2-fluorophenyl)-4a,5,6,7,8,8a-hexahydro-4H-benzo[d][1,3]thiazin-2-yl]carbamate obtained in Preparation Example 63-(5) (402 mg) according to the method of Preparation Example 57-(9) using fuming nitric acid (87.1 μl, two equivalents with respect to the raw material).

¹H-NMR (400 MHz, CDCl₃) δ (ppm): 1.55 (s, 9H), 1.80-1.88 (m, 2H), 2.06 (br, 3H), 2.18-2.27 (m, 1H), 2.56 (dd, J=2.8, 12.8 Hz, 1H), 2.75-2.80 (m, 1H), 2.87 (br, 1H), 4.66-4.86 (m, 1H), 7.19-7.25 (m, 1H), 8.14-8.22 (m, 2H)

(7) Synthesis of tert-butyl(±)-[(4aR*,6R*,8aS*)-8a-(5-amino-2-fluorophenyl)-6-fluoro-4a,5,6,7,8,8a-hexahydro-4H-benzo[d][1,3]thiazin-2-yl]carbamate The title compound (330 mg) was obtained from tert-butyl (±)-[(4aR*,6R*,8aS*)-6-fluoro-8a-(2-fluoro-5-nitrophenyl)-4a,5,6,7,8,8a-hexahydro-4H-benzo[d][1,3]thiazin-2-yl]carbamate obtained in Preparation Example 63-(6) (406 mg) according to the method of Preparation Example 57-(10).

¹H-NMR (400 MHz, CDCl₃) δ (ppm): 1.54 (s, 9H), 1.80-1.88 (m, 2H), 2.04-2.11 (m, 3H), 2.38-2.47 (m, 1H), 2.48-2.53 (m, 1H), 2.89-2.95 (m, 2H), 3.65 (s, 2H), 4.68-4.88 (m, 1H), 6.51-6.57 (m, 2H), 6.83-6.88 (m, 1H)

HPLC (CHIRALPAK™ AD-H manufactured by Daicel Chemical Industries, Ltd., 2 cm×25 cm, mobile phase: hexane:ethanol=80:20, flow rate: 1 mL/min): 4.4 minutes (optical rotation (+)), 6.8 minutes (optical rotation (−))

(8) Synthesis of tert-butyl (−)-[(4aR*,6R*,8aS*)-8a-(5-amino-2-fluorophenyl)-6-fluoro-4a,5,6,7,8,8a-hexahydro-4H-benzo[d][1,3]thiazin-2-yl]carbamate tert-Butyl (±)-[(4aR*,6R*,8aS*)-8a-(5-amino-2-fluorophenyl)-6-fluoro-4a,5,6,7,8,8a-hexahydro-4H-benzo[d][1,3]thiazin-2-yl]carbamate obtained in Preparation Example 58-(12) (330 mg) was optically resolved by CHIRALPAK™ AD-H manufactured by Daicel Chemical Industries, Ltd. (2 cm×25 cm, mobile phase: hexane:ethanol=50:50, flow rate: 10 mL/min, charged with a solution of about 40 mg in 1 mL of ethanol for one cycle). The component having a retention time of 12.2 to 15.5 minutes among the two main components was collected to obtain the title compound (155 mg, >99% ee, optical rotation (−)).

HPLC (CHIRALPAK™ AD-H manufactured by Daicel Chemical Industries, Ltd., 2 cm×25 cm, mobile phase: hexane:ethanol=80:20, flow rate: 1 mL/min): 7.0 minutes ¹H-NMR (400 MHz, CDCl₃) δ (ppm): 1.54 (s, 9H), 1.80-1.88 (m, 2H), 2.04-2.12 (m, 3H), 2.38-2.46 (m, 1H), 2.48-2.53 (m, 1H), 2.89-2.94 (m, 2H), 3.66 (br, 2H), 4.68-4.88 (m, 1H), 6.51-6.57 (m, 2H), 6.83-6.88 (m, 1H)

Preparation Example 64

Synthesis of tert-butyl (−)-[(4aR*,6S*,8aS*)-8a-(5-amino-2-fluorophenyl)-6-fluoro-4a,5,6,7,8,8a-hexahydro-4H-benzo[d][1,3]thiazin-2-yl]carbamate

[Formula 86]

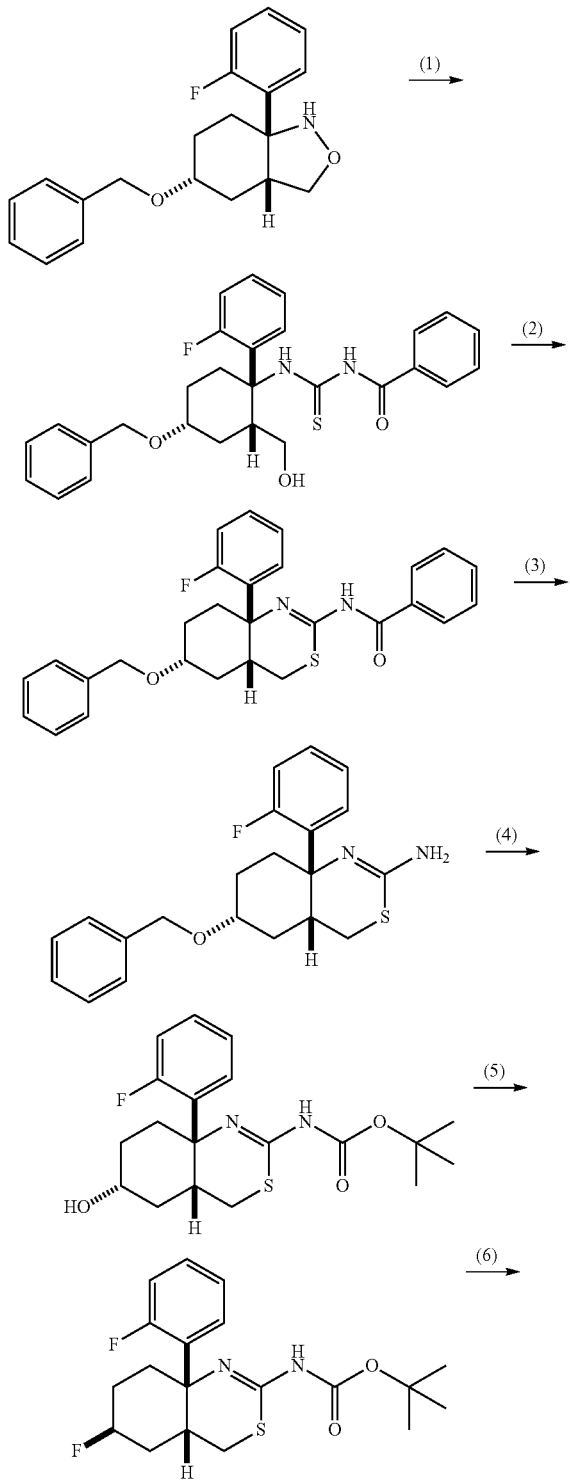

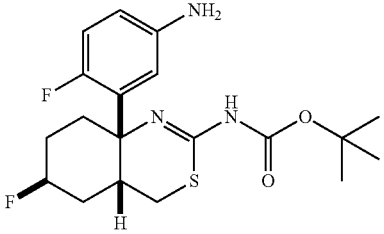

racemic

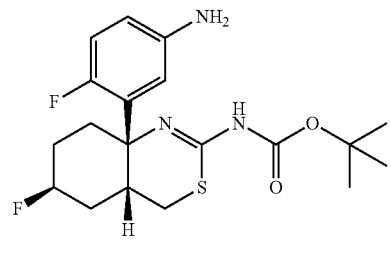

chiral

(1) Synthesis of (±)-1-benzoyl-3-[(1S*,2R*,4R*)-4-benzyloxy-1-(2-fluorophenyl)-2-hydroxymethylcyclohexyl]thiourea The title compound (3.13 g) was obtained from (±)-(3aR*,5R*,7aS*)-5-benzyloxy-7a-(2-fluorophenyl)-octahydrobenz[c]isoxazole obtained in Preparation Example 62-(4) (2.48 g) according to the method of Preparation Example 57-(6).

$^1$H-NMR (400 MHz, CDCl$_3$) δ (ppm): 1.59-1.69 (m, 2H), 1.95-2.10 (m, 2H), 2.31-2.34 (m, 2H), 3.58-3.72 (m, 3H), 3.85 (br, 1H), 4.64 (s, 2H), 7.02-7.08 (m, 1H), 7.12-7.16 (m, 1H), 7.27-7.30 (m, 2H), 7.35-7.46 (m, 5H), 7.51-7.55 (m, 2H), 7.61-7.65 (m, 1H), 7.86-7.89 (m, 2H), 8.89 (br, 1H), 11.56 (br, 1H)

(2) Synthesis of (±)-N-[(4aR*,6R*,8aS*)-6-benzyloxy-8a-(2-fluorophenyl)-4a,5,6,7,8,8a-hexahydro-4H-benzo[d][1,3]thiazin-2-yl]benzamide The title compound (2.03 g) was obtained from (±)-1-benzoyl-3-[(1S*,2R*,4R*)-4-benzyloxy-1-(2-fluorophenyl)-2-hydroxymethylcyclohexyl]thiourea obtained in Preparation Example 64-(1) (3.13 g) according to the method of Preparation Example 57-(7).

ESI-MS; m/z 475 [M+H]

$^1$H-NMR (400 MHz, CDCl$_3$) δ (ppm): 1.80 (q, J=12.8 Hz, 1H), 1.93 (d, J=14.8 Hz, 1H), 2.01-2.17 (m, 3H), 2.42-2.49 (m, 1H), 2.59 (d, J=12.4 Hz, 1H), 2.93 (d, J=12.8 Hz, 1H), 3.00 (d, J=10.8, 1H), 3.68-3.73 (m, 1H), 4.62 (s, 2H), 7.05-7.11 (m, 1H), 7.14-7.18 (m, 1H), 7.29-7.36 (m, 7H), 7.41-7.45 (m, 2H), 7.48-7.52 (m, 1H), 8.24 (d, J=7.2 Hz, 2H), 12.30 (br, 1H)

(3) Synthesis of (±)-(4aR*,6S*,8aS*)-6-benzyloxy-8a-(2-fluorophenyl)-4a,5,6,7,8,8a-hexahydro-4H-benzo[d][1,3]thiazin-2-ylamine The title compound (1.50 g) was obtained from (±)-N-[(4aR*,6R*,8aS*)-6-benzyloxy-8a-(2-fluorophenyl)-4a,5,6,7,8,8a-hexahydro-4H-benzo[d][1,3]thiazin-2-yl]benzamide obtained in Preparation Example 64-(2) (2.03 g) according to the method of Preparation Example 58-(7).

$^1$H-NMR (400 MHz, CDCl$_3$) δ (ppm): 1.64-1.77 (m, 1H), 1.80-1.86 (m, 2H), 1.88-1.94 (m, 1H), 2.00-2.06 (m, 1H), 2.26-2.33 (m, 1H), 2.53-2.57 (m, 1H), 2.71-2.76 (m, 1H), 2.84-2.88 (m, 1H), 3.61-3.69 (m, 1H), 4.43 (br, 2H), 4.62 (d, J=4.4 Hz, 2H), 7.00 (ddd, J=1.2, 8.0, 12.8 Hz, 1H), 7.07-7.11 (m, 1H), 7.19-7.24 (m, 1H), 7.28-7.31 (m, 2H), 7.33-7.39 (m, 4H)

(4) Synthesis of tert-butyl(±)-[(4aR*,6R*,8aS*)-8a-(2-fluorophenyl)-6-hydroxy-4a,5,6,7,8,8a-hexahydro-4H-benzo[d][1,3]thiazin-2-yl]carbamate The title compound (1.59 g) was obtained from (±)-(4aR*,6R*,8aS*)-6-benzyloxy-8a-(2-fluorophenyl)-4a,5,6,7,8,8a-hexahydro-4H-benzo[d][1,3]thiazin-2-ylamine obtained in Preparation Example 64-(3) (1.50 g) according to the method of Preparation Example 58-(8).

$^1$H-NMR (400 MHz, CDCl$_3$) δ (ppm): 1.53 (s, 9H), 1.62-1.73 (m, 1H), 1.80-2.02 (m, 4H), 2.42-2.54 (m, 2H), 2.80-2.84 (m, 1H), 2.93-2.99 (m, 1H), 3.90-3.98 (m, 1H), 7.04-7.09 (m, 1H), 7.15-7.20 (m, 1H), 7.28-7.34 (m, 2H)

(5) Synthesis of tert-butyl(±)-[(4aR*,6S*,8aS*)-6-fluoro-8a-(2-fluorophenyl)-4a,5,6,7,8,8a-hexahydro-4H-benzo[d][1,3]thiazin-2-yl]carbamate tert-Butyl (±)-[(4aR*,6R*,8aS*)-8a-(2-fluorophenyl)-6-hydroxy-4a,5,6,7,8,8a-hexahydro-4H-benzo[d][1,3]thiazin-2-yl]carbamate obtained in Preparation Example 64-(4) (500 mg) was dissolved in THF. Then, perfluorobutanesulfonyl fluoride (0.43 mL, specific gravity: 1.682 g/cm$^3$), a triethylamine-trihydrofluoric acid complex (0.39 mL, specific gravity: 0.989 g/cm$^3$) and triethylamine (0.99 mL, specific gravity: 0.73 g/cm$^3$) were sequentially added at room temperature. After completion of the addition, the mixture was stirred for 15 hours. The reaction solution was concentrated under reduced pressure and then the residue was purified by silica gel column chromatography to obtain the title compound (351 mg).

$^1$H-NMR (400 MHz, CDCl$_3$) δ (ppm): 1.53 (s, 9H), 1.63-1.67 (m, 1H), 1.76-2.19 (m, 4H), 2.46-2.49 (m, 1H), 2.76-2.83 (m, 1H), 2.88-2.92 (m, 1H), 3.29-3.32 (m, 1H), 5.04 (d, J=48.0 Hz, 1H), 7.07-7.12 (m, 1H), 7.16-7.20 (m, 1H), 7.30-7.32 (m, 2H)

(6) Synthesis of tert-butyl(±)-[(4aR*,6S*,8aS*)-6-fluoro-8a-(2-fluoro-5-nitrophenyl)-4a,5,6,7,8,8a-hexahydro-4H-benzo[d][1,3]thiazin-2-yl]carbamate The title compound (266 mg) was obtained from tert-butyl (±)-[(4aR*,6S*,8aS*)-6-fluoro-8a-(2-fluorophenyl)-4a,5,6,7,8,8a-hexahydro-4H-benzo[d][1,3]thiazin-2-yl]carbamate obtained in Preparation Example 64-(5) (351 mg) according to the method of Preparation Example 57-(9), by adding di-tert-butyl dicarbonate (401 mg), stirring at room temperature for 14 hours, and then adding di-tert-butyl dicarbonate (200 mg) again.

$^1$H-NMR (400 MHz, CDCl$_3$) δ (ppm): 1.54 (s, 9H), 1.65-1.68 (m, 1H), 1.77-1.91 (m, 1H), 1.98-2.14 (m, 3H), 2.54 (dd, J=2.8, 12.8 Hz, 1H), 2.61-2.67 (m, 1H), 2.86 (dd, J=3.6, 12.8 Hz, 1H), 3.27 (br, 1H), 5.03 (d, J=48.4 Hz, 1H), 7.23-7.28 (m, 1H), 8.18-8.23 (m, 2H)

(7) Synthesis of tert-butyl(±)-[(4aR*,6S*,8aS*)-8a-(5-amino-2-fluorophenyl)-6-fluoro-4a,5,6,7,8,8a-hexahydro-4H-benzo[d][1,3]thiazin-2-yl]carbamate The title compound (191 mg) was obtained from tert-butyl (±)-[(4aR*,6S*,8aS*)-6-fluoro-8a-(2-fluoro-5-nitrophenyl)-4a,5,6,7,8,8a-hexahydro-4H-benzo[d][1,3]thiazin-2-yl]carbamate obtained in Preparation Example 64-(6) (266 mg) according to the method of Preparation Example 57-(10).

$^1$H-NMR (400 MHz, CDCl$_3$) δ (ppm): 1.53 (s, 9H), 1.56-1.68 (m, 1H), 1.75-1.93 (m, 1H), 1.99-2.16 (m, 3H), 2.47 (d, J=13.2 Hz, 1H), 2.78 (t, J=13.2 Hz, 1H), 2.98 (d, J=12.0 Hz, 1H), 3.26-3.28 (m, 1H), 3.65 (br, 2H), 5.03 (d, J=48.0 Hz, 1H), 6.53-6.58 (m, 2H), 6.85-6.90 (m, 1H)

HPLC (CHIRALPAK™ AD-H manufactured by Daicel Chemical Industries, Ltd., 2 cm×25 cm, mobile phase: hexane:ethanol=80:20, flow rate: 1 mL/min): 3.3 minutes (optical rotation (+)), 5.9 minutes (optical rotation (−))

(8) Synthesis of tert-butyl (−)-[(4aR*,6S*,8aS*)-8a-(5-amino-2-fluorophenyl)-6-fluoro-4a,5,6,7,8,8a-hexahydro-4H-benzo[d][1,3]thiazin-2-yl]carbamate tert-Butyl (±)-[(4aR*,6S*,8aS*)-8a-(5-amino-2-fluorophenyl)-6-fluoro-4a,5,6,7,8,8a-hexahydro-4H-benzo[d][1,3]thiazin-2-yl]carbamate obtained in Preparation Example 58-(12) (191 mg) was optically resolved by CHIRALPAK™ AD-H manufactured by Daicel Chemical Industries, Ltd. (2 cm×25 cm, mobile phase: hexane:ethanol=50:50, flow rate: 10 mL/min, charged with a solution of about 6 mg in 2 mL of ethanol for one cycle). The component having a retention time of 10.9 to 12.6 minutes among the two main components was collected to obtain the title compound (72 mg, >99% ee, optical rotation (−)).

HPLC (CHIRALPAK™ AD-H manufactured by Daicel Chemical Industries, Ltd., 2 cm×25 cm, mobile phase: hexane:ethanol=80:20, flow rate: 1 mL/min): 5.9 minutes $^1$H-NMR (400 MHz, CDCl$_3$) δ (ppm): 1.52 (s, 9H), 1.60-1.68 (m, 1H), 1.74-1.93 (m, 1H), 1.98-2.15 (m, 3H), 2.47 (d, J=12.8 Hz, 1H), 2.77 (t, J=13.2 Hz, 1H), 2.97 (d, J=12.4 Hz, 1H), 3.26 (d, J=10.0 Hz, 1H), 3.72 (br, 2H), 5.02 (d, J=48.0 Hz, 1H), 6.53-6.58 (m, 2H), 6.85-6.90 (m, 1H)

Preparation Example 65

Synthesis of (±)-N,N-bis(t-butoxycarbonyl)[(4aR*,7aS*)-7a-(3-bromophenyl)-6-pyrazin-2-yl-4,4a,5,6,7,7a-hexahydropyrrolo[3,4-d][1,3]thiazin-2-yl]amine

[Formula 87]

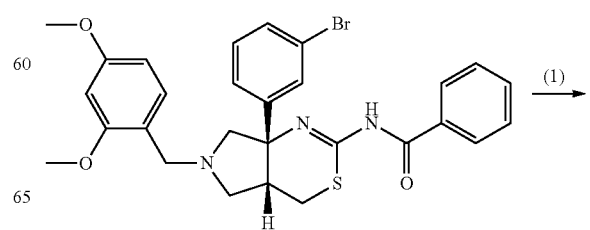

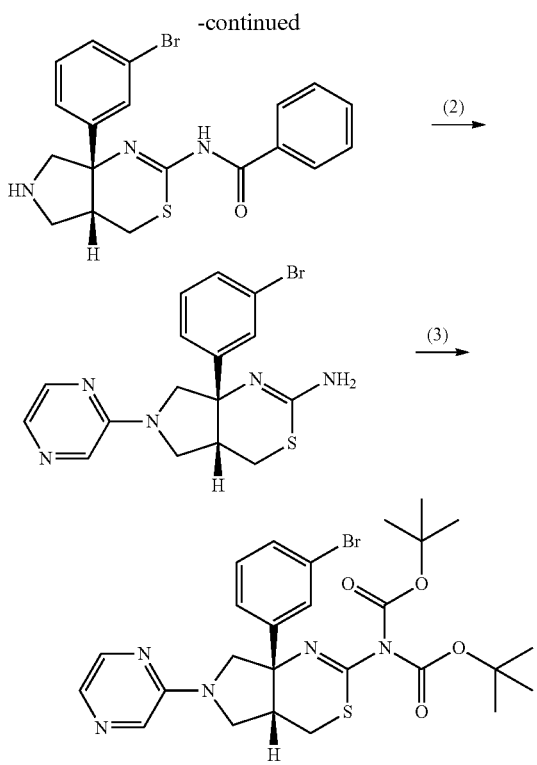

(1) Synthesis of (±)-N-[(4aR*,7aS*)-7a-(3-bromophenyl)-4,4a,5,6,7,7a-hexahydropyrrolo[3,4-d][1,3]thiazin-2-yl]benzamide The title compound (7.52 g) was obtained from (±)-N-[(4aR*,7aS*)-7a-(3-bromophenyl)-6-(2,4-dimethoxybenzyl)-4,4a,5,6,7,7a-hexahydropyrrolo[3,4-d][1,3]thiazin-2-yl]benzamide obtained in Preparation Example 18-(5) (14.5 g) according to the method of Preparation Example 18-(9).
ESI-MS; m/z 416 [M+H]

(2) Synthesis of (±)-N-(4aR*,7aS*)-7a-(3-bromophenyl)-6-pyrazin-2-yl-4,4a,5,6,7,7a-hexahydropyrrolo[3,4-d][1,3]thiazin-2-ylamine 2-Chloropyrazine (2.14 mL, specific gravity: 1.284 g/cm³) was added to (±)-N-[(4aR*,7aS*)-7a-(3-bromophenyl)-4,4a,5,6,7,7a-hexahydropyrrolo[3,4-d][1, 3]thiazin-2-yl]benzamide obtained in Preparation Example 65-(1) (2 g), and the mixture was heated to 90° C. and stirred under a nitrogen atmosphere. After 13 hours, the reaction solution was cooled to room temperature. Chloroform and a saturated sodium bicarbonate solution were added, followed by extraction with chloroform three times. The resulting organic layers were dried over anhydrous magnesium sulfate, and the solid was removed by filtration. The resulting filtrate was concentrated under reduced pressure and then purified by NH-silica gel column chromatography. Methanol (9.6 mL) was added to a mixture containing the resulting N-aryl compound. Then, a solution of sodium methoxide in methanol (373 μL, 25%, specific gravity: 0.945 g/cm³) was added and the mixture was stirred with heating under reflux. After three hours and 50 minutes, the reaction solution was cooled to room temperature. Chloroform, a saturated sodium bicarbonate solution and brine were added, followed by extraction with chloroform three times. The resulting organic layers were dried over anhydrous magnesium sulfate, and the solid was removed by filtration. The resulting filtrate was concentrated under reduced pressure and then purified by NH-silica gel column chromatography to obtain the title compound (138 mg).
ESI-MS; m/z 390 [M+H]

(3) Synthesis of (±)-N,N-bis(t-butoxycarbonyl)[(4aR*,7aS*)-7a-(3-bromophenyl)-6-pyrazin-2-yl-4,4a,5,6,7,7a-hexahydropyrrolo[3,4-d][1,3]thiazin-2-yl]amine (±)-N-(4aR*,7aS*)-7a-(3-Bromophenyl)-6-pyrazin-2-yl-4,4a,5,6,7,7a-hexahydropyrrolo[3,4-d][1,3]thiazin-2-ylamine obtained in Preparation Example 65-(2) (138 mg) was dissolved in THF (10 mL). Then, di-tert-butyl dicarbonate (232 mg) and 4-dimethylaminopyridine (151 mg) were added and the mixture was stirred at room temperature. After 11 hours and 30 minutes, the reaction solution was diluted with ethyl acetate. Then, a saturated ammonium chloride solution was added, followed by extraction with ethyl acetate. The resulting organic layer was sequentially washed with water and brine and dried over anhydrous magnesium sulfate. The solid was removed by filtration. The filtrate was concentrated under reduced pressure and then the residue was purified by silica gel column chromatography to obtain the title compound (154 mg).
¹H-NMR (400 MHz, CDCl₃) δ (ppm): 1.41 (m, 18H), 2.88-3.12 (m, 3H), 3.17-3.21 (m, 1H), 3.80-3.96 (m, 3H), 7.40-7.47 (m, 3H), 7.65-7.66 (m, 1H), 7.85 (d, J=2.0 Hz, 1H), 7.88 (d, J=1.6 Hz, 1H), 8.04-8.05 (m, 1H)

The following compounds were synthesized from ethyl 2-trifluoromethanesulfonyloxycyclohex-1-enecarboxylate and the corresponding boronic acids according to Preparation Example 1.

Preparation Example 66

Synthesis of tert-butyl(±)-[(4aR*,8aS*)-8a-(5-amino-2,4-difluorophenyl)-4a,5,6,7,8,8a-hexahydro-4H-benzo[d][1,3]thiazin-2-yl]carbamate

[Formula 88]

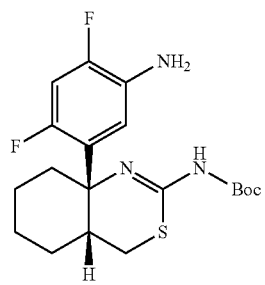

¹H-NMR (400 MHz, CDCl₃) δ (ppm): 1.53 (s, 9H), 1.46-1.73 (m, 6H), 1.83-1.89 (m, 1H), 2.28-2.34 (m, 1H), 2.48 (dd, J=3.2, 12.4 Hz, 1H), 2.77-2.81 (m, 1H), 2.87 (dd, J=4.0, 12.4 Hz, 1H), 3.68 (s, 2H), 6.66 (dd, J=8.0, 9.6 Hz, 1H), 6.78 (dd, J=10.4, 11.6 Hz, 1H).

Preparation Example 67

Synthesis of tert-butyl(±)-[(4aR*,8aS*)-8a-(5-amino-2,6-difluorophenyl)-4a,5,6,7,8,8a-hexahydro-4H-benzo[d][1,3]thiazin-2-yl]carbamate

[Formula 89]

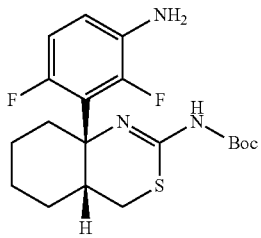 [SMILES: CC(C)(C)OC(=O)NC1=N[C@@]2(c3c(F)ccc(N)c3F)CCCC[C@H]2CS1]

¹H-NMR (400 MHz, CDCl₃) δ (ppm): 1.51 (s, 9H), 1.43-2.05 (m, 7H), 2.16-2.24 (m, 1H), 2.54-2.58 (m, 1H), 2.97-3.01 (m, 1H), 3.18 (dd, J=4.4, 12.8 Hz, 1H), 3.63 (s, 2H), 6.64-6.73 (m, 2H).

Preparation Example 68

Synthesis of 5-(1-ethoxy-vinyl)-pyridine-2-carboxylic acid

[Formula 90]

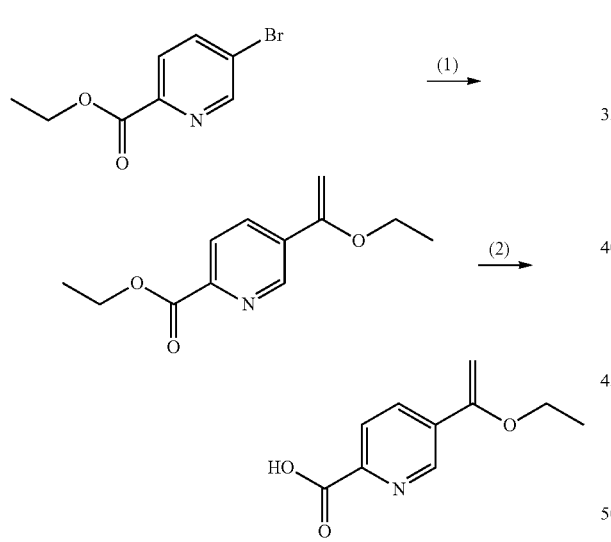

(1) Synthesis of ethyl 5-(1-ethoxyvinyl)pyridine-2-carboxylate

1-Ethoxyvinyltri-N-butyltin (880 μL) and tetrakis(triphenylphosphine)palladium (125 mg) were added to a solution of 5-bromopyridine-2-carboxylic acid (500 mg) in DMF (10 mL). After replacement with nitrogen, the mixture was heated to 85° C. and stirred overnight. After cooling to room temperature, ethyl acetate was added to the reaction mixture. The organic layer was washed with water and brine and dried over anhydrous magnesium sulfate. The solvent was evaporated under reduced pressure and the residue was purified by silica gel column chromatography to obtain the title compound (342 mg).

¹H-NMR (400 MHz, CDCl₃) δ (ppm): 1.42-1.47 (m, 6H), 3.96 (q, J=6.4 Hz, 2H). 4.40 (d, J=3.4 Hz, 1H), 4.49 (q, J=6.8 Hz, 2H), 4.81 (d, J=3.4 Hz, 1H), 8.03 (dd, J=2.2, 8.4 Hz, 1H), 8.10 (dd, J=0.8, 8.4 Hz, 1H), 8.98 (dd, J=0.8, 2.2 Hz, 1H).

(2) Synthesis of 5-(1-ethoxyvinyl)pyridine-2-carboxylic acid

A 5 N sodium hydroxide solution (2 mL) was added to a solution of ethyl 5-(1-ethoxyvinyl)pyridine-2-carboxylate (100 mg) in ethanol (5 mL). The mixture was stirred at room temperature for two hours. After confirming completion of the reaction, the reaction solution was neutralized with 1 N hydrochloric acid. The aqueous layer was extracted with ethyl acetate, and the organic layer was dried over anhydrous magnesium sulfate. The solvent was evaporated under reduced pressure to obtain the title compound (92 mg).

¹H-NMR (400 MHz, CD OD) δ (ppm): 1.44 (t, J=6.8 Hz, 3H), 3.99 (q, J=6.8 Hz, 2H), 4.52 (d, J=3.4 Hz, 1H), 4.96 (d, J=3.4 Hz, 1H), 8.13 (dd, J=0.8, 8.4 Hz, 1H), 8.21 (dd, J=2.4, 8.4 Hz, 1H), 8.90 (dd, J=0.8, 2.4 Hz, 1H).

Preparation Example 69

Synthesis of 3-methoxypyridine-2-carboxylic acid

[Formula 91]

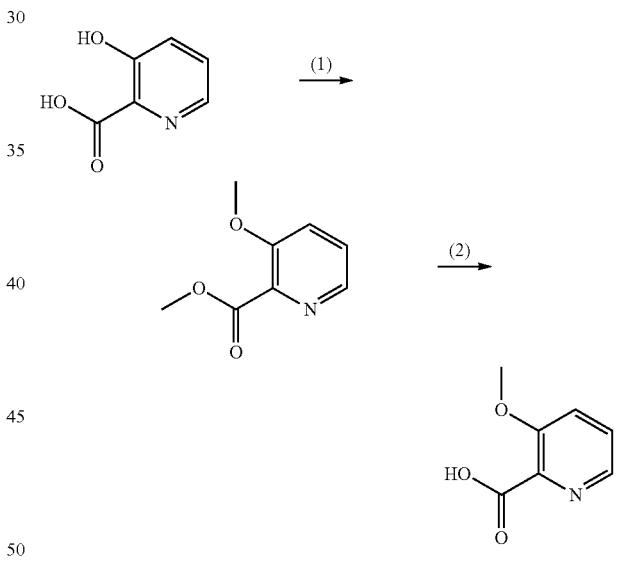

(1) Synthesis of methyl 3-methoxypyridine-2-carboxylate

Sodium hydride (60%, 253 mg) was added to a solution of 3-hydroxypicolinic acid (440 mg) in DMF (4 mL) in an ice bath. After stirring at room temperature for 30 minutes, iodomethane (393 μL) was added and the mixture was stirred at room temperature overnight. Ice was added to the reaction mixture to terminate the reaction. The aqueous layer was extracted with ethyl acetate, and the organic layer was washed with water and brine. The organic layer was dried over anhydrous magnesium sulfate, and then the solvent was evaporated under reduced pressure. The residue was purified by silica gel column chromatography to obtain the title compound (112 mg).

$^1$H-NMR (400 MHz, CDCl$_3$) δ (ppm): 3.85 (s, 3H), 3.90 (s, 3H), 7.30 (dd, J=1.2, 8.6 Hz, 1H), 7.35 (dd, J=4.4, 8.6 Hz, 1H), 8.20 (dd, J=1.2, 4.4 Hz, 1H).

(2) Synthesis of 3-methoxypyridine-2-carboxylic acid

A 5 N sodium hydroxide solution (147 μL) was added to a solution of methyl 3-methoxypyridine-2-carboxylate (112 mg) in methanol (2 mL), and the mixture was stirred at room temperature overnight. The excess of methanol was evaporated under reduced pressure, and the residue was diluted with water. The aqueous layer was washed with ether and then made weak acidic with 5 N hydrochloric acid. The aqueous layer was extracted with a THF-ethyl acetate mixed solvent, and then the organic layer was dried over anhydrous magnesium sulfate. The solvent was evaporated under reduced pressure to obtain the title compound (19 mg).

$^1$H-NMR (400 MHz, CD$_3$OD) δ (ppm): 3.95 (s, 3H), 7.96 (dd, J=4.4, 8.2 Hz, 1H), 7.71 (d, J=8.2 Hz, 1H), 8.18 (d, J=4.4 Hz, 1H).

Preparation Example 70

Synthesis of 5-(1-methyl-1H-pyrazol-4-yl)-pyridine-2-carboxylic acid

[Formula 92]

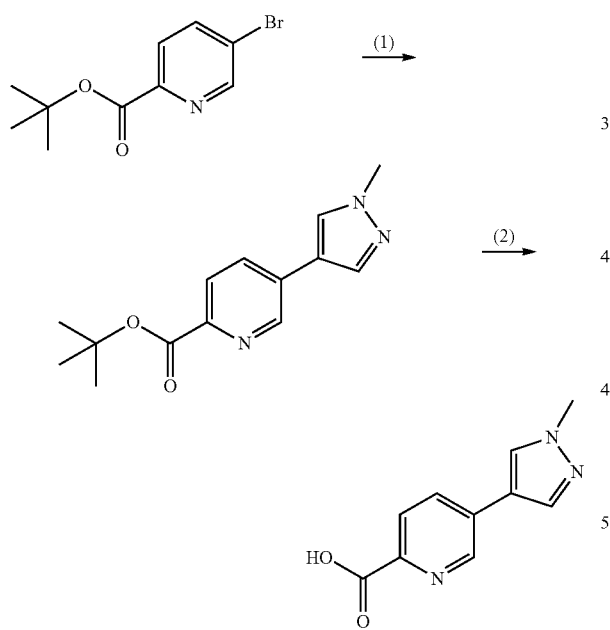

(1) Synthesis of tert-butyl 5-(1-methyl-1H-pyrazol-4-yl)-pyridine-2-carboxylate

1-Methyl-4-(4,4,5,5-tetramethyl-1,3,2-dioxaborolan-2-yl)-1H-pyrazole (80.7 mg), bis(tri-tert-butylphosphine)palladium (0) (9.91 mg) and a 1 N potassium phosphate solution (388 μL) were added to a solution of tert-butyl 5-bromopyridine-2-carboxylate (50 mg) in 1,4-dioxane (2 mL). After replacement with nitrogen, the mixture was heated to 100° C. and stirred for eight hours. The reaction solution was cooled to room temperature, and the solvent was evaporated under reduced pressure. The residue was purified by silica gel column chromatography to obtain the title compound as a mixture (81 mg).

NMR $^1$H-NMR (400 MHz, CDCl$_3$) δ (ppm): 1.65 (s, 9H), 3.99 (s, 3H), 7.74 (s, 1H), 7.82-7.85 (m, 2H), 8.04 (dd, J=1.2, 8.4 Hz, 1H), 8.85 (dd, J=0.8, 2.4 Hz, 1H). ESI-MS; m/z 260 [M$^+$+H]

(2) Synthesis of 5-(1-methyl-1H-pyrazol-4-yl)-pyridine-2-carboxylic acid

TFA (1 mL) was added to a solution of tert-butyl 5-(1-methyl-1H-pyrazol-4-yl)-pyridine-2-carboxylate (81 mg) in dichloromethane (4 mL), and the mixture was stirred at room temperature overnight. The solvent was evaporated under reduced pressure to obtain a crude product of the title compound (170 mg).

$^1$H-NMR (400 MHz, DMSO-d$_6$) δ (ppm): 3.90 (s, 3H), 8.03 (dd, J=0.8, 8.2 Hz, 1H), 8.09 (d, J=0.8 Hz, 1H), 8.14 (dd, J=2.0, 8.2 Hz, 1H), 8.41 (s, 1H), 8.95 (dd, J=0.8, 2.0 Hz, 1H).

Preparation Example 71

Synthesis of (±)-N,N-bis(t-butoxycarbonyl) [(4aR*,7aS*)-7a-(3-amino-5-chlorophenyl)-4,4a,5,6,7,7a-hexahydro-cyclopenta[d][1,3]thiazin-2-yl]amine

[Formula 93]

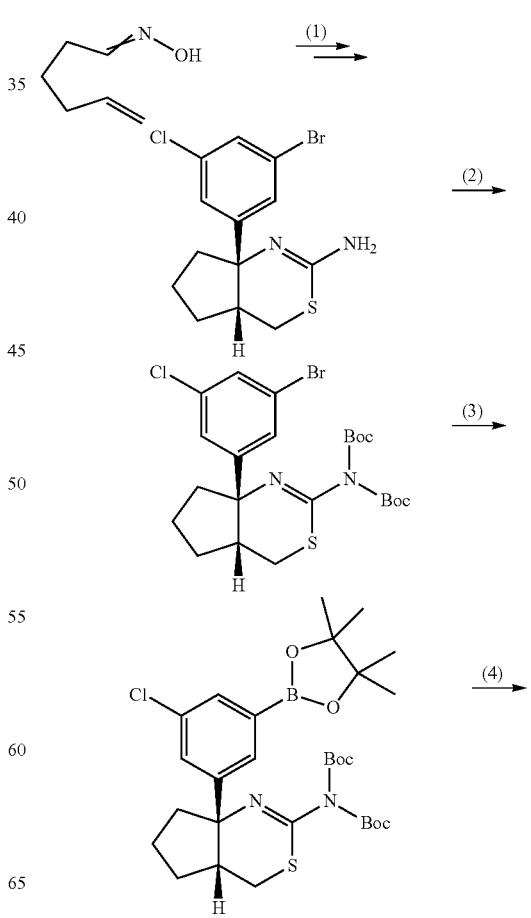

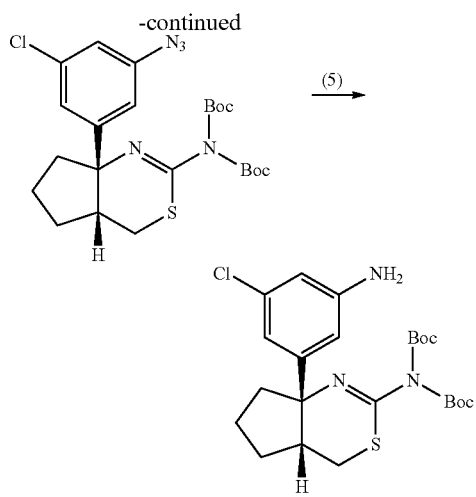

(1) Synthesis of (±)-(4aR*,7aS*)-7a-(3-bromo-5-chlorophenyl)-4,4a,5,6,7,7a-hexahydrocyclopenta[d][1,3]thiazin-2-ylamine The title compound was synthesized from hex-5-enal oxime (JOC, 41(5), 863-9; 1976) according to the method of Preparation Example 8, using 1,3-dibromo-5-chlorobenzene instead of 2-fluorobromobenzene.

$^1$H-NMR (400 MHz, CDCl$_3$) δ (ppm): 1.66-2.00 (m, 5H), 2.17-2.24 (m, 1H), 2.33-2.39 (m, 1H), 2.73 (dd, J=4.0, 12.6 Hz, 1H), 2.97 (dd, J=3.2, 12.6 Hz, 1H), 4.36 (br, 2H), 7.27 (t, J=2.0 Hz, 1H), 7.36 (t, J=2.0 Hz, 1H), 7.37 (t, J=1.6 Hz, 1H).

(2) Synthesis of (±)-N,N-bis(t-butoxycarbonyl)[(4aR*,7aS*)-7a-(3-bromo-5-chlorophenyl)-4,4a,5,6,7,7a-hexahydrocyclopenta[d][1,3]thiazin-2-yl]amine Di-tert-butyl dicarbonate (1.05 g) and 4-dimethylaminopyridine (393 mg) were added to a solution of (±)-(4aR*,7aS*)-7a-(3-bromo-5-chlorophenyl)-4,4a,5,6,7,7a-hexahydrocyclopenta[d][1,3]thiazin-2-ylamine (555 mg) in dichloromethane (30 mL). The mixture was stirred at room temperature overnight, and then the solvent was evaporated under reduced pressure at room temperature or lower. The residue was purified by silica gel column chromatography to obtain the title compound (140 mg).

$^1$H-NMR (400 MHz, CDCl$_3$) δ (ppm): 1.53 (s, 18H), 1.77-2.14 (m, 5H), 2.22-2.30 (m, 1H), 2.48-2.54 (m, 1H), 2.82 (dd, J=3.2, 13.0 Hz, 1H), 3.06 (dd, J=3.6, 13.0 Hz, 1H), 7.34 (t, J=2.0 Hz, 1H), 7.38 (t, J=1.6 Hz, 1H), 7.44 (t, J=1.6 Hz, 1H).
ESI-MS; m/z 547 [M$^+$+H].

(±)-N-(t-Butoxycarbonyl)-N-(methoxycarbonyl)[(4aR*,7aS*)-7a-(3-bromo-5-chlorophenyl)-4,4a,5,6,7,7a-hexahydrocyclopenta[d][1,3]thiazin-2-yl]amine generated during purification (575 mg) was obtained as a by-product.

$^1$H-NMR (400 MHz, CDCl$_3$) δ (ppm): 1.55 (s, 9H), 1.78-2.04 (m, 4H), 2.12 (ddd, J=3.2, 7.2, 13.2 Hz, 1H), 2.26-2.33 (m, 1H), 2.44-2.50 (m, 1H), 2.83 (dd, J=3.6, 12.8 Hz, 1H), 3.06 (dd, J=3.2, 12.8 Hz, 1H), 3.92 (s, 3H), 7.32 (t, J=2.0 Hz, 1H), 7.40 (t, J=2.0 Hz, 1H), 7.42 (t, J=1.6 Hz, 1H). ESI-MS; m/z 505 [M$^+$+H].

(3) Synthesis of (±)-N,N-bis(t-butoxycarbonyl){(4aR*,7aS*)-7a-[3-chloro-5-(4,4,5,5-tetramethyl-[1,3,2]dioxaborolan-2-yl)phenyl]-4,4a,5,6,7,7a-hexahydro-cyclopenta[d][1,3]thiazin-2-yl}amine 1,1'-Bis(diphenylphosphino)ferrocene dichloropalladium (II) (40.2 mg), bis(pinacolato)diboron (1.40 g) and potassium acetate (216 mg) were added to a solution of (±)-N,N-bis(t-butoxycarbonyl) [(4aR*,7aS*)-7a-(3-bromo-5-chlorophenyl)-4,4a,5,6,7,7a-hexahydrocyclopenta[d][1,3]thiazin-2-yl]amine (300 mg) in DMF (6 mL). After replacement with nitrogen, the mixture was stirred at 80° C. for six hours. The reaction mixture was cooled to room temperature and diluted with ethyl acetate. The organic layer was washed with water twice and brine once and dried over anhydrous magnesium sulfate. The solvent was evaporated under reduced pressure and the residue was purified by silica gel column chromatography to obtain the title compound (1.16 g) as a mixture.

$^1$H-NMR (400 MHz, CDCl$_3$) δ (ppm): 1.34 (s, 12H), 1.52 (s, 18H), 1.76-2.14 (m, 5H), 2.22-2.30 (m, 1H), 2.48-2.54 (m, 1H), 2.80 (dd, J=3.6, 13.2 Hz, 1H), 3.08 (dd, J=3.6, 13.2 Hz, 1H), 7.50 (t, J=2.0 Hz, 1H), 7.65 (m, 2H).
ESI-MS; m/z 593 [M$^+$+H].

(4) Synthesis of (±)-N,N-bis(t-butoxycarbonyl)[(4aR*,7aS*)-7a-(3-azido-5-chlorophenyl)-4,4a,5,6,7,7a-hexahydrocyclopenta[d][1,3]thiazin-2-yl]amine Sodium azide (53 mg) and copper (II) acetate (19.9 mg) were added to a solution of (±)-N,N-bis(t-butoxycarbonyl){(4aR*,7aS*)-7a-[3-chloro-5-(4,4,5,5-tetramethyl-[1,3,2]dioxaborolan-2-yl)phenyl]-4,4a,5,6,7,7a-hexahydrocyclopenta[d][1,3]thiazin-2-yl}amine (1.16 g) in methanol (20 mL). The mixture was stirred at room temperature for six days. Brine was added to the reaction mixture, followed by extraction with ethyl acetate. The organic layer was dried over anhydrous magnesium sulfate, and the solvent was evaporated under reduced pressure. The residue was purified by silica gel column chromatography to obtain the title compound (58.0 mg).

$^1$H-NMR (400 MHz, CDCl$_3$) δ (ppm): 1.53 (s, 18H), 1.78-2.15 (m, 5H), 2.25-2.32 (m, 1H), 2.46-2.51 (m, 1H), 2.81 (dd, J=3.2, 12.8 Hz, 1H), 3.05 (dd, J=3.2, 12.8 Hz, 1H), 6.89 (t, J=2.0 Hz, 1H), 7.03 Hz (t, J=2.0 Hz, 1H), 7.16 (t, J=1.6 Hz, 1H).
ESI-MS; m/z 508 [M$^+$+H].

(5) Synthesis of (±)-N,N-bis(t-butoxycarbonyl)[(4aR*,7aS*)-7a-(3-amino-5-chlorophenyl)-4,4a,5,6,7,7a-hexahydrocyclopenta[d][1,3]thiazin-2-yl]amine Ammonium formate (12.4 mg) and zinc (3.86 mg) were added to a solution of (±)-N,N-bis(t-butoxycarbonyl) [(4aR*,7aS*)-7a-(3-azido-5-chlorophenyl)-4,4a,5,6,7,7a-hexahydrocyclopenta[d][1,3]thiazin-2-yl]amine (20.0 mg) in methanol (2 mL). The mixture was stirred at room temperature overnight, and then the excess of methanol was evaporated under reduced pressure. The residue was diluted with ethyl acetate, and the organic layer was washed with an ammonium chloride solution. The solvent was evaporated under reduced pressure and the residue was purified by pTLC to obtain the title compound (13.0 mg).

$^1$H-NMR (400 MHz, CDCl$_3$) δ (ppm): 1.52 (s, 18H), 1.75-2.11 (m, 5H), 2.25-2.33 (m, 1H), 2.44-2.50 (m, 1H), 2.81 (dd, J=3.6, 12.8 Hz, 1H), 3.12 (dd, J=3.6, 12.8 Hz, 1H), 3.72 (brs, 2H) 6.53 (t, J=2.0 Hz, 1H), 6.65 Hz (t, J=1.6 Hz, 1H), 6.74 (t, J=1.6 Hz, 1H). ESI-MS; m/z 482 [M$^+$+H].

Preparation Example 72

Synthesis of (±)-N,N-bis(tert-butoxycarbonyl)[(4aR*,7aS*)-7a-(5-bromo-2-fluorophenyl)-4,4a,5,6,7,7a-hexahydrocyclopenta[d][1,3]thiazin-2-yl]amine

[Formula 94]

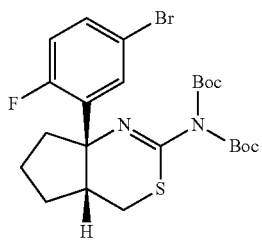 [SMILES: CC(C)(C)OC(=O)N(C(=O)OC(C)(C)C)C1=N[C@@]2(c3cc(Br)ccc3F)CCC[C@H]2CS1]

4-Dimethylaminopyridine (1.62 g) and di-tert-butyl dicarbonate (2.31 g) were added to a solution of the compound obtained in Preparation Example 54-(4) (1.00 g) in dichloromethane (25 mL). After stirring at room temperature for 14 hours, water was added to the reaction mixture to terminate the reaction. The aqueous layer was extracted with dichloromethane, and the organic layer was dried over anhydrous magnesium sulfate. The solvent was evaporated under reduced pressure and the residue was purified by silica gel column chromatography to obtain the title compound (1.13 g).

ESI-MS; m/z 531 [M$^+$+H].

Preparation Example 73

Synthesis of (±)-N,N-bis(tert-butyloxycarbonyl)[(4aR*,6R*,7aS*)-7a-(5-bromo-2-fluorophenyl)-6-methoxy-4,4a,5,6,7,7a-hexahydro-cyclopenta[d][1,3]thiazin-2-yl]amine and (±)-N,N-bis(tert-butyloxycarbonyl)[(4aR*,6R*,7aS*)-7a-(5-bromo-2-fluorophenyl)-6-methoxy-4,4a,5,6,7,7a-hexahydro-cyclopenta[d][1,3]thiazin-2-yl]amine

[Formula 95]

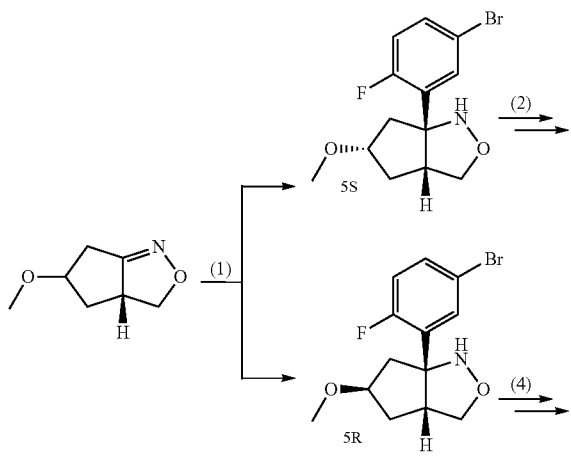

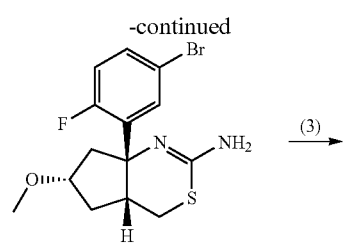

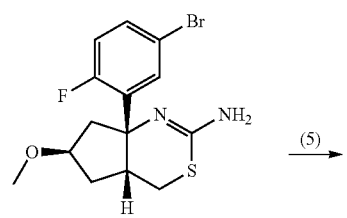

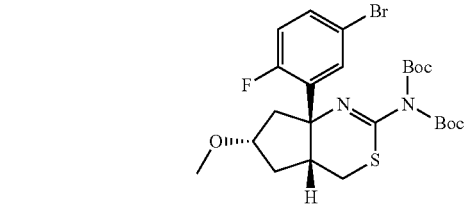

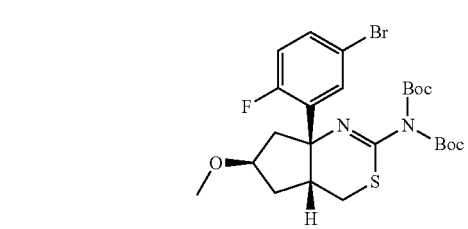

(1) Synthesis of (±)-(3aR*,5S*,6aS*)-6a-(5-bromo-2-fluorophenyl)-5-methoxy-hexahydro-cyclopenta[c]isoxazole and (±)-(3aR*,5R*,6aS*)-6a-(5-bromo-2-fluorophenyl)-5-methoxy-hexahydro-cyclopenta[c]isoxazole The less polar title compound (5S; 62 mg) and the more polar title compound (5R; 170 mg) were obtained from the compound of Preparation Example 10-(3) (mixture of more polar and less polar compounds; 450 mg) and 2,4-dibromo-1-fluorobenzene (1.78 g) according to Preparation Example 21-(3).

Less Polar Title Compound $^1$H-NMR (400 MHz, CDCl$_3$) δ (ppm): 2.08-2.26 (m, 3H), 3.21-3.29 (m, 2H), 3.30 (s, 3H). 3.68 (t, J=8.0 Hz, 1H), 4.08 (t, J=5.2 Hz, 1H), 4.40 (t, J=8.4 Hz, 1H), 6.88 (dd, J=8.4, 11.2 Hz, 1H), 7.31 (ddd, J=2.8, 4.4, 8.4 Hz, 1H), 8.09 (dd, J=2.8, 7.2 Hz, 1H).

More Polar Title Compound $^1$H-NMR (400 MHz, CDCl$_3$) δ (ppm): 2.03-2.20 (m, 3H), 2.33 (dd, J=5.8, 13.4 Hz, 1H), 3.23-3.29 (m, 1H), 3.35 (s, 3H), 3.59 (brs, 1H), 4.10-4.16 (m, 1H), 4.25-4.28 (m, 1H), 6.94 (dd, J=9.0, 10.8 Hz, 1H), 7.35 (ddd, J=2.8, 4.8, 8.8 Hz, 1H), 7.85-7.87 (m, 1H).

(2) Synthesis of (±)-(4aR*,6S*,7aS*)-7a-(5-bromo-2-fluorophenyl)-6-methoxy-4,4a,5,6,7,7a-hexahydro-cyclopenta[d][1,3]thiazin-2-ylamine The title compound was obtained from (±)-(3aR*,5S*,6aS*)-6a-(5-bromo-2-fluorophenyl)-5-methoxy-hexahydro-cyclopenta[c]isoxazole according to the method of Preparation Example 28.

$^1$H-NMR (400 MHz, CDCl$_3$) δ (ppm): 1.98-2.10 (m, 2H), 2.16-2.22 (m, 1H), 2.57-2.64 (m, 1H), 2.76 (dd, J=4.4, 13.2 Hz, 1H) 2.87-2.93 (m, 2H), 3.33 (s, 3H), 4.10-4.17 (m, 1H), 6.90 (dd, J=4.4, 11.6 Hz, 1H), 7.32 (ddd, J=2.4, 4.0, 8.4 Hz, 1H), 7.43 (dd, J=2.4, 7.6 Hz, 1H).

ESI-MS; m/z 359 [M$^+$+H].

(3) Synthesis of (±)-N,N-bis(tert-butyloxycarbonyl)[(4aR*,6S*,7aS*)-7a-(5-bromo-2-fluorophenyl)-6-methoxy-4,4a,5,6,7,7a-hexahydro-cyclopenta[d][1,3]thiazin-2-yl]amine The title compound (22 mg) was obtained from (±)-(4aR*,6S*,7aS*)-7a-(5-bromo-2-fluorophenyl)-6-methoxy-4,4a,5,6,7,7a-hexahydro-cyclopenta[d][1,3]thiazin-2-ylamine (15 mg) according to Preparation Example 72.

ESI-MS; m/z 559 [M$^+$+H].

(4) Synthesis of (±)-(4aR*,6R*,7aS*)-7a-(5-bromo-2-fluorophenyl)-6-methoxy-4,4a,5,6,7,7a-hexahydro-cyclopenta[d][1,3]thiazin-2-ylamine The title compound was obtained from (±)-(3aR*,5R*,6aS*)-6a-(5-bromo-2-fluorophenyl)-5-methoxy-hexahydro-cyclopenta[c]isoxazole according to the method of Preparation Example 19.

$^1$H-NMR (400 MHz, CDCl$_3$) δ (ppm): 1.87 (ddd, J=4.0, 9.6, 13.6 Hz, 1H), 2.25-2.30 (m, 2H), 2.56 (dd, J=7.0, 13.0 Hz, 1H), 2.72 (dd, 3.6, 12.8 Hz, 1H), 2.94 (dd, J=3.2, 12.8 Hz, 1H), 3.06-3.12 (m, 1H), 3.32 (s, 3H), 3.87-3.94 (m, 1H), 4.41 (br, 2H), 6.91 (dd, J=8.8, 12.0 Hz, 1H), 7.33 (ddd, J=2.4, 4.4, 8.8 Hz, 1H), 7.40 (dd, J=2.4, 7.2 Hz, 1H). ESI-MS; m/z 361 [M$^+$+H].

(5) Synthesis of (±)-N,N-bis(tert-butyloxycarbonyl)[(4aR*,6R*,7aS*)-7a-(5-bromo-2-fluorophenyl)-6-methoxy-4,4a,5,6,7,7a-hexahydro-cyclopenta[d][1,3]thiazin-2-yl]amine The title compound (92 mg) was obtained from (±)-(4aR*,6R*,7aS*)-7a-(5-bromo-2-fluorophenyl)-6-methoxy-4,4a,5,6,7,7a-hexahydro-cyclopenta[d][1,3]thiazin-2-ylamine (65 mg) according to Preparation Example 72.

ESI-MS; m/z 559 [M$^+$+H].

Preparation Example 74

Synthesis of benzyl (±)-[(4aR*,8aS*)-8a-(5-bromo-2,4-difluorophenyl)-4a,5,6,7,8,8a-hexahydro-4H-benzo[d][1,3]thiazin-2-yl]carbamate

[Formula 96]

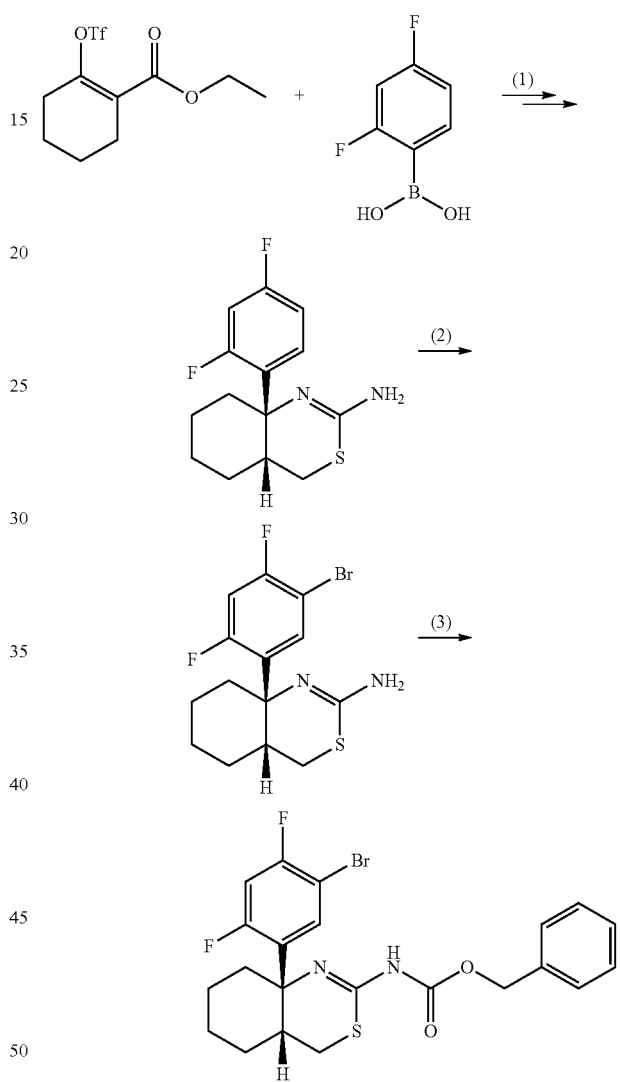

(1) Synthesis of (±)-(4aR*,8aS*)-8a-(2,4-difluorophenyl)-4a,5,6,7,8,8a-hexahydro-4H-benzo[d][1,3]thiazin-2-ylamine The title compound was synthesized from ethyl 2-trifluoromethanesulfonyloxycyclohex-1-enecarboxylate and 2,4-difluorophenylboronic acid according to Preparation Example 1.

$^1$H-NMR (400 MHz, CDCl$_3$) δ (ppm): 1.43-1.80 (m, 7H), 2.16-2.24 (m, 1H), 2.48 (dd, J=3.2, 12.0 Hz, 1H), 2.60-2.66 (m, 1H), 2.85 (dd, J=4.0, 12.0 Hz, 1H), 4.47 (s, 2H), 6.74-6.84 (m, 1H), 7.21-7.28 (m, 1H).

(2) Synthesis of (±)-(4aR*,8aS*)-8a-(5-bromo-2,4-difluorophenyl)-4a,5,6,7,8,8a-hexahydro-4H-benzo[d][1,3]thiazin-2-ylamine (±)-(4aR*,8aS*)-8a-(2,4-Difluoro-phenyl)-4a,5,6,7,8,8a-hexahydro-4H-benzo[d][1,3]thiazin-2-ylamine (270 mg) was dissolved in concentrated sulfuric acid (3 mL). N-Bromosuccinimide (170 mg) was added in an ice bath, and the mixture was stirred at the same temperature for two hours. Ice was added to terminate the reaction, followed by dilution with ether. The reaction solution was neutralized with a sodium bicarbonate solution, and the aqueous layer was extracted with ethyl acetate. The organic layer was dried over anhydrous magnesium sulfate, and the solvent was evaporated under reduced pressure. The residue was purified by silica gel column chromatography to obtain the title compound (330 mg).

$^1$H-NMR (400 MHz, CDCl$_3$) δ (ppm): 1.43-1.80 (m, 7H), 2.09-2.16 (m, 1H), 2.56 (dd, J=2.8, 12.0 Hz, 1H), 2.59-2.63 (m, 1H), 2.85 (dd, J=4.0, 12.0 Hz, 1H), 6.86 (dd, J=8.0, 11.6 Hz, 1H), 7.45 (t, J=8.4, 1H). ESI-MS; m/z 361 [M$^+$+H].

(3) Synthesis of benzyl (±)-[(4aR*,8aS*)-8a-(5-bromo-2,4-difluorophenyl)-4a,5,6,7,8,8a-hexahydro-4H-benzo[d][1,3]thiazin-2-yl]carbamate (±)-(4aR*,8aS*)-8a-(5-Bromo-2,4-difluorophenyl)-4a,5,6,7,8,8a-hexahydro-4H-benzo[d][1,3]thiazin-2-ylamine (330 mg) was suspended in 1,4-dioxane (10 mL) and a saturated sodium carbonate solution (10 mL).

Benzyl chloroformate (156 μL) was added and the mixture was stirred at room temperature overnight. The aqueous layer was extracted with ethyl acetate, and the organic layer was dried over anhydrous magnesium sulfate. The solvent was evaporated under reduced pressure and the residue was purified by silica gel column chromatography to obtain the title compound (501 mg).

$^1$H-NMR (400 MHz, CDCl$_3$) δ (ppm): 1.47-1.90 (m, 7H), 2.25-2.30 (m, 1H), 2.55 (dd, J=2.4, 12.8 Hz, 1H), 2.81-2.87 (m, 2H), 4.71 (s, 1H), 5.18 (s, 2H), 6.93 (dd, J=8.0, 12.0 Hz, 1H), 7.26-7.45 (m, 6H).

Preparation Example 75

Synthesis of tert-butyl(±)-[(3aS*,7aR*)-7a-(3-aminophenyl)-3a,6,7,7a-tetrahydro-4H-pyrano[4,3-d]thiazol-2-yl]carbamate

[Formula 97]

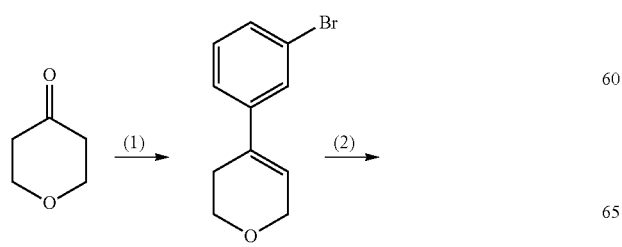

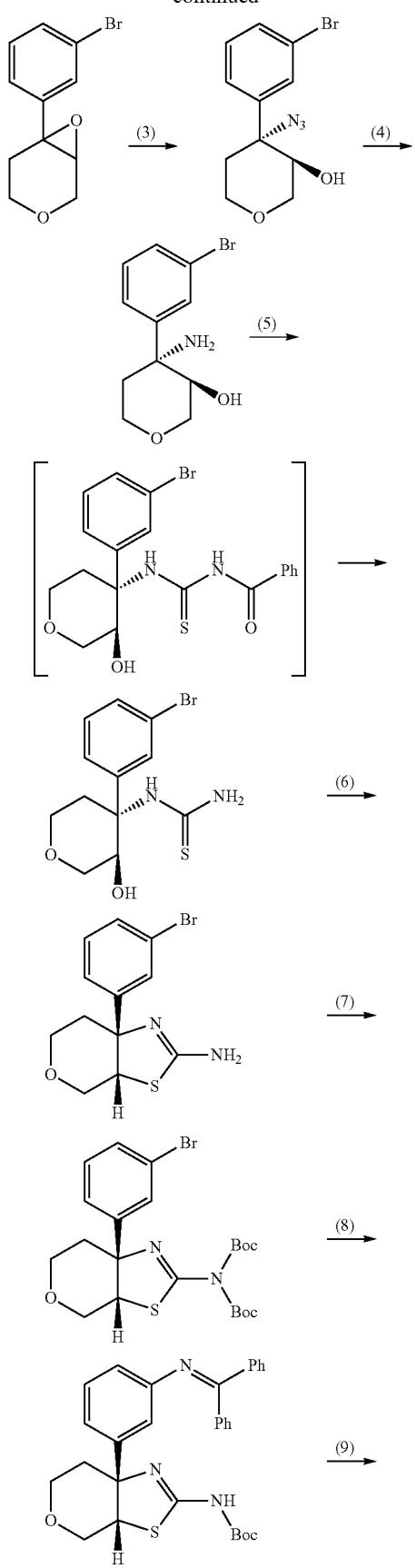

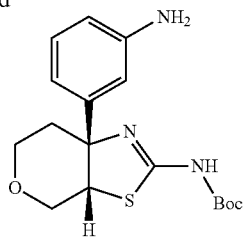

(1) Synthesis of 4-(3-bromophenyl)-3,6-dihydro-2H-pyran n-Butyllithium (2.64 M, 37.9 mL) was added dropwise to a solution of 1,3-dibromobenzene (23.5 g) in tetrahydrofuran (469 mL) at −78° C. The mixture was stirred at the same temperature for 30 minutes, and then tetrahydro-4H-pyran-4-one (10.0 g) was added dropwise. The mixture was stirred at the same temperature for 30 minutes and then warmed to room temperature. After stirring at room temperature for four hours, an ammonium chloride solution was added to the reaction mixture to terminate the reaction. The aqueous layer was extracted with ethyl acetate, and the organic layer was washed with water and brine. The organic layer was dried over anhydrous magnesium sulfate. The solvent was evaporated under reduced pressure, and the resulting residue was dissolved in toluene (400 mL). p-Toluenesulfonic acid monohydrate (2 g) was added and the mixture was stirred with heating under reflux for two hours. The reaction mixture was cooled to room temperature and purified by NH-silica gel column chromatography to obtain the title compound (21.4 g).

$^1$H-NMR (400 MHz, CDCl$_3$) δ (ppm): 2.46-2.50 (m, 2H), 3.94 (t, J=5.6 Hz, 2H), 4.32 (dd, J=2.4, 5.6 Hz, 2H), 6.13-6.15 (m, 1H), 7.20 (t, J=8.0 Hz, 1H), 7.30-7.32 (m, 1H), 7.38 (ddd, J=1.2, 1.6, 8.0 Hz, 1H), 7.52 (t, J=1.6 Hz, 1H).

(2) Synthesis of (±)-6-(3-bromophenyl)-3,7-dioxa-bicyclo[4.1.0]heptane

3-Chloroperbenzoic acid (purity: 80%, 25.1 g) was added to a solution of 4-(3-bromophenyl)-3,6-dihydro-2H-pyran (21.4 g) in dichloromethane (400 mL) in an ice bath. The mixture was stirred at the same temperature for three hours, and then warmed to room temperature and stirred for five hours. Ice and a saturated sodium bicarbonate solution were added to the reaction mixture, and the organic layer was separated. The organic layer was sequentially washed with a saturated sodium bicarbonate solution, a sodium thiosulfate solution and brine. The aqueous layers were combined and extracted with ethyl acetate, and the organic layer was sequentially washed with a sodium bicarbonate solution, a sodium thiosulfate solution and brine. The organic layers were combined and dried over anhydrous magnesium sulfate, and the solvent was evaporated under reduced pressure. The residue was purified by silica gel column chromatography to obtain the title compound (17.5 g).

$^1$H-NMR (400 MHz, CDCl$_3$) δ (ppm): 2.09 (dt, J=3.6, 14.8 Hz, 1H), 2.51 (ddd, 6.0, 8.0, 14.8 Hz, 1H), 3.17 (d, J=3.2 Hz, 1H), 3.65-3.68 (m, 2H), 4.01 (d, J=13.6 Hz, 1H), 4.13 (dd, J=3.2, 13.2 Hz, 1H), 7.24 (t, J=8.0 Hz, 1H), 7.33 (ddd, J=1.2, 1.6, 8.0 Hz, 1H), 7.44 (ddd, 1.2, 2.0, 8.0 Hz, 1H), 7.55 (t, J=2.0 Hz, 1H).

(3) Synthesis of (±)-(3R*,4R*)-4-azido-4-(3-bromophenyl)tetrahydropyran-3-ol Water (88 mL) and ammonium chloride (11.7 g) were added to a solution of (±)-6-(3-bromophenyl)-3,7-dioxa-bicyclo[4.1.0]heptane (17.5 g) in methanol (700 mL), followed by stirring at room temperature. Then, sodium azide (32.1 g) was added, followed by stirring at 80° C. for eight hours. After returning to room temperature, the excess of methanol was evaporated under reduced pressure. The residual aqueous layer was extracted with chloroform three times, and the organic layers were dried over anhydrous magnesium sulfate. The solvent was evaporated under reduced pressure and the residue was purified by silica gel column chromatography to obtain the title compound (22.1 g).

$^1$H-NMR (400 MHz, CDCl$_3$) δ (ppm): 1.94 (ddd, J=1.6, 3.6, 14.4 Hz, 1H), 2.09 (d, J=7.2 Hz, 1H), 2.61 (ddd, J=5.2, 12.4, 14.4 Hz, 1H), 3.71 (dd, J=1.6, 7.2 Hz, 1H), 3.84 (d, J=1.6 Hz, 1H), 3.88 (t, J=1.6 Hz, 1H), 3.97-4.00 (m, 1H), 4.03 (dd, J=1.2, 12.4 Hz, 1H), 7.34 (t, J=8.0 Hz, 1H), 7.42 (ddd, J=1.2, 2.0, 8.0 Hz, 1H), 7.52 (ddd, J=1.2, 2.0, 8.0 Hz, 1H), 7.62 (t, J=2.0 Hz, 1H).

(4) Synthesis of (±)-(3R*,4R*)-4-amino-4-(3-bromophenyl)tetrahydropyran-3-ol Ammonium formate (16.9 g) and zinc (5.25 g) were added to a solution of (±)-(3R*,4R*)-4-azido-4-(3-bromophenyl)tetrahydropyran-3-ol (16.0 g) in methanol (250 mL). The mixture was stirred at room temperature overnight, and then the excess of methanol was evaporated under reduced pressure. The residue was diluted with an ammonium chloride solution, and the aqueous layer was extracted with chloroform. The organic layer was washed with an ammonium chloride solution and brine and dried over anhydrous magnesium sulfate. The solvent was evaporated under reduced pressure and the residue was purified by silica gel column chromatography to obtain the title compound (10.9 g).

$^1$H-NMR (400 MHz, CDCl$_3$) δ (ppm): 1.62 (dd, J=2.0, 14.0 Hz, 1H), 2.58 (dt, 8.8, 14.0 Hz, 1H), 3.68 (d, 1.6 Hz, 1H), 3.85 (dd, J=2.0, 12.0 Hz, 1H), 3.92 (d, J=2.0 Hz, 1H), 3.95 (d, J=2.0 Hz, 1H), 4.14 (dd, J=1.6, 12.0 Hz, 1H), 7.27 (dd, J=8.0 Hz, 10.0 Hz, 1H), 7.40-7.43 (m, 2H), 7.63 (t, J=2.0 Hz, 1H).

(5) Synthesis of (±)-[(3R*,4R*)-4-(3-bromophenyl)-3-hydroxytetrahydropyran-4-yl]thiourea Benzoyl isothiocyanate (7.20 g) was added to a suspension of (±)-(3R*,4R*)-4-amino-4-(3-bromophenyl)tetrahydropyran-3-ol (10.9 g) in toluene (200 mL). The mixture was stirred at room temperature overnight and then diluted with tetrahydrofuran, followed by addition of silica gel. The solvent was evaporated under reduced pressure and the residue was purified by silica gel column chromatography to obtain an intermediate crude product. The resulting intermediate was suspended in methanol (300 mL), and potassium carbonate (20.0 g) was added. The mixture was stirred at room temperature overnight. Then, the insoluble matter was removed by filtration through celite, and the solvent was evaporated under reduced pressure. The residue was diluted with ethyl acetate, and the resulting solid was removed by filtration through celite. The solvent was evaporated under reduced pressure and the residue was purified by silica gel column chromatography to obtain the title compound (8.63 g).

$^1$H-NMR (400 MHz, CDCl$_3$) δ (ppm): 2.12 (d, J=13.6 Hz, 1H), 2.34 (d, J=6.4 Hz, 1H), 2.58 (ddd, J=4.4, 10.8, 14.0 Hz, 1H), 3.77-3.83 (m, 2H), 3.88 (dt, J=4.0, 12.0 Hz, 1H), 3.95

(dd, J=2.8, 12.8 Hz, 1H), 4.03 (dd, J=2.0, 12.8 Hz, 1H), 6.60 (s, 1H), 7.35 (t, J=8.0 Hz, 1H), 7.50 (ddd, J=1.2, 2.0, 8.0 Hz, 1H), 7.54 (ddd, J=1.2, 2.0, 8.0 Hz, 1H), 7.71 (t, J=2.0 Hz, 1H).
ESI-MS; m/z 333 [M$^+$+H].

(6) Synthesis of (±)-(3aS*, 7aR*)-7a-(3-bromophenyl)-3a,6,7,7a-tetrahydro-4H-pyrano[4,3-d]thiazol-2-ylamine Diethyl azodicarbonate (13.0 mL) was added dropwise to a solution of triphenylphosphine (7.51 g) in tetrahydrofuran (200 mL) in an ice bath. The mixture was warmed to room temperature and stirred for 30 minutes. The reaction solution was cooled to 0° C., and a solution of (±)-[(3R*,4R*)-4-(3-bromophenyl)-3-hydroxytetrahydropyran-4-yl]thiourea (6.33 g) in tetrahydrofuran (44 mL) was added dropwise. The mixture was stirred overnight while gradually warming to room temperature. Water was added to the reaction mixture, and the aqueous layer was extracted with ethyl acetate. The solvent was evaporated under reduced pressure and the residue was purified by silica gel column chromatography to obtain a crude product. The resulting crude product was purified by silica gel column chromatography again to obtain the title compound (3.55 g).
$^1$H-NMR (400 MHz, CDCl$_3$) δ (ppm): 2.13-2.23 (m, 2H), 3.36 (dd, J=10.8, 11.6 Hz, 1H), 3.71 (dt, J=3.4 Hz, 1H), 3.89-3.96 (m, 2H), 4.08 (dd, J=6.4, 12.0 Hz, 1H), 7.21 (t, J=8.0 Hz, 1H), 7.37-7.40 (m, 2H), 7.60 (t, J=2.0 Hz, 1H).

(7) Synthesis of (±)-N,N-bis(tert-butoxycarbonyl)[(3aS*,7aR*)-7a-(3-bromophenyl)-3a,6,7,7a-tetrahydro-4H-pyrano[4,3-d]thiazol-2-yl]amine 4-Dimethylaminopyridine (2.77 g) and di-tert-n-butyl dicarbonate (12.3 g) were added to a solution of (±)-(3aS*, 7aR*)-7a-(3-bromophenyl)-3a,6,7,7a-tetrahydro-4H-pyrano[4,3-d]thiazol-2-ylamine (3.55 g) in tetrahydrofuran (500 mL). The mixture was stirred at room temperature for four hours, and then the solvent was evaporated under reduced pressure at room temperature or lower. The residue was purified by silica gel column chromatography to obtain the title compound (4.49 g).
$^1$H-NMR (400 MHz, CDCl$_3$) δ (ppm): 1.54 (s, 18H), 2.11 (ddd, J=5.2, 12.4, 14.4 Hz, 1H), 2.31 (dt, J=2.0, 14.4 Hz, 1H), 3.41 (dd, J=10.4, 12.0 Hz, 1H), 3.60-3.67 (m, 1H), 3.83-3.94 (m, 2H), 4.10 (dd, J=6.2, 11.8 Hz, 1H), 7.20 (t, J=8.0 Hz, 1H), 7.37-7.40 (m, 2H), 7.59 (d, J=2.0 Hz, 1H).

(8) Synthesis of tert-butyl(±)-{(3aS*,7aR*)-7a-[3-(benzhydrylidene-amino)phenyl]-3a,6,7,7a-tetrahydro-4H-pyrano[4,3-d]thiazol-2-yl}carbamate Benzophenone imine (244 μL), BINAP (60.6 mg), tris(dibenzylideneacetone)dipalladium (0) (44.6 mg) and sodium tert-butoxide (233 mg) were added to a solution of (±)-N,N-bis(tert-butoxycarbonyl)[(3aS*,7aR*)-7a-(3-bromophenyl)-3a,6,7,7a-tetrahydro-4H-pyrano[4,3-d]thiazol-2-yl]amine (250 mg) in toluene (20 mL). After replacement with nitrogen, the mixture was stirred at 85° C. for four hours. The reaction solution was returned to room temperature, and water was added to the reaction mixture. The aqueous layer was extracted with ethyl acetate, and the organic layer was washed with brine. The organic layer was dried over anhydrous magnesium sulfate, and the solvent was evaporated under reduced pressure. The residue was purified by silica gel column chromatography to obtain the title compound (165 mg).
$^1$H-NMR (400 MHz, CDCl$_3$) δ (ppm): 1.38 (s, 9H), 1.98-2.06 (br, 2H), 3.24 (dd, J=6.0, 10.8 Hz, 1H), 3.35 (t, J=10.8 Hz, 1H), 3.61 (t, J=12.6 Hz, 1H), 3.80-3.87 (m, 1H), 3.96 (dd, J=6.0, 11.6 Hz, 1H), 6.57 (brs, 1H), 6.82 (d, J=7.6 Hz, 1H), 6.95-6.97 (m, 1H), 7.06-7.08 (m, 2H), 7.17 (t, J=8.0 Hz, 1H), 7.25-7.28 (m, 4H), 7.39-7.44 (m, 2H), 7.47-7.51 (m, 1H), 7.75-7.77 (m, 2H).
ESI-MS; m/z 536 [M$^+$+Na].

(9) Synthesis of tert-butyl(±)-[(3aS*,7aR*)-7a-(3-aminophenyl)-3a,6,7,7a-tetrahydro-4H-pyrano[4,3-d]thiazol-2-yl]carbamate 1 N hydrochloric acid (1 mL) was added to a solution of tert-butyl(±)-{(3aS*,7aR*)-7a-[3-(benzhydrylidene-amino)phenyl]-3a,6,7,7a-tetrahydro-4H-pyrano[4,3-d]thiazol-2-yl}carbamate (165 mg) in ether (1 mL), and the mixture was stirred at room temperature for one hour. The reaction solution was neutralized with a sodium bicarbonate solution, the organic layer was dried over anhydrous magnesium sulfate. The solvent was evaporated under reduced pressure and the residue was purified by NH-silica gel column chromatography to obtain the title compound (77 mg).
$^1$H-NMR (400 MHz, CDCl$_3$) δ (ppm): 1.41 (s, 9H), 2.04-2.28 (m, 2H), 3.38 (t, J=11.2 Hz, 1H), 3.65-4.12 (m, 4H), 6.56-6.60 (m, 1H), 6.69-6.85 (m, 2H), 7.10-7.15 (m, 1H).
ESI-MS; m/z 350 [M$^+$+H].

Preparation Example 76

Synthesis of (±)-N-tert-butoxycarbonyl-N-[(4aS*, 8aS*)-8a-(4-bromo-thiophen-2-yl)-4a,7,8,8a-tetrahydro-4H,5H-6-oxa-3-thia-1-azanaphthalen-2-yl]benzamide

[Formula 98]

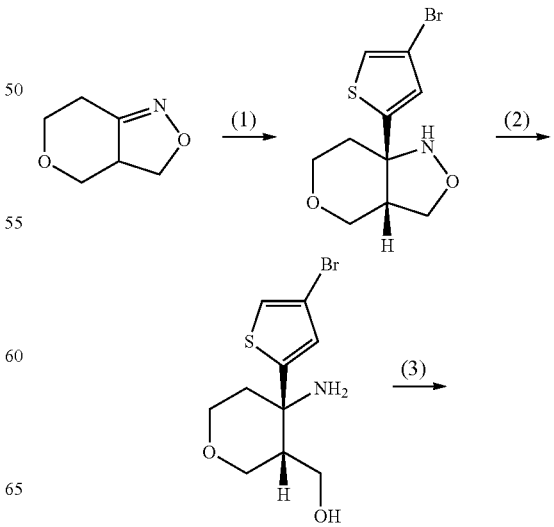

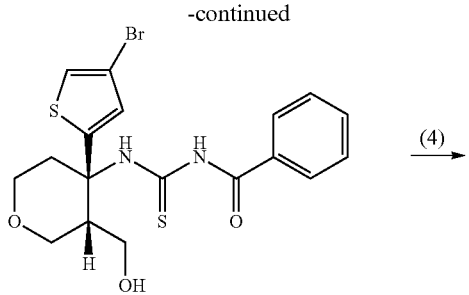

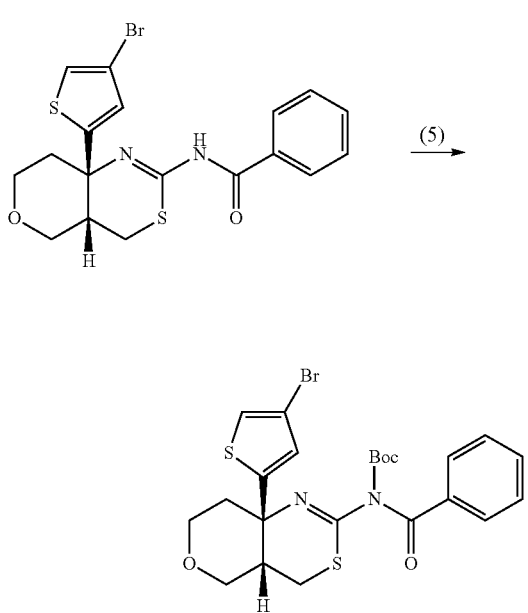

(1) Synthesis of (±)-(3aS*,7aS*)-7a-(4-bromo-thiophen-2-yl)-hexahydro-pyrano[4,3-c]isoxazole The title compound (166 mg) was obtained from the compound obtained in Preparation Example 8-(2) (100 mg) and 2,4-dibromothiophene (400 mg) according to the method of Preparation Example 21-(3).

$^1$H-NMR (400 MHz, CDCl$_3$) δ (ppm): 2.05 (br, 1H), 2.26 (br, 1H), 2.80 (br, 1H), 3.44-4.23 (m, 6H), 7.03 (s, 1H), 7.21 (s, 1H).

(2) Synthesis of (±)-[(3R*,4S*)-4-amino-4-(4-bromo-thiophen-2-yl)-tetrahydro-pyran-3-yl]methanol Zinc (374 mg) was added to a solution of (±)-(3aS*,7aS*)-7a-(4-bromo-thiophen-2-yl)-hexahydro-pyrano[4,3-c]isoxazole (166 mg) in acetic acid (5 mL), and the mixture was stirred at room temperature overnight. The insoluble matter was removed by filtration through celite, and the solvent was evaporated under reduced pressure. Ice was added to the residue, followed by neutralization with a 2 N sodium hydroxide solution. The aqueous layer was extracted with ethyl acetate, and the organic layer was dried over anhydrous magnesium sulfate. The solvent was evaporated under reduced pressure and the residue was purified by silica gel column chromatography to obtain the title compound (147 mg).

$^1$H-NMR (400 MHz, CDCl$_3$) δ (ppm): 1.65 (dt, J=2.8, 14.0 Hz, 1H), 2.00-2.06 (m, 1H), 2.25 (ddd, J=5.2, 10.8, 14.0 Hz, 1H), 3.62 (dd, J=4.0, 11.6 Hz, 1H), 3.70 (dd, J=4.4, 11.6 Hz, 1H), 3.81-3.95 (m, 4H), 6.94 (d, J=1.4 Hz, 1H), 7.14 (d, J=1.4 Hz, 1H).

(3) Synthesis of (±)-1-benzoyl-3-[(3R*,4S*)-4-(4-bromo-thiophen-2-yl)-3-hydroxymethyl-tetrahydro-pyran-4-yl]thiourea Benzoyl isothiocyanate (66.5 μL) was added to a solution of (±)-[(3R*,4S*)-4-amino-4-(4-bromo-thiophen-2-yl)-tetrahydro-pyran-3-yl]methanol (144 mg) in dichloromethane (5 mL). The mixture was stirred at room temperature overnight, and then the solvent was evaporated under reduced pressure. The residue was purified by silica gel column chromatography to obtain the title compound (233 mg).

$^1$H-NMR (400 MHz, CDCl$_3$) δ (ppm): 1.65 (dd, 4.4, 6.0 Hz, 1H), 2.19 (ddd, J=3.6, 10.8, 14.4 Hz, 1H), 2.27 (brs, 1H), 3.74-4.06 (m, 6H), 6.94 (d, J=1.6 Hz, 1H), 7.18 (d, J=1.6 Hz, 1H), 7.52-7.56 (m, 2H), 7.63-7.67 (m, 1H), 7.86-7.88 (m, 2H), 8.88 (s, 1H), 11.64 (s, 1H).

(4) Synthesis of (±)-N-[(4aS*,8aS*)-8a-(4-bromo-thiophen-2-yl)-4a,7,8,8a-tetrahydro-4H,5H-6-oxa-3-thia-1-azanaphthalen-2-yl]benzamide (±)-1-Benzoyl-3-[(3R*,4S*)-4-(4-bromo-thiophen-2-yl)-3-hydroxymethyl-tetrahydro-pyran-4-yl]thiourea (233 mg) was dissolved in methanol (5 mL). Several drops of concentrated hydrochloric acid were added, followed by stirring for two hours. The reaction solution was returned to room temperature and the solvent was evaporated under reduced pressure to obtain the title compound.

ESI-MS; m/z 439 [M$^+$+H].

(5) Synthesis of (±)-N-tert-butoxycarbonyl-N-[(4aS*,8aS*)-8a-(4-bromo-thiophen-2-yl)-4a,7,8,8a-tetrahydro-4H,5H-6-oxa-3-thia-1-azanaphthalen-2-yl]benzamide 4-Dimethylaminopyridine (40.3 mg) and di-tert-butyl dicarbonate (48 mg) were added to a solution of (±)-N-[(4aS*,8aS*)-8a-(4-bromo-thiophen-2-yl)-4a,7,8,8a-tetrahydro-4H,5H-6-oxa-3-thia-1-azanaphthalen-2-yl]benzamide (48 mg) in tetrahydrofuran (2 mL). The mixture was stirred at room temperature for two hours, and then the solvent was evaporated under reduced pressure. The residue was purified by silica gel column chromatography to obtain the title compound (60.0 mg).

$^1$H-NMR (400 MHz, CDCl$_3$) δ (ppm): 1.36 (s, 9H), 2.06 (d, J=12.8 Hz, 1H), 2.26 (dt, J=4.4, 12.8 Hz, 1H), 2.37-2.43 (m, 1H), 2.65 (dd, J=2.8, 13.2 Hz, 1H), 3.25 (dd, J=4.0, 13.2 Hz, 1H), 3.36 (dt, J=2.0 Hz, 12.4 Hz, 1H), 3.78-3.83 (m, 3H), 7.01 (d, J=1.8 Hz, 1H), 7.15 (d, J=1.8 Hz, 1H), 7.44-7.48 (m, 2H), 7.54-7.58 (m, 1H), 7.74-7.76 (m, 2H).

Preparation Example 77

Synthesis of (±)-6-{(E)-2-[3-((4aR*,7aS*)-2-amino-4a,5,6,7,-tetrahydro-4H-cyclopenta[d][1,3]thiazin-7a-yl)-4-fluorophenyl]vinyl}nicotinonitrile

[Formula 99]

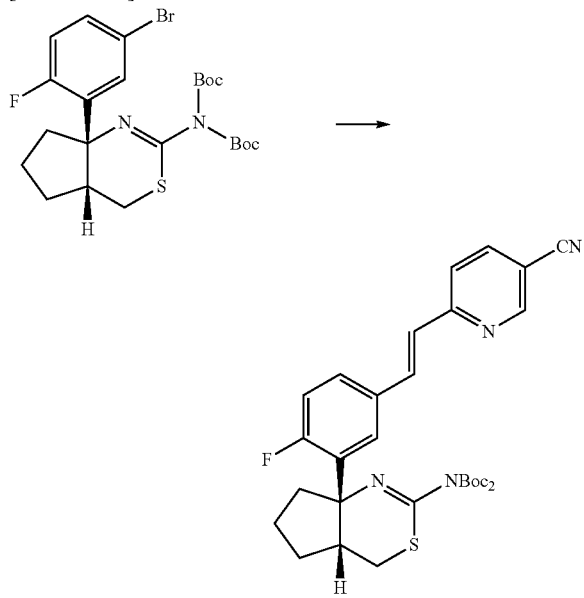

Synthesis of (±)-N,N-bis(t-butoxycarbonyl)-6-{(E)-2-[3-((4aR*,7aS*)-2-amino-4a,5,6,7,7a-tetrahydro-4H-cyclopenta[d][1,3]thiazin-7a-yl)-4-fluorophenyl]vinyl}nicotinonitrile The compound obtained in Preparation Example 72 (100 mg) was mixed with trans-1,2-bis(tri-n-butylstannyl) (114 mg), 2-bromo-5-cyanopyridine (35 mg), tri(o-tolyl)phosphine (9.2 mg) and bis(acetonitrile)dichloropalladium (II) (2.8 mg) in toluene (3 mL), and the mixture was stirred under a nitrogen atmosphere at 80° C. overnight. The reaction suspension was concentrated and then the residue was purified by preparative HPLC. The resulting product was purified again by pTLC to obtain the title compound (17 mg).

$^1$H-NMR (400 MHz, CDCl$_3$) δ (ppm): 1.57 (s, 18H), 1.80-2.20 (m, 5H), 2.68-2.88 (m, 3H), 3.07 (dd, J=3.4, 13.3 Hz, 1H), 7.07 (dd, J=8.5, 12.2 Hz, 1H), 7.32 (d, J=15.8 Hz, 1H), 7.41 (m, 2H), 7.81 (d, J=12.2 Hz, 1H), 7.87 (dd, (dd, J=2.1, 8.2 Hz, 2H), 8.81 (d, J=2.1 Hz, 1H).

Preparation Example 78

Synthesis of (±)-(4aR*,7aS*)-7a-(5-ethynyl-2-fluorophenyl)-4,4a,5,6,7,7a-hexahydrocyclopenta[d][1,3]thiazin-2-amine

[Formula 100]

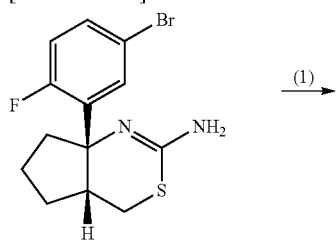

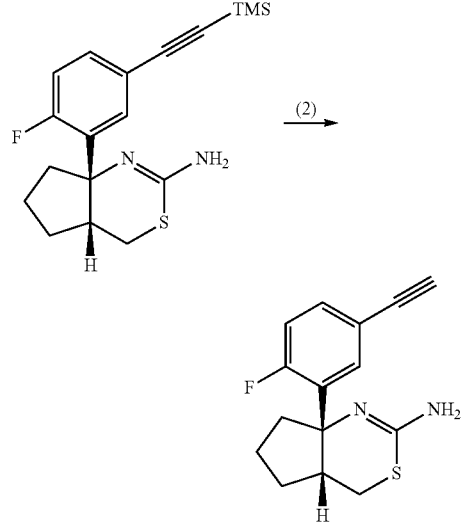

(1) Synthesis of (±)-(4aR*,7aS*)-7a-{2-fluoro-5-[(trimethylsilyl)ethynyl]phenyl}-4,4a,5,6,7,7a-hexahydrocyclopenta[d][1,3]thiazin-2-amine The compound obtained in Preparation Example 54-(4) (100 mg) was mixed with bis(triphenylphosphine)palladium (II)dichloride (60 mg), copper (I) iodide (2.3 mg) and ethynyltrimethylsilane (60 mg) in triethylamine (1.75 mL) and tetrahydrofuran (0.25 mL), and the mixture was stirred under a nitrogen atmosphere at 90° C. overnight. The reaction suspension was filtered and concentrated. Then, the resulting residue was purified by preparative HPLC to obtain the title compound (31 mg).

$^1$H-NMR (400 MHz, CDCl$_3$) δ (ppm): 0.26 (s, 9H), 2.00 (m, 4H), 2.30 (m, 1H), 2.55 (m, 1H), 2.88 (dd, J=3.5, 12.5 Hz, 1H), 3.00-3.14 (m, 2H), 7.00 (dd, J=8.4, 12.3 Hz, 1H), 7.34 (dd, J=2.0, 7.9 Hz, 1H), 7.40 (m, 1H), 9.31 (brs, NH$_2$)

(2) Synthesis of (±)-(4aR*,7aS*)-7a-(5-ethynyl-2-fluorophenyl)-4,4a,5,6,7,7a-hexahydrocyclopenta[d][1,3]thiazin-2-amine Tetrabutylammonium fluoride (2.9 mL) was added to a solution of the compound obtained in Preparation Example 78-(1) (500 mg) in tetrahydrofuran (30 mL), and the mixture was stirred at room temperature for 30 minutes. Brine was added to the reaction mixture, followed by extraction with ethyl acetate. The organic layer was dried over anhydrous magnesium sulfate. The drying agent was removed by filtration and the filtrate was concentrated under reduced pressure to obtain a residue. The residue was purified by silica gel column chromatography to obtain the title compound (59 mg).

ESI-MS; m/z 275 [M$^+$+H].

$^1$H-NMR (400 MHz, CDCl$_3$) δ (ppm): 1.74-2.00 (m, 5H), 2.58 (m, 1H), 2.81 (m, 2H), 2.97 (dd, J=3.1, 12.5 Hz, 1H), 3.05 (s, 1H), 6.99 (dd, J=8.3, 12.2 Hz, 1H), 7.37 (m, 1H), 7.48 (dd, J=2.2, 8.00 Hz, 1H).

Example 1

Synthesis of tert-butyl(±)-((4aR*,8aS*)-8a-{5-[(5-chloropyridine-2-carbonyl)-amino]-2-fluorophenyl}-4a,5,6,7,8,8a-hexahydro-4H-benzo[d][1,3]thiazin-2-yl)carbamate

[Formula 101]

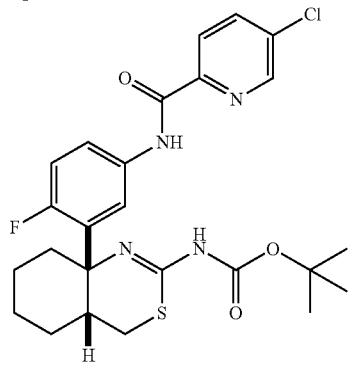

5-Chloropyridine-2-carboxylic acid (30.4 mg) and triethylamine (89.0 μL) were added to a solution of the compound of Preparation Example 1-(8) (58.0 mg) in DMF (5.63 mL). 1-Hydroxybenzotriazole (26.0 mg) and EDC.HCl (61.4 mg) were added to the reaction solution in an ice bath. The reaction solution was warmed to room temperature, followed by stirring overnight. Ice was added to the reaction mixture, followed by extraction with ethyl acetate. The organic layer was washed with water and a saturated sodium chloride solution and dried over anhydrous magnesium sulfate. The drying agent was removed by filtration and the filtrate was concentrated under reduced pressure. The resulting crude product was purified by silica gel column chromatography to obtain the title compound (23.0 mg).

ESI-MS; m/z 519 [M+H].

$^1$H-NMR (400 MHz, CDCl$_3$) δ (ppm): 1.57 (s, 9H), 1.64-1.89 (m, 7H), 2.37 (m, 1H), 2.53 (m, 1H), 2.88 (brs, 1H), 2.91 (d, J=2.4 Hz, 1H), 7.12 (dd, J=8.8, 12.0 Hz, 1H), 7.18 (m, 1H), 7.88 (dd, J=2.8, 8.4 Hz, 1H), 8.22 (d, J=8.4 Hz, 1H), 8.23 (m, 1H), 8.59 (d, J=2.0 Hz, 1H), 9.84 (s, 1H).

Example 2

Synthesis of (±)-N-[3-((4aR*,8aS*)-2-amino-4a,5,6,7,8,8a-hexahydro-4H-benzo[d][1,3]thiazin-8a-yl)-4-fluorophenyl]-5-chloropyridine-2-carboxamide

[Formula 102]

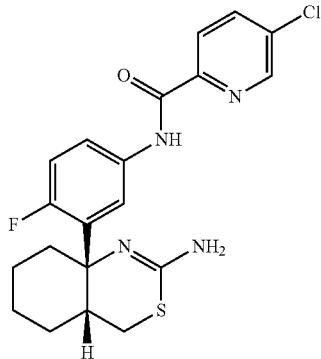

Trifluoroacetic acid (200 μL) was added to a solution of the compound of Example 1 (23.0 mg) in dichloromethane (1.00 mL), and the mixture was stirred at room temperature for four hours. The reaction solution was diluted with diethyl ether and neutralized with a sodium bicarbonate solution. The reaction mixture was extracted with ethyl acetate, and the organic layer was washed with a saturated sodium chloride solution. The organic layer was dried over anhydrous magnesium sulfate. The drying agent was removed by filtration and the filtrate was concentrated under reduced pressure to obtain a residue. The residue was purified by NH-silica gel column chromatography to obtain the title compound (18.0 mg).

$^1$H-NMR (400 MHz, CDCl$_3$) δ (ppm): 1.37-1.90 (m, 7H), 2.20 (m, 1H), 2.56 (dd, J=2.8, 12.2 Hz, 1H), 2.74 (m, 1H), 2.94 (dd, J=4.0, 12.2 Hz, 1H), 7.06 (dd, J=8.8, 12.0 Hz, 1H), 7.27 (m, 1H), 7.87 (dd, J=2.8, 8.4 Hz, 1H), 7.98 (m, 1H), 8.24 (dd, J=0.8, 8.4 Hz, 1H), 8.56 (dd, J=0.8, 2.4 Hz, 1H), 9.77 (s, 1H).

Example 3

Synthesis of (+)-N-[3-((4aR*,8aS*)-2-amino-4a,5,6,7,8,8a-hexahydro-4H-benzo[d][1,3]thiazin-8a-yl)-4-fluorophenyl]-5-chloropyridine-2-carboxamide

[Formula 103]

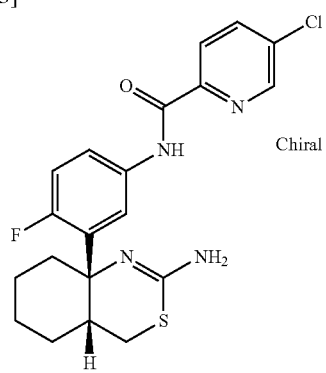

(±)-2-[(4aR*,8aS*)-2-Amino-4a,5,6,7,8,8a-hexahydro-4H-benzo[d][1,3]thiazin-8a-yl]-4-(5-chloropyridine-2-carbonylamino)fluorobenzene obtained in Example 2 (10 mg) was optically resolved by CHIRALPAK™ OD-H manufactured by Daicel Chemical Industries, Ltd. (2 cm×25 cm, mobile phase: hexane:ethanol=8:2, flow rate: 20 mL/min). The component having a retention time of six minutes was collected and purified sequentially again by NH-pTLC, LCMS and NH-silica gel column chromatography to obtain the title (+)-isomer (2.0 mg; >99% ee).

ESI-MS; m/z 419 [M+H].

$^1$H-NMR (400 MHz, CDCl$_3$) δ (ppm): 1.37-1.90 (m, 7H), 2.20 (m, 1H), 2.56 (dd, J=2.8, 12.2 Hz, 1H), 2.74 (m, 1H), 2.94 (dd, J=4.0, 12.2 Hz, 1H), 7.06 (dd, J=8.8, 12.0 Hz, 1H), 7.27 (m, 1H), 7.87 (dd, J=2.8, 8.4 Hz, 1H), 7.98 (m, 1H), 8.24 (dd, J=0.8, 8.4 Hz, 1H), 8.56 (dd, J=0.8, 2.4 Hz, 1H), 9.77 (s, 1H).

Example 4

Alternative Method to Example 3

Synthesis of (+)-N-[3-((4aR*,8aS*)-2-amino-4a,5,6,7,8,8a-hexahydro-4H-benzo[d][1,3]thiazin-8a-yl)-4-fluorophenyl]-5-chloropyridine-2-carboxamide

[Formula 104]

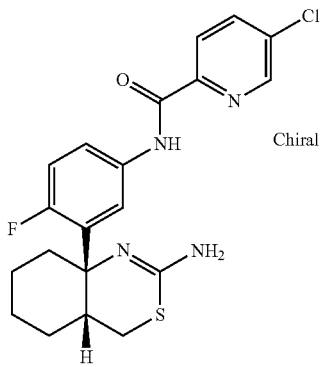

N,N-Dimethylformamide (one drop) and thionyl chloride (1 mL) were added to a suspension of 5-chloropyridinecarboxylic acid (55.2 mg) in toluene (5 mL). The mixture was heated under reflux for one hour. The reaction solution was cooled to room temperature and then the solvent was evaporated under reduced pressure to obtain 5-chloropyridinecarboxylic acid chloride. A solution of 5-chloropyridinecarboxylic acid chloride in THF (5 mL) and pyridine (115 μL) were sequentially added to a solution of the compound of Preparation Example 2-(2) (111 mg) in THF (10 mL) under ice-cooling. The mixture was warmed to room temperature and stirred for 30 minutes. After confirming completion of the reaction, a saturated sodium bicarbonate solution was added to the mixture, followed by extraction with ethyl acetate. The organic layer was washed with a saturated sodium chloride solution and dried over anhydrous magnesium sulfate. The drying agent was removed by filtration and the filtrate was concentrated under reduced pressure to obtain an amide compound of a synthetic intermediate. The resulting amide was dissolved in dichloromethane (10 mL). Trifluoroacetic acid (2 mL) was added and the mixture was stirred at room temperature for three hours. The reaction solution was diluted with diethyl ether. Then, the reaction mixture was neutralized with a sodium bicarbonate solution, followed by extraction with ethyl acetate. The organic layer was washed with a saturated sodium chloride solution and then dried over anhydrous magnesium sulfate. The drying agent was removed by filtration and the filtrate was concentrated under reduced pressure. The crude product was purified by NH-silica gel column chromatography to obtain the title compound (115 mg; >99% ee).

Example 5

Synthesis of (+)-N-[3-((4aR*,7aS*)-2-amino-4,4a,5,6,7,7a-hexahydrocyclopenta[d][1,3]thiazin-7a-yl)-4-fluorophenyl]-5-chloropyridine-2-carboxamide

[Formula 105]

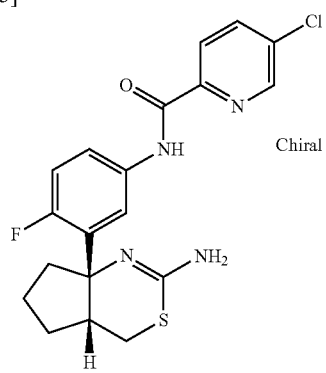

The title compound (39.5 mg; >99% ee) was obtained from the compound obtained in Preparation Example 3-(8) (45.0 mg) and 5-chloropyridine-2-carboxylic acid (23.3 mg) according to Example 4.

$^1$H-NMR (400 MHz, CDCl$_3$) δ (ppm): 1.73-2.00 (m, 5H), 2.61 (m, 1H), 2.75 (dd, J=4.0, 12.6 Hz, 1H), 2.83 (m, 1H), 2.99 (dd, J=3.2, 12.6 Hz, 1H), 7.05 (dd, J=8.8, 12.0 Hz, 1H), 7.40 (dd, J=2.8, 7.2 Hz, 1H), 7.87 (dd, J=2.4, 8.4 Hz, 1H), 7.94 (m, 1H), 8.23 (d, J=8.4 Hz, 1H), 8.55 (dd, J=0.8, 2.4 Hz, 1H), 9.79 (s, 1H).

Example 6

Synthesis of N-[3-((4aR*,7aS*)-2-amino-4,4a,5,6,7,7a-hexahydrocyclopenta[d][1,3]thiazin-7a-yl)-4-fluorophenyl]pyridine-2-carboxamide

[Formula 106]

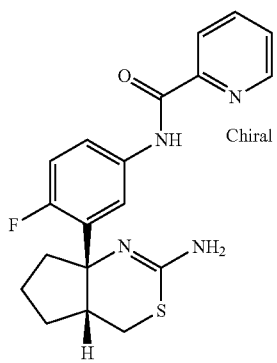 [SMILES: NC1=N[C@@]2(c3cc(NC(=O)c4ccccn4)ccc3F)CCC[C@H]2CS1]

The title compound (4.20 mg) was obtained from the compound obtained in Preparation Example 3-(8) (15.0 mg) and picolinoyl chloride hydrochloride (8.76 mg) according to the method of Example 5.

$^1$H-NMR (400 MHz, CDCl$_3$) δ (ppm): 1.76-2.02 (m, 5H), 2.62 (m, 1H), 2.76 (dd, J=4.0, 12.8 Hz, 1H), 2.84 (m, 1H), 3.01 (dd, J=3.2, 12.8 Hz, 1H), 7.06 (dd, J=8.8, 12.0 Hz, 1H), 7.39 (dd, 2.4, 6.8 Hz, 1H), 7.49 (dd, J=4.4, 7.6 Hz, 1H), 7.91 (m, 1H), 8.00 (m, 1H), 8.29 (dd, J=1.2, 7.6 Hz, 1H), 8.62 (ddd, J=0.8, 1.2, 4.8 Hz, 1H), 9.99 (s, 1H).

Example 7

Synthesis of N-[3-((4aR*,7aS*)-2-amino-4,4a,5,6,7,7a-hexahydrocyclopenta[d][1,3]thiazin-7a-yl)-4-fluorophenyl]nicotinamide

[Formula 107]

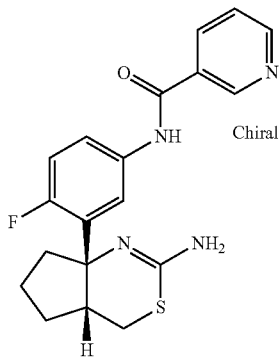 [SMILES: NC1=N[C@@]2(c3cc(NC(=O)c4cccnc4)ccc3F)CCC[C@H]2CS1]

Triethylamine (30.4 μL), 1-hydroxybenzotriazole (12.2 mg) and EDC.HCl (21.0 mg) were added to a solution of the compound obtained in Preparation Example 3-(8) (10.0 mg) and nicotinic acid (10.1 mg) in DMF (2.00 mL). The reaction solution was stirred at room temperature for four days. Then, ice water was added to the reaction mixture, followed by extraction with ethyl acetate. The organic layer was washed with water and a saturated sodium chloride solution and then dried over anhydrous magnesium sulfate. The drying agent was removed by filtration and then the solvent was evaporated under reduced pressure. The resulting crude product was purified by pTLC to obtain a corresponding amide. TFA (2.00 mL) was added to a solution of the resulting amide in dichloromethane (5.00 mL), and the mixture was stirred at room temperature for three hours. After confirming completion of the reaction, the reaction solution was diluted with toluene and the solvent was evaporated under reduced pressure at room temperature or lower. The residue was purified by NH-pTLC to obtain the title compound (3.80 mg).

$^1$H-NMR (400 MHz, CDCl$_3$) δ (ppm): 1.75-1.94 (m, 5H), 2.36 (br, 2H), 2.60 (m, 1H), 2.76 (dd, J=4.0, 12.8 Hz, 1H), 2.85 (m, 1H), 2.97 (dd, 3.6, 12.8 Hz, 1H), 7.06 (dd, J=8.8, 12.0 Hz, 1H), 7.26 (m, 1H), 7.43 (dd, J=4.8, 7.2 Hz, 1H), 7.89 (m, 1H), 8.20 (d, J=8.0 Hz, 1H), 8.77 (dd, J=1.6, 4.8 Hz, 1H), 9.09 (d, J=1.6 Hz, 1H).

Example 8

Synthesis of N-[3-((4aR*,7aS*)-2-amino-4,4a,5,6,7,7a-hexahydrocyclopenta[d][1,3]thiazin-7a-yl)-4-fluorophenyl]isonicotinamide

[Formula 108]

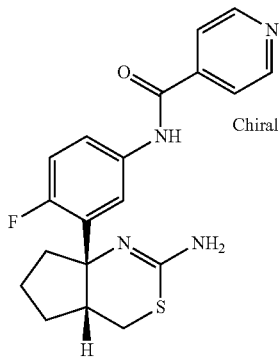 [SMILES: NC1=N[C@@]2(c3cc(NC(=O)c4ccncc4)ccc3F)CCC[C@H]2CS1]

The title compound (3.20 mg) was obtained from the compound obtained in Preparation Example 3-(8) (10.0 mg) and isonicotinic acid (10.1 mg) according to the method of Example 7.

$^1$H-NMR (400 MHz, CDCl$_3$) δ (ppm): 1.75-1.97 (m, 5H), 2.59 (m, 1H), 2.76 (dd, J=4.0, 12.8 Hz, 1H), 2.84 (m, 1H), 2.96 (dd, J=3.2, 12.8 Hz, 1H), 7.07 (dd, J=8.8, 12.4 Hz, 1H), 7.27 (m, 1H), 7.69 (dd, J=1.6, 4.4 Hz, 2H), 7.88 (m, 1H), 8.79 (dd, J=1.2, 4.4 Hz, 2H).

Example 9

Synthesis of N-[3-((4aR*,7aS*)-2-amino-4,4a,5,6,7,7a-hexahydrocyclopenta[d][1,3]thiazin-7a-yl)-4-fluorophenyl]-5-fluoropyridine-2-carboxamide

[Formula 109]

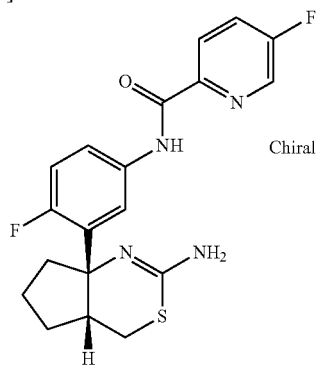

The title compound (7.20 mg) was obtained from the compound obtained in Preparation Example 3-(8) (12.0 mg) and 5-fluoropyridine-2-carboxylic acid (10.5 mg) according to the method of Example 4.

$^1$H-NMR (400 MHz, CDCl$_3$) δ (ppm): 1.63-2.00 (m, 5H), 2.61 (m, 1H), 2.76 (dd, J=4.0, 12.8 Hz, 1H), 2.82 (m, 1H), 3.00 (dd, J=3.2, 12.8 Hz, 1H), 4.43 (br, 2H), 7.05 (dd, J=8.8, 12.4 Hz, 1H), 7.38 (dd, J=2.8, 7.2 Hz, 1H), 7.59 (m, 1H), 7.95 (m, 1H), 8.33 (dd, J=4.8, 8.8 Hz, 1H), 8.45 (d, J=2.8 Hz, 1H), 9.77 (s, 1H).

Example 10

Synthesis of N-[3-((4aR*,7aS*)-2-amino-4,4a,5,6,7,7a-hexahydrocyclopenta[d][1,3]thiazin-7a-yl)-4-fluorophenyl]-6-chloropyridine-2-carboxamide

[Formula 110]

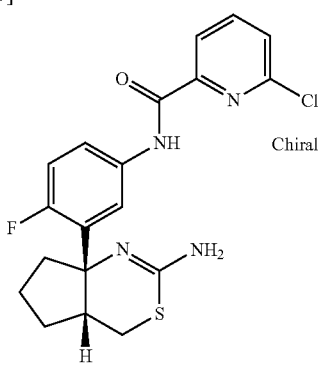

The title compound (10.8 mg) was obtained from the compound obtained in Preparation Example 3-(8) (10.0 mg) and 6-chloropyridine-2-carboxylic acid (7.75 mg) according to the method of Example 4.

¹H-NMR (400 MHz, CDCl₃) δ (ppm): 1.70-2.07 (m, 5H), 2.60 (m, 1H), 2.76 (dd, J=4.0, 12.8 Hz, 1H), 2.85 (m, 1H), 3.01 (dd, J=3.2, 12.8 Hz, 1H), 7.05 (dd, J=8.8, 12.0 Hz, 1H), 7.41 (dd, J=2.8, 7.2 Hz, 1H), 7.51 (dd, J=1.2, 8.0 Hz, 1H), 7.87 (t, J=8.0 Hz, 1H), 7.95 (m, 1H), 8.22 (dd, J=0.8, 7.6 Hz, 1H), 9.66 (s, 1H).

Example 11

Synthesis of N-[3-((4aR*,7aS*)-2-amino-4,4a,5,6,7,7a-hexahydrocyclopenta[d][1,3]thiazin-7a-yl)-4-fluorophenyl]-4-chloropyridine-2-carboxamide

[Formula 111]

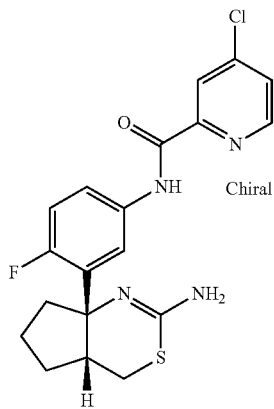 [SMILES: NC1=N[C@@]2(c3cc(NC(=O)c4cc(Cl)ccn4)ccc3F)CCC[C@H]2CS1]

The title compound (9.60 mg) was obtained from the compound obtained in Preparation Example 3-(8) (10.0 mg) and 4-chloropyridine-2-carboxylic acid (7.75 mg) according to the method of Example 4.

¹H-NMR (400 MHz, CDCl₃) δ (ppm): 1.69-1.98 (m, 5H), 2.61 (m, 1H), 2.76 (dd, J=4.0, 12.8 Hz, 1H), 2.83 (m, 1H), 2.99 (dd, 3.2, 12.8 Hz, 1H), 7.06 (dd, J=8.8, 12.0 Hz, 1H), 7.39 (dd, J=2.8, 7.2 Hz, 1H), 7.48 (dd, J=2.0, 5.2 Hz, 1H), 7.96 (m, 1H), 8.29 (dd, J=0.4, 2.0 Hz, 1H), 8.51 (dd, J=0.4, 5.2 Hz, 1H), 9.87 (s, 1H).

Example 12

Synthesis of N-[3-((4aR*,7aS*)-2-amino-4,4a,5,6,7,7a-hexahydrocyclopenta[d][1,3]thiazin-7a-yl)-4-fluorophenyl]-3-chloropyridine-2-carboxamide

[Formula 112]

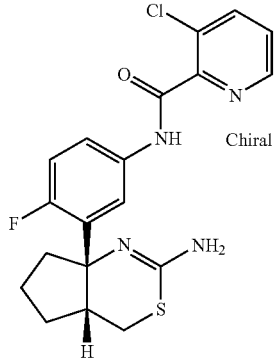 [SMILES: NC1=N[C@@]2(c3cc(NC(=O)c4ncccc4Cl)ccc3F)CCC[C@H]2CS1]

The title compound (4.20 mg) was obtained from the compound obtained in Preparation Example 3-(8) (11.0 mg) and 3-chloropyridine-2-carboxylic acid (7.11 mg) according to the method of Example 4.

¹H-NMR (400 MHz, CDCl₃) δ (ppm): 1.69-1.97 (m, 5H), 2.60 (m, 1H), 2.76 (dd, J=4.0, 12.6 Hz, 1H), 2.84 (m, 1H), 9.40 (dd, J=3.2, 12.6, 1H), 7.05 (dd, J=8.8, 12.0 Hz, 1H), 7.25 (m, 1H), 7.43 (dd, J=4.4, 8.0 Hz, 1H), 7.88 (dd, 1.2, 8.0 Hz, 1H), 8.08 (m, 1H), 8.53 (dd, J=1.2, 4.8 Hz, 1H), 9.86 (s, 1H).

Example 13

Synthesis of (+)-N-[3-((4aR*,8aS*)-2-amino-4a,5,6,7,8,8a-hexahydro-4H-benzo[d][1,3]thiazin-8a-yl)phenyl]5-chloropyridine-2-carboxamide

[Formula 113]

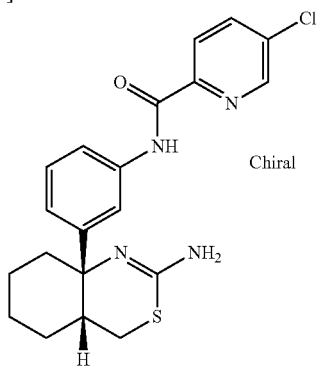

The title compound (66.1 mg; >99% ee) was obtained from tert-butyl[(4aR*,8aS*)-8a-(3-aminophenyl)-4a,5,6,7,8,8a-hexahydro-4H-benzo[d][1,3]thiazin-2-yl]carbamate obtained in Preparation Example 4-(8) (110 mg) and 5-chloropyridine-2-carboxylic acid (62.3 mg) according to the method of Example 4.

¹H-NMR (400 MHz, CDCl₃)) δ (ppm): 1.49-1.89 (m, 8H), 2.26 (m, 1H), 2.47 (dd, J=2.8, 12.0 Hz, 1H), 2.93 (dd, J=4.4, 12.0 Hz, 1H), 7.12 (dt, J=1.6, 8.0 Hz, 1H), 7.35 (t, J=8.0 Hz, 1H), 7.67 (m, 2H), 7.88 (dd, J=2.4, 8.4 Hz, 1H), 8.25 (d, J=8.4 Hz, 1H), 8.58 (d, J=0.8 Hz, 1H), 9.83 (s, 1H).

Example 14

Synthesis of (+)-N-[3-((4aR*,8aS*)-2-amino-4a,5,6,7,8,8a-hexahydro-4H-benzo[d][1,3]thiazin-8a-yl)-4,5-difluorophenyl]-5-chloropyridine-2-carboxamide

[Formula 114]

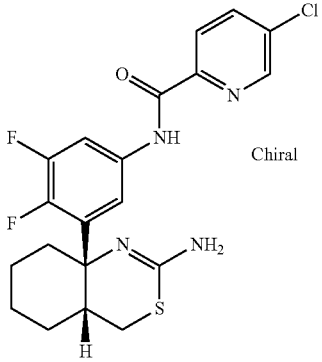 [SMILES: NC1=N[C@@]2(c3cc(NC(=O)c4ccc(Cl)cn4)cc(F)c3F)CCCC[C@H]2CS1]

5-Chloropyridinecarboxylic acid (4.16 mg), N,N-diisopropylethylamine (8.98 μL) and PyBOP (22.9 mg) were added to a solution of the compound obtained in Preparation Example 5-(8) (7.00 mg) in dichloromethane (4.00 mL). The reaction solution was stirred at room temperature for three days. Then, the reaction mixture was purified by NH-silica gel column chromatography to obtain an amide. The resulting amide was dissolved in dichloromethane (4.00 mL) and trifluoroacetic acid (1.00 mL) was added. The reaction solution was stirred at room temperature for three hours. Then, a saturated sodium bicarbonate solution was added, followed by extraction with ethyl acetate. The organic layer was dried over anhydrous magnesium sulfate. The drying agent was removed by filtration and then the solvent was evaporated under reduced pressure. The residue was purified by silica gel column chromatography to obtain the title compound (5.80 mg; >99% ee).

ESI-MS; m/z 437 [M+H].

$^1$H-NMR (400 MHz, CDCl$_3$)) δ (ppm): 1.51-1.95 (m, 7H), 2.20 (m, 1H), 2.62 (dd, J=2.8, 12.2 Hz, 1H), 2.79 (m, 1H), 2.98 (dd, J=4.0, 12.2 Hz, 1H), 6.95 (m, 1H), 7.89 (dd, J=2.4, 8.4 Hz, 1H), 8.12 (m, 1H), 8.22 (d, J=8.4 Hz, 1H), 8.58 (d, J=2.0 Hz, 1H), 9.84 (s, 1H).

Example 15

Synthesis of N-[3-((4aR*,8aS*)-2-amino-4a,5,6,7,8,8a-hexahydro-4H-benzo[d][1,3]thiazin-8a-yl)-4,5-difluorophenyl]-pyridine-2-carboxamide

[Formula 115]

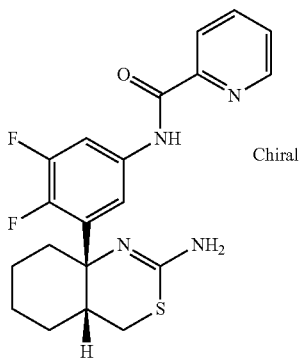 [SMILES: NC1=N[C@@]2(c3cc(NC(=O)c4ccccn4)cc(F)c3F)CCCC[C@H]2CS1]

Chiral

The title compound (6.30 mg) was obtained from the compound obtained in Preparation Example 5-(8) (7.00 mg) and picolinic acid (4.16 mg) according to the method of Example 14.

$^1$H-NMR (400 MHz, CDCl$_3$)) δ (ppm): 1.52-1.84 (m, 7H), 2.21 (m, 1H), 2.59 (dd, J=2.8, 12.0 Hz, 1H), 2.73 (m, 1H), 2.96 (dd, J=4.0, 12.0 Hz, 1H), 6.96 (m, 1H), 7.50 (ddd, J=1.2, 4.8, 8.0 Hz, 1H), 7.91 (dt, J=1.6, 8.0 Hz, 1H), 8.12 (ddd, J=2.8, 6.8, 11.6 Hz, 1H), 8.27 (dd, J=1.2, 8.0 Hz, 1H), 8.61 (ddd, J=0.8, 1.6, 4.8 Hz, 1H), 9.99 (s, 1H).

Example 16

Synthesis of N-[3-((4aR*,8aS*)-2-amino-4a,5,6,7,8,8a-hexahydro-4H-benzo[d][1,3]thiazin-8a-yl)-4,5-difluorophenyl]-5-fluoropyridine-2-carboxamide

[Formula 116]

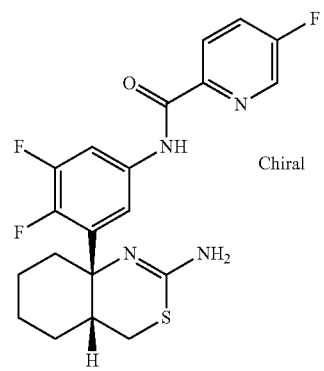 [SMILES: NC1=N[C@@]2(c3cc(NC(=O)c4ccc(F)cn4)cc(F)c3F)CCCC[C@H]2CS1]

Chiral

The title compound (2.30 mg) was obtained from the compound obtained in Preparation Example 5-(8) (7.00 mg) and 5-fluoropyridine-2-carboxylic acid (7.45 mg) according to the method of Example 14.

$^1$H-NMR (400 MHz, CDCl$_3$)) δ (ppm): 1.53-1.83 (m, 7H), 2.21 (m, 1H), 2.60 (d, J=12.0 Hz, 1H), 2.73 (m, 1H), 2.96 (dd, J=3.2, 12.0 Hz, 1H), 6.95 (m, 1H), 7.60 (dt, J=2.8, 8.4 Hz, 1H), 8.08 (ddd, J=2.0, 6.8, 11.6 Hz, 1H), 8.31 (dd, J=4.8, 8.8 Hz, 1H), 8.45 (d, J=2.8 Hz, 1H), 9.78 (s, 1H).

Example 17

Synthesis of N-[3-((4aR*,8aS*)-2-amino-4a,5,6,7,8,8a-hexahydro-4H-benzo[d][1,3]thiazin-8a-yl)-4,5-difluorophenyl]-3-chloropyridine-2-carboxamide

[Formula 117]

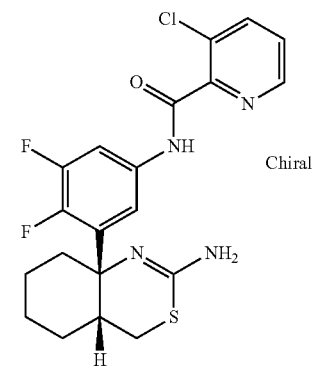 [SMILES: NC1=N[C@@]2(c3cc(NC(=O)c4ncccc4Cl)cc(F)c3F)CCCC[C@H]2CS1]

Chiral

The title compound (6.20 mg) was obtained from the compound obtained in Preparation Example 5-(8) (7.00 mg) and 3-chloropicolinic acid (4.16 mg) according to the method of Example 14.

$^1$H-NMR (500 MHz, CDCl$_3$)) δ (ppm): 1.52-1.82 (m, 7H), 2.19 (m, 1H), 2.59 (dd, J=2.8, 12.4 Hz, 1H), 2.72 (m, 1H), 2.96 (dd, J=4.0, 12.4 Hz, 1H), 6.82 (m, 1H), 7.44 (dd, J=4.8, 8.0 Hz, 1H), 7.89 (dd, J=1.2, 8.0 Hz, 1H), 8.21 (ddd, J=2.8, 6.8, 11.6 Hz, 1H), 8.52 (dd, J=1.2, 4.8 Hz, 1H), 9.89 (s, 1H).

Example 18

Synthesis of N-[3-((4aR*,8aS*)-2-amino-4a,5,6,7,8,8a-hexahydro-4H-benzo[d][1,3]thiazin-8a-yl)-4,5-difluorophenyl]-3,5-difluoropyridine-2-carboxamide

[Formula 118]

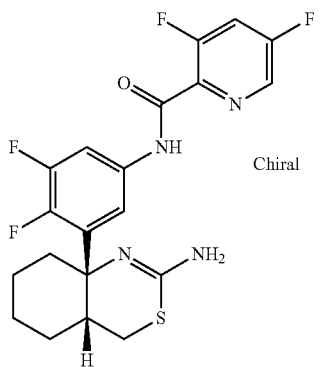 [SMILES: NC1=N[C@@]2(c3cc(NC(=O)c4ncc(F)cc4F)cc(F)c3F)CCCC[C@H]2CS1]

The title compound (5.20 mg) was obtained from the compound obtained in Preparation Example 5-(8) (7.00 mg) and 3,5-difluoropicolinic acid (4.16 mg) according to the method of Example 14.

$^1$H-NMR (400 MHz, CDCl$_3$)) δ (ppm): 1.49-1.82 (m, 7H), 2.19 (m, 1H), 2.59 (dd, J=2.8, 12.2 Hz, 1H), 2.72 (m, 1H), 2.96 (dd, J=4.0, 12.2 Hz, 1H), 6.87 (m, 1H), 7.39 (ddd, J=2.4, 8.0, 10.4 Hz, 1H), 8.12 (ddd, J=2.8, 6.8, 11.6 Hz, 1H), 8.35 (d, J=2.4 Hz, 1H), 9.57 (s, 1H).

Example 19

Synthesis of N-[3-((4aR*,8aS*)-2-amino-4a,5,6,7,8,8a-hexahydro-4H-benzo[d][1,3]thiazin-8a-yl)-4-fluorophenyl]-5-cyanopyridine-2-carboxamide

[Formula 119]

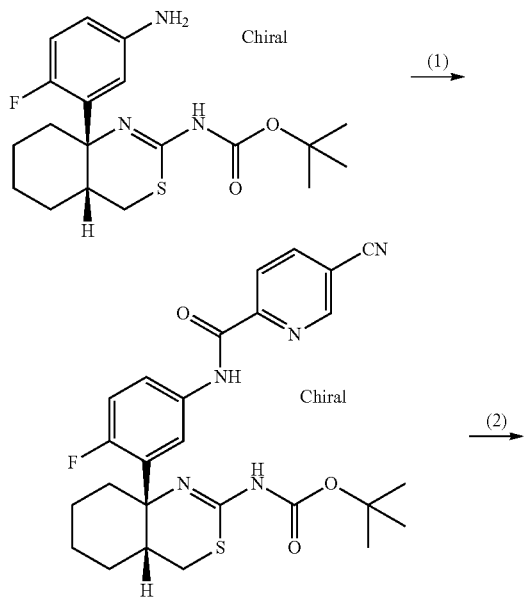

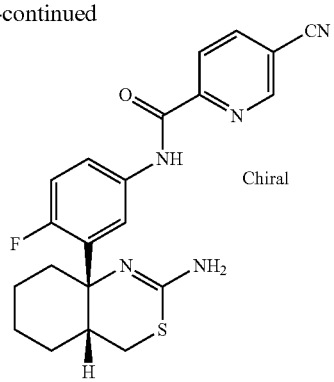

(1) Synthesis of tert-butyl ((4aR*,8aS*)-8a-{5-[(5-cyanopyridine-2-carbonyl)amino]-2-fluorophenyl}-4a,5,6,7,8,8a-hexahydro-4H-benzo[d][1,3]thiazin-2-yl)carbamate PyBOP (219 mg) was added to a solution of the compound of Preparation Example 13-(2) (46 mg), N,N-diisopropylethylamine (0.11 mL) and the compound of Preparation Example 2-(2) (40 mg) in dichloromethane (4 mL). The mixture was stirred at room temperature for 1.5 hours. The reaction solution was poured into a sodium bicarbonate solution, followed by extraction with ethyl acetate. The extract was washed with a saturated sodium chloride solution and dried over anhydrous magnesium sulfate. The drying agent was removed by filtration and the filtrate was concentrated under reduced pressure. The crude product was purified by silica gel column chromatography (ethyl acetate-heptane system) to obtain the title compound (47 mg).

ESI-MS; m/z 510 [M+H].

2) Synthesis of N-[3-((4aR*,8aS*)-2-amino-4a,5,6,7,8,8a-hexahydro-4H-benzo[d][1,3]thiazin-8a-yl)-4-fluorophenyl]-5-cyanopyridine-2-carboxamide Trifluoroacetic acid (1.0 mL) was added to a solution of the compound obtained in Example 19-(1) (47 mg) in dichloromethane (2 mL), and the reaction solution was stirred at room temperature for 1.5 hours. The reaction solution was poured into aqueous sodium bicarbonate, followed by extraction with ethyl acetate. The extract was washed with a saturated sodium chloride solution and dried over anhydrous magnesium sulfate. The drying agent was removed by filtration and the filtrate was concentrated under reduced pressure. The crude product was purified by NH-silica gel column chromatography (ethyl acetate-heptane system) to obtain the title compound (28 mg).

ESI-MS; m/z 410 [M+H].

$^1$H-NMR (400 MHz, CDCl$_3$) δ (ppm): 1.40-1.86 (m, 7H), 2.16-2.30 (m, 1H), 2.50-2.60 (m, 1H), 2.66-2.78 (m, 1H), 2.92 (dd, J=4.0, 12.0 Hz, 1H), 7.01 (dd, J=8.8, 12.0 Hz, 1H), 7.24-7.36 (m, 1H), 7.86-7.98 (m, 1H), 8.18 (d, J=8.0 Hz, 1H), 8.39 (d, J=8.0 Hz, 1H), 8.84 (s, 1H), 9.73 (s, 1H).

Example 20

Synthesis of N-[3-((4aR*,7aS*)-2-amino-4,4a,5,6,7,7a-hexahydrocyclopenta[d][1,3]thiazin-7a-yl-4-fluorophenyl]-5-difluoromethoxypyrazine-2-carboxamide

[Formula 120]

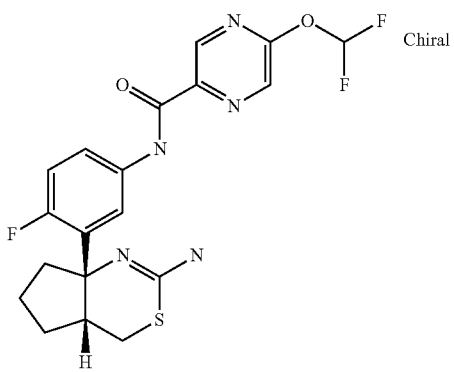 [SMILES: NC1=N[C@@]2(c3cc(NC(=O)c4cnc(OC(F)F)cn4)ccc3F)CCC[C@H]2CS1]

The title compound (275 mg) was obtained from the compound obtained in Preparation Example 3-(8) (230 mg) and 5-difluoromethoxypyrazine-2-carboxylic acid obtained in Preparation Example 14-(2) (180 mg) according to the method of Example 14.

$^1$H-NMR (400 MHz, CDCl$_3$) δ (ppm): 1.78-1.99 (m, 6H), 2.60-3.00 (m, 3H), 7.00-7.10 (m, 1H), 7.28-7.35 (m, 1H), 7.51 (t, J=71.6 Hz, 1H), 7.94-7.97 (m, 1H), 8.34 (s, 1H), 9.08 (s, 1H), 9.45 (s, 1H).

Example 21

Synthesis of N-[3-((4aR*,7aS*)-2-amino-4,4a,5,6,7,7a-hexahydrocyclopenta[d][1,3]thiazin-7a-yl)-4-fluorophenyl]-5-fluoromethoxypyrazine-2-carboxamide

[Formula 121]

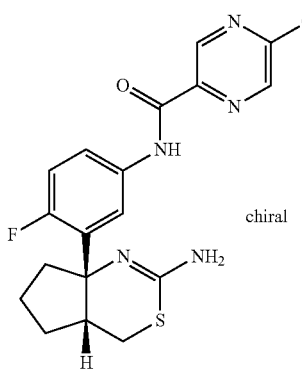

5-Fluoromethoxypyrazine-2-carboxylic acid obtained in Preparation Example 15-(2) (10.2 mg), N,N-diisopropylethylamine (24.7 µL) and PyBOP (61.5 mg) were added to a solution of the compound obtained in Preparation Example 3-(8) (17.3 mg) in dichloromethane (1.0 mL). The reaction solution was stirred at room temperature for one hour. Then, the reaction mixture was purified by silica gel column chromatography to obtain an amide. The resulting amide was dissolved in dichloromethane (750 µL) and trifluoroacetic acid (250 µL) was added. The reaction solution was allowed to stand at room temperature for 55 minutes, and then the solvent was evaporated under reduced pressure. A saturated sodium bicarbonate solution was added to the residue, followed by extraction with ethyl acetate. The organic layer was concentrated under reduced pressure. The residue was purified by NH-silica gel column chromatography to obtain the title compound (12.1 mg).

$^1$H-NMR (400 MHz, CDCl$_3$) δ (ppm): 1.69-2.02 (m, 5H), 2.55-2.66 (m, 1H), 2.76 (dd, J=12.6, 4.9 Hz, 1H), 2.79-2.88 (m, 1H), 3.00 (dd, J=12.6, 4.0 Hz, 1H), 6.07-6.11 (m, 1H), 6.19-6.23 (m, 1H), 7.06 (dd, J=12.0, 8.6 Hz, 1H), 7.36 (dd, J=7.2, 3.0 Hz, 1H), 7.92-7.98 (m, 1H), 8.29 (d, J=1.2 Hz, 1H), 9.08 (d, J=1.2 Hz, 1H), 9.47 (brs, 1H).

Example 22

Synthesis of N-[3-((4aR*,7aS*)-2-amino-4,4a,5,6,7,7a-hexahydrocyclopenta[d][1,3]thiazin-7a-yl)-4-fluorophenyl]-5-cyanopyridine-2-carboxamide

[Formula 122]

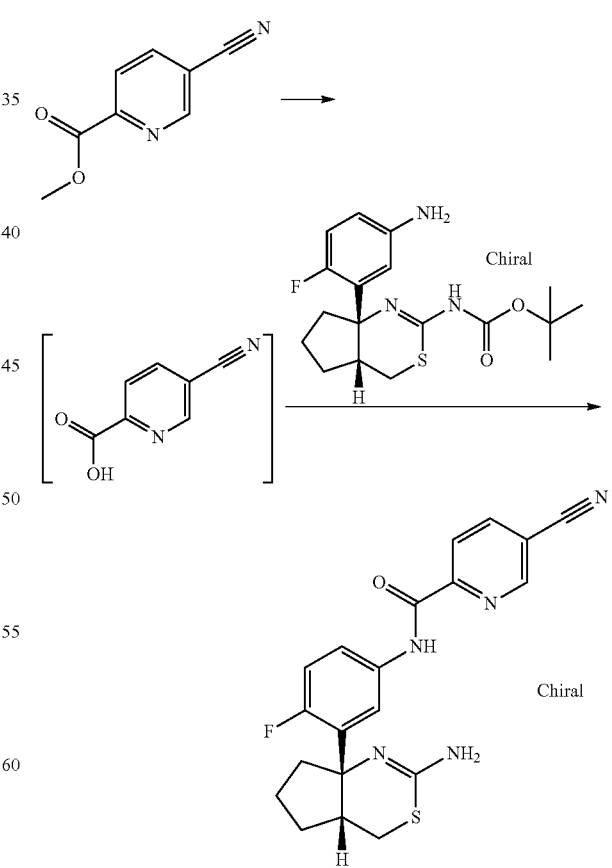

A 5 N sodium hydroxide solution (50.1 µL) was added to a solution of the compound obtained in Preparation Example 13-(1), methyl 5-cyanopyridine-2-carboxylate (30 mg) in ethanol, and the mixture was stirred at room temperature for 15 minutes. The reaction solution was made acidic with 5 N hydrochloric acid. Ethyl acetate and brine were added to the reaction solution, and the organic layer was separated. The organic layer was dried over anhydrous magnesium sulfate, and the solvent was evaporated under reduced pressure. The title compound (28 mg) was obtained from the resulting 5-cyanopyridine-2-carboxylic acid and the compound obtained in Preparation Example 3-(8) (35 mg) according to the method of Example 14.

ESI-MS; m/z 396 [M$^+$+H].

$^1$H-NMR (CDCl$_3$) δ (ppm): 1.74-2.00 (m, 5H), 2.57-2.64 (m, 1H), 2.78 (dd, J=4.0, 12.8 Hz, 1H), 2.85-2.91 (m, 1H), 3.00 (dd, J=3.2, 12.8 Hz, 1H), 7.08 (dd, J=8.8, 12.4 Hz, 1H), 7.40 (dd, J=2.8, 7.2 Hz, 1H), 7.95-7.99 (m, 1H), 8.20 (dd, J=2.0, 8.0 Hz, 1H), 8.42 (dd, J=0.8, 8.0 Hz, 1H), 8.90 (dd, J=0.8, 2.0 Hz, 1H), 9.84 (brs, 1H).

Example 23

Synthesis of N-[3-((4aR*,7aS*)-2-amino-4,4a,5,6,7,7a-hexahydrocyclopenta[d][1,3]thiazin-7a-yl)-4-fluorophenyl]-5-fluoromethoxypyridine-2-carboxamide

[Formula 123]

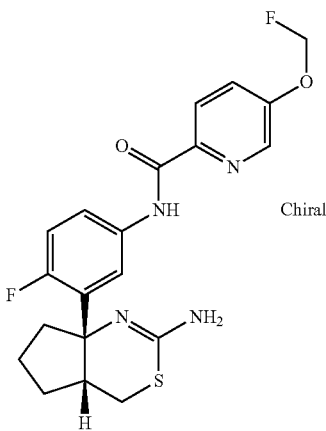 [SMILES: NC1=N[C@@]2(c3cc(NC(=O)c4ccc(OCF)cn4)ccc3F)CCC[C@H]2CS1]

The title compound (31 mg) was obtained from 5-fluoromethoxypyridine-2-carboxylic acid obtained in Preparation Example 16-(2) (22.4 mg) and the compound obtained in Preparation Example 3-(8) (35 mg) according to the method of Example 14.

ESI-MS; m/z 419 [M$^+$+H].

$^1$H-NMR (CDCl$_3$) δ (ppm): 1.60-2.00 (m, 5H), 2.57-2.64 (m, 1H), 2.76 (dd, J=4.0, 12.4 Hz, 1H), 2.80-2.85 (m, 1H), 2.99 (dd, J=3.2, 12.4 Hz, 1H), 5.80 (d, J=53.2 Hz, 2H), 7.05 (dd, J=8.8, 12.4 Hz, 1H), 7.37 (dd, J=2.8, 7.2 Hz, 1H), 7.57 (dd, J=2.8, 8.8 Hz, 1H), 7.94-7.98 (m, 1H), 8.29 (d, J=8.8 Hz, 1H), 8.41 (d, J=2.8 Hz, 1H), 9.80 (brs, 1H).

Example 24

Synthesis of N-[3-((4aS*,7aS*)-2-amino-4a,5-dihydro-4H-furo[3,4-d][1,3]thiazin-7a-yl)-4-fluorophenyl]-5-cyanopyridine-2-carboxamide

[Formula 124]

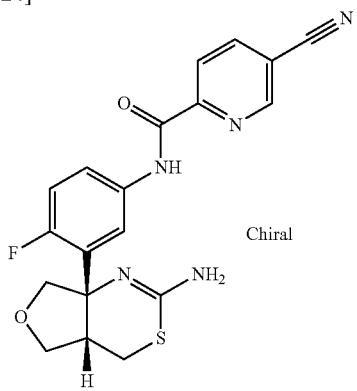

The title compound (30 mg) was obtained from 5-cyanopyridine-2-carboxylic acid obtained in Preparation Example 13-(2) (21.2 mg) and the compound obtained in Preparation Example 9-(10) (35 mg) according to the method of Example 14.

ESI-MS; m/z 398 [M$^+$+H].

$^1$H-NMR (CDCl$_3$) δ (ppm): 2.82-2.88 (m, 1H), 3.07-3.10 (m, 2H), 3.84 (dd, J=2.4, 8.8 Hz, 1H), 4.08-4.19 (m, 2H), 4.46 (dd, J=2.4, 8.8 Hz, 1H), 7.11 (dd, J=8.4, 12.0 Hz, 1H), 7.62 (dd, J=2.8, 7.2 Hz, 1H), 7.94-7.98 (m, 1H), 8.21 (dd, J=1.6, 8.0 Hz, 1H), 8.43 (d, J=8.0 Hz, 1H), 8.90 (d, J=1.6 Hz, 1H), 9.86 (s, 1H).

Example 25

Synthesis of N-[3-((4aS*,7aS*)-2-amino-4a,5-dihydro-4H-furo[3,4-d][1,3]thiazin-7a-yl)-4-fluorophenyl]-5-difluoromethoxypyrazine-2-carboxamide

[Formula 125]

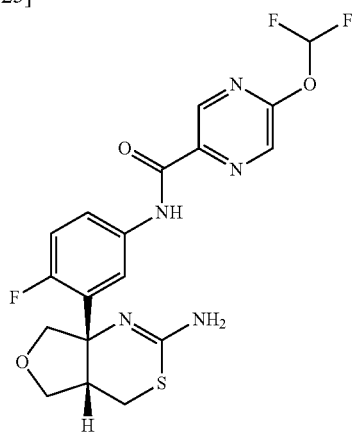

The title compound (27 mg) was obtained from 5-difluoromethoxypyrazine-2-carboxylic acid obtained in Preparation Example 14-(2) (21.7 mg) and the compound obtained in Preparation Example 9-(10) (35 mg) according to the method of Example 14.

ESI-MS; m/z 440 [M$^+$+H].

¹H-NMR (CDCl₃) δ (ppm): 2.82-2.87 (m, 1H), 3.06-3.13 (m, 2H), 3.83 (dd, J=2.4, 9.2 Hz, 1H), 4.07-4.18 (m, 2H), 4.46 (dd, J=1.2, 8.4 Hz, 1H), 7.09 (dd, J=8.8, 11.6 Hz, 1H), 7.51 (t, J=71.6 Hz, 1H), 7.59 (dd, J=2.8, 7.2 Hz, 1H), 7.91-7.95 (m, 1H), 8.34 (d, J=0.8 Hz, 1H), 9.07 (d, J=1.2 Hz, 1H), 9.45 (s, 1H).

Example 26

Synthesis of N-[3-((4aS*,7aS*)-2-amino-4a,5-dihydro-4H-furo[3,4-d][1,3]thiazin-7a-yl)-4-fluorophenyl]-5-chloropyridine-2-carboxamide

[Formula 126]

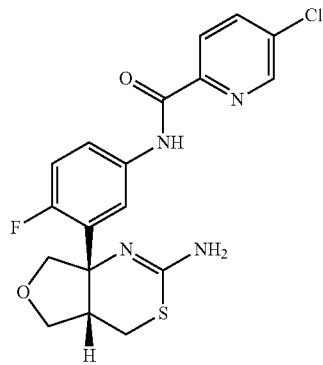

The title compound (30 mg) was obtained from 5-chloropyridine-2-carboxylic acid (21.7 mg) and the compound obtained in Preparation Example 9-(10) (35 mg) according to the method of Example 14.

ESI-MS; m/z 407 [M⁺+H].

¹H-NMR (CDCl₃) δ (ppm): 2.81-2.86 (m, 1H), 3.07-3.13 (m, 2H), 3.83 (dd, J=2.4, 8.8 Hz, 1H), 4.08-4.18 (m, 2H), 4.46 (dd, J=1.6, 8.4 Hz, 1H), 7.09 (dd, J=8.8, 11.6 Hz, 1H), 7.61 (dd, J=2.4, 7.2 Hz, 1H), 7.88 (dd, J=2.4, 8.4 Hz, 1H), 7.91-7.95 (m, 1H), 8.24 (d, J=8.4 Hz, 1H), 8.56 (dd, J=0.8, 2.4 Hz, 1H), 9.83 (s, 1H).

Example 27

Synthesis of N-[3-((7S*,7aS*)-2-amino-4a,5-dihydro-4H-furo[3,4-d][1,3]thiazin-7a-yl)-4-fluorophenyl]-5-fluoromethoxypyrazine-2-carboxamide

[Formula 127]

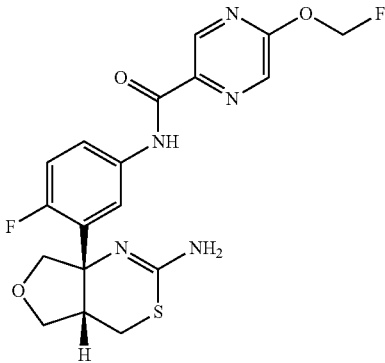 [SMILES: NC1=N[C@@]2(c3cc(NC(=O)c4cnc(OCF)cn4)ccc3F)COC[C@H]2CS1]

The compound obtained in Preparation Example 15-(2) (18.4 mg), N,N-diisopropylethylamine (39.8 μL) and PyBOP (99.1 mg) were added to a solution of the compound obtained by Preparation Example 9-(10) (28.0 mg) in dichloromethane (800 μL). The reaction solution was stirred at room temperature for 16 hours and 30 minutes. Then, the reaction mixture was purified by silica gel column chromatography to obtain an amide. The resulting amide was dissolved in dichloromethane (600 μL) and trifluoroacetic acid (200 μL) was added. The reaction solution was allowed to stand at room temperature for one hour, and then the solvent was evaporated under reduced pressure. A saturated sodium bicarbonate solution was added to the residue, followed by extraction with ethyl acetate. The organic layer was concentrated under reduced pressure. The residue was purified by NH-silica gel column chromatography to obtain the title compound (14.5 mg).

¹H-NMR (400 MHz, CDCl₃) δ (ppm): 2.80-2.88 (m, 1H), 3.05-3.14 (m, 2H), 3.81-3.85 (m, 1H), 4.06-4.19 (m, 2H), 4.44-4.49 (m, 1H), 6.08-6.10 (m, 1H), 6.21-6.23 (m, 1H), 7.10 (dd, J=11.6, 8.8 Hz, 1H), 7.58 (dd, J=7.0, 3.0 Hz, 1H), 7.93-7.97 (m, 1H), 8.29 (d, J=1.2 Hz, 1H), 9.08 (d, J=1.2 Hz, 1H), 9.50 (brs, 1H).

Example 28

Synthesis of N-[3-((4aS*,8aS*)-2-amino-4a,5,7,8-tetrahydro-4H-6-oxa-3-thia-1-azanaphthalen-8a-yl)-4-fluorophenyl]-5-cyanopyridine-2-carboxamide

[Formula 128]

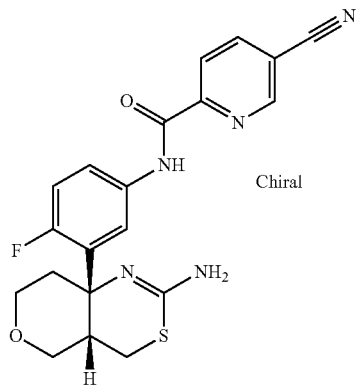 [SMILES: N#Cc1ccc(C(=O)Nc2ccc(F)c([C@]34CCOC[C@H]3CSC(N)=N4)c2)nc1]

The title compound (135 mg) was obtained from 5-cyanopyridine-2-carboxylic acid obtained in Preparation Example 13-(2) (113 mg) and the compound obtained in Preparation Example 8-(9) (195 mg) according to the method of Example 14.

ESI-MS; m/z 412 [M⁺+H].

¹H-NMR (CDCl₃) δ (ppm): 1.68 (d, J=13.6 Hz, 1H), 2.58 (dd, J=2.4, 13.2 Hz, 1H), 2.63-2.71 (m, 1H), 2.95 (dd, J=4.4, 12.4 Hz, 1H), 3.03-3.06 (m, 1H), 3.69-3.82 (m, 3H), 3.90 (dd, J=4.0, 11.2 Hz, 1H), 7.10 (dd, J=9.2, 12.0 Hz, 1H), 7.42 (dd, J=2.8, 6.8 Hz, 1H), 7.91-7.95 (m, 1H), 8.20 (dd, J=2.0, 8.4 Hz, 1H), 8.42 (d, J=8.0 Hz, 1H), 8.89 (d, J=2.4 Hz, 1H), 9.82 (s, 1H).

Example 29

Synthesis of N-[3-((4aS*,8aS*)-2-amino-4a,5,7,8-tetrahydro-4H-6-oxa-3-thia-1-azanaphthalen-8a-yl)-4-fluorophenyl]-5-difluoromethoxypyrazine-2-carboxamide

[Formula 129]

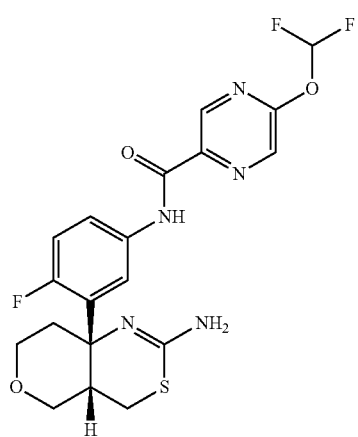 [SMILES: NC1=N[C@@]2(c3cc(NC(=O)c4cnc(OC(F)F)cn4)ccc3F)CCOC[C@H]2CS1]

The title compound (24 mg) was obtained from 5-difluoromethoxypyrazine-2-carboxylic acid obtained in Preparation Example 14-(2) (26.1 mg) and the compound obtained in Preparation Example 8-(9) (35 mg) according to the method of Example 14.

ESI-MS; m/z 454 [M$^+$+H].

$^1$H-NMR (CDCl$_3$) δ (ppm): 1.68 (d, J=12.8 Hz, 1H), 2.58 (dd, J=2.4, 12.8 Hz, 1H), 2.63-2.71 (m, 1H), 2.95 (dd, J=4.4, 12.4 Hz, 1H), 3.03-3.07 (m, 1H), 3.69-3.82 (m, 3H), 3.89 (dd, J=4.4, 11.6 Hz, 1H), 7.10 (dd, J=9.2, 12.4 Hz, 1H), 7.36 (dd, J=2.8, 6.8 Hz, 1H), 7.90-7.94 (m, 1H), 8.34 (d, J=1.2 Hz, 1H), 9.07 (d, J=1.2 Hz, 1H), 9.44 (s, 1H).

Example 30

Synthesis of N-[3-((4aS*,8aS*)-2-amino-4a,5,7,8-tetrahydro-4H-6-oxa-3-thia-1-azanaphthalen-8a-yl)-4-fluorophenyl]-5-chloropyridine-2-carboxamide

[Formula 130]

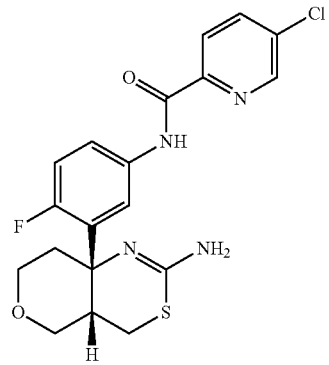 [SMILES: NC1=N[C@@]2(c3cc(NC(=O)c4ccc(Cl)cn4)ccc3F)CCOC[C@H]2CS1]

The title compound (21 mg) was obtained from 5-chloropyridine-2-carboxylic acid (21.7 mg) and the compound obtained in Preparation Example 8-(9) (35 mg) according to the method of Example 14.

ESI-MS; m/z 421 [M$^+$+H].

$^1$H-NMR (CDCl$_3$) δ (ppm): 1.70-1.83 (m, 1H), 2.62 (dd, J=3.2, 12.8 Hz, 1H), 2.68 (dd, J=4.4, 12.8 Hz, 1H), 2.99 (dd, J=4.0, 12.4 Hz, 1H), 3.08-3.15 (m, 1H), 3.70-3.77 (m, 2H), 3.83 (dd, J=4.4, 11.6 Hz, 1H), 3.92 (dd, J=4.0, 11.2 Hz, 1H), 7.10 (dd, J=8.8, 12.0 Hz, 1H), 7.41 (dd, J=2.4, 7.2 Hz, 1H), 7.88 (dd, J=2.4, 8.4 Hz, 1H), 7.92-7.96 (m, 1H), 8.24 (d, J=8.4 Hz, 1H), 8.58 (d, J=2.4 Hz, 1H), 9.82 (s, 1H).

Example 31

Synthesis of (+)-N-[3-((4aR*,6S*,7aS*)-2-amino-6-methoxy-4,4a,5,6,7,7a-hexahydrocyclopenta[d][1,3]thiazin-7a-yl)-4-fluorophenyl]-5-cyanopyridine-2-carboxamide

[Formula 131]

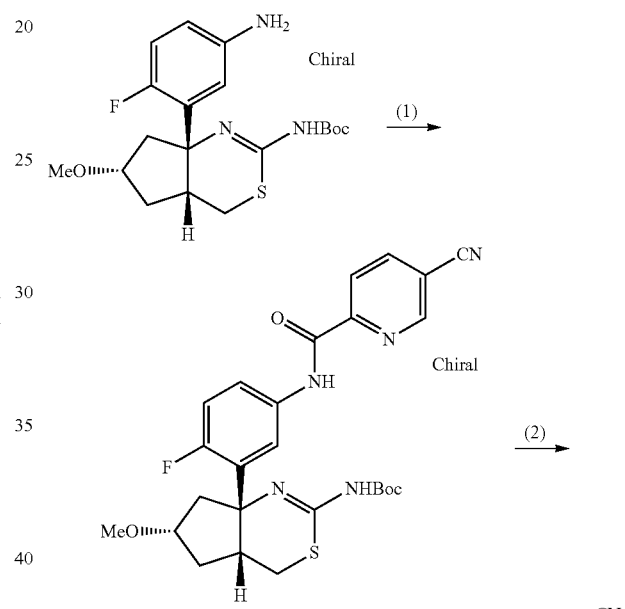

(1) Synthesis of tert-butyl ((4aR*,6S*,7aS*)-7a-{5-[(5-cyanopyridine-2-carbonyl)amino]-2-fluorophenyl}-6-methoxy-4,4a,5,6,7,7a-hexahydrocyclopenta[d][1,3]thiazin-2-yl)carbamate PyBOP (86.9 mg) was added to a solution of tert-butyl (−)-[(4aR*,6S*,7aS*)-7a-(5-amino-2-fluorophenyl)-6-methoxy-4,4a,5,6,7,7a-hexahydrocyclopenta[d][1,3]thiazin-2-yl]carbamate (22 mg), the compound of Preparation Example 26-(2) (11.6 mg) and N,N-diisopropylethylamine (0.11 mL) in dichloromethane (2.2 mL). The mixture was stirred at room temperature for one hour. The reaction solution was poured into a saturated sodium bicarbonate solution, followed by extraction with ethyl acetate. The extract was washed with a saturated sodium chloride solution and dried over anhydrous magnesium sulfate. The drying agent was removed by filtration and the filtrate was concentrated under reduced pressure. The crude product was purified by silica gel column chromatography to obtain the title compound (29 mg).

ESI-MS; m/z 526 [M$^+$+H].

(2) Synthesis of (+)-N-[3-((4aR*,6S*,7aS*)-2-amino-6-methoxy-4,4a,5,6,7,7a-hexahydrocyclopenta[d][1,3]thiazin-7a-yl)-4-fluorophenyl]-5-cyanopyridine-2-carboxamide Trifluoroacetic acid (1.0 mL) was added to a solution of tert-butyl (4aR*,6S*,7aS*)-7a-{5-[(5-cyanopyridine-2-carbonyl)amino]-2-fluorophenyl}-6-methoxy-4,4a,5,6,7,7a-hexahydrocyclopenta[d][1,3]thiazin-2-yl]carbamate (29 mg) in dichloromethane (2 mL), and the reaction solution was stirred at room temperature for one hour. The reaction solution was poured into a saturated sodium bicarbonate solution, followed by extraction with ethyl acetate. The extract was washed with a saturated sodium chloride solution and dried over anhydrous magnesium sulfate. The drying agent was removed by filtration and the filtrate was concentrated under reduced pressure. The crude product was purified by NH-silica gel column chromatography to obtain the title compound (12 mg).

optical rotation (+)

$^1$H-NMR (400 MHz, CDCl$_3$) δ (ppm): 1.98-2.14 (m, 2H), 2.22 (ddd, J=6.8, 6.8, 13.2 Hz, 1H), 2.64-2.74 (m, 1H), 2.78 (dd, J=4.4, 13.2 Hz, 1H), 2.88-3.02 (m, 2H), 3.34 (s, 3H), 4.08-4.24 (m, 1H), 7.07 (dd, J=8.8, 12.0 Hz, 1H), 7.38 (dd, J=2.8, 7.2 Hz, 1H), 7.90-8.02 (m, 1H), 8.20 (dd, J=2.0, 8.0 Hz, 1H), 8.42 (d, J=8.0 Hz, 1H), 8.90 (s, 1H), 9.82 (s, 1H).

Example 32

Synthesis of (+)-N-[3-((4aR*,6R*,7aS*)-2-amino-6-methoxy-4,4a,5,6,7,7a-hexahydrocyclopenta[d][1,3]thiazin-7a-yl)-4-fluorophenyl]-5-cyanopyridine-2-carboxamide

[Formula 132]

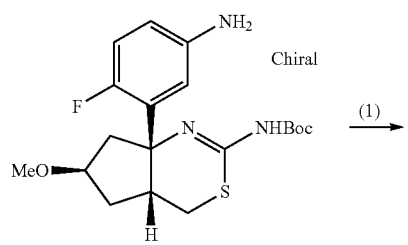

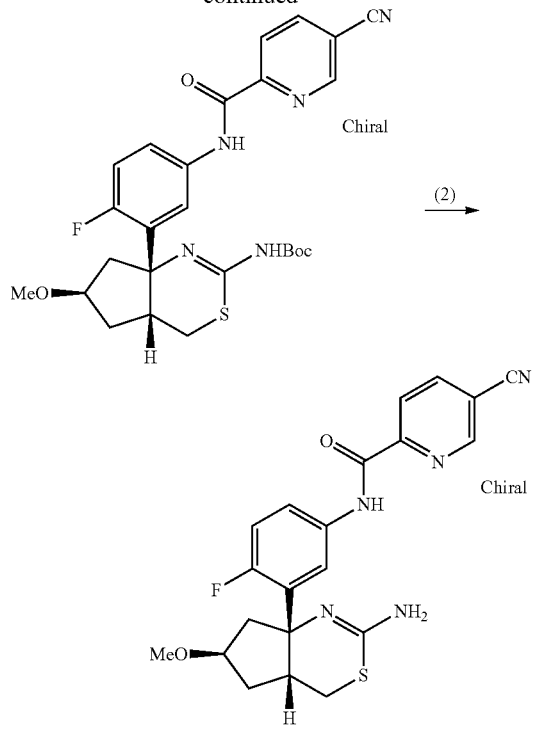

(1) Synthesis of tert-butyl ((4aR*,6R*,7aS*)-7a-{5-[(5-cyanopyridine-2-carbonyl)amino]-2-fluorophenyl}-6-methoxy-4,4a,5,6,7,7a-hexahydrocyclopenta[d][1,3]thiazin-2-yl)carbamate PyBOP (86.9 mg) was added to a solution of tert-butyl (−)-[(4aR*,6R*,7aS*)-7a-(5-amino-2-fluorophenyl)-6-methoxy-4,4a,5,6,7,7a-hexahydrocyclopenta[d][1,3]thiazin-2-yl]carbamate (22 mg), the compound of Preparation Example 26-(2) (11.6 mg) and N,N-diisopropylethylamine (0.11 mL) in dichloromethane (2.2 mL). The mixture was stirred at room temperature for one hour. The reaction solution was poured into a saturated sodium bicarbonate solution, followed by extraction with ethyl acetate. The extract was washed with a saturated sodium chloride solution and dried over anhydrous magnesium sulfate. The drying agent was removed by filtration and the filtrate was concentrated under reduced pressure. The crude product was purified by silica gel column chromatography to obtain the title compound (29 mg).

ESI-MS; m/z 526 [M$^+$+H].

(2) Synthesis of (+)-N-[3-((4aR*,6R*,7aS*)-2-amino-6-methoxy-4,4a,5,6,7,7a-hexahydrocyclopenta[d][1,3]thiazin-7a-yl)-4-fluorophenyl]-5-cyanopyridine-2-carboxamide Trifluoroacetic acid (1.0 mL) was added to a solution of tert-butyl ((4aR*,6R*,7aS*)-7a-{5-[(5-cyanopyridine-2-carbonyl)amino]-2-fluorophenyl}-6-methoxy-4,4a,5,6,7,7a-hexahydrocyclopenta[d][1,3]thiazin-2-yl)carbamate (29 mg)

in dichloromethane (2 mL), and the reaction solution was stirred at room temperature for one hour. The reaction solution was poured into a saturated sodium bicarbonate solution, followed by extraction with ethyl acetate. The extract was washed with a saturated sodium chloride solution and dried over anhydrous magnesium sulfate. The drying agent was removed by filtration and the filtrate was concentrated under reduced pressure. The crude product was purified by NH-silica gel column chromatography to obtain the title compound (12 mg).

optical rotation (+)

¹H-NMR (400 MHz, CDCl₃) δ (ppm): 1.91 (ddd, J=3.6, 9.6, 13.2 Hz, 1H), 2.22-2.40 (m, 2H), 2.62 (dd, J=6.8, 12.8 Hz, 1H), 2.76 (dd, J=3.2, 12.8 Hz, 1H), 2.99 (dd, J=3.2, 12.8 Hz, 1H), 3.10-3.22 (m, 1H), 3.34 (s, 3H), 3.88-4.00 (m, 1H), 7.08 (dd, J=8.8, 12.0 Hz, 1H), 7.34-7.46 (m, 1H), 7.86-7.98 (m, 1H), 8.20 (dd, J=1.2, 8.0 Hz, 1H), 8.42 (d, J=8.0 Hz, 1H), 8.89 (s, 1H), 9.82 (s, 1H).

Example 33

Synthesis of (+)-N-[3-((4aR*,9aS*)-2-amino-4,4a,5,6,7,8,9,9a-octahydrocyclohepta[d][1,3]thiazin-9a-yl)-4-fluorophenyl]-5-cyanopyridine-2-carboxamide

[Formula 133]

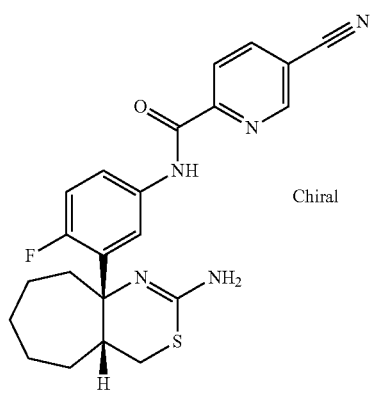 [SMILES: N#Cc1ccc(C(=O)Nc2ccc(F)c([C@]34CCCCC[C@H]3CSC(N)=N4)c2)nc1]

The title compound (41 mg) was obtained from tert-butyl (−)-[(4aR*,9aS*)-9a-(5-amino-2-fluorophenyl)-4,4a,5,6,7,8,9,9a-octahydrocyclohepta[d][1,3]thiazin-2-yl]carbamate obtained in Preparation Example 7-(8) (60.0 mg) and 5-cyanopyridine-2-carboxylic acid obtained in Preparation Example 13-(2) (97.8 mg) according to the method of Example 14.

ESI-MS; m/z 424 [M+H].

¹H-NMR (400 MHz, CDCl₃) δ (ppm): 1.50-1.91 (m, 9H), 2.39 (m, 1H), 2.56 (dd, J=3.2, 12.0 Hz, 1H), 2.71 (m, 1H), 2.86 (dd, J=3.2, 12.0 Hz, 1H), 7.07 (dd, J=8.8, 12.0 Hz, 1H), 7.27 (m, 1H), 7.97 (ddd, J=2.4, 4.8, 8.8 Hz, 1H), 8.19 (dd, J=2.0, 8.0 Hz, 1H), 8.42 (dd, J=1.2, 8.0 Hz, 1H), 8.88 (dd, J=1.2, 2.4 Hz, 1H), 9.79 (s, 1H).

Example 34

Synthesis of (±)-N-[3-((4aR*,7aS*)-2-amino-4,4a,5,6,7,7a-hexahydrocyclopenta[d][1,3]thiazin-7a-yl)-4-methoxyphenyl]-5-chloropyridine-2-carboxamide

[Formula 134]

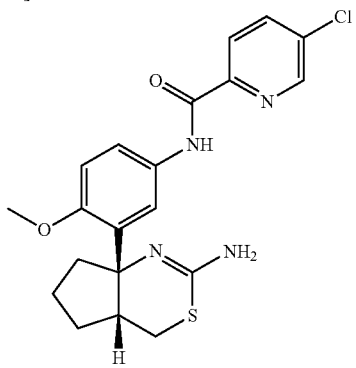

5-Chloropyridine-2-carboxylic acid (6.26 mg), N,N-diisopropylethylamine (13.8 μL) and PyBOP (34.5 mg) were added to a solution of the compound obtained in Preparation Example 6-(2) (10.0 mg) in dichloromethane (1.0 mL). The reaction solution was stirred at room temperature for one hour and 50 minutes, and then trifluoroacetic acid (250 μL) was added. The reaction solution was allowed to stand at room temperature for 40 minutes, and then the solvent was evaporated under reduced pressure. A saturated sodium bicarbonate solution was added to the residue, followed by extraction with ethyl acetate. The organic layer was concentrated under reduced pressure. The residue was purified by NH-silica gel column chromatography to obtain the title compound (1.0 mg).

¹H-NMR (400 MHz, CDCl₃) δ (ppm): 1.72-1.98 (m, 5H) 2.72 (dd, J=12.8, 4.7 Hz, 1H), 2.74-2.82 (m, 1H), 2.97 (dd, J=12.8, 4.0 Hz, 1H), 3.05-3.12 (m, 1H), 3.86 (s, 3H), 6.93 (d, J=8.8 Hz, 1H), 7.31 (brd, J=3.5 Hz, 1H), 7.86 (dd, J=8.4, 3.5 Hz, 1H), 7.99 (dd, J=8.8, 3.5 Hz, 1H), 8.24 (d, J=8.4 Hz, 1H), 8.56 (d, J=3.5 Hz, 1H), 9.73 (brs, 1H).

Example 35

Synthesis of N-[3-((4aS*,7aS*)-2-amino-4a,5-dihydro-4H-furo[3,4-d][1,3]thiazin-7a-yl)-4-fluorophenyl]-5-difluoromethylpyrazine-2-carboxamide

[Formula 135]

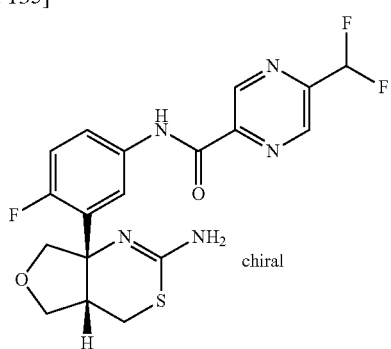

The title compound (27 mg) was obtained from 5-difluoromethylpyrazine-2-carboxylic acid prepared in Preparation Example 17-(5) (17.0 mg) and the compound obtained in Preparation Example 9-(10) (30 mg) according to the method of Example 14.

ESI-MS; m/z 424 [M⁺+H].

¹H-NMR (CDCl₃) δ (ppm): 2.82-2.87 (m, 1H), 3.07-3.13 (m, 2H), 3.83 (dd, J=2.4, 8.8 Hz, 1H), 4.08-4.18 (m, 2H), 4.47 (dd, J=1.6, 8.4 Hz, 1H), 6.80 (t, J=54.8 Hz, 1H), 7.13 (dd, J=8.8, 12.0 Hz, 1H), 7.62 (dd, J=2.8, 6.8 Hz, 1H), 7.94-7.98 (m, 1H), 8.93 (s, 1H), 9.53 (s, 1H), 9.65 (s, 1H).

Example 36

Synthesis of (±)-(4aR,7aS)-7a-[3-(2-fluoro-pyridin-3-yl)phenyl]-6-phenyl-4,4a,5,6,7,7a-hexahydropyr-rolo[3,4-d][1,3]thiazin-2-ylamine

[Formula 136]

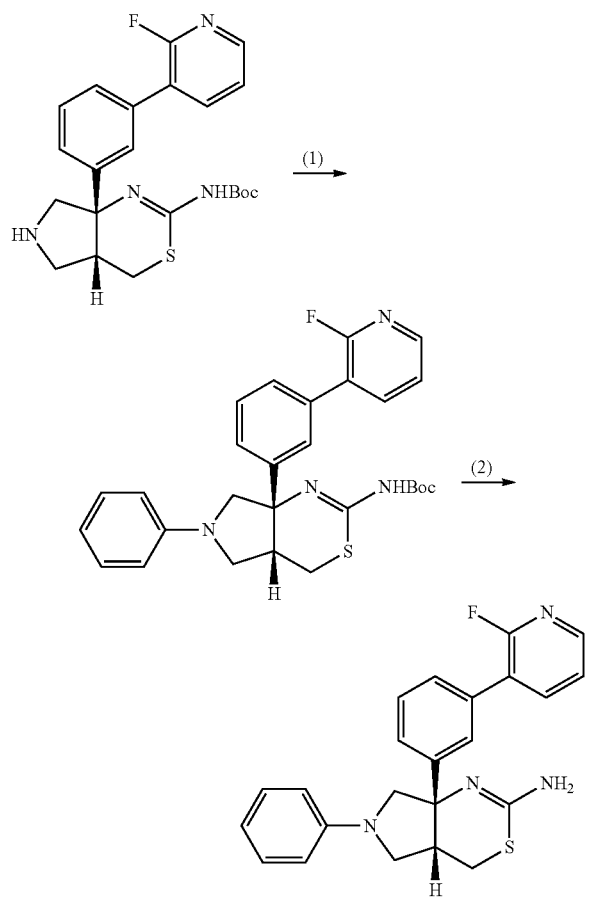

(1) Synthesis of tert-butyl(±)-{(4aR*,7aS*)-7a-[3-(2-fluoropyridin-3-yl)phenyl]-6-phenyl-4,4a,5,6,7,7a-hexahydropyrrolo[3,4-d][1,3]thiadiazin-2-yl}carbamate The compound obtained in Preparation Example 18-(9) (50.00 mg) was mixed with phenylboronic acid (23.9 mg), copper (II) acetate (3.56 mg), triethylamine (54.3 μL) and molecular sieves 4A (powder) (40.00 mg) in THF, and the mixture was stirred under a nitrogen atmosphere at room temperature for 23 hours. The reaction suspension was purified by NH-silica gel column chromatography. The resulting product was purified again by NH-pTLC to obtain the title compound (8 mg).

¹H-NMR (400 MHz, CDCl₃) δ (ppm): 1.49 (s, 9H), 2.91 (dd, J=4.8, 13.2 Hz, 1H), 3.01-3.08 (m, 2H), 3.60-3.64 (m, 1H), 3.69 (d, J=10.4 Hz, 1H), 3.75-3.79 (m, 1H), 4.00 (d, J=10.0 Hz, 1H), 6.58 (d, J=8.0 Hz, 2H), 6.75 (t, J=7.2 Hz, 1H) 7.21-7.32 (m, 3H), 7.41-7.44 (m, 1H), 7.46-7.55 (m, 3H), 7.85 (ddd, J=2.0, 3.6, 9.6 Hz, 1H), 8.21-8.23 (m, 1H).

(2) Synthesis of (±)-(4aR*,7aS*)-7a-[3-(2-fluoropy-ridin-3-yl)phenyl]-6-phenyl-4,4a,5,6,7,7a-hexahydropyrrolo[3,4-d][1, 3]thiazin-2-ylamine TFA (0.50 mL) was added to a solution of the compound obtained in Example 36-(1) (8.00 mg) in chloroform (0.50 mL). After stirring at room temperature for 2.5 hours, the reaction solution was diluted with chloroform and poured into a mixture of a saturated sodium bicarbonate solution and a saturated sodium chloride solution, followed by vigorous shaking. The aqueous layer was separated and then the organic layer was dried over anhydrous magnesium sulfate. The drying agent was removed by filtration and then the solvent was evaporated under reduced pressure. TFA (0.50 mL) was added to a solution of the residue in chloroform (0.50 mL). After stirring at room temperature for 23 hours, the reaction solution was diluted with chloroform and poured into a mixture of a saturated sodium bicarbonate solution and a saturated sodium chloride solution, followed by vigorous shaking. The aqueous layer was separated and then the organic layer was dried over anhydrous magnesium sulfate. The drying agent was removed by filtration and then the solvent was evaporated under reduced pressure. The residue was purified by NH-silica gel column chromatography. The resulting product was dissolved in chloroform and methanol and the solvent was evaporated under a nitrogen stream. Diethyl ether was added to the residue and the solid was sufficiently precipitated. Then, the solvent was evaporated under a nitrogen stream. The residue was dried under reduced pressure to obtain the title compound (6.50 mg).

¹H-NMR (400 MHz, CDCl₃) δ (ppm): 2.75-2.78 (m, 1H), 2.96-3.08 (m, 2H), 3.60 (d, J=7.6 Hz, 2H), 3.67 (d, J=9.6 Hz, 1H), 4.02 (d, J=10.0 Hz, 1H), 6.59 (d, J=8.4 Hz, 2H), 6.72 (t, J=7.2 Hz, 1H), 7.24-7.28 (m, 3H), 7.41-7.46 (m, 3H), 7.54 (s, 1H), 7.82-7.86 (m, 1H), 8.19 (d, J=4.4 Hz, 1H).

Example 37

Synthesis of (±)-(4aR*,7aS*)-7a-[3-(2-fluoropyridin-3-yl)phenyl]-6-pyrimidin-2-yl-4,4a,5,6,7,7a-hexahy-dropyrrolo[3,4-d][1,3]thiazin-2-ylamine

[Formula 137]

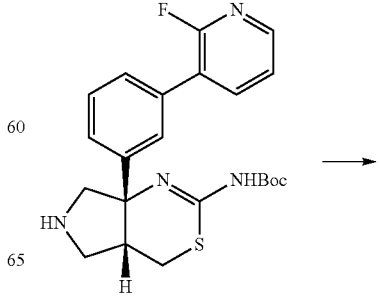

-continued

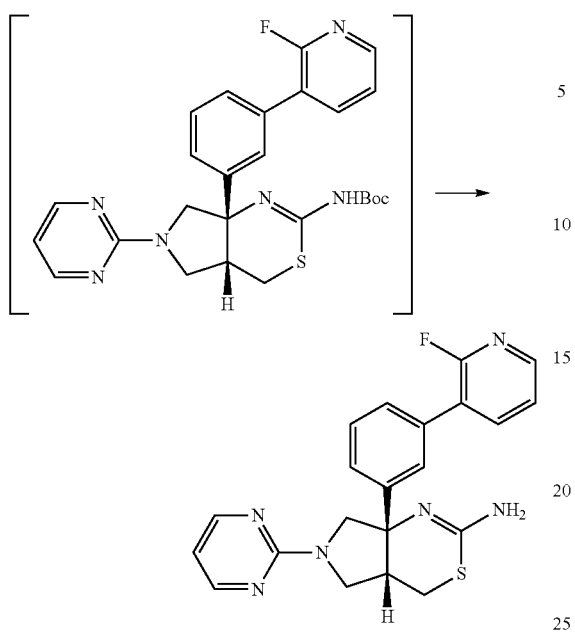

2-Bromopyrimidine (93.00 mg), tris(dibenzylideneacetone)dipalladium (0) (10.70 mg), rac-2,2-bis(diphenylphosphino)-1,1-binaphthyl (10.90 mg) and sodium tert-butoxide (45.00 mg) were added to a 1 solution of the compound obtained in Preparation Example 18-(9) (50.00 mg) in toluene (1.00 mL). The mixture was heated with stirring under a nitrogen atmosphere at 70° C. for five hours and 45 minutes. The reaction mixture was cooled to room temperature and diluted with ethyl acetate. Then, the reaction solution was filtered through NH-silica gel under reduced pressure and washed with ethyl acetate. The resulting filtrate was concentrated under reduced pressure and then purified by NH-silica gel column chromatography to obtain a Boc-protected compound as a synthetic intermediate. TFA (0.50 mL) was added to a solution of the resulting product in chloroform (0.50 mL). After stirring at room temperature for six hours, the reaction solution was diluted with chloroform and poured into a mixture of a saturated sodium bicarbonate solution and a saturated sodium chloride solution, followed by vigorous shaking. The aqueous layer was separated and then the organic layer was dried over anhydrous magnesium sulfate. The drying agent was removed by filtration and then the solvent was evaporated under reduced pressure. The residue was purified by NH-silica gel column chromatography. The resulting product was dissolved in ethyl acetate and the solvent was evaporated under a nitrogen stream. Diethyl ether was added to the residue and the solid was sufficiently precipitated. Then, the solvent was evaporated under a nitrogen stream. The residue was dried under reduced pressure to obtain the title compound (1.60 mg).

$^1$H-NMR (400 MHz, CDCl$_3$) δ (ppm): 2.82-2.88 (m, 1H), 2.98 (dd, J=5.2, 13.2 Hz, 1H), 3.13 (dd, J=4.0, 5.2 Hz, 1H), 3.87 (dd, J=2.8, 4.0 Hz, 2H), 4.07 (d, J=11.6 Hz, 1H), 4.23 (d, J=11.6 Hz, 1H), 6.53 (t, J=4.8 Hz, 1H), 7.24-7.29 (m, 1H), 7.44-7.48 (m, 3H), 7.56-7.57 (m, 1H), 7.86 (ddd, J=2.0, 7.6, 9.6 Hz, 1H), 8.19-8.21 (m, 1H), 8.34 (d, J=4.8 Hz, 2H).

Example 38

Synthesis of N-[3-((4aS,7R,8aS)-2-amino-7-methoxymethyl-4a,5,7,8-tetrahydro-4H-6-oxa-3-thia-1-azanaphthalen-8a-yl)-4-fluorophenyl]-5-fluoromethoxypyrazine-2-carboxamide

[Formula 138]

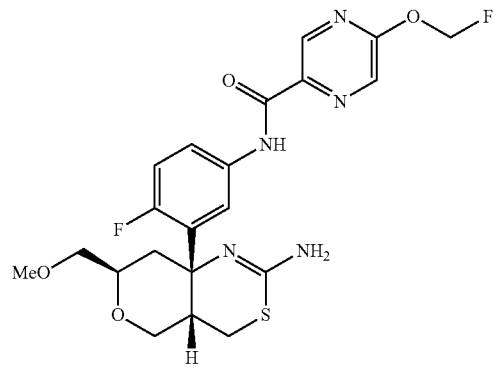 [SMILES: COC[C@H]1C[C@]2(c3cc(NC(=O)c4cnc(OCF)cn4)ccc3F)N=C(N)SC[C@@H]2CO1]

The compound obtained in Preparation Example 19-(14) (45 mg) was dissolved in dichloromethane (2 mL). 5-Fluoromethoxypyrazine-2-carboxylic acid (28 mg), N,N-diisopropylethylamine (48 μL) and PyBOP (113 mg) were added thereto, followed by stirring at room temperature. After three hours, the reaction solution was concentrated and the residue was subjected to silica gel column chromatography to obtain an amide compound (66 mg). The amide compound (66 mg) was dissolved in dichloromethane (2 mL). TFA (1 mL) was added and the mixture was stirred at room temperature for 1.5 hours. The reaction solution was concentrated. Chloroform, a saturated sodium bicarbonate solution and a 1 N sodium hydroxide solution were added to the residue, and the organic layer was separated. The organic layer was dried over anhydrous magnesium sulfate. The drying agent was removed by filtration and the filtrate was concentrated under reduced pressure to obtain a residue. The residue was precipitated using t-butyl methyl ether, ethyl acetate and hexane. The solid was collected by filtration to obtain the title compound (36 mg).

ESI-MS; m/z 480 [M$^+$+H].

$^1$H-NMR (400 MHz, CDCl$_3$) δ (ppm): 1.69 (dd, J=1.6, 12.8 Hz, 1H), 2.38 (t, J=12.0 Hz, 1H), 2.56-2.64 (m, 1H), 2.96 (dd, J=4.4, 12.8 Hz, 1H), 2.98-3.06 (m, 1H), 3.40 (s, 3H), 3.37-3.51 (m, 2H), 3.79-3.95 (m, 3H), 6.09 (dd, J=2.0, 3.6 Hz, 1H), 6.22 (dd, J=2.0, 3.6 Hz, 1H), 7.08 (dd, J=8.8, 12.0 Hz, 1H), 7.30-7.40 (m, 1H), 7.85-7.95 (m, 1H), 8.29 (d, J=1.6 Hz, 1H), 9.08 (d, J=1.2 Hz, 1H) 9.45 (brs, 1H).

Examples 39 to 40

The compounds of Examples 39 to 40 as shown in Table 1 below were synthesized according to Example 38 using the corresponding carboxylic acids.

[Table 1]

TABLE 1

| Example | Chemical structure | Compound name: |
|---|---|---|
| 39 | 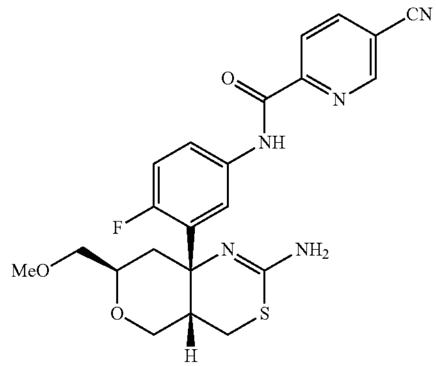 [SMILES: COC[C@H]1C[C@]2(c3cc(NC(=O)c4ccc(C#N)cn4)ccc3F)N=C(N)SC[C@@H]2CO1] | N-[3-((4aS,7R,8aS)-2-amino-7-methoxymethyl-4a,5,7,8-tetrahydro-4H-6-oxa-3-thia-1-azanaphthalen-8a-yl)-4-fluorophenyl]-5-cyanopyridine-2-carboxamide<br>ESI-MS m/z 456 [M⁺ + H] |
| 40 | 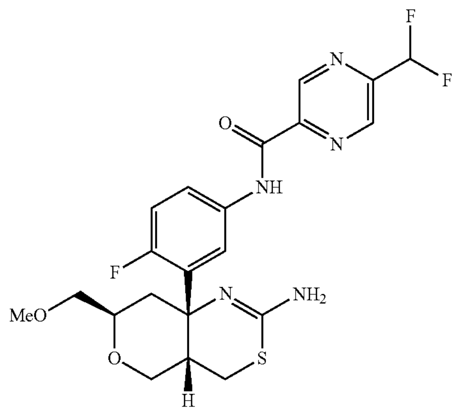 [SMILES: COC[C@H]1C[C@]2(c3cc(NC(=O)c4cnc(C(F)F)cn4)ccc3F)N=C(N)SC[C@@H]2CO1] | N-[3-((4aS,7R,8aS)-2-amino-7-methoxymethyl-4a,5,7,8-tetrahydro-4H-6-oxa-3-thia-1-azanaphthalen-8a-yl)-4-fluorophenyl]-5-difluoromethylpyrazine-2-carboxamide<br>ESI-MS m/z 482 [M⁺ + H] |

Example 41

Synthesis of N-[3-((4aS,7R,8aS)-2-amino-7-fluoromethyl-4a,5,7,8-tetrahydro-4H-6-oxa-3-thia-1-azanaphthalen-8a-yl)-4-fluorophenyl]-5-fluoromethoxypyrazine-2-carboxamide

[Formula 139]

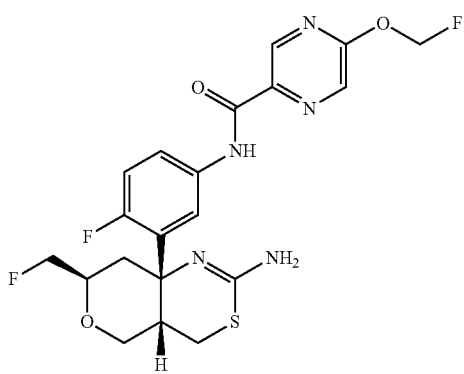 [SMILES: NC1=N[C@@]2(c3cc(NC(=O)c4cnc(OCF)cn4)ccc3F)C[C@H](CF)OC[C@H]2CS1]

The compound obtained in Preparation Example 20-(3) (45 mg) was dissolved in dichloromethane (2 mL). 5-Fluoromethoxypyrazine-2-carboxylic acid (28 mg), N,N-diisopropylethylamine (48 µL) and PyBOP (113 mg) were added thereto, followed by stirring at room temperature. After three hours, the reaction solution was concentrated and the residue was subjected to silica gel column chromatography to obtain an amide compound (67 mg). The amide compound (67 mg) was dissolved in dichloromethane (2 mL). Then, TFA (1 mL) was added and the mixture was stirred at room temperature for 1.5 hours. The reaction solution was concentrated under reduced pressure. Then, chloroform, a saturated sodium bicarbonate solution and a 1 N sodium hydroxide solution were added to the residue, and the organic layer was separated. The organic layer was dried over anhydrous magnesium sulfate. The drying agent was removed by filtration and the filtrate was concentrated under reduced pressure to obtain a residue. The residue was solidified by addition of t-butyl methyl ether and hexane. The solid was collected by filtration to obtain the title compound (41 mg). ESI-MS; m/z 468 [M⁺+H].

¹H-NMR (400 MHz, CDCl₃) δ (ppm): 1.50-1.90 (m, 1H), 2.36-2.48 (m, 1H), 2.58-2.66 (m, 1H), 2.92-3.10 (m, 2H), 3.80-4.04 (m, 3H), 4.32-4.43 (m, 1H), 4.44-4.54 (m, 1H), 6.09 (dd, J=2.0, 4.0 Hz, 1H), 6.22 (dd, J=2.0, 4.0 Hz, 1H), 7.10 (dd, J=8.8, 12.0 Hz, 1H), 7.35-7.45 (m, 1H), 7.85-7.95 (m, 1H), 8.29 (d, J=1.6 Hz, 1H), 9.08 (d, J=1.6 Hz, 1H) 9.46 (brs, 1H).

Examples 42 to 45

The compounds of Examples 42 to 45 as shown in Table 2 below were synthesized according to Example 41 using the corresponding carboxylic acids.

TABLE 2

| Example | Chemical structure | Compound name: |
|---|---|---|
| 42 | 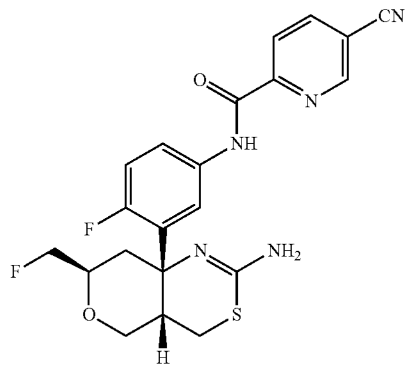 [SMILES: N#Cc1ccc(C(=O)Nc2ccc(F)c([C@]34C[C@H](CF)OC[C@H]3CSC(N)=N4)c2)nc1] | N-[3-((4aS,7R,8aS)-2-amino-7-fluoromethyl-4a,5,7,8-tetrahydro-4H-6-oxa-3-thia-1-azanaphthalen-8a-yl)-4-fluorophenyl]-5-cyanopyridine-2-carboxamide<br>ESI-MS m/z 444 [M⁺ + H] |
| 43 | 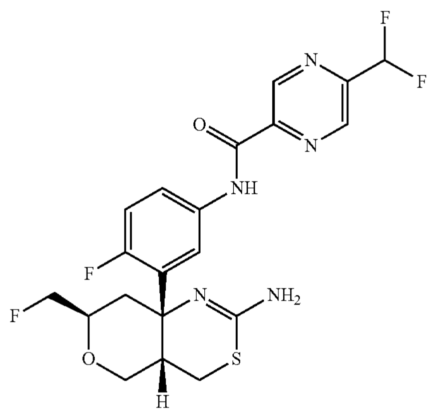 [SMILES: NC1=N[C@@]2(c3cc(NC(=O)c4cnc(C(F)F)cn4)ccc3F)C[C@H](CF)OC[C@H]2CS1] | N-[3-((4aS,7R,8aS)-2-amino-7-fluoromethyl-4a,5,7,8-tetrahydro-4H-6-oxa-3-thia-1-azanaphthalen-8a-yl)-4-fluorophenyl]-5-difluoromethylpyrazine-2-carboxamide<br>ESI-MS m/z 470 [M⁺ + H] |
| 44 | 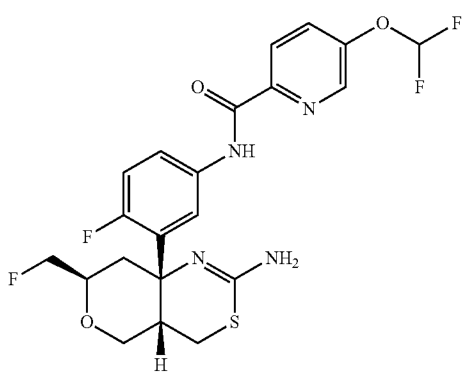 [SMILES: NC1=N[C@@]2(c3cc(NC(=O)c4ccc(OC(F)F)cn4)ccc3F)C[C@H](CF)OC[C@H]2CS1] | N-[3-((4aS,7R,8aS)-2-amino-7-fluoromethyl-4a,5,7,8-tetrahydro-4H-6-oxa-3-thia-1-azanaphthalen-8a-yl)-4-fluorophenyl]-5-difluoromethoxypyridine-2-carboxamide<br>ESI-MS m/z 485 [M⁺ + H] |
| 45 | 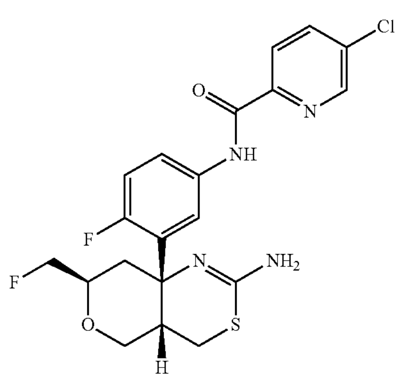 [SMILES: NC1=N[C@@]2(c3cc(NC(=O)c4ccc(Cl)cn4)ccc3F)C[C@H](CF)OC[C@H]2CS1] | N-[3-((4aS,7R,8aS)-2-amino-7-fluoromethyl-4a,5,7,8-tetrahydro-4H-6-oxa-3-thia-1-azanaphthalen-8a-yl)-4-fluorophenyl]-5-chloropyridine-2-carboxamide<br>ESI-MS m/z 453 [M⁺ + H] |

Example 46

Synthesis of (±)-(4aR*,7aS*)-7a-[3-(2-fluoropyridin-3-yl)phenyl]-6-(2,2,2-trifluoroethyl)-4,4a,5,6,7,7a-hexahydropyrrolo[3,4-d][1,3]thiazin-2-ylamine

[Formula 140]

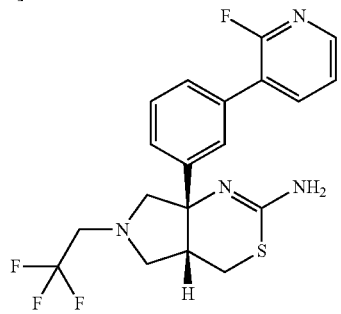

The compound obtained in Preparation Example 18-(9) (50 mg) and N,N-diisopropylethylamine (45 μL) were dissolved in acetonitrile (1 mL). Then, 2,2,2-trifluoroethyl trifluoromethanesulfonate (24 μL) was added, followed by stirring at room temperature. After 14 hours, water and ethyl acetate were added to the reaction solution, and the organic layer was separated. The organic layer was sequentially washed with brine and a saturated sodium bicarbonate solution. The organic layer was dried over magnesium sulfate. The drying agent was removed by filtration and the filtrate was concentrated under reduced pressure. The residue was subjected to NH-silica gel column chromatography to obtain an N-alkyl compound (38 mg) as a crude product. The N-alkyl compound (38 mg) was dissolved in dichloromethane (2 mL). Then, TFA (0.5 mL) was added, followed by stirring for two hours. The reaction solution was concentrated under reduced pressure. Chloroform and 2 N sodium hydroxide were added to the residue, and the organic layer was separated. The organic layer was dried over anhydrous magnesium sulfate. The drying agent was removed by filtration. The filtrate was concentrated under reduced pressure to obtain a residue. The residue was subjected to NH-silica gel column chromatography to obtain the title compound (18 mg).

ESI-MS; m/z 411 [M$^+$+H].

Example 47

Synthesis of (±)-1-{(4aR*,7aS*)-2-amino-7a-[3-(2-fluoropyridin-3-yl)phenyl]-4a,5,7,7a-tetrahydro-4H-pyrrolo[3,4-d][1,3]thiazin-6-yl}-3,3,3-trifluoropropan-1-one

[Formula 141]

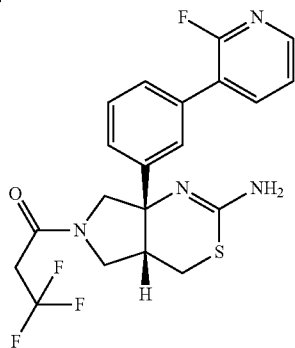

The compound obtained in Preparation Example 18-(9) (45 mg), 3,3,3-trifluoropropionic acid (10 μL), N,N-diisopropylethylamine (17 μL) were dissolved in tetrahydrofuran (1 mL). Then, PyBOP (51 mg) was added, followed by stirring at room temperature. After 14 hours, a saturated sodium bicarbonate solution and ethyl acetate were added to the reaction solution, and the organic layer was separated. The organic layer was sequentially washed with brine and a saturated ammonium chloride solution. The organic layer was dried over magnesium sulfate. The drying agent was removed by filtration and the filtrate was concentrated under reduced pressure. The residue was subjected to NHpTLC to obtain an amide compound (26 mg) as a crude product. The amide compound (26 mg) was dissolved in dichloromethane (2 mL). Then, TFA (0.5 mL) was added, followed by stirring for two hours. The reaction solution was concentrated under reduced pressure. Chloroform and 2 N sodium hydroxide were added to the residue, and the organic layer was separated. The organic layer was dried over anhydrous magnesium sulfate. The drying agent was removed by filtration and the filtrate was concentrated under reduced pressure to obtain a residue. This was subjected to silica gel column chromatography to obtain the title compound (15 mg).

ESI-MS; m/z 439 [M$^+$+H].

Example 48

The compound of Example 48 as shown in Table 3 below was synthesized according to Example 47 using the corresponding carboxylic acids.

[Table 3]

TABLE 3

| Example | Chemical structure | |
|---|---|---|
| 48 | 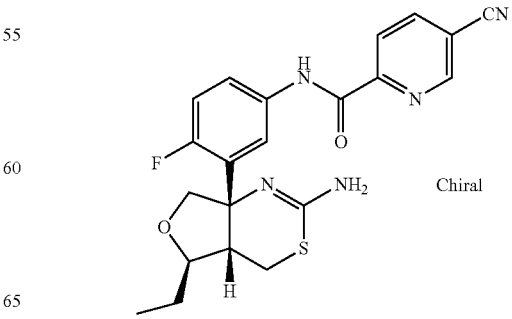 | ESI-MS; m/z 411 [M$^+$ + H]. |

Example 49

Synthesis of N-[3-((4aS*,5R*,7aS*)-2-amino-5-ethyl-4a,5-dihydro-4H-furo[3,4-d][1,3]thiazin-7a-yl)-4-fluorophenyl]-5-cyanopyridine-2-carboxamide

[Formula 142]

The title compound (28.0 mg) was obtained from the compound obtained in Preparation Example 21-(10) (30.0 mg) and 5-cyanopyridine-2-carboxylic acid obtained in Preparation Example 13-(2) (22.5 mg) according to the method of Example 14.

$^{1}$H-NMR (400 MHz, CDCl$_{3}$) δ (ppm): 1.04-1.07 (m, 3H), 1.65-1.72 (m, 2H), 2.68-2.77 (m, 2H), 3.08-3.12 (m, 1H), 3.80-3.82 (m, 1H), 4.17-4.22 (m, 1H), 4.54-4.57 (m, 1H), 7.07-7.13 (m, 1H), 7.52-7.54 (m, 1H), 7.96-8.00 (m, 1H), 8.19-8.21 (m, 1H), 8.42-8.44 (m, 1H), 8.90 (s, 1H), 9.85 (br, 1H).

Example 50

Synthesis of N-[3-((4aS*,5R*,7aS*)-2-amino-5-ethyl-4a,5-dihydro-4H-furo[3,4-d][1,3]thiazin-7a-yl)-4-fluorophenyl]-5-difluoromethoxypyrazine-2-carboxamide

[Formula 143]

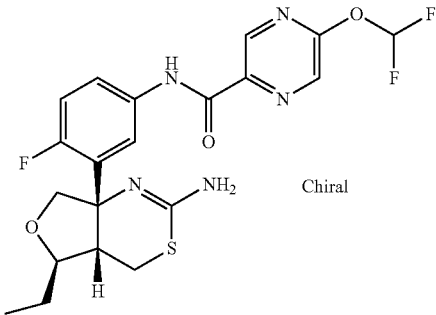 [SMILES: CC[C@H]1OC[C@]2(c3cc(NC(=O)c4cnc(OC(F)F)cn4)ccc3F)N=C(N)SC[C@H]12]

The title compound (22.0 mg) was obtained from the compound obtained in Preparation Example 21-(10) (28.0 mg) and 5-difluoromethoxypyrazine-2-carboxylic acid obtained in Preparation Example 14-(2) (20.2 mg) according to the method of Example 14.

$^{1}$H-NMR (400 MHz, CDCl$_{3}$) δ (ppm): 1.04-1.07 (m, 3H), 1.67-1.70 (m, 2H), 2.70-2.76 (m, 2H), 3.08-3.11 (m, 1H), 3.80-3.83 (m, 1H), 4.17-4.20 (m, 1H), 4.54-4.56 (m, 1H), 7.06-7.11 (m, 1H), 7.51 (t, J=72 Hz, 1H), 7.93-7.95 (m, 1H), 8.33 (s, 1H), 9.06 (s, 1H), 9.48 (br, 1H).

Example 51

Synthesis of N-[3-((4aS*,5R*,7aS*)-2-amino-5-ethyl-4a,5-dihydro-4H-furo[3,4-d][1,3]thiazin-7a-yl)-4-fluorophenyl]-5-chloropyridine-2-carboxamide

[Formula 144]

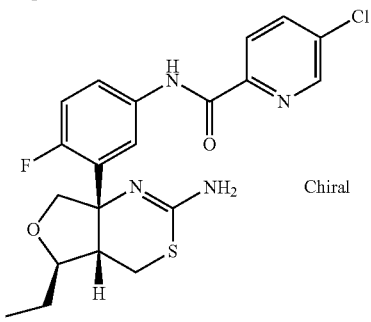 [SMILES: CC[C@H]1OC[C@]2(c3cc(NC(=O)c4ccc(Cl)cn4)ccc3F)N=C(N)SC[C@H]12]

The title compound (26.0 mg) was obtained from the compound obtained in Preparation Example 21-(10) (28.0 mg) and 5-chloropyridine-2-carboxylic acid (23.2 mg) according to the method of Example 14.

$^{1}$H-NMR (400 MHz, CDCl$_{3}$) δ (ppm): 1.05 (t, J=7.2 Hz, 3H), 1.65-1.72 (m, 2H), 2.68-2.76 (m, 2H), 3.08-3.13 (m, 1H), 3.81-3.83 (m, 1H), 4.17-4.22 (m, 1H), 4.54-4.56 (m, 1H), 7.05-7.10 (m, 1H), 7.51-7.53 (m, 1H), 7.87-7.98 (m, 2H), 8.23-8.25 (m, 1H), 8.56-8.56 (m, 1H), 9.83 (br, 1H).

Example 52

Synthesis of N-[3-((4aS*,5R*,7aS*)-2-amino-5-ethyl-4a,5-dihydro-4H-furo[3,4-d][1,3]thiazin-7a-yl)-4-fluorophenyl]-5-fluoromethoxypyrazine-2-carboxamide

[Formula 145]

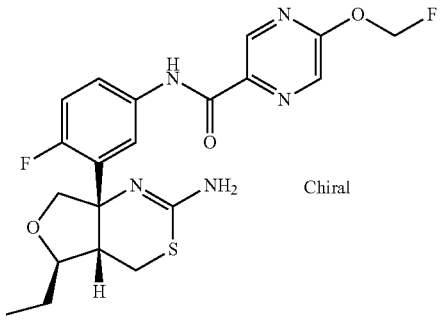 [SMILES: CC[C@H]1OC[C@]2(c3cc(NC(=O)c4cnc(OCF)cn4)ccc3F)N=C(N)SC[C@H]12]

The title compound (23.0 mg) was obtained from the compound obtained in Preparation Example 21-(10) (30.0 mg) and 5-fluoromethoxypyrazine-2-carboxylic acid obtained in Preparation Example 15-(2) (18.8 mg) according to the method of Example 14.

$^{1}$H-NMR (400 MHz, CDCl$_{3}$) δ (ppm): 1.04-1.07 (m, 3H), 1.65-1.70 (m, 2H), 2.71-2.76 (m, 2H), 3.09-3.13 (m, 1H), 3.80-3.83 (m, 1H), 4.15-4.20 (m, 1H), 4.54-4.56 (m, 1H), 6.15 (d, J=51 Hz, 1H), 7.06-7.11 (m, 1H), 7.48-7.49 (m, 1H), 7.96-7.97 (m, 1H), 8.29 (s, 1H), 9.08 (s, 1H), 9.50 (br, 1H).

Example 53

Synthesis of N-[3-((4aS*,5R*,7aS*)-2-amino-5-ethyl-4a,5-dihydro-4H-furo[3,4-d][1,3]thiazin-7a-yl)-4-fluorophenyl]-5-difluoromethylpyrazine-2-carboxamide

[Formula 146]

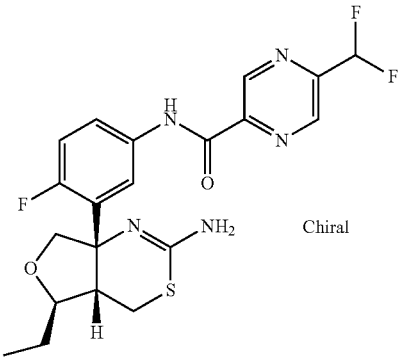 [SMILES: CC[C@H]1OC[C@]2(c3cc(NC(=O)c4cnc(C(F)F)cn4)ccc3F)N=C(N)SC[C@H]12]

The title compound (30.0 mg) was obtained from the compound obtained in Preparation Example 21-(10) (28.0 mg) and 5-difluoromethylpyrazine-2-carboxylic acid prepared in Preparation Example 17-(5) (18.5 mg) according to the method of Example 14.

¹H-NMR (400 MHz, CDCl₃) δ (ppm): 1.04-1.08 (m, 3H), 1.66-1.73 (m, 2H), 2.69-2.78 (m, 2H), 3.09-3.13 (m, 1H), 3.81-3.83 (m, 1H), 4.18-4.23 (m, 1H), 4.55-4.57 (m, 1H), 6.80 (t, J=55 Hz, 1H), 7.09-7.12 (m, 1H), 7.53-7.56 (m, 1H), 7.95-7.99 (m, 1H), 8.93 (s, 1H), 9.53 (s, 1H), 9.65 (br, 1H).

Example 54

Synthesis of N-[3-((4aS*,5R*,7aS*)-2-amino-5-methyl-4a,5-dihydro-4H-furo[3,4-d][1,3]thiazin-7a-yl)-4-fluorophenyl]-5-cyanopyridine-2-carboxamide

[Formula 147]

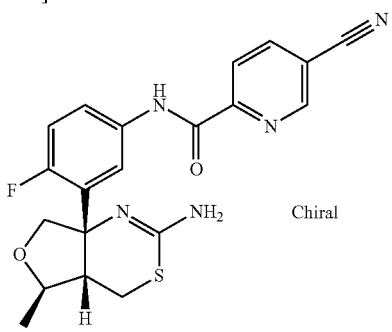

The title compound (18.0 mg) was obtained from the compound obtained in Preparation Example 22-(11) (30.0 mg) and 5-cyanopyridine-2-carboxylic acid obtained in Preparation Example 13-(2) (23.3 mg) according to the method of Example 14.

¹H-NMR (400 MHz, CDCl₃) δ (ppm): 1.37-1.39 (m, 3H), 2.57-2.58 (m, 1H), 2.73-2.76 (m, 1H), 3.10-3.13 (m, 1H), 3.81-3.83 (m, 1H), 4.35-4.38 (m, 1H), 4.59-4.61 (m, 1H), 7.08-7.13 (m, 1H), 7.52-7.53 (m, 1H), 7.96-7.98 (m, 1H), 8.20 (d, J=8.0 Hz, 1H), 8.43 (d, J=8.0 Hz, 1H), 8.90 (s, 1H), 9.85 (br, 1H).

Example 55

Synthesis of N-[3-((4aS*,5R*,7aS*)-2-amino-5-methyl-4a,5-dihydro-4H-furo[3,4-d][1,3]thiazin-7a-yl)-4-fluorophenyl]-5-difluoromethoxypyrazine-2-carboxamide

[Formula 148]

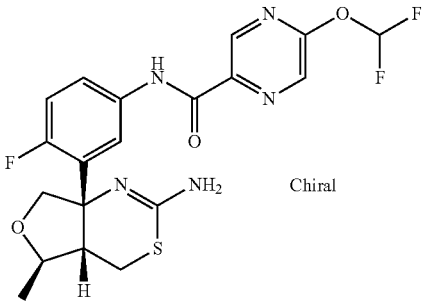 [SMILES: C[C@H]1OC[C@]2(c3cc(NC(=O)c4cnc(OC(F)F)cn4)ccc3F)N=C(N)SC[C@H]12]

The title compound (22.0 mg) was obtained from the compound obtained in Preparation Example 22-(11) (30.0 mg) and 5-difluoromethoxypyrazine-2-carboxylic acid obtained in Preparation Example 14-(2) (22.5 mg) according to the method of Example 14.

¹H-NMR (400 MHz, CDCl₃) δ (ppm): 1.37-1.39 (m, 3H), 2.56-2.60 (m, 1H), 2.72-2.76 (m, 1H), 3.10-3.14 (m, 1H), 3.81-3.84 (m, 1H), 4.35-4.38 (m, 1H), 4.59-4.61 (m, 1H), 7.07-7.12 (m, 1H), 7.49-7.51 (m, 1H), 7.51 (t, J=71.6 Hz, 1H), 7.93-7.96 (m, 1H), 8.34 (d, J=1.6 Hz, 1H), 9.07 (d, J=1.6 Hz, 1H), 9.47 (br, 1H).

Example 56

Synthesis of N-[3-((4aS*,5R*,7aS*)-2-amino-5-methyl-4a,5-dihydro-4H-furo[3,4-d][1,3]thiazin-7a-yl)-4-fluorophenyl]-5-chloropyridine-2-carboxamide

[Formula 149]

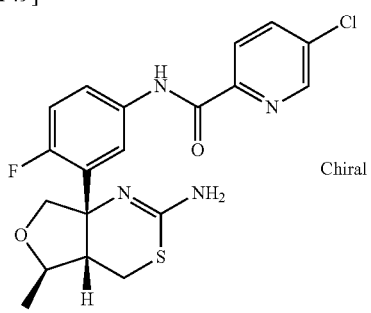

The title compound (17.0 mg) was obtained from the compound obtained in Preparation Example 22-(11) (28.0 mg) and 5-chloropyridine-2-carboxylic acid (23.2 mg) according to the method of Example 14.

¹H-NMR (400 MHz, CDCl₃) δ (ppm): 1.37-1.39 (m, 3H), 2.57-2.61 (m, 1H), 2.72-2.76 (m, 1H), 3.11-3.15 (m, 1H), 3.82-3.85 (m, 1H), 4.35-4.38 (m, 1H), 4.59-4.62 (m, 1H), 7.06-7.11 (m, 1H), 7.50-7.52 (m, 1H), 7.88-7.98 (m, 2H), 8.24 (d, J=8.4 Hz, 1H), 8.57 (s, 1H), 9.82 (br, 1H).

Example 57

Synthesis of N-[3-((4aS*,5R*,7aS*)-2-amino-5-methyl-4a,5-dihydro-4H-furo[3,4-d][1,3]thiazin-7a-yl)-4-fluorophenyl]-5-fluoromethoxypyrazine-2-carboxamide

[Formula 150]

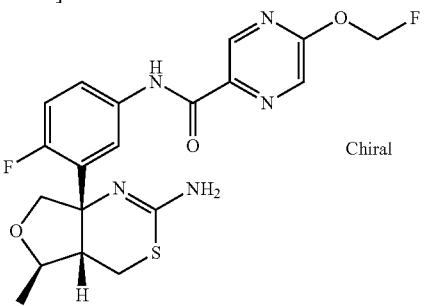

The title compound (22.0 mg) was obtained from the compound obtained in Preparation Example 22-(11) (28.0 mg) and 5-fluoromethoxypyrazine-2-carboxylic acid obtained in Preparation Example 15-(2) (19.0 mg) according to the method of Example 14.

¹H-NMR (400 MHz, CDCl₃) δ (ppm): 1.37-1.39 (m, 3H), 2.59-2.61 (m, 1H), 2.73-2.77 (m, 1H), 3.10-3.15 (m, 1H), 3.82-3.85 (m, 1H), 4.35-4.37 (m, 1H), 4.59-4.61 (m, 1H), 6.08-6.22 (m, 1H), 7.07-7.12 (m, 1H), 7.49-7.51 (m, 1H), 7.93-7.97 (m, 1H), 8.29 (s, 1H), 9.08 (s, 1H), 9.50 (br, 1H).

Example 58

Synthesis of N-[3-((4aS*,5R*,7aS*)-2-amino-5-methyl-4a,5-dihydro-4H-furo[3,4-d][1,3]thiazin-7a-yl)-4-fluorophenyl]-5-difluoromethylpyrazine-2-carboxamide

[Formula 151]

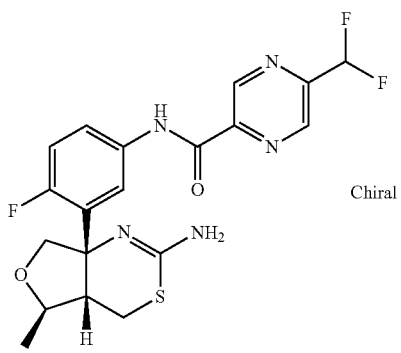 [SMILES: C[C@H]1OC[C@]2(c3cc(NC(=O)c4cnc(C(F)F)cn4)ccc3F)N=C(N)SC[C@H]12]

The title compound (21.0 mg) was obtained from the compound obtained in Preparation Example 22-(11) (25.0 mg) and 5-difluoromethylpyrazine-2-carboxylic acid prepared in Preparation Example 17-(5) (17.0 mg) according to the method of Example 14.

$^1$H-NMR (400 MHz, CDCl$_3$) δ (ppm): 1.37-1.39 (m, 3H), 2.57-2.61 (m, 1H), 2.73-2.77 (m, 1H), 3.10-3.14 (m, 1H), 3.81-3.84 (m, 1H), 4.35-4.39 (m, 1H), 4.60-4.62 (m, 1H), 6.66-6.93 (m, 1H), 7.09-7.14 (m, 1H), 7.53-7.55 (m, 1H), 7.93-7.97 (m, 1H), 8.92 (d, J=8.0 Hz, 1H), 9.53 (s, 1H), 9.64 (br, 1H).

Example 59

Synthesis of N-[3-((4aS*,5R*,7aS*)-2-amino-5-methyl-4a,5-dihydro-4H-furo[3,4-d][1,3]thiazin-7a-yl)-4-fluorophenyl]-5-difluoromethoxypyridine-2-carboxamide

[Formula 152]

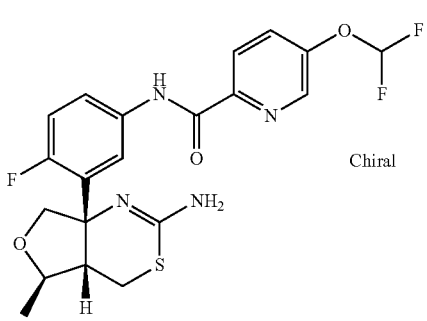 [SMILES: C[C@H]1OC[C@]2(c3cc(NC(=O)c4ccc(OC(F)F)cn4)ccc3F)N=C(N)SC[C@H]12]

The title compound (28.0 mg) was obtained from the compound obtained in Preparation Example 22-(11) (30.0 mg) and 5-difluoromethoxypyridine-2-carboxylic acid (22.3 mg) according to the method of Example 14.

$^1$H-NMR (400 MHz, CDCl$_3$) δ (ppm): 1.37-1.39 (m, 3H), 2.58-2.61 (m, 1H), 2.72-2.76 (m, 1H), 3.11-3.15 (m, 1H), 3.82-3.84 (m, 1H), 4.34-4.40 (m, 1H), 4.60-4.62 (m, 1H), 6.65 (t, J=72 Hz, 1H), 7.08-7.11 (m, 1H), 7.51-7.53 (m, 1H), 7.65-7.67 (m, 1H), 7.93-7.97 (m, 1H), 8.31-8.33 (m, 1H), 8.46 (s, 1H), 9.83 (br, 1H).

Example 60

Synthesis of N-[3-((4aS*,5R*,7aS*)-2-amino-5-methyl-4a,5-dihydro-4H-furo[3,4-d][1,3]thiazin-7a-yl)-4-fluorophenyl]-pyrimidine-4-carboxamide

[Formula 153]

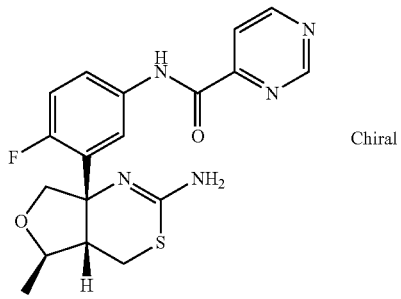 [SMILES: C[C@H]1OC[C@]2(c3cc(NC(=O)c4ccncn4)ccc3F)N=C(N)SC[C@H]12]

The title compound (16.0 mg) was obtained from the compound obtained in Preparation Example 22-(11) (20.0 mg) and pyrimidine-4-carboxylic acid (15.0 mg) according to the method of Example 14.

$^1$H-NMR (400 MHz, CDCl$_3$) δ (ppm): 1.37-1.39 (m, 3H), 2.59-2.61 (m, 1H), 2.73-2.77 (m, 1H), 3.10-3.14 (m, 1H), 3.83-3.86 (m, 1H), 4.35-4.39 (m, 1H), 4.59-4.62 (m, 1H), 7.08-7.14 (m, 1H), 7.53-7.56 (m, 1H), 7.94-7.96 (m, 1H), 8.21-8.23 (m, 1H), 9.04-9.05 (m, 1H), 9.32-9.32 (m, 1H), 9.87 (br, 1H).

Example 61

Synthesis of N-[3-((4aS*,5R*,7aS*)-2-amino-5-methyl-4a,5-dihydro-4H-furo[3,4-d][1,3]thiazin-7a-yl)-4-fluorophenyl]-pyridine-2-carboxamide

[Formula 154]

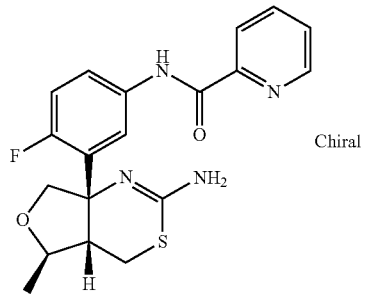 [SMILES: C[C@H]1OC[C@]2(c3cc(NC(=O)c4ccccn4)ccc3F)N=C(N)SC[C@H]12]

The title compound (18.0 mg) was obtained from the compound obtained in Preparation Example 22-(11) (20.0 mg) and picolinic acid (12.9 mg) according to the method of Example 14.

$^1$H-NMR (400 MHz, CDCl$_3$) δ (ppm): 1.37-1.39 (m, 3H), 2.58-2.62 (m, 1H), 2.72-2.77 (m, 1H), 3.12-3.16 (m, 1H), 3.84-3.87 (m, 1H), 4.35-4.39 (m, 1H), 4.60-4.62 (m, 1H), 7.06-7.11 (m, 1H), 7.48-7.54 (m, 2H), 7.89-8.01 (m, 2H), 8.28-8.30 (m, 1H), 8.62-8.63 (m, 1H).

Example 62

Synthesis of N-[3-((4aS*,5R*,7aS*)-2-amino-5-methyl-4a,5-dihydro-4H-furo[3,4-d][1,3]thiazin-7a-yl)-4-fluorophenyl]-5-fluoropyridine-2-carboxamide

[Formula 155]

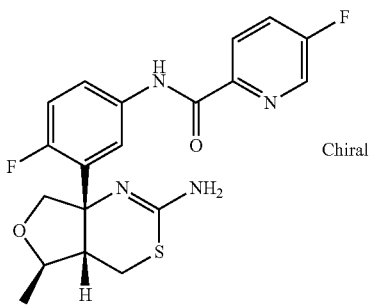 [SMILES: C[C@H]1OC[C@]2(c3cc(NC(=O)c4ccc(F)cn4)ccc3F)N=C(N)SC[C@H]12]

The title compound (13.0 mg) was obtained from the compound obtained in Preparation Example 22-(11) (20.0 mg) and 5-fluoropyridine-2-carboxylic acid (15.0 mg) according to the method of Example 14.

$^1$H-NMR (400 MHz, CDCl$_3$) δ (ppm): 1.37-1.39 (m, 3H), 2.59-2.61 (m, 1H), 2.72-2.77 (m, 1H), 3.11-3.15 (m, 1H), 3.83-3.86 (m, 1H), 4.35-4.39 (m, 1H), 4.59-4.62 (m, 1H), 7.06-7.12 (m, 1H), 7.49-7.62 (m, 2H), 7.95-7.97 (m, 1H), 8.31-8.47 (m, 2H), 9.80 (br, 1H).

Example 63

Synthesis of N-[3-((4aS*,5S*,7aS*)-2-amino-5-methoxy-4,4a,5,6,7,7a-hexahydrocyclopenta[d][1,3]thiazin-7a-yl)-4-fluorophenyl]-5-cyanopyridine-2-carboxamide

[Formula 156]

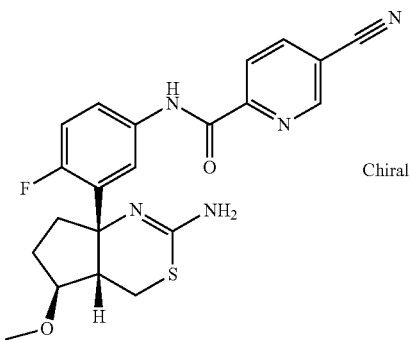

The title compound (7.0 mg) was obtained from the compound obtained in Preparation Example 23-(15) (20.0 mg) and 5-cyanopyridine-2-carboxylic acid obtained in Preparation Example 13-(2) (15.0 mg) according to the method of Example 14.

$^1$H-NMR (400 MHz, CDCl$_3$) δ (ppm): 1.84-2.09 (m, 3H), 2.73-2.85 (m, 2H), 2.96-2.97 (m, 2H), 3.41 (s, 3H), 4.01-4.06 (m, 1H), 7.06-7.11 (m, 1H), 7.39-7.40 (m, 1H), 7.93-7.97 (m, 1H), 8.19-8.20 (m, 1H), 8.42-8.44 (m, 1H), 8.90 (s, 1H), 9.82 (br, 1H).

Example 64

Synthesis of N-[3-((4aS*,5S*,7aS*)-2-amino-5-methoxy-4,4a,5,6,7,7a-hexahydrocyclopenta[d][1,3]thiazin-7a-yl)-4-fluorophenyl]-5-difluoromethoxypyrazine-2-carboxamide

[Formula 157]

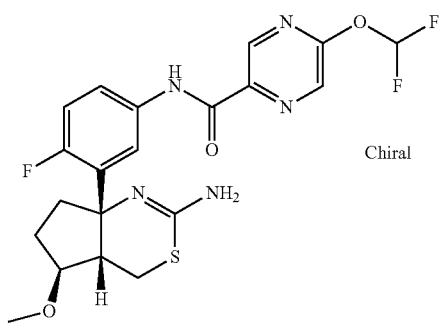 [SMILES: CO[C@H]1CC[C@]2(c3cc(NC(=O)c4cnc(OC(F)F)cn4)ccc3F)N=C(N)SC[C@H]12]

The title compound (10.0 mg) was obtained from the compound obtained in Preparation Example 23-(15) (18.0 mg) and 5-difluoromethoxypyrazine-2-carboxylic acid obtained in Preparation Example 14-(2) (13.0 mg) according to the method of Example 14.

$^1$H-NMR (400 MHz, CDCl$_3$) δ (ppm): 1.85-2.06 (m, 3H), 2.75-2.84 (m, 2H), 2.96-2.97 (m, 2H), 3.41 (s, 3H), 4.02-4.04 (m, 1H), 7.05-7.10 (m, 1H), 7.35-7.38 (m, 1H), 7.51 (t, J=72 Hz, 1H), 7.90-7.94 (m, 1H), 8.33 (s, 1H), 9.07 (s, 1H), 9.45 (br, 1H).

Example 65

Synthesis of N-[3-((4aS*,5R*,7aS*)-2-amino-5-methoxy-4,4a,5,6,7,7a-hexahydrocyclopenta[d][1,3]thiazin-7a-yl)-4-fluorophenyl]-5-cyanopyridine-2-carboxamide

[Formula 158]

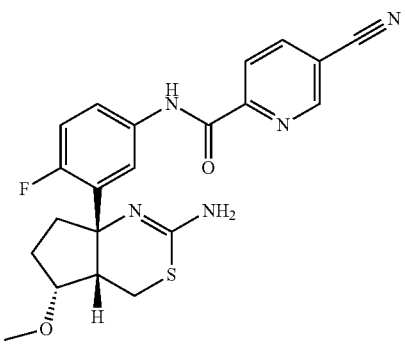 [SMILES: CO[C@@H]1CC[C@]2(c3cc(NC(=O)c4ccc(C#N)cn4)ccc3F)N=C(N)SC[C@H]12]

The title compound (11.0 mg) was obtained from the compound obtained in Preparation Example 23-(14) (20.0 mg) and 5-cyanopyridine-2-carboxylic acid obtained in Preparation Example 13-(2) (15.0 mg) according to the method of Example 14.

$^1$H-NMR (400 MHz, CDCl$_3$) δ (ppm): 1.77-2.26 (m, 3H), 2.53-2.58 (m, 1H), 2.83-3.06 (m, 3H), 3.32 (s, 3H), 3.94-3.96 (m, 1H), 7.05-7.10 (m, 1H), 7.67-7.68 (m, 1H), 7.76-7.78 (m, 1H), 8.20-8.22 (m, 1H), 8.42-8.44 (m, 1H), 8.91 (s, 1H), 9.84 (br, 1H).

Example 66

Synthesis of N-[3-((4aS,5S,7aS)-2-amino-5-methoxymethyl-4a,5-dihydro-4H-furo[3,4-d][1,3]thiazin-7a-yl)-4-fluorophenyl]-5-cyanopyridine-2-carboxamide

[Formula 159]

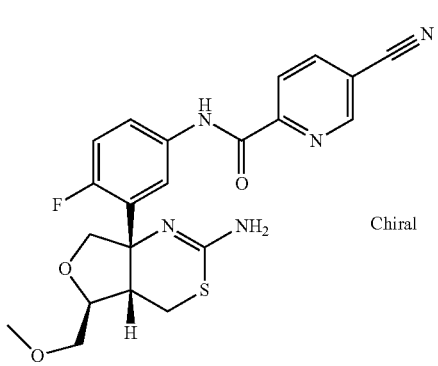 [SMILES: COC[C@H]1OC[C@]2(c3cc(NC(=O)c4ccc(C#N)cn4)ccc3F)N=C(N)SC[C@H]12]

The following compound was synthesized according to Example 14 using the compound obtained in Preparation Example 24-(11) and the corresponding carboxylic acid.

$^1$H-NMR (400 MHz, CDCl$_3$) δ (ppm): 2.83-2.86 (m, 1H), 2.96-3.00 (m, 1H), 3.09-3.13 (m, 1H), 3.44 (s, 3H), 3.53-3.57 (m, 1H), 3.63-3.67 (m, 1H), 3.86-3.88 (m, 1H), 4.44-4.48 (m, 1H), 4.55-4.57 (m, 1H), 7.08-7.13 (m, 1H), 7.53-7.54 (m, 1H), 7.97-8.00 (m, 1H), 8.20-8.22 (m, 1H), 8.42-8.44 (m, 1H), 8.90 (s, 1H), 9.86 (br, 1H).

Example 67

Synthesis of N-[3-((4aS,5S,7aS)-2-amino-5-methoxymethyl-4a,5-dihydro-4H-furo[3,4-d][1,3]thiazin-7a-yl)-4-fluorophenyl]-5-difluoromethoxy-pyrazine-2-carboxamide

[Formula 160]

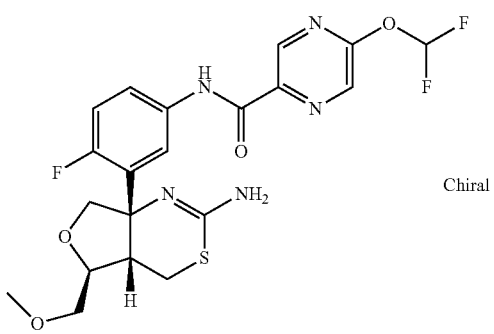 [SMILES: COC[C@H]1OC[C@]2(c3cc(NC(=O)c4cnc(OC(F)F)cn4)ccc3F)N=C(N)SC[C@H]12]

The following compound was synthesized according to Example 14 using the compound obtained in Preparation Example 24-(11) and the corresponding carboxylic acid.

$^1$H-NMR (400 MHz, CDCl$_3$) δ (ppm): 2.82-2.85 (m, 1H), 2.96-2.98 (m, 1H), 3.10-3.13 (m, 1H), 3.43 (s, 3H), 3.53-3.56 (m, 1H), 3.64-3.66 (m, 1H), 3.85-3.87 (m, 1H), 4.45-4.46 (m, 1H), 4.54-4.57 (m, 1H), 7.07-7.12 (m, 1H), 7.49-7.51 (m, 1H), 7.51 (t, J=72 Hz, 1H), 7.95-7.97 (m, 1H), 8.34 (s, 1H), 9.07 (s, 1H), 9.49 (br, 1H).

Example 68

Synthesis of N-[3-((4aS,5S,7aS)-2-amino-5-methoxymethyl-4a,5-dihydro-4H-furo[3,4-d][1,3]thiazin-7a-yl)-4-fluorophenyl]-5-difluoromethylpyrazine-2-carboxamide

[Formula 161]

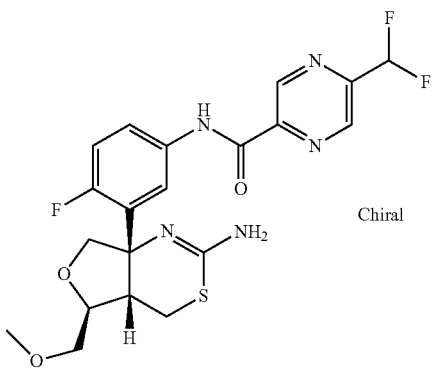 [SMILES: COC[C@H]1OC[C@]2(c3cc(NC(=O)c4cnc(C(F)F)cn4)ccc3F)N=C(N)SC[C@H]12]

The following compound was synthesized according to Example 14 using the compound obtained in Preparation Example 24-(11) and the corresponding carboxylic acid.

$^1$H-NMR (400 MHz, CDCl$_3$) δ (ppm): 2.82-2.86 (m, 1H), 2.95-2.99 (m, 1H), 3.09-3.14 (m, 1H), 3.44 (s, 3H), 3.54-3.57 (m, 1H), 3.65-3.67 (m, 1H), 3.85-3.87 (m, 1H), 4.44-4.48 (m, 1H), 4.55-4.57 (m, 1H), 6.80 (t, J=55 Hz, 1H), 7.08-7.14 (m, 1H), 7.55-7.56 (m, 1H), 7.95-7.99 (m, 1H), 8.92 (s, 1H), 9.52 (s, 1H), 9.65 (br, 1H).

Example 69

Synthesis of N-[3-((4aS,5S,7aS)-2-amino-5-methoxymethyl-4a,5-dihydro-4H-furo[3,4-d][1,3]thiazin-7a-yl)-4-fluorophenyl]-5-fluoromethoxypyrazine-2-carboxamide

[Formula 162]

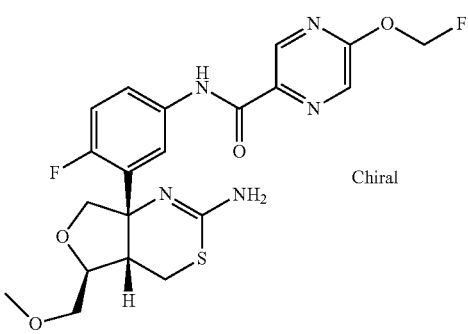 [SMILES: COC[C@H]1OC[C@]2(c3cc(NC(=O)c4cnc(OCF)cn4)ccc3F)N=C(N)SC[C@H]12]

The following compound was synthesized according to Example 14 using the compound obtained in Preparation Example 24-(11) and the corresponding carboxylic acid.

$^1$H-NMR (400 MHz, CDCl$_3$) δ (ppm): 2.83-2.86 (m, 1H), 2.97-2.99 (m, 1H), 3.10-3.43 (m, 1H), 3.44 (s, 3H), 3.54-3.56 (m, 1H), 3.64-3.67 (m, 1H), 3.86-3.89 (m, 1H), 4.45-4.47 (m, 1H), 4.54-4.57 (m, 1H), 6.09-6.22 (m, 1H), 7.07-7.12 (m, 1H), 7.47-7.49 (m, 1H), 7.97-7.99 (m, 1H), 8.30 (s, 1H), 9.08 (s, 1H), 9.52 (br, 1H).

Example 70

Synthesis of N-[3-((4aS,5S,7aS)-2-amino-5-fluoromethyl-4a,5-dihydro-4H-furo[3,4-d][1,3]thiazin-7a-yl)-4-fluorophenyl]-5-trifluoromethylpyridine-2-carboxamide

[Formula 163]

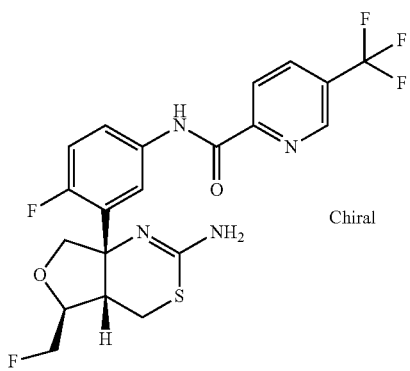 [SMILES: NC1=N[C@@]2(c3cc(NC(=O)c4ccc(C(F)(F)F)cn4)ccc3F)CO[C@H](CF)[C@H]2CS1]

The title compound (29.0 mg) was obtained from the compound obtained in Preparation Example 25-(13) (25.0 mg) and 5-trifluoromethylpyridine-2-carboxylic acid (17.9 mg) according to the method of Example 14.

$^1$H-NMR (400 MHz, CDCl$_3$) δ (ppm): 2.79-2.83 (m, 1H), 3.08-3.19 (m, 2H), 3.88-3.91 (m, 1H), 4.51-4.66 (m, 4H), 7.09-7.14 (m, 1H), 7.58-7.61 (m, 1H), 7.96-8.00 (m, 1H), 8.16-8.18 (m, 1H), 8.42-8.44 (m, 1H), 8.90 (s, 1H).

Example 71

Synthesis of N-[3-((4aS,5S,7aS)-2-amino-5-fluoromethyl-4a,5-dihydro-4H-furo[3,4-d][1,3]thiazin-7a-yl)-4-fluorophenyl]-5-chloropyridine-2-carboxamide

[Formula 164]

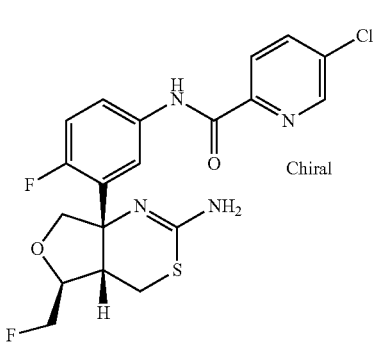 [SMILES: NC1=N[C@@]2(c3cc(NC(=O)c4ccc(Cl)cn4)ccc3F)CO[C@H](CF)[C@H]2CS1]

The title compound (16.0 mg) was obtained from the compound obtained in Preparation Example 25-(13) (25.0 mg) and 5-chloropyridine-2-carboxylic acid (14.8 mg) according to the method of Example 14.

$^1$H-NMR (400 MHz, CDCl$_3$) δ (ppm): 2.79-2.83 (m, 1H), 3.08-3.19 (m, 2H), 3.88-3.91 (m, 1H), 4.51-4.66 (m, 4H), 7.07-7.12 (m, 1H), 7.54-7.56 (m, 1H), 7.87-8.00 (m, 2H), 8.23-8.25 (m, 1H), 8.57 (m, 1H), 9.83 (br, 1H).

Example 72

Synthesis of N-[3-((4aS,5,7aS)-2-amino-5-fluoromethyl-4a,5-dihydro-4H-furo[3,4-d][1,3]thiazin-7a-yl)-4-fluorophenyl]-5-difluoromethoxypyridine-2-carboxamide

[Formula 165]

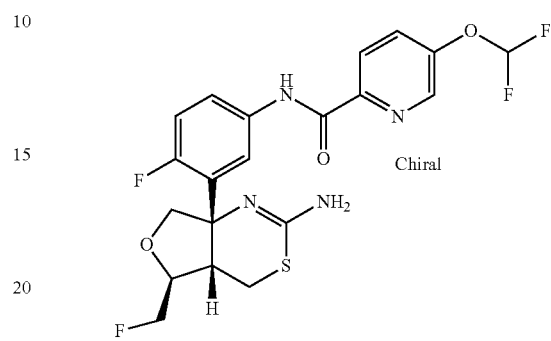

The title compound (27.0 mg) was obtained from the compound obtained in Preparation Example 25-(13) (25.0 mg) and 5-difluoromethoxypyridine-2-carboxylic acid (17.8 mg) according to the method of Example 14.

$^1$H-NMR (400 MHz, CDCl$_3$) δ (ppm): 2.79-2.83 (m, 1H), 3.08-3.19 (m, 2H), 3.88-3.91 (m, 1H), 4.51-4.66 (m, 4H), 6.65 (t, J=72.0 Hz, 1H), 7.08-7.13 (m, 1H), 7.55-7.57 (m, 1H), 7.66-7.69 (m, 1H), 7.95-7.99 (m, 1H), 8.31-8.34 (m, 1H), 8.47-8.48 (m, 1H), 9.84 (br, 1H).

Example 73

Synthesis of N-[3-((4aS,5S,7aS)-2-amino-5-fluoromethyl-4a,5-dihydro-4H-furo[3,4-d][1,3]thiazin-7a-yl)-4-fluorophenyl]-5-difluoromethylpyrazine-2-carboxamide

[Formula 166]

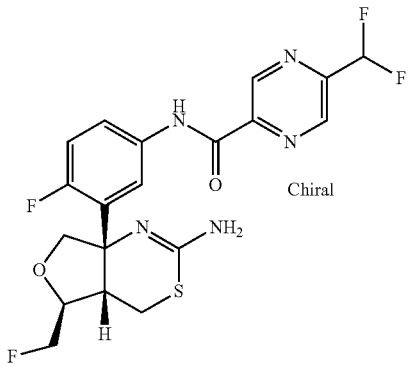 [SMILES: NC1=N[C@@]2(c3cc(NC(=O)c4cnc(C(F)F)cn4)ccc3F)CO[C@H](CF)[C@H]2CS1]

The title compound (16.0 mg) was obtained from the compound obtained in Preparation Example 25-(13) (25.0 mg) and 5-difluoromethylpyrazine-2-carboxylic acid prepared in Preparation Example 17-(5) (16.3 mg) according to the method of Example 14.

$^1$H-NMR (400 MHz, CDCl$_3$) δ (ppm): 2.80-2.84 (m, 1H), 3.11-3.19 (m, 2H), 3.91-3.94 (m, 1H), 4.51-4.66 (m, 4H), 6.80 (t, J=54.4 Hz, 1H), 7.10-7.16 (m, 1H), 7.56-7.59 (m, 1H), 7.96-8.00 (m, 1H), 8.94 (s, 1H), 9.53 (s, 1H), 9.66 (br, 1H).

Example 74

Synthesis of N-[3-((4aS,5S,7aS)-2-amino-5-fluoromethyl-4a,5-dihydro-4H-furo[3,4-d][1,3]thiazin-7a-yl)-4-fluorophenyl]-5-difluoromethoxypyrazine-2-carboxamide

[Formula 167]

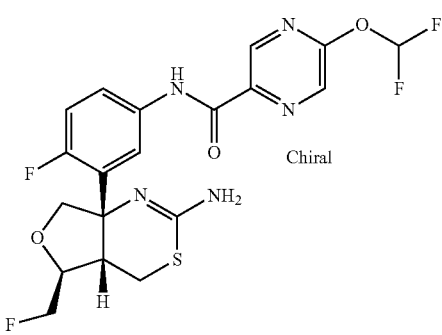 [SMILES: NC1=N[C@@]2(c3cc(NC(=O)c4cnc(OC(F)F)cn4)ccc3F)CO[C@H](CF)[C@H]2CS1]

The title compound (26.0 mg) was obtained from the compound obtained in Preparation Example 25-(13) (25.0 mg) and 5-difluoromethoxypyrazine-2-carboxylic acid obtained in Preparation Example 14-(2) (17.9 mg) according to the method of Example 14.

$^1$H-NMR (400 MHz, CDCl$_3$) δ (ppm): 2.79-2.83 (m, 1H), 3.09-3.18 (m, 2H), 3.89-3.92 (m, 1H), 4.51-4.65 (m, 4H), 7.09-7.14 (m, 1H), 7.52 (t, J=71.6 Hz, 1H), 7.52-7.55 (m, 1H), 7.94-7.97 (m, 1H), 8.35 (s, 1H), 9.07 (s, 1H), 9.49 (br, 1H).

Example 75

Synthesis of N-[3-((4aS,5S,7aS)-2-amino-5-fluoromethyl-4a,5-dihydro-4H-furo[3,4-d][1,3]thiazin-7a-yl)-4-fluorophenyl]-5-fluoromethoxypyrazine-2-carboxamide

[Formula 168]

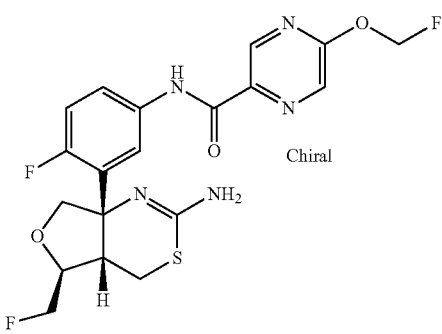 [SMILES: NC1=N[C@@]2(c3cc(NC(=O)c4cnc(OCF)cn4)ccc3F)CO[C@H](CF)[C@H]2CS1]

The title compound (28.0 mg) was obtained from the compound obtained in Preparation Example 25-(13) (25.0 mg) and 5-fluoromethoxypyrazine-2-carboxylic acid obtained in Preparation Example 15-(2) (16.2 mg) according to the method of Example 14.

$^1$H-NMR (400 MHz, CDCl$_3$) δ (ppm): 2.80-2.84 (m, 1H), 3.11-3.19 (m, 2H), 3.92-3.95 (m, 1H), 4.50-4.66 (m, 4H), 6.09-6.10 (m, 1H), 6.22-6.23 (m, 1H), 7.08-7.13 (m, 1H), 7.51-7.53 (m, 1H), 7.95-7.99 (m, 1H), 8.30 (s, 1H), 9.09 (s, 1H), 9.51 (br, 1H).

Example 76

Synthesis of N-[3-((4aS,5S,7aS)-2-amino-5-fluoromethyl-4a,5-dihydro-4H-furo[3,4-d][1,3]thiazin-7a-yl)-4-fluorophenyl]-pyrimidine-4-carboxamide

[Formula 169]

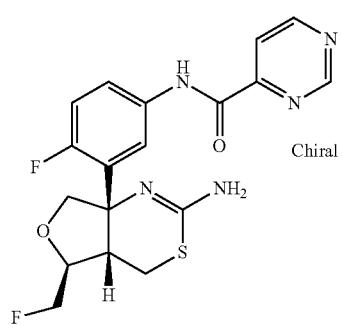

The title compound (15.0 mg) was obtained from the compound obtained in Preparation Example 25-(13) (20.0 mg) and pyrimidine-4-carboxylic acid (12.4 mg) according to the method of Example 14.

$^1$H-NMR (400 MHz, CDCl$_3$) δ (ppm): 2.79-2.83 (m, 1H), 3.09-3.18 (m, 2H), 3.87-3.90 (m, 1H), 4.52-4.66 (m, 4H), 7.09-7.14 (m, 1H), 7.58-7.61 (m, 1H), 7.95-7.99 (m, 1H), 8.21-8.23 (m, 1H), 9.05 (d, J=5.6 Hz, 1H), 9.32 (d, J=5.6 Hz, 1H), 9.88 (br, 1H).

Example 77

Synthesis of N-[3-((4aS,5S,7aS)-2-amino-5-fluoromethyl-4a,5-dihydro-4H-furo[3,4-d][1,3]thiazin-7a-yl)-4-fluorophenyl]-pyridine-2-carboxamide

[Formula 170]

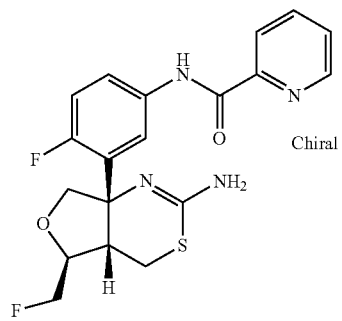 [SMILES: NC1=N[C@@]2(c3cc(NC(=O)c4ccncn4)ccc3F)CO[C@H](CF)[C@H]2CS1]

The title compound (18.0 mg) was obtained from the compound obtained in Preparation Example 25-(13) (20.0 mg) and picolinic acid (12.9 mg) according to the method of Example 14.

$^1$H-NMR (400 MHz, CDCl$_3$) δ (ppm): 2.79-2.83 (m, 1H), 3.08-3.20 (m, 2H), 3.90-3.92 (m, 1H), 4.51-4.66 (m, 4H), 7.07-7.20 (m, 2H), 7.48-7.58 (m, 2H), 7.90-8.01 (m, 1H), 8.28-8.30 (m, 1H), 8.63-8.65 (m, 1H).

Example 78

Synthesis of N-[3-((4aS,5S,7aS)-2-amino-5-fluoromethyl-4a,5-dihydro-4H-furo[3,4-d][1,3]thiazin-7a-yl)-4-fluorophenyl]-5-fluoropyridine-2-carboxamide

[Formula 171]

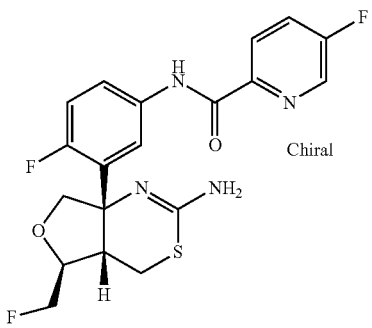 [SMILES: NC1=N[C@@]2(c3cc(NC(=O)c4ccc(F)cn4)ccc3F)CO[C@H](CF)[C@H]2CS1]

The title compound (13.0 mg) was obtained from the compound obtained in Preparation Example 25-(13) (20.0 mg) and picolinic acid (15.0 mg) according to the method of Example 14.

$^1$H-NMR (400 MHz, CDCl$_3$) δ (ppm): 2.78-2.82 (m, 1H), 3.06-3.19 (m, 2H), 3.88-3.90 (m, 1H), 4.51-4.67 (m, 4H), 7.07-7.12 (m, 1H), 7.55-7.62 (m, 1H), 7.93-7.97 (m, 1H), 8.31-8.45 (m, 2H).

Example 79

Synthesis of N-[3-((4aS*,8aS*)-2-amino-4a,5,7,8-tetrahydro-4H-6-oxa-3-thia-1-azanaphthalen-8a-yl)-4-fluorophenyl]-5-difluoromethylpyrazine-2-carboxamide

[Formula 172]

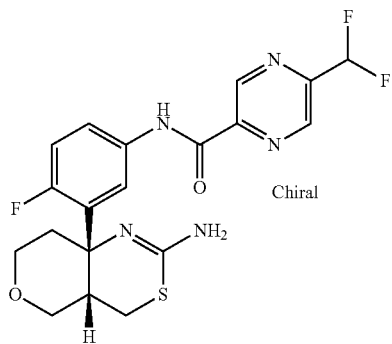 [SMILES: NC1=N[C@@]2(c3cc(NC(=O)c4cnc(C(F)F)cn4)ccc3F)CCOC[C@H]2CS1]

The title compound (29.0 mg) was obtained from the compound obtained in Preparation Example 8 (30.0 mg) and 5-difluoromethylpyrazine-2-carboxylic acid prepared in Preparation Example 17-(5) (22.3 mg) according to the method of Example 14.

$^1$H-NMR (400 MHz, CDCl$_3$) δ (ppm): 1.70-1.73 (m, 1H), 2.60-2.70 (m, 2H), 2.93-3.05 (m, 2H), 3.70-3.91 (m, 4H), 4.59 (br, 1H), 6.79 (t, J=54 Hz, 1H), 7.04-7.09 (m, 1H), 7.45-7.46 (m, 1H), 7.87-7.89 (m, 1H), 8.89 (s, 1H), 9.49 (s, 1H), 9.59 (br, 1H).

Example 80

Synthesis of N-[3-((4aS*,8aS*)-2-amino-4a,5,7,8-tetrahydro-4H-6-oxa-3-thia-1-azanaphthalen-8a-yl)-4-fluorophenyl]-5-fluoromethoxypyrazine-2-carboxamide

[Formula 173]

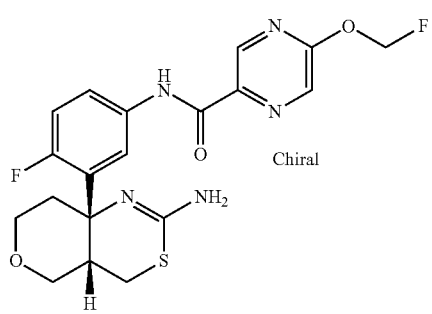 [SMILES: NC1=N[C@@]2(c3cc(NC(=O)c4cnc(OCF)cn4)ccc3F)CCOC[C@H]2CS1]

The title compound (24.0 mg) was obtained from the compound obtained in Preparation Example 8 (30.0 mg) and 5-fluoromethoxypyrazine-2-carboxylic acid obtained in Preparation Example 15-(2) (20.3 mg) according to the method of Example 14.

$^1$H-NMR (400 MHz, CDCl$_3$) δ (ppm): 1.68-1.71 (m, 1H), 2.57-2.69 (m, 2H), 2.93-3.06 (m, 2H), 3.70-3.91 (m, 4H), 6.08-6.21 (m, 1H), 7.05-7.10 (m, 1H), 7.37-7.38 (m, 1H), 7.89-7.93 (m, 1H), 8.27 (s, 1H), 9.07 (s, 1H), 9.45 (br, 1H).

Example 81

Synthesis of N-[3-((4aS*,8aS*)-2-amino-4a,5,7,8-tetrahydro-4H-6-oxa-3-thia-1-azanaphthalen-8a-yl)-4-fluorophenyl]-5-difluoromethoxypyridine-2-carboxamide

[Formula 174]

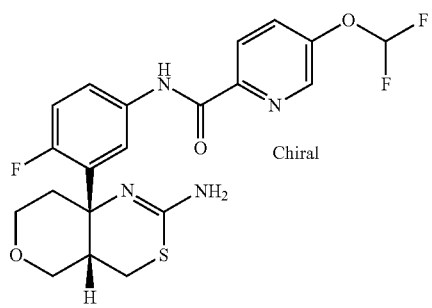 [SMILES: NC1=N[C@@]2(c3cc(NC(=O)c4ccc(OC(F)F)cn4)ccc3F)CCOC[C@H]2CS1]

The title compound (31.0 mg) was obtained from the compound obtained in Preparation Example 8 (30.0 mg) and 5-difluoromethoxypyridine-2-carboxylic acid (21.5 mg) according to the method of Example 14.

$^1$H-NMR (400 MHz, CDCl$_3$) δ (ppm): 1.69-1.72 (m, 1H), 2.56-2.71 (m, 2H), 2.94-3.05 (m, 2H), 3.70-3.91 (m, 4H), 6.65 (t, J=72 Hz, 1H), 7.03-7.09 (m, 1H), 7.40-7.41 (m, 1H), 7.64-7.66 (m, 1H), 7.89-7.93 (m, 1H), 8.28-8.30 (m, 1H), 8.43-8.43 (m, 1H), 9.77 (br, 1H).

Examples 82 to 86

The compounds of Examples 82 to 86 as shown in Table 4 below were synthesized according to Example 47.

[Table 4]

TABLE 4

| Example | Chemical structure | |
|---|---|---|
| 82 | (structure) | ESI-MS m/z 433 [M⁺ + H] |
| 83 | (structure) | ESI-MS m/z 371 [M⁺ + H] |
| 84 | (structure) | ESI-MS m/z 397 [M⁺ + H] |
| 85 | (structure) | ESI-MS m/z 469 [M⁺ + H] |

TABLE 4-continued

| Example | Chemical structure | |
|---|---|---|
| 86 | (structure) | ESI-MS m/z 434 [M⁺ + H] |

Examples 87 to 88

The compounds of Examples 87 to 88 as shown in Table 5 below were synthesized according to Example 37.

[Table 5]

TABLE 5

| Example | Chemical structure | |
|---|---|---|
| 87 | (structure) | ESI-MS m/z 407 [M⁺ + H] |
| 88 | (structure) | ESI-MS m/z 424 [M⁺ + H] |

Example 89

Synthesis of (+)-N-[3-((4aR*,6S*,7aS*)-2-amino-6-ethoxy-4,4a,5,6,7,7a-hexahydrocyclopenta[d][1,3]thiazin-7a-yl)-4-fluorophenyl]-5-cyanopyridine-2-carboxamide

[Formula 175]

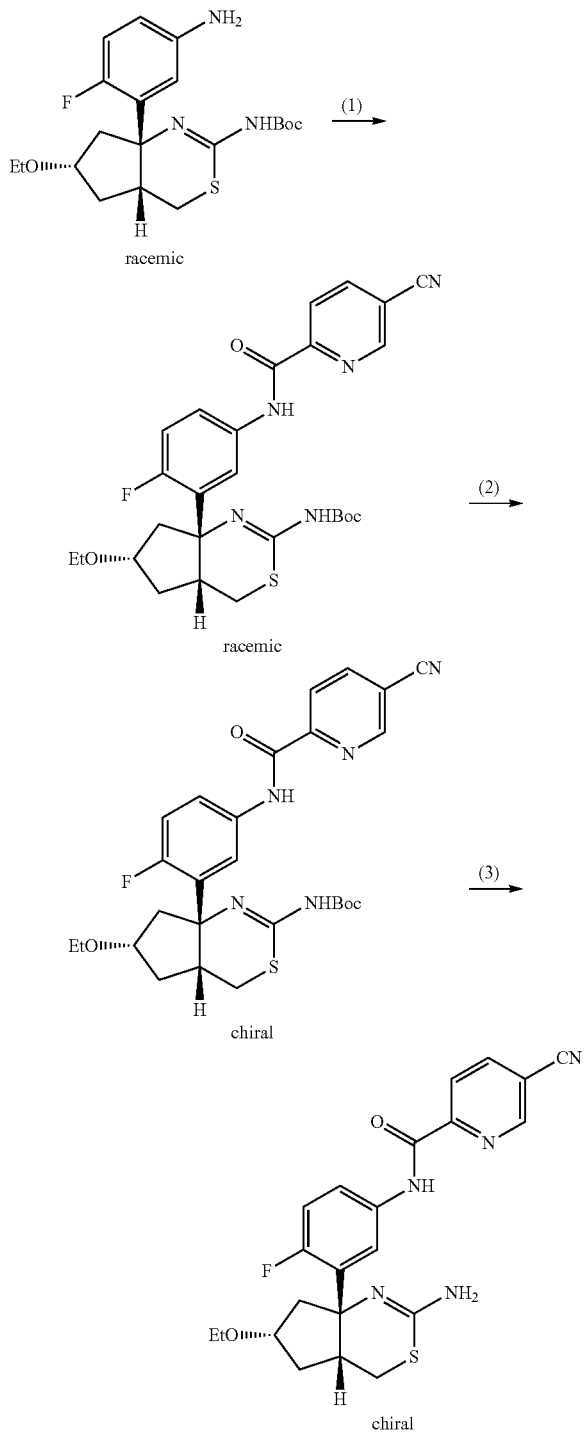

(1) Synthesis of tert-butyl ((4aR*,6S*,7aS*)-7a-{5-[(5-cyanopyridine-2-carbonyl)amino]-2-fluorophenyl}-6-ethoxy-4,4a,5,6,7,7a-hexahydrocyclopenta[d][1,3]thiazin-2-yl)carbamate PyBOP (205 mg) was added to a solution of tert-butyl(±)-[(4aR*,6S*,7aS*)-7a-(5-amino-2-fluorophenyl)-6-ethoxy-4,4a,5,6,7,7a-hexahydrocyclopenta[d][1,3]thiazin-2-yl]carbamate (52 mg), the compound of Preparation Example 26-(2) (27.3 mg) and N,N-diisopropylethylamine (0.26 mL) in dichloromethane (5.2 mL). The mixture was stirred at room temperature for one hour. The reaction solution was poured into a saturated sodium bicarbonate solution, followed by extraction with ethyl acetate. The extract was washed with a saturated sodium chloride solution and dried over anhydrous magnesium sulfate. The drying agent was removed by filtration and the filtrate was concentrated under reduced pressure. The crude product was purified by silica gel column chromatography to obtain the title compound (45 mg).
ESI-MS; m/z 540 [M⁺+H].

(2) Synthesis of tert-butyl (−)-((4aR*,6S*,7aS*)-7a-{5-[(5-cyanopyridine-2-carbonyl)amino]-2-fluorophenyl}-6-ethoxy-4,4a,5,6,7,7a-hexahydrocyclopenta[d][1,3]thiazin-2-yl)carbamate The tert-butyl ester obtained in (1) (45 mg) was optically resolved by CHIRALPAK™ IB manufactured by Daicel Chemical Industries, Ltd. (2 cm×25 cm, mobile phase: hexane:ethanol=7:3, flow rate: 10 mL/min). The components having a retention time of 21 to 28 minutes were collected to obtain the title (−)-isomer (17 mg).
optical rotation (−)
ESI-MS; m/z 540 [M⁺+H].

(3) Synthesis of (+)-N-[3-((4aR*,6S*,7aS*)-2-amino-6-ethoxy-4,4a,5,6,7,7a-hexahydrocyclopenta[d][1,3]thiazin-7a-yl)-4-fluorophenyl]-5-cyanopyridine-2-carboxamide Trifluoroacetic acid (1.0 mL) was added to a solution of the tert-butyl (−)-carbamate obtained in (2) (17 mg) in dichloromethane (1.0 mL), and the reaction solution was stirred at room temperature for one hour. The reaction solution was poured into a saturated sodium bicarbonate solution, followed by extraction with ethyl acetate. The extract was washed with a saturated sodium chloride solution and dried over anhydrous magnesium sulfate. The drying agent was removed by filtration and the filtrate was concentrated under reduced pressure. The crude product was purified by NH-silica gel column chromatography to obtain the title compound (12 mg).
optical rotation (+)
ESI-MS m/z 440 [M⁺+H]
$^1$H-NMR (400 MHz, CDCl$_3$) δ (ppm): 1.22 (t, J=6.8 Hz, 3H), 1.95-2.25 (m, 3H), 2.60-2.70 (m, 1H), 2.78 (dd, J=4.4, 13.2 Hz, 1H), 2.90-3.00 (m, 2H), 3.51 (q, J=6.8 Hz, 2H), 4.20-4.35 (m, 1H), 7.07 (dd, J=8.8, 12.0 Hz, 1H), 7.38 (dd, J=2.8, 7.2 Hz, 1H), 7.90-8.00 (m, 1H), 8.20 (dd, J=2.0, 8.0 Hz, 1H), 8.42 (d, J=8.0 Hz, 1H), 8.86-8.92 (m, 1H), 9.82 (s, 1H).

The compounds Examples 90 to 103 below were synthesized according to Example 19 using the corresponding carboxylic acids and the corresponding aniline intermediates in the Preparation Examples.

Example 90

Synthesis of (+)-N-[3-((4aR*,6R*,7aS*)-2-amino-6-ethoxy-4,4a,5,6,7,7a-hexahydrocyclopenta[d][1,3]thiazin-7a-yl)-4-fluorophenyl]-5-cyanopyridine-2-carboxamide

[Formula 176]

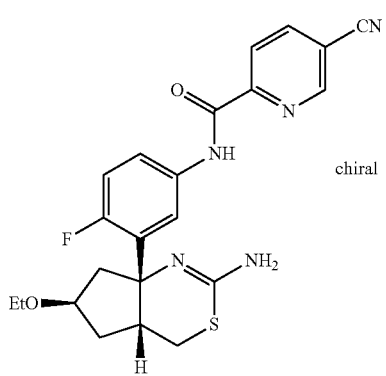 [SMILES: CCO[C@@H]1C[C@H]2CSC(N)=N[C@@]2(c2cc(NC(=O)c3ccc(C#N)cn3)ccc2F)C1]

¹H-NMR (400 MHz, CDCl₃) δ (ppm): 1.23 (t, J=7.2 Hz, 3H), 1.85-1.95 (m, 1H), 2.25-2.35 (m, 2H), 2.63 (dd, J=7.2, 12.8 Hz, 1H), 2.75 (dd, J=3.6, 12.8 Hz, 1H), 2.99 (dd, J=3.6, 12.8 Hz, 1H), 3.10-3.23 (m, 1H), 3.40-3.55 (m, 2H), 3.95-4.05 (m, 1H), 7.08 (dd, J=8.8, 12.0 Hz, 1H), 7.39 (dd, J=2.8, 7.2 Hz, 1H), 7.88-7.98 (m, 1H), 8.19 (dd, J=2.0, 8.0 Hz, 1H), 8.42 (d, J=8.0 Hz, 1H), 8.84-8.94 (m, 1H), 9.82 (s, 1H).
ESI-MS m/z 440 [M⁺+H]

Example 91

Synthesis of (+)-N-[3-((4aR*,6R*,7aS*)-2-amino-6-fluoro-4a,5,6,7-tetrahydro-4H-cyclopenta[d][1,3]thiazin-7a-yl)-4-fluorophenyl]-5-cyanopyridine-2-carboxamide

[Formula 177]

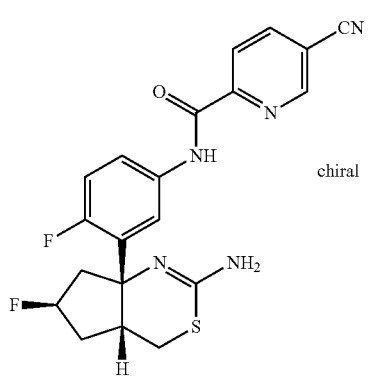 [SMILES: N#Cc1ccc(C(=O)Nc2ccc(F)c([C@]34C[C@H](F)C[C@H]3CSC(N)=N4)c2)nc1]

¹H-NMR (400 MHz, CDCl₃) δ (ppm): 1.95-2.60 (m, 3H), 2.75-3.10 (m, 3H), 3.15-3.28 (m, 1H), 5.15-5.38 (m, 1H), 7.11 (dd, J=8.8, 12.0 Hz, 1H), 7.42 (dd, J=2.8, 7.2 Hz, 1H), 7.86-7.96 (m, 1H), 8.20 (dd, J=2.0, 8.0 Hz, 1H), 8.42 (d, J=8.0 Hz, 1H), 8.86-8.92 (m, 1H), 9.83 (s, 1H).
ESI-MS m/z 414 [M⁺+H]

Example 92

Synthesis of (+)-N-[3-((4aR*,6R*,7aS*)-2-amino-6-fluoro-4,4a,5,6,7,7a-hexahydrocyclopenta[d][1,3]thiazin-7a-yl)-4-fluorophenyl]-5-cyanopyridine-2-carboxamide

[Formula 178]

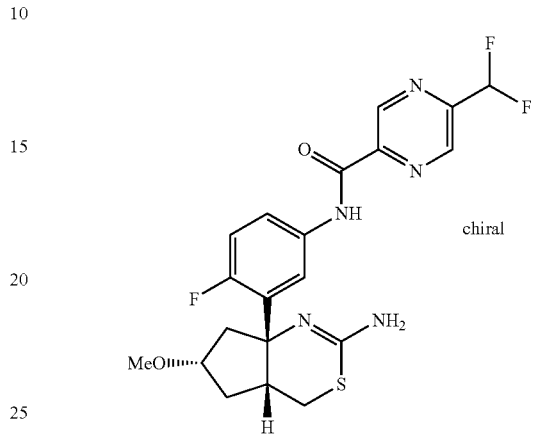

¹H-NMR (400 MHz, CDCl₃) δ (ppm): 2.00-2.14 (m, 2H), 2.18-2.28 (m, 1H), 2.64-2.74 (m, 1H), 2.78 (dd, J=4.0, 13.2 Hz, 1H), 2.90-3.00 (m, 2H), 3.34 (s, 3H), 4.08-4.24 (m, 1H), 6.79 (t, J=54.4 Hz, 1H), 7.00-7.13 (m, 1H), 7.39 (dd, J=2.8, 7.2 Hz, 1H), 7.90-8.00 (m, 1H), 8.91 (s, 1H), 9.51 (s, 1H), 9.61 (s, 1H).
ESI-MS m/z 452 [M⁺+H]

Example 93

Synthesis of (+)-N-[3-((4aR*,6R*,7aS*)-2-amino-6-methoxy-4,4a,5,6,7,7a-hexahydrocyclopenta[d][1,3]thiazin-7a-yl)-4-fluorophenyl]-5-difluoromethylpyrazine-2-carboxamide

[Formula 179]

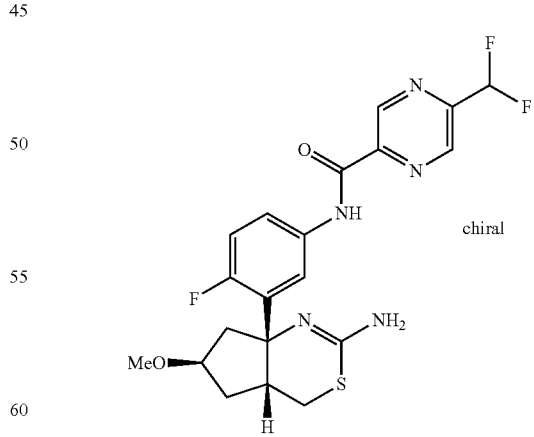

¹H-NMR (400 MHz, CDCl₃) δ (ppm): 1.85-1.94 (m, 1H), 2.24-2.38 (m, 2H), 2.63 (dd, J=6.8, 12.8 Hz, 1H), 2.76 (dd, J=3.6, 12.8 Hz, 1H), 2.99 (dd, J=3.6, 12.8 Hz, 1H), 3.12-3.22 (m, 1H), 3.34 (s, 3H), 3.90-4.00 (m, 1H), 6.79 (t, J=54.8 Hz, 1H), 7.08 (dd, J=8.8, 12.0 Hz, 1H), 7.43 (dd, J=2.8, 7.2 Hz, 1H), 7.85-7.95 (m, 1H), 8.90 (d, J=0.8 Hz, 1H), 9.51 (d, J=0.8 Hz, 1H), 9.62 (s, 1H). ESI-MS m/z 452 [M++H]

Example 94

Synthesis of (+)-N-[3-((4aR*,7aS*)-2-amino-6,6-difluoro-4,4a,5,6,7,7a-hexahydrocyclopenta[d][1,3]thiazin-7a-yl)-4-fluorophenyl]-5-cyanopyridine-2-carboxamide

[Formula 180]

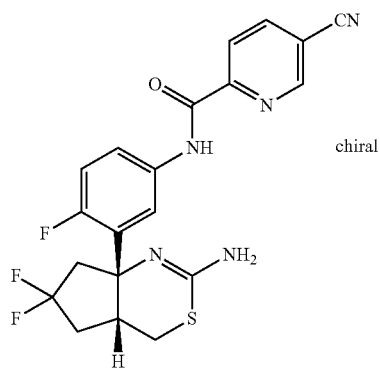 [SMILES: N#Cc1ccc(C(=O)Nc2ccc(F)c([C@]34CC(F)(F)C[C@H]3CSC(N)=N4)c2)nc1]

$^1$H-NMR (400 MHz, CDCl$_3$) δ (ppm): 2.26-2.44 (m, 1H), 2.46-2.70 (m, 2H), 2.72-2.83 (m, 1H), 3.00 (d, J=13.2 Hz, 1H), 3.10-3.28 (m, 2H), 7.11 (dd, J=8.8, 11.6 Hz, 1H), 7.36-7.46 (m, 1H), 7.90-8.00 (m, 1H), 8.21 (dd, J=2.0, 8.0 Hz, 1H), 8.43 (d, J=8.0 Hz, 1H), 8.90 (d, J=0.8 Hz, 1H), 9.83 (s, 1H). ESI-MS m/z 432 [M++H]

Example 95

Synthesis of (+)-N-[3-((4aR*,6R*,7aS*)-2-amino-6-methoxy-4,4a,5,6,7,7a-hexahydrocyclopenta[d][1,3]thiazin-7a-yl)-4-fluorophenyl]-5-difluoromethylpyrazine-2-carboxamide

[Formula 181]

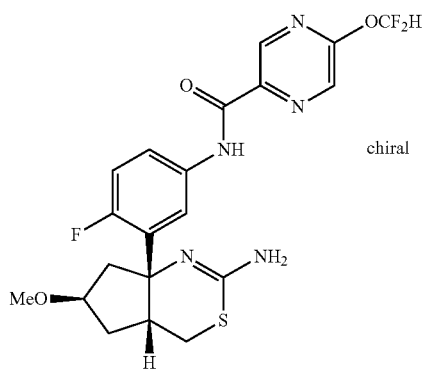

$^1$H-NMR (400 MHz, CDCl$_3$) δ (ppm): 1.80-1.95 (m, 1H), 2.25-2.40 (m, 2H), 2.62 (dd, J=6.8, 12.8 Hz, 1H), 2.76 (dd, J=3.6, 12.8 Hz, 1H), 2.99 (dd, J=3.6, 12.8 Hz, 1H), 3.10-3.20 (m, 1H), 3.34 (s, 3H), 3.85-4.00 (m, 1H), 7.07 (dd, J=8.8, 12.0 Hz, 1H), 7.38 (dd, J=2.4, 7.2 Hz, 1H), 7.51 (t, J=71.2 Hz, 1H), 7.84-7.94 (m, 1H), 8.32 (d, J=1.2 Hz, 1H), 9.06 (d, J=1.2 Hz, 1H), 9.45 (s, 1H). ESI-MS m/z 468 [M++H]

Example 96

Synthesis of (+)-N-[3-((4aR*,6R*,7aS*)-2-amino-6-methoxy-4,4a,5,6,7,7a-hexahydrocyclopenta[d][1,3]thiazin-7a-yl)-4-fluorophenyl]-5-fluoromethoxypyrazine-2-carboxamide

[Formula 182]

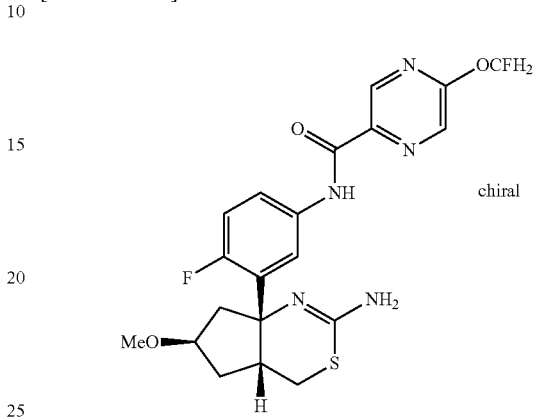

$^1$H-NMR (400 MHz, CDCl$_3$) δ (ppm): 1.84-1.94 (m, 1H), 2.24-2.36 (m, 2H), 2.62 (dd, J=7.2, 12.8 Hz, 1H), 2.72-2.80 (m, 1H), 2.96-3.04 (m, 1H), 3.12-3.20 (m, 1H), 3.34 (s, 3H), 3.88-3.98 (m, 1H), 6.05-6.25 (m, 2H), 7.07 (dd, J=4.8, 12.0 Hz, 1H), 7.37 (dd, J=2.8, 7.2 Hz, 1H), 7.85-7.95 (m, 1H), 8.27 (d, J=1.2 Hz, 1H), 9.07 (d, J=1.2 Hz, 1H), 9.46 (s, 1H).

ESI-MS m/z 450 [M++H]

Example 97

Synthesis of (+)-N-[3-((4aR*,6S*,7aS*)-2-amino-6-fluoro-4,4a,5,6,7,7a-hexahydrocyclopenta[d][1,3]thiazin-7a-yl)-4-fluorophenyl]-5-difluoromethylpyrazine-2-carboxamide

[Formula 183]

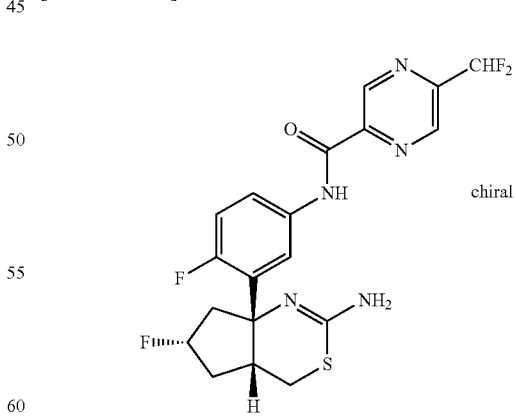

$^1$H-NMR (400 MHz, CDCl$_3$) δ (ppm): 2.20-2.50 (m, 3H), 2.73-3.05 (m, 4H), 5.25-5.50 (m, 1H), 6.80 (t, J=54.8 Hz, 1H), 7.00-7.10 (m, 1H), 7.41 (dd, J=2.8, 7.2 Hz, 1H), 7.90-8.02 (m, 1H), 8.90 (s, 1H), 9.51 (s, 1H), 9.60 (s, 1H).

ESI-MS m/z 440 [M++H]

Example 98

Synthesis of (+)-N-[3-((4aR*,6R*,7aS*)-2-amino-6-fluoro-4,4a,5,6,7,7a-hexahydrocyclopenta[d][1,3]thiazin-7a-yl)-4-fluorophenyl]-5-difluoromethoxy-pyrazine-2-carboxamide

[Formula 184]

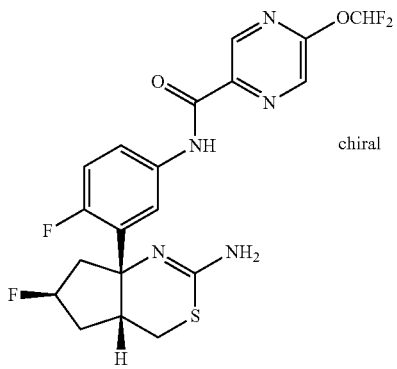 [SMILES: NC1=N[C@@]2(c3cc(NC(=O)c4cnc(OC(F)F)cn4)ccc3F)C[C@H](F)C[C@H]2CS1]

¹H-NMR (400 MHz, CDCl₃) δ (ppm): 2.00-2.20 (m, 1H), 2.25-2.60 (m, 2H), 2.70-3.10 (m, 3H), 3.10-3.25 (m, 1H), 5.10-5.35 (m, 1H), 7.10 (dd, J=8.8, 12.0 Hz, 1H), 7.38 (dd, J=2.8, 7.2 Hz, 1H), 7.51 (t, J=71.6 Hz, 1H), 7.86-7.92 (m, 1H), 8.33 (d, J=1.2 Hz, 1H), 9.07 (d, J=1.2 Hz, 1H), 9.45 (s, 1H). ESI-MS m/z 456 [M⁺+H]

Example 99

Synthesis of (+)-N-[3-((4aR*,6R*,7aS*)-2-amino-6-methoxy-4,4a,5,6,7,7a-hexahydrocyclopenta[d][1,3]thiazin-7a-yl)-4-fluorophenyl]-5-chloropyridine-2-carboxamide

[Formula 185]

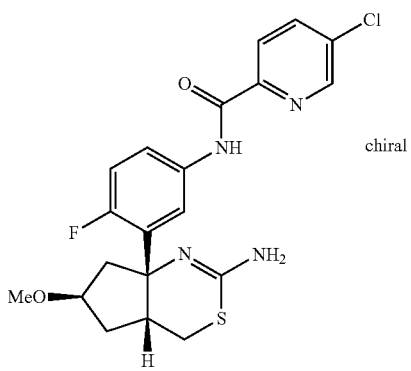 [SMILES: CO[C@@H]1C[C@H]2CSC(N)=N[C@@]2(c2cc(NC(=O)c3ccc(Cl)cn3)ccc2F)C1]

¹H-NMR (400 MHz, CDCl₃) δ (ppm): 1.84-1.94 (m, 1H), 2.24-2.36 (m, 2H), 2.62 (dd, J=7.2, 12.8 Hz, 1H), 2.75 (dd, J=3.6, 12.8 Hz, 1H), 3.00 (dd, J=3.6, 12.8 Hz, 1H), 3.12-3.20 (m, 1H), 3.34 (s, 3H), 3.88-3.98 (m, 1H), 7.07 (dd, J=8.8, 12.0 Hz, 1H), 7.36 (dd, J=2.8, 7.2 Hz, 1H), 7.87 (dd, J=2.8, 8.4 Hz, 1H), 7.90-8.00 (m, 1H), 8.24 (d, J=8.4 Hz, 1H), 8.55 (d, J=2.4 Hz, 1H), 9.78 (s, 1H).
ESI-MS m/z 435 [M⁺+H]

Example 100

Synthesis of (+)-N-[3-((4aR*,6R*,7aS*)-2-amino-6-methoxy-4,4a,5,6,7,7a-hexahydrocyclopenta[d][1,3]thiazin-7a-yl)-4-fluorophenyl]-5-difluoromethoxypyridine-2-carboxamide

[Formula 186]

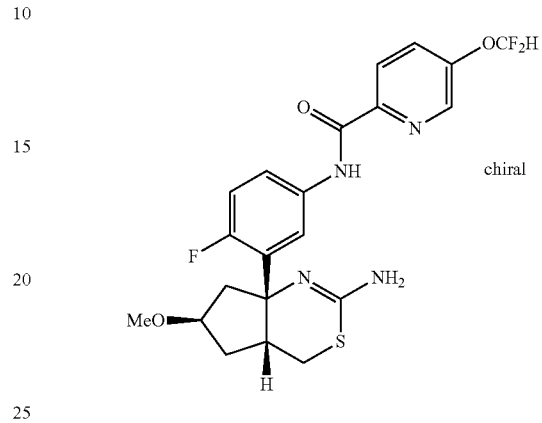

¹H-NMR (400 MHz, CDCl₃) δ (ppm): 1.84-1.96 (m, 1H), 2.22-2.40 (m, 2H), 2.62 (dd, J=6.8, 12.8 Hz, 1H), 2.77 (dd, J=3.6, 12.8 Hz, 1H), 3.01 (dd, J=3.6, 12.8 Hz, 1H), 3.12-3.24 (m, 1H), 3.33 (s, 3H), 3.88-3.98 (m, 1H), 6.64 (t, J=72.0 Hz, 1H), 7.07 (dd, J=8.8, 12.4 Hz, 1H), 7.40 (dd, J=2.8, 7.2 Hz, 1H), 7.65 (dd, J=2.8, 8.8 Hz, 1H), 7.85-7.95 (m, 1H), 8.30 (d, J=8.8 Hz, 1H), 8.45 (d, J=2.0 Hz, 1H), 9.80 (s, 1H).
ESI-MS m/z 467 [M⁺+H]

Example 101

Synthesis of (±)-N-[3-((4aR*,6S*,7aS*)-2-amino-6-methoxy-4,4a,5,6,7,7a-hexahydrocyclopenta[d][1,3]thiazin-7a-yl)-4-fluorophenyl]-5-fluoropyridine-2-carboxamide

[Formula 187]

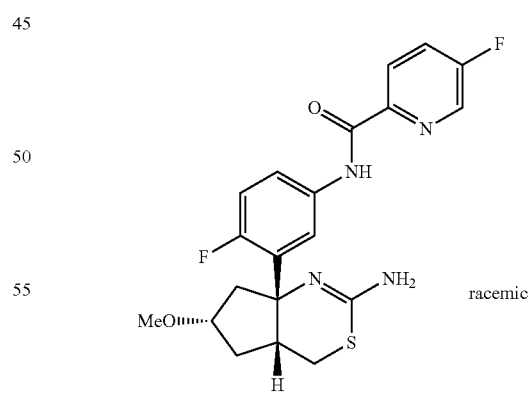

¹H-NMR (400 MHz, CDCl₃) δ (ppm): 1.98-2.14 (m, 2H), 2.16-2.26 (m, 1H), 2.62-2.72 (m, 1H), 2.78 (dd, J=4.4, 12.8 Hz, 1H), 2.90-3.02 (m, 2H), 3.40 (s, 3H), 4.08-4.24 (m, 1H), 7.05 (dd, J=8.8, 12.0 Hz, 1H), 7.35 (dd, J=2.4, 7.2 Hz, 1H), 7.60 (dt, J=2.4, 8.8 Hz, 1H), 7.90-8.02 (m, 1H), 8.33 (dd, J=4.4, 8.8 Hz, 1H), 8.46 (d, J=2.4 Hz, 1H), 9.77 (s, 1H).
ESI-MS m/z 419 [M⁺+H]

Example 102

Synthesis of (±)-N-[3-((4aR*,6S*,7aS*)-2-amino-6-methoxy-4,4a,5,6,7,7a-hexahydrocyclopenta[d][1,3]thiazin-7a-yl)-4-fluorophenyl]-pyridine-2-carboxamide

[Formula 188]

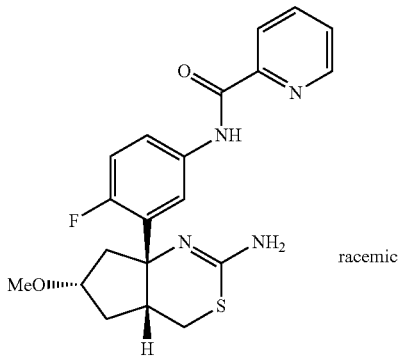

racemic

¹H-NMR (400 MHz, CDCl₃) δ (ppm): 1.96-2.12 (m, 2H), 2.16-2.26 (m, 1H), 2.62-2.74 (m, 1H), 2.78 (dd, J=4.8, 12.8 Hz, 1H), 2.90-3.02 (m, 2H), 3.34 (s, 3H), 4.08-4.24 (m, 1H), 7.05 (dd, J=8.8, 12.0 Hz, 1H), 7.38 (dd, J=2.8, 7.6 Hz, 1H), 7.45-7.55 (m, 1H), 7.85-7.95 (m, 1H), 7.95-8.05 (m, 1H), 8.25-8.35 (m, 1H), 8.60-8.70 (m, 1H), 9.99 (s, 1H). ESI-MS m/z 401 [M⁺+H]

Example 103

Synthesis of (±)-N-[3-((4aR*,6S*,7aS*)-2-amino-6-methoxy-4,4a,5,6,7,7a-hexahydrocyclopenta[d][1,3]thiazin-7a-yl)-4-fluorophenyl]-pyrimidine-4-carboxamide

[Formula 189]

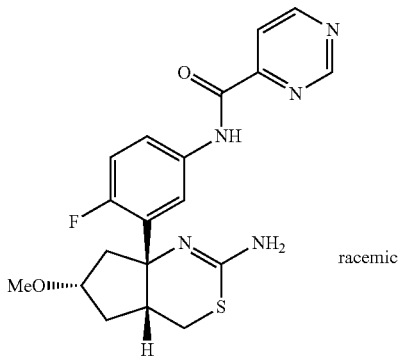 [SMILES: CO[C@H]1C[C@H]2CSC(N)=N[C@@]2(c2cc(NC(=O)c3ccccn3)ccc2F)C1]

racemic

¹H-NMR (400 MHz, CDCl₃) δ (ppm): 2.00-2.14 (m, 2H), 2.16-2.28 (m, 1H), 2.64-2.74 (m, 1H), 2.78 (dd, J=4.4, 12.8 Hz, 1H), 2.90-3.00 (m, 2H), 3.34 (s, 3H), 4.10-4.24 (m, 1H), 7.07 (dd, J=8.8, 12.0 Hz, 1H), 7.40 (dd, J=2.8, 7.2 Hz, 1H), 7.90-8.00 (m, 1H), 8.21 (dd, J=1.6, 4.8 Hz, 1H), 9.04 (d, J=4.8 Hz, 1H), 9.31 (d, J=1.6 Hz, 1H), 9.85 (s, 1H).

ESI-MS m/z 402 [M⁺+H]

Examples 104 to 107

The compounds of Examples 104 to 107 as shown in Table 6 below were synthesized according to Example 19 using the corresponding carboxylic acids and the corresponding aniline intermediates in the Preparation Examples.

[Table 6]

Table 6

TABLE 6

| Example | Chemical structure | | Compound name: |
|---|---|---|---|
| 104 | (structure with 5-chloropyrazine) | racemic | N-[3-((4aR*,8aS*)-2-amino-4a,5,6,7,8,8a-hexahydro-4H-benzo[d][1,3]thiazin-8a-yl)-4-fluorophenyl]-5-chloropyrazine-2-carboxamide ESI-MS m/z 420 [M⁺ + H] |
| 105 | (structure with 3,5-difluoropyridine) | chiral | N-[3-((4aR*,8aS*)-2-amino-4a,5,6,7,8,8a-hexahydro-4H-benzo[d][1,3]thiazin-8a-yl)-4-fluorophenyl]-3,5-difluoropyridine-2-carboxamide ESI-MS m/z 421 [M⁺ + H] |
| 106 | (structure with 5-trifluoromethylpyridine) | chiral | N-[3-((4aR*,8aS*)-2-amino-4a,5,6,7,8,8a-hexahydro-4H-benzo[d][1,3]thiazin-8a-yl)-4-fluorophenyl]-5-trifluoromethyl-pyridine-2-carboxamide ESI-MS m/z 453 [M⁺ + H] |

TABLE 6-continued

| Example | Chemical structure | Compound name: |
|---|---|---|
| 107 | (structure) | N-[3-((4aR*,8aS*)-2-amino-4a,5,6,7,8,8a-hexahydro-4H-benzo[d][1,3]thiazin-8a-yl)-4-fluorophenyl]-5-methoxypyrazine-2-carboxamide ESI-MS m/z 416 [M+ + H] |

Examples 108 to 110

The compounds of Examples 108 to 110 as shown in Table 7 were synthesized according to Example 19 or 89 using the corresponding carboxylic acids and the corresponding aniline compounds in the Preparation Examples.

[Table 7]
Table 7

TABLE 7

| Example | Chemical structure | Compound name: |
|---|---|---|
| 108 | (structure) | (+)-N-[3-((4aR*,6R*,7aS*)-2-amino-6-butoxy-4,4a,5,6,7,7a-hexahydrocyclopenta[d][1,3]thiazin-7a-yl)-4-fluorophenyl]-5-cyanopyridine-2-carboxamide ESI-MS m/z 468 [M+ + H] |
| 109 | (structure) | (+)-N-[3-((4aR*,6S*,7aS*)-2-amino-6-butoxy-4,4a,5,6,7,7a-hexahydrocyclopenta[d][1,3]thiazin-7a-yl)-4-fluorophenyl]-5-cyanopyridine-2-carboxamide ESI-MS m/z 468 [M+ + H] |

TABLE 7-continued

| Example | Chemical structure | Compound name: |
|---|---|---|
| 110 | (structure) | (+)-N-[3-((4aR*,6S*,7aS*)-2-amino-6-fluoro-4,4a,5,6,7,7a-hexahydrocyclopenta[d][1,3]thiazin-7a-yl)-4-fluorophenyl]-5-cyanopyridine-2-carboxamide ESI-MS m/z 414 [M+ + H] |

Examples 111 to 125

The compounds of Examples 111 to 125 as shown in Table 8 below were synthesized according to Example 1 or 19 using the corresponding carboxylic acids or sulfonyl chlorides and the compound of Preparation Examples 1-(8). [Table 8]

TABLE 8

| Example | Chemical structure | |
|---|---|---|
| 111 | (structure) | ESI-MS m/z 436 [M+ + H] |
| 112 | (structure) | ESI-MS m/z 419 [M+ + H] |

TABLE 8-continued

| Example | Chemical structure | |
|---|---|---|
| 113 | 2-methoxy-4-chlorobenzamide derivative | ESI-MS m/z 448 [M+ + H] |
| 114 | 3-fluoroisonicotinamide derivative | ESI-MS m/z 403 [M+] |
| 115 | pyridine-2-sulfonamide derivative | ESI-MS m/z 421 [M+ + H] |
| 116 | 6-chloropyridazine-3-carboxamide derivative | ESI-MS m/z 420 [M+ + H] |
| 117 | 5-methylpyrazine-2-carboxamide derivative | ESI-MS m/z 400 [M+ + H] |
| 118 | 5-(dimethylamino)pyrazine-2-carboxamide derivative | ESI-MS m/z 429 [M+ + H] |
| 119 | tetrahydrofuran-2-carboxamide derivative | ESI-MS m/z 378 [M+ + H] |
| 120 | 5-bromopyrimidine-2-carboxamide derivative | ESI-MS m/z 466 [M+ + H] |

TABLE 8-continued

| Example | Chemical structure | |
|---|---|---|
| 121 | 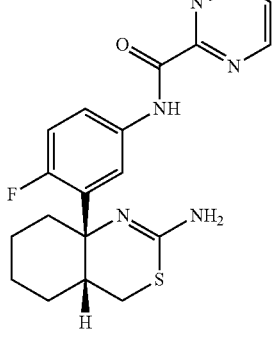 | ESI-MS m/z 386 [M+ + H] |
| 122 | 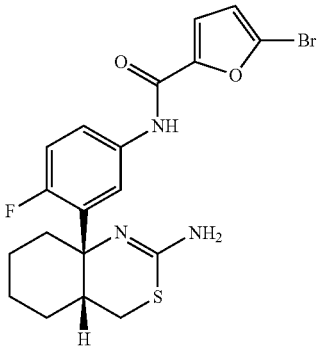 [SMILES: NC1=N[C@@]2(c3cc(NC(=O)c4ccc(Br)o4)ccc3F)CCCC[C@H]2CS1] | ESI-MS m/z 454 [M+ + H] |
| 123 | 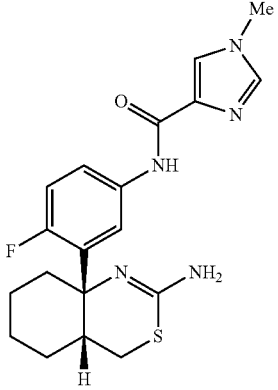 [SMILES: Cn1cnc(C(=O)Nc2ccc(F)c([C@]34CCCC[C@H]3CSC(N)=N4)c2)c1] | ESI-MS m/z 388 [M+ + H] |
| 124 | 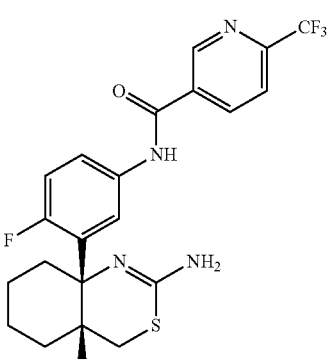 | ESI-MS m/z 453 [M+ + H] |
| 125 | 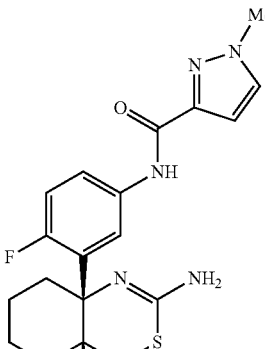 | ESI-MS m/z 388 [M+ + H] |

Example 126 to 129

The compounds of Examples 126 to 129 as shown in Table 9 below were synthesized according to Example 1 or 19 using the corresponding carboxylic acids and the compound of Preparation Examples 3-(8).

[Table 9]

TABLE 9

| Example | Chemical structure | |
|---|---|---|
| 126 | 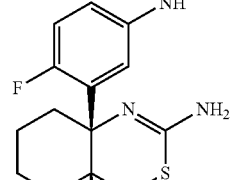 | ESI-MS m/z 397 [M+ + H] |
| 127 | 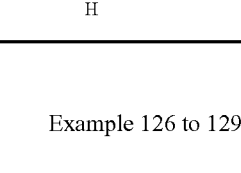 | ESI-MS m/z 428 [M+ + H] |

TABLE 9-continued

| Example | Chemical structure | |
|---|---|---|
| 128 | 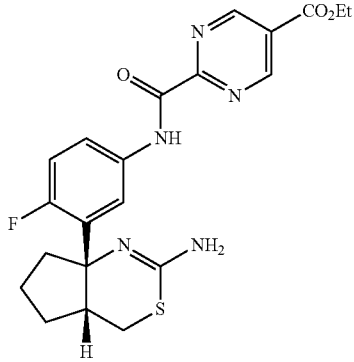 [SMILES: CCOC(=O)c1cnc(C(=O)Nc2ccc(F)c([C@]34CCC[C@H]3CSC(N)=N4)c2)nc1] | ESI-MS m/z 444 [M+ + H] |
| 129 | 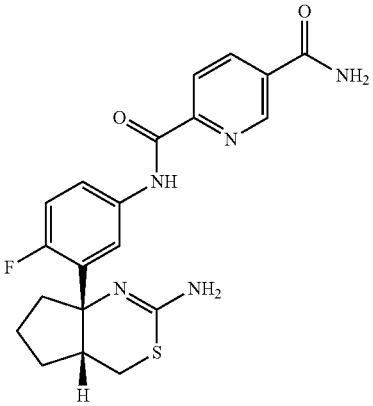 [SMILES: NC(=O)c1ccc(C(=O)Nc2ccc(F)c([C@]34CCC[C@H]3CSC(N)=N4)c2)nc1] | ESI-MS m/z 414 [M+ + H] |

Example 130

Synthesis of (±)-(4aR*,7aS*)-7a-{5-[(5-chloropyridin-2-yl)amino]-2-fluorophenyl}-4,4a,5,6,7,7a-hexahydrocyclopenta[d][1,3]thiazin-2-amine

[Formula 190]

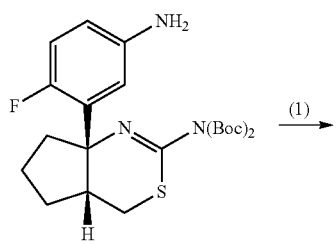

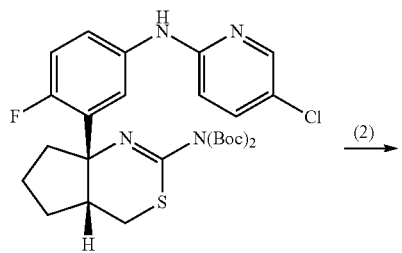

(1) Synthesis of (±)-di-tert-butyl[(4aR*,7aS*)-7a-{5-[(5-chloropyridin-2-yl)amino]-2-fluorophenyl}-4,4a,5,6,7,7a-hexahydrocyclopenta[d][1,3]thiazin-2-yl]imidodicarbonate 2-Bromo-5-chloropyridine (10 mg), (R)-(+)-2,2'-bis(diphenylphosphino)-1,1'-binaphthyl (4.86 mg), tris(dibenzylideneacetone)dipalladium (0) (2.38 mg) and tert-butoxysodium (6.5 mg) were added to a solution of (±)-di-tert-butyl [(4aR*,7aS*)-7a-(5-amino-2-fluorophenyl)-4,4a,5,6,7,7a-hexahydrocyclopenta[d][1,3]thiazin-2-yl]imidodicarbonate (29.1 mg) in toluene (10 mL). The mixture was heated with stirring under a nitrogen atmosphere at 100° C. for five hours. The reaction solution was returned to room temperature and poured into water, followed by extraction with ethyl acetate. The extract was washed with brine and dried over anhydrous magnesium sulfate. The title compound (60 mg) was obtained by removal of the drying agent and concentration under reduced pressure.

ESI-MS; m/z 577 [M$^+$].

(2) (±)-(4aR*,7aS*)-7a-{5-[(5-Chloropyridin-2-yl)amino]-2-fluorophenyl}-4,4a,5,6,7,7a-hexahydrocyclopenta[d][1,3]thiazin-2-amine TFA (0.5 mL) was added to a solution of the condensate obtained in the previous step (60 mg) in dichloromethane (3 mL), and the mixture was stirred at room temperature for two hours. The reaction solution was poured into a saturated sodium bicarbonate solution, followed by extraction with ethyl acetate. The extract was washed with brine and dried over anhydrous magnesium sulfate. The drying agent was removed, followed by concentration under reduced pressure. The residue was purified by column chromatography to obtain the title compound (2.4 mg).

ESI-MS; m/z 377 [M$^+$+H].

Example 131

The compound of Example 131 as shown in Table 10 below was obtained according to the method of Example 130.

[Table 10]

TABLE 10

| Example | Chemical structure | |
|---|---|---|
| 131 | (structure shown) | ESI-MS m/z 421 [M$^+$] |

Examples 132 to 142

The compounds of Examples 132 to 142 as shown in Table 11 below were synthesized according to Example 14 using the corresponding carboxylic acids and the compound obtained in Preparation Example 3-(8).

[Table 11]

Table 11

TABLE 11

| Example | Chemical structure | Compound name: |
|---|---|---|
| 132 | (structure shown) chiral | N-[3-((4aR*,7aS*)-2-amino-4,4a,5,6,7,7a-hexahydrocyclopenta[d][1,3]thiazin-7a-yl)-4-fluorophenyl]-5-cyclopropylethynyl-pyridine-2-carboxamide ESI-MS m/z 435 [M$^+$ + H] |

TABLE 11-continued

| Example | Chemical structure | Compound name: |
|---|---|---|
| 133 | 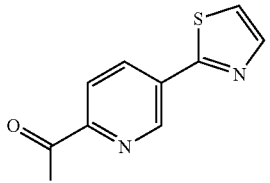 chiral | N-[3-((4aR*,7aS*)-2-amino-4,4a,5,6,7,7a-hexahydrocyclo-penta[d][1,3]thiazin-7a-yl)-4-fluorophenyl]-5-thiazol-2-yl-pyridine-2-carboxamide<br>ESI-MS m/z 454 [M+ + H] |
| 134 | 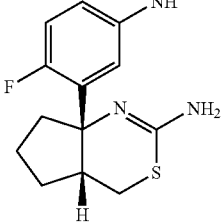 chiral | ESI-MS m/z 411 [M+ + H] |
| 135 | 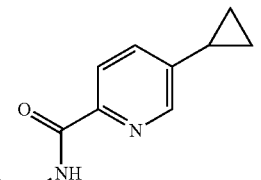 chiral | N-[3-((4aR*,7aS*)-2-amino-4,4a,5,6,7,7a-hexahydrocyclo-penta[d][1,3]thiazin-7a-yl)-4-fluorophenyl]-5-methylsulfanyl-pyrazine-2-carboxamide<br>ESI-MS m/z 418 [M+ + H] |
| 136 | 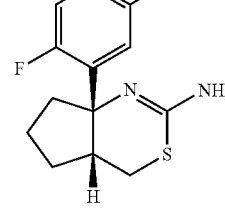 chiral | N-[3-((4aR*,7aS*)-2-amino-4,4a,5,6,7,7a-hexahydrocyclo-penta[d][1,3]thiazin-7a-yl)-4-fluorophenyl]-5-(3-methoxypropyn-1-yl)-pyridine-2-carboxamide<br>ESI-MS m/z 439 [M+ + H] |

TABLE 11-continued
| Example | Chemical structure | Compound name: |
|---|---|---|
| 137 | 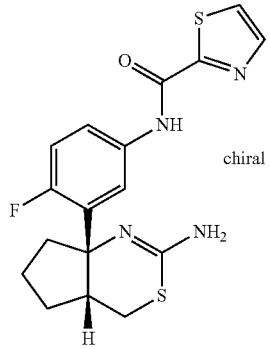 [SMILES: NC1=N[C@@]2(c3cc(NC(=O)c4nccs4)ccc3F)CCC[C@H]2CS1] | N-[3-((4aR*,7aS*)-2-amino-4,4a,5,6,7,7a-hexahydrocyclopenta[d][1,3]thiazin-7a-yl)-4-fluorophenyl]-thiazole-2-carboxamide<br>ESI-MS m/z 377 [M$^+$ + H] |
| 138 | 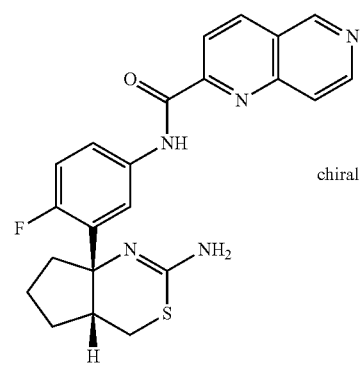 [SMILES: NC1=N[C@@]2(c3cc(NC(=O)c4ccc5cnccc5n4)ccc3F)CCC[C@H]2CS1] | ESI-MS m/z 422 [M$^+$ + H] |
| 139 | 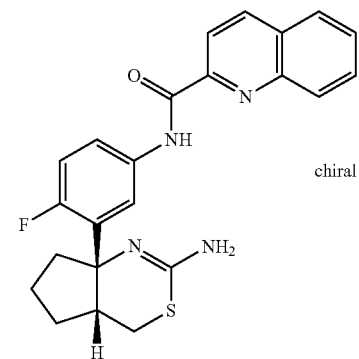 [SMILES: NC1=N[C@@]2(c3cc(NC(=O)c4ccc5ccccc5n4)ccc3F)CCC[C@H]2CS1] | ESI-MS m/z 421 [M$^+$ + H] |
| 140 | 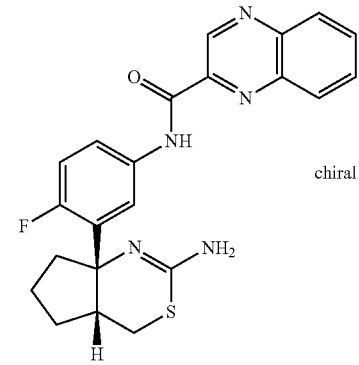 [SMILES: NC1=N[C@@]2(c3cc(NC(=O)c4cnc5ccccc5n4)ccc3F)CCC[C@H]2CS1] | ESI-MS m/z 422 [M$^+$ + H] |

TABLE 11-continued

| Example | Chemical structure | Compound name: |
|---|---|---|
| 141 | 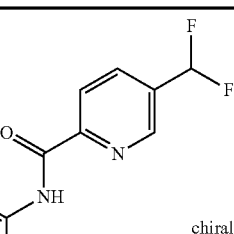 | N-[3-((4aR*,7aS*)-2-amino-4,4a,5,6,7,7a-hexahydrocyclopenta[d][1,3]thiazin-7a-yl)-4-fluorophenyl]-5-difluoromethylpyridine-2-carboxamide<br>ESI-MS m/z 421 [M+ + H] |
| 142 | 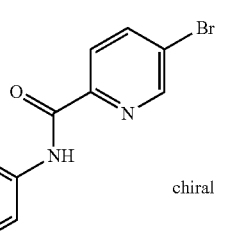 | N-[3-((4aS*,8aS*)-2-amino-4a,5,7,8-tetrahydro-4H-6-oxa-3-thia-1-azanaphthalen-8a-yl)-4-fluorophenyl]-5-bromopyridine-2-carboxamide<br>ESI-MS m/z 467 [M+ + H] |

The compounds of Examples 143 to 148 below were synthesized according to Example 14 using the corresponding carboxylic acids and the compound obtained in Preparation Example 44-(16).

Example 143

Synthesis of N-[3-((4aS*,5S*,8aS*)-2-amino-5-fluoromethyl-4a,5,7,8-tetrahydro-4H-6-oxa-3-thia-1-azanaphthalen-8a-yl)-4-fluorophenyl]-5-cyanopyridine-2-carboxamide

[Formula 191]

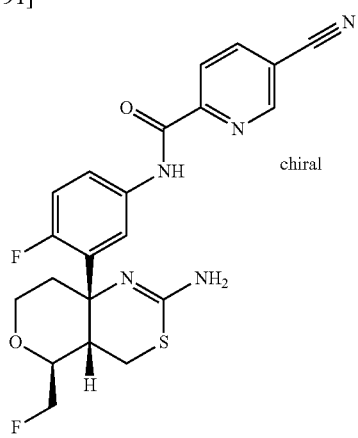

$^1$H-NMR (400 MHz, CDCl$_3$) δ (ppm): 1.64-1.72 (m, 1H), 2.66-2.73 (m, 1H), 2.73-2.81 (m, 1H), 2.89-2.97 (m, 1H), 2.99-3.06 (m, 1H), 3.76-4.02 (m, 3H), 4.64 (dd, J=48.0, 3.8 Hz, 2H), 7.11 (dd, J=11.6, 8.8 Hz, 1H), 7.46 (dd, J=6.8, 2.8 Hz, 1H), 7.88-7.94 (m, 1H), 8.20 (dd, J=8.0, 2.5 Hz, 1H), 8.41-8.45 (m, 1H), 8.88-8.92 (m, 1H), 9.82 (brs, 1H).
ESI-MS m/z 444 [M++H]

Example 144

Synthesis of N-[3-((4aS*,5S*,8aS*)-2-amino-5-fluoromethyl-4a,5,7,8-tetrahydro-4H-6-oxa-3-thia-1-azanaphthalen-8a-yl)-4-fluorophenyl]-5-fluoromethoxypyrazine-2-carboxamide

[Formula 192]

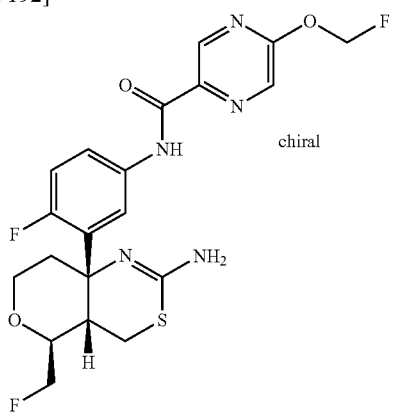

¹H-NMR (400 MHz, CDCl₃) δ (ppm): 1.66-1.72 (m, 1H), 2.66-2.82 (m, 2H), 2.89-2.98 (m, 1H), 2.98-3.06 (m, 1H), 3.77-4.02 (m, 3H), 4.64 (brd, J=47.6 Hz, 2H), 6.16 (d, J=51.2 Hz, 2H), 7.05-7.16 (m, 1H), 7.37-7.46 (m, 1H), 7.84-7.93 (m, 1H), 8.29 (d, J=1.4 Hz, 1H), 9.08 (d, J=1.4 Hz, 1H), 9.47 (brs, 1H). ESI-MS m/z 468 [M⁺+H]

Example 145

Synthesis of N-[3-((4aS*,5S*,8aS*)-2-amino-5-fluoromethyl-4a,5,7,8-tetrahydro-4H-6-oxa-3-thia-1-azanaphthalen-8a-yl)-4-fluorophenyl]-5-difluoromethoxypyrazine-2-carboxamide

[Formula 193]

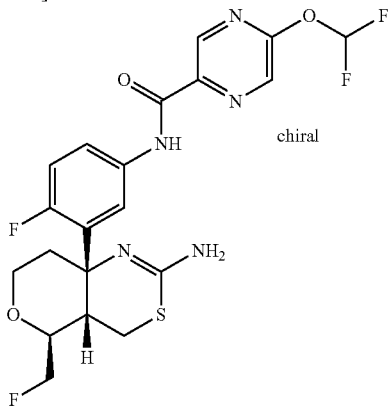

¹H-NMR (400 MHz, CDCl₃) δ (ppm): 1.63-1.73 (m, 1H), 2.65-2.82 (m, 2H), 2.89-2.98 (m, 1H), 2.98-3.06 (m, 1H), 3.77-4.03 (m, 3H), 4.64 (dd, J=47.6, 3.5 Hz, 2H), 7.06-7.15 (m, 1H), 7.41-7.47 (m, 1H), 7.51 (t, J=71.4 Hz, 1H), 7.84-7.92 (m, 1H), 8.32-8.36 (m, 1H), 9.05-9.10 (m, 1H), 9.45 (brs, 1H). ESI-MS m/z 486 [M⁺+H]

Example 146

Synthesis of N-[3-((4aS*,5S*,8aS*)-2-amino-5-fluoromethyl-4a,5,7,8-tetrahydro-4H-6-oxa-3-thia-1-azanaphthalen-8a-yl)-4-fluorophenyl]-5-difluoromethylpyrazine-2-carboxamide

[Formula 194]

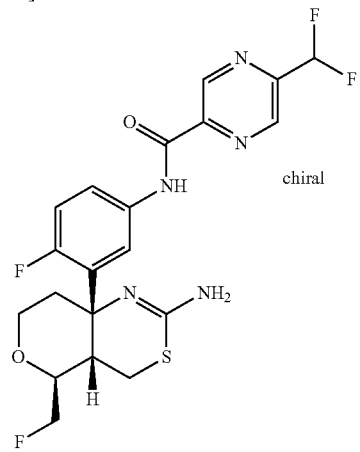

¹H-NMR (400 MHz, CDCl₃) δ (ppm): 1.63-1.74 (m, 1H), 2.66-2.82 (m, 2H), 2.89-2.98 (m, 1H), 2.98-3.08 (m, 1H), 3.76-4.03 (m, 3H), 4.64 (dd, J=48.0, 2.8 Hz, 2H), 6.80 (t, J=54.4 Hz, 1H), 7.07-7.17 (m, 1H), 7.45-7.52 (m, 1H), 7.85-7.94 (m, 1H), 8.93 (s, 1H), 9.53 (s, 1H), 9.62 (brs, 1H). ESI-MS m/z 470 [M⁺+H]

Example 147

Synthesis of N-[3-((4aS*,5S*,8aS*)-2-amino-5-fluoromethyl-4a,5,7,8-tetrahydro-4H-6-oxa-3-thia-1-azanaphthalen-8a-yl)-4-fluorophenyl]-5-difluoromethoxypyridine-2-carboxamide

[Formula 195]

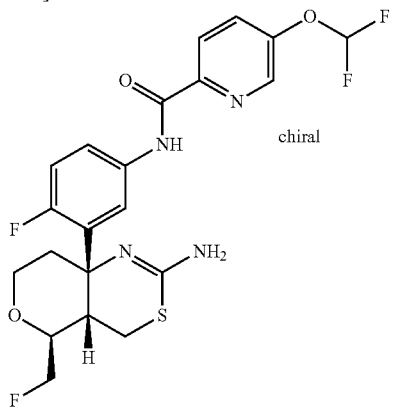

¹H-NMR (400 MHz, CDCl₃) δ (ppm): 1.63-1.72 (m, 1H), 2.67-2.81 (m, 2H), 2.88-2.98 (m, 1H), 2.98-3.07 (m, 1H), 3.76-4.02 (m, 3H), 4.64 (d, J=48.0 Hz, 2H), 6.65 (t, J=72.0 Hz, 1H), 7.03-7.15 (m, 1H), 7.38-7.47 (m, 1H), 7.62-7.71 (m, 1H), 7.84-7.95 (m, 1H), 8.27-8.36 (m, 1H) 8.42-8.50 (m, 1H), 9.80 (brs, 1H).
ESI-MS m/z 485 [M⁺+H]

Example 148

Synthesis of N-[3-((4aS*,5S*,8aS*)-2-amino-5-fluoromethyl-4a,5,7,8-tetrahydro-4H-6-oxa-3-thia-1-azanaphthalen-8a-yl)-4-fluorophenyl]-5-chloropyridine-2-carboxamide

[Formula 196]

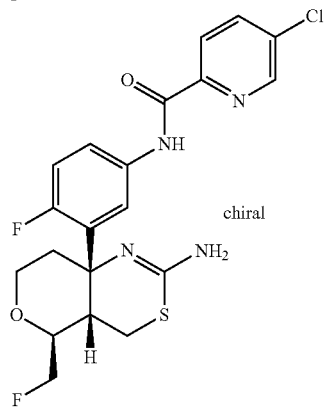 [SMILES: NC1=N[C@@]2(c3cc(NC(=O)c4ccc(Cl)cn4)ccc3F)CCO[C@H](CF)[C@H]2CS1]

¹H-NMR (400 MHz, CDCl₃) δ (ppm): 1.63-1.72 (m, 1H), 2.67-2.80 (m, 2H), 2.90-2.98 (m, 1H), 2.98-3.06 (m, 1H), 3.77-4.01 (m, 3H), 4.64 (dd, J=47.6, 2.8 Hz, 2H), 7.06-7.14 (m, 1H), 7.41-7.47 (m, 1H), 7.86-7.93 (m, 2H), 8.22-8.28 (m, 1H), 8.55-8.60 (m, 1H), 9.80 (brs, 1H).
ESI-MS m/z 453 [M⁺+H]

Examples 149 to 151

The compounds of Examples 149 to 151 as shown in Table 12 below were synthesized according to Example 14 using the corresponding carboxylic acids and the corresponding aniline intermediates in Preparation Examples.

[Table 12]

TABLE 12

| Example | Chemical structure | | |
|---|---|---|---|
| 149 | 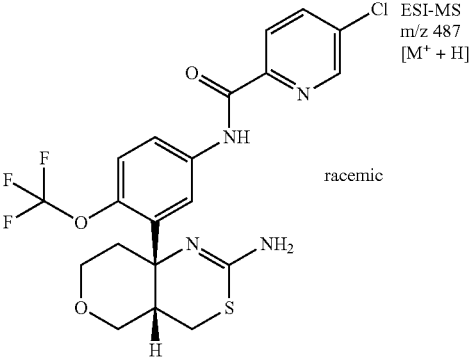 | racemic | ESI-MS m/z 487 [M+ + H] |
| 150 | 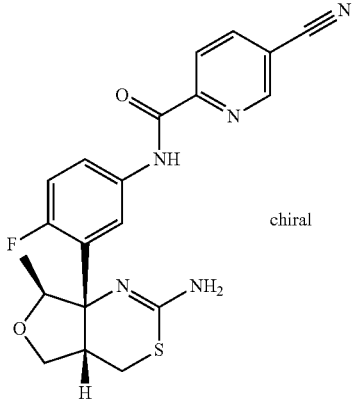 [SMILES: C[C@@H]1OC[C@H]2CSC(N)=N[C@]21c1cc(NC(=O)c2ccc(C#N)cn2)ccc1F] | chiral | ESI-MS m/z 412 [M+ + H] |
| 151 | 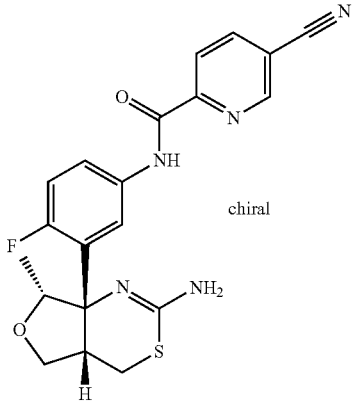 [SMILES: C[C@H]1OC[C@H]2CSC(N)=N[C@]21c1cc(NC(=O)c2ccc(C#N)cn2)ccc1F] | chiral | ESI-MS m/z 412 [M+ + H] |

The compounds of Examples 152 to 157 below were synthesized according to Example 14 using the corresponding carboxylic acids and the compound obtained in Preparation Example 48-(13).

Example 152

Synthesis of N-[3-((4aS*,5R*,8aS*)-2-amino-5-methyl-4a,5,7,8-tetrahydro-4H-6-oxa-3-thia-1-aza-naphthalen-8a-yl)-4-fluorophenyl]-5-chloropyridine-2-carboxamide

[Formula 197]

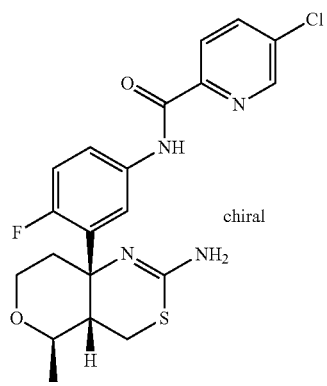 [SMILES: C[C@H]1OCC[C@]2(c3cc(NC(=O)c4ccc(Cl)cn4)ccc3F)N=C(N)SC[C@H]12]

$^1$H-NMR (400 MHz, CDCl$_3$) δ (ppm): 1.34 (d, J=6.4 Hz, 3H), 1.72-1.82 (m, 1H), 2.64-2.82 (m, 3H), 2.92-3.00 (m, 1H), 3.75-3.86 (m, 2H), 3.92-3.97 (m, 1H), 7.08-7.16 (m, 1H), 7.40-7.46 (m, 1H), 7.87-7.96 (m, 2H), 8.22-8.26 (m, 1H), 8.57-8.60 (m, 1H), 9.84 (brs, 1H).

ESI-MS m/z 435 [M$^+$+H]

Example 153

Synthesis of N-[3-((4aS*,5R*,8aS*)-2-amino-5-methyl-4a,5,7,8-tetrahydro-4H-6-oxa-3-thia-1-aza-naphthalen-8a-yl)-4-fluorophenyl]-5-fluoromethoxy-pyrazine-2-carboxamide

[Formula 198]

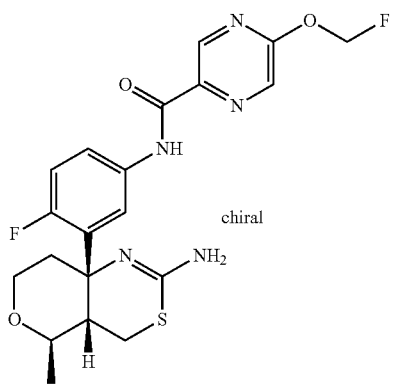 [SMILES: C[C@H]1OCC[C@]2(c3cc(NC(=O)c4cnc(OCF)cn4)ccc3F)N=C(N)SC[C@H]12]

$^1$H-NMR (400 MHz, CDCl$_3$) δ (ppm): 1.33 (d, J=6.0 Hz, 3H), 1.75-1.84 (m, 1H), 2.62-2.80 (m, 3H), 2.89-2.97 (m, 1H), 3.74-3.85 (m, 2H), 3.89-3.97 (m, 1H), 6.06-6.12 (m, 1H), 6.19-6.25 (m, 1H), 7.06-7.15 (m, 1H), 7.35-7.41 (m, 1H), 7.88-7.96 (m, 1H), 8.30 (d, J=1.2 Hz, 1H), 9.07 (d, J=1.2 Hz, 1H), 9.50 (brs, 1H). ESI-MS m/z 450 [M$^+$+H]

Example 154

Synthesis of N-[3-((4aS*,5R*,8aS*)-2-amino-5-methyl-4a,5,7,8-tetrahydro-4H-6-oxa-3-thia-1-aza-naphthalen-8a-yl)-4-fluorophenyl]-5-difluoromethoxypyrazine-2-carboxamide

[Formula 199]

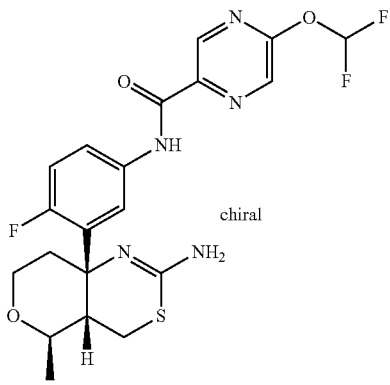 [SMILES: C[C@H]1OCC[C@]2(c3cc(NC(=O)c4cnc(OC(F)F)cn4)ccc3F)N=C(N)SC[C@H]12]

$^1$H-NMR (400 MHz, CDCl$_3$) δ (ppm): 1.32 (d, J=6.0 Hz, 3H), 1.68-1.77 (m, 1H), 2.59-2.77 (m, 3H), 2.86-2.94 (m, 1H), 3.73-3.86 (m, 2H), 3.87-3.95 (m, 1H), 7.07-7.14 (m, 1H), 7.36-7.40 (m, 1H), 7.51 (t, J=71.4 Hz, 1H), 7.88-7.94 (m, 1H), 8.35 (d, J=1.2 Hz, 1H), 9.07 (d, J=1.2 Hz, 1H), 9.47 (brs, 1H).

ESI-MS m/z 468 [M$^+$+H]

Example 155

Synthesis of N-[3-((4aS*,5R*,8aS*)-2-amino-5-methyl-4a,5,7,8-tetrahydro-4H-6-oxa-3-thia-1-aza-naphthalen-8a-yl)-4-fluorophenyl]-5-difluoromethoxypyridine-2-carboxamide

[Formula 200]

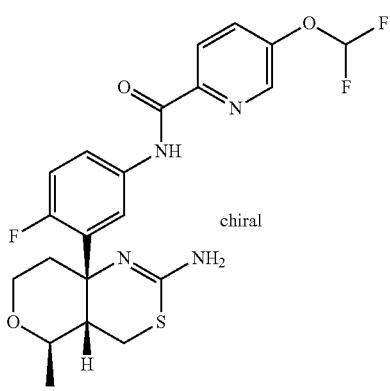 [SMILES: C[C@H]1OCC[C@]2(c3cc(NC(=O)c4ccc(OC(F)F)cn4)ccc3F)N=C(N)SC[C@H]12]

$^1$H-NMR (400 MHz, CDCl$_3$) δ (ppm): 1.33 (d, J=6.0 Hz, 3H), 1.74-1.83 (m, 1H), 2.62-2.79 (m, 3H), 2.89-2.97 (m, 1H), 3.74-3.86 (m, 2H), 3.88-3.96 (m, 1H), 6.65 (t, J=72.0 Hz, 1H), 7.05-7.14 (m, 1H), 7.37-7.42 (m, 1H), 7.64-7.69 (m, 1H), 7.90-7.96 (m, 1H), 8.30-8.34 (m, 1H), 8.46-8.50 (m, 1H), 9.82 (brs, 1H). ESI-MS m/z 467 [M$^+$+H]

Example 156

Synthesis of N-[3-((4aS*,5R*,8aS*)-2-amino-5-methyl-4a,5,7,8-tetrahydro-4H-6-oxa-3-thia-1-aza-naphthalen-8a-yl)-4-fluorophenyl]-5-difluoromethylpyrazine-2-carboxamide

[Formula 201]

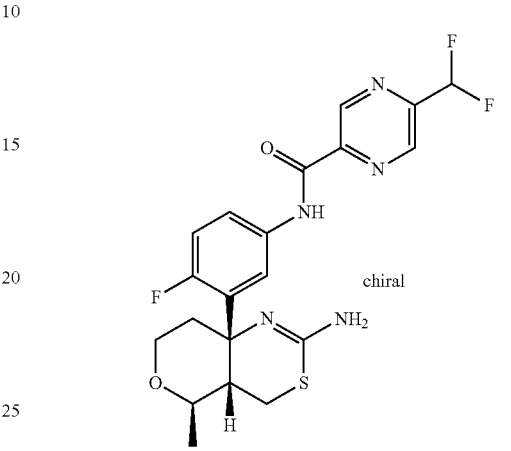

$^1$H-NMR (400 MHz, CDCl$_3$) δ (ppm): 1.33 (d, J=6.4 Hz, 3H), 1.72-1.81 (m, 1H), 2.62-2.79 (m, 3H), 2.88-2.95 (m, 1H), 3.74-3.86 (m, 2H), 3.89-3.96 (m, 1H), 6.79 (t, J=54.4 Hz, 1H), 7.08-7.16 (m, 1H), 7.41-7.46 (m, 1H), 7.88-7.96 (m, 1H), 8.92-8.95 (m, 1H), 9.51-9.54 (m, 1H), 9.64 (brs, 1H).

ESI-MS m/z 452 [M$^+$+H]

Example 157

Synthesis of (±)-N-[3-((4aR*,7aS*)-2-amino-4,4a,5,6,7,7a-hexahydrocyclopenta[d][1,3]thiazin-7a-yl)-5-fluorophenyl]-5-cyanopyridine-2-carboxamide

[Formula 202]

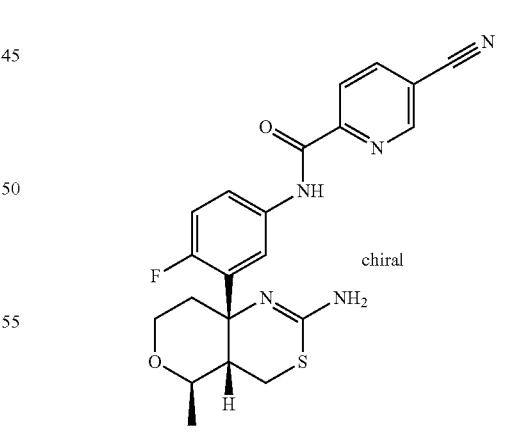

$^1$H-NMR (400 MHz, CDCl$_3$) δ (ppm): 1.32 (d, J=6.4 Hz, 3H), 1.62-1.69 (m, 1H), 2.54-2.62 (m, 1H), 2.65-2.75 (m, 2H), 2.84-2.92 (m, 1H), 3.73-3.86 (m, 2H), 3.86-3.93 (m, 1H), 7.06-7.14 (m, 1H), 7.36-7.42 (m, 1H), 7.92-7.98 (m, 1H), 8.20 (dd, J=8.2, 1.8 Hz, 1H), 8.43 (dd, J=8.2, 1.0 Hz, 1H), 8.90 (dd, J=1.8, 1.0 Hz, 1H), 9.81 (brs, 1H).

ESI-MS m/z 426 [M$^+$+H]

Example 158

Synthesis of (±)-N-[3-((4aR*,7aS*)-2-amino-4a,5,6,7-tetrahydro-4H-cyclopenta[d][1,3]thiazin-7a-yl)-5-fluorophenyl]-5-cyanopyridine-2-carboxamide

[Formula 203]

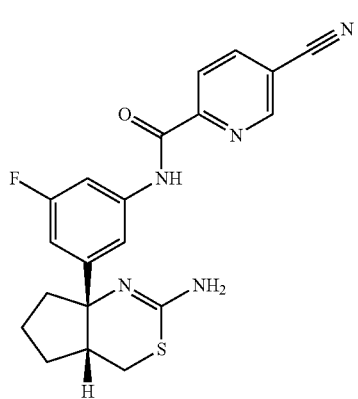 [SMILES: N#Cc1ccc(C(=O)Nc2cc(F)cc([C@]34CCC[C@H]3CSC(N)=N4)c2)nc1]

The title compound (52 mg) was obtained from 5-cyanopyridine-2-carboxylic acid obtained in Preparation Example 13 (49.3 mg) and the compound obtained in Preparation Example 55-(11) (85 mg) according to the method of Example 14.

ESI-MS; m/z 396 [M$^+$+H].

Example 159

Synthesis of N-[3-((4aR*,8aS*)-2-amino-4a,5,7,8-tetrahydro-4H-6-oxa-3-thia-1-azanaphthalen-8a-yl)-4-fluorophenyl]-5-cyanopyridine-2-carboxamide

[Formula 204]

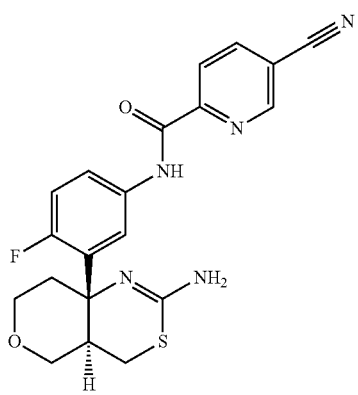 [SMILES: N#Cc1ccc(C(=O)Nc2ccc(F)c([C@]34CCOC[C@@H]3CSC(N)=N4)c2)nc1]

The title compound (15 mg) was obtained from 5-cyanopyridine-2-carboxylic acid (12.9 mg) and the compound obtained in Preparation Example 56-(16) (23 mg) according to the method of Example 14.

ESI-MS; m/z 412 [M$^+$+H].

Example 160

Synthesis of (±)-(4aR*,7aS*)-7a-[2-fluoro-5-(2-fluoropyridin-3-yl)phenyl]-4,4a,5,6,7,7a-hexahydrocyclopenta[d][1,3]thiazin-2-ylamine

[Formula 205]

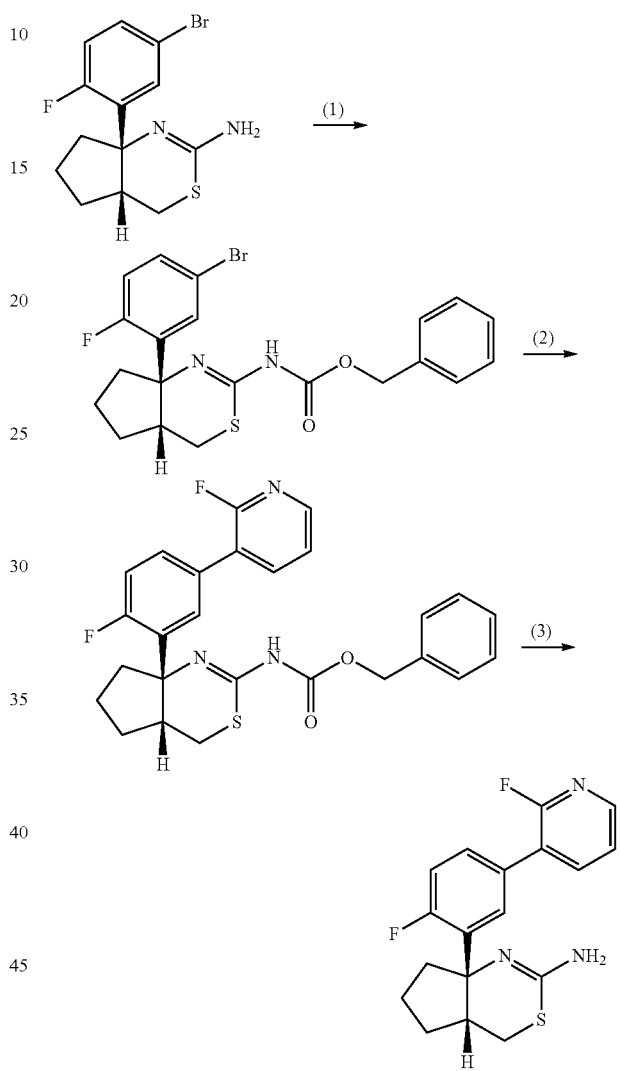

(1) Synthesis of benzyl (±)-[(4aR*,7aS*)-7a-(5-bromo-2-fluorophenyl)-4,4a,5,6,7,7a-hexahydrocyclopenta[d][1,3]thiazin-2-yl]carbamate Benzyl chloroformate (1.16 mL) was added to a solution of the compound obtained in Preparation Example 54-(4) (2.24 g) in 1,4-dioxane and a saturated sodium bicarbonate solution (60 mL/60 mL). The reaction solution was stirred at room temperature for three hours. Ethyl acetate and saturated aqueous sodium chloride were added to the reaction solution, and the organic layer was separated. The organic layer was washed with saturated aqueous sodium chloride again. The organic layer was dried over anhydrous magnesium sulfate. The organic layer was concentrated under reduced pressure. The residue was purified by silica gel chromatography to obtain the title compound (2.35 g).

ESI-MS; m/z 463 [M$^+$+H].

335

(2) Synthesis of benzyl (±)-{(4aR*,7aS*)-7a-[2-fluoro-5-(2-fluoropyridin-3-yl)phenyl]-4,4a,5,6,7,7a-hexahydrocyclopenta[d][1,3]thiazin-2-yl}carbamate 1 M aqueous sodium bicarbonate (432 L), 2-fluoropyridine-3-boronic acid (67.1 mg) and tetrakis(triphenylphosphine)palladium (0) (25.1 mg) were added to a solution of the compound obtained in Example 160-(1) (200 mg) in toluene (4 mL)/ethanol (2 mL), and the mixture was stirred at 85° C. for 16 hours. The reaction solution was returned to room temperature. Saturated aqueous sodium chloride and ethyl acetate were added to the reaction solution. The organic layer was separated and dried over anhydrous magnesium sulfate. The organic layer was concentrated under reduced pressure. The residue was purified by silica gel column chromatography to obtain a crude purified product containing the title compound (156 mg). ESI-MS; m/z 480 [M$^+$+H].

(3) Synthesis of (±)-(4aR*,7aS*)-7a-[2-fluoro-5-(2-fluoropyridin-3-yl)phenyl]-4,4a,5,6,7,7a-hexahydro-cyclopenta[d][1,3]thiazin-2-ylamine Iodotrimethylsilane (116 μL) was added to a solution of the compound obtained in Example 160-(2) (78 mg) in chloroform (4 mL), and the mixture was stirred at room temperature overnight. Iodotrimethylsilane (116 μL) was added to the reaction solution again, and the mixture was heated under reflux for 20 hours. The reaction solution was returned to room temperature. The reaction solution was made basic with 5 N sodium hydroxide, and chloroform was added. The organic layer was separated and washed with saturated aqueous sodium chloride. The organic layer was dried over anhydrous magnesium sulfate and concentrated under reduced pressure. The residue was purified by NH-silica gel column chromatography to obtain the title compound (11 mg).
ESI-MS; m/z 346 [M$^+$+H].

Example 161

Synthesis of (±)-(4aR*,7aS*)-7a-(4-fluoro-3'-methoxybiphenyl-3-yl)-4,4a,5,6,7,7a-hexahydro-cyclopenta[d][1,3]thiazin-2-ylamine

[Formula 206]

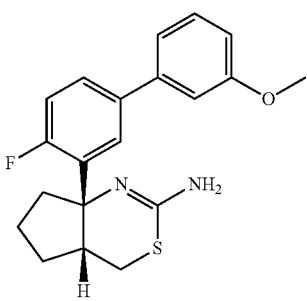 [SMILES: COc1cccc(-c2ccc(F)c([C@]34CCC[C@H]3CSC(N)=N4)c2)c1]

Synthesis of (±)-(4aR*,7aS*)-7a-(4-fluoro-3'-methoxybiphenyl-3-yl)-4,4a,5,6,7,7a-hexahydro-cyclopenta[d][1,3]thiazin-2-ylamine The title compound (1.3 mg) was obtained from the compound obtained in Example 160-(1) (100 mg) according to Example 160 using the corresponding boronic acid.
ESI-MS; m/z 357 [M$^+$+H].

Example 162

Synthesis of (+)-(4aR*,7aS*)-7a-(3',5'-dichloro-4-fluorobiphenyl-3-yl)-4,4a,5,6,7,7a-hexahydro-cyclopenta[d][1,3]thiazin-2-ylamine

[Formula 207]

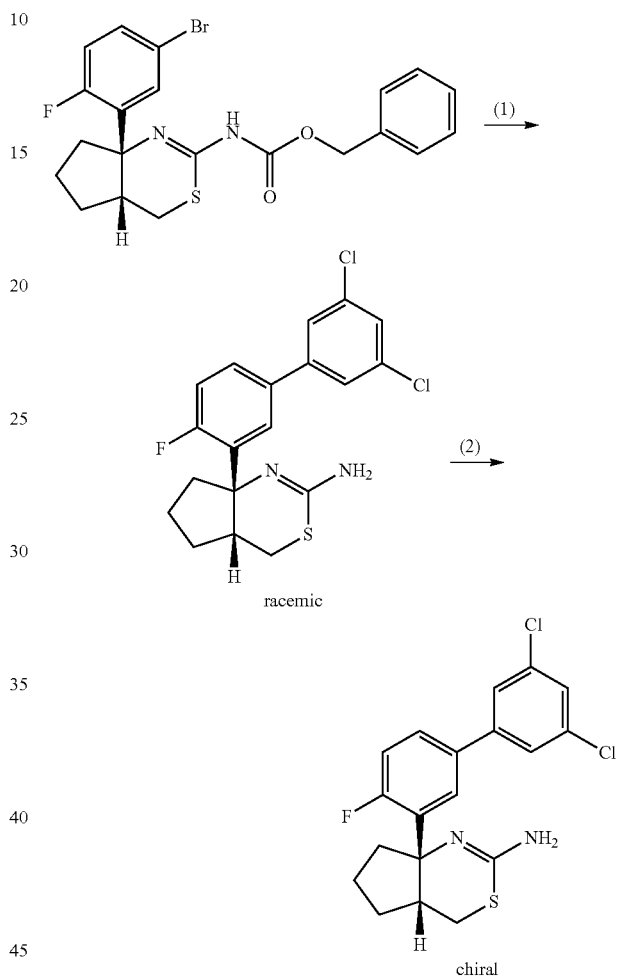

(1) Synthesis of (±)-(4aR*,7aS*)-7a-(3',5'-dichloro-4-fluorobiphenyl-3-yl)-4,4a,5,6,7,7a-hexahydro-cyclopenta[d][1,3]thiazin-2-ylamine 1 M aqueous sodium bicarbonate (486 μL), 3,5-dichlorophenylboronic acid (80.4 mg) and tetrakis(triphenylphosphine)palladium (0) (18.8 mg) were added to a solution of the compound obtained in Example 160-(1) (120 mg) in DMF (3 mL), and the mixture was stirred at 110° C. for eight hours. The reaction solution was returned to room temperature. Saturated aqueous sodium chloride and ethyl acetate were added to the reaction solution. The organic layer was separated and dried over anhydrous magnesium sulfate. The organic layer was concentrated under reduced pressure. The residue was purified by silica gel column chromatography to obtain a crude purified product containing the title compound (69 mg).

ESI-MS; m/z 395 [M$^+$+H].

(2) Synthesis of (+)-(4aR*,7aS*)-7a-(3',5'-dichloro-4-fluorobiphenyl-3-yl)-4,4a,5,6,7,7a-hexahydro-cyclopenta[d][1,3]thiazin-2-ylamine The compound obtained in Example 162-(1) (69 g) was washed with a mixed solvent of ethyl acetate (0.5 mL) and heptane (3 mL). The resulting solid was diluted with 8 mL of ethanol, and the compound was optically resolved by CHIRALPAK™ IA manufactured by Daicel Chemical Industries, Ltd. (2 cm×25 cm, mobile phase: hexane:ethanol=7:3, flow rate: 5 mL/min). The component having a retention time of 24 to 28 minutes was collected to obtain the title compound (11 mg).

ESI-MS; m/z 395 [M$^+$+H].

Example 163

Synthesis of (+)-(4aR*,7aS*)-7a-[2-fluoro-5-(5-methoxypyridin-3-yl)phenyl]-4,4a,5,6,7,7a-hexahydrocyclopenta[d][1,3]thiazin-2-ylamine

[Formula 208]

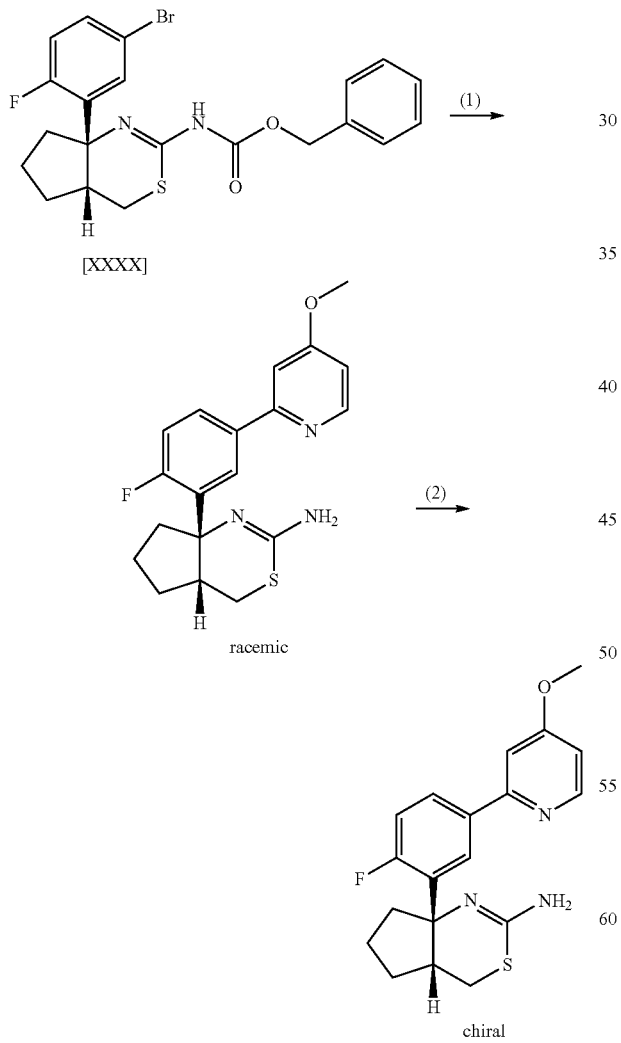

[XXXX]

(1) Synthesis of (±)-(4aR*,7aS*)-7a-[2-fluoro-5-(5-methoxypyridin-3-yl)phenyl]-4,4a,5,6,7,7a-hexahydrocyclopenta[d][1,3]thiazin-2-ylamine A crude purified product containing the title compound (150 mg) was obtained from the compound obtained in Example 160-(1) (200 mg) according to Example 162 using the corresponding boronic acid.

ESI-MS; m/z 358 [M$^+$+H].

(2) Synthesis of (+)-(4aR*,7aS*)-7a-[2-fluoro-5-(5-methoxypyridin-3-yl)phenyl]-4,4a,5,6,7,7a-hexahydrocyclopenta[d][1,3]thiazin-2-ylamine The compound obtained in Example 163-(1) (150 mg) was purified by silica gel chromatography again, and the resulting solid was diluted with 12 mL of ethanol. The compound was optically resolved by CHIRALPAK™ IA manufactured by Daicel Chemical Industries, Ltd. (2 cm×25 cm, mobile phase: hexane:ethanol=1:1, flow rate: 5 mL/min). The component having a retention time of 27 to 30 minutes was collected to obtain the title compound (18 mg). ESI-MS; m/z 358 [M$^+$+H].

The compounds of Examples 164 to 167 below were synthesized according to Example 14 using the corresponding carboxylic acids and the corresponding aniline intermediates in Preparation Examples below.

Example 164

Synthesis of N-[3-((4aS,5S,7aS)-2-amino-5-fluoromethyl-4a,5-dihydro-4H-furo[3,4-d][1,3]thiazin-7a-yl)-4-fluorophenyl]-5-cyanopyridine-2-carboxamide

[Formula 209]

$^1$H-NMR (400 MHz, CDCl$_3$) δ (ppm): 2.80 (dd, J=4.0, 13.2 Hz, 1H), 3.05-3.10 (m, 1H), 3.15 (dd, J=3.6, 13.2 Hz, 1H), 3.87 (dd, J=2.8, 8.8 Hz, 1H), 4.51-4.66 (m, 4H), 7.11 (dd, J=8.8, 12.0H, 1H), 7.58 (dd, J=2.8, 7.2 Hz, 1H), 7.93-7.97 (m, 1H), 8.21 (dd, J=2.4, 8.4 Hz, 1H), 8.42 (dd, J=0.8, 8.0 Hz, 1H), 8.90 (dd, J=0.8, 2.0 Hz, 1H), 9.86 (s, 1H).

ESI-MS m/z 430 [M$^+$+H]

Example 165

Synthesis of N-[3-((4aS*,7aS*)-2-amino-4a,5-dihydro-4H-furo[3,4-d][1,3]thiazin-7a-yl)-4-fluorophenyl]-5-trifluoromethylpyridine-2-carboxamide

[Formula 210]

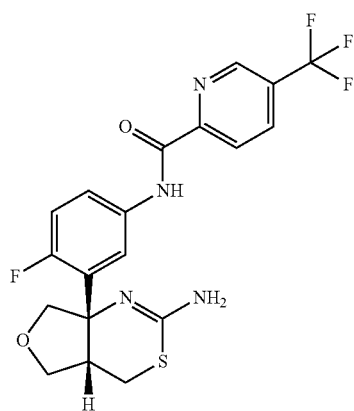 [SMILES: NC1=N[C@@]2(c3cc(NC(=O)c4ccc(C(F)(F)F)cn4)ccc3F)COC[C@H]2CS1]

$^1$H-NMR (400 MHz, CDCl$_3$) δ (ppm): 2.84 (dd, J=5.6, 14.0 Hz, 1H), 3.08-3.13 (m, 2H), 3.83 (dd, J=2.0, 8.4 Hz, 1H), 4.08-4.15 (m, 2H), 4.47 (dd, J=1.2, 8.4 Hz, 1H), 7.10 (dd, J=8.8, 12.0 Hz, 1H), 7.65 (dd, J=2.8, 6.8 Hz, 1H), 7.93-7.97 (m, 1H), 8.17 (dd, J=2.4, 8.0 Hz, 1H), 8.43 (d, J=8.0 Hz, 1H), 8.90 (s, 1H), 9.94 (s, 1H).
ESI-MS m/z 441 [M$^+$+H]

Example 166

Synthesis of N-[3-((4aS*,7aS*)-2-amino-4a,5-dihydro-4H-furo[3,4-d][1,3]thiazin-7a-yl)-4-fluorophenyl]-5-bromopyridine-2-carboxamide

[Formula 211]

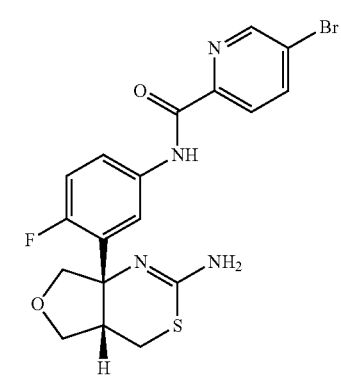

$^1$H-NMR (400 MHz, CDCl$_3$) δ (ppm): 2.84 (dd, J=6.0, 14.0 Hz, 1H), 3.08-3.13 (m, 2H), 3.84 (dd, J=2.0, 8.8 Hz, 1H), 4.08-4.15 (m, 2H), 4.46 (dd, J=1.2, 8.4 Hz, 1H), 7.09 (dd, J=8.8, 11.6 Hz, 1H), 7.59 (dd, J=2.8, 6.8 Hz, 1H), 7.93-7.97 (m, 1H), 8.04 (dd, J=2.4, 8.0 Hz, 1H), 8.18 (d, J=8.4 Hz, 1H), 8.67 (d, J=1.6 Hz, 1H), 9.83 (s, 1H).
ESI-MS m/z 451[M$^+$+H]

Example 167

Synthesis of N-[3-((4aS*,7aS*)-2-amino-4a,5-dihydro-4H-furo[3,4-d][1,3]thiazin-7a-yl)-4-fluorophenyl]-5-difluoromethoxypyridine-2-carboxamide

[Formula 212]

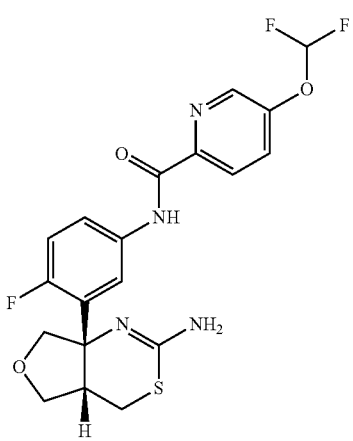 [SMILES: NC1=N[C@@]2(c3cc(NC(=O)c4ccc(OC(F)F)cn4)ccc3F)COC[C@H]2CS1]

$^1$H-NMR (400 MHz, CDCl$_3$) δ (ppm): 2.84 (dd, J=6.4, 14.0 Hz, 1H), 3.07-3.12 (m, 2H), 3.83 (dd, J=2.0, 8.8 Hz, 1H), 4.08-4.18 (m, 2H), 4.46 (dd, J=1.2, 8.4 Hz, 1H), 6.65 (t, J=72.0 Hz, 1H), 7.09 (dd, J=8.8, 12.0 Hz, 1H), 7.59 (dd, J=2.8, 7.2 Hz, 1H), 7.67 (dd, J=2.8, 8.8 Hz, 1H), 7.94-7.98 (m, 1H), 8.32 (d, J=8.8 Hz, 1H), 8.47 (d, J=2.4 Hz, 1H), 9.83 (s, 1H).
ESI-MS m/z 439 [M$^+$+H]

Examples 168 to 191

The compounds of Examples 168 to 191 as shown in Table 13 below were synthesized according to Example 14 using the corresponding carboxylic acids and the corresponding aniline intermediates in Preparation Examples.

[Table 13]

Table 13

| Example | | Compound name: |
|---|---|---|
| 168 | 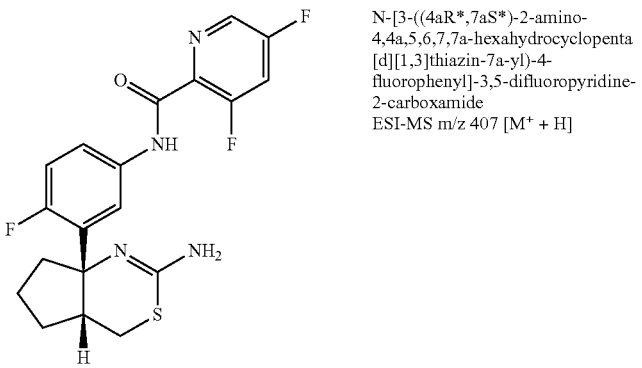 | N-[3-((4aR*,7aS*)-2-amino-4,4a,5,6,7,7a-hexahydrocyclopenta[d][1,3]thiazin-7a-yl)-4-fluorophenyl]-3,5-difluoropyridine-2-carboxamide<br>ESI-MS m/z 407 [M$^+$ + H] |
| 169 | 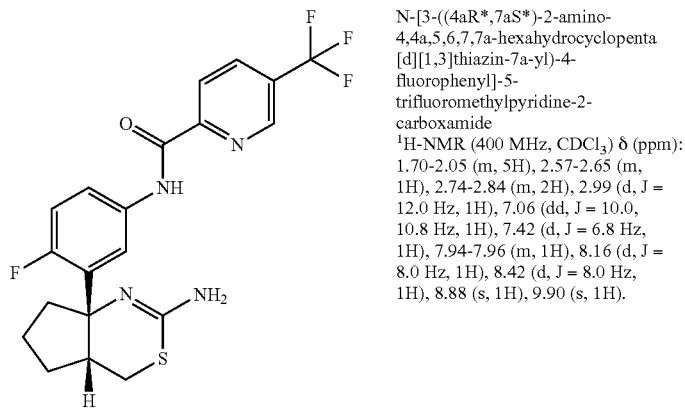 | N-[3-((4aR*,7aS*)-2-amino-4,4a,5,6,7,7a-hexahydrocyclopenta[d][1,3]thiazin-7a-yl)-4-fluorophenyl]-5-trifluoromethylpyridine-2-carboxamide<br>$^1$H-NMR (400 MHz, CDCl$_3$) δ (ppm): 1.70-2.05 (m, 5H), 2.57-2.65 (m, 1H), 2.74-2.84 (m, 2H), 2.99 (d, J = 12.0 Hz, 1H), 7.06 (dd, J = 10.0, 10.8 Hz, 1H), 7.42 (d, J = 6.8 Hz, 1H), 7.94-7.96 (m, 1H), 8.16 (d, J = 8.0 Hz, 1H), 8.42 (d, J = 8.0 Hz, 1H), 8.88 (s, 1H), 9.90 (s, 1H). |
| 170 | 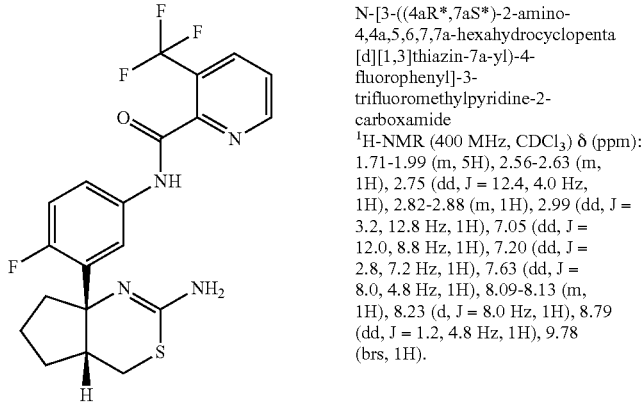 | N-[3-((4aR*,7aS*)-2-amino-4,4a,5,6,7,7a-hexahydrocyclopenta[d][1,3]thiazin-7a-yl)-4-fluorophenyl]-3-trifluoromethylpyridine-2-carboxamide<br>$^1$H-NMR (400 MHz, CDCl$_3$) δ (ppm): 1.71-1.99 (m, 5H), 2.56-2.63 (m, 1H), 2.75 (dd, J = 12.4, 4.0 Hz, 1H), 2.82-2.88 (m, 1H), 2.99 (dd, J = 3.2, 12.8 Hz, 1H), 7.05 (dd, J = 12.0, 8.8 Hz, 1H), 7.20 (dd, J = 2.8, 7.2 Hz, 1H), 7.63 (dd, J = 8.0, 4.8 Hz, 1H), 8.09-8.13 (m, 1H), 8.23 (d, J = 8.0 Hz, 1H), 8.79 (dd, J = 1.2, 4.8 Hz, 1H), 9.78 (brs, 1H). |
| 171 | 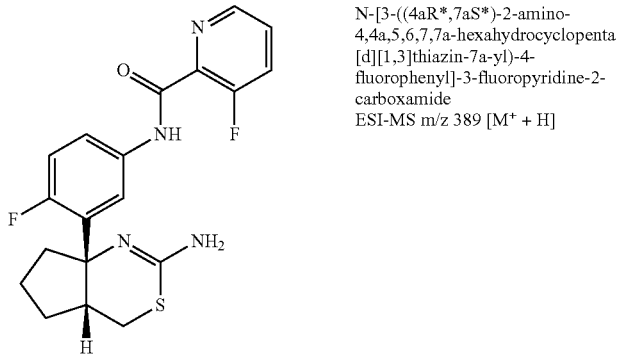 | N-[3-((4aR*,7aS*)-2-amino-4,4a,5,6,7,7a-hexahydrocyclopenta[d][1,3]thiazin-7a-yl)-4-fluorophenyl]-3-fluoropyridine-2-carboxamide<br>ESI-MS m/z 389 [M$^+$ + H] |

| Example | | Compound name: |
|---|---|---|
| 172 | 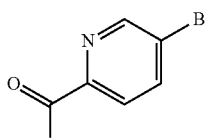 | N-[3-((4aR*,7aS*)-2-amino-4a,5,6,7,7a-hexahydrocyclopenta[d][1,3]thiazin-7a-yl)-4-fluorophenyl]-5-bromopyridine-2-carboxamide<br>ESI-MS m/z 449 [M+ + H] |
| 173 | 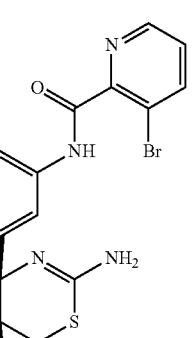 | N-[3-((4aR*,7aS*)-2-amino-4a,5,6,7,7a-hexahydrocyclopenta[d][1,3]thiazin-7a-yl)-4-fluorophenyl]-3-bromopyridine-2-carboxamide<br>ESI-MS m/z 449 [M+ + H] |
| 174 | 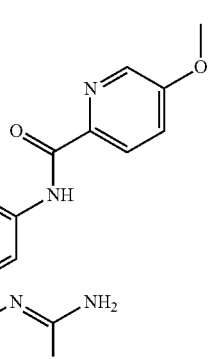 | N-[3-((4aR*,7aS*)-2-amino-4a,5,6,7,7a-hexahydrocyclopenta[d][1,3]thiazin-7a-yl)-4-fluorophenyl]-5-methoxypyridine-2-carboxamide<br>ESI-MS m/z 401 [M+ + H] |
| 175 | 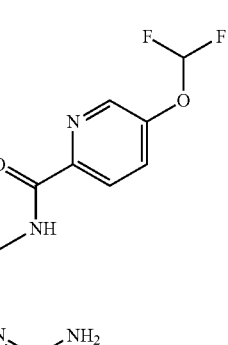 | N-[3-((4aR*,7aS*)-2-amino-4a,5,6,7,7a-hexahydrocyclopenta[d][1,3]thiazin-7a-yl)-4-fluorophenyl]-5-difluoromethoxypyridine-2-carboxamide<br>ESI-MS m/z 437 [M+ + H] |

-continued

| Example | | Compound name: |
|---|---|---|
| 176 | 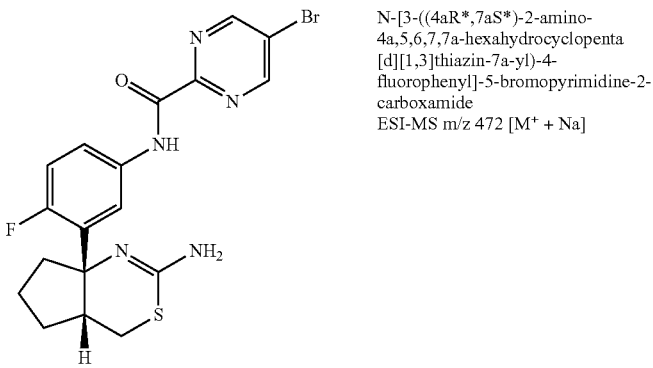 | N-[3-((4aR*,7aS*)-2-amino-4a,5,6,7,7a-hexahydrocyclopenta[d][1,3]thiazin-7a-yl)-4-fluorophenyl]-5-bromopyrimidine-2-carboxamide<br>ESI-MS m/z 472 [M+ + Na] |
| 177 | 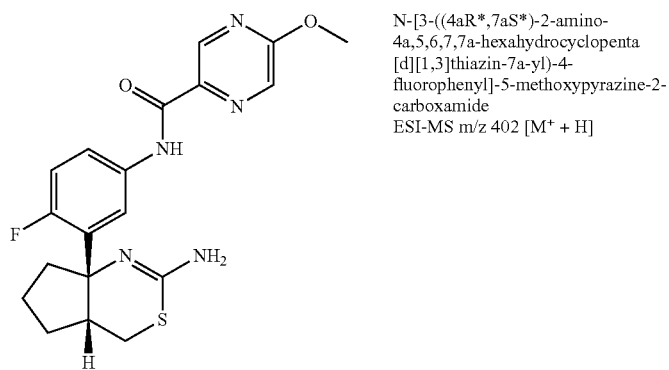 | N-[3-((4aR*,7aS*)-2-amino-4a,5,6,7,7a-hexahydrocyclopenta[d][1,3]thiazin-7a-yl)-4-fluorophenyl]-5-methoxypyrazine-2-carboxamide<br>ESI-MS m/z 402 [M+ + H] |
| 178 | 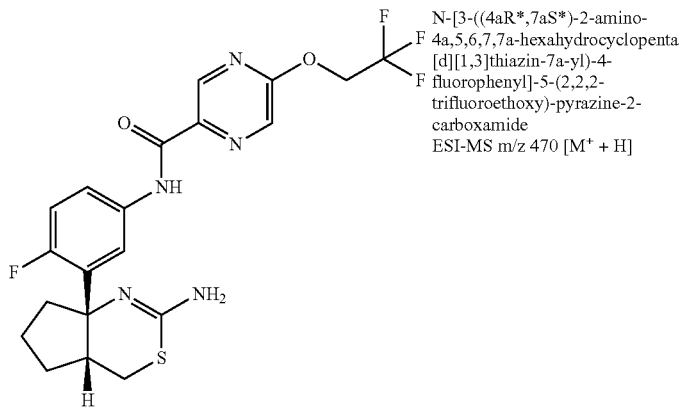 | N-[3-((4aR*,7aS*)-2-amino-4a,5,6,7,7a-hexahydrocyclopenta[d][1,3]thiazin-7a-yl)-4-fluorophenyl]-5-(2,2,2-trifluoroethoxy)-pyrazine-2-carboxamide<br>ESI-MS m/z 470 [M+ + H] |
| 179 | 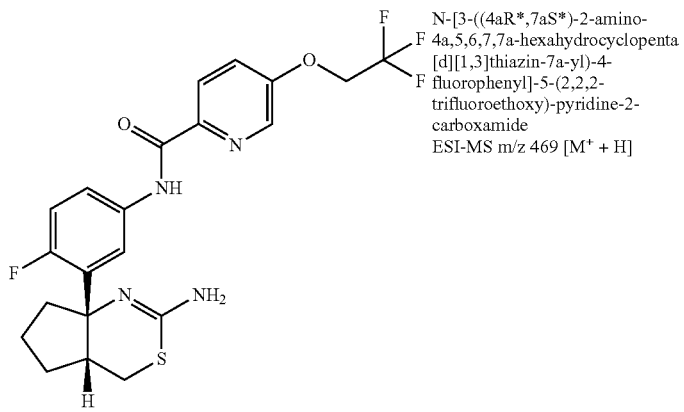 | N-[3-((4aR*,7aS*)-2-amino-4a,5,6,7,7a-hexahydrocyclopenta[d][1,3]thiazin-7a-yl)-4-fluorophenyl]-5-(2,2,2-trifluoroethoxy)-pyridine-2-carboxamide<br>ESI-MS m/z 469 [M+ + H] |

| Example | | Compound name: |
|---|---|---|
| 180 | 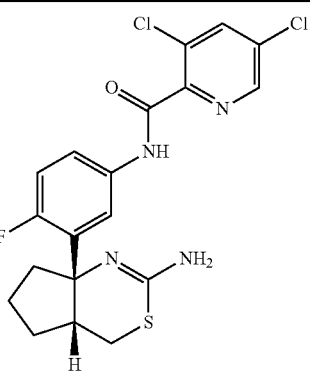 | N-[3-((4aR*,7aS*)-2-amino-4a,5,6,7,7a-hexahydrocyclopenta[d][1,3]thiazin-7a-yl)-4-fluorophenyl]-3,5-dichloropyridine-2-carboxamide<br>ESI-MS m/z 439 [M$^+$ + H] |
| 181 | 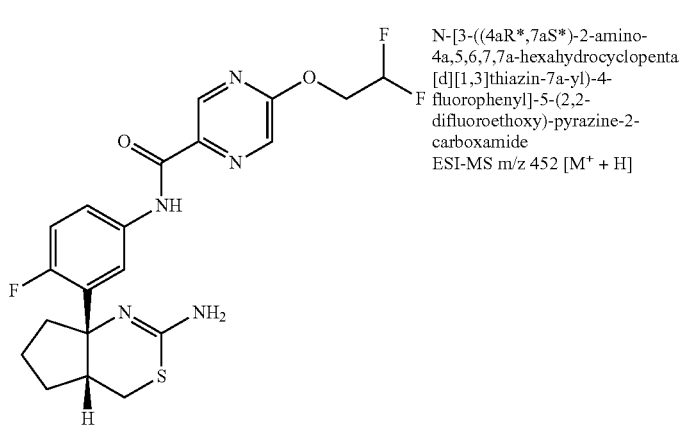 | N-[3-((4aR*,7aS*)-2-amino-4a,5,6,7,7a-hexahydrocyclopenta[d][1,3]thiazin-7a-yl)-4-fluorophenyl]-5-(2,2-difluoroethoxy)-pyrazine-2-carboxamide<br>ESI-MS m/z 452 [M$^+$ + H] |
| 182 | 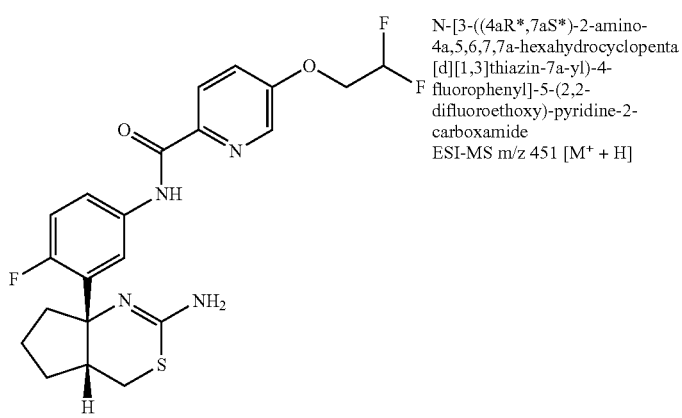 | N-[3-((4aR*,7aS*)-2-amino-4a,5,6,7,7a-hexahydrocyclopenta[d][1,3]thiazin-7a-yl)-4-fluorophenyl]-5-(2,2-difluoroethoxy)-pyridine-2-carboxamide<br>ESI-MS m/z 451 [M$^+$ + H] |
| 183 | 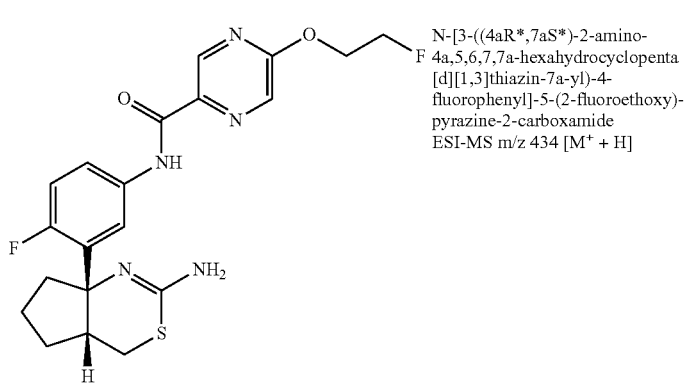 | N-[3-((4aR*,7aS*)-2-amino-4a,5,6,7,7a-hexahydrocyclopenta[d][1,3]thiazin-7a-yl)-4-fluorophenyl]-5-(2-fluoroethoxy)-pyrazine-2-carboxamide<br>ESI-MS m/z 434 [M$^+$ + H] |

-continued

| Example | | Compound name: |
|---|---|---|
| 184 | 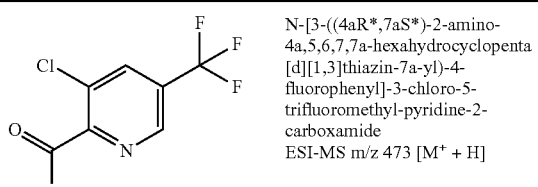 | N-[3-((4aR*,7aS*)-2-amino-4a,5,6,7,7a-hexahydrocyclopenta[d][1,3]thiazin-7a-yl)-4-fluorophenyl]-3-chloro-5-trifluoromethyl-pyridine-2-carboxamide<br>ESI-MS m/z 473 [M$^+$ + H] |
| 185 | 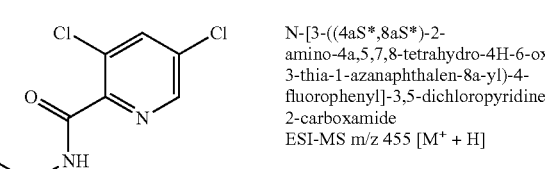 | N-[3-((4aS*,8aS*)-2-amino-4a,5,7,8-tetrahydro-4H-6-oxa-3-thia-1-azanaphthalen-8a-yl)-4-fluorophenyl]-3,5-dichloropyridine-2-carboxamide<br>ESI-MS m/z 455 [M$^+$ + H] |
| 186 | 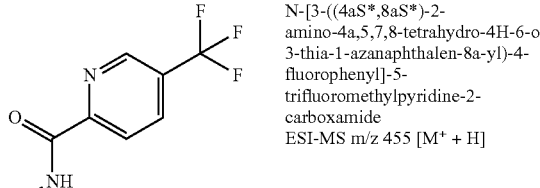 | N-[3-((4aS*,8aS*)-2-amino-4a,5,7,8-tetrahydro-4H-6-oxa-3-thia-1-azanaphthalen-8a-yl)-4-fluorophenyl]-5-trifluoromethylpyridine-2-carboxamide<br>ESI-MS m/z 455 [M$^+$ + H] |
| 187 | 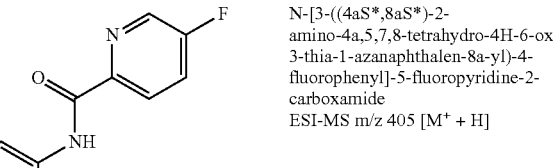 | N-[3-((4aS*,8aS*)-2-amino-4a,5,7,8-tetrahydro-4H-6-oxa-3-thia-1-azanaphthalen-8a-yl)-4-fluorophenyl]-5-fluoropyridine-2-carboxamide<br>ESI-MS m/z 405 [M$^+$ + H] |

-continued

| Example | | Compound name: |
|---|---|---|
| 188 | 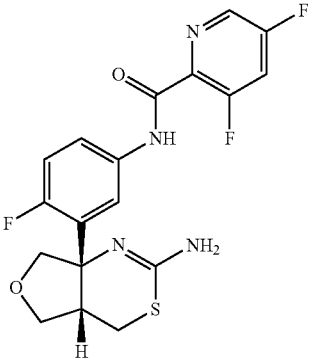 [SMILES: NC1=N[C@@]2(c3cc(NC(=O)c4ncc(F)cc4F)ccc3F)COC[C@H]2CS1] | N-[3-((4aS*,7aS*)-2-amino-4a,5-dihydro-4H-furo[3,4-d][1,3]thiazin-7a-yl)-4-fluorophenyl]-3,5-difluoropyridine-2-carboxamide<br>ESI-MS m/z 409 [M+ + H] |
| 189 | 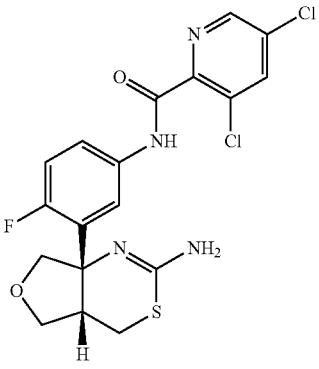 [SMILES: NC1=N[C@@]2(c3cc(NC(=O)c4ncc(Cl)cc4Cl)ccc3F)COC[C@H]2CS1] | N-[3-((4aS*,7aS*)-2-amino-4a,5-dihydro-4H-furo[3,4-d][1,3]thiazin-7a-yl)-4-fluorophenyl]-3,5-dichloropyridine-2-carboxamide<br>ESI-MS m/z 441 [M+ + H] |
| 190 | 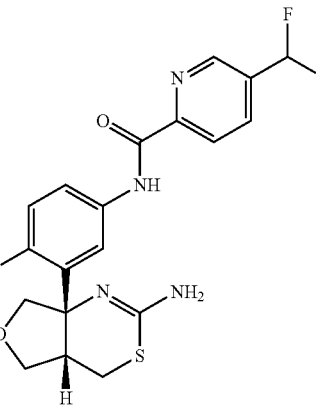 | N-[3-((4aS*,7aS*)-2-amino-4a,5-dihydro-4H-furo[3,4-d][1,3]thiazin-7a-yl)-4-fluorophenyl]-5-difluoromethylpyridine-2-carboxamide<br>ESI-MS m/z 423 [M+ + H] |
| 191 | 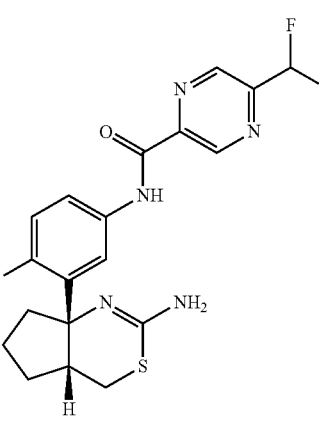 | N-[3-((4aR*,7aS*)-2-amino-4a,5,6,7,7a-hexahydrocyclopenta[d][1,3]thiazin-7a-yl)-4-fluorophenyl]-5-difluoromethylpyrazine-2-carboxamide<br>ESI-MS m/z 422 [M+ + H] |

Examples 192 to 200

The compounds of Examples 192 to 200 as shown in Table 14 below were synthesized according to Example 14 using the corresponding carboxylic acids and the corresponding aniline intermediates in Preparation Examples.

[Table 14]

TABLE 14

| Example | | |
|---|---|---|
| 192 | 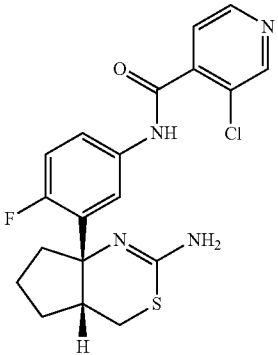 [SMILES: NC1=N[C@@]2(c3cc(NC(=O)c4ccncc4Cl)ccc3F)CCC[C@H]2CS1] | ESI-MS m/z 405 [M+ + H] |
| 193 | 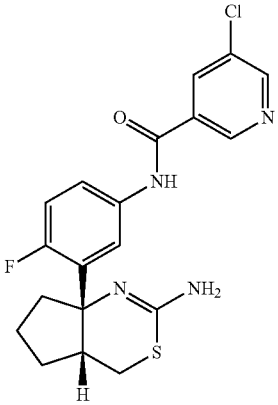 [SMILES: NC1=N[C@@]2(c3cc(NC(=O)c4cncc(Cl)c4)ccc3F)CCC[C@H]2CS1] | ESI-MS m/z 405 [M+ + H] |
| 194 | 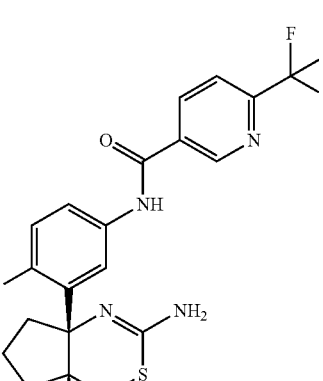 | ESI-MS m/z 439 [M+ + H] |

TABLE 14-continued

| Example | | |
|---|---|---|
| 195 | 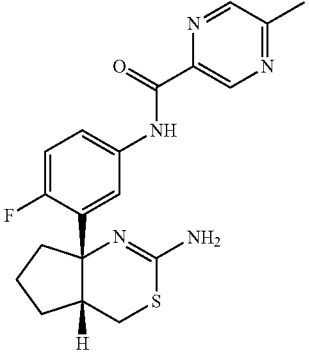 [SMILES: Cc1cnc(C(=O)Nc2ccc(F)c([C@]34CCC[C@H]3CSC(N)=N4)c2)cn1] | ESI-MS m/z 386 [M+ + H] |
| 196 | 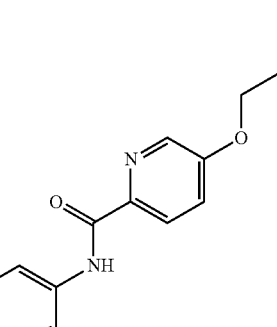 | ESI-MS m/z 477 [M+ + H] |
| 197 | 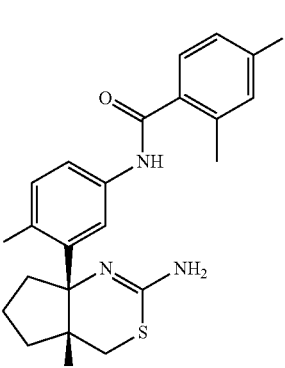 | ESI-MS m/z 418 [M+ + H] |
| 198 | 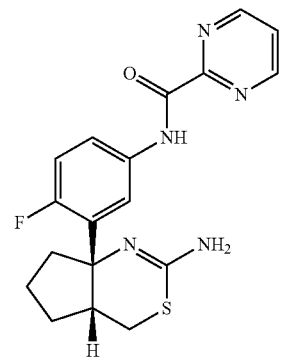 [SMILES: NC1=N[C@@]2(c3cc(NC(=O)c4ncccn4)ccc3F)CCC[C@H]2CS1] | ESI-MS m/z 372 [M+ + H] |

TABLE 14-continued

| Example | | |
|---|---|---|
| 199 | 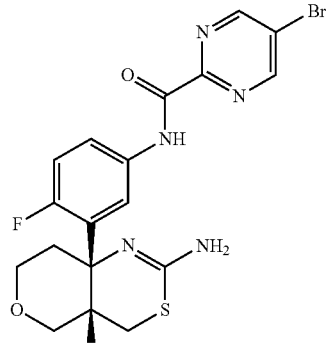 | ESI-MS m/z 468 [M⁺ + H] |
| 200 | 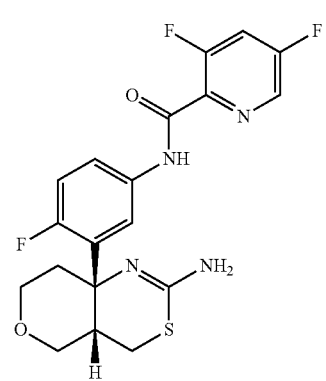 [SMILES: NC1=N[C@@]2(c3cc(NC(=O)c4ncc(F)cc4F)ccc3F)CCOC[C@H]2CS1] | ESI-MS m/z 423 [M⁺ + H] |

Example 201

Synthesis of N-[3-((4aR*,7S*,8aS*)-2-amino-7-methoxy-4a,5,6,7,8,8a-hexahydro-4H-benzo[d][1,3]thiazin-8a-yl)-4-fluorophenyl]-5-cyanopyridine-2-carboxamide

[Formula 213]

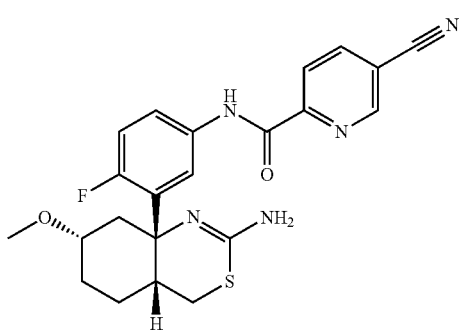 [SMILES: CO[C@H]1CC[C@H]2CSC(N)=N[C@@]2(c2cc(NC(=O)c3ccc(C#N)cn3)ccc2F)C1]

tert-Butyl (−)-[(4aR*,7S*,8aS*)-8a-(5-amino-2-fluorophenyl)-7-methoxy-4a,5,6,7,8,8a-hydro-4H-benzo[d][1,3]thiazin-2-yl]carbamate obtained in Preparation Example 57-(11) (41 mg) was mixed with 5-fluoromethoxypyrazine-2-carboxylic acid (18 mg), N,N-diisopropylethylamine (87 μL, specific gravity: 0.742 g/cm³) and PyBOP (104 mg) in dichloromethane (2 mL), and the mixture was stirred under a nitrogen atmosphere at room temperature. After stirring for five hours, the reaction solution was directly purified by silica gel column chromatography. Chloroform (0.5 mL) and TFA (0.5 mL) were added to the resulting amide compound, and the mixture was stirred at room temperature for two hours and 30 minutes. The reaction solution was slowly poured into a saturated sodium bicarbonate solution, followed by extraction with chloroform three times. The resulting organic layers were dried over anhydrous magnesium sulfate, and the solid was removed by filtration. The filtrate was concentrated under reduced pressure and then purified by NH-silica gel column chromatography to obtain the title compound (34 mg). ESI-MS; m/z 440 [M⁺+H].

¹H-NMR (400 MHz, CDCl₃) δ (ppm): 1.40-1.43 (m, 1H), 1.69-1.75 (m, 1H), 2.08-2.28 (m, 3H), 2.32-2.35 (m, 1H), 2.61-2.64 (m, 1H), 2.76-2.79 (m, 1H), 2.88-2.91 (m, 1H), 3.36 (s, 3H), 3.63 (br, 1H), 7.05-7.10 (m, 1H), 7.37-7.38 (m, 1H), 8.04-8.07 (m, 1H), 8.19-8.20 (m, 1H), 8.41-8.43 (m, 1H), 8.90 (s, 1H), 9.84 (s, 1H).

Example 202

Synthesis of N-[3-((4aR*,7R*,8aS*)-2-amino-7-methoxy-4a,5,6,7,8,8a-hexahydro-4H-benzo[d][1,3]thiazin-8a-yl)-4-fluorophenyl]-5-cyanopyridine-2-carboxamide

[Formula 214]

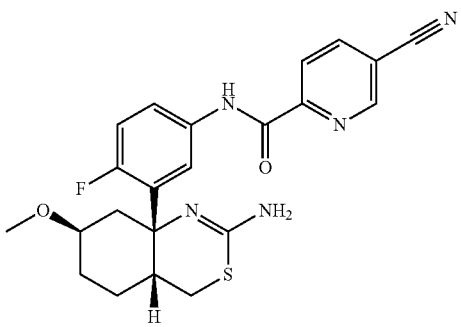 [SMILES: CO[C@@H]1CC[C@H]2CSC(N)=N[C@@]2(c2cc(NC(=O)c3ccc(C#N)cn3)ccc2F)C1]

The title compound (39 mg) was obtained from tert-butyl (−)-[(4aR*,7R*,8aS*)-8a-(5-amino-2-fluorophenyl)-7-methoxy-4a,5,6,7,8,8a-hexahydro-4H-benzo[d][1,3]thiazin-2-yl]carbamate obtained in Preparation Example 58-(13) (50 mg) according to the method of Example 201.

ESI-MS; m/z 440 [M⁺+H].

¹H-NMR (400 MHz, CDCl₃) δ (ppm): 1.42-1.53 (m, 1H), 1.61-1.65 (m, 1H), 1.77-1.89 (m, 1H), 2.09-2.24 (m, 3H), 2.61-2.64 (m, 1H), 2.71-2.74 (m, 1H), 2.92 (dd, J=4.0, 12.0 Hz, 1H), 3.36 (s, 3H), 3.39-3.45 (m, 1H), 7.08 (dd, J=8.8, 12.0 Hz, 1H), 7.32-7.34 (m, 1H), 7.92-7.95 (m, 1H), 8.18-8.21 (m, 1H), 8.42 (dd, J=0.8, 8.4 Hz, 1H), 8.88-8.89 (m, 1H), 9.80 (s, 1H).

Example 203

The compound of Example 203 as shown in Table 15 below was synthesized according to Example 202 using the corresponding carboxylic acid.

Table 15

| Example | Chemical structure | Compound name: |
|---|---|---|
| 203 | 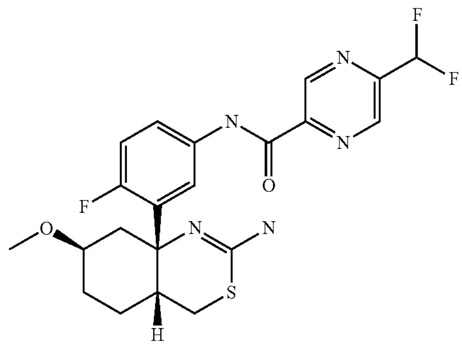 [SMILES: CO[C@@H]1CC[C@H]2CSC(N)=N[C@@]2(c2cc(NC(=O)c3cnc(C(F)F)cn3)ccc2F)C1] | N-[3-((4aR*,7R*,8aS*)-2-amino-7-methoxy-4a,5,6,7,8,8a-hexahydro-4H-benzo[d][1,3]thiazin-8a-yl)-4-fluorophenyl]-5-difluoromethylpyrazine-2-carboxamide ESI-MS; m/z 466 [M+ + H]. |

Example 204

Synthesis of N-[3-((4aR*,6S*,8aS*)-2-amino-6-methoxy-4a,5,6,7,8,8a-hexahydro-4H-benzo[d][1,3]thiazin-8a-yl)-4-fluorophenyl]-5-cyanopyridine-2-carboxamide

[Formula 215]

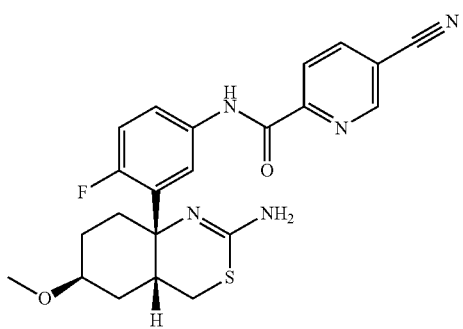 [SMILES: CO[C@H]1CC[C@]2(c3cc(NC(=O)c4ccc(C#N)cn4)ccc3F)N=C(N)SC[C@@H]2C1]

The title compound (37 mg) was obtained from tert-butyl (−)-[(4aR*,6S*,8aS*)-8a-(5-amino-2-fluorophenyl)-6-methoxy-4a,5,6,7,8,8a-hexahydro-4H-benzo[d][1,3]thiazin-2-yl]carbamate obtained in Preparation Example 60-(4) (50 mg) according to the method of Example 201.

ESI-MS; m/z 440 [M++H].

$^1$H-NMR (400 MHz, CDCl$_3$) δ (ppm): 1.52-1.57 (m, 1H), 1.66-1.76 (m, 1H), 1.82-1.92 (m, 3H), 2.52-2.62 (m, 2H), 2.95-2.99 (m, 1H), 3.10-3.15 (m, 1H), 3.39 (s, 3H), 3.60-3.62 (m, 1H), 7.07 (dd, J=8.8, 11.6 Hz, 1H), 7.34 (dd, J=2.8, 7.2 Hz, 1H), 7.93 (ddd, J=2.8, 4.0, 8.8 Hz, 1H), 8.18-8.21 (m, 1H), 8.42 (dd, J=0.8, 4.4 Hz, 1H), 8.89 (dd, J=0.8, 2.0 Hz, 1H), 9.79 (s, 1H).

The compound of Example 205 as shown in Table 16 below was synthesized according to Example 204 using the corresponding carboxylic acid.

TABLE 16

| Example | Chemical structure | |
|---|---|---|
| 205 | 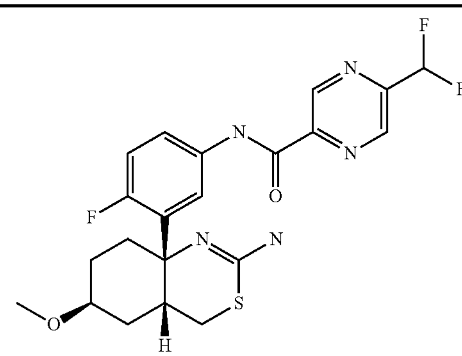 | ESI-MS; m/z 466 [M+ + H]. |

Example 206

Synthesis of N-[3-((4aR*,6R*,8aS*)-2-amino-6-methoxy-4a,5,6,7,8,8a-hexahydro-4H-benzo[d][1,3]thiazin-8a-yl)-4-fluorophenyl]-5-cyanopyridine-2-carboxamide

[Formula 216]

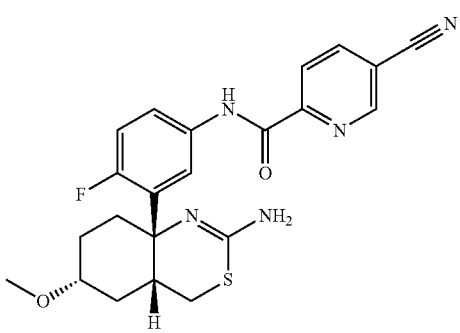 [SMILES: CO[C@@H]1CC[C@]2(c3cc(NC(=O)c4ccc(C#N)cn4)ccc3F)N=C(N)SC[C@@H]2C1]

The title compound (33 mg) was obtained from tert-butyl (−)-[(4aR*,6R*,8aS*)-8a-(5-amino-2-fluorophenyl)-6-methoxy-4a,5,6,7,8,8a-hexahydro-4H-benzo[d][1,3]thiazin-2-yl]carbamate obtained in Preparation Example 61-(4) (50 mg) according to the method of Example 201.

ESI-MS; m/z 440 [M$^+$+H].

$^1$H-NMR (400 MHz, CDCl$_3$) δ (ppm): 1.60-1.74 (m, 2H), 1.82-1.91 (m, 2H), 1.97-2.00 (m, 1H), 2.23-2.30 (m, 1H), 2.58-2.61 (m, 1H), 2.77-2.80 (m, 1H), 2.92-2.95 (m, 1H), 3.41 (s, 3H), 3.41-3.49 (m, 1H), 7.05-7.10 (m, 1H), 7.30-7.32 (m, 1H), 7.97-8.00 (m, 1H), 8.19 (d, J=8.4 Hz, 1H), 8.42 (d, J=8.0 Hz, 1H), 8.90 (s, 1H), 9.80 (s, 1H).

Examples 207 to 211

The compounds of Examples 207 to 211 as shown in Table 17 below were synthesized according to Example 206 using the corresponding carboxylic acids.

[Table 17]

Table 17

| Example | Chemical structure | Compound name: |
|---|---|---|
| 207 | 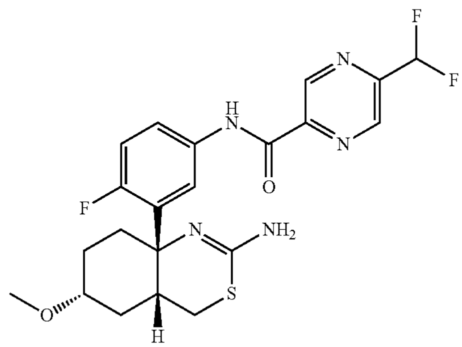 [SMILES: CO[C@@H]1CC[C@]2(c3cc(NC(=O)c4cnc(C(F)F)cn4)ccc3F)N=C(N)SC[C@@H]2C1] | N-[3-((4aR*,6R*,8aS*)-2-amino-6-methoxy-4a,5,6,7,8,8a-hexahydro-4H-benzo[d][1,3]thiazin-8a-yl)-4-fluorophenyl]-5-difluoromethylpyrazine-2-carboxamide ESI-MS; m/z 466 [M$^+$ + H]. |
| 208 | 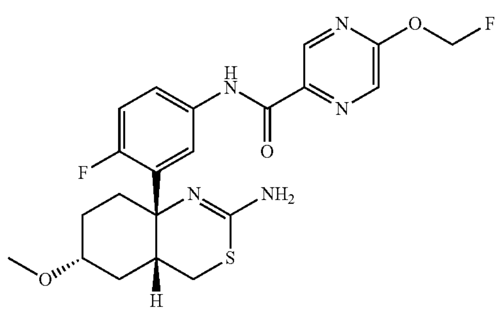 [SMILES: CO[C@@H]1CC[C@]2(c3cc(NC(=O)c4cnc(OCF)cn4)ccc3F)N=C(N)SC[C@@H]2C1] | N-[3-((4aR*,6R*,8aS*)-2-amino-6-methoxy-4a,5,6,7,8,8a-hexahydro-4H-benzo[d][1,3]thiazin-8a-yl)-4-fluorophenyl]-5-fluoromethoxypyrazine-2-carboxamide $^1$H-NMR (400 MHz, CDCl$_3$): δ (ppm): 1.53-1.61 (m, 1H), 1.65-1.75 (m, 1H), 1.81-1.91 (m, 2H), 1.97-1.99 (m, 1H), 2.27 (dt, J = 2.4, 13.6 Hz, 1H), 2.59 (dd, J = 2.8, 12.4 Hz, 1H), 2.76-2.80 (m, 1H), 2.95 (dd, J = 4.0, 12.4 Hz, 1H), 3.41-3.52 (m, 4H), 6.16 (qd, J = 2.0, 51.2 Hz, 2H), 7.06 (dd, J = 8.8, 12.0 Hz, 1H), 7.23-7.25 (m, 1H), 8.00 (ddd, J = 2.8, 4.0, 8.8 Hz, 1H), 8.29 (d, J = 1.6 Hz, 1H), 9.07 (d, J = 1.6 Hz, 1H), 9.44 (br, 1H). ESI-MS; m/z 464 [M$^+$ + H]. |
| 209 | 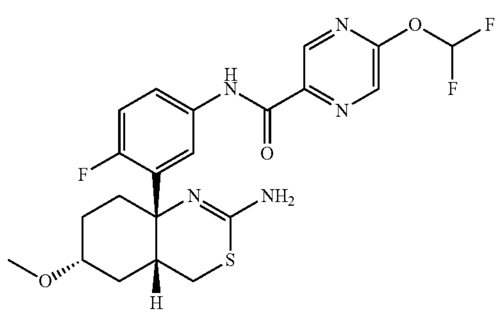 [SMILES: CO[C@@H]1CC[C@]2(c3cc(NC(=O)c4cnc(OC(F)F)cn4)ccc3F)N=C(N)SC[C@@H]2C1] | N-[3-((4aR*,6R*,8aS*)-2-amino-6-methoxy-4a,5,6,7,8,8a-hexahydro-4H-benzo[d][1,3]thiazin-8a-yl)-4-fluorophenyl]-5-difluoromethoxypyrazine-2-carboxamide ESI-MS; m/z 482 [M$^+$ + H]. |

-continued

| Example | Chemical structure | Compound name: |
|---|---|---|
| 210 | 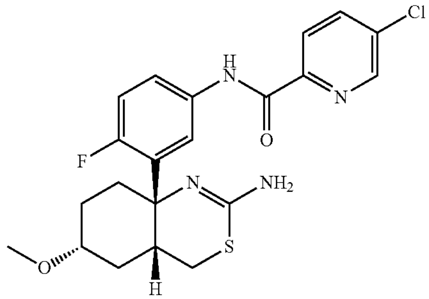 [SMILES: CO[C@@H]1CC[C@]2(c3cc(NC(=O)c4ccc(Cl)cn4)ccc3F)N=C(N)SC[C@@H]2C1] | N-[3-((4aR*,7R*,8aS*)-2-amino-6-methoxy-4a,5,6,7,8,8a-hexahydro-4H-benzo[d][1,3]thiazin-8a-yl)-4-fluorophenyl]-5-chloropyridine-2-carboxamide<br>$^1$H-NMR (400 MHz, CDCl$_3$): 1.52-1.75 (m, 2H), 1.81-1.92 (m, 2H), 1.96-1.99 (m, 1H), 2.23-2.31 (m, 1H), 2.57-2.61 (m, 1H), 2.75-2.81 (m, 1H) 2.93-2.97 (m, 1H), 3.41-3.49 (m, 4H), 4.52 (br, 2H), 7.05 (dd, J = 8.8, 12.0 Hz, 1H), 7.25-7.28 (m, 1H), 7.87 (dd, J = 2.4, 8.4 Hz, 1H), 8.00 (ddd, J = 2.8, 4.0, 8.8 Hz, 1H), 8.23 (dd, J = 0.4, 8.4 Hz, 1H), 8.56 (dd, J = 0.4, 2.4 Hz, 1H), 9.77 (br, 1H).<br>ESI-MS; m/z 449 [M$^+$ + H]. |
| 211 | 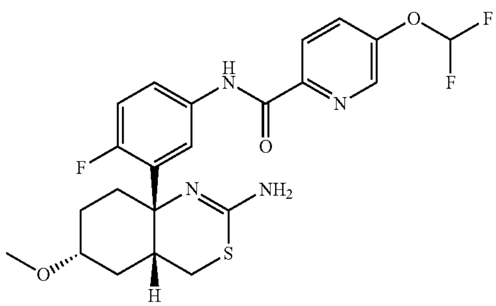 [SMILES: CO[C@@H]1CC[C@]2(c3cc(NC(=O)c4ccc(OC(F)F)cn4)ccc3F)N=C(N)SC[C@@H]2C1] | N-[3-((4aR*,6R*,8aS*)-2-amino-6-methoxy-4a,5,6,7,8,8a-hexahydro-4H-benzo[d][1,3]thiazin-8a-yl)-4-fluorophenyl]-5-difluoromethoxypyridine-2-carboxamide<br>$^1$H-NMR (400 MHz, CDCl$_3$): 1.53-1.63 (m, 1H), 1.65-1.75 (m, 1H), 1.81-1.91 (m, 2H), 1.95-2.01 (m, 1H), 2.27 (dt, 2.4, 13.6 Hz, 1H), 2.57-2.60 (m, 1H), 2.75-2.81 (m, 1H), 2.95 (dd, J = 4.0, 12.4 Hz, 1H), 3.39-3.49 (m, 4H), 4.50 (br, 2H), 6.64 (t, J = 72.0 Hz, 1H), 7.05 (dd, J = 8.8, 12.0 Hz, 1H), 7.25-7.27 (m, 1H), 7.65 (dd, J = 2.8, 8.8 Hz, 1H), 8.01 (ddd, J = 2.8, 4.0, 8.8 Hz, 1H), 8.31 (dd, J = 0.8, 8.8 Hz, 1H), 8.46 (dd, J = 0.8, 2.8 Hz, 1H), 9.77 (br, 1H).<br>ESI-MS; m/z 481 [M$^+$ + H]. |

Example 212

Synthesis of N-[3-((4aR*,6R*,8aS*)-2-amino-6-fluoro-4a,5,6,7,8,8a-hexahydro-4H-benzo[d][1,3]thiazin-8a-yl)-4-fluorophenyl]-5-cyanopyridine-2-carboxamide

[Formula 217]

The title compound (37 mg) was obtained from tert-butyl (−)-[(4aR*,6R*,8aS*)-8a-(5-amino-2-fluorophenyl)-6-fluoro-4a,5,6,7,8,8a-hexahydro-4H-benzo[d][1,3]thiazin-2-yl]carbamate obtained in Preparation Example 63-(8) (52 mg) according to the method of Example 201.

ESI-MS; m/z 428 [M$^+$+H].

$^1$H-NMR (400 MHz, CDCl$_3$) δ (ppm): 1.79-1.91 (m, 2H), 1.92-2.07 (m, 3H), 2.24-2.32 (m, 1H), 2.61 (dd, J=2.8, 12.0 Hz, 1H), 2.78-2.82 (m, 1H), 2.94 (ddd, J=3.2, 4.0, 12.0 Hz, 1H), 4.58 (br, 2H), 4.68-4.88 (m, 1H), 7.07 (dd, J=8.8, 12.0 Hz, 1H), 7.34 (dd, J=2.8, 7.2 Hz, 1H), 7.97 (ddd, J=2.8, 4.4, 8.8 Hz, 1H), 8.20 (dd, J=2.4, 8.4 Hz, 1H), 8.42 (dd, J=1.2, 4.4 Hz, 1H), 8.89 (dd, J=1.2, 2.4 Hz, 1H), 9.80 (br, 1H).

Examples 213 to 214

The compounds of Examples 213 to 214 as shown in Table 18 below were synthesized according to Example 210 using the corresponding carboxylic acids.

[Table 18]

Table 18

| Example | Chemical structure | Compound name: |
|---|---|---|
| 213 | 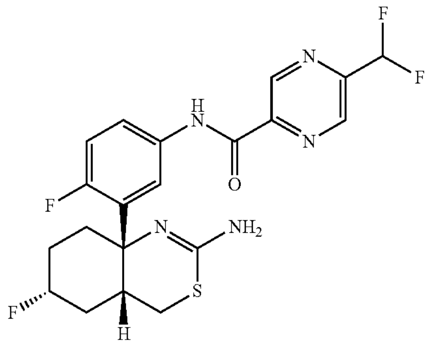 [SMILES: NC1=N[C@@]2(c3cc(NC(=O)c4cnc(C(F)F)cn4)ccc3F)CC[C@@H](F)C[C@H]2CS1] | N-[3-((4aR*,6R*,8aS*)-2-amino-6-fluoro-4a,5,6,7,8,8a-hexahydro-4H-benzo[d][1,3]thiazin-8a-yl)-4-fluorophenyl]-5-difluoromethylpyrazine-2-carboxamide<br>$^1$H-NMR (400 MHz, CDCl$_3$) δ (ppm): 1.82-1.90 (m, 2H), 1.92-2.07 (m, 3H), 2.25-2.32 (m, 1H), 2.59-2.63 (m, 1H), 2.79-2.82 (m, 1H), 2.92-2.97 (m, 1H), 4.59 (br, 2H), 4.68-4.88 (m, 1H), 6.79 (t, J = 54.4 Hz, 1H), 7.08 (dd, J = 8.8, 12.0 Hz, 1H), 7.35 (dd, J = 2.8, 7.2 Hz, 1H), 7.96 (ddd, J = 2.8, 4.0, 8.8 Hz, 1H), 8.92 (d, J = 1.2 Hz, 1H), 9.52 (d, J = 1.2 Hz, 1H), 9.59 (br, 1H).<br>ESI-MS; m/z 454 [M$^+$ + H]. |
| 214 | 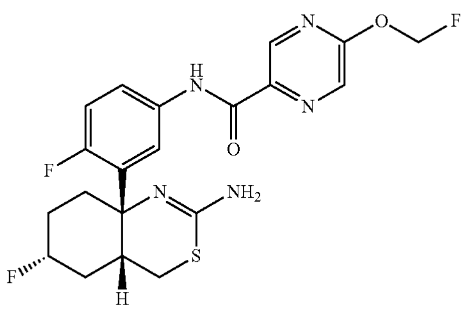 [SMILES: NC1=N[C@@]2(c3cc(NC(=O)c4cnc(OCF)cn4)ccc3F)CC[C@@H](F)C[C@H]2CS1] | N-[3-((4aR*,6R*,8aS*)-2-amino-6-fluoro-4a,5,6,7,8,8a-hexahydro-4H-benzo[d][1,3]thiazin-8a-yl)-4-fluorophenyl]-5-fluoromethoxypyrazine-2-carboxamide<br>$^1$H-NMR (400 MHz, CDCl$_3$) δ (ppm): 1.82-1.89 (m, 2H), 1.92-2.06 (m, 3H), 2.24-2.32 (m, 1H), 2.58-2.62 (m, 1H), 2.77-2.81 (m, 1H), 2.92-2.97 (m, 1H) 4.59 (br, 2H), 4.67-4.88 (m, 1H), 6.15 (qd, J = 2.0, 51.2 Hz, 2H), 7.06 (dd, J = 8.8, 12.0 Hz, 1H), 7.29 (dd, J = 2.8, 7.2 Hz, 1H), 7.93-7.97 (m, 1H), 8.28 (d, J = 1.6 Hz, 1H), 9.07 (d, J = 1.6 Hz, 1H), 9.44 (br, 1H).<br>ESI-MS; m/z 452 [M$^+$ + H]. |

Example 215

Synthesis of N-[3-((4aR*,6S*,8aS*)-2-amino-6-fluoro-4a,5,6,7,8,8a-hexahydro-4H-benzo[d][1,3]thiazin-8a-yl)-4-fluorophenyl]-5-cyanopyridine-2-carboxamide

[Formula 218]

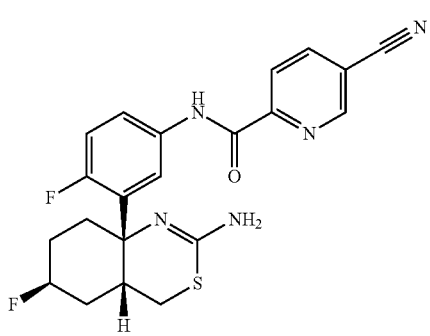 [SMILES: N#Cc1ccc(C(=O)Nc2ccc(F)c([C@]34CC[C@H](F)C[C@H]3CSC(N)=N4)c2)nc1]

The title compound (22 mg) was obtained from tert-butyl (−)-[(4aR*,6S*,8aS*)-8a-(5-amino-2-fluorophenyl)-6-fluoro-4a,5,6,7,8,8a-hexahydro-4H-benzo[d][1,3]thiazin-2-yl]carbamate obtained in Preparation Example 64-(8) (36 mg) according to the method of Example 201.

ESI-MS; m/z 428 [M$^+$+H].

$^1$H-NMR (400 MHz, CDCl$_3$) δ (ppm): 1.51-1.66 (m, 1H), 1.72-1.83 (m, 1H), 1.87-2.03 (m, 3H), 2.57 (dd, J=2.8, 12.4 Hz, 1H), 2.62-2.70 (m, 1H), 3.01 (dd, J=4.0, 12.0 Hz, 1H), 3.16-3.34 (m, 1H), 4.99 (d, J=48.8 Hz, 1H) 7.10 (dd, J=8.8, 11.6 Hz, 1H), 7.36-7.38 (m, 1H), 7.91-7.95 (m, 1H), 8.19-8.21 (m, 1H), 8.42-8.44 (m, 1H), 8.89-8.90 (m, 1H), 9.80 (br, 1H).

Examples 216 to 219

The compounds of Examples 216 to 219 as shown in Table 19 below were synthesized according to Example 202 using the corresponding carboxylic acids.

| Example | Chemical structure | Compound name: |
|---|---|---|
| 216 | 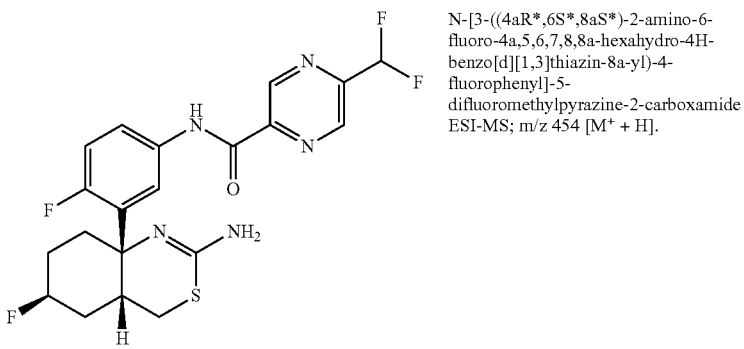 | N-[3-((4aR*,6S*,8aS*)-2-amino-6-fluoro-4a,5,6,7,8,8a-hexahydro-4H-benzo[d][1,3]thiazin-8a-yl)-4-fluorophenyl]-5-difluoromethylpyrazine-2-carboxamide<br>ESI-MS; m/z 454 [M+ + H]. |
| 217 | 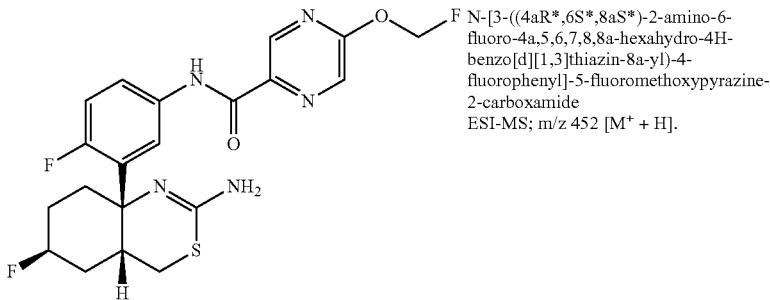 | N-[3-((4aR*,6S*,8aS*)-2-amino-6-fluoro-4a,5,6,7,8,8a-hexahydro-4H-benzo[d][1,3]thiazin-8a-yl)-4-fluorophenyl]-5-fluoromethoxypyrazine-2-carboxamide<br>ESI-MS; m/z 452 [M+ + H]. |
| 218 | 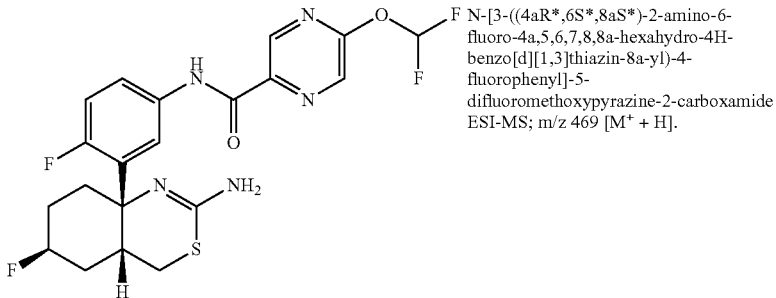 | N-[3-((4aR*,6S*,8aS*)-2-amino-6-fluoro-4a,5,6,7,8,8a-hexahydro-4H-benzo[d][1,3]thiazin-8a-yl)-4-fluorophenyl]-5-difluoromethoxypyrazine-2-carboxamide<br>ESI-MS; m/z 469 [M+ + H]. |
| 219 | 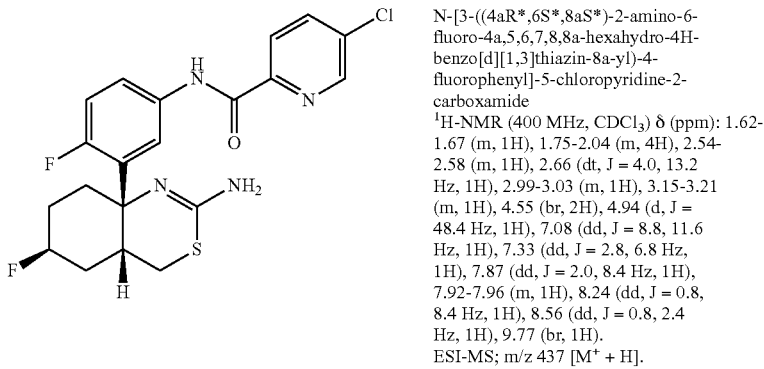 | N-[3-((4aR*,6S*,8aS*)-2-amino-6-fluoro-4a,5,6,7,8,8a-hexahydro-4H-benzo[d][1,3]thiazin-8a-yl)-4-fluorophenyl]-5-chloropyridine-2-carboxamide<br>$^1$H-NMR (400 MHz, CDCl$_3$) δ (ppm): 1.62-1.67 (m, 1H), 1.75-2.04 (m, 4H), 2.54-2.58 (m, 1H), 2.66 (dt, J = 4.0, 13.2 Hz, 1H), 2.99-3.03 (m, 1H), 3.15-3.21 (m, 1H), 4.55 (br, 2H), 4.94 (d, J = 48.4 Hz, 1H), 7.08 (dd, J = 8.8, 11.6 Hz, 1H), 7.33 (dd, J = 2.8, 6.8 Hz, 1H), 7.87 (dd, J = 2.0, 8.4 Hz, 1H), 7.92-7.96 (m, 1H), 8.24 (dd, J = 0.8, 8.4 Hz, 1H), 8.56 (dd, J = 0.8, 2.4 Hz, 1H), 9.77 (br, 1H).<br>ESI-MS; m/z 437 [M+ + H]. |

Example 220

Synthesis of (±)-N-[3-((4aR*,8aS*)-2-amino-4a,5,6,7,8,8a-hexahydro-4H-benzo[d][1,3]thiazin-8a-yl)-4-fluorophenyl]benzamide

[Formula 219]

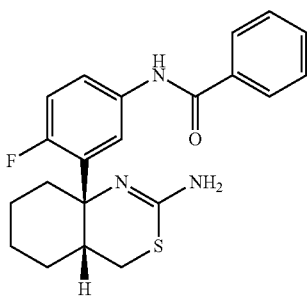 [SMILES: NC1=N[C@@]2(c3cc(NC(=O)c4ccccc4)ccc3F)CCCC[C@H]2CS1]

tert-Butyl (±)-[(4aR*,8aS*)-8a-(5-amino-2-fluorophenyl)-4a,5,6,7,8,8a-hexahydro-4H-benzo[d][1,3]thiazin-2-yl]carbamate obtained in Preparation Example 1-(8) (100 mg) was dissolved in THF (5 mL). Then, pyridine (107 μL, specific gravity: 0.978 g/cm³) was added and the mixture was cooled in an ice bath under a nitrogen atmosphere. After sufficiently cooling, benzyl chloride (46 μL, specific gravity: 1.211 g/cm³) was added, followed by stirring for one hour and 30 minutes. After diluting with ethyl acetate, a saturated ammonium chloride solution was added, followed by extraction with ethyl acetate. The resulting organic layer was sequentially washed with a saturated ammonium chloride solution, water and brine. The organic layer was dried over anhydrous magnesium sulfate, and the solid was removed by filtration. The filtrate was concentrated under reduced pressure and purified by pTLC to obtain an amide compound (93 mg). This was dissolved in a mixed solvent of ethyl acetate (1 mL) and chloroform (2 mL). Then, a solution of hydrogen chloride in ethyl acetate (4 N, 1 mL) was added and the mixture was stirred at room temperature. After five hours, TFA (2 mL) was further added, followed by further stirring. After 17 hours, the solvent was concentrated under reduced pressure. TFA (3 mL) was added to the resulting residue, followed by stirring. After 23 hours and 30 minutes, the reaction solution was concentrated under reduced pressure. Ethyl acetate and a saturated sodium bicarbonate solution were added to the resulting residue, followed by extraction with ethyl acetate three times. The resulting organic layers were washed with brine and dried over anhydrous magnesium sulfate. The solid was removed by filtration. After concentration under reduced pressure, the residue was purified by NH-pTLC to obtain the title compound (40 mg).

ESI-MS; m/z 384 [M⁺+H].

$^1$H-NMR (400 MHz, CDCl$_3$) δ (ppm): 1.47-1.81 (m, 7H), 2.20-2.27 (m, 1H), 2.55 (dd, J=2.8, 12.4 Hz, 1H), 2.70-2.75 (m, 1H), 2.94 (dd, J=4.0, 12.0 Hz, 1H), 7.30-7.09 (m, 2H), 7.47-7.52 (m, 2H), 7.53-7.58 (m, 1H), 7.84-7.86 (m, 3H), 7.93-7.97 (m, 1H).

Example 221

Synthesis of (±)-N-[3-((4aR*,8aS*)-2-amino-4a,5,6,7,8,8a-hexahydro-4H-benzo[d][1,3]thiazin-8a-yl)-4-fluorophenyl]-furan-2-carboxamide

[Formula 220]

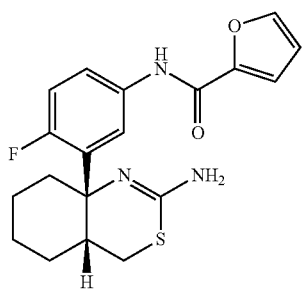 [SMILES: NC1=N[C@@]2(c3cc(NC(=O)c4ccco4)ccc3F)CCCC[C@H]2CS1]

tert-Butyl (±)-[(4aR*,8aS*)-8a-(5-amino-2-fluorophenyl)-4a,5,6,7,8,8a-hexahydro-4H-benzo[d][1,3]thiazin-2-yl]carbamate obtained in Preparation Example 1-(8) (100 mg) was dissolved in THF (5 mL). Then, pyridine (107 μL, specific gravity: 0.978 g/cm³) was added and the mixture was cooled in an ice bath under a nitrogen atmosphere. After sufficiently cooling, furan-2-carbonyl chloride (39 specific gravity: 1.324 g/cm³) was added, followed by stirring for one hour and 30 minutes. After diluting with ethyl acetate, a saturated ammonium chloride solution was added, followed by extraction with ethyl acetate. The resulting organic layer was sequentially washed with a saturated ammonium chloride solution, water and brine. The organic layer was dried over anhydrous magnesium sulfate, and the solid was removed by filtration. The filtrate was concentrated under reduced pressure and purified by pTLC to obtain an amide compound (59 mg). This was dissolved in a mixed solvent of ethyl acetate (2 mL) and chloroform (2 mL). Then, a solution of hydrogen chloride in ethyl acetate (4 N, 2 mL) was added and the mixture was stirred at room temperature. After five hours, TFA (2 mL) was further added, followed by further stirring. After 16 hours and 30 minutes, the solvent was concentrated under reduced pressure. Ethyl acetate and a saturated sodium bicarbonate solution were added to the resulting residue, followed by extraction with ethyl acetate three times. The resulting organic layers were washed with brine and dried over anhydrous magnesium sulfate. The solid was removed by filtration. After concentration under reduced pressure, the residue was purified by NH-pTLC to obtain the title compound (20 mg).

ESI-MS; m/z 374 [M⁺+H].

$^1$H-NMR (400 MHz, CDCl$_3$) δ (ppm): 1.50-1.81 (m, 7H), 2.19-2.26 (m, 1H), 2.56 (dd, J=2.4, 12.0 Hz, 1H), 2.71-2.74 (m, 1H), 2.94 (dd, J=4.0, 12.0 Hz, 1H), 6.56 (dd, J=1.6, 3.6 Hz, 1H), 7.05 (dd, J=8.8, 12.0 Hz, 1H), 7.13 (dd, J=2.4, 6.8 Hz, 1H), 7.23-7.25 (m, 1H), 7.52 (d, J=1.2 Hz, 1H), 7.89-7.93 (m, 1H), 8.07 (bs, 1H).

Examples 222 to 225

The compounds of Examples 222 to 225 as shown in Table 20 below were synthesized according to Example 221 using the corresponding carboxylic acids.

TABLE 20

| Example | Chemical structure | |
|---|---|---|
| 222 | 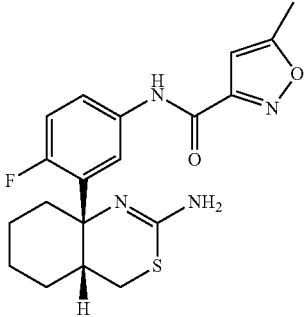 [SMILES: Cc1cc(C(=O)Nc2ccc(F)c([C@]34CCCC[C@H]3CSC(N)=N4)c2)no1] | ¹H-NMR (400 MHz, CDCl₃) δ (ppm): 1.47-1.54 (m, 2H), 1.61 (br, 2H), 1.68-1.81 (m, 3H), 2.19-2.27 (m, 1H), 2.51 (s, 3H), 2.56 (dd, J = 2.8, 4.0 Hz, 1H), 2.70-2.76 (m, 1H), 2.92 (dd, J = 4.0, 12.0 Hz, 1H), 6.52 (d, J = 0.8 Hz, 1H), 7.05 (dd, J = 8.8, 12.0 Hz, 1H), 7.20 (dd, J = 2.8, 7.2 Hz, 1H), 7.88 (ddd, J = 2.8, 4.0, 8.8 Hz, 1H) |
| 223 | 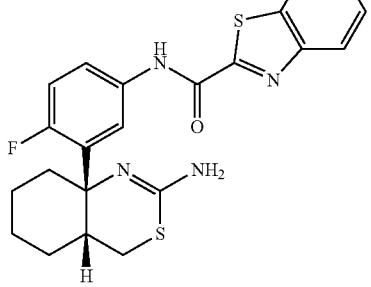 | ESI-MS; m/z 441 [M⁺ + H] |
| 224 | 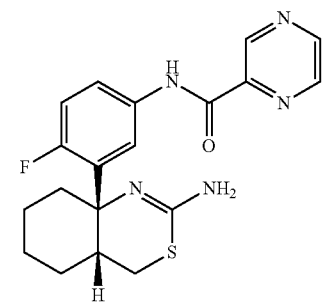 [SMILES: NC1=N[C@@]2(c3cc(NC(=O)c4cnccn4)ccc3F)CCCC[C@H]2CS1] | ESI-MS; m/z 386 [M⁺ + H] |
| 225 | 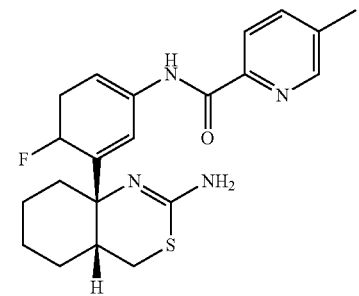 [SMILES: Cc1ccc(C(=O)NC2=CCC(F)C([C@]34CCCC[C@H]3CSC(N)=N4)=C2)nc1] | ESI-MS; m/z 399 [M⁺ + H] |

Example 226

Synthesis of (±)-(4aR*,7aS*)-6-(4-fluorophenyl)-7a-[3-(2-fluoropyridin-3-yl)phenyl]-4,4a,5,6,7,7a-hexahydropyrrolo[3,4-d][1,3]thiazin-2-ylamine

[Formula 221]

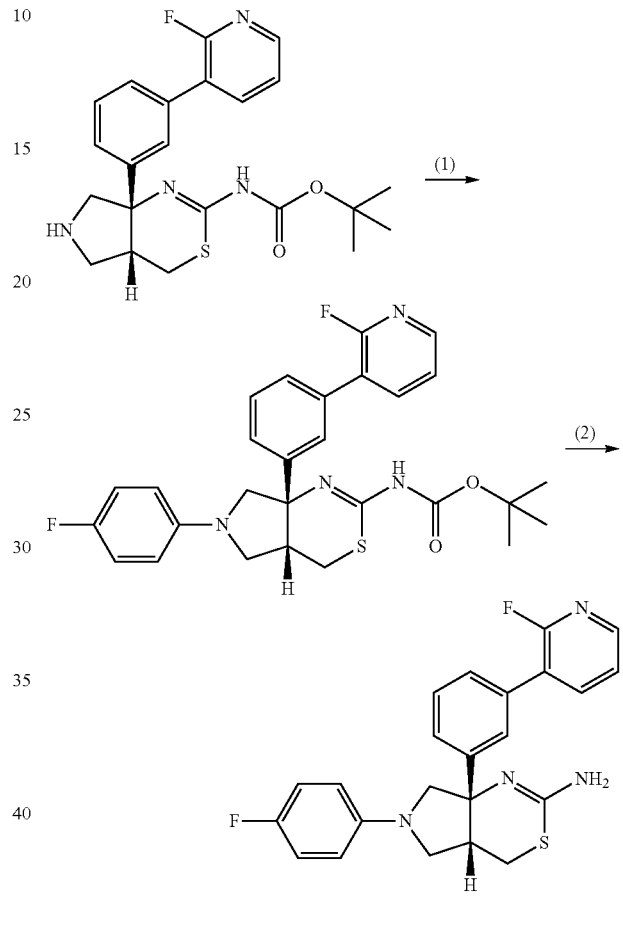

(1) Synthesis of tert-butyl(±)-{(4aR*,7aS*)-6-(4-fluorophenyl)-7a-[3-(2-fluoropyridin-3-yl)phenyl]-4,4a,5,6,7,7a-hexahydropyrrolo[3,4-d][1,3]thiazin-2-yl}carbamate tert-Butyl (±)-{(4aR*,7aS*)-7a-[3-(2-fluoropyridin-3-yl)phenyl]-4,4a,5,6,7,7a-hexahydropyrrolo[3,4-d][1,3]thiazin-2-yl}carbamate obtained in Preparation Example 18-(9) (72 mg) was mixed with 4-fluorobenzeneboronic acid (24.7 mg), copper (II) acetate (6.1 mg), triethylamine (93.2 μL, specific gravity: 0.73 g/cm³) and molecular sieves 4A (powder) (57.6 mg) in dichloromethane (3 mL), and the mixture was stirred under a nitrogen atmosphere at room temperature for 11 hours and 30 minutes. 4-Fluorobenzeneboronic acid (23.5 mg) and copper (II) acetate (12 mg) were further added. The atmosphere was changed to an open system, followed by further stirring. After 23 hours and 45 minutes, the reaction suspension was purified by NH-silica gel column chromatography. The resulting product was purified again by pTLC to obtain the title compound (15 mg).

¹H-NMR (400 MHz, CDCl₃) δ (ppm): 1.49 (s, 9H), 2.28-2.93 (m, 1H), 3.00-3.08 (m, 2H), 3.55-3.59 (m, 1H), 3.64 (d, J=10.0 Hz, 1H), 3.73-3.77 (m, 1H), 3.95 (d, J=10.0 Hz, 1H), 6.47-6.50 (m, 2H), 6.95-7.00 (m, 2H) 7.27-7.31 (m, 1H), 7.41-7.44 (m, 1H), 7.48-7.55 (m, 3H), 7.83-7.88 (m, 1H), 8.22 (td, J=1.6, 4.8 Hz, 1H).

(2) Synthesis of (±)-(4aR*,7aS*)-6-(4-fluorophenyl)-7a-[3-(2-fluoropyridin-3-yl)phenyl]-4,4a,5,6,7,7a-hexahydropyrrolo[3,4-d][1,3]thiazin-2-ylamine The title compound (7.8 mg) was obtained from tert-butyl (±)-{(4aR*,7aS*)-6-(4-fluorophenyl)-7a-[3-(2-fluoropyridin-3-yl)phenyl]-4,4a,5,6,7,7a-hexahydropyrrolo[3,4-d][1,3]thiazin-2-yl}carbamate obtained in Example 226-(1) (15 mg) according to Example 36-(2).
ESI-MS; m/z 423 [M⁺+H]

Example 227

Synthesis of (±)-(4aR*,7aS*)-7a-[3-(2-fluoropyridin-3-yl)phenyl]-6-o-tolyl-4,4a,5,6,7,7a-hexahydropyrrolo[3,4-d][1,3]thiazin-2-ylamine

[Formula 222]

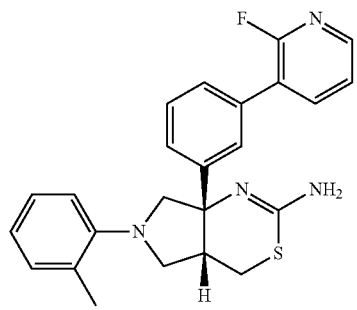 [SMILES: Cc1ccccc1N1C[C@H]2CSC(N)=N[C@@]2(c2cccc(-c3cccnc3F)c2)C1]

tert-Butyl (±)-{(4aR*,7aS*)-7a-[3-(2-fluoropyridin-3-yl)phenyl]-4,4a,5,6,7,7a-hexahydropyrrolo[3,4-d][1,3]thiazin-2-yl}carbamate obtained in Preparation Example 18-(9) (50 mg) was mixed with o-tolylboronic acid (19.1 mg), copper (II) acetate (4.3 mg), triethylamine (64.9 µL, specific gravity: 0.73 g/cm³) and molecular sieves 4A (powder) (40 mg) in dichloromethane (2 mL), followed by stirring at room temperature. After 20 hours, o-tolylboronic acid (12.7 mg), copper (II) acetate (4.3 mg) and triethylamine (64.9 µL) were added and the mixture was further stirred in an oxygen atmosphere. After two days, o-tolylboronic acid (31.8 mg) was further added, followed by further stirring. After one day, o-tolylboronic acid (63.6 mg), triethylamine (130 µL) and dichloromethane (1 mL) were further added, followed by further stirring. After three days, the reaction suspension was purified by NH-silica gel column chromatography. The resulting product was purified again by pTLC to obtain an N-aryl compound. This was dissolved in chloroform (1 mL) and then TFA was added at room temperature, followed by stirring. After 12 hours, the reaction solution was diluted with chloroform, and then the excess of TFA was neutralized with saturated sodium bicarbonate. The mixture was extracted with chloroform three times. The resulting organic layers were dried over anhydrous magnesium sulfate, and the solid was removed by filtration. The filtrate was concentrated under reduced pressure and then purified by NH-silica gel column chromatography to obtain the title compound (6.4 mg).
ESI-MS; m/z 419 [M⁺+H]

Example 228

The compound of Example 228 as shown in Table 21 below was synthesized according to Example 227 using the corresponding carboxylic acid.
[Table 21]

TABLE 21

| Example | Chemical structure | |
|---|---|---|
| 228 | 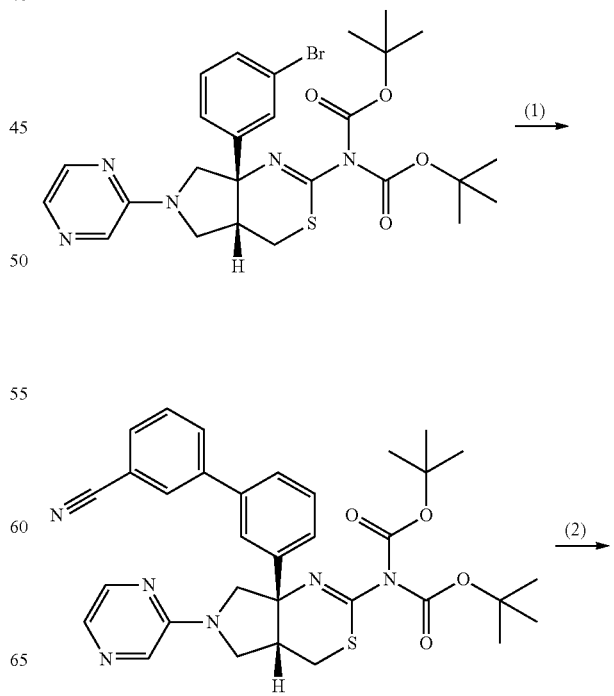 | ESI-MS; m/z 430 [M⁺ + H] |

Example 229

Synthesis of (±)-3'-((4aR*,7aS*)-2-amino-6-pyrazin-2-yl-4a,5,6,7-tetrahydro-4H-pyrrolo[3,4-d][1,3]thiazin-7a-yl)biphenyl-3-carbonitrile

[Formula 223]

-continued

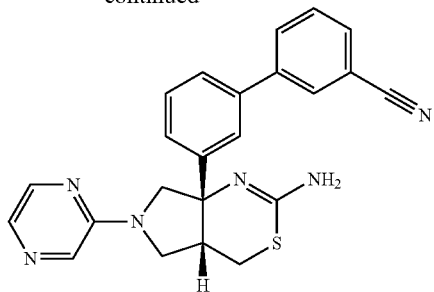

(1) Synthesis of (±)-3'-{(4aR*,7aS*)-2-[N,N-bis(t-butoxycarbonyl)amino]-6-pyrazin-2-yl-4a,5,6,7-tetrahydro-4H-pyrrolo[3,4-d][1,3]thiazin-7a-yl}biphenyl-3-carbonitrile The title compound (23 mg) was obtained from (±)-N,N-bis(t-butoxycarbonyl)[(4aR*,7aS*)-7a-(3-bromophenyl)-6-pyrazin-2-yl-4,4a,5,6,7,7a-hexahydropyrrolo[3,4-d][1,3]thiazin-2-yl]amine obtained in Preparation Example 65-(3) (51 mg) according to Preparation Example 18-(8).

$^1$H-NMR (400 MHz, CDCl$_3$) δ (ppm): 1.41 (s, 18H), 2.99-3.07 (m, 2H), 3.20-3.23 (m, 1H), 3.87-3.98 (m, 2H), 4.07-4.21 (m, 2H), 7.40-7.55 (m, 4H), 7.63-7.66 (m, 1H), 7.83-7.84 (m, 2H), 7.88-7.93 (m, 2H), 7.96 (br, 1H), 8.06 (br, 1H).

(2) Synthesis of (±)-3'-((4aR*,7aS*)-2-amino-6-pyrazin-2-yl-4a,5,6,7-tetrahydro-4H-pyrrolo[3,4-d][1,3]thiazin-7a-yl)-biphenyl-3-carbonitrile The title compound (9.8 mg) was obtained from (±)-3'-{(4aR*,7aS*)-2-[N,N-bis(t-butoxycarbonyl)amino]-6-pyrazin-2-yl-4a,5,6,7-tetrahydro-4H-pyrrolo[3,4-d][1,3]thiazin-7a-yl}biphenyl-3-carbonitrile obtained in Example 229-(1) (23 mg) according to Example 36-(2). ESI-MS; m/z 413 [M$^+$+H]

Example 230

The compound of Example 230 as shown in Table 22 below was synthesized according to Example 229 using the corresponding carboxylic acid.

[Table 22]

TABLE 22

| Example | Chemical structure | |
|---|---|---|
| 230 | (structure) | ESI-MS; m/z 390 [M$^+$ + H] |

Example 231

The compound of Example 231 as shown in Table 23 below was synthesized from the compound of Preparation Example 66 and the corresponding carboxylic acid according to Example 14.

[Table 23]

TABLE 23

| Example | Chemical structure | |
|---|---|---|
| 231 | (structure) | ESI-MS m/z 437 [M$^+$ + H] |

Example 232

The compound of Example 232 as shown in Table 24 below was synthesized from the compound of Preparation Example 67 and the corresponding carboxylic acid according to Example 14.

[Table 24]

TABLE 24

| Example | Chemical structure | |
|---|---|---|
| 232 | (structure) | ESI-MS m/z 403 [M$^+$ + H] |

Examples 233 to 239

The compounds of Examples 233 to 239 as shown in Table 25 below were synthesized according to Example 14 using the compound of Preparation Example 3-(8) and the corresponding carboxylic acids.

TABLE 25

| Example | Chemical structure | |
|---|---|---|
| 233 | 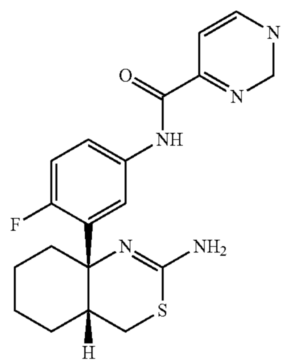 [SMILES: NC1=N[C@@]2(c3cc(NC(=O)C4=NCNC=C4)ccc3F)CCCC[C@H]2CS1] | ESI-MS m/z 372 [M+ + H] |
| 234 | 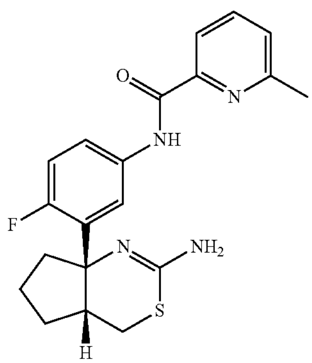 [SMILES: Cc1cccc(C(=O)Nc2ccc(F)c([C@]34CCC[C@H]3CSC(N)=N4)c2)n1] | ESI-MS m/z 385 [M+ + H] |
| 235 | 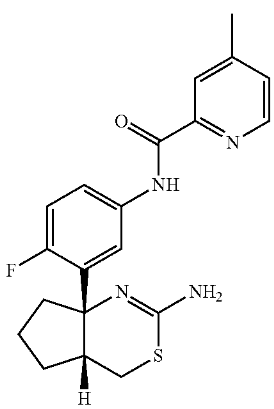 [SMILES: Cc1ccnc(C(=O)Nc2ccc(F)c([C@]34CCC[C@H]3CSC(N)=N4)c2)c1] | ESI-MS m/z 385 [M+ + H] |
| 236 | 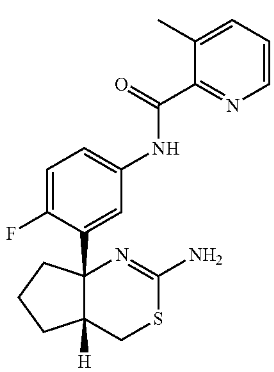 [SMILES: Cc1cccnc1C(=O)Nc1ccc(F)c([C@]23CCC[C@H]2CSC(N)=N3)c1] | ESI-MS m/z 385 [M+ + H] |

TABLE 25-continued

| Example | Chemical structure | |
|---|---|---|
| 237 | 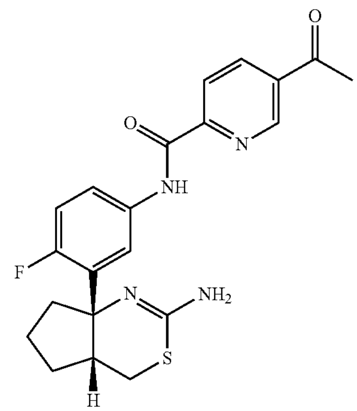 [SMILES: CC(=O)c1ccc(C(=O)Nc2ccc(F)c([C@]34CCC[C@H]3CSC(N)=N4)c2)nc1] | ESI-MS m/z 413 [M+ + H] |
| 238 | 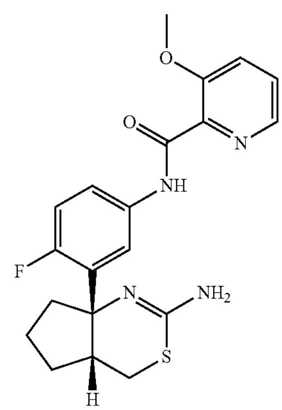 [SMILES: COc1cccnc1C(=O)Nc1ccc(F)c([C@]23CCC[C@H]2CSC(N)=N3)c1] | ESI-MS m/z 401 [M+ + H] |
| 239 | 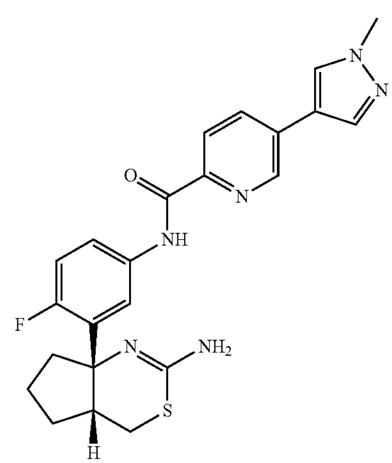 [SMILES: Cn1cc(-c2ccc(C(=O)Nc3ccc(F)c([C@]45CCC[C@H]4CSC(N)=N5)c3)nc2)cn1] | ESI-MS m/z 451 [M+ + H] |

Example 240

Synthesis of (±)-N-[3-((4aR*,7aS*)-2-amino-4,4a,5,6,7,7a-hexahydrocyclopenta[d][1,3]thiazin-7a-yl)-5-chlorophenyl]-5-cyanopyridine-2-carboxamide

[Formula 224]

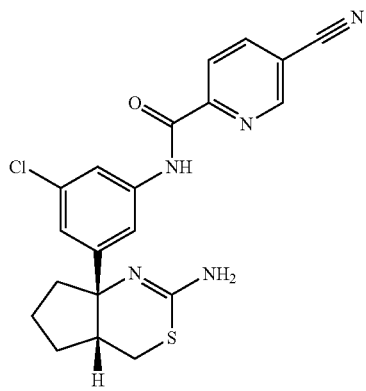 [SMILES: N#Cc1ccc(C(=O)Nc2cc(Cl)cc([C@]34CCC[C@H]3CSC(N)=N4)c2)nc1]

The title compound (1 mg) was obtained from the compound obtained in Preparation Example 71-(5) (13 mg) and 5-cyanopyridine-2-carboxylic acid (4.80 mg) according to the method of Example 14.

$^1$H-NMR (400 MHz, CDCl$_3$) δ (ppm): 1.70-2.03 (m, 5H), 2.25-2.33 (m, 1H), 2.41-2.48 (m, 1H), 2.76 (dd, J=3.6, 12.8 Hz, 1H), 3.02 (dd, J=3.6, 12.8 Hz, 1H), 6.53 (dd, J=0.4, 3.6 Hz, 1H), 7.51 (dd, J=2.0, 3.6 Hz, 1H), 7.86 (t, J=2.0 Hz, 1H), 8.22 (dd, J=2.0, 8.0 Hz, 1H), 8.43 (dd, J=1.2, 8.0 Hz, 1H), 8.90 (dd, J=1.2, 3.2 Hz, 1H), 9.87 (s, 1H).

Example 241

Synthesis of (±)-(4aR*,7aS*)-7a-[3-chloro-5-(2-fluoropyridin-3-yl)phenyl]-4,4a,5,6,7,7a-hexahydrocyclopenta[d][1,3]thiazin-2-ylamine

[Formula 225]

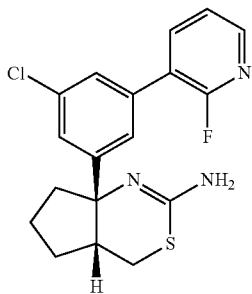 [SMILES: NC1=N[C@@]2(c3cc(Cl)cc(-c4cccnc4F)c3)CCC[C@H]2CS1]

2-Fluoropyridine-3-boronic acid (55.8 mg), tetrakis(triphenylphosphine)palladium (0) (22.9 mg) and a 1 N sodium carbonate solution (396 μL) were added to a solution of the by-product (±)-N-(t-butoxycarbonyl)-N-(methoxycarbonyl) [(4aR*,7aS*)-7a-(3-bromo-5-chlorophenyl)-4,4a,5,6,7,7a-hexahydrocyclopenta[d][1,3]thiazin-2-yl]amine obtained in Preparation Example 71-(2) (100 mg) in DMF (5 mL). After replacement with nitrogen, the mixture was stirred at 85° C. for three hours. The reaction solution was returned to room temperature, and the solvent was evaporated under reduced pressure. The residue was purified by NH-silica gel column chromatography to obtain a crude product. The crude product was further sequentially purified by NH-pTLC and silica gel column chromatography to obtain the title compound (25.6 mg).

$^1$H-NMR (400 MHz, CDCl$_3$) δ (ppm): 1.74-2.06 (m, 5H), 2.26-2.34 (m, 1H), 2.43-2.48 (m, 1H), 2.78 (dd, J=3.6, 12.8 Hz, 1H), 3.04 (dd, J=3.3.6, 12.8 Hz, 1H), 7.28-7.31 (m, 1H), 7.39 (t, J=2.0 Hz, 1H), 7.41-7.42 (m, 2H), 7.87 (ddd, J=2.0, 7.2, 9.6 Hz, 1H), 8.22 (dt, J=1.6, 4.4 Hz, 1H).

ESI-MS; m/z 362 [M$^+$+H].

Example 242

Synthesis of (±)-5-[3-((4aR*,7aS*)-2-amino-4,4a,5,6,7,7a-hexahydrocyclopenta[d][1,3]thiazin-7a-yl)-4-fluorophenyl]nicotinonitrile

[Formula 226]

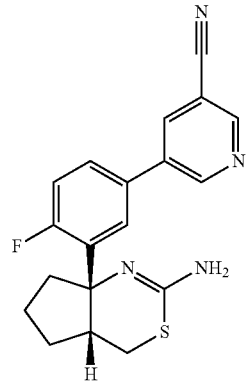 [SMILES: N#Cc1cncc(-c2ccc(F)c([C@]34CCC[C@H]3CSC(N)=N4)c2)c1]

5-Cyano-3-pyridinylboronic acid (37.9 mg), tetrakis(triphenylphosphine)palladium and a 1 N sodium carbonate solution (256 μL) were added to a solution of (±)-N,N-bis(tert-butoxycarbonyl) [(4aR*,7aS*)-7a-(5-bromo-2-fluorophenyl)-4,4a,5,6,7,7a-hexahydrocyclopenta[d][1,3]thiazin-2-yl]amine (70.0 mg) in DMF (5 mL). After replacement with nitrogen, the mixture was stirred at 80° C. for two hours. After cooling to room temperature, water was added to the reaction mixture. The aqueous layer was extracted with ethyl acetate, and the organic layer was washed with water and brine. The organic layer was dried over anhydrous magnesium sulfate, and the solvent was evaporated under reduced pressure. The residue was dissolved in dichloromethane (3 mL). Trifluoroacetic acid (1 mL) was added and the mixture was stirred at room temperature for two hours. The reaction mixture was diluted with water, followed by neutralization with a saturated sodium bicarbonate solution. The aqueous layer was extracted with ethyl acetate, and the organic layer was dried over anhydrous magnesium sulfate. The solvent was evaporated under reduced pressure and the residue was purified by NH-silica gel column chromatography to obtain the title compound.

$^1$H-NMR (400 MHz, CDCl$_3$) δ (ppm): 1.74-2.01 (m, 5H), 2.59-2.66 (m, 1H), 2.78 (dd, J=4.0, 12.4 Hz, 1H), 2.81-2.87 (m, 1H), 2.96 (dd, J=3.2, 12.4 Hz, 1H), 7.17 (dd, J=8.4, 12.0 Hz, 1H), 7.41 (ddd, J=2.8, 4.4, 8.4 Hz, 1H), 7.56 (dd, J=2.8, 7.6 Hz, 1H), 8.09 (t, J=2.0 Hz, 1H), 8.83 (d, J=2.0 Hz, 1H), 8.99 (d, J=2.0 Hz, 1H).

Example 243

Synthesis of (±)-(4aR*,6S*,7aS*)-7a-[2-Fluoro-5-(2-fluoro-pyridin-3-yl)phenyl-6-methoxy-4,4a,5,6,7,7a-hexahydrocyclopenta[d][1,3]thiazin-2-ylamine

[Formula 227]

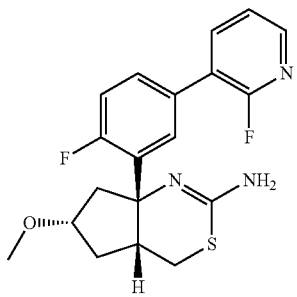 [SMILES: CO[C@H]1C[C@H]2CSC(N)=N[C@@]2(c2cc(-c3cccnc3F)ccc2F)C1]

The title compound (2.1 mg) was obtained from (±)-N,N-bis(tert-butyloxycarbonyl)[(4aR*,6S*,7aS*)-7a-(5-bromo-2-fluorophenyl)-6-methoxy-4,4a,5,6,7,7a-hexahydro-cyclopenta[d][1,3]thiazin-2-yl]amine (22.0 mg) and 2-fluoropyridine-3-boronic acid (11.0 mg) according to Example 242.

ESI-MS; m/z 376 [M$^+$+H].

Example 244

Synthesis of (4aR,6R,7aS)-7a-[2-Fluoro-5-(2-fluoro-pyridin-3-yl)phenyl-6-methoxy-4,4a,5,6,7,7a-hexahydrocyclopenta[d][1,3]thiazin-2-ylamine

[Formula 228]

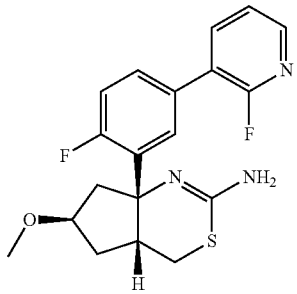 [SMILES: CO[C@@H]1C[C@H]2CSC(N)=N[C@@]2(c2cc(-c3cccnc3F)ccc2F)C1]

A racemate of the title compound (30.0 mg) was obtained from (±)-N,N-bis(tert-butyloxycarbonyl)[(4aR*,6R*,7aS*)-7a-(5-bromo-2-fluorophenyl)-6-methoxy-4,4a,5,6,7,7a-hexahydro-cyclopenta[d][1,3]thiazin-2-yl]amine (92.0 mg) and 2-fluoropyridine-3-boronic acid (46.2 mg) according to Example 242. The resulting racemate (10.0 mg) was optically resolved by CHIRALPAK™ AD-H manufactured by Daicel Chemical Industries, Ltd. (2 cm×25 cm, mobile phase: hexane:ethanol=8:2, flow rate: 10 mL/min), and the component having a retention time of 33.8 to 38.1 minutes was collected. This operation was repeated to obtain the title compound (9.9 mg) from the racemate (26 mg).

ESI-MS; m/z 376 [M$^+$+H].

Example 245

Synthesis of (±)-(4aR*,8aS*)-8a-[2,4-difluoro-5-(2-fluoropyridin-3-yl)phenyl]-4a,5,6,7,8,8a-hexahydro-4H-benzo[d][1,3]thiazin-2-ylamine

[Formula 229]

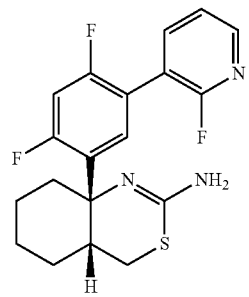 [SMILES: NC1=N[C@@]2(c3cc(-c4cccnc4F)c(F)cc3F)CCCC[C@H]2CS1]

Isopropyl alcohol (1 mL), 2-fluoro-3-pyridineboronic acid (49.8 mg), a 1 N sodium carbonate solution (354 μL) and bis(tri-tert-butylphosphine)palladium (0) (3.61 mg) were added to a solution of benzyl (±)-[(4aR*,8aS)-8a-(5-bromo-2,4-difluorophenyl)-4a,5,6,7,8,8a-hexahydro-4H-benzo[d][1,3]thiazin-2-yl]carbamate (35 mg) in toluene (2 mL). After replacement with nitrogen, the mixture was stirred at 85° C. for 9.5 hours. The reaction solution was cooled to room temperature, and the solvent was evaporated under reduced pressure. The residue was purified by NH-silica gel column chromatography to obtain an intermediate. The resulting intermediate was dissolved in chloroform (2 mL). Iodotrimethylsilane (30 μL) was added, followed by stirring for 14 hours. The reaction solution was returned to room temperature, and a sodium bicarbonate solution was added to the reaction mixture. The mixture was diluted with ethyl acetate and sodium thiosulfate was added, followed by stirring for 30 minutes. The reaction mixture was extracted with ethyl acetate when it became transparent. The organic layer was washed with brine. The organic layer was dried over anhydrous magnesium sulfate, and the solvent was evaporated under reduced pressure. The residue was sequentially purified by NH-pTLC and pTLC to obtain the title compound (2.0 mg).

$^1$H-NMR (400 MHz, CDCl$_3$) δ (ppm): 1.43-1.81 (m, 7H), 2.18-2.25 (m, 1H), 2.58 (dd, J=3.2, 12.4 Hz, 1H), 2.65-2.69 (m, 1H), 2.85 (dd, J=4.0, 12.4 Hz, 1H), 6.92 (dd, J=9.6, 12.0 Hz, 1H), 7.18-7.33 (m, 2H), 7.77-7.81 (m, 1H), 8.24 (d, J=4.8 Hz, 1H). ESI-MS; m/z 378 [M$^+$+H].

Example 246

Synthesis of (±)-N-[3-((3aS*,7aR*)-2-amino-3a,6,7,7a-tetrahydro-4H-pyrano[4,3-d]thiazol-7a-yl)phenyl]-5-chloropyridine-2-carboxamide

[Formula 230]

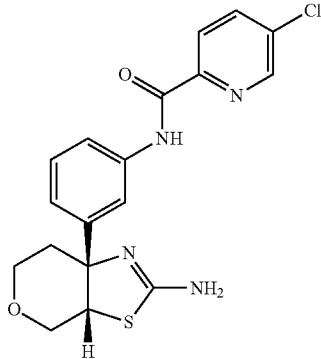 [SMILES: NC1=N[C@@]2(c3cccc(NC(=O)c4ccc(Cl)cn4)c3)CCOC[C@H]2S1]

The title compound (39.5 mg) was obtained from the compound of Preparation Example 75-(9) (99.0 mg) according to the method of Example 14.
ESI-MS; m/z 389 [M$^+$+H].

Example 247

Synthesis of (±)-(4aS*,8aS*)-8a-[4-(2-fluoro-pyridin-3-yl)-thiophen-2-yl]-4a,7,8,8a-tetrahydro-4H,5H-6-oxa-3-thia-1-azanaphthalen-2-ylamine

[Formula 231]

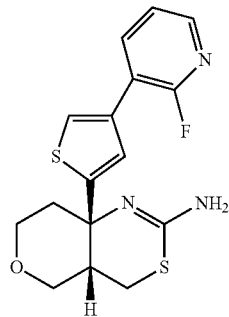 [SMILES: NC1=N[C@@]2(c3cc(-c4cccnc4F)cs3)CCOC[C@H]2CS1]

2-Fluoropyridine-3-boronic acid (15.7 mg), tetrakis(triphenylphosphine)palladium (4.3 mg) and a 1 N sodium carbonate solution (112 μL) were added to a solution of (±)-N-tert-butoxycarbonyl-N-[(4aS*,8aS*)-8a-(4-bromo-thiophen-2-yl)-4a,7,8,8a-tetrahydro-4H,5H-6-oxa-3-thia-1-azanaphthalen-2-yl]benzamide (20.0 mg) in DMF (1 mL). After replacement with nitrogen, the mixture was stirred at 90° C. for seven hours. After cooling to room temperature, ethyl acetate was added to the reaction mixture. The organic layer was washed with water and brine and dried over anhydrous magnesium sulfate. The solvent was evaporated under reduced pressure and the residue was purified by NH-silica gel column chromatography to obtain the title compound (4.7 mg).

$^1$H-NMR (400 MHz, CDCl$_3$) δ (ppm): 1.98-2.02 (m, 1H), 2.27 (ddd, J=4.4, 12.8, 13.6 Hz, 1H), 2.44-2.50 (m, 1H), 2.59 (dd, J=3.0, 12.8 Hz, 1H), 3.24 (dd, J=4.4, 12.8 Hz, 1H), 3.66-3.92 (m, 4H), 7.18 (t, J=1.4 Hz, 7.22-7.26 (m, 2H), 7.56 (t, J=1.6 Hz, 1H), 7.95 (ddd, J=1.6, 7.2, 9.6 Hz, 1H), 8.12 (dt, J=1.6, 4.8 Hz, 1H).

ESI-MS; m/z 350 [M$^+$+H].

Examples 248 to 253

The compounds of Examples 248 to 253 as shown in Table 26 below were synthesized according to Example 33 using the compound of Preparation Example 7-(8) and the corresponding carboxylic acids.

[Table 26]

Table 26

| Example | Chemical structure | Compound name: |
|---------|-------------------|----------------|
| 248 | 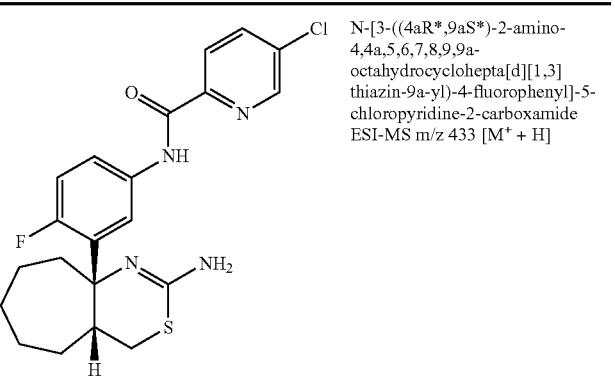 | N-[3-((4aR*,9aS*)-2-amino-4,4a,5,6,7,8,9,9a-octahydrocyclohepta[d][1,3]thiazin-9a-yl)-4-fluorophenyl]-5-chloropyridine-2-carboxamide ESI-MS m/z 433 [M$^+$ + H] |

-continued

| Example | Chemical structure | Compound name: |
|---|---|---|
| 249 | 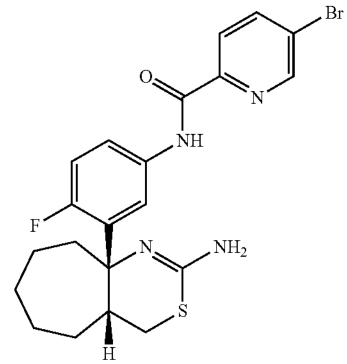 [SMILES: NC1=N[C@@]2(c3cc(NC(=O)c4ccc(Br)cn4)ccc3F)CCCCC[C@H]2CS1] | N-[3-((4aR*,9aS*)-2-amino-4,4a,5,6,7,8,9,9a-octahydrocyclohepta[d][1,3]thiazin-9a-yl)-4-fluorophenyl]-5-bromopyridine-2-carboxamide<br>ESI-MS m/z 479 [M+ + H] |
| 250 | 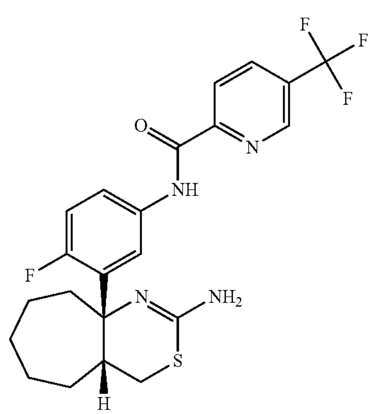 [SMILES: NC1=N[C@@]2(c3cc(NC(=O)c4ccc(C(F)(F)F)cn4)ccc3F)CCCCC[C@H]2CS1] | N-[3-((4aR*,9aS*)-2-amino-4,4a,5,6,7,8,9,9a-octahydrocyclohepta[d][1,3]thiazin-9a-yl)-4-fluorophenyl]-5-trifluoromethylpyridine-2-carboxamide<br>ESI-MS m/z 467 [M+ + H] |

Example 254

The compound synthesized from the compound of Preparation Example 1-(8) and 5-bromopyridine-2-carboxylic acid according to Example 14 was optically resolved by CHIRAL-PAK™ OD-H manufactured by Daicel Chemical Industries, Ltd. (2.5 cm×25 cm, mobile phase: hexane:ethanol=8:2, flow rate: 20 mL/min), and the component having a retention time of 4.9 to 5.7 minutes was collected to obtain the compound of Example 254 as shown in Table 27 below.

[Table 27]

Table 27

| Example | Chemical structure | Compound name: |
|---|---|---|
| 254 | (structure) | N-[3-((4aR*,8aS*)-2-amino-4a,5,6,7,8,8a-hexahydro-4H-benzo[d][1,3]thiazin-8a-yl)-4-fluorophenyl]-5-bromopyridine-2-carboxamide<br>ESI-MS m/z 465 [M$^+$ + H] |

Example 255

The compound synthesized from the compound of Preparation Example 1-(8) and pyridine-2-carboxylic acid according to Example 14 was optically resolved by CHIRALPAK™ OD-H manufactured by Daicel Chemical Industries, Ltd. (2.5 cm×25 cm, mobile phase: hexane:ethanol=8:2, flow rate: 20 mL/min), and the component having a retention time of 5.1 to 6.4 minutes was collected to obtain the compound of Example 255 as shown in Table 28 below.

[Table 28]

TABLE 28

| Example | Chemical structure | |
|---|---|---|
| 255 | (structure) | ESI-MS m/z 385 [M$^+$ + H] |

Examples 256 to 261

The compounds of Examples 256 to 261 as shown in Table 29 below were synthesized according to Example 14 using the compound of Preparation Example 2-(2) and the corresponding carboxylic acids.

| Example | Chemical structure | Compound name: |
|---|---|---|
| 256 | 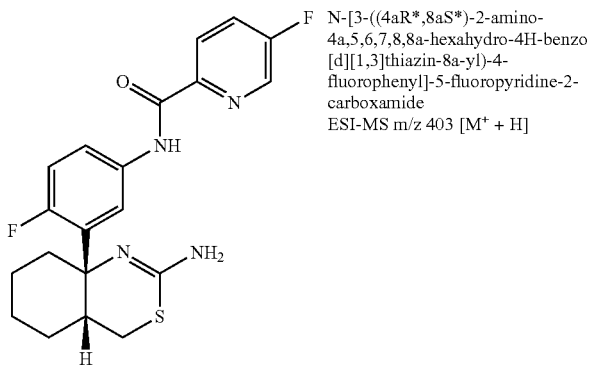 | N-[3-((4aR*,8aS*)-2-amino-4a,5,6,7,8,8a-hexahydro-4H-benzo[d][1,3]thiazin-8a-yl)-4-fluorophenyl]-5-fluoropyridine-2-carboxamide<br>ESI-MS m/z 403 [M+ + H] |
| 257 | 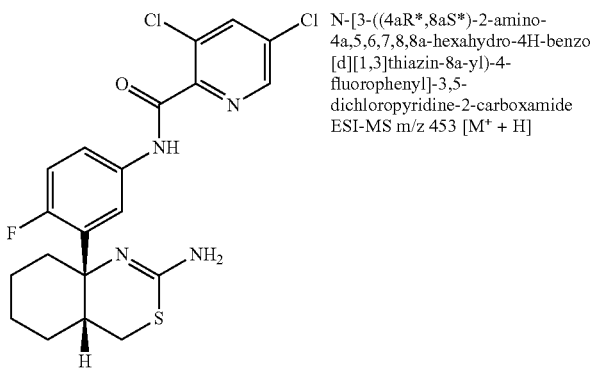 | N-[3-((4aR*,8aS*)-2-amino-4a,5,6,7,8,8a-hexahydro-4H-benzo[d][1,3]thiazin-8a-yl)-4-fluorophenyl]-3,5-dichloropyridine-2-carboxamide<br>ESI-MS m/z 453 [M+ + H] |
| 258 | 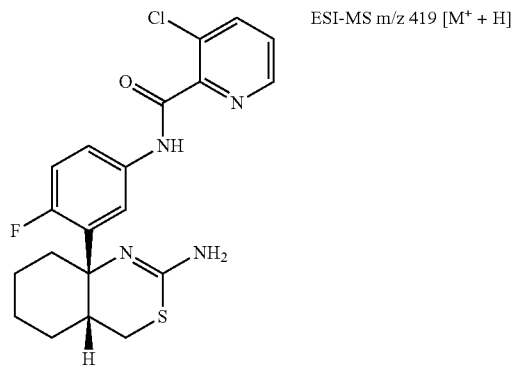 | ESI-MS m/z 419 [M+ + H] |
| 259 | 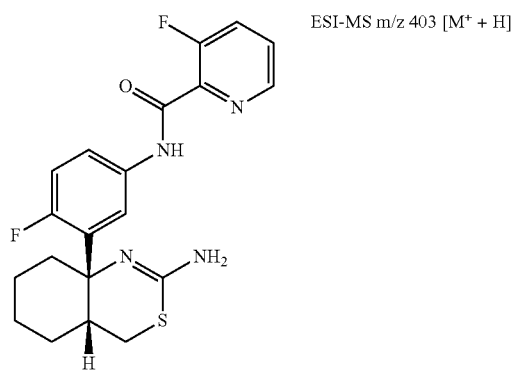 | ESI-MS m/z 403 [M+ + H] |

| Example | Chemical structure | Compound name: |
|---|---|---|
| 260 | 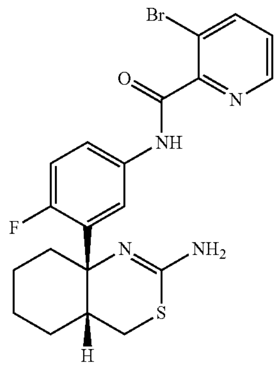 [SMILES: NC1=N[C@@]2(c3cc(NC(=O)c4ncccc4Br)ccc3F)CCCC[C@H]2CS1] | ESI-MS m/z 465 [M⁺ + H] |
| 261 | 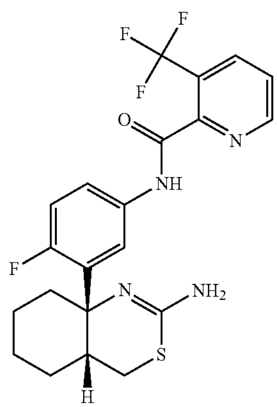 [SMILES: NC1=N[C@@]2(c3cc(NC(=O)c4ncccc4C(F)(F)F)ccc3F)CCCC[C@H]2CS1] | ESI-MS m/z 453 [M⁺ + H] |

Example 262

Synthesis of N-[3-((4aR*,7aS*)-2-amino-4,4a,5,6,7,7a-hexahydrocyclopenta[d][1,3]thiazin-7a-yl)-4-fluorophenyl]-2-chlorooxazole-4-carboxamide

[Formula 232]

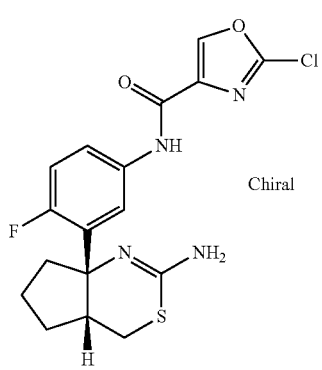 [SMILES: NC1=N[C@@]2(c3cc(NC(=O)c4csc(Br)n4)ccc3F)CCC[C@H]2CS1]

The title compound (12.4 mg) was obtained from the compound obtained in Preparation Example 3-(8) (20.0 mg) and 2-chlorooxazole-4-carboxylic acid (12.1 mg) according to Example 14.

ESI-MS; m/z 393, 395 [M⁺+H].

$^1$H-NMR (400 MHz, CDCl$_3$) δ (ppm): 1.70-2.00 (m, 5H), 2.55-2.65 (m, 1H), 2.71-2.84 (m, 2H), 2.97 (dd, J=3.1, 12.5 Hz, 1H), 7.03 (dd, J=8.8, 12.0 Hz, 1H), 7.30 (dd, J=2.8, 7.2 Hz, 1H), 7.84 (ddd, J=2.4, 3.9, 8.8 Hz, 1H), 8.24 (s, 1H), 8.50 (s, 1H).

Examples 263 to 267

The compounds of Examples 263 to 267 as shown in Table 30 below were synthesized according to Example 14 using the corresponding carboxylic acids.

[Table 30]

Table 30

| Example | Chemical structure | Compound name: |
|---|---|---|
| 263 | 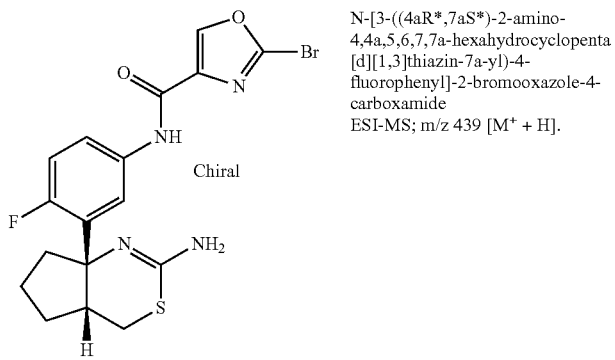 | N-[3-((4aR*,7aS*)-2-amino-4,4a,5,6,7,7a-hexahydrocyclopenta[d][1,3]thiazin-7a-yl)-4-fluorophenyl]-2-bromooxazole-4-carboxamide<br>ESI-MS; m/z 439 [M⁺ + H]. |
| 264 | 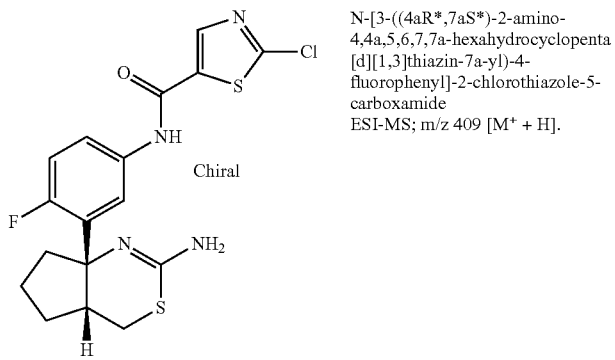 | N-[3-((4aR*,7aS*)-2-amino-4,4a,5,6,7,7a-hexahydrocyclopenta[d][1,3]thiazin-7a-yl)-4-fluorophenyl]-2-chlorothiazole-5-carboxamide<br>ESI-MS; m/z 409 [M⁺ + H]. |
| 265 | 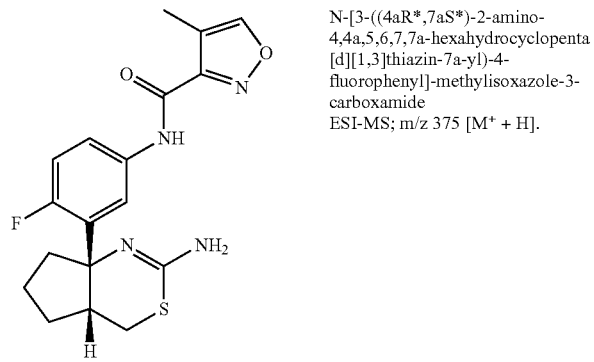 | N-[3-((4aR*,7aS*)-2-amino-4,4a,5,6,7,7a-hexahydrocyclopenta[d][1,3]thiazin-7a-yl)-4-fluorophenyl]-methylisoxazole-3-carboxamide<br>ESI-MS; m/z 375 [M⁺ + H]. |
| 266 | 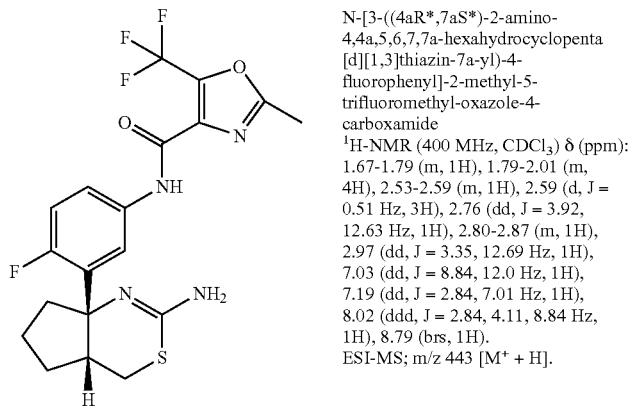 | N-[3-((4aR*,7aS*)-2-amino-4,4a,5,6,7,7a-hexahydrocyclopenta[d][1,3]thiazin-7a-yl)-4-fluorophenyl]-2-methyl-5-trifluoromethyl-oxazole-4-carboxamide<br>$^1$H-NMR (400 MHz, CDCl$_3$) δ (ppm): 1.67-1.79 (m, 1H), 1.79-2.01 (m, 4H), 2.53-2.59 (m, 1H), 2.59 (d, J = 0.51 Hz, 3H), 2.76 (dd, J = 3.92, 12.63 Hz, 1H), 2.80-2.87 (m, 1H), 2.97 (dd, J = 3.35, 12.69 Hz, 1H), 7.03 (dd, J = 8.84, 12.0 Hz, 1H), 7.19 (dd, J = 2.84, 7.01 Hz, 1H), 8.02 (ddd, J = 2.84, 4.11, 8.84 Hz, 1H), 8.79 (brs, 1H).<br>ESI-MS; m/z 443 [M⁺ + H]. |

| Example | Chemical structure | Compound name: |
|---|---|---|
| 267 | (see structure) | N-[3-((4aR*,7aS*)-2-amino-4,4a,5,6,7,7a-hexahydrocyclopenta[d][1,3]thiazin-7a-yl)-4-fluorophenyl]-6-chloro-imidazo[1,2a]pyridine-2-carboxamide<br>$^1$H-NMR (400 MHz, CDCl$_3$) δ (ppm): 1.66-2.03 (m, 5H), 2.55-2.66 (m, 1H), 2.75(dd, J = 4.04, 12.51 Hz, 1H), 2.78-2.85 (m, 1H), 2.98 (dd, J = 8.78, 12.06 Hz, 1H), 7.04 (dd, J = 8.84, 12.0 Hz, 1H), 7.25 (dd, J = 2.02, 9.73 Hz, 1H), 7.41 (dd, J = 2.78, 7.20 Hz, 1H), 7.55 (dt, J = 9.66, 0.85 Hz, 1H), 7.94 (ddd, J = 0.63 Hz, 1H), 8.24 (dd, J = 0.88, 2.02 Hz, 1H), 9.19 (brs, 1H).<br>ESI-MS; m/z 444 [M$^+$ + H]. |

Example 268

Synthesis of N-[3-((4aR*,7aS*)-2-amino-4,4a,5,6,7,7a-hexahydrocyclopenta[d][1,3]thiazin-7a-yl)-4-fluorophenyl]cyclopentanecarboxamide

[Formula 233]

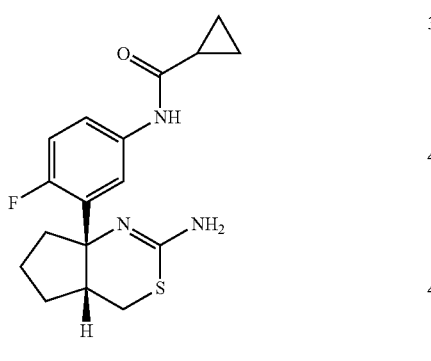

The title compound (12.4 mg) was obtained from the compound obtained in Preparation Example 3-(7) (20.0 mg) and 2-chlorooxazole-4-carboxylic acid (12.1 mg) according to Example 14.

ESI-MS; m/z 334 [M$^+$+H].

$^1$H-NMR (400 MHz, CDCl$_3$) δ (ppm): 0.79-0.86 (m, 2H), 1.03-1.07 (m, 2H), 1.53-1.62 (m, 1H), 1.76-2.04 (m, 5H), 2.60 (dt, J=13.4, 8.5 Hz, 1H), 2.79 (dd, J=3.7, 12.7 Hz, 1H), 2.91-3.06 (m, 1H), 6.98 (dd, J=8.8, 12.1 Hz, 1H), 7.09 (dd, J=2.2, 6.7 Hz, 1H), 7.88 (dd, J=3.3, 4.7 Hz, 1H), 8.39 (brs, 1H).

Example 269

Synthesis of (+)-N-[3-((4aR*,7aS*)-2-amino-4,4a,5,6,7,7a-hexahydrocyclopenta[d][1,3]thiazin-7a-yl)-4-fluorophenyl]-3-bromothiazole-4-carboxamide

[Formula 234]

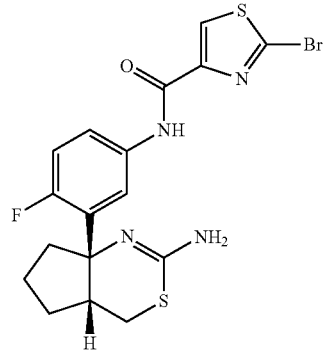

The title compound (12.5 mg) was obtained from the compound obtained in Preparation Example 3-(8) (21.0 mg) and 2-bromothiazole-4-carboxylic acid (18.0 mg) according to Example 14.

$^1$H-NMR (400 MHz, CDCl$_3$) δ (ppm): 1.67-2.02 (m, 5H), 2.51-2.68 (m, 1H), 2.76 (dd, J=8.72, 12.0 Hz, 1H), 2.78-2.86 (m, 1H), 2.99 (dd, J=3.22, 12.57 Hz, 1H), 7.04 (dd, J=8.72, 12.00 Hz, 1H), 7.30 (dd, J=2.84, 7.14 Hz, 1H), 7.87 (ddd, J=2.78, 11.9, 8.78 Hz, 1H), 8.15 (s, 1H), 8.98 (s, 1H).

Example 270

Synthesis of (+)-N-[3-((4aR*,7aS*)-2-amino-4,4a,5,6,7,7a-hexahydrocyclopenta[d][1,3]thiazin-7a-yl)-4-fluorophenyl]-1-methyl-1H-imidazole-4-carboxamide

[Formula 235]

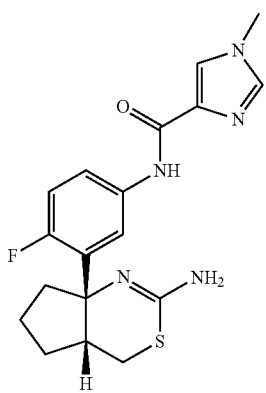 [SMILES: Cn1cnc(C(=O)Nc2ccc(F)c([C@]34CCC[C@H]3CSC(N)=N4)c2)c1]

The title compound (7 mg) was obtained from the compound obtained in Preparation Example 3-(8) (20.0 mg) and 1-methyl-1H-imidazole-4-carboxylic acid (10.0 mg) according to Example 14.

$^1$H-NMR (400 MHz, CDCl$_3$) δ (ppm): 1.74-2.01 (m, 5H), 2.61 (dt, J=12.00, 8.40 Hz, 1H), 2.74 (dd, J=4.04, 12.13 Hz, 1H), 2.77-2.83 (m, 1H), 2.99 (dd, J=3.03, 12.63 Hz, 1H), 3.77 (s, 3H), 7.01 (dd, J=8.84, 11.87 Hz, 1H), 7.30 (dd, J=2.53, 12.63 Hz, 1H), 7.42 (d, 1.52 Hz, 1H), 7.61 (d, 1.52 Hz, 1H), 7.92 (ddd, J=2.78, 4.04, 8.84, 1H), 8.89 (s, 1H).

Example 271

Synthesis of (+)-N-[3-((4aR*,7aS*)-2-amino-4,4a,5,6,7,7a-hexahydrocyclopenta[d][1,3]thiazin-7a-yl)-4-fluorophenyl]-3-methyl-3H-imidazole-4-carboxamide

[Formula 236]

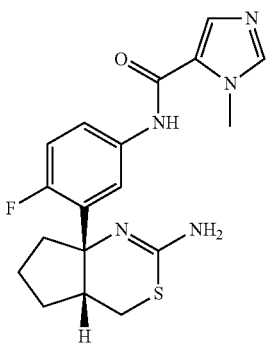 [SMILES: Cn1cncc1C(=O)Nc1ccc(F)c([C@]23CCC[C@H]2CSC(N)=N3)c1]

The title compound (10.5 mg) was obtained from the compound obtained in Preparation Example 3-(8) (15.0 mg) and 3-methyl-3H-imidazole-4-carboxylic acid (10.0 mg) according to Example 14.

ESI-MS; m/z 374 [M$^+$+H].

$^1$H-NMR (400 MHz, CDCl$_3$) δ (ppm): 1.70-2.01 (m, 5H), 2.53-2.66 (m, 1H), 2.75 (dd, J=4.04, 12.76 Hz, 1H), 2.79-2.88 (m, 1H), 2.97 (dd, J=3.35, 12.69 Hz, 1H), 3.94 (s, 3H), 7.03 (dd, J=8.84, 12.00 Hz, 1H), 7.21 (dd, J=2.78, 7.07 Hz, 1H), 7.53 (s, 1H), 7.61 (d, J=0.76 Hz, 1H), 7.79 (ddd, J=2.78, 4.01, 8.75 Hz, 1H).

Example 272

Synthesis of (+)-N-[3-((4aR*,7aS*)-2-amino-4,4a,5,6,7,7a-hexahydrocyclopenta[d][1,3]thiazin-7a-yl)-4-fluorophenyl]-1-methyl-1H-pyrazole-4-carboxamide

[Formula 237]

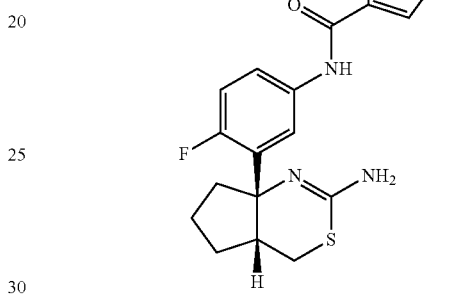

The title compound (14.7 mg) was obtained from the compound obtained in Preparation Example 3-(8) (25.0 mg) and 1-methyl-1H-pyrazole-4-carboxylic acid (17.0 mg) according to Example 14.

ESI-MS; m/z 374 [M$^+$+H].

$^1$H-NMR (400 MHz, CDCl$_3$+several drops of MeOD) δ (ppm): 1.64-2.01 (m, 5H), 2.51-2.65 (m, 1H), 2.73 (dd, J=3.79, 12.63 Hz, 1H), 2.84-2.92 (m, 1H), 2.96 (dd, J=3.41, 12.63 Hz, 1H), 3.93 (s, 3H), 6.95-7.04 (m, 2H), 7.97 (m, 3H).

Example 273

Synthesis of (+)-N-[3-((4aR*,7aS*)-2-amino-4,4a,5,6,7,7a-hexahydrocyclopenta[d][1,3]thiazin-7a-yl)-4-fluorophenyl]-4-chloro-1-methyl-1H-pyrazole-3-carboxamide

[Formula 238]

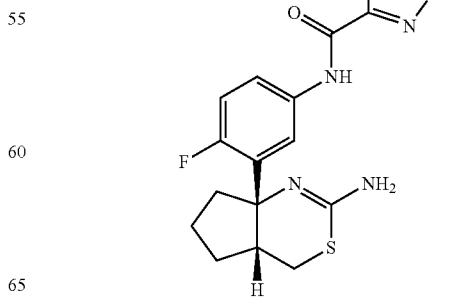

The title compound (8.5 mg) was obtained from the compound obtained in Preparation Example 3-(8) (24.0 mg) and 4-chloro-1-methyl-1H-pyrazole-3-carboxylic acid (21.0 mg) according to Example 14.

ESI-MS; m/z 408 [M++H].

$^1$H-NMR (400 MHz, CDCl$_3$) δ (ppm): 1.66-2.02 (m, 5H), 2.50-2.66 (m, 1H), 2.76 (dd, J=4.04, 12.76 Hz, 1H), 2.79-2.89 (m, 1H), 2.99 (dd, J=3.28, 12.63 Hz, 1H), 3.93 (s, 3H), 7.02 (dd, J=8.78, 12.06 Hz, 1H), 7.20 (dd, J=2.78, 7.20 Hz, 1H), 7.45 (s, 1H), 7.99 (ddd, J=2.78, 4.11, 8.78 Hz, 1H), 8.58 (s, 1H).

Example 274

Synthesis of (±)-6-{(E)-2-[3-((4aR*,7aS*)-2-amino-4a,5,6,7,7a-tetrahydro-4H-cyclopenta[d][1,3]thiazin-7a-yl)-4-fluorophenyl]vinyl}nicotinonitrile

[Formula 239]

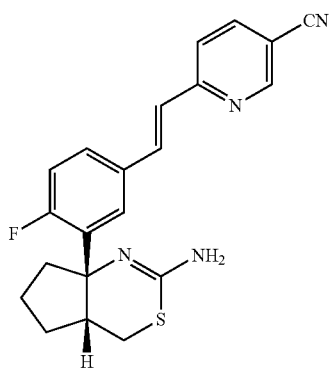 [SMILES: N#Cc1ccc(/C=C/c2ccc(F)c([C@]34CCC[C@H]3CSC(N)=N4)c2)nc1]

Trifluoroacetic acid (0.3 mL) was added to a solution of the compound obtained in Preparation Example 77 (17 mg) in dichloromethane (2 mL), and the mixture was stirred at room temperature for 30 minutes. The reaction solution was neutralized with a sodium carbonate solution. The reaction mixture was extracted with dichloromethane. The organic layer was dried over anhydrous magnesium sulfate. The drying agent was removed by filtration and the filtrate was concentrated under reduced pressure to obtain a residue. The residue was purified by preparative HPLC to obtain the title compound (5.1 mg).

$^1$H-NMR (400 MHz, CDCl$_3$) δ (ppm): 2.00 (m, 4H), 2.31 (m, 1H), 2.55 (m, 1H), 2.87 (dd, J=4.0, 12.9 Hz, 1H), 3.07 (dd, J=4.0, 12.9 Hz, 1H), 3.14 (m, 1H), 7.09 (dd, J=8.3, 12.2 Hz, 1H), 7.14 (d, J=16.2 Hz, 1H), 7.49 (dd, J=0.7, 8.3 Hz, 1H), 7.53 (m, 1H), 7.59 (dd, J=2.2, 8.0 Hz, 1H), 7.78 (d, J=16.2 Hz, 1H), 7.91 (dd, J=2.2, 8.2 Hz, 1H) 8.84 (dd, J=0.5, 2.1 Hz, 1H)

Example 275

Synthesis of (±)-(4aR*,7aS*)-7a-(5((E)-2-(5-chloropyridin-2-yl)vinyl)-2-fluorophenoxy)-4,4a,5,6,7,7a-hexahydrocyclopenta[d][1,3]thiazin-2-amine

[Formula 240]

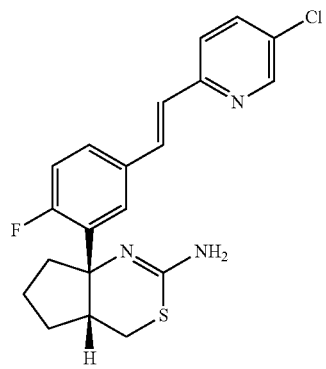 [SMILES: NC1=N[C@@]2(c3cc(/C=C/c4ccc(Cl)cn4)ccc3F)CCC[C@H]2CS1]

The title compound (13.4 mg) was obtained from the compound obtained in Preparation Example 72 (200 mg) and 2-bromo-5-chloropyridine (73 mg) according to Example 274.

$^1$H-NMR (400 MHz, CDCl$_3$) δ (ppm): 1.70-2.00 (m, 4H), 2.19 (m, 1H), 2.40 (m, 1H), 2.76 (dd, J=3.8, 13.0 Hz, 1H), 2.96 (dd, J=3.8, 13.0 Hz, 1H), 3.06 (m, 1H), 6.90 (m, 2H), 7.18 (d, J=8.5 Hz, 1H), 7.28 (dd, J=2.1, 8.0 Hz, 1H), 7.34 (m, 1H), 7.39 (d, J=16.1 Hz, 1H), 7.49 (dd, J=2.5, 8.4 Hz, 1H), 8.36 (d, J=2.4 Hz, 1H)

Example 276

Synthesis of (±)-6-{[3-(2-amino-4a,5,6,7,-tetrahydro-4H-cyclopenta[d][1,3]thiazin-7a(4H)-yl)-4-fluorophenyl]ethynyl}nicotinonitrile

[Formula 241]

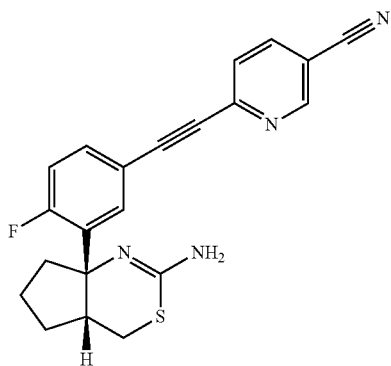 [SMILES: N#Cc1ccc(C#Cc2ccc(F)c([C@]34CCC[C@H]3CSC(N)=N4)c2)nc1]

The compound obtained in Preparation Example 78-(2) (135 mg) was mixed with bis(triphenylphosphine)palladium (II)dichloride (35 mg), copper (I) iodide (9.4 mg) and 2-bromo-5-cyanopyridine (180 mg) in triethylamine (3.5 mL) and tetrahydrofuran (0.45 mL), and the mixture was stirred under a nitrogen atmosphere at 90° C. for five hours. The reaction suspension was filtered and concentrated. Then, the resulting residue was purified by preparative LCMS to obtain the title compound (113 mg).

$^1$H-NMR (400 MHz, CDCl$_3$) δ (ppm): 1.60-1.90 (m, 5H), 2.43 (m, 1H), 2.72 (m, 1H), 2.84 (m, 2H), 5.77 (brs, 2H), 7.32 (dd, J=8.5, 12.3 Hz, 1H), 7.62 (m, 2H), 7.88 (d, J=8.2 Hz, 1H), 8.39 (dd, J=1.8, 8.1 Hz, 1H), 9.06 (s, 1H)

ESI-MS; m/z 377 [M$^+$+H].

Example 277

Synthesis of (±)-(4aR*,7aS*)-7a-[2-fluoro-5-(5-fluoropyridin-2-yl)ethynyl]phenyl}-4,4a,5,6,7,7a-hexahydrocyclopenta[d][1,3]thiazin-2-amine

[Formula 242]

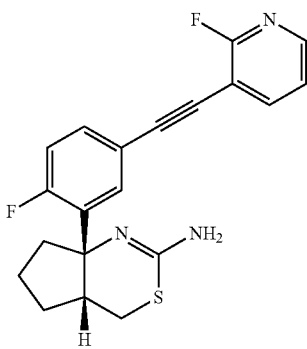 [SMILES: NC1=N[C@@]2(c3cc(C#Cc4cccnc4F)ccc3F)CCC[C@H]2CS1]

The title compound (59 mg) was obtained from the compound obtained in Preparation Example 78-(2) (200 mg) and 3-bromo-2-fluoropyridine (257 mg) according to Example 276.

ESI-MS; m/z 370 [M$^+$+H].

Example 278

Synthesis of (±)-(4aR*,7aS*)-7a-{2-fluoro-5-[2-(2-fluoropyridin-3-yl)ethyl]phenyl]-4,4a,5,6,7,7a-hexahydrocyclopenta[d][1,3]thiazin-2-ylamine

[Formula 243]

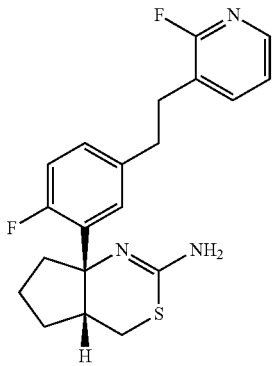 [SMILES: NC1=N[C@@]2(c3cc(CCc4cccnc4F)ccc3F)CCC[C@H]2CS1]

A 10% palladium hydroxide catalyst was added to a mixed solution of the compound obtained in Example 277 (20 mg) in methanol (5 mL) and ethyl acetate (5 mL), and the mixture was stirred in a hydrogen atmosphere at room temperature overnight. The reaction suspension was filtered through Celite and concentrated. Then, the resulting residue was purified by preparative LCMS to obtain the title compound (18 mg).

ESI-MS; m/z 374[M$^+$+H].

Example 279

The compound of Example 279 as shown in Table 31 below was synthesized according to Example 278 using the corresponding alkyne compound.

[Table 31]

TABLE 31

| Example | Chemical structure | Compound name: |
|---|---|---|
| 279 | 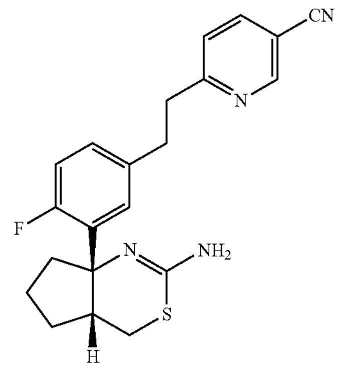 [SMILES: N#Cc1ccc(CCc2ccc(F)c([C@]34CCC[C@H]3CSC(N)=N4)c2)nc1] | (±)-6-{2-[3-(2-amino-4a,5,6,7-tetrahydrocyclopenta[d][1,3]thiazin-7a(4H)-yl)-4-fluorophenyl]ethyl}pyridine-3-carbonitrile ESI-MS; m/z 381 [M$^+$ + H] |

Example 280

Synthesis of N-[3-((4aS,5S,7aS)-2-amino-5-difluoromethyl-4a,5-dihydro-4H-furo[3,4-d][1,3]thiazin-7a-yl)-4-fluorophenyl]-5-dihydropyridine-2-carboxamide

[Formula 244]

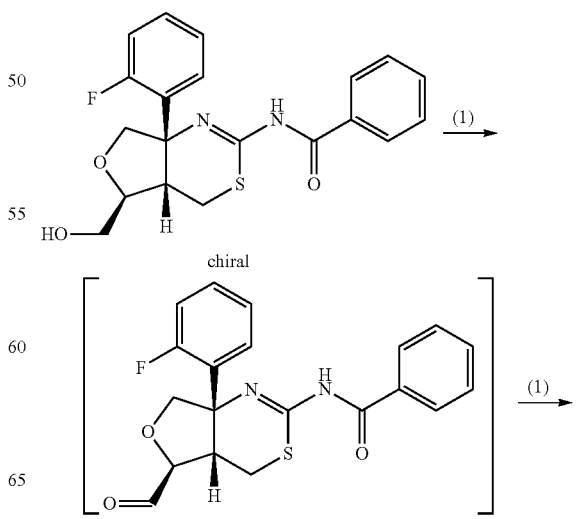

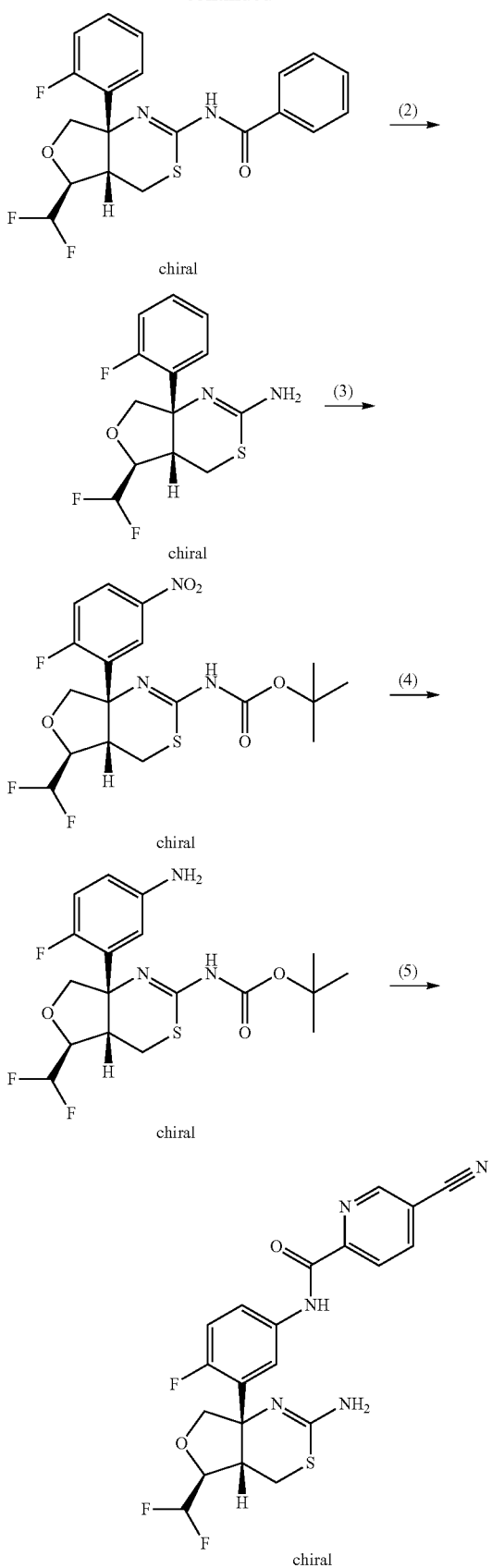

(1) Synthesis of N-[(4aS,5S,7aS)-5-difluoromethyl-7a-(2-fluorophenyl)-4a,5,7,7a-tetrahydro-4H-furo[3,4-d][1,3]thiazin-2-yl]benzamide A solution of DMSO (165 µL) in dichloromethane (0.5 mL) was added dropwise to a solution of oxarylchloride (166 µL) in dichloromethane (12 mL) under a nitrogen atmosphere at −78° C. After the mixture was stirred for 10 minutes at the same temperature, a solution of the compound obtained in Preparation Example 25-(9) (500 mg) in dichloromethane (2.5 mL) was added dropwise. The mixture was stirred for 45 minutes at the same temperature. Diisopropylamine (1.12 mL) was added to the reaction solution at the same temperature, and warmed to room temperature. The reaction solution was stirred for one hour at room temperature. Aqueous ammonium chloride solution and ethylacetate were added, and an organic layer was separated. The organic layer was washed with an aqueous saturated sodium chloride solution, and dried over anhydrous magnesium sulfate. The organic layer was concentrated under reduced pressure to obtain a crude aldehyde body. Dichloromethane (10 mL) was added to the crude aldehyde body, and the mixture was cooled by ice. Diethylaminosulfurtrifluoride (676 µL) was added dropwise to the mixture, and the mixture was stirred for 30 minutes, followed by warming to room temperature. The reaction solution was further stirred for two hours. Aqueous saturated sodium bicarbonate solution and chloroform were added to the reaction solution and the organic layer was separated. The organic layer was dried over anhydrous magnesium sulfate, and concentrated under reduced pressure. The residue was purified by a silica gel chromatography to obtain the title compound (170 mg).

The reactions as described above were conducted at the same scale using [bis(2-methoxyethyl)amino]sulfurtrifluoride (0.95 mL), instead of diethylaminosulfurtrifluoride, to obtain the title compound (140 mg).

ESI-MS; m/z 407[M$^+$+H].
$^1$H-NMR (400 MHz, CDCl$_3$) δ (ppm): 2.85-2.91 (m, 1H), 3.14-3.29 (m, 1H), 3.51-3.60 (m, 1H), 4.00-4.09 (m, 1H), 4.53 (d, J=9.2 Hz, 1H), 4.60-4.70 (m, 1H), 5.86-6.15 (m, 1H), 7.12-7.27 (m, 2H), 7.35-7.53 (m, 5H), 8.00-8.18 (m, 2H).

(2) Synthesis of (4aS,5S,7aS)-5-difluoro-7a-(2-fluorophenyl)-4a,5,7,7a-tetrahydro-4H-furo[3,4-d][1,3]thiazin-2-ylamine Hydrazine hydrate (738 µL) was added to a solution of the compound obtained in Example 280-(1) (310 mg) in ethanol (8 mL), and stirred for three hours at room temperature. Aqueous saturated sodium chloride solution and ethylacetate were added to the reaction solution and the organic layer was separated. The organic layer was dried over anhydrous magnesium sulfate, and concentrated under reduced pressure. The residue was purified by a slica gel chromatography to obtain the title compound (185 mg).

ESI-MS; m/z 303[M$^+$+H].
$^1$H-NMR (400 MHz, CDCl$_3$) δ(ppm): 2.84 (dd, J=3.6, 13.2 Hz, 1H), 3.10 (dd, J=3.6, 13.2 Hz, 1H), 3.23-3.27 (m, 1H), 3.85-3.88 (m, 1H), 4.45-4.58 (m, 4H), 5.77-6.07 (m, 1H), 7.06 (ddd, J=1.2, 8.4, 12.8 Hz, 1H), 7.13-7.18 (m, 1H), 7.28-7.31 (m, 1H), 7.41-7.45 (m, 1H).

(3) Synthesis of tert-butyl[(4aS,5S,7aS)-difluoromethyl-7a-(2-fluoro-5-nitrophenyl)-4a,5,7,7a-tetrahydro-4H-furo[3,4-d][1,3]thiazin-2-yl]carbamate White fumic nitric acid (39.7 µL) was added dropwise to a solution of the compound obtained in Example 280-(2) (185 mg) under ice cooling. The reaction solution was stirred for 30 minutes at room temperature, and then poured onto ice. The resulting mixture was made basic with 5N sodium hydroxide under ice cooling. Chloroform was added to the reaction solution and the organic layer was separated. The organic layer was dried over anhydrous magnesium sulfate, and concentrated under reduced pressure. The residue was dissolved in THF (801 mL), and triethylamine (0.85 mL) and di-tert-butyl dicarbonate (801 mg) were added, and the resulting mixture was stirred for twenty hours. Triethylamine (0.85 mL) and di-tert-butyl dicarbonate (801 mg) were added again to the reaction solution, and the mixture was stirred for five hours. An aqueous saturated sodium chloride and ethyacetate were added to the reaction solution and the organic layer was separated. The organic layer was dried over anhydrous magnesium sulfate, and concentrated under reduced pressure. The residue was purified by a slica gel chromatography to obtain the title compound (213 mg).

ESI-MS; m/z 448[M$^+$+H].
$^1$H-NMR (400 MHz, CDCl$_3$) δ (ppm): 1.53 (s, 9H), 2.78 (dd, J=3.6, 14.0 Hz, 1H), 2.91-2.98 (m, 1H), 3.37-3.44 (m, 1H), 3.79-3.84 (m, 1H), 4.46 (d, J=8.0 Hz, 1H), 4.58-4.64 (m, 1H), 5.83-6.13 (m, 1H), 7.27-7.33 (m, 1H), 8.21-8.25 (m, 1H), 8.31 (dd, J=2.8, 6.8 Hz, 1H).

(4) Synthesis of tert-butyl[(4aS,5S,7aS)-7a-(5-amino-2-fluorophenyl)-5-difluoromethyl-4a,5,7,7a-tetrahydro-4H-furo[3,4-d][1,3]thiazin-2-yl]carbamate Aqueous saturated ammonium chloride (2 mL) and iron powder (276 mg) were added to a solution of the compound obtained in Example 280-(3) (210 mg) in ethanol (10 mL), and heated under reflux for 30 minutes. The temperature of the reaction solution was returned to room temperature, and diluted with ethylacetate. The materials insoluble in the reaction solution were removed by Celitefiltration. Aqueous saturated sodium chloride and ethyl acetate were added to the filtrate and the organic layer was separated. The organic layer was dried over anhydrous magnesium sulfate, and concentrated under reduced pressure. The residue was purified by a NH-slica gel chromatography to obtain the title compound (144 mg).

ESI-MS; m/z 418[M$^+$+H].
$^1$H-NMR (400 MHz, CDCl$_3$) δ (ppm): 1.51 (s, 9H), 2.76 (dd, J=3.6, 14.0 Hz, 1H), 3.04-3.12 (m, 1H), 3.33-3.42 (m, 1H), 3.62 (brs, 2H), 3.80-3.85 (m, 1H), 4.50 (d, J=8.4 Hz, 1H), 4.49-4.59 (m, 1H), 5.94 (dt, J=3.6, 55.6 Hz, 1H), 6.55-6.62 (m, 2H), 6.87 (dd, J=8.4, 12.4 Hz, 1H).

(5) Synthesis of N-[3-((4aS,5S,7aS)-2-amino-5-difluoromethyl-4a,5-dihydro-4H-furo[3,4-d][1,3]thiazin-7a-yl)-4-fluorophenyl]-5-cyanopyridine-2-carboxamide The title compound (15 mg) was obtained according to the methods of Example 14 from the compound obtained in Example 280-(4) (28 mg) and the compound obtained in Preparation Example 13-(2) (19 mg).

ESI-MS; m/z 448[M$^+$+H].
$^1$H-NMR (400 MHz, CDCl$_3$) δ (ppm): 3.05 (dd, J=3.6, 14.0 Hz, 1H), 3.40 (dd, J=3.6, 13.6 Hz, 1H), 3.70-3.76 (m, 1H), 4.27-4.33 (m, 1H), 4.47-4.57 (m, 2H), 6.05 (dt, J=3.2, 54.8 Hz, 1H), 7.19 (dd, J=9.2, 12.0 Hz, 1H), 7.70 (dd, J=2.8, 7.2 Hz, 1H), 7.94-7.98 (m, 1H), 8.22 (dd, J=2.0, 8.0 Hz, 1H), 8.41 (dd, J=0.8, 8.0 Hz, 1H), 8.92 (dd, J=0.8, 2.0 Hz, 1H), 9.96 (s, 1H).

Examples 281 to 284

The compounds of Examples 281 to 284 as shown in Table 32 below were synthesized according to the methods of Example 280, using the corresponding carboxylic acids.
[Table 32]

TABLE 32

| Example | | Compound name: |
|---|---|---|
| 281 | 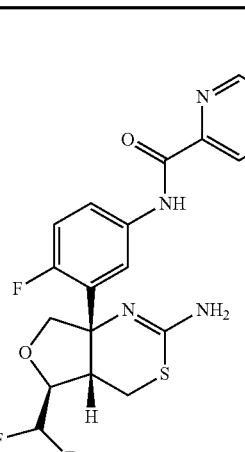 | N-[3-((4aS,5S,7aS)-2-amino-5-difluoromethyl-4a,5-dihydro-4H-furo[3,4-d][1,3]thiazin-7a-yl)-4-fluorophenyl]-5-difluoromethyl pyrazine-2-carboxamide<br>$^1$H-NMR (400 MHz, CDCl$_3$) δ (ppm): 2.87 (dd, J = 2.0, 13.2 Hz, 1H), 3.14 (dd, J = 3.2, 13.6 Hz, 1H), 3.29-3.34 (m, 1H), 3.86-3.89 (m, 1H), 4.48-4.57 (m, 2H), 5.81-6.10 (m, 1H), 6.80 (t, J = 54.4 Hz, 1H), 7.13 (dd, J = 8.4, 11.6 Hz, 1H), 7.62 (dd, J = 2.8, 7.2 Hz, 1H), 7.93-7.97 (m, 1H), 8.92 (d, J = 1.2 Hz, 1H), 9.53 (d, J = 0.8 Hz, 1H), 9.65 (s, 1H).<br>ESI-MS; m/z 474 [M$^+$ + H] |

TABLE 32-continued

| Example | | Compound name: |
|---|---|---|
| 282 | 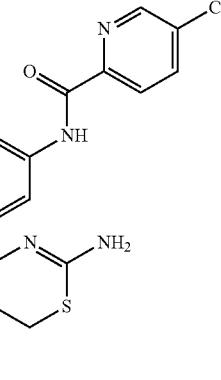 | N-[3-((4aS,5S,7aS)-2-amino-5-difluoromethyl-4a,5-dihydro-4H-furo[3,4-d][1,3]thiazin-7a-yl)-4-fluorophenyl]-5-chloro pyridine-2-carboxamide<br>$^1$H-NMR (400 MHz, CDCl$_3$), δ (ppm): 3.01-3.04 (m, 1H), 3.35-3.41 (m, 1H), 3.63-3.72 (m, 1H), 4.24-4.31 (m, 1H), 4.45-4.58 (m, 2H), 5.89-6.18 (m, 1H), 7.17 (dd, J = 8.8, 12.0 Hz, 1H), 7.66 (dd, J = 2.8, 7.2 Hz, 1H), 7.90 (dd, J = 2.4, 8.4 Hz, 1H), 7.93-7.99 (m, 1H), 8.23 (d, J = 8.4 Hz, 1H), 8.59 (d, J = 2.4 Hz, 1H), 9.19 (s, 1H).<br>ESI-MS; m/z 457 [M$^+$ + H] |
| 283 | 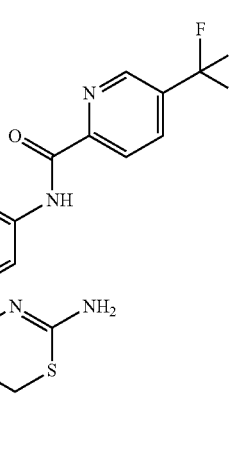 | N-[3-((4aS,5S,7aS)-2-amino-5-difluoromethyl-4a,5-dihydro-4H-furo[3,4-d][1,3]thiazin-7a-yl)-4-fluorophenyl]-5-trifluoro Methylpyridine-2-carboxamide<br>$^1$H-NMR (400 MHz, CDCl$_3$) δ (ppm): 2.87 (dd, J = 4.0, 13.6 Hz, 1H), 3.15 (dd, J = 3.2, 13.6 Hz, 1H), 3.29-3.33 (m, 1H), 3.86-3.90 (m, 1H), 4.49-4.57 (m, 2H), 5.95 (dt, J = 4.0, 55.6 Hz, 1H), 7.12 (dd, J = 8.8, 12.0 Hz, 1H), 7.62 (dd, J = 2.8, 7.2 Hz, 1H), 7.94-7.99 (m, 1H), 8.18 (dd, J = 2.8, 8.0 Hz, 1H), 8.43 (d, J = 8.0 Hz, 1H), 8.89 (d, J = 0.8 Hz, 1H), 9.94 (s, 1H).<br>ESI-MS; m/z 491 [M$^+$ + H] |
| 284 | 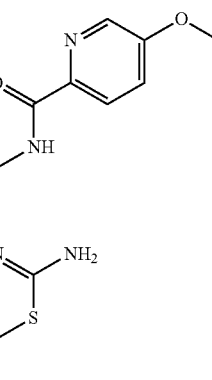 | N-[3-((4aS,5S,7aS)-2-amino-5-difluoromethyl-4a,5-dihydro-4H-furo[3,4-d][1,3]thiazin-7a-yl)-4-fluorophenyl]-5-difluoro methoxypryridine-2-carboxamide<br>$^1$H-NMR (400 MHz, CDCl$_3$) δ (ppm): 2.86 (dd, J = 4.0, 13.6 Hz, 1H), 3.13 (dd, J = 3.2, 13.2 Hz, 1H), 3.28-3.32 (m, 1H), 3.86-3.89 (m, 1H), 4.48-4.56 (m, 2H), 5.94 (dt, J = 4.4, 55.6 Hz, 1H), 6.65 (t, J = 72.0 Hz, 1H), 7.10 (dd, J = 8.8, 11.6 Hz, 1H), 7.60 (dd, J = 2.8, 6.8 Hz, 1H), 7.66 (dd, J = 2.4, 8.8 Hz, 1H), 7.92-7.96 (m, 1H), 8.31 (d, J = 8.4 Hz, 1H), 8.45 (d, J = 2.8 Hz, 1H), 9.84 (s, 1H).<br>ESI-MS; m/z 489 [M$^+$ + H] |

Example 285

Synthesis of (±)-N-[5-((4aS*,5R*,7aR*)-2-amino-5-methyl-4a,5-dihydro-4H-furo[3,4-d][1,3]thiazin-7a-yl)-thiophene-3-yl]-5-cyanopyridine-2-carboxamide

[Formula 245]

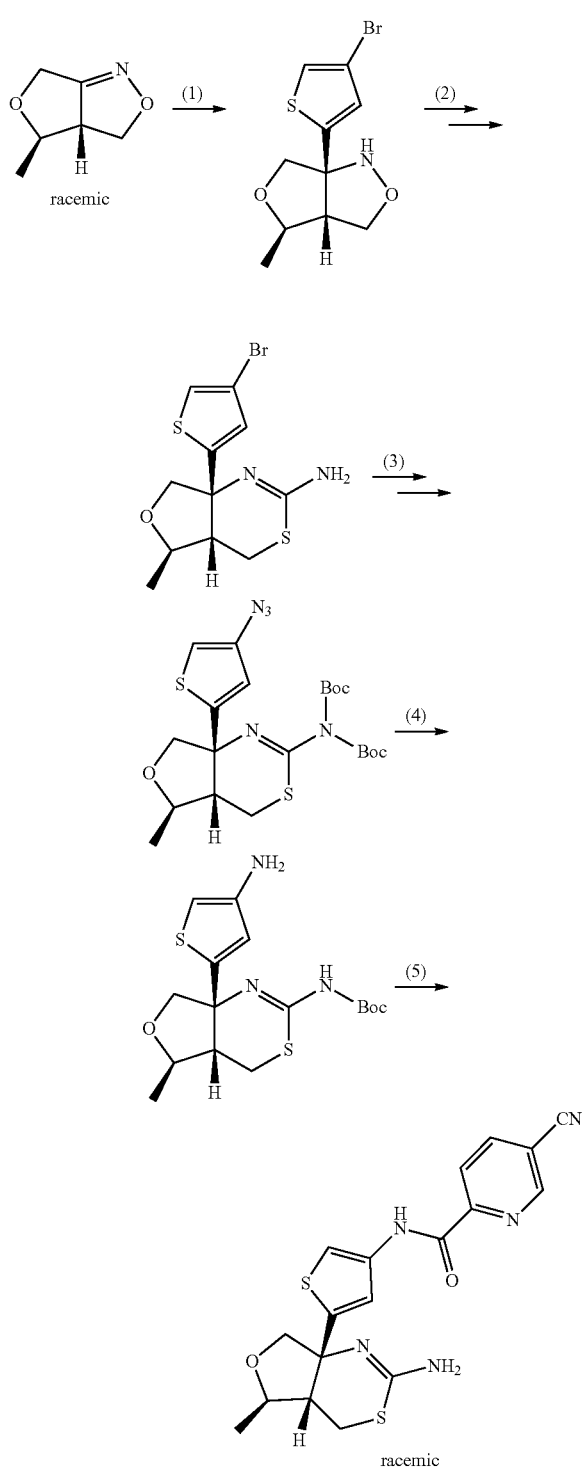

(1) Synthesis of (±)-(3aR*,4R*,6aR*)-6a-(4-bromothiophene-2-yl)-4-methyl-tetrahydro-furo[3,4-c]isoxazole The title compound (956 mg) was obtained according to the methods of Preparation Example 76 from the compound obtained in Preparation Example 22-(2)(410 mg) and 2,4-dibromothiophene (1.64 g). ESI-MS; m/z 290[M++H].

(2) Synthesis of (±)-(4aS*,5R*,7aR*)-7a-(4-bromo-2-thienyl)-5-methyl-4a,5,7,7a-tetrahydro-4H-furo[3,4-d][1,3]thiazin-2-ylamine The title compound (270 mg) was obtained according to the methods of Preparation Example 22 from (±)-(3aR*,4R*,6aR*)-6a-(4-bromothiophene-2-yl)-4-methyl-tetrahydro-flo[3,4-c]isoxazole. However, the debenzoyl reaction corresponding to Preparation Example 22-(7) was conducted according to the methods of Preparation Example 19-(9).
ESI-MS; m/z 335[M++H].

(3) Synthesis of (±)-di-tert-butyl[(4aS*,5R*,7aR*)-7a-(4-azido-2-thienyl)-5-methyl-4a,5,7,7a-tetrahydro-4H-furo[3,4-d][1,3]thiazin-2-yl]imidodicarbonate The title compound (75 mg) was obtained according to the methods of Preparation Example 71 from (±)-(4aS*,5R*,7aR*)-7a-(4-bromo-2-thienyl)-5-methyl-4a,5,7,7a-tetrahydro-4H-flo[3,4-d][1,3]thiazin-2-ylamine.
ESI-MS; m/z 496[M++H].

(4) Synthesis of (±)-tert-butyl[(4aS*,5R*,7aR*)-7a-(4-aminothiophene-2-yl)-5-methyl-4a,5,7,7a-tetrahydro-4H-furo[3,4-d][1,3]thiazin-2-yl]carbamate Zinc (19.7 mg) and ammonium formate were added to a solution of (±)-di-tert-butyl[(4aS*,5R*,7aR*)-7a-(4-azido-2-thienyl)-5-methyl-4a,5,7,7a-tetrahydro-4H-flo[3,4-d][1,3]thiazin-2-yl]imidodicarbonate (75 mg) in methanol (5 mL). The mixture was stirred for three days at room temperature. Further, methanol (50 mL), zinc (197 mg) and ammonium formate (476 mg) were added to the reaction mixture, and then the mixture was stirred for three hours. The excess of ethanol was evaporated under reduced pressure. Water and ethylacetate were added to the residue to dissolve insoluble materials. The water layer was extracted with ethylacetate, and the organic layer was washed with water. The organic layer was dried over anhydrous magnesium sulfate, and the solvent was evaporated under reduced pressure. The residue was purified by a NH-slica gel chromatography to obtain the title compound (35 mg).
ESI-MS; m/z 370[M++H].

(5) Synthesis of (±)-N-[5-((4aS*,5R*,7aR*)-2-amino-5-methyl-4a,5-dihydro-4H-furo[3,4-d][1,3]thiazin-7a-yl)-thiophene-3-yl]-5-cyanopyridine-2-carboxamide The title compound (27 mg) was obtained according to the methods of Example 14 from the compound obtained in Example 285-(4) and the compound obtained in Preparation Example 13-(2).
ESI-MS; m/z 400[M++H].

Example 286

Synthesis of (±)-N-[5-((4aS*,8aR*)-2-amino-4a,5,7,8-tetrahydro-4H-6-oxa-3-thia-1-azanaphtalene-8a-yl)-thiophene-3-yl]-5-cyanopyridine-2-carboxamide

[Formula 246]

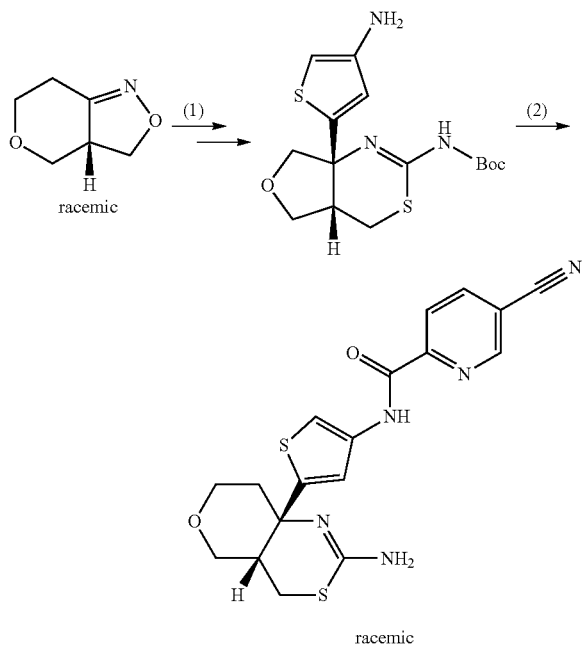

(1) Synthesis of tert-butyl(±)-[(4aS*,8aR*)-8a-(4-amino-thiophene-2-yl)-4a,7,8,8a-tetrahydro-4H,5H-6-oxa-3-thia-1-aza-naphtalene-2-yl]carbamate The title compound (89 mg) was obtained according to the methods of Example 285 from the compound obtained in Preparation Example 8-(2) and 2,4-dibromothiophene.
ESI-MS; m/z 370[M$^+$+H].

(2) Synthesis of (±)-N-[5-((4aS*,8aR*)-2-amino-4a,5,7,8-tetrahydro-4H-6-oxa-3-thia-1-axa-naphtalen-8a-yl)-thiophene-3-yl]-5-cyanopyridine-2-carboxamide The title compound (23 mg) was obtained according to the methods of Example 14 from the compound obtained in Example 286-(1) and the compound obtained in Preparation Example 13-(2).
ESI-MS; m/z 400[M$^+$+H].

Test Example 1

Quantification of Aβ Peptide in Culture of Neurons from Rat Fetus Brain (1) Rat Primary Neuronal Culture Primary neuronal cultures were prepared from the cerebral cortex of embryonic day 18 Wistar rats (Charles River Japan, Yokohama, Japan). Specifically, the embryos were aseptically removed from pregnant rats under ether anesthesia. The brain was isolated from the embryo and immersed in an ice-cold L-15 medium (such as Invitrogen Corp. Cat #11415-064, Carlsbad, Calif., USA, or SIGMA L1518). The cerebral cortex was collected from the isolated brain under a stereoscopic microscope. The cerebral cortex fragments collected were enzymatically treated in an enzyme solution containing 0.25% trypsin (Invitrogen Corp. Cat #15050-065, Carlsbad, Calif., USA) and 0.01% DNase (Sigma D5025, St. Louis, Mo., USA) at 37° C. for 30 minutes to disperse the cells. Here, the enzymatic reaction was stopped by adding inactivated horse serum to the solution. The enzymatically treated solution was centrifuged at 1,500 rpm for five minutes to remove the supernatant. 5 to 10 mL of a medium was added to the resulting cell mass. Neurobasal medium (Invitrogen Corp. Cat #21103-049, Carlsbad, Calif., USA) supplemented with 2% B27 supplement (Invitrogen Corp. Cat #17504-044, Carlsbad, Calif., USA), 25 μM 2-mercaptoethanol (2-ME, WAKO Cat #139-06861, Osaka, Japan), 0.5 mM L-glutamine (Invitrogen Corp. Cat #25030-081, Carlsbad, Calif., USA), and Antibiotics-Antimycotics (Invitrogen Corp. Cat #15240-062, Carlsbad, Calif., USA) was used as the medium (Neurobasal/B27/2-ME). However, the above Neurobasal medium not supplemented with 2-ME (Neurobasal/B27) was used for the assay. The cells were redispersed by mild pipetting of the cell mass to which the medium was added. The cell dispersion was filtered through a 40-μm nylon mesh (Cell Strainer, Cat #35-2340, Becton Dickinson Labware, Franklin Lakes, N.J., USA) to remove the remaining cell mass, and thus a neuronal cell suspension was obtained. The neuronal cell suspension was diluted with the medium and then plated in a volume of 100 μL/well at an initial cell density of 5×10$^5$ cells/cm$^2$ in a 96-well polystyrene culture plate pre-coated with poly-L or D-lysine (Falcon Cat #35-3075, Becton Dickinson Labware, Franklin Lakes, N.J., USA coated with poly-L-lysine using the method shown below, or BIOCOAT™ cell environments Poly-D-lysine cell ware 96-well plate, Cat #35-6461, Becton Dickinson Labware, Franklin Lakes, N.J., USA). Poly-L-lysine coating was carried out as follows. 100 μg/mL of a poly-L-lysine (SIGMA P2636, St. Louis, Mo., USA) solution was aseptically prepared with a 0.15 M borate buffer (pH 8.5). 100 μg/well of the solution was added to the 96-well polystyrene culture plate and incubated at room temperature for one or more hours or at 4° C. overnight or longer. Thereafter, the coated 96-well polystyrene culture plate was washed with sterile water four or more times, and then dried or rinsed with, for example, sterile PBS or medium, and used for cell plating. The plated cells were cultured in the culture plate at 37° C. in 5% $CO_2$-95% air for one day. Then, the total amount of the medium was replaced with a fresh Neurobasal™/B27/2-ME medium, and then the cells were cultured for further three days.

(2) Addition of Compound

The drug was added to the culture plate on Day 4 of culture as follows. The total amount of the medium was removed from the wells, and 180 μL/well of Neurobasal medium not containing 2-ME and containing 2% B-27 (Neurobasal/B27) was added thereto. A solution of the test compound in dimethyl sulfoxide (hereinafter abbreviated as DMSO) was diluted with Neurobasal/B27 to a concentration 10-fold higher than the final concentration. 20 μL/well of the dilution was added to and sufficiently mixed with the medium. The final DMSO concentration was 1% or less. Only DMSO was added to the control group.

(3) Sampling

The cells were cultured for three days after addition of the compound, and the total amount of the medium was collected. The resulting medium was used as an ELISA sample. The sample was not diluted for ELISA measurement of Aβx-42 and diluted to 5-fold with a diluent supplied with an ELISA kit for ELISA measurement of Aβx-40.

(4) Evaluation of Cell Survival

Cell survival was evaluated by an MTT assay according to the following procedure. After collecting the medium, 100 μL/well of a pre-warmed medium was added to the wells. Further, 8 μL/well of a solution of 8 mg/mL of MTT (SIGMA M2128, St. Louis, Mo., USA) in D-PBS(−) (Dulbecco's phosphate buffered Saline, SIGMA D8537, St. Louis, Mo., USA) was added to the wells. The 96-well polystyrene culture plate was incubated in an incubator at 37° C. in 5% $CO_2$-95% air for 20 minutes. 100 μL/well of an MTT lysis buffer was added thereto, and MTT formazan crystals were sufficiently dissolved in the buffer in the incubator at 37° C. in 5% $CO_2$-95% air. Then, the absorbance at 550 nm in each well was measured. The MTT lysis buffer was prepared as follows. 100 g of SDS (sodium dodecyl sulfate (sodium lauryl sulfate), WAKO 191-07145, Osaka, Japan) was dissolved in a mixed solution of 250 mL of N,N-dimethylformamide (WAKO 045-02916, Osaka, Japan) with 250 mL of distilled water. 350 μL each of concentrated hydrochloric acid and acetic acid were further added to the solution to allow the solution to have a final pH of about 4.7.

Upon measurement, wells having no cells plated and containing only the medium and MTT solution were set as background (bkg). The measured values were respectively applied to the following formula including subtracting bkg values from them. Thus, the proportion against the control group (group not treated with the drug, CTRL) (% of CTRL) was calculated to compare and evaluate cell survival activities.

% of CTRL=(A550_sample−A550_bkg)/(A550_CTRL−bkg)×100

(A550_sample: absorbance at 550 nm of sample well, A550_bkg: absorbance at 550 nm of background well, A550_CTRL: absorbance at 550 nm of control group well)

(5) Aβ ELISA

Human/Rat β Amyloid (42) ELISA Kit Wako (#290-62601) and Human/Rat β Amyloid (40) ELISA Kit Wako (#294-62501) from Wako Pure Chemical Industries, Ltd. were used for Aβ ELISA. Aβ ELISA was carried out according to the protocols recommended by the manufacturers (methods described in the attached documents). However, the Aβ calibration curve was created using beta-amyloid peptide 1-42, rat and beta-amyloid peptide 1-40, rat (Calbiochem, #171596 [Aβ$_{42}$], #171593 [Aβ$_{40}$]). The results are shown in Tables 33, 34 and 35 below as percentage to the Aβ concentration in the medium of the control group (% of CTRL).

[Table 33]

TABLE 33

| Test compound | Aβ42 production reducing effect IC50 (μM) |
|---|---|
| 3 | 0.009 |
| 5 | 0.003 |
| 6 | 0.088 |
| 9 | 0.028 |
| 19 | 0.045 |
| 20 | 0.005 |
| 21 | 0.013 |
| 22 | 0.005 |
| 23 | 0.01 |
| 24 | 0.0043 |
| 25 | 0.0061 |
| 26 | 0.0069 |
| 27 | 0.011 |
| 28 | 0.012 |

TABLE 33-continued

| Test compound | Aβ42 production reducing effect IC50 (μM) |
|---|---|
| 29 | 0.004 |
| 30 | 0.011 |
| 31 | 0.004 |
| 32 | 0.0011 |
| 33 | 0.01 |
| 34 | 0.115 |
| 36 | 0.384 |
| 37 | 0.029 |

[Table 34]

TABLE 34

| Test compound | Aβ42 production reducing effect IC50 (μM) |
|---|---|
| 38 | 0.006 |
| 39 | 0.007 |
| 40 | 0.026 |
| 41 | 0.006 |
| 42 | 0.004 |
| 43 | 0.019 |
| 48 | 0.575 |
| 49 | 0.0008 |
| 50 | 0.0009 |
| 51 | 0.0016 |
| 52 | 0.002 |
| 53 | 0.002 |
| 54 | 0.0017 |
| 55 | 0.0011 |
| 56 | 0.003 |
| 57 | 0.003 |
| 58 | 0.007 |
| 59 | 0.002 |
| 60 | 0.012 |
| 63 | 0.011 |
| 64 | 0.008 |
| 65 | 0.038 |
| 66 | 0.0013 |
| 67 | 0.0014 |
| 68 | 0.006 |
| 69 | 0.002 |
| 70 | 0.002 |
| 71 | 0.001 |
| 72 | 0.002 |
| 73 | 0.007 |
| 75 | 0.003 |
| 79 | 0.028 |
| 80 | 0.008 |
| 81 | 0.014 |
| 82 | 0.425 |
| 84 | 0.893 |
| 87 | 0.062 |
| 88 | 0.075 |
| 89 | 0.0032 |
| 90 | 0.0025 |
| 91 | 0.0014 |
| 92 | 0.005 |
| 93 | 0.003 |
| 94 | 0.002 |
| 95 | 0.001 |
| 96 | 0.001 |
| 98 | 0.001 |
| 99 | 0.001 |
| 100 | 0.002 |
| 104 | 0.212 |
| 105 | 0.121 |
| 106 | 0.088 |
| 107 | 0.017 |
| 108 | 0.001 |
| 109 | 0.0018 |
| 110 | 0.005 |
| 117 | 0.158 |

TABLE 34-continued

| Test compound | Aβ42 production reducing effect IC50 (μM) |
|---|---|
| 120 | 0.038 |
| 121 | 0.263 |
| 122 | 0.123 |
| 126 | 0.07 |
| 127 | 0.214 |
| 128 | 0.231 |
| 129 | 0.065 |
| 132 | 0.044 |
| 133 | 0.063 |
| 134 | 0.086 |
| 135 | 0.015 |
| 136 | 0.025 |
| 137 | 0.047 |
| 138 | 0.063 |
| 139 | 0.169 |
| 140 | 0.067 |
| 141 | 0.016 |
| 142 | 0.01 |
| 143 | 0.016 |
| 144 | 0.011 |
| 145 | 0.003 |

[Table 35]

TABLE 35

| Test compound | Aβ42 production reducing effect IC50 (μM) |
|---|---|
| 146 | 0.032 |
| 147 | 0.012 |
| 148 | 0.009 |
| 149 | 0.414 |
| 151 | 0.167 |
| 158 | 0.053 |
| 160 | 0.521 |
| 163 | 0.367 |
| 164 | 0.001 |
| 165 | 0.012 |
| 166 | 0.004 |
| 167 | 0.006 |
| 168 | 0.016 |
| 169 | 0.027 |
| 170 | 0.21 |
| 171 | 0.089 |
| 172 | 0.007 |
| 173 | 0.072 |
| 174 | 0.011 |
| 175 | 0.009 |
| 176 | 0.01 |
| 177 | 0.018 |
| 178 | 0.044 |
| 179 | 0.098 |
| 180 | 0.003 |
| 181 | 0.047 |
| 182 | 0.09 |
| 183 | 0.028 |
| 184 | 0.013 |
| 185 | 0.01 |
| 186 | 0.03 |
| 187 | 0.054 |
| 188 | 0.022 |
| 189 | 0.008 |
| 190 | 0.012 |
| 191 | 0.009 |
| 195 | 0.068 |
| 196 | 0.977 |
| 197 | 0.22 |
| 198 | 0.129 |
| 199 | 0.012 |
| 200 | 0.044 |
| 202 | 0.003 |
| 204 | 0.023 |

TABLE 35-continued

| Test compound | Aβ42 production reducing effect IC50 (μM) |
|---|---|
| 205 | 0.025 |
| 206 | 0.002 |
| 207 | 0.003 |
| 215 | 0.01 |
| 223 | 0.316 |
| 224 | 0.271 |
| 225 | 0.198 |
| 226 | 0.233 |
| 229 | 0.544 |
| 230 | 0.202 |
| 233 | 0.086 |
| 236 | 0.059 |
| 237 | 0.08 |
| 238 | 0.35 |
| 239 | 0.238 |
| 240 | 0.039 |
| 243 | 0.069 |
| 245 | 1.159 |
| 248 | 0.016 |
| 249 | 0.018 |
| 250 | 0.027 |
| 251 | 0.12 |
| 252 | 0.187 |
| 253 | 0.171 |
| 254 | 0.043 |
| 255 | 0.158 |
| 256 | 0.038 |
| 257 | 0.017 |
| 258 | 0.376 |
| 259 | 0.372 |
| 260 | 0.17 |
| 261 | 0.277 |

As is clear from the results of Table 1, the compound of the present invention was proved to have an Aβ42 production reducing effect.

The compound of the general formula (I) or pharmaceutically acceptable salt thereof or solvate thereof according to the present invention have an Aβ42 production reducing effect. Thus, the present invention can particularly provide a prophylactic or therapeutic agent for a neurodegenerative disease caused by Aβ such as Alzheimer-type dementia or Down's syndrome.

The invention claimed is:
1. A compound represented by the formula:

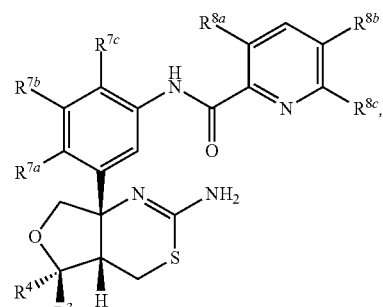

or a pharmaceutically acceptable salt thereof, wherein:
R$^3$ and R$^4$ are independently selected from the group consisting of H and C$_{1-6}$ alkyl, wherein the C$_{1-6}$ alky is optionally substituted by 1, 2, or 3 substituents;
R$^{7a}$, R$^{7b}$, and R$^{7C}$ are independently selected from the group consisting of H and X;

$R^{8a}$, $R^{8b}$, and $R^{8C}$ are independently selected from the group consisting of H, X, $CH_mX_n$, and $OCH_mX_n$; wherein m is 0, 1, or 2;

n is 1, 2, or 3; and

X is halogen selected from the group consisting of fluorine, chlorine, bromine and iodine.

2. The compound of claim 1, or a pharmaceutically acceptable salt thereof, wherein $R^3$ and $R^4$ are H; and only one of $R^{7a}$, $R^{7b}$, and $R^{7C}$ is X.

3. The compound of claim 2, or a pharmaceutically acceptable salt thereof, wherein $R^{8a}$, $R^{8b}$, and $R^{8C}$ are independently selected from the group consisting of H, X, and $CH_mX_n$.

4. The compound of claim 3, or a pharmaceutically acceptable salt thereof, wherein $R^{7b}$ and $R^{7c}$ are H and $R^{7a}$ is X.

5. The compound of claim 4, or a pharmaceutically acceptable salt thereof, wherein $R^{8a}$, $R^{8b}$, and $R^{8C}$ are independently selected from the group consisting of H and X.

6. The compound of claim 5, or a pharmaceutically acceptable salt thereof, wherein $R^{8a}$ and $R^{8C}$ are H and $R^{8b}$ is X.

7. The compound of claim 6, wherein $R^{7a}$ is fluorine.

8. A pharmaceutical composition comprising the compound or pharmaceutically acceptable salt thereof according to any one of claims 1 to 7 as an active ingredient.

9. A method of treating a neurodegenerative disease, comprising administering an effective amount of the pharmaceutical composition according to claim 8 to a subject in need thereof, wherein the neurodegenerative disease is Alzheimer-type dementia or Down's syndrome.

10. A method of treating Alzheimer's disease, comprising administering an effective amount of the pharmaceutical composition according to claim 8 to a subject in need thereof.

\* \* \* \* \*

UNITED STATES PATENT AND TRADEMARK OFFICE
CERTIFICATE OF CORRECTION

PATENT NO. : 8,946,211 B2  
APPLICATION NO. : 13/804691  
DATED : February 3, 2015  
INVENTOR(S) : Yuichi Suzuki et al.

Page 1 of 1

It is certified that error appears in the above-identified patent and that said Letters Patent is hereby corrected as shown below:

In the Claims

Column 414, claim 1

Line 64, delete "alky" and replace it with --alkyl--.

Line 66, delete "$R^{7C}$" and replace it with --$R^{7c}$--.

Column 415, claim 1

Line 1, delete "$R^{8C}$" and replace it with --$R^{8c}$--.

Column 415, claim 2

Line 10, delete "$R^{7C}$" and replace it with --$R^{7c}$--.

Column 415, claim 3

Line 12, delete "$R^{8C}$" and replace it with --$R^{8c}$--.

Column 415, claim 5

Line 17, delete "$R^{8C}$" and replace it with --$R^{8c}$--.

Column 415, claim 6

Line 20, delete "$R^{8C}$" and replace it with --$R^{8c}$--.

Signed and Sealed this  
Eighth Day of September, 2015

Michelle K. Lee  
*Director of the United States Patent and Trademark Office*